United States Patent
Zhao et al.

(10) Patent No.: US 12,297,191 B2
(45) Date of Patent: May 13, 2025

(54) HETEROCYCLIC DERIVATIVE AND ORGANIC ELECTROLUMINESCENT DEVICE THEREOF

(71) Applicant: Changchun Hyperions Technology Co., Ltd, Changchun (CN)

(72) Inventors: Qian Zhao, Changchun (CN); Xiaohui Wang, Changchun (CN); Dongda Zhu, Changchun (CN)

(73) Assignee: Changchun Hyperions Technology Co., Ltd, Changchun (CN)

( * ) Notice: Subject to any disclaimer, the term of this patent is extended or adjusted under 35 U.S.C. 154(b) by 774 days.

(21) Appl. No.: 17/535,110

(22) Filed: Nov. 24, 2021

(65) Prior Publication Data

US 2022/0173333 A1   Jun. 2, 2022

(30) Foreign Application Priority Data

Nov. 30, 2020   (CN) .......................... 202011377608.8

(51) Int. Cl.
   *C07D 403/14*   (2006.01)
   *C07C 211/54*   (2006.01)
   (Continued)

(52) U.S. Cl.
   CPC .......... *C07D 403/14* (2013.01); *C07C 211/54* (2013.01); *C07C 211/61* (2013.01);
   (Continued)

(58) Field of Classification Search
   CPC .. C07D 403/10; C07D 403/14; C07D 413/10; C07D 413/14; C07D 417/10;
   (Continued)

(56) References Cited

U.S. PATENT DOCUMENTS

| 6,171,715 B1 | 1/2001 | Sato et al. |
| 9,266,851 B2 | 2/2016 | Yoshida et al. |

(Continued)

FOREIGN PATENT DOCUMENTS

| CN | 104193738 A | 12/2014 |
| CN | 106536485   | 3/2017  |

(Continued)

OTHER PUBLICATIONS

Extended European Search Report dated Apr. 25, 2022 in EP Patent Application No. 21208948.6, pp. 1-7.

(Continued)

*Primary Examiner* — Vu A Nguyen
(74) *Attorney, Agent, or Firm* — Byrne Poh LLP; Nina R. Horan

(57) ABSTRACT

Provided are a heterocyclic derivative and an organic electroluminescent device thereof, which relates to the field of organic photoelectric materials. The heterocyclic derivative of Formula I has high electron mobility and great hole blocking performance, and thus the organic electroluminescent device prepared by using the heterocyclic derivative as the electron transport region material, especially the hole blocking material, has low drive voltage and high luminous efficiency. The organic electroluminescent device can also include a hole transport region, and the hole transport region, especially the emissive auxiliary layer, contains the triarylamine compound of Formula II. Since the electron transport region and the hole transport region of the device can effectively balance carriers, which reduces the quenching of excitons and improves the recombination probability of carriers, the device shows low drive voltage and high luminous efficiency.

10 Claims, 4 Drawing Sheets

(51) Int. Cl.

| | | |
|---|---|---|
| *C07C 211/61* | (2006.01) | |
| *C07D 235/18* | (2006.01) | |
| *C07D 413/14* | (2006.01) | |
| *C07D 417/14* | (2006.01) | |
| *C09K 11/06* | (2006.01) | |
| *H10K 50/16* | (2023.01) | |
| *H10K 50/18* | (2023.01) | |
| *H10K 85/60* | (2023.01) | |

(52) U.S. Cl.
CPC ......... *C07D 235/18* (2013.01); *C07D 413/14* (2013.01); *C07D 417/14* (2013.01); *C09K 11/06* (2013.01); *H10K 85/615* (2023.02); *H10K 85/624* (2023.02); *H10K 85/633* (2023.02); *H10K 85/657* (2023.02); *H10K 85/6572* (2023.02); *H10K 85/6574* (2023.02); *H10K 85/6576* (2023.02); *C07B 2200/05* (2013.01); *C07C 2603/18* (2017.05); *C07C 2603/42* (2017.05); *C07C 2603/74* (2017.05); *C09K 2211/1007* (2013.01); *C09K 2211/1011* (2013.01); *C09K 2211/1014* (2013.01); *C09K 2211/1018* (2013.01); *H10K 50/16* (2023.02); *H10K 50/18* (2023.02); *H10K 50/181* (2023.02); *H10K 85/622* (2023.02); *H10K 85/626* (2023.02)

(58) Field of Classification Search
CPC ............. C07D 417/14; H10K 85/6672; H10K 85/6574; H10K 85/6576
See application file for complete search history.

(56) References Cited

U.S. PATENT DOCUMENTS

| | | | | |
|---|---|---|---|---|
| 10,903,430 | B2 * | 1/2021 | Jatsch | ............ C07D 235/18 |
| 2015/0318487 | A1 | 11/2015 | Ito et al. | |
| 2015/0318510 | A1 | 11/2015 | Ito et al. | |
| 2019/0027695 | A1 | 1/2019 | Zhang et al. | |
| 2022/0173333 | A1 | 6/2022 | Zhao et al. | |

FOREIGN PATENT DOCUMENTS

| | | | |
|---|---|---|---|
| CN | 106753340 | A | 5/2017 |
| CN | 108997322 | A | 12/2018 |
| CN | 109206420 | | 1/2019 |
| CN | 109879812 | A | 6/2019 |
| CN | 110229145 | A | 9/2019 |
| CN | 111253332 | | 6/2020 |
| CN | 111943902 | A | 11/2020 |
| CN | 112442023 | | 3/2021 |
| EP | 4006025 | | 6/2022 |
| JP | 2017-524699 | A | 8/2017 |
| JP | 2022-087059 | A | 6/2022 |
| JP | 7262138 | | 4/2023 |
| KR | 20170032414 | | 3/2017 |
| WO | WO 2011/046182 | | 4/2011 |
| WO | WO 2016/012075 | | 1/2016 |
| WO | WO 2019/114478 | | 6/2019 |
| WO | WO 2019/166206 | | 9/2019 |

OTHER PUBLICATIONS

First Search Report in CN Patent Application No. 202011377608.8, Date: Unknown, pp. 1.
Office Action dated Apr. 20, 2021 in CN Patent Application No. 202011377608.8, pp. 1-8.
Office Action dated Nov. 4, 2022 in JP Patent Application No. 2021-192199, pp. 1-10.
Office Action dated Jan. 12, 2024 in KR Patent Application No. 10-2021-0167964, pp. 1-15.
European Search Report dated Apr. 25, 2022 in EP Patent Application No. 21214051.1, pp. 1-12.
European Search Report dated Aug. 1, 2022 in EP Patent Application No. 21214051.1, pp. 1-11.
Negi, S., et al., "Impact of Different Layers on Performance of OLED", In Microsystem Technologies, vol. 24, No. 12, Berlin, DE, May 4, 2018, pp. 4981-4989.
Office Action dated Feb. 20, 2024 in JP Patent Application No. 2021-206236, pp. 1-6.
Office Action dated Jun. 16, 2023 in JP Patent Application No. 2021-206236, pp. 1-13.
Office Action dated Nov. 21, 2024 in U.S. Appl. No. 17/557,595, pp. 1-134.
Office Action dated Dec. 14, 2022 in JP Patent Application No. 2021-206236, pp. 1-14.
Office Action undated in CN Patent Application No. 2020115350376, pp. 1-11.

* cited by examiner

HETEROCYCLIC DERIVATIVE AND ORGANIC ELECTROLUMINESCENT DEVICE THEREOF

CROSS-REFERENCE TO RELATED APPLICATION(S)

This application claims priority to Chinese Patent Application No. CN 202011377608.8 filed on Nov. 30, 2020, the disclosure of which is incorporated herein by reference in its entirety.

TECHNICAL FIELD

The present disclosure relates to the technical field of organic photoelectric materials and specifically, relates to a heterocyclic derivative and an organic electroluminescent device thereof.

BACKGROUND

OLED technology refers to the technology that organic materials emit light under the action of the electric field. According to the difference in driving modes, OLED can be divided into passive-matrix OLED (PMOLED) and active-matrix OLED (AMOLED). OLED is a new generation of flat panel display technology after CRT and LCD. It has the characteristics of wide viewing angle, fast response speed, low power consumption, good shock resistance of solid structure, wide working temperature range, thinness, and flexibility, and is known as "fantastic display technology".

The electroluminescence process of organic electroluminescent devices is a process of energy transfer. In this process, the organic electroluminescent device converts electric energy into light energy, and the organic electroluminescent device is regarded as an injection-type light-emitting diode in this conversion process. A voltage is applied to both ends of the organic electroluminescent device. Through the electric field generated by this voltage, holes are injected into the hole transport layer from the anode of the device, while electrons are injected into the electron transport layer from the cathode of the device. These two kinds of carriers migrate into the emissive layer and combine to form excitons, and the radiative transition of excitons causes light emission.

The structure of organic electroluminescent devices is a simple "sandwich" structure, and a basic device is formed by placing an organic functional layer between the anode and the cathode. The organic functional layer can be a single-layer organic functional layer, a double-layer organic functional layer, a three-layer organic functional layer, and a multi-layer organic functional layer, and the types of the organic functional layer can be a hole injection layer, a hole transport layer, an electron blocking layer, an emissive layer, a hole blocking layer, an electron transport layer, an electron injection layer, etc.

It can be seen from the above that the organic electroluminescent device is a stacked structure composed of a variety of functional layers with different properties, and these functional layers have different functions and cooperate with each other to form an organic whole. Each functional layer corresponds to related functional material, that is, the hole injection material, the hole transport material, the electron blocking material, the light-emitting material, the hole blocking material, the electron transport material, the electron injection material, and so on. Although the properties of the light-emitting material are very important for organic electroluminescent devices, in order to improve the performance of devices comprehensively, it is necessary not only to have high-quality light-emitting materials but also to have many auxiliary materials with excellent properties, such as hole injection materials, hole transport materials, electron blocking materials, hole blocking materials, electron transport materials, electron injection materials and so on. The improvement of the properties of these auxiliary materials is helpful to improve the performance of organic electroluminescent devices. Therefore, it is of great significance to research and develop new auxiliary materials.

SUMMARY

In view of the preceding problems in the related art, the present disclosure provides a heterocyclic derivative and an organic electroluminescent device thereof.

The present disclosure provides a heterocyclic derivative having a general structural formula as shown in Formula I:

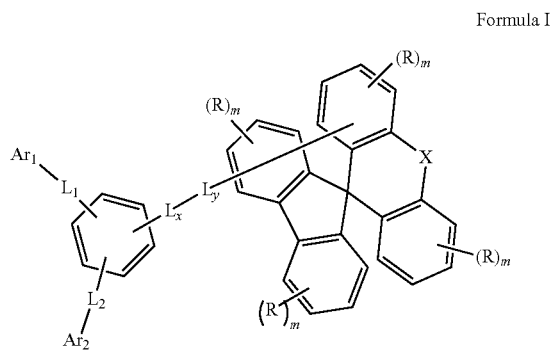

Formula I wherein $Ar_1$ and $Ar_2$ are identical or different and selected from the following group:

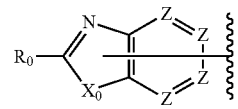

wherein $R_0$ is selected from one of hydrogen, deuterium, halogen, cyano, nitro, substituted or unsubstituted C1 to C30 alkyl, substituted or unsubstituted C3 to C30 cycloalkyl, substituted or unsubstituted C6 to C60 aryl or substituted or unsubstituted C3 to C60 heteroaryl, $X_0$ is selected from one of O, S, N($R_x$) or C($R_x$)$_2$, wherein $R_x$ is selected from one of substituted or unsubstituted C1 to C30 alkyl, substituted or unsubstituted C3 to C30 cycloalkyl, substituted or unsubstituted C6 to C60 aryl or substituted or unsubstituted C3 to C60 heteroaryl, Z is selected from C(Ry) or N, wherein Ry is selected from one of hydrogen, deuterium, halogen, cyano, nitro, substituted or unsubstituted C1 to C30 alkyl, substituted or unsubstituted C3 to C30 cycloalkyl, substituted or unsubstituted C2 to C30 alkenyl, substituted or unsubstituted C2 to C30 alkynyl, substituted or unsubstituted C6 to C60 aryl or substituted or unsubstituted C3 to C60 heteroaryl, or two adjacent groups are joined to form a ring;

X is selected from one of O, S, N(Ar), C(Ar)$_2$ or Si(Ar)$_2$, wherein Ar is selected from one of substituted or unsubstituted C1 to C30 alkyl, substituted or unsubstituted C3 to C30 cycloalkyl, substituted or unsubstituted C6 to C60 aryl or substituted or unsubstituted C3 to C60 heteroaryl;

m is selected from 0, 1, 2, 3 or 4, and R is identically or differently selected from one of deuterium, cyano, nitro, substituted or unsubstituted C1 to C30 alkyl, substituted or unsubstituted C3 to C30 cycloalkyl, substituted or unsubstituted C2 to C30 alkenyl, substituted or unsubstituted C2 to C30 alkynyl, substituted or unsubstituted C6 to C60 aryl or substituted or unsubstituted C3 to C60 heteroaryl, or two adjacent groups are joined to form a ring;

$L_x$ and $L_y$ are independently selected from one of a single bond, substituted or unsubstituted C1 to C30 alkylene, substituted or unsubstituted C3 to C30 cycloalkylene, substituted or unsubstituted C6 to C60 arylene or substituted or unsubstituted C3 to C60 heteroarylene; and $L_1$ and $L_2$ are independently selected from one of a single bond, substituted or unsubstituted C6 to C60 arylene or substituted or unsubstituted C3 to C60 heteroarylene.

The present disclosure further provides an organic electroluminescent device including an anode, an organic layer, and a cathode, wherein the organic layer is disposed between the anode and the cathode, and the organic layer includes an electron transport region containing the above-mentioned heterocyclic derivative of the present disclosure.

Beneficial effects: The heterocyclic derivative as shown in Formula I of the present disclosure has high electron mobility and great hole blocking performance, and can not only balance carriers well, but also block holes from entering the electron transport region, so the organic electroluminescent device prepared by using the heterocyclic derivative as the hole blocking layer shows low drive voltage and high luminous efficiency.

In addition, since the triarylamine compound of Formula II has high hole mobility, the hole transport region where the triarylamine compound is located when used as the emissive auxiliary layer and the electron transport region where the hole blocking layer is located can effectively balance carriers, which reduces the quenching of excitons and improves the recombination probability of carriers, and thus the device shows great photoelectric performance.

DETAILED DESCRIPTION

Figure 1:
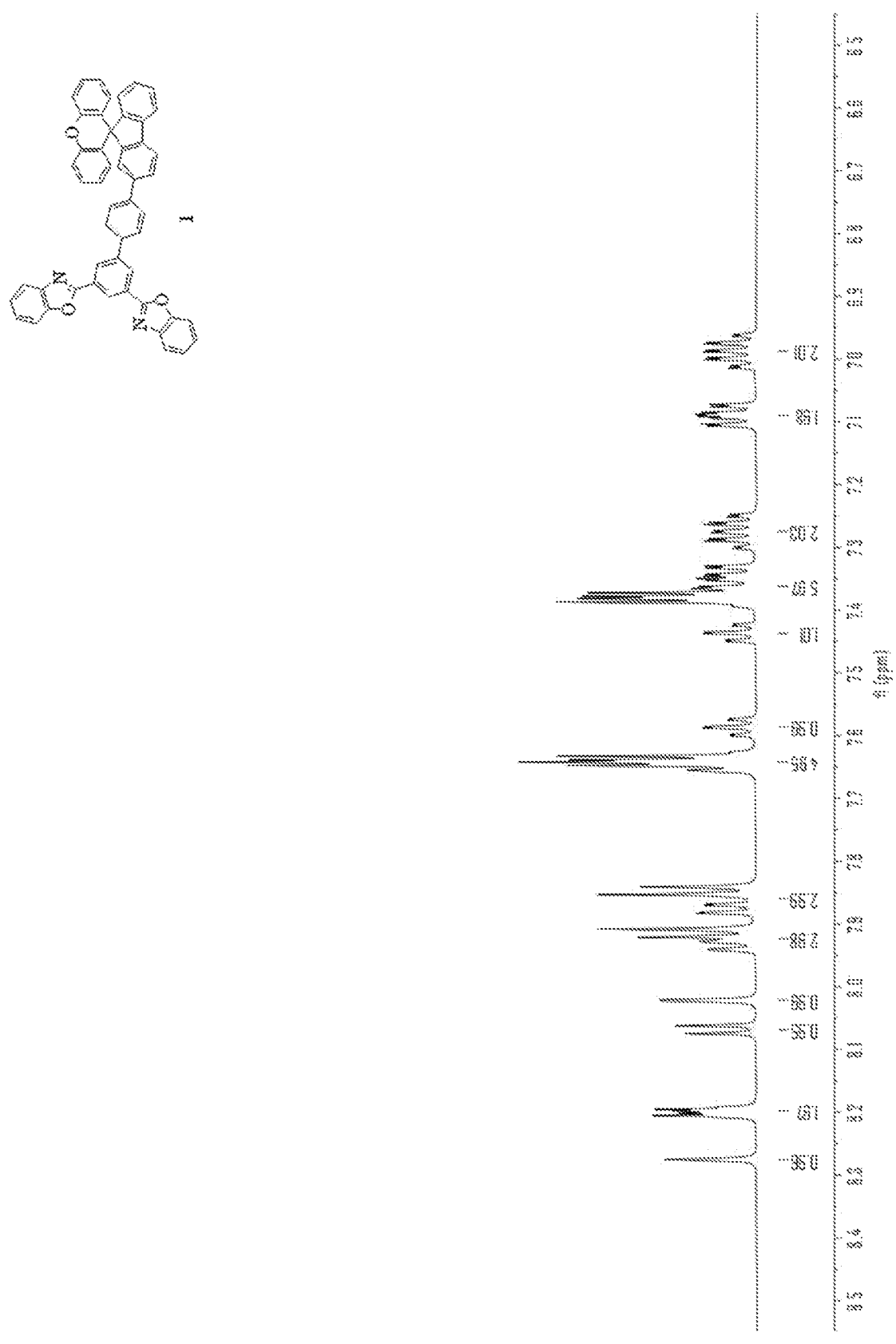
FIG. 1 is a $^1$H NMR graph of Compound 1 of the present disclosure.
Figure 2:
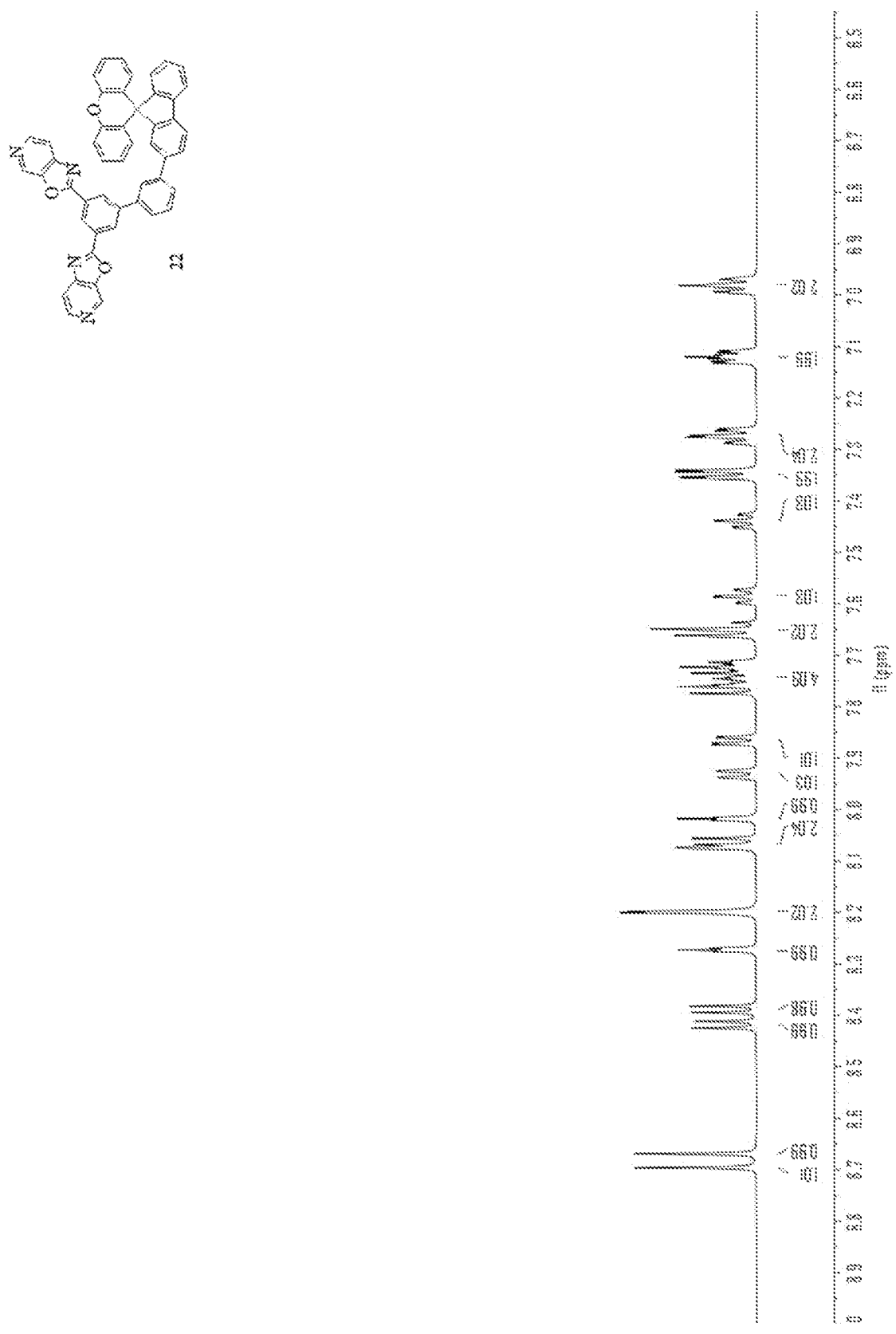
FIG. 2 is a $^1$H NMR graph of Compound 22 of the present disclosure.
Figure 3:
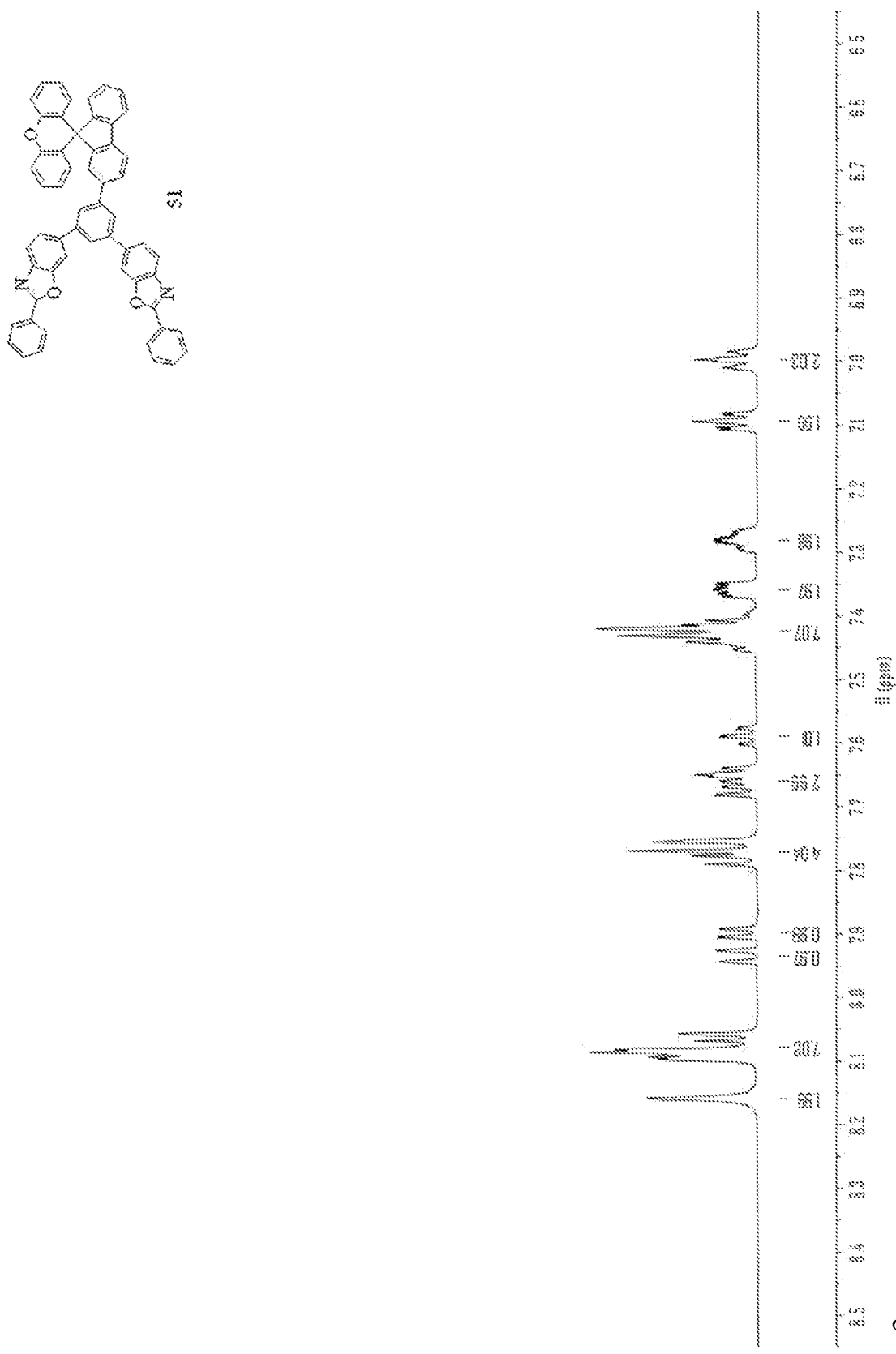
FIG. 3 is a $^1$H NMR graph of Compound 51 of the present disclosure.
Figure 4:
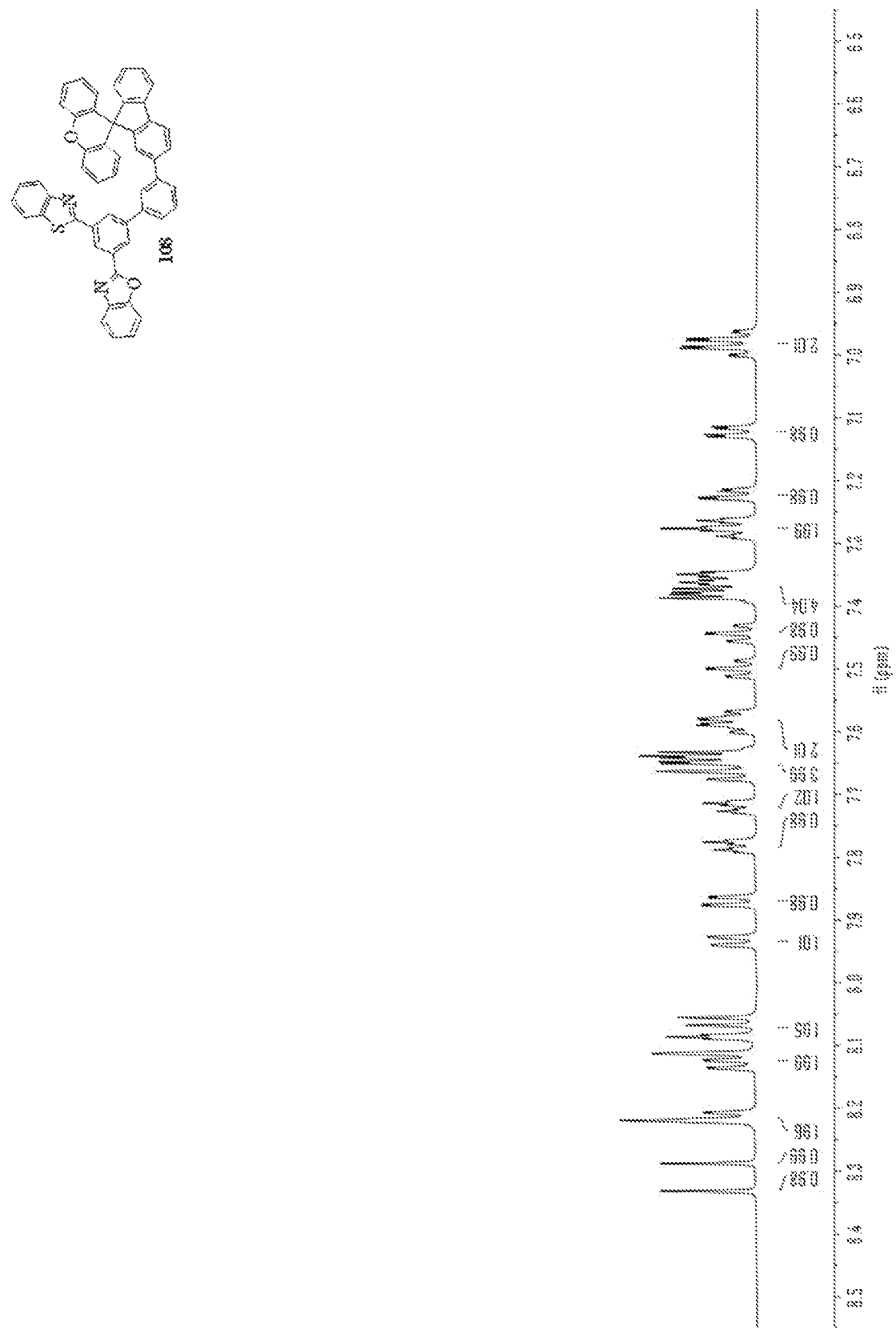
FIG. 4 is a $^1$H NMR graph of Compound 108 of the present disclosure.

The present disclosure is further illustrated below in conjunction with specific embodiments. It is understood that these embodiments are intended to illustrate the present disclosure and not to limit the scope thereof, and modifications of various equivalents of the present disclosure by those skilled in the art after reading the present disclosure fall within the scope of the claims of the present application.

In the present disclosure, "halogen" includes fluorine, chlorine, bromine, and iodine.

In the present disclosure, "unsubstituted" in "substituted or unsubstituted" means that the hydrogen atom on the group is not replaced with any substituent.

In the present disclosure, "substituted" in "substituted or unsubstituted" means that at least one hydrogen atom on the group is replaced with substituents. When a plurality of hydrogen is replaced with a plurality of substituents, the plurality of substituents may be identical or different. The position of the hydrogen replaced with the substituent can be any position. The substituent represented in the "substitution" includes, but is not limited to, at least one of deuterium, halogen, cyano, nitro, C1 to C30 alkyl, C3 to C30 cycloalkyl, C6 to C60 aryl, C3 to C60 heteroaryl or C6 to C60 amine.

In the present disclosure, the expression of being joined to form a ring means that two groups are attached to each other through a chemical bond. In the present disclosure, the formed ring can be a five-membered ring, a six-membered ring or a fused ring, such as a benzene ring, a naphthalene ring, a phenanthrene ring, an anthracene ring, a triphenylene ring, a fluorene ring, a quinoline ring, a dibenzofuran ring, a dibenzothiophene ring, a carbazole ring, etc., but is not limited thereto.

In the present disclosure, the alkyl refers to a monovalent group formed by removing a hydrogen atom from an alkane molecule. The alkyl includes straight and branched chain alkyl groups. The number of carbon atoms of the alkyl is not particularly limited and is preferably C1 to C60, further preferably C1 to C30, more preferably C1 to C15, and most preferably C1 to C10. Examples of the alkyl include, but are not limited to, the following groups: methyl, ethyl, propyl, butyl, amyl, hexyl, heptyl, octyl, nonyl, decyl, etc. The chain alkyl group having more than three carbons in the present disclosure includes its isomers, for example, propyl includes n-propyl, isopropyl, t-butyl includes n-butyl, t-butyl, isobutyl, sec-butyl group, and so on.

In the present disclosure, the cycloalkyl refers to a monovalent group formed by removing a hydrogen atom from a cycloalkane molecule. The number of carbon atoms of the cycloalkyl is not particularly limited and is preferably C3 to C60, further preferably C3 to C30, more preferably C3 to C15, and most preferably C3 to C10. Examples of the cycloalkyl include, but are not limited to, the following groups: cyclopropyl, cyclobutyl, cyclopentyl, cyclohexyl, cyclooctane, adamantyl, camphanyl, norbornyl, cubyl, etc.

In the present disclosure, the aryl refers to a monovalent group formed by removing a hydrogen atom from the parent nucleus of an arene molecule. The aryl includes monocyclic aryl, polycyclic aryl, and fused aryl. The number of carbon atoms of the aryl is not particularly limited and is preferably C6 to C60, further preferably C6 to C30, more preferably C6 to C18, and most preferably C6 to C14. Examples of the aryl include, but are not limited to, the following groups: phenyl, biphenyl, triphenyl, tetraphenyl, naphthyl, anthryl, benzoanthryl, phenanthryl, triphenylenyl, pyrenyl, benzopyrenyl, perylenyl, fluoranthenyl, indenyl, fluorenyl, benzofluorenyl, dibenzofluorenyl, spirofluorenyl, benzospirofluorenyl, dibenzospirofluorenyl, etc.

In the present disclosure, the heteroaryl refers to a monovalent group formed by removing a hydrogen atom from the parent nucleus of a heterocyclic arene molecule. The heteroatoms in the heteroaryl include, but are not limited to, the following atoms: O, S, N, Si, B, P, Se, etc. The heteroaryl includes monocyclic heteroaryl, polycyclic heteroaryl, and fused ring heteroaryl. The number of carbon atoms of the heteroaryl is not particularly limited and is preferably C3 to C60, further preferably C3 to C30, more preferably C3 to C15, and most preferably C3 to C8. Examples of the heteroaryl include, but are not limited to, the following groups: pyridyl, pyrazinyl, pyridazinyl, pyrimidinyl, triazinyl, quinolinyl, isoquinolinyl, quinoxalinyl, quinazolinyl, phenanthrolinyl, oxadiazolyl, oxazolyl, benzoxazolyl, naphthoxazolyl, phenanthroxazolyl, thiazolyl, benzothiazolyl, naphthothiazolyl, phenanthrothiazolyl, imidazolyl, benzimidazolyl, naphthoimidazolyl, phenanthroimidazolyl, furanyl, benzofuranyl, dibenzofuranyl, benzodibenzofuranyl, thiophenyl, benzothiophenyl, dibenzothiophenyl, benzodibenzothiophenyl, carbazolyl, benzocarbazolyl, dibenzocarbazolyl, acridinyl, etc.

In the present disclosure, the alkenyl refers to a monovalent group formed by removing a hydrogen atom from an olefin molecule, and the alkenyl includes monoalkenyl, dialkenyl, polyalkenyl, etc. The number of carbon atoms of the alkenyl is not particularly limited and is preferably C2 to C60, further preferably C2 to C30, more preferably C2 to C15, and most preferably C2 to C10. Examples of the alkenyl include, but are not limited to, the following groups: vinyl, butadienyl, etc.

In the present disclosure, the alkynyl refers to a monovalent group formed by removing a hydrogen atom from an alkyne molecule, and the alkynyl includes monoalkynyl, dialkynyl, polyalkynyl, etc. The number of carbon atoms of the alkynyl is not particularly limited and is preferably C2 to C60, further preferably C2 to C30, more preferably C2 to C15, and most preferably C2 to C10. Examples of the alkynyl include, but are not limited to, the following groups: ethynyl, butadiynyl, etc.

In the present disclosure, the alkylene refers to a divalent group formed by removing two hydrogens from an alkane molecule. The number of carbon atoms of the alkylene is not particularly limited and is preferably C1 to C60, further preferably C1 to C30, more preferably C1 to C15, and most preferably C1 to C10. Examples of the alkylene include, but are not limited to, the following groups: methylene, ethylene, etc.

In the present disclosure, the cycloalkylene refers to a divalent group formed by removing two hydrogens from a cycloalkane molecule. The number of carbon atoms of the cycloalkylene is not particularly limited and is preferably C3 to C60, further preferably C3 to C30, more preferably C3 to C15, and most preferably C3 to C10. Examples of the cycloalkylene include, but are not limited to, the following groups: adamantylene, camphanylene, norbornylene, etc.

In the present disclosure, the arylene refers to a divalent group formed by removing two hydrogen atoms from the parent nucleus of an aromatic hydrocarbon molecule. The arylene includes monocyclic arylene, polycyclic arylene, fused ring arylene or combinations thereof. The number of carbon atoms of the arylene is not particularly limited and is preferably C6 to C60, further preferably C6 to C30, more preferably C6 to C18, and most preferably C6 to C14. Examples of the arylene include, but are not limited to, the following groups: phenylene, biphenylene, triphenylene, tetraphenylene, naphthylene, phenanthrylene, anthrylene, triphenylenylene, pyrenylene, fluorenylene, benzofluorenylene, spirodifluorenylene, benzospirodifluorenylene, etc. The arylene of the present disclosure also includes a divalent group formed by connecting a monocyclic arene with a polycyclic arene through a single bond, a divalent group formed by connecting a fused ring arene with a fused ring arene through a single bond, such as

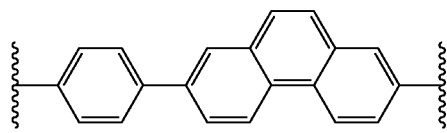

which is a divalent group formed by connecting benzene with phenanthrene through a single bond, and so on.

In the present disclosure, the heteroarylene refers to a divalent group formed by removing two hydrogen atoms from the parent nucleus of a heterocyclic arene molecule. The heteroatoms include, but are not limited to, the following atoms: O, S, N, Si, B, P, Se, etc. The heteroarylene includes monocyclic heteroarylene, polycyclic heteroarylene, fused ring heteroarylene or combinations thereof. The polycyclic heteroarylene can have only one benzene ring substituted by heteroatoms or a plurality of benzene rings substituted by heteroatoms. The number of carbon atoms of the heteroarylene is not particularly limited and is preferably C6 to C60, further preferably C6 to C30, more preferably C3 to C15, and most preferably C3 to C8. Examples of the heteroarylene include, but are not limited to, the following groups: pyridinylene, pyrimidinylene, pyrazinylene, pyridazinylene, triazinylene, furanylene, thiophenylene, quinolinylene, isoquinolinylene, quinoxalinylene, quinazolinylene, phenanthrolinylene, benzofuranylene, dibenzofuranylene, benzodibenzofuranylene, benzothiophenylene, dibenzothiophenylene, benzodibenzothiophenylene, carbazolylene, benzocarbazolylene, etc. The heteroarylene of the present disclosure also includes a divalent group formed by connecting a heterocyclic arene with a heterocyclic arene through a single bond, a divalent group formed by connecting an arene with a heterocyclic arene through a single bond, such as

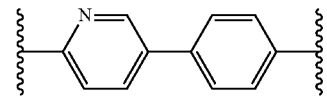 [SMILES: *c1ccc(-c2ccc(*)nc2)cc1]

which is a divalent group formed by connecting pyridine with benzene through a single bond, and so on.

"C1 to C30" in the "substituted or unsubstituted C1 to C30 alkyl" represents the number of carbon atoms in the unsubstituted "alkyl" and does not include the number of carbon atoms in the substituent; "C6 to C60" in the "substituted or unsubstituted C6 to C60 aryl" represents the number of carbon atoms in the unsubstituted "aryl" and does not include the number of carbon atoms in the substituent; "C3 to C60" in the "substituted or unsubstituted C3 to C60 heteroaryl" represents the number of carbon atoms in the unsubstituted "heteroaryl" and does not include the number of carbon atoms in the substituent; "C6 to C60" in the "substituted or unsubstituted C6 to C60 arylene" represents the number of carbon atoms in the unsubstituted "arylene" and does not include the number of carbon atoms in the substituent; "C3 to C60" in the "substituted or unsubstituted C3 to C60 heteroarylene" represents the number of carbon atoms in the unsubstituted "heteroarylene" and does not include the number of carbon atoms in the substituent; and son on.

The present disclosure provides a heterocyclic derivative having a general structural formula as shown in Formula I:

Formula I

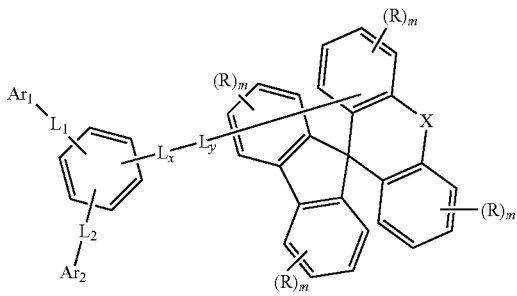

wherein Ar₁ and Ar₂ are identical or different and selected from the following group:

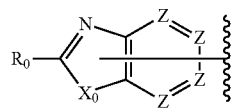

wherein $R_0$ is selected from one of hydrogen, deuterium, halogen, cyano, nitro, substituted or unsubstituted C1 to C30 alkyl, substituted or unsubstituted C3 to C30 cycloalkyl, substituted or unsubstituted C6 to C60 aryl or substituted or unsubstituted C3 to C60 heteroaryl, $X_0$ is selected from one of O, S, $N(R_x)$ or $C(R_x)_2$, and $R_x$ is selected from one of substituted or unsubstituted C1 to C30 alkyl, substituted or unsubstituted C3 to C30 cycloalkyl, substituted or unsubstituted C6 to C60 aryl or substituted or unsubstituted C3 to C60 heteroaryl, Z is selected from C(Ry) or N, wherein Ry is selected from one of hydrogen, deuterium, halogen, cyano, nitro, substituted or unsubstituted C1 to C30 alkyl, substituted or unsubstituted C3 to C30 cycloalkyl, substituted or unsubstituted C2 to C30 alkenyl, substituted or unsubstituted C2 to C30 alkynyl, substituted or unsubstituted C6 to C60 aryl or substituted or unsubstituted C3 to C60 heteroaryl, or two adjacent groups are joined to form a ring;

X is selected from one of O, S, N(Ar), C(Ar)₂ or Si(Ar)₂, wherein Ar is selected from one of substituted or unsubstituted C1 to C30 alkyl, substituted or unsubstituted C3 to C30 cycloalkyl, substituted or unsubstituted C6 to C60 aryl or substituted or unsubstituted C3 to C60 heteroaryl;

m is selected from 0, 1, 2, 3 or 4, and R is identically or differently selected from one of deuterium, cyano, nitro, substituted or unsubstituted C1 to C30 alkyl, substituted or unsubstituted C3 to C30 cycloalkyl, substituted or unsubstituted C2 to C30 alkenyl, substituted or unsubstituted C2 to C30 alkynyl, substituted or unsubstituted C6 to C60 aryl or substituted or unsubstituted C3 to C60 heteroaryl, or two adjacent groups are joined to form a ring;

$L_x$ and $L_y$ are independently selected from one of a single bond, substituted or unsubstituted C1 to C30 alkylene, substituted or unsubstituted C3 to C30 cycloalkylene, substituted or unsubstituted C6 to C60 arylene or substituted or unsubstituted C3 to C60 heteroarylene; and $L_1$ and $L_2$ are independently selected from one of a single bond, substituted or unsubstituted C6 to C60 arylene or substituted or unsubstituted C3 to C60 heteroarylene.

Preferably, $L_x$ and $L_y$ are independently selected from a single bond, substituted or unsubstituted adamantylene, substituted or unsubstituted camphanylene, substituted or unsubstituted norbornylene, substituted or unsubstituted phenylene, substituted or unsubstituted biphenylene, substituted or unsubstituted terphenylene, substituted or unsubstituted naphthylene, substituted or unsubstituted phenanthrylene, substituted or unsubstituted triphenylenylene, substituted or unsubstituted fluorenylene, substituted or unsubstituted benzofluorenylene, substituted or unsubstituted spirodifluorenylene, substituted or unsubstituted benzospirodifluorenylene, substituted or unsubstituted dibenzofuranylene, substituted or unsubstituted dibenzothiophenylene, substituted or unsubstituted carbazolylene, substituted or unsubstituted quinolinylene, substituted or unsubstituted isoquinolinylene, substituted or unsubstituted naphthyridinylene, substituted or unsubstituted quinoxalinylene, substituted or unsubstituted quinazolinylene or substituted or unsubstituted phenanthrolinylene; and $L_1$ and $L_2$ are independently selected from a single bond or one of the following groups:

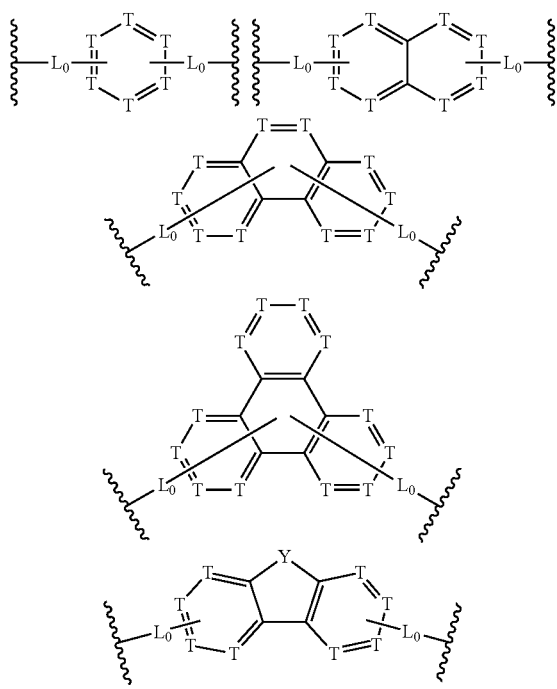

wherein T is identically or differently selected from N or $C(R_m)$, wherein $R_m$ is selected from one of hydrogen, deuterium, cyano, nitro, substituted or unsubstituted C1 to C30 alkyl, substituted or unsubstituted C3 to C30 cycloalkyl, substituted or unsubstituted C6 to C60 aryl or substituted or unsubstituted C3 to C60 heteroaryl;

Y is selected from O, S, $N(R_n)$ or $C(R_n)_2$, wherein $R_n$ is selected from one of hydrogen, deuterium, substituted or unsubstituted C1 to C30 alkyl, substituted or unsubstituted C3 to C30 cycloalkyl, substituted or unsubstituted C2 to C30 alkenyl, substituted or unsubstituted C2 to C30 alkynyl, substituted or unsubstituted C6 to C60 aryl or substituted or unsubstituted C3 to C60 heteroaryl, or two adjacent groups are joined to form a ring; and $L_0$ is identically or differently selected from one of a single bond, substituted or unsubstituted C6 to C60 arylene or substituted or unsubstituted C3 to C60 heteroarylene.
Preferably, $Ar_1$ and $Ar_2$ are independently selected from one of the following groups:
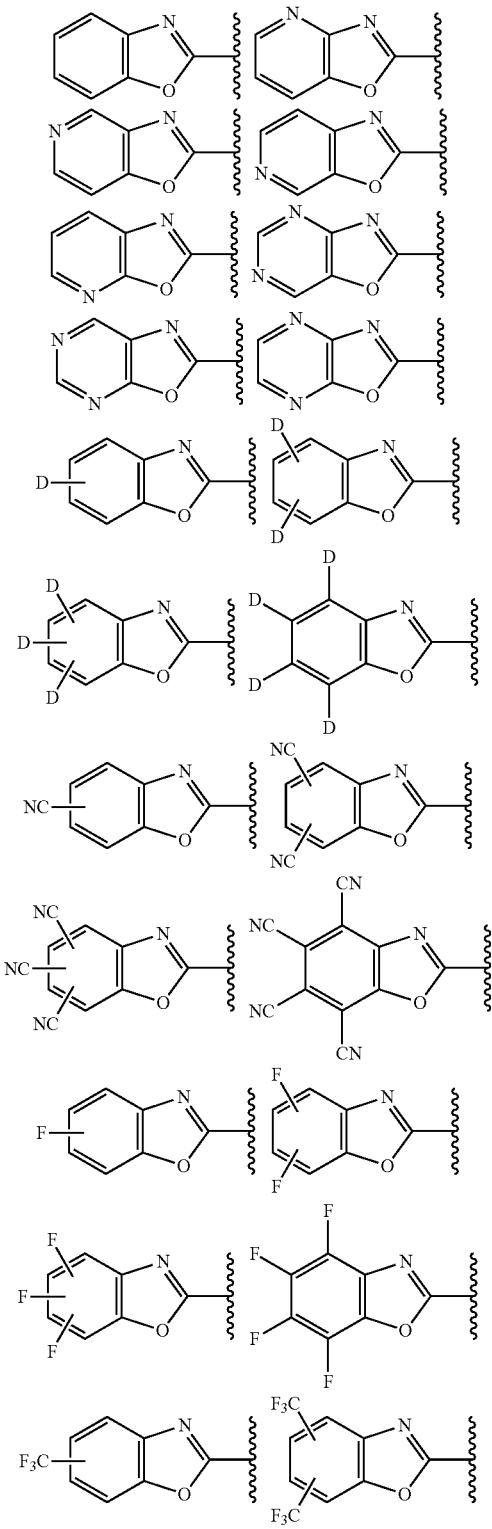
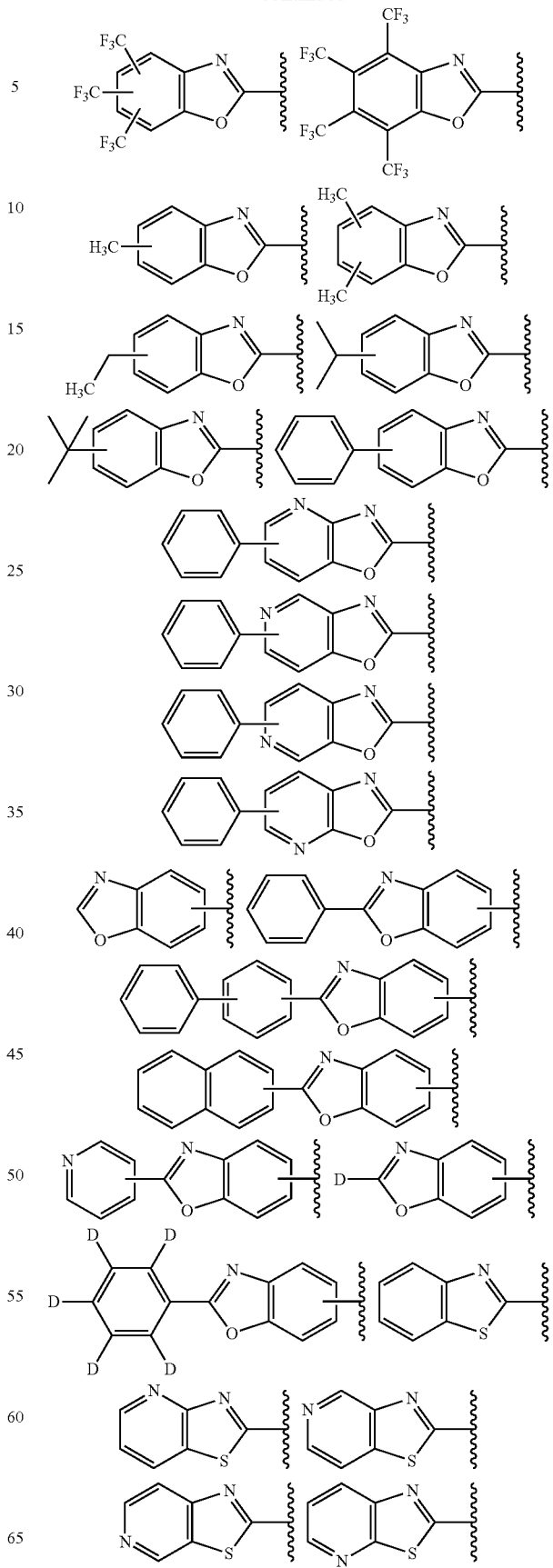

-continued
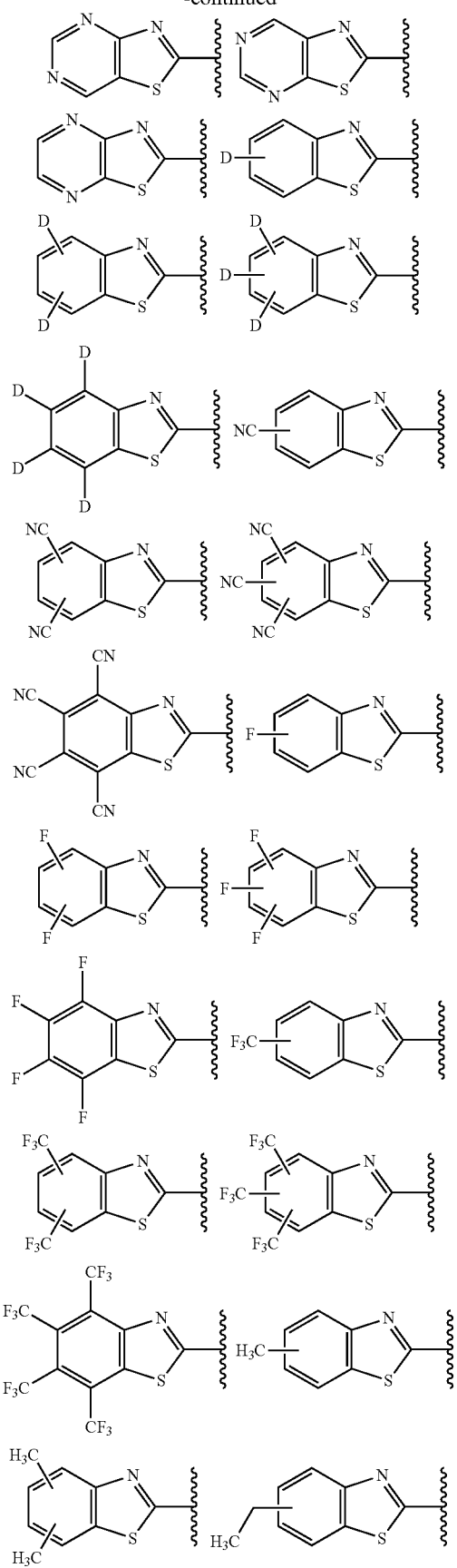
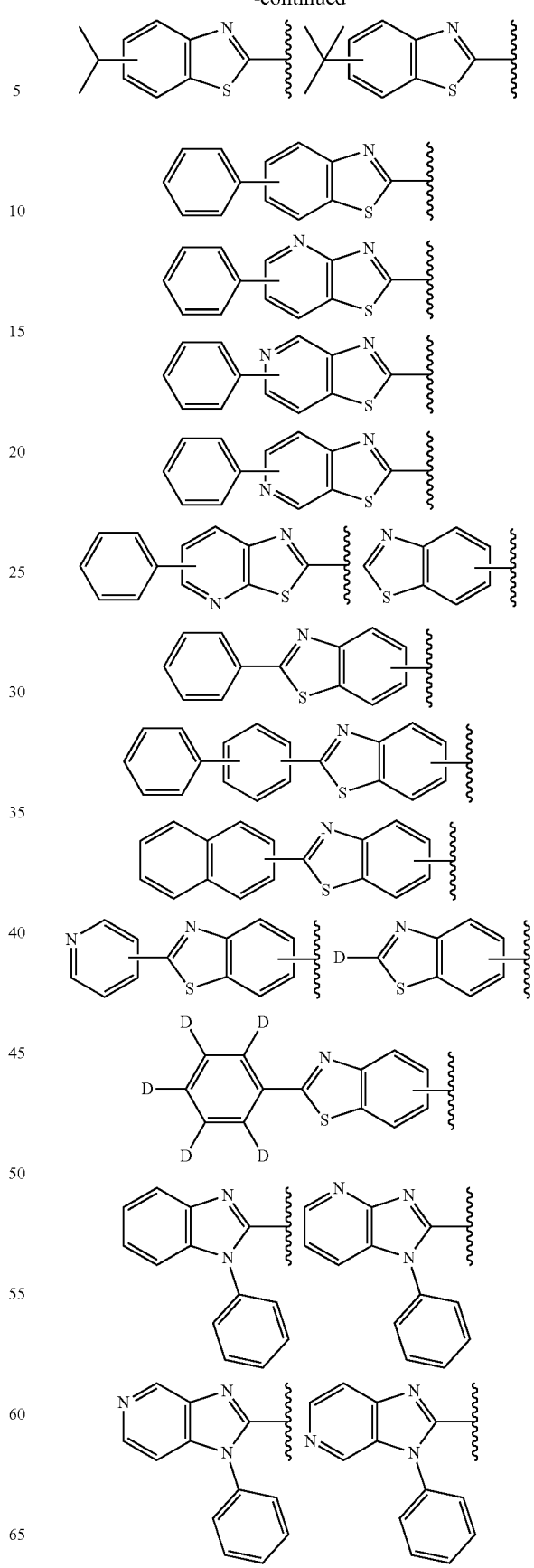

-continued
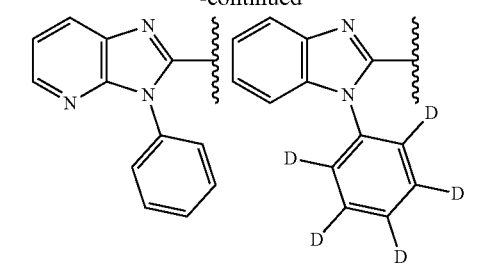
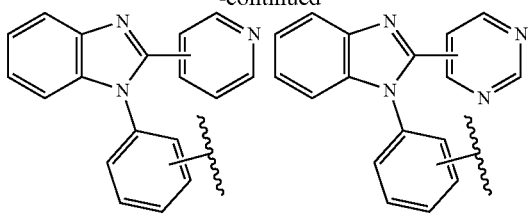
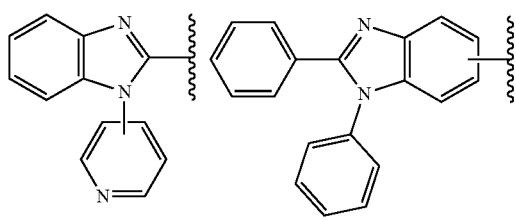
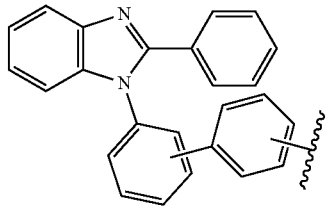
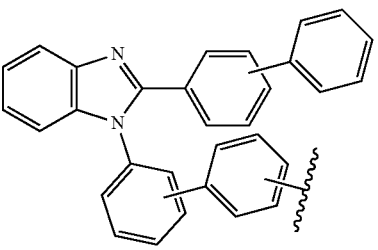
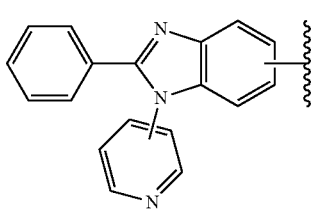
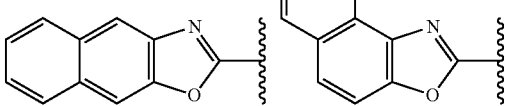
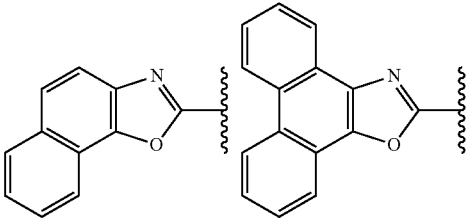
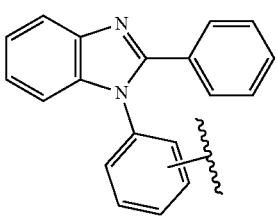
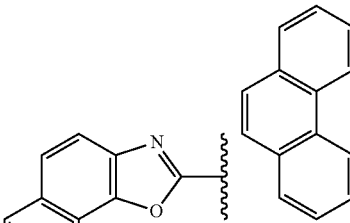
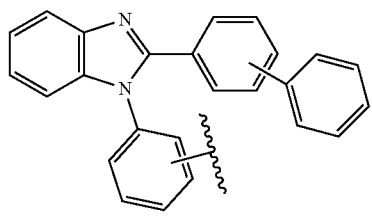
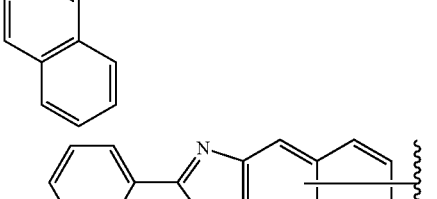
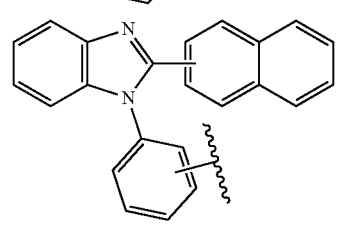

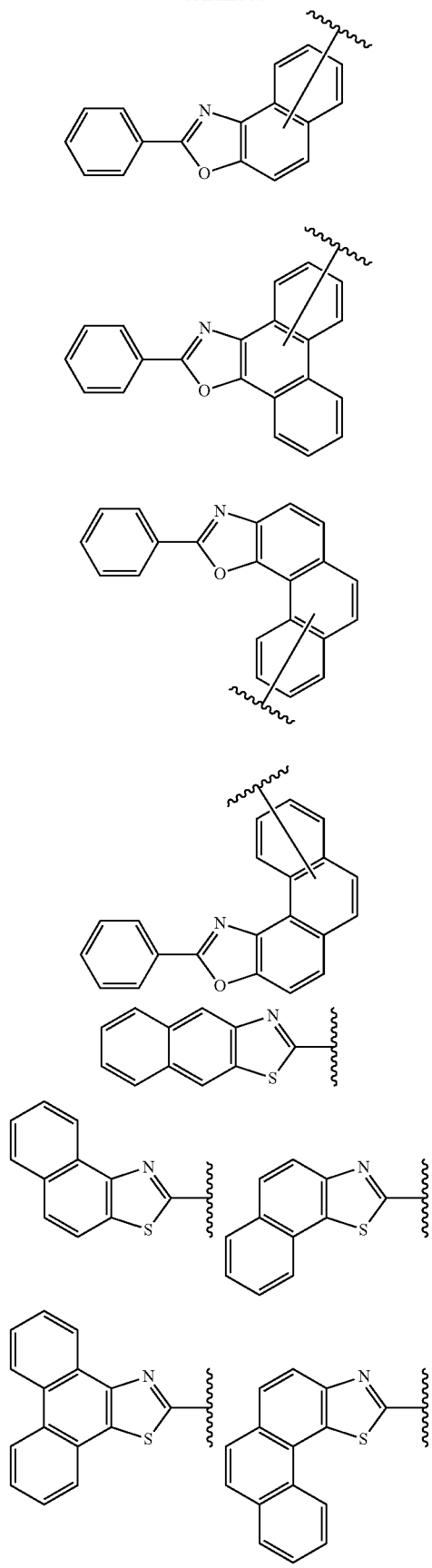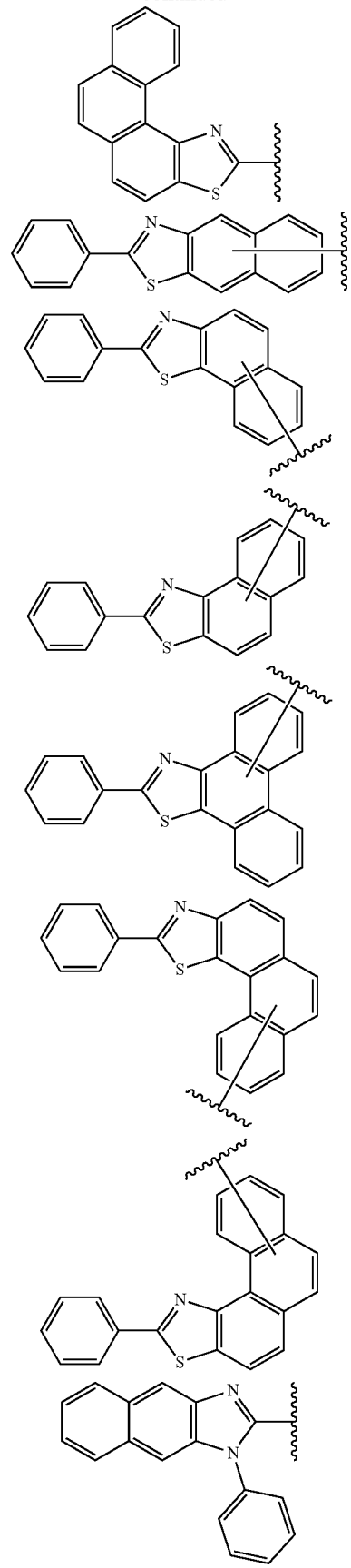

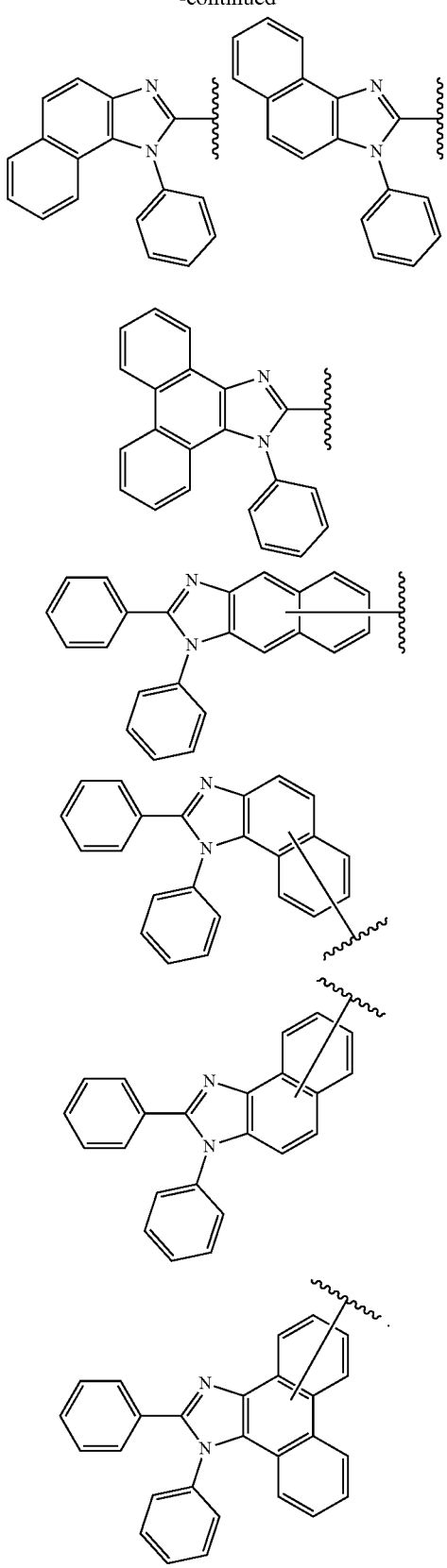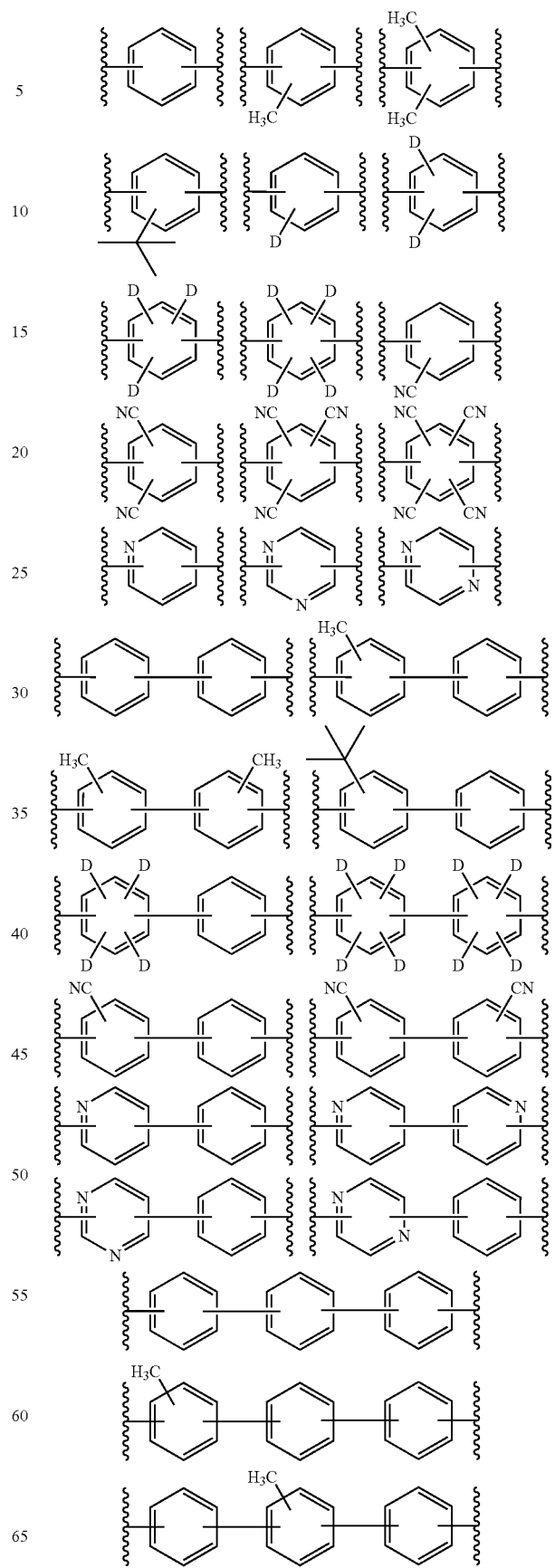
Preferably, L₁ and L₂ are independently selected from a single bond or one of the following groups:

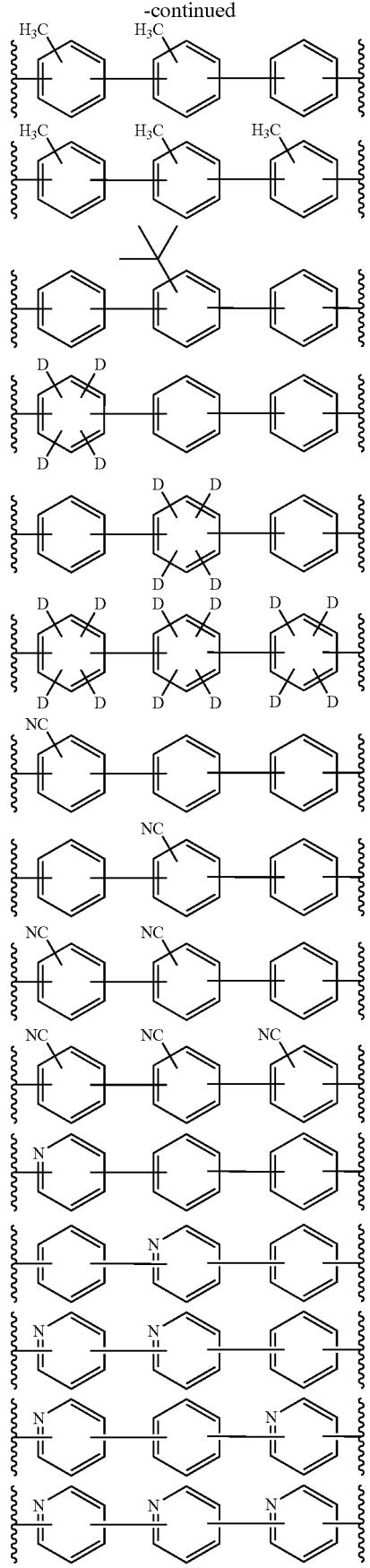
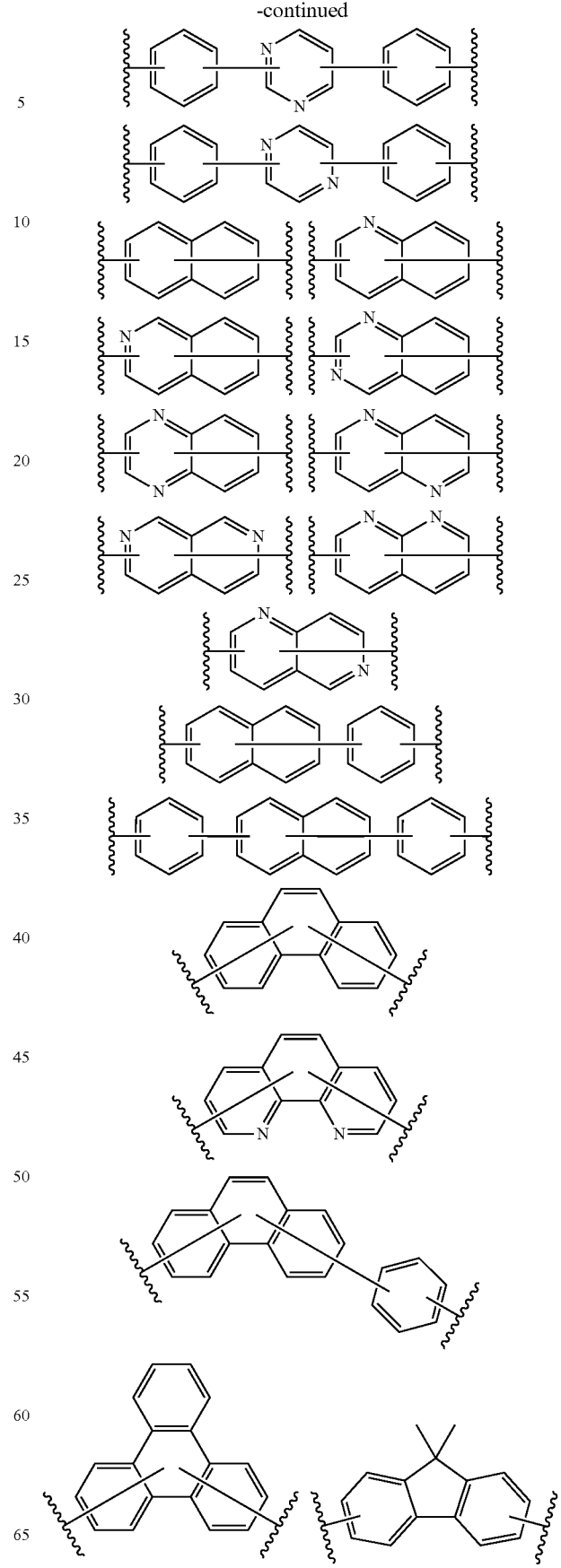

-continued
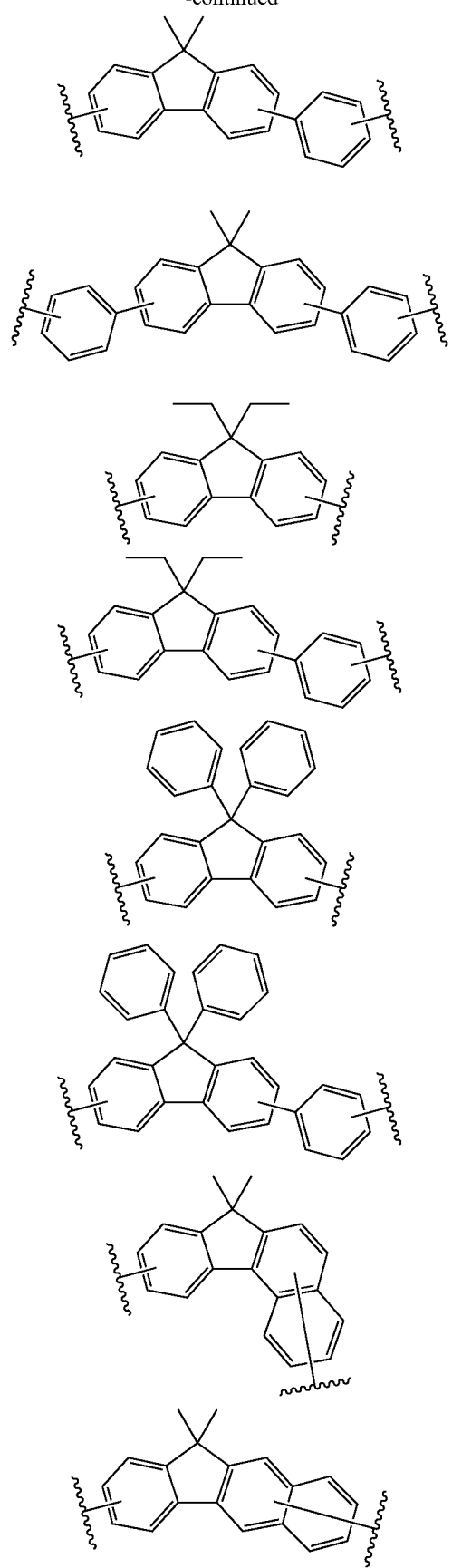
-continued
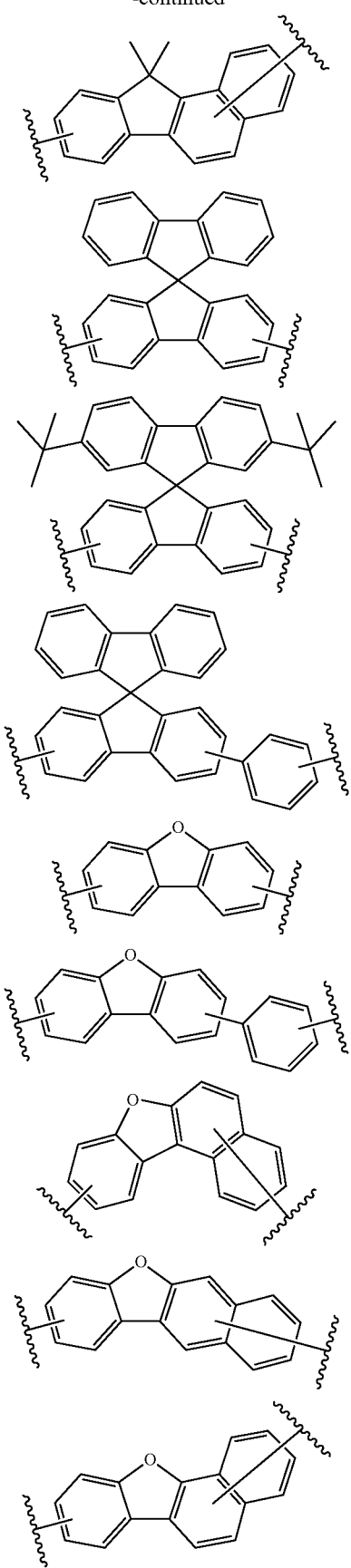

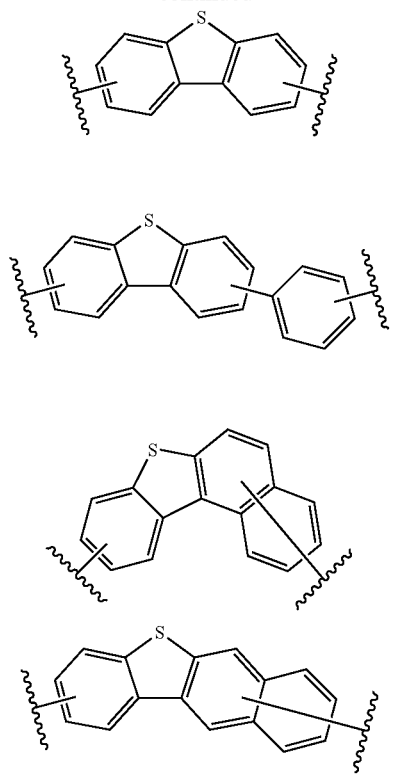
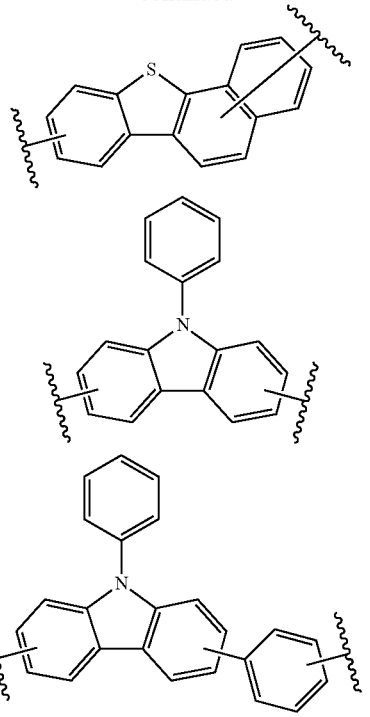
Preferably, the heterocyclic derivative is selected from one of the following structures:
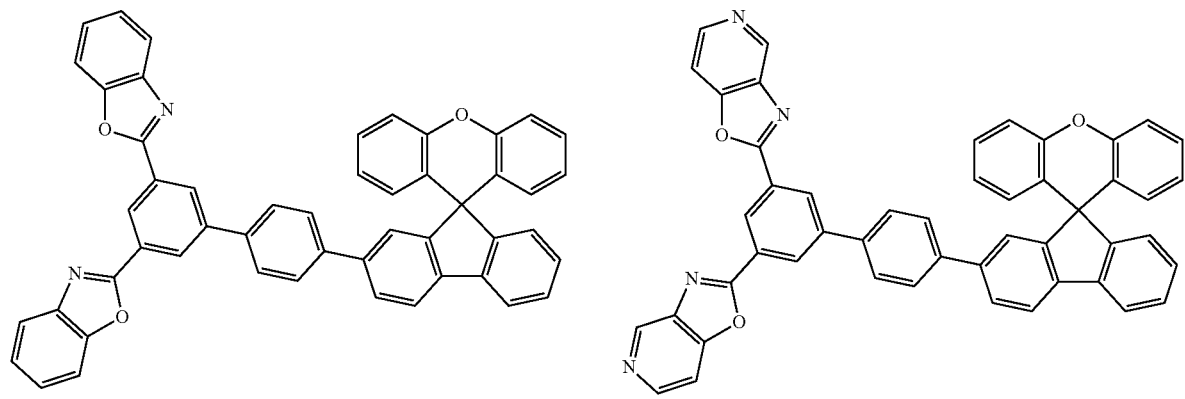
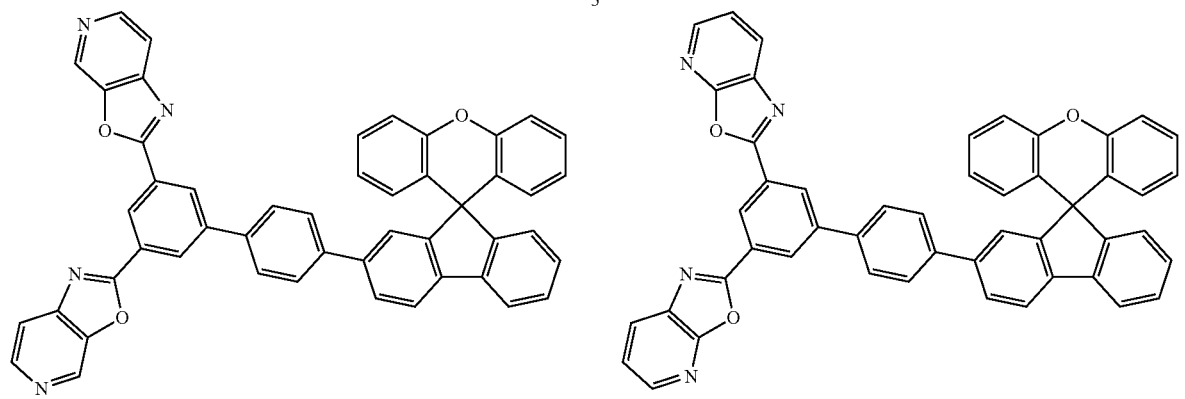

-continued
5
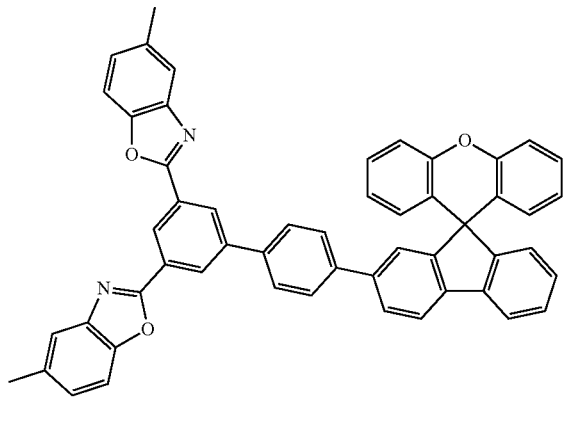
6
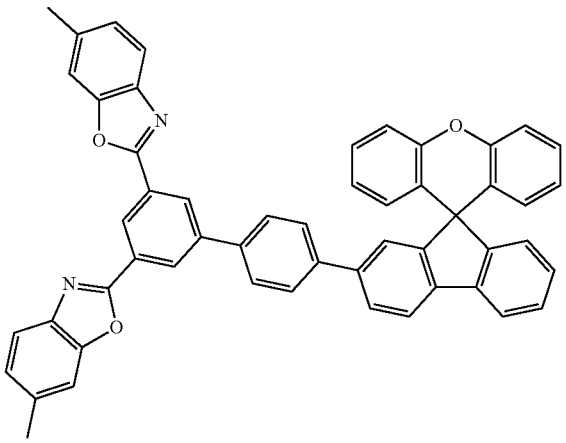
7
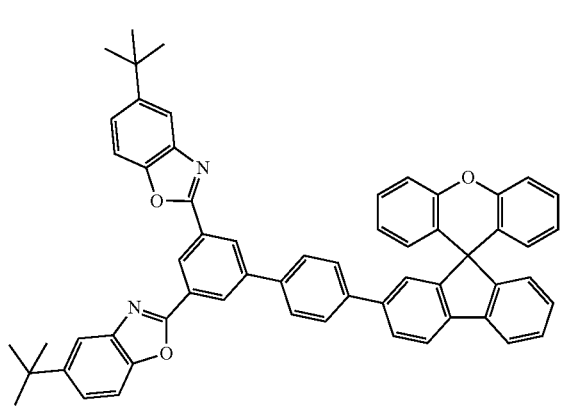
8
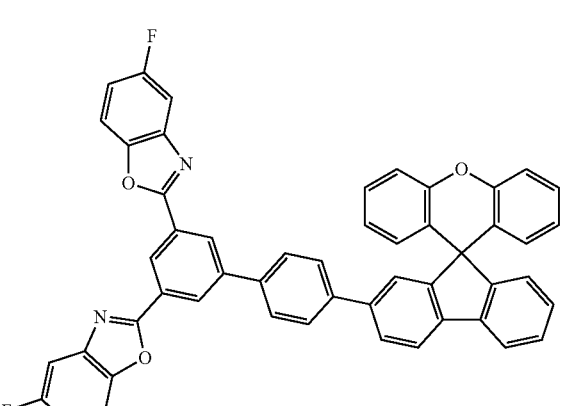
9
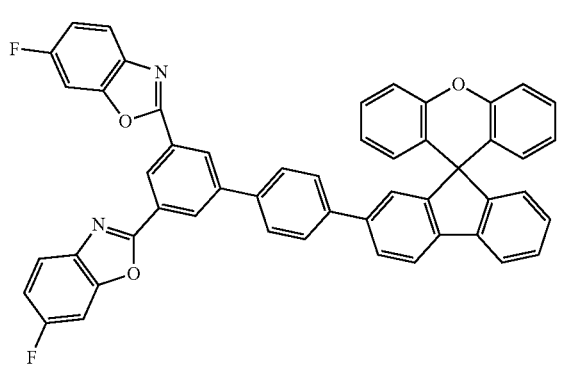
10
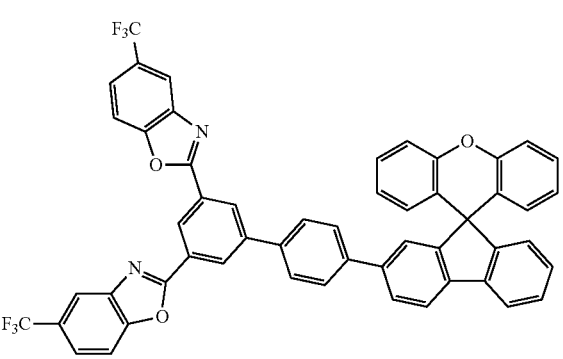
11
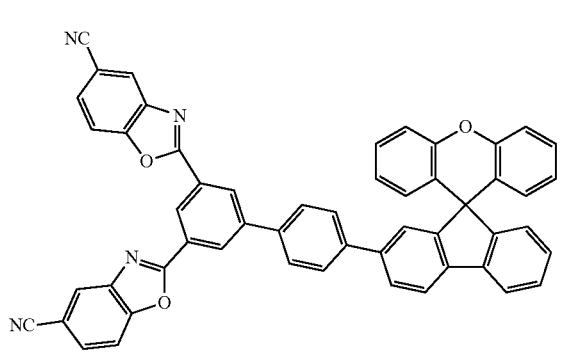
12
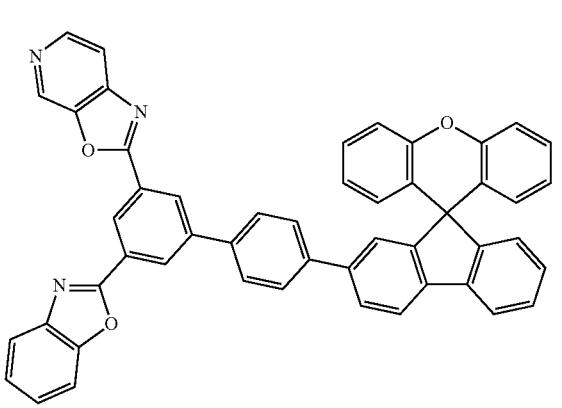

-continued
13
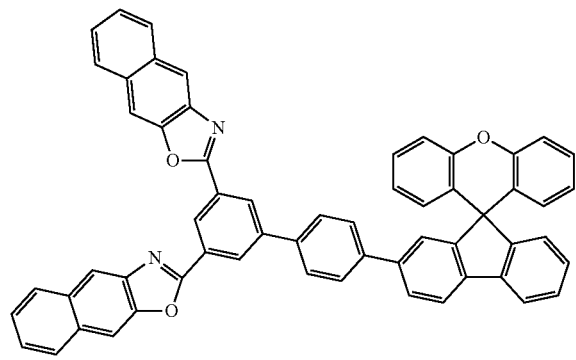
14
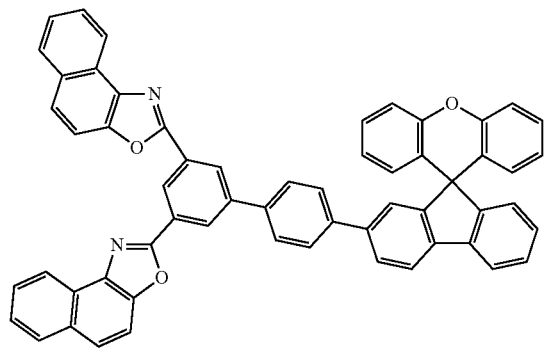
15
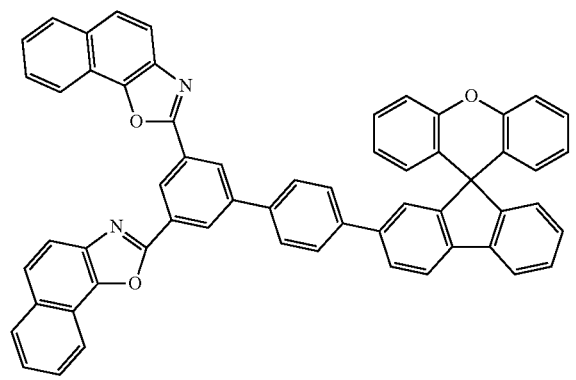
16
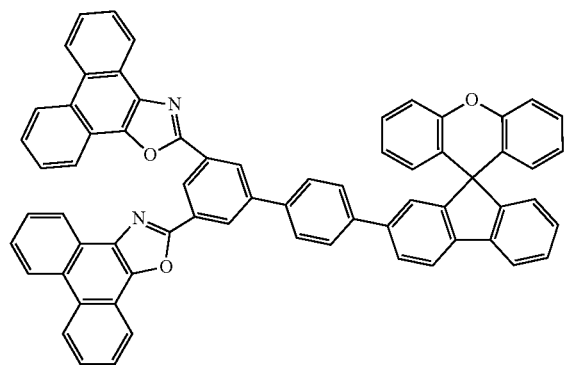
17
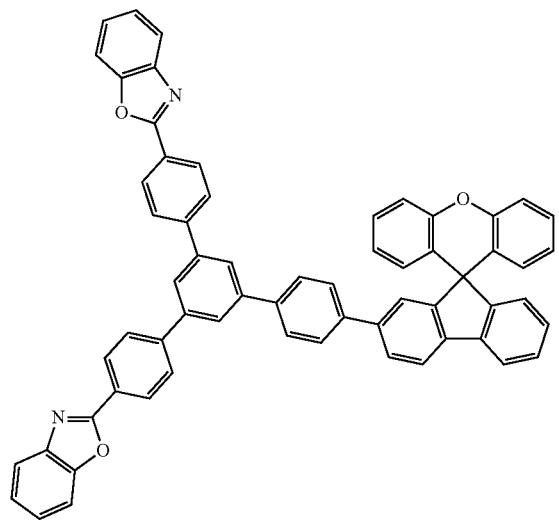
18
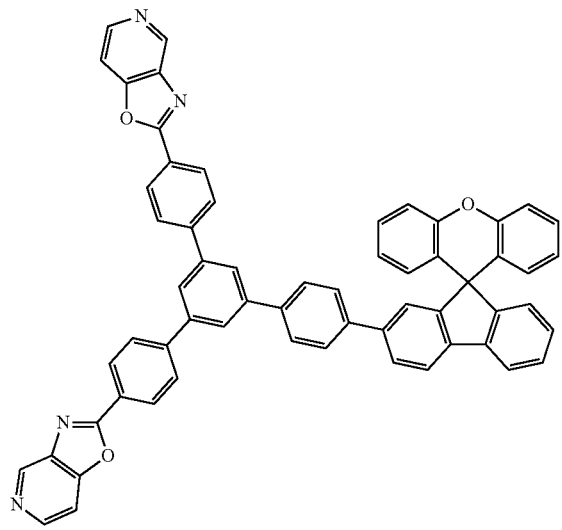

-continued
19
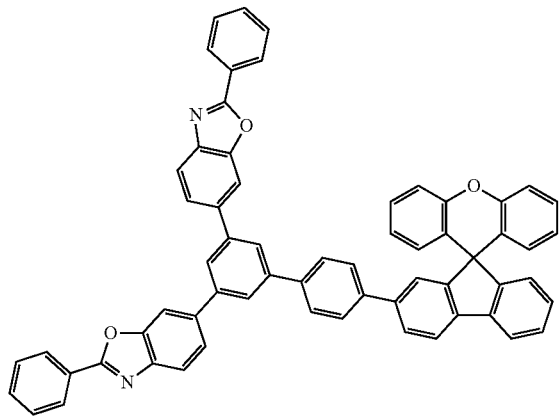
20
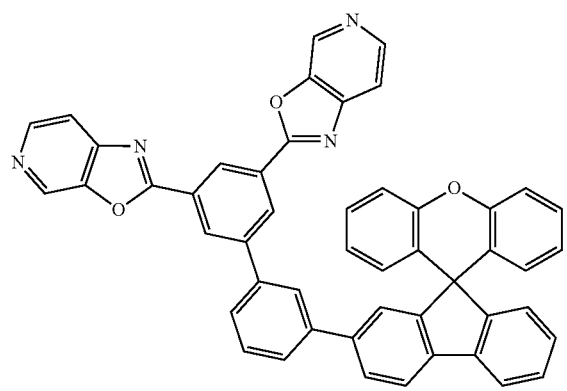
21
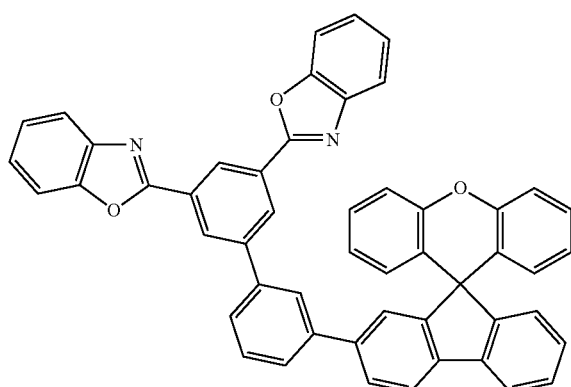
22
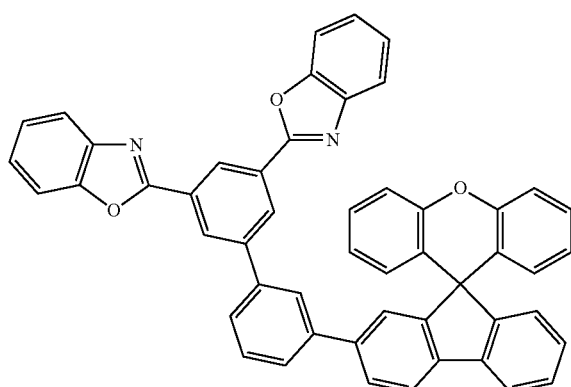
23
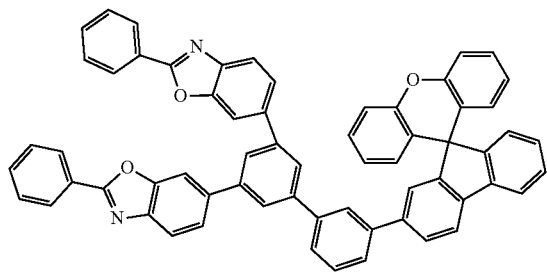
24
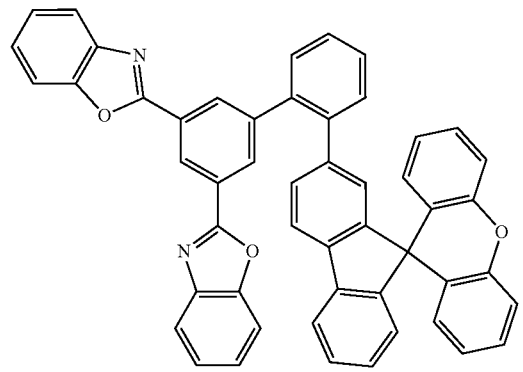
25
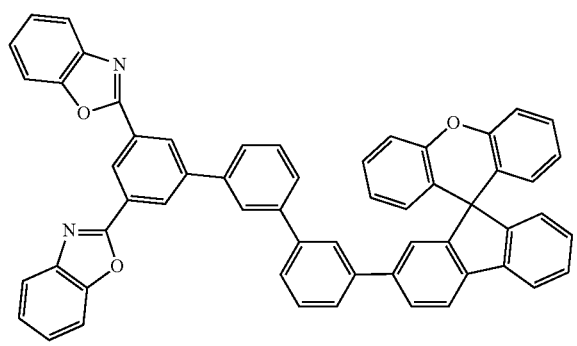
26
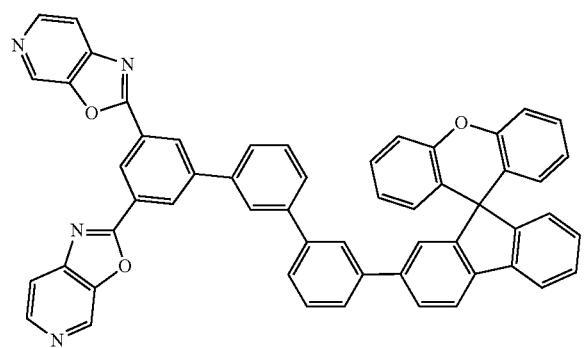

-continued
27
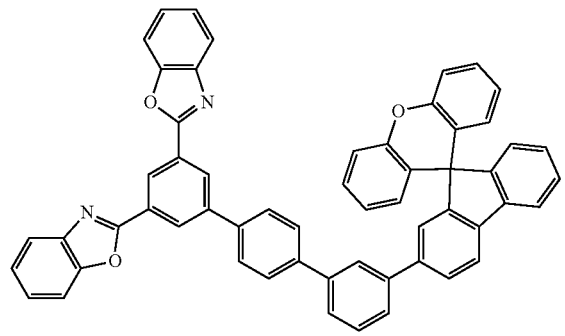
28
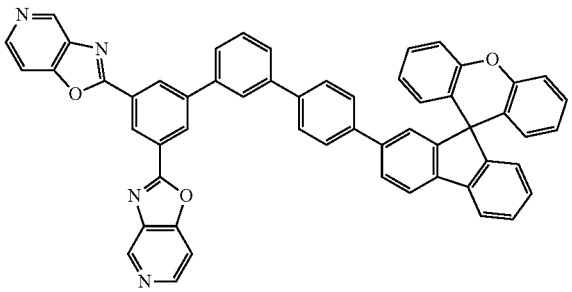
29
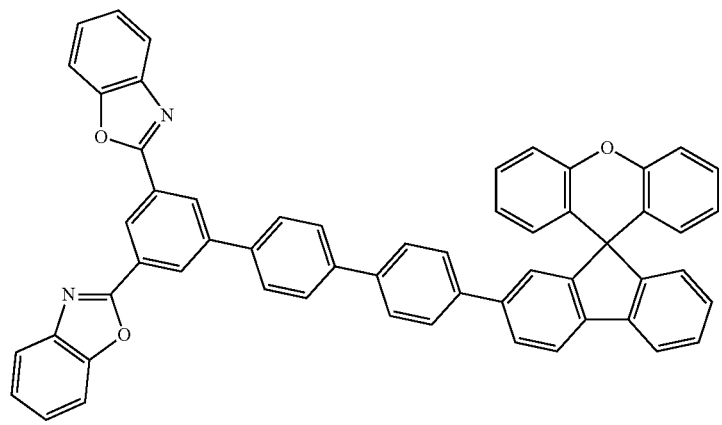
30
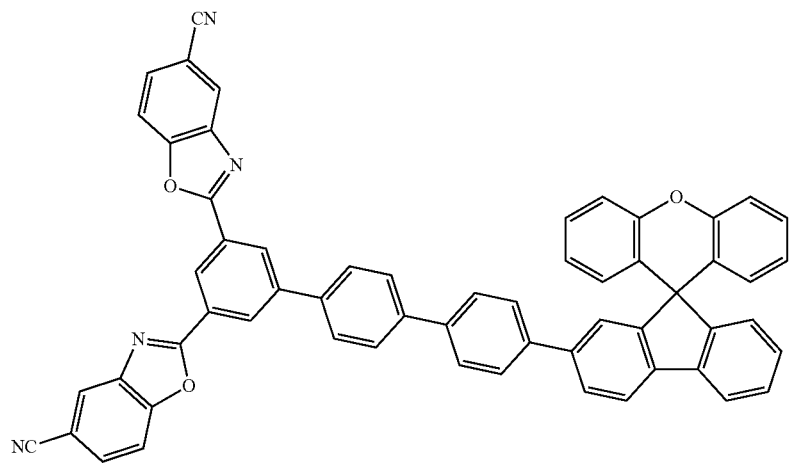
31
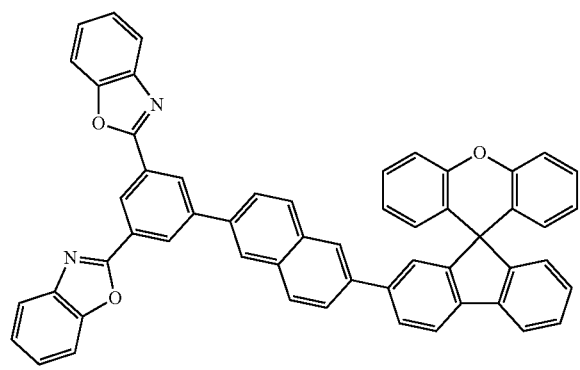
32
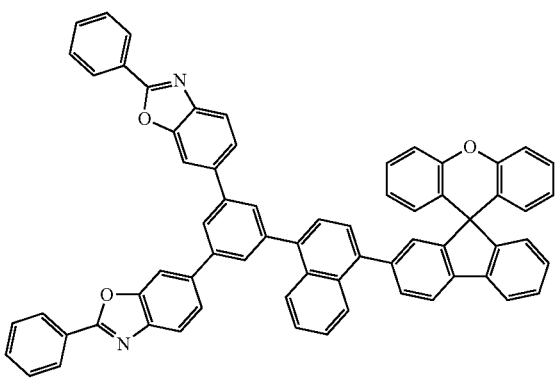

33
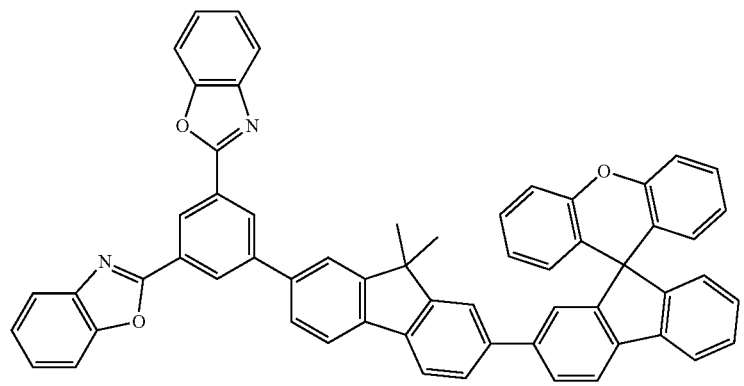
34
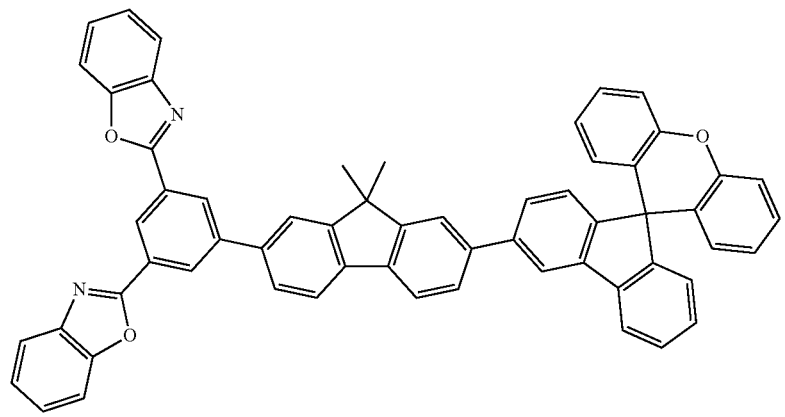
35
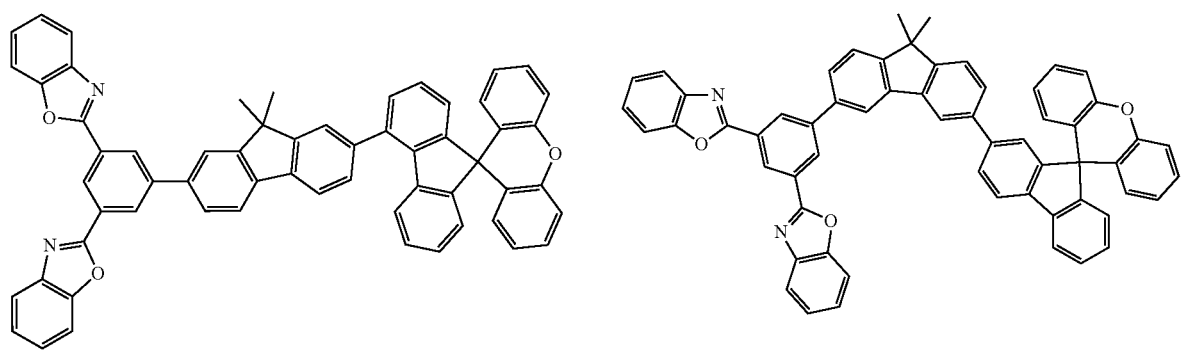
36
37
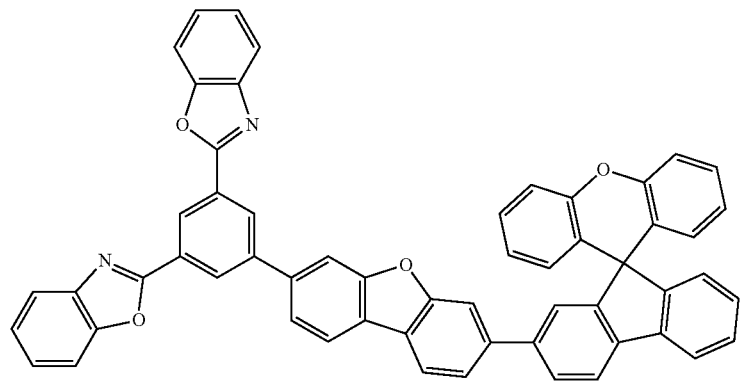

38
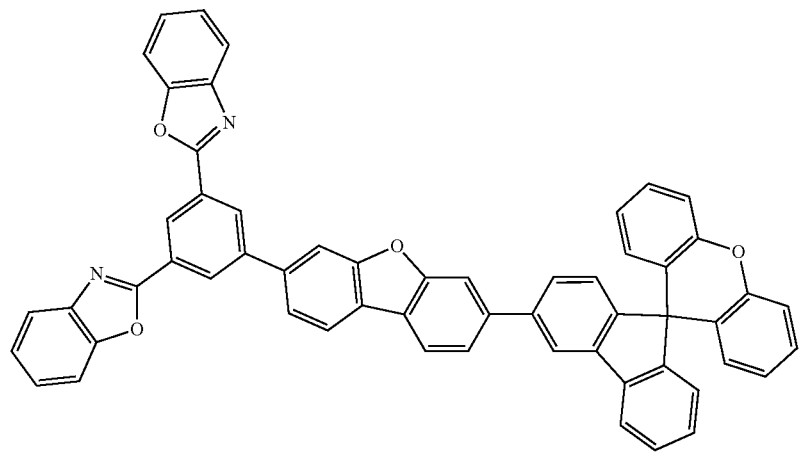
39 40
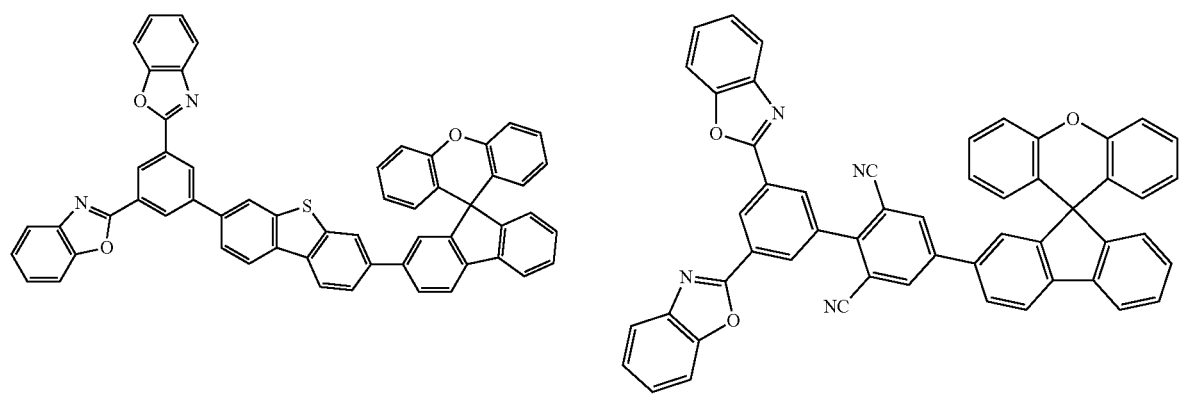
41 42
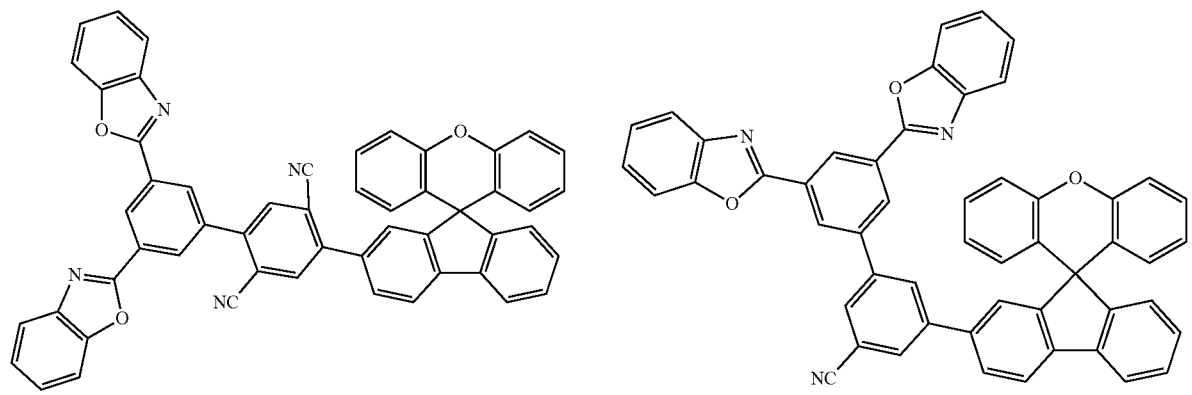

-continued
43
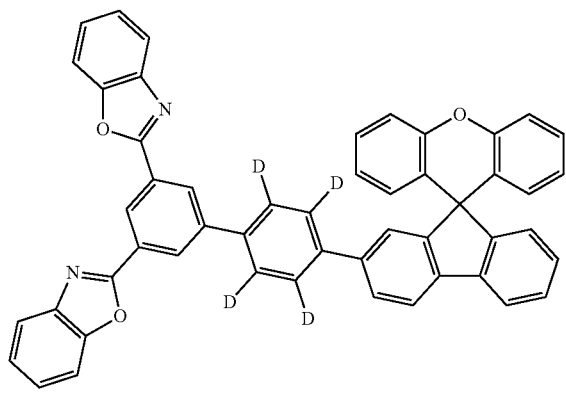
44
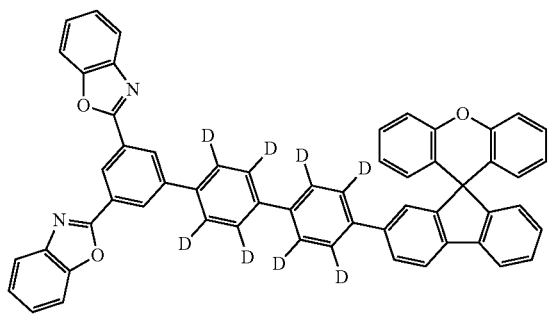
45
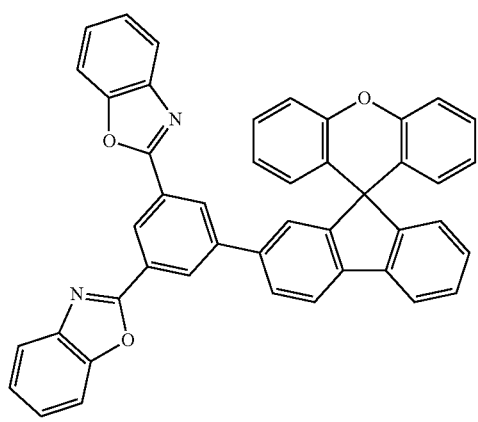
46
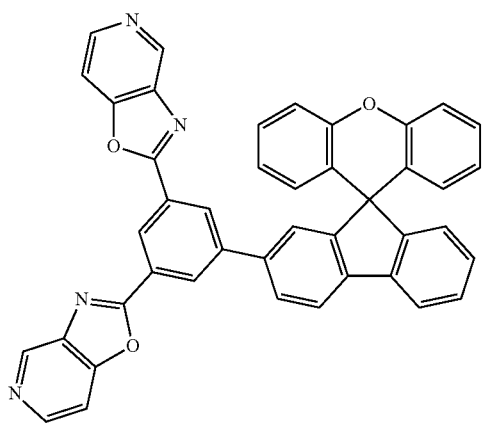
47
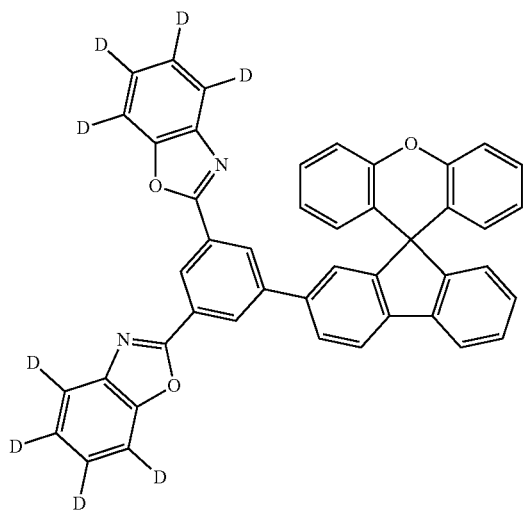
48
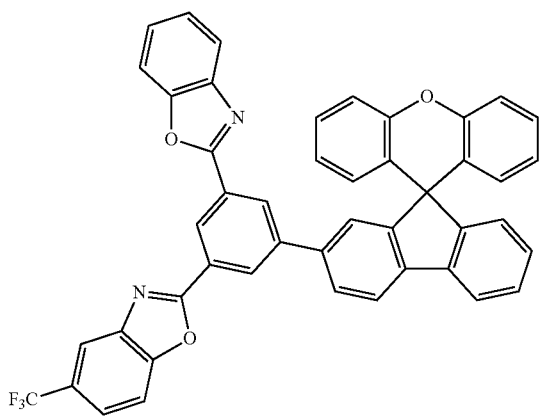

-continued
49
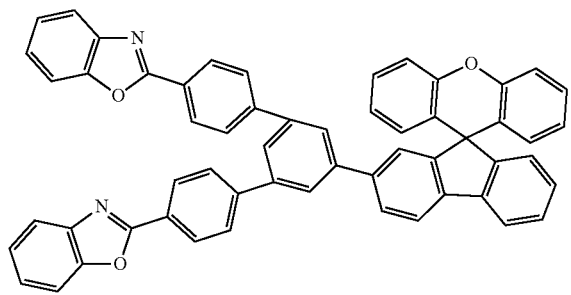
50
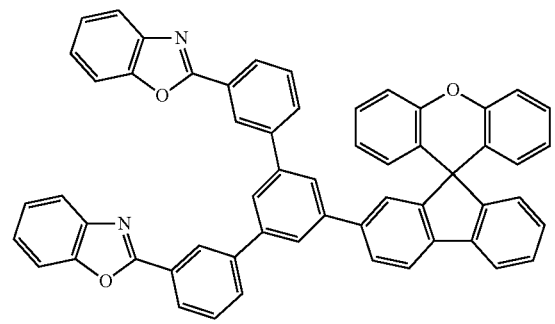
51
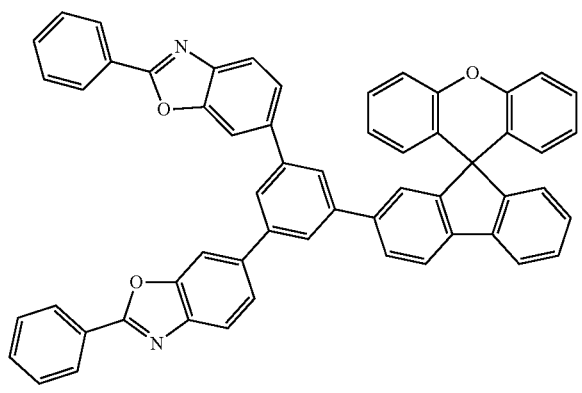
52
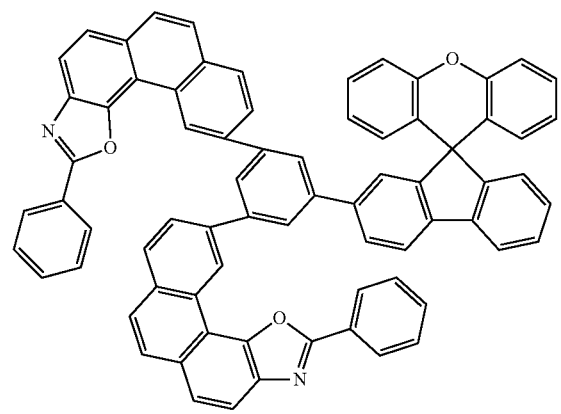
53
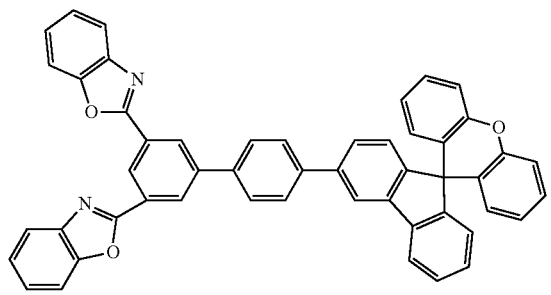
54
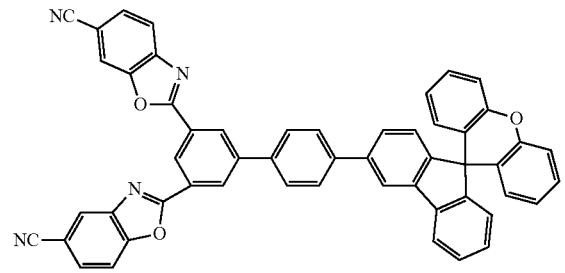
55
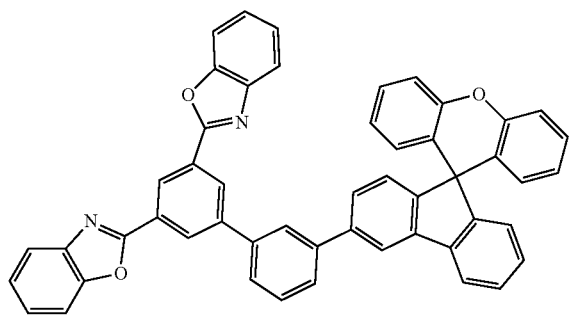
56
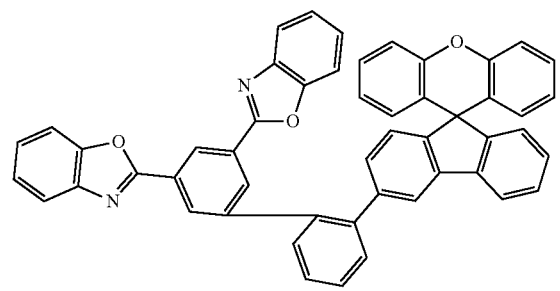

-continued
57
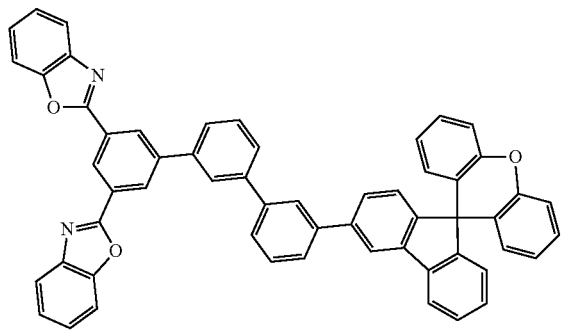
58
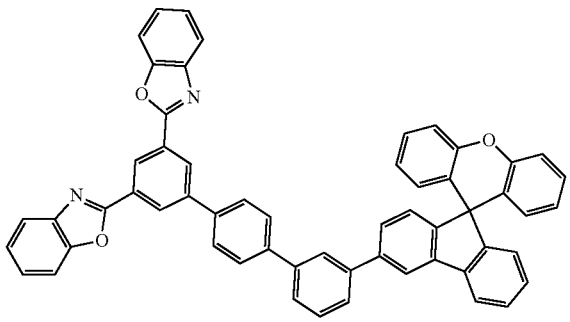
59
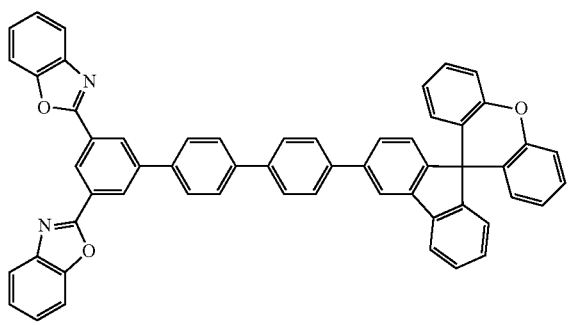
60
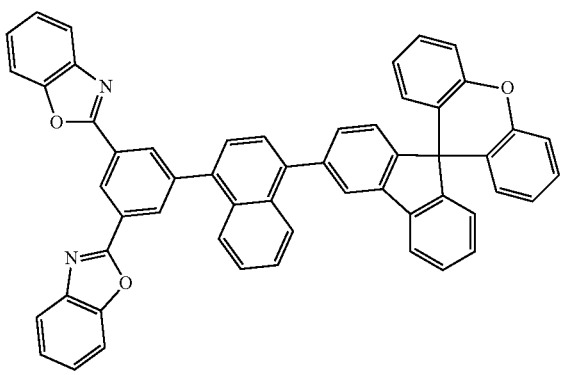
61
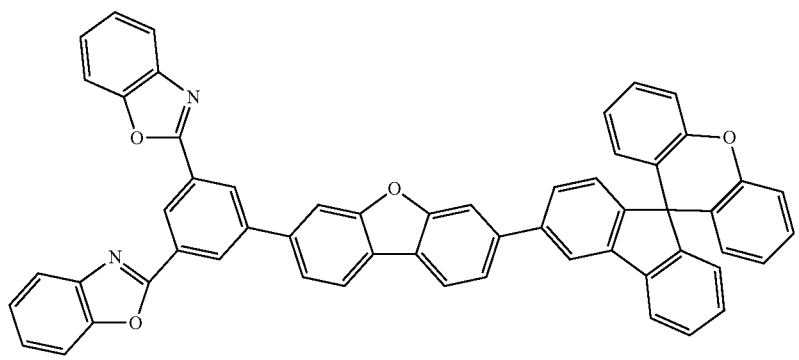
62
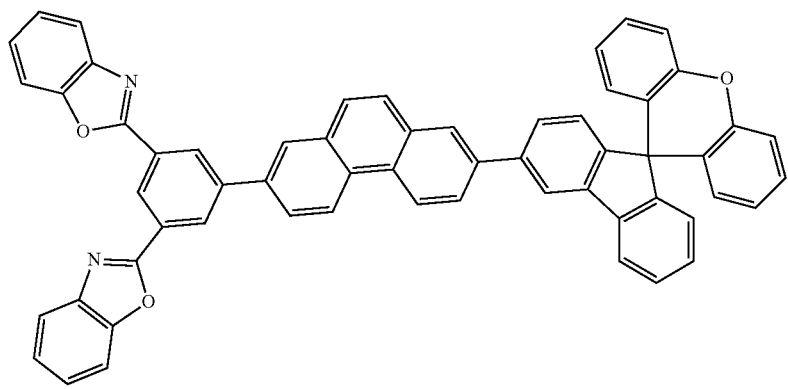

63
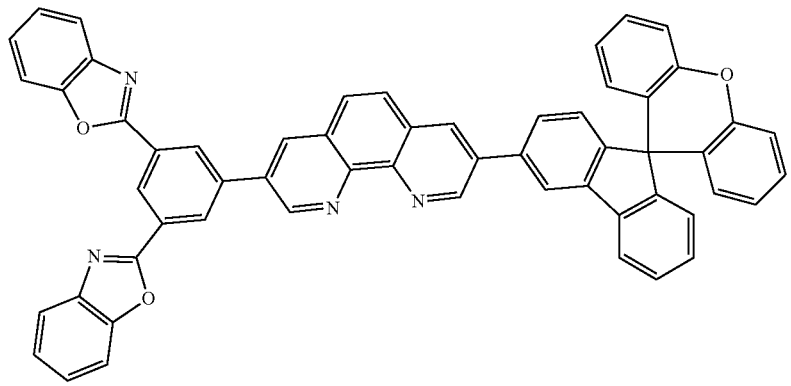
64
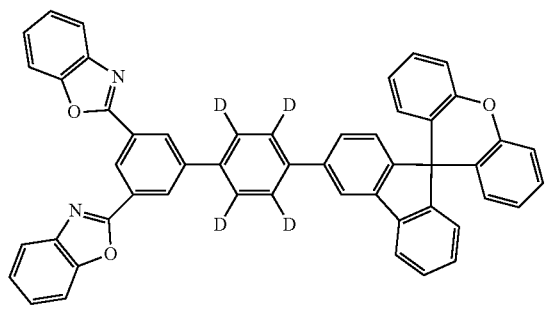
65
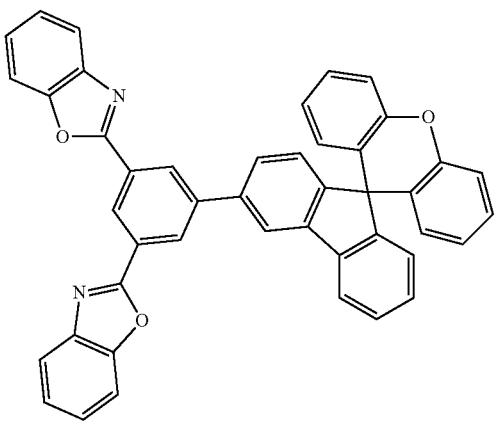
66
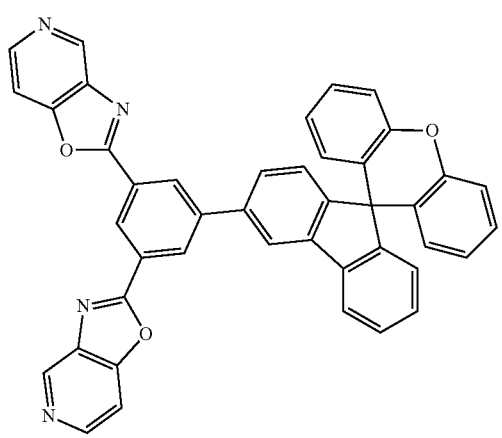
67
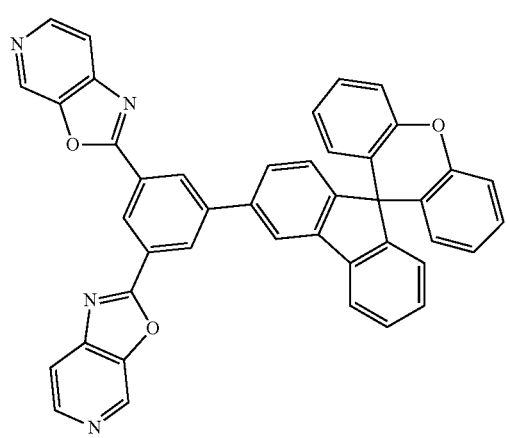

-continued
68
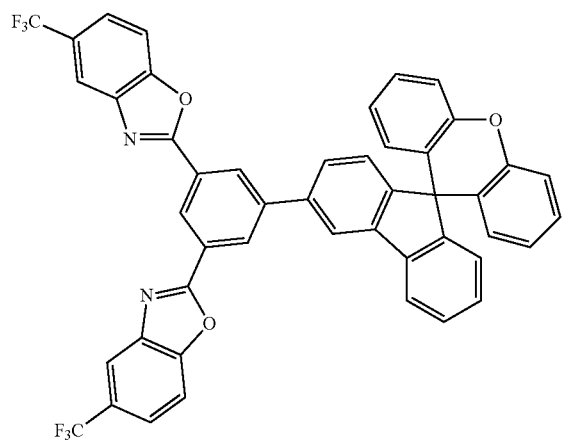
69
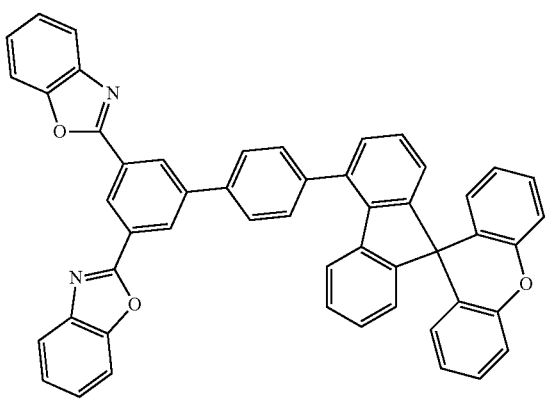
70
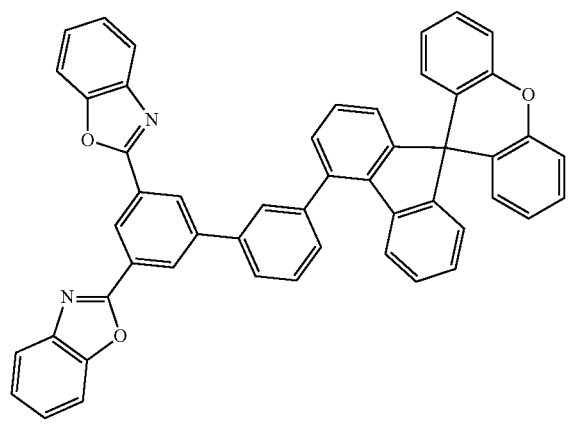
71
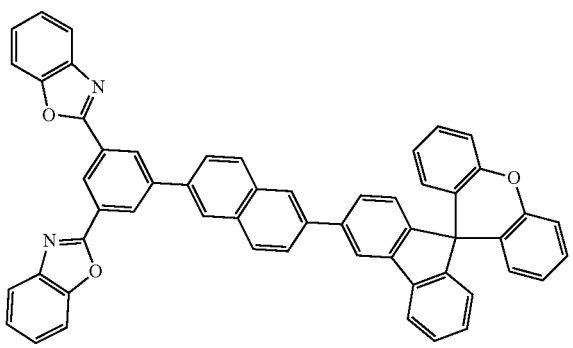
72
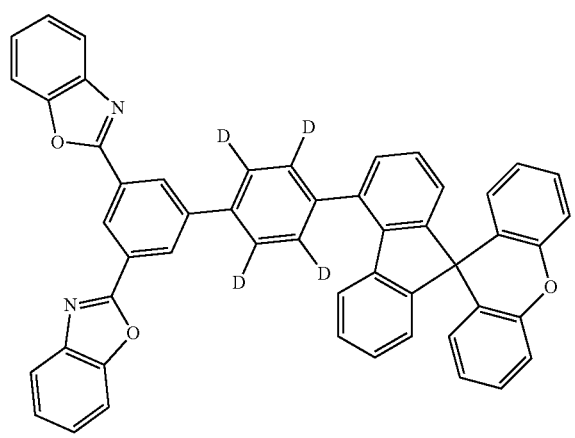
73
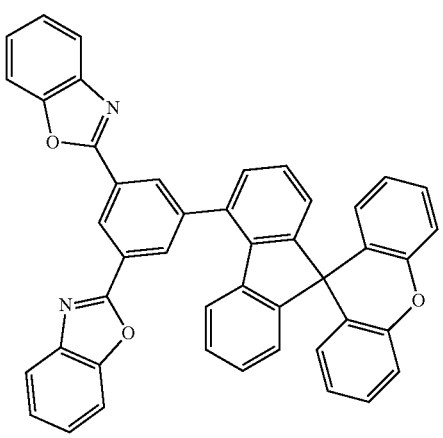

-continued
74
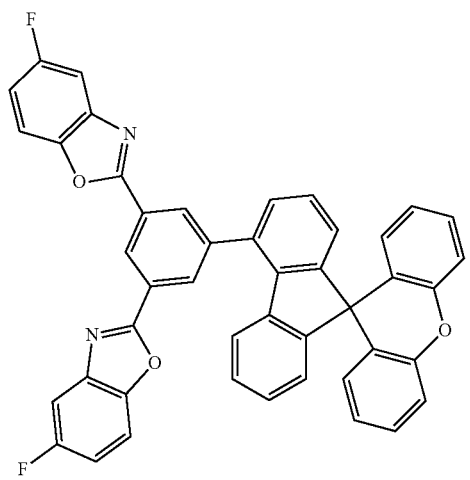
75
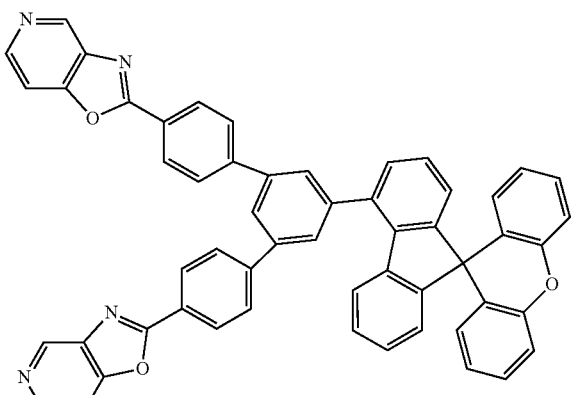
76
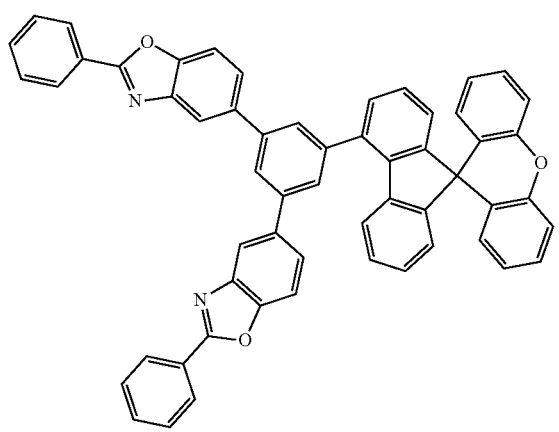
77
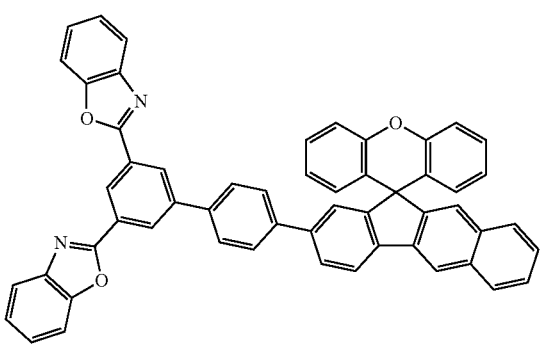
78
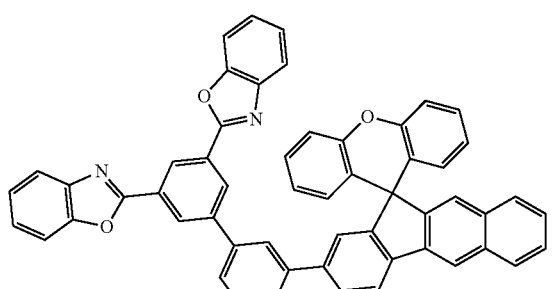
79
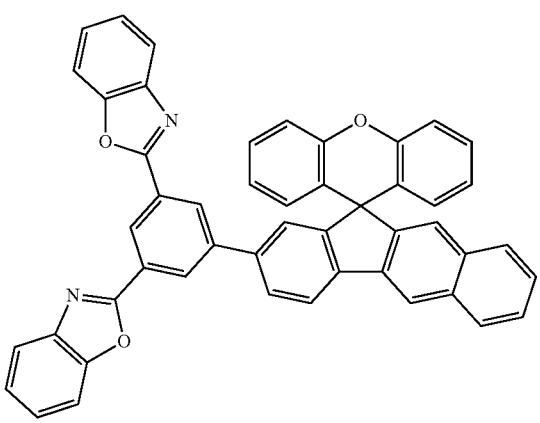

-continued
80
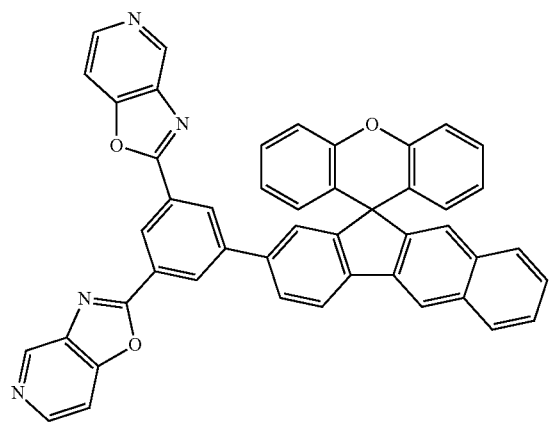
81
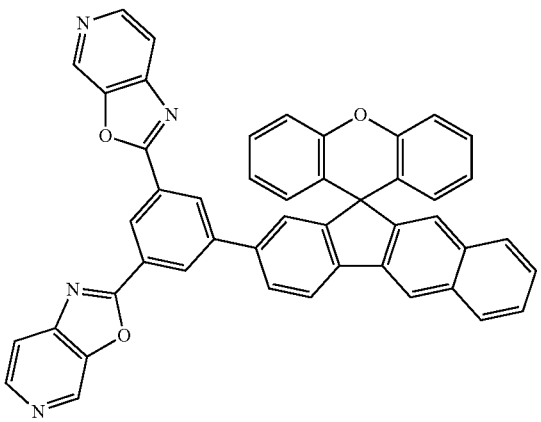
82
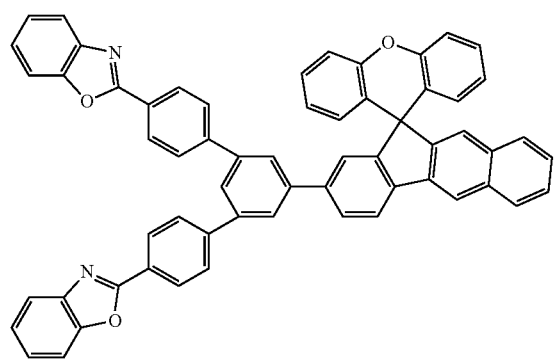
83
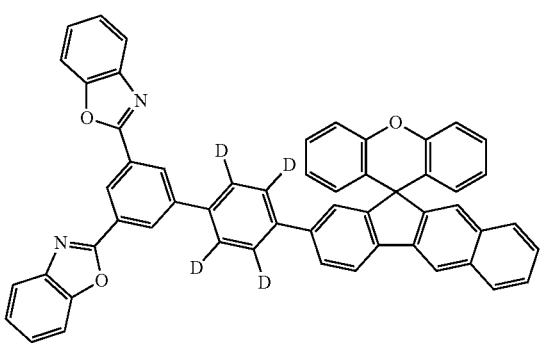
84
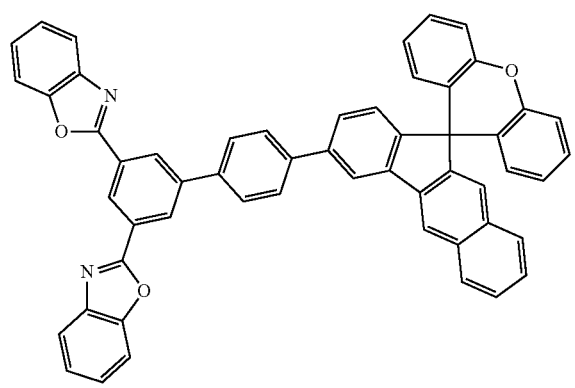
85
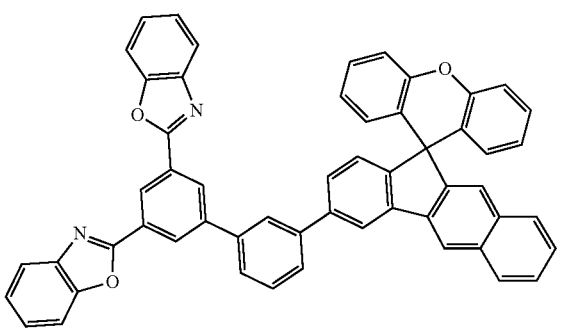
86
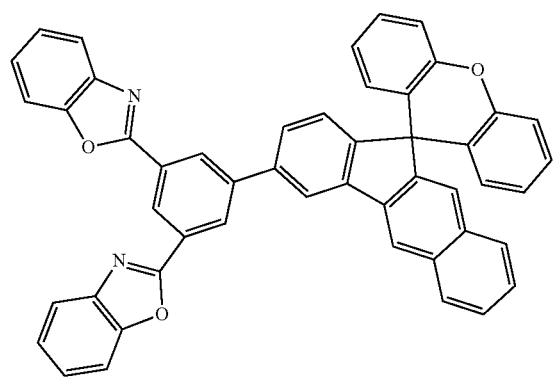
87
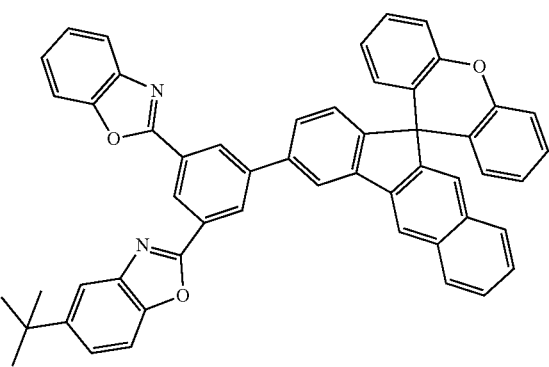

-continued
88
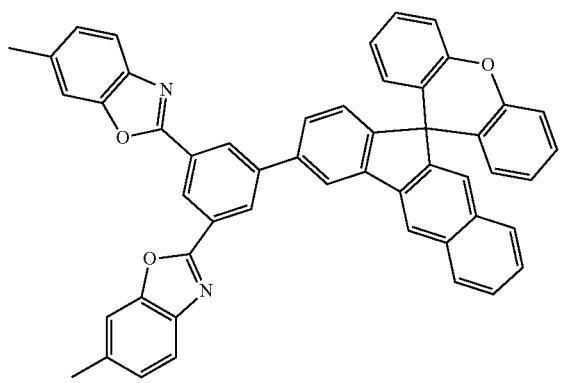
89
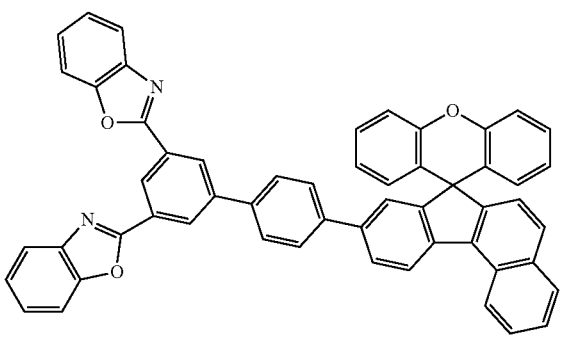
90
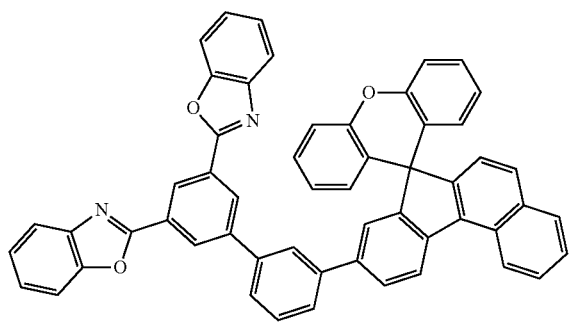
91
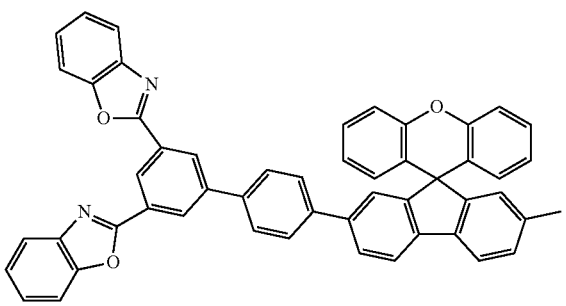
92
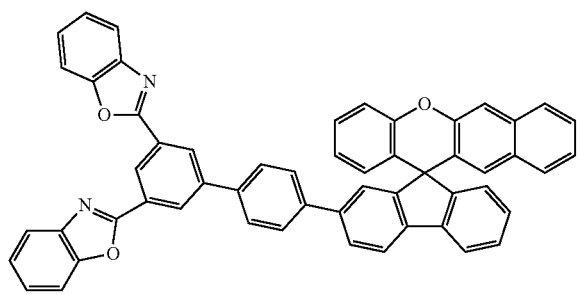
93
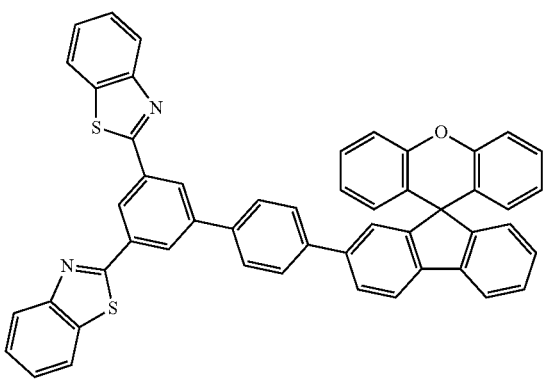
94
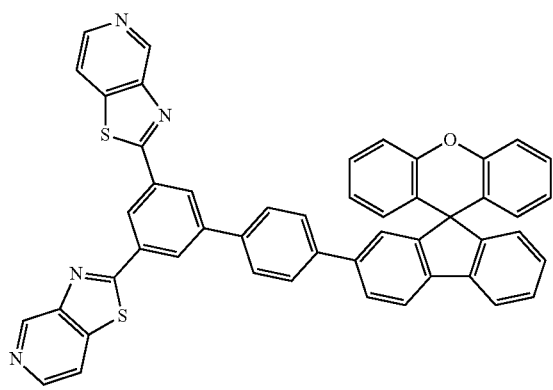
95
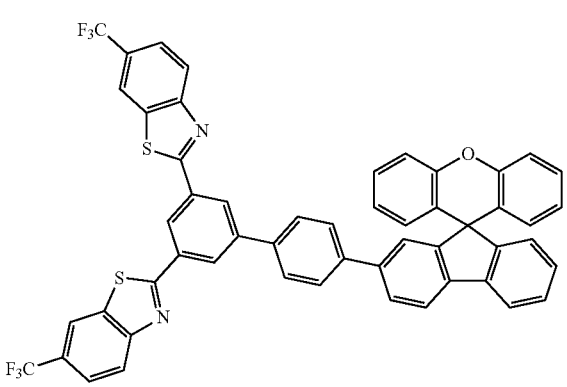

-continued
96
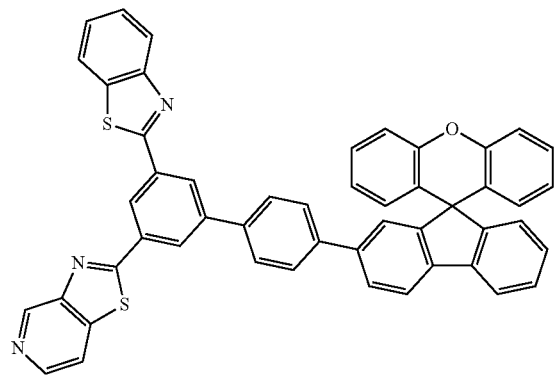
97
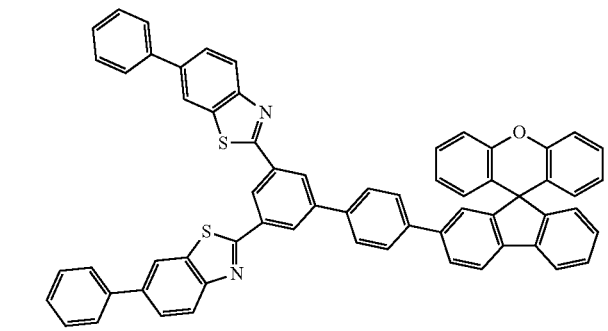
98
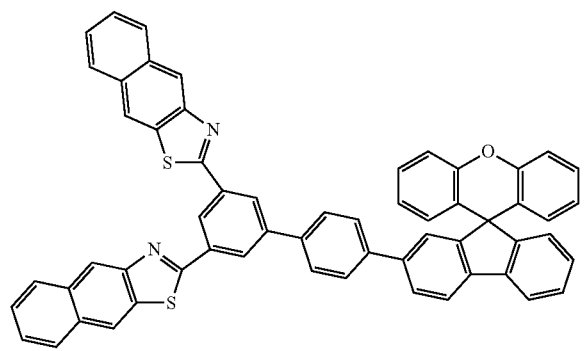
99
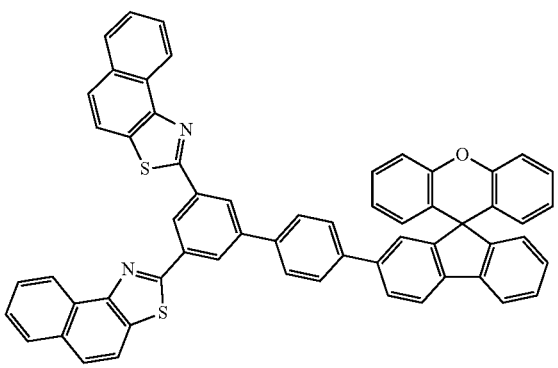
100
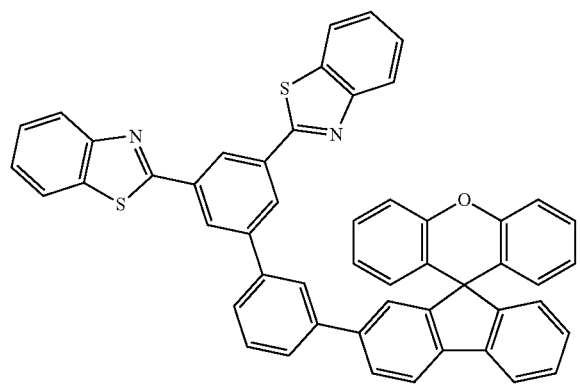
101
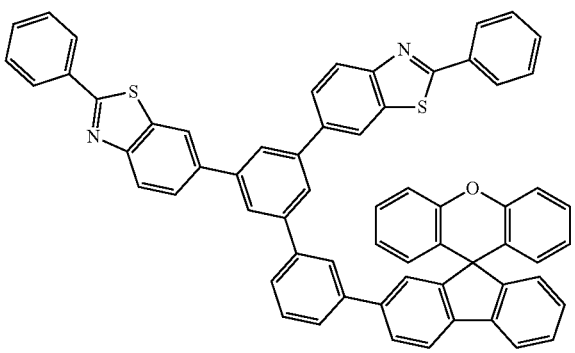
102
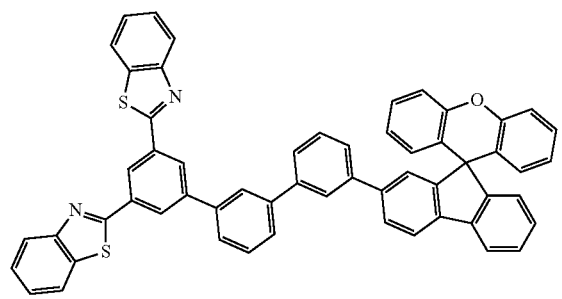
103
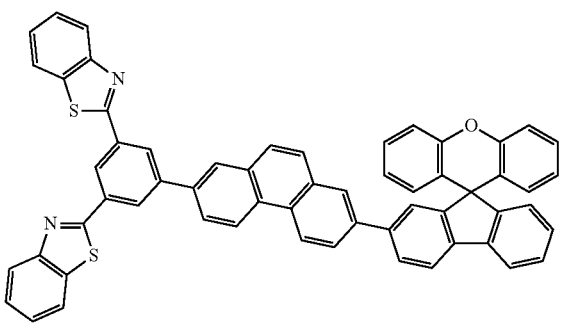

-continued
104
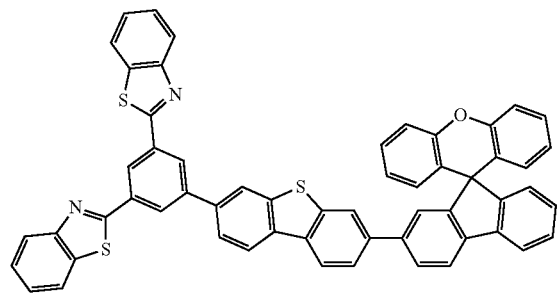
105
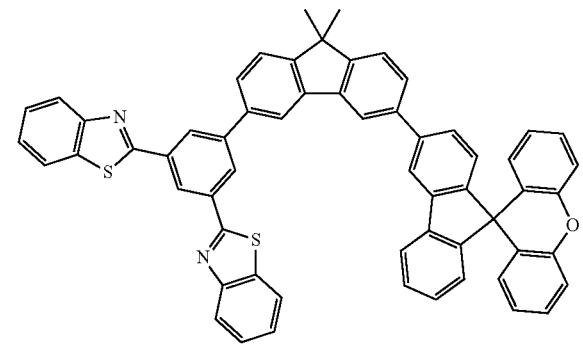
106
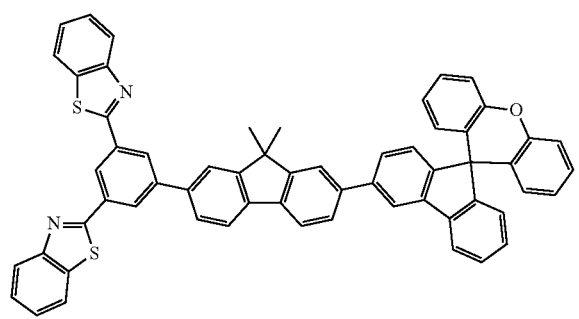
107
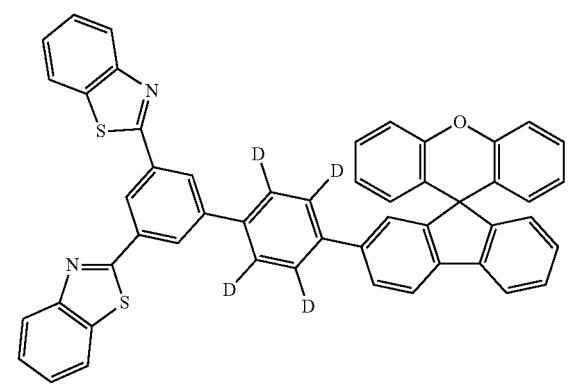
108
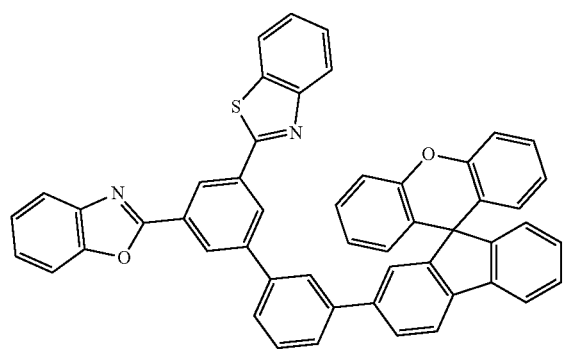
109
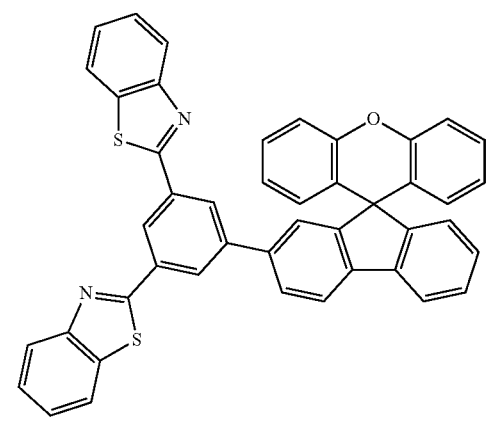
110
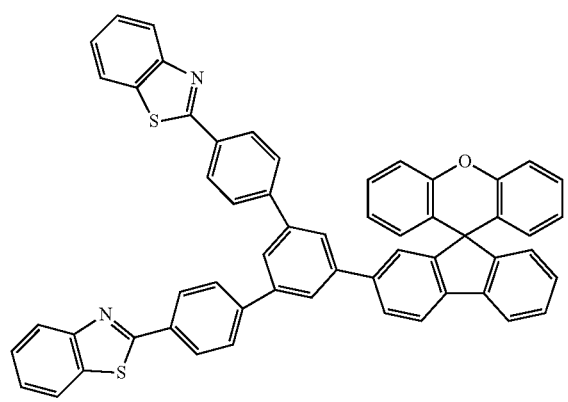
111
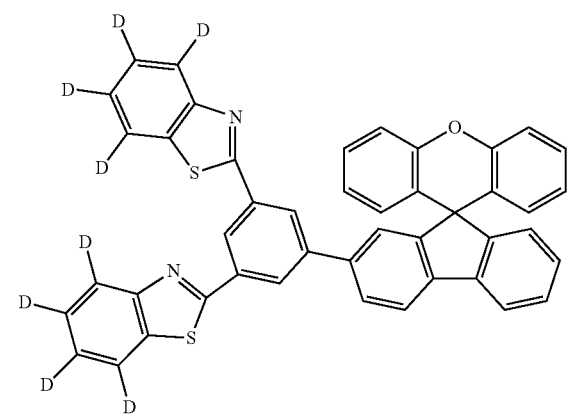

-continued
112
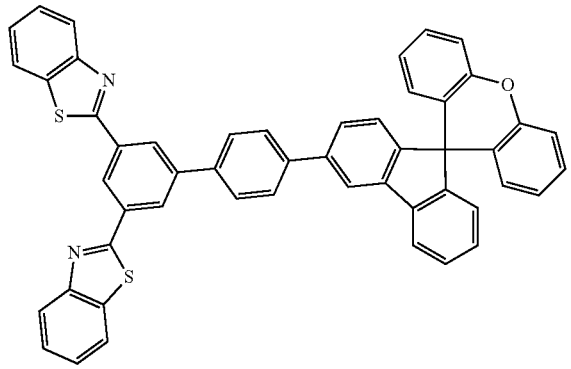
113
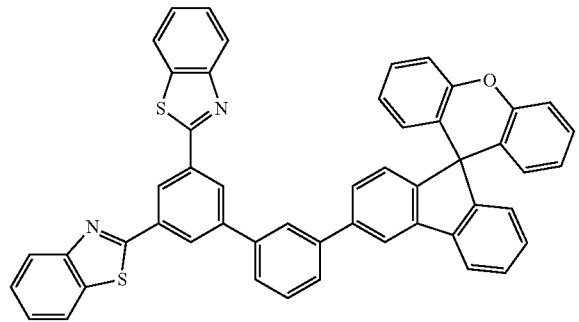
114
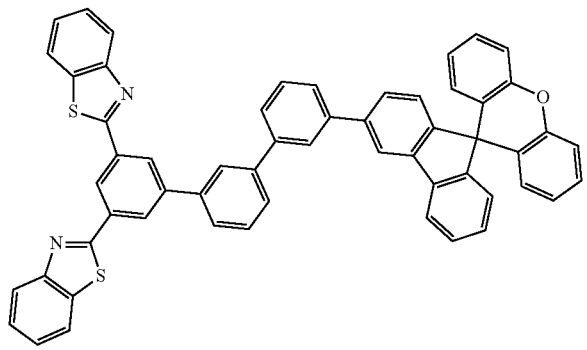
115
116
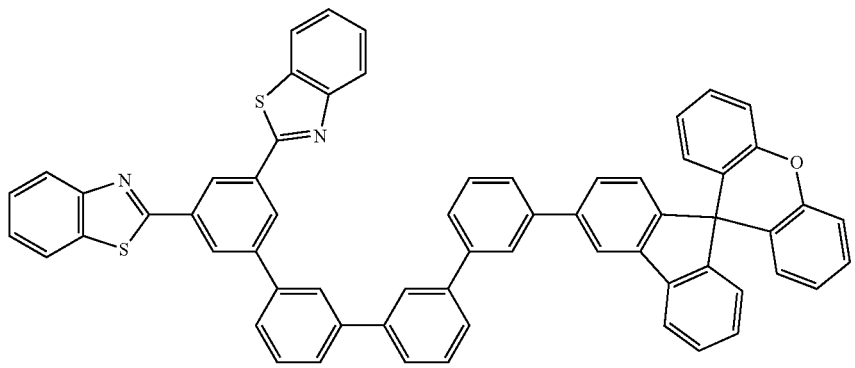
117
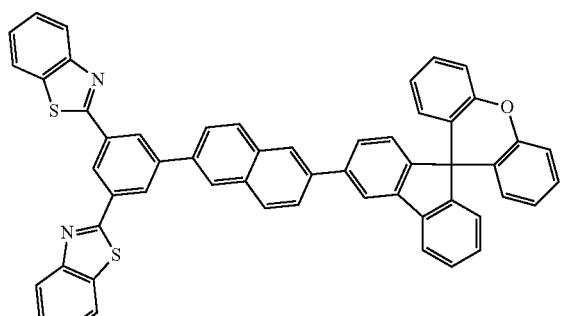
118
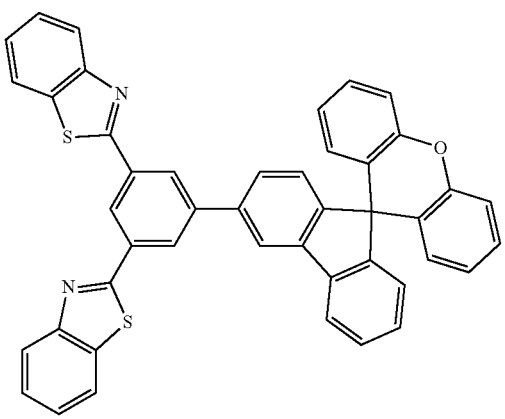

-continued
119
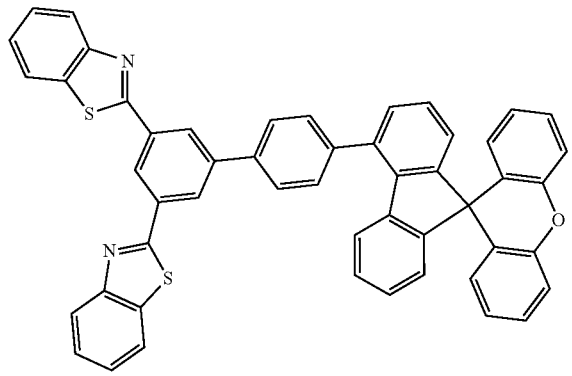
120
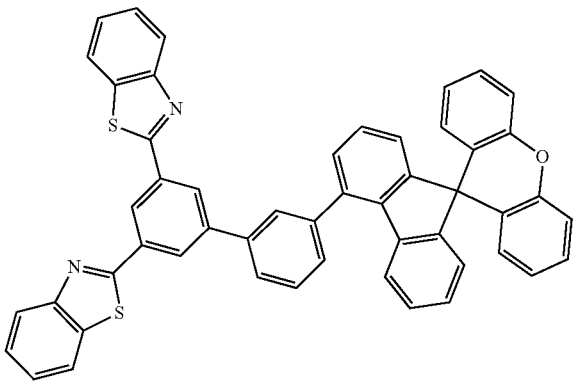
121
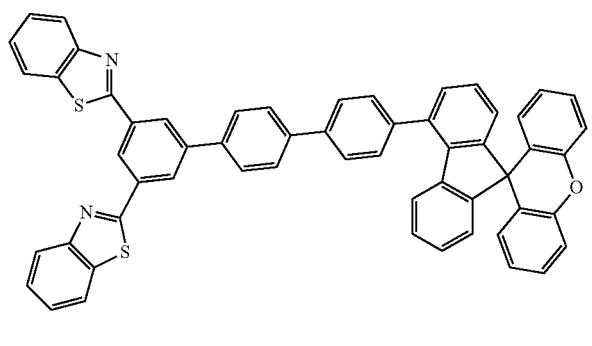
122
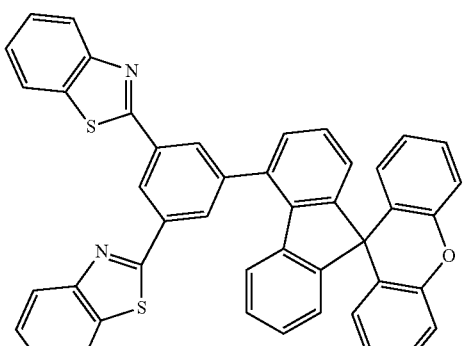
123
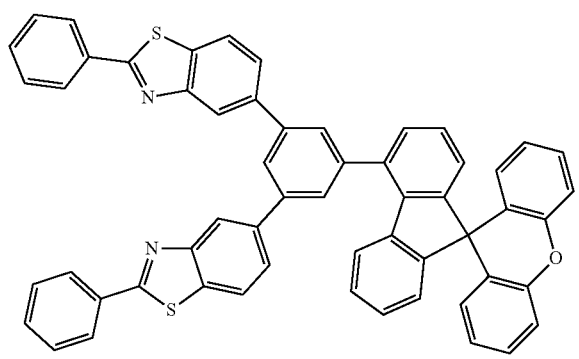
124
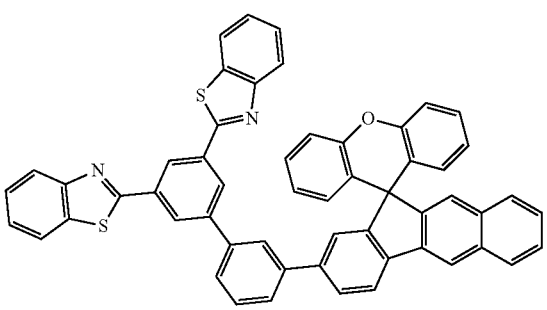
125
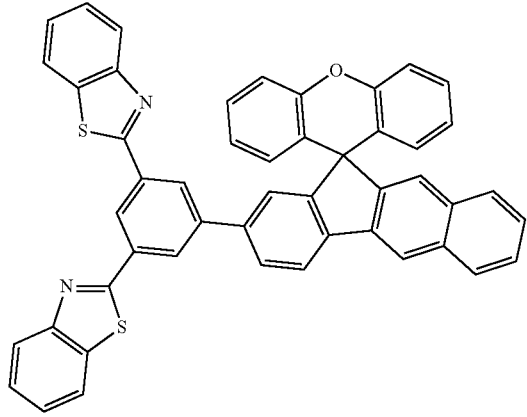
126
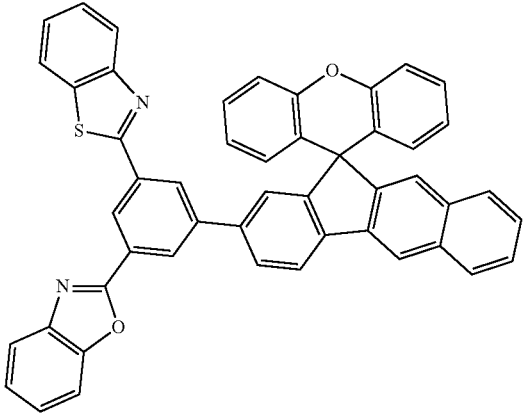

-continued
127
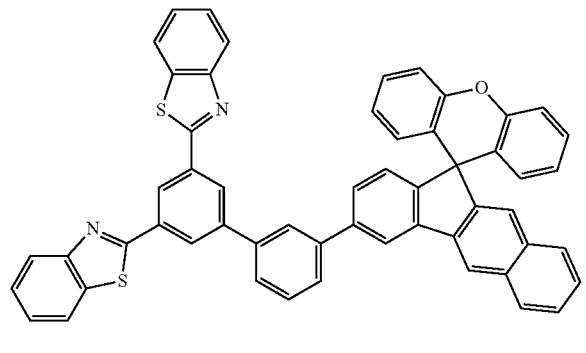
128
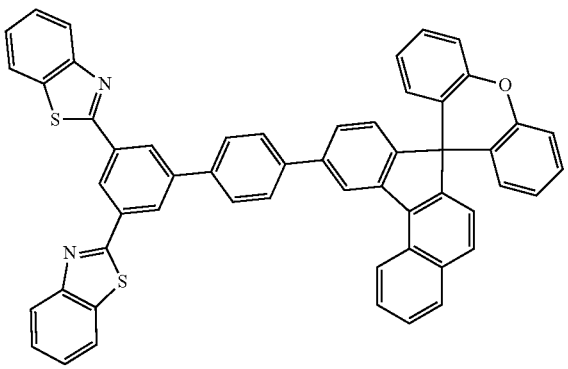
129
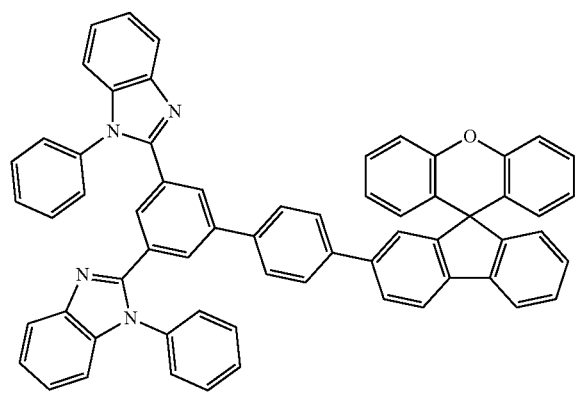
130
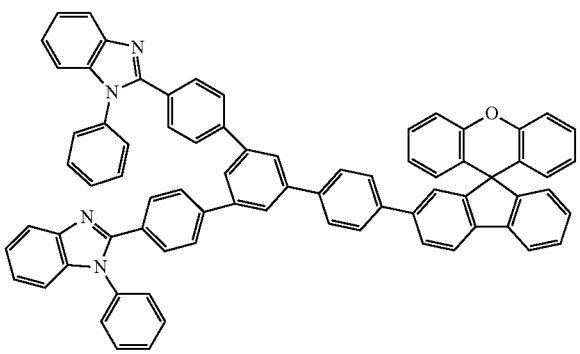
131
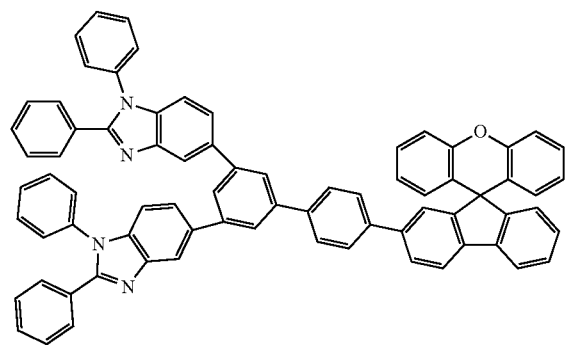
132
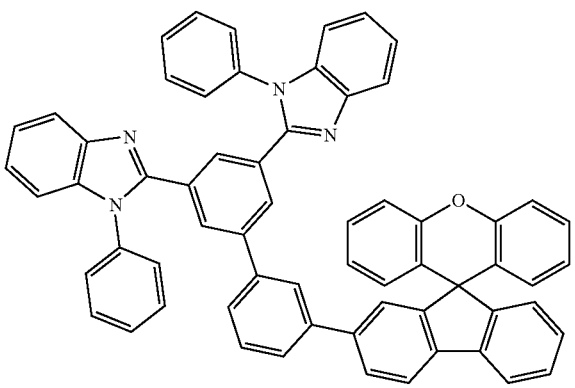
133
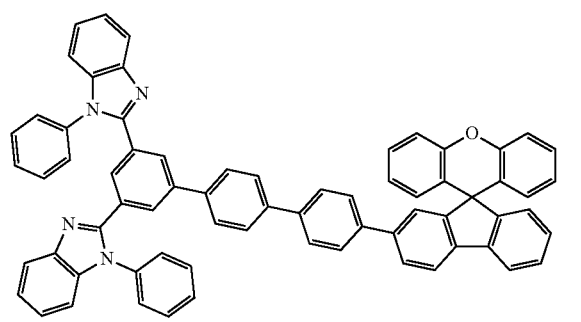
134
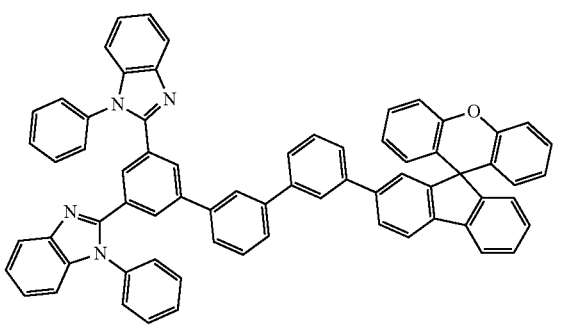

135
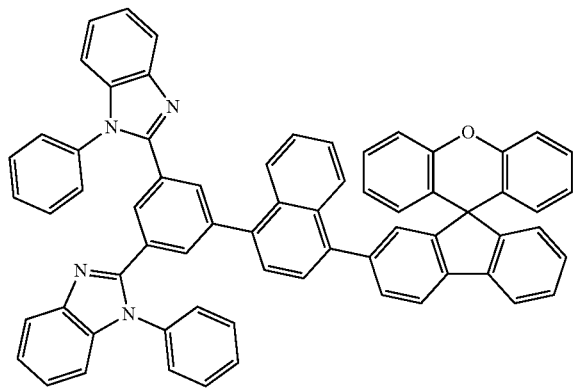
136
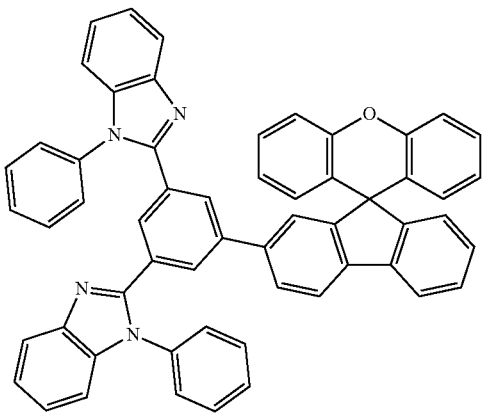
137
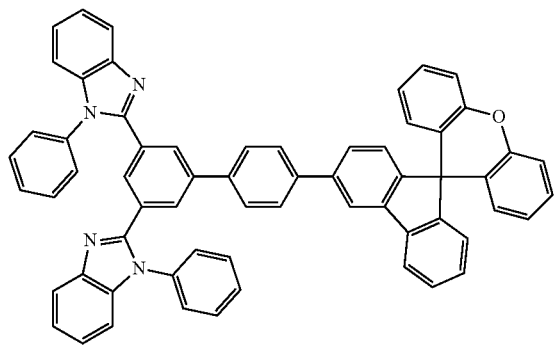
138
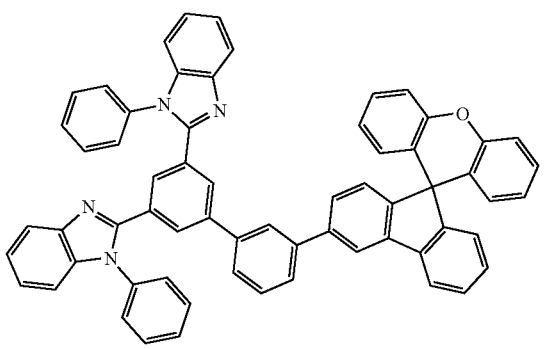
139
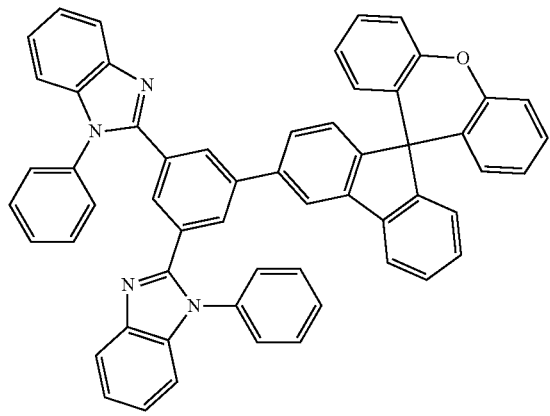
140
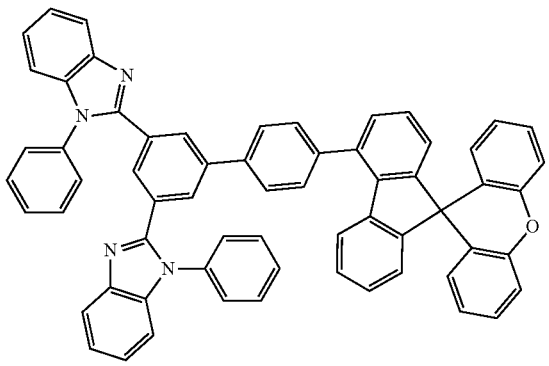

141
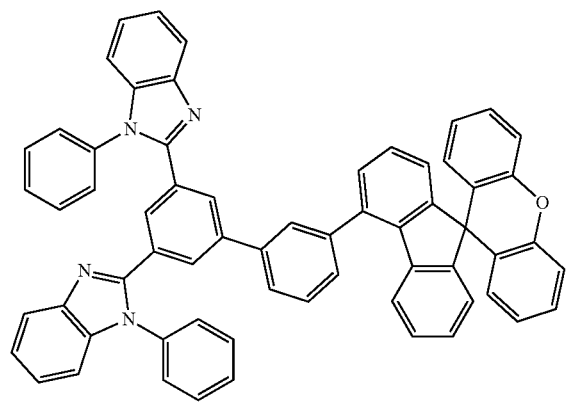
142
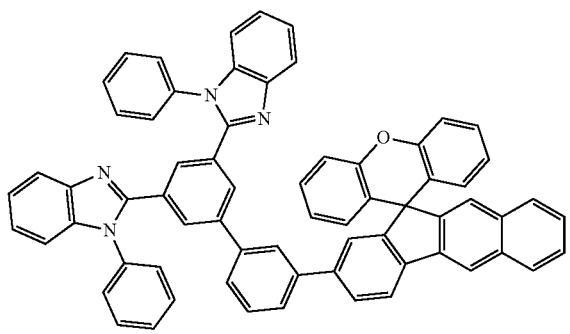
143
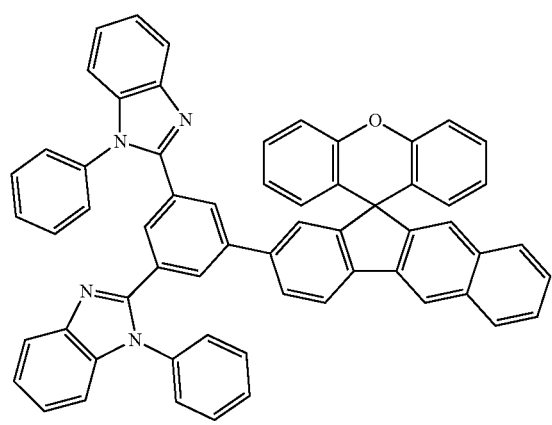
144
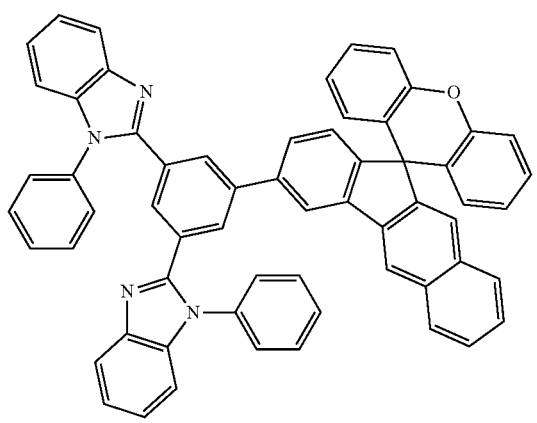
145
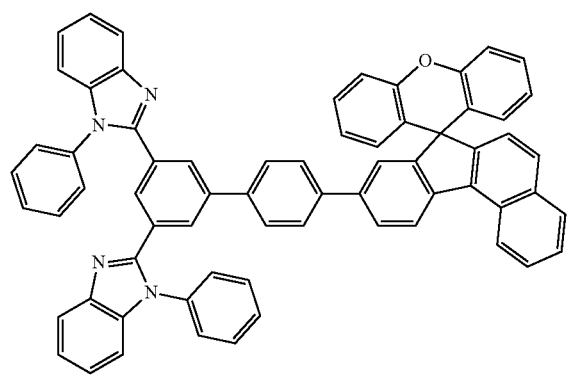
146
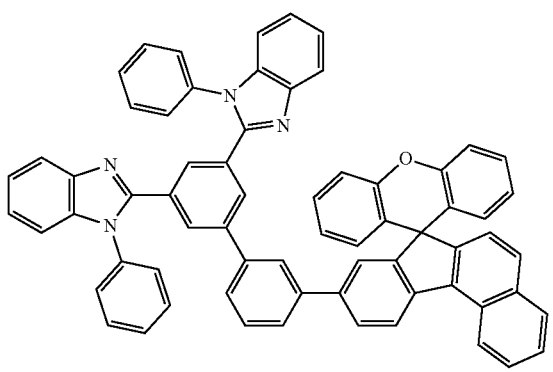

-continued
147
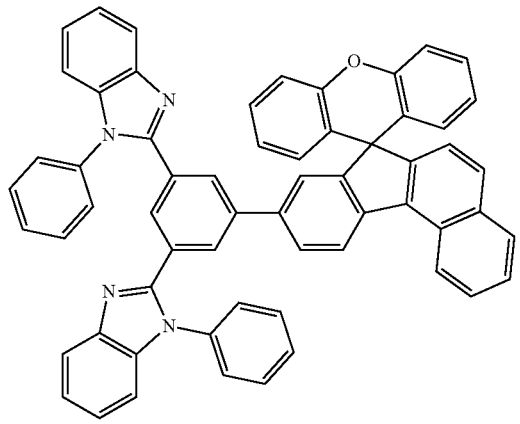
148
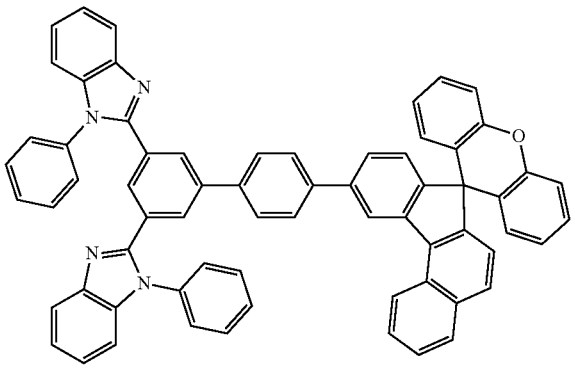
149
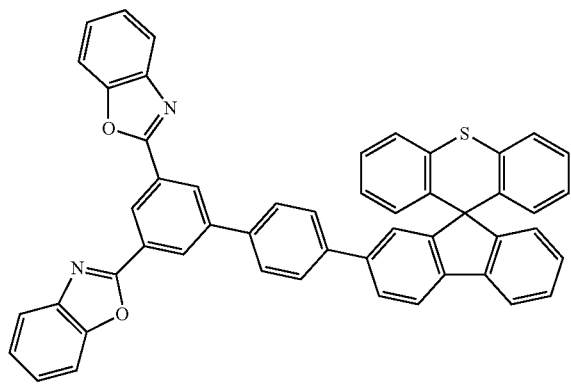
150
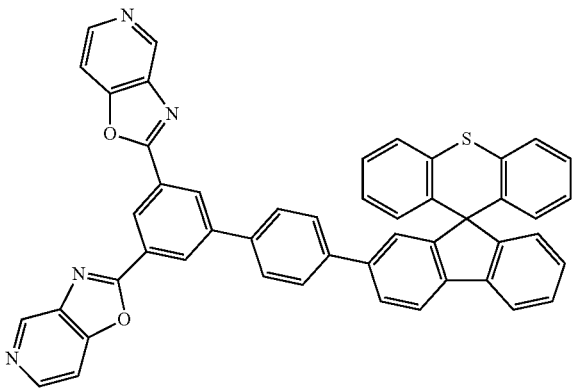
151
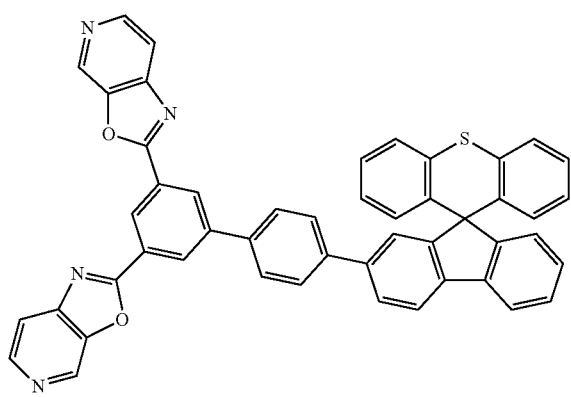
152
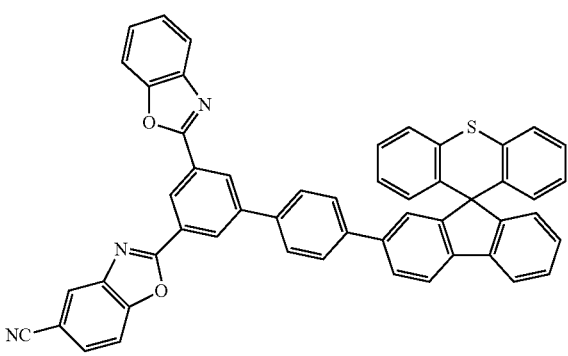
153
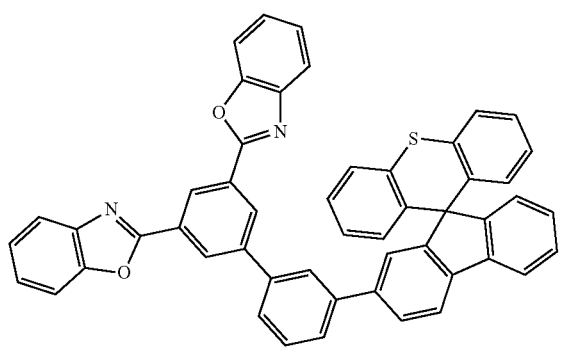
154
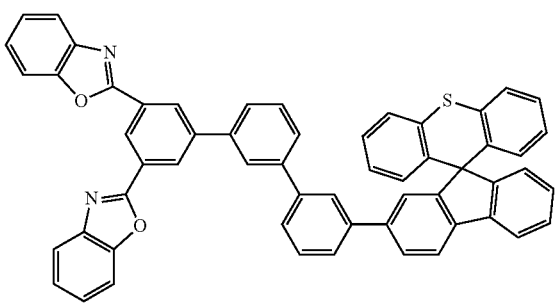

-continued
155
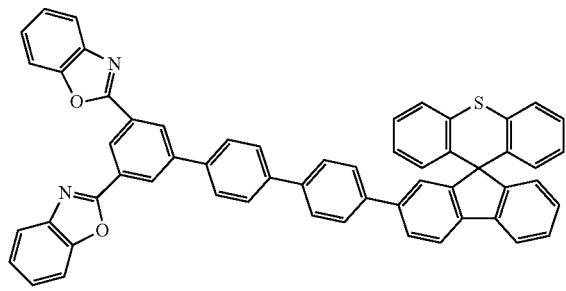
156
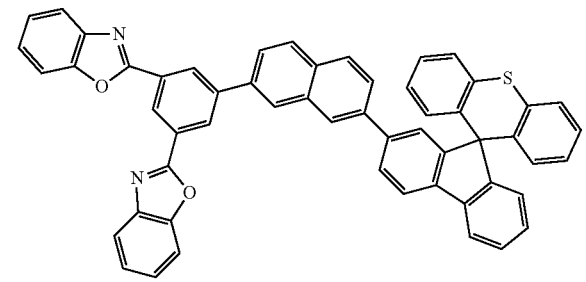
157
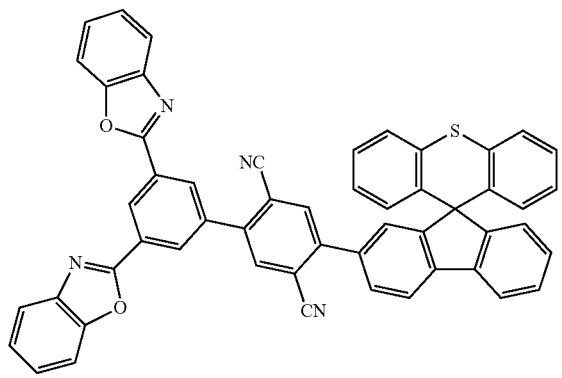
158
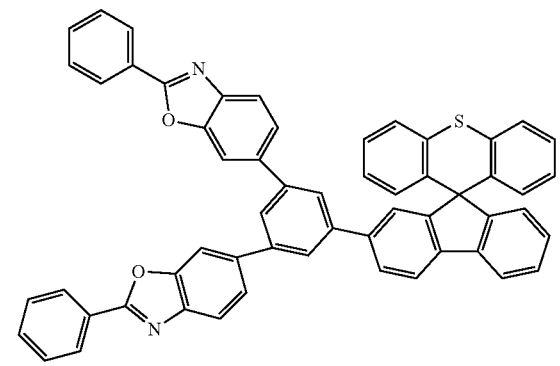
159
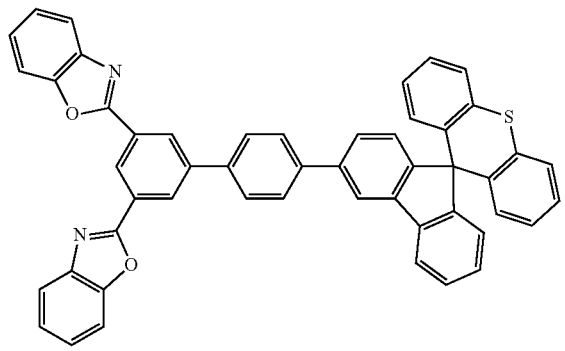
160
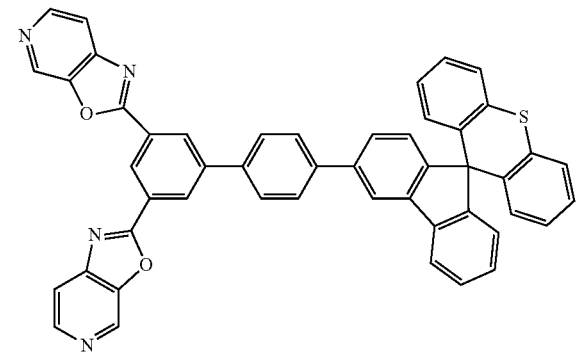
161
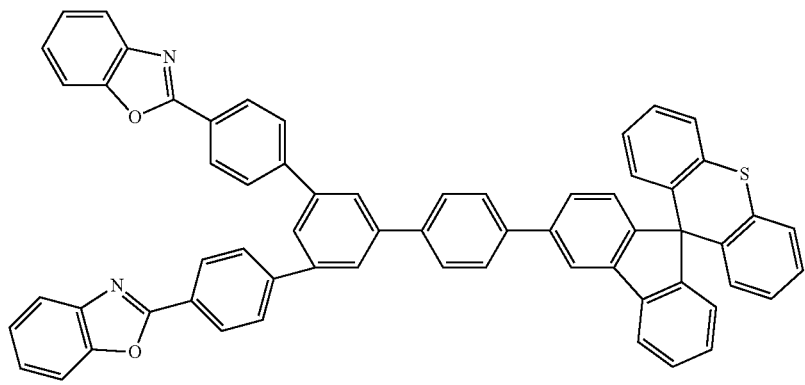

-continued
162
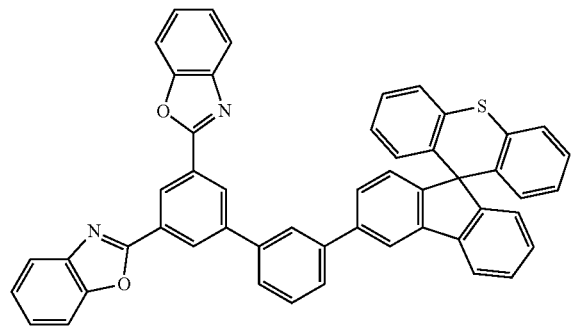
163
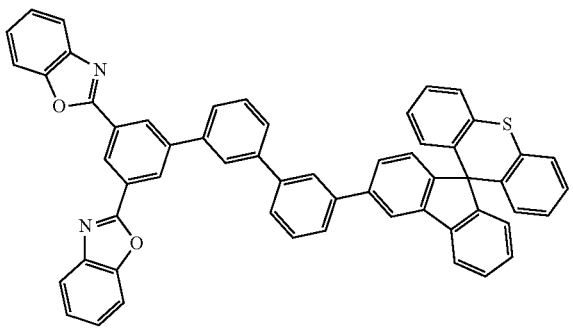
164
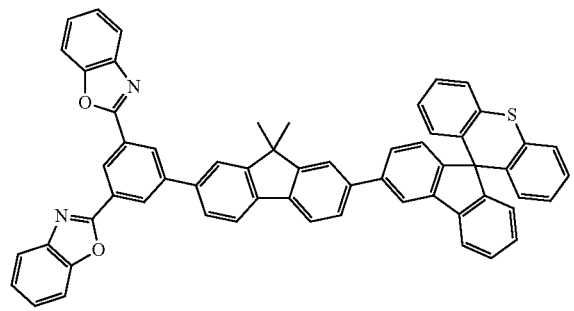
165
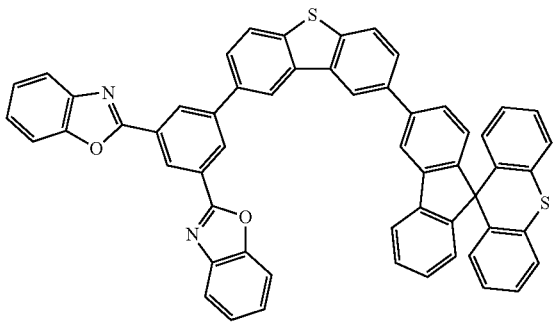
166
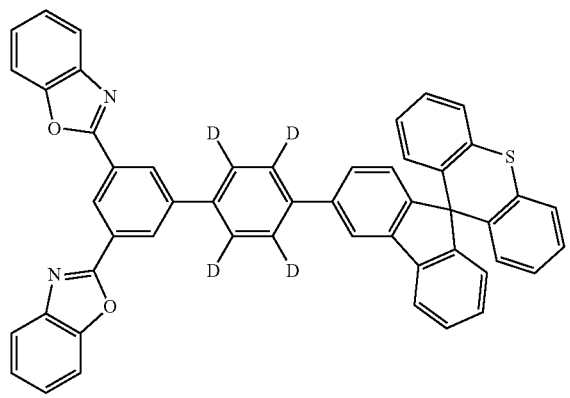
167
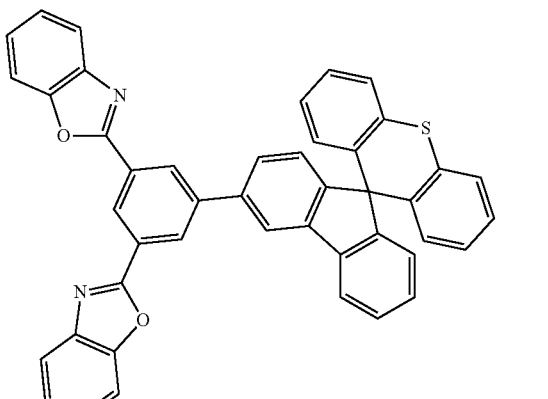
168
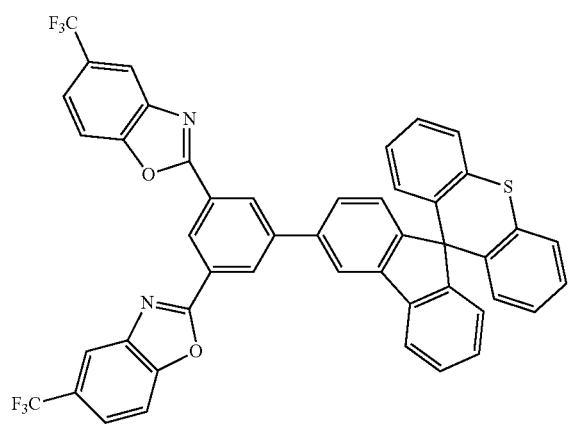
169
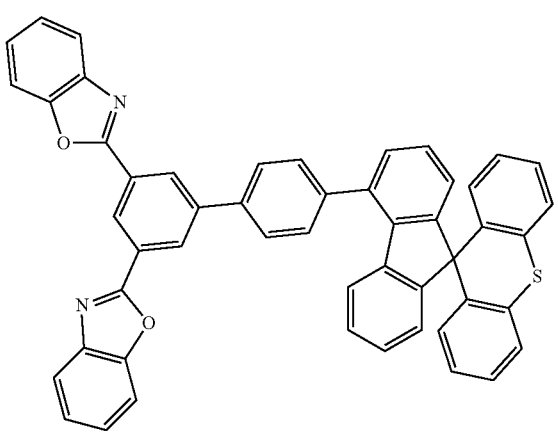

-continued
170
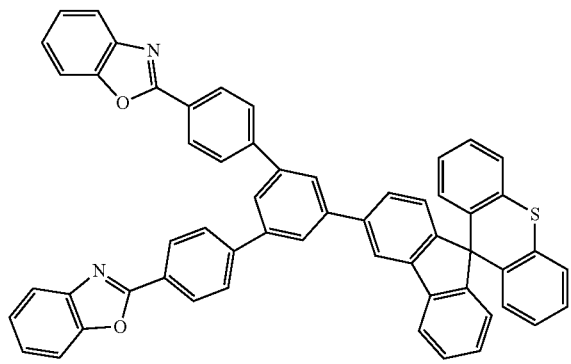
171
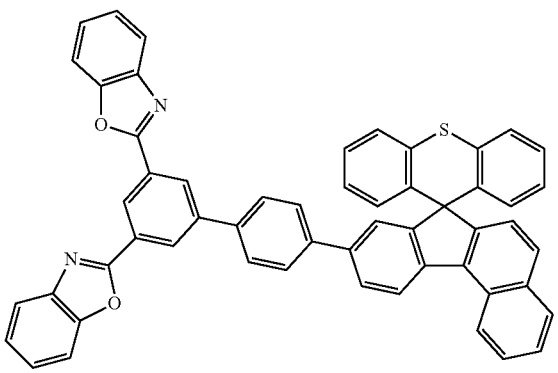
172
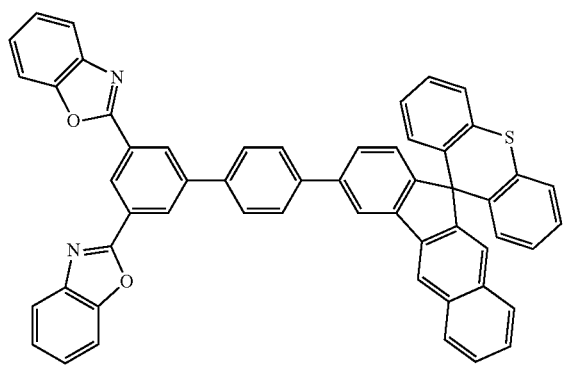
173
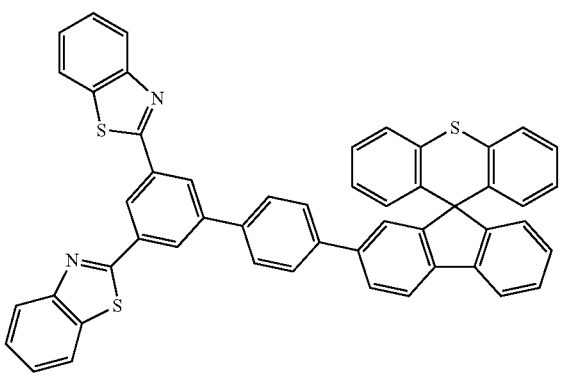
174
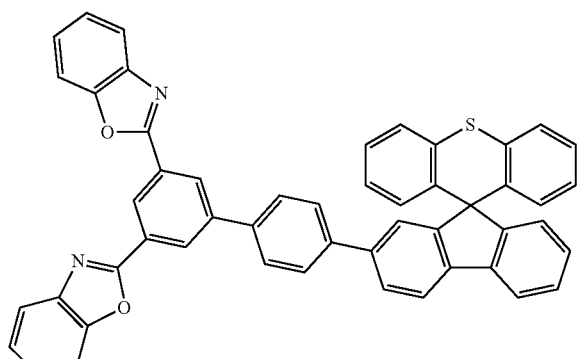
175
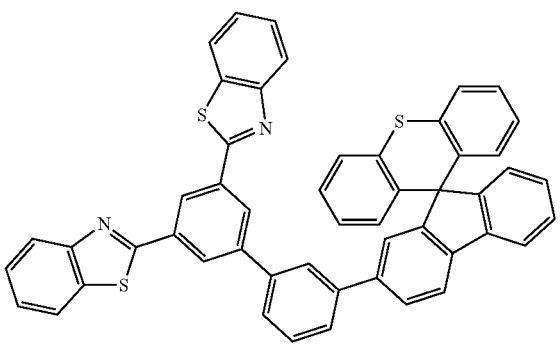
176
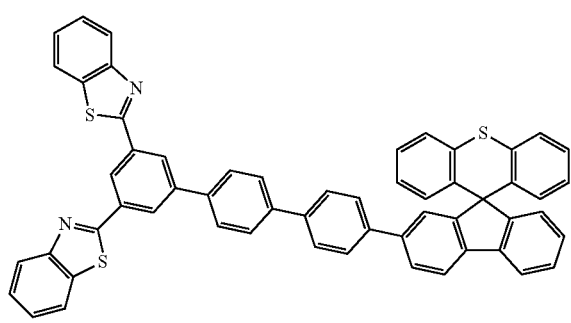
177
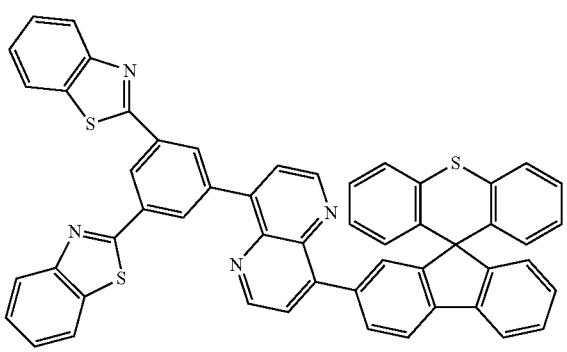

-continued
178
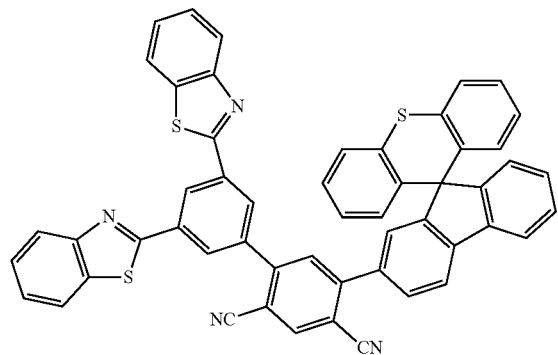
179
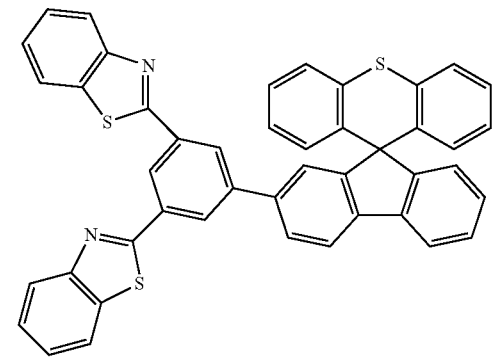
180
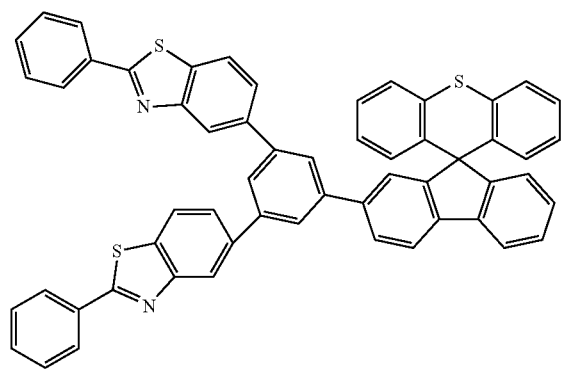
181
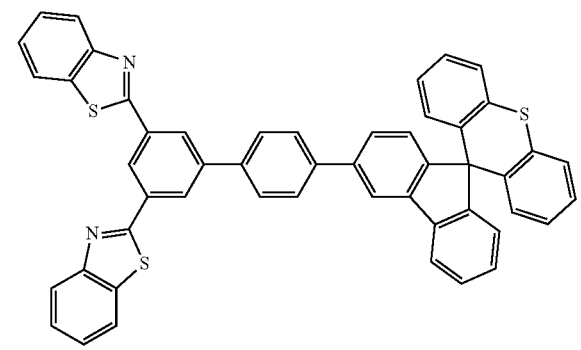
182
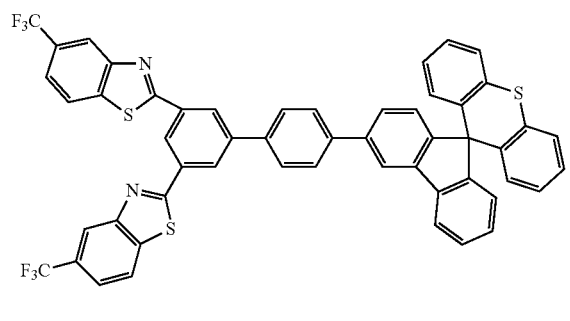
183
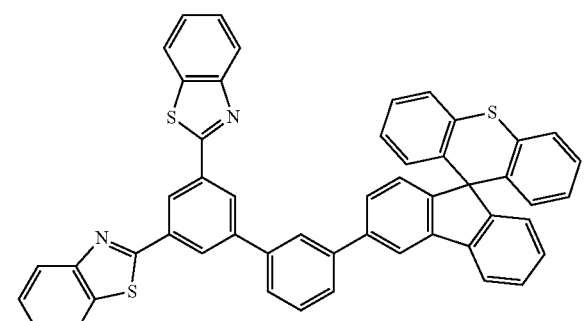
184
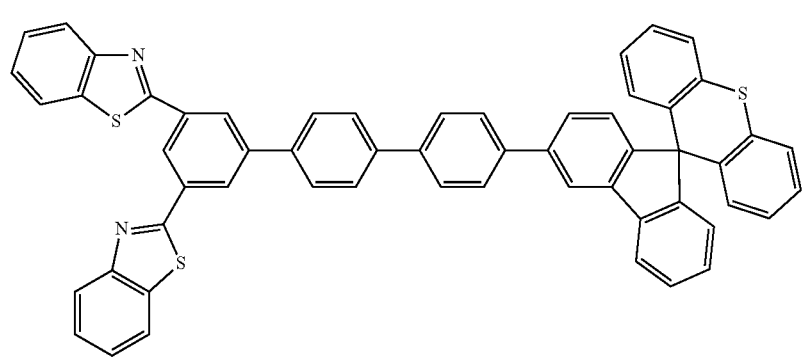

-continued
185
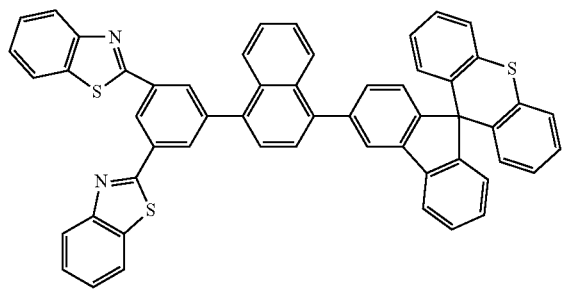
186
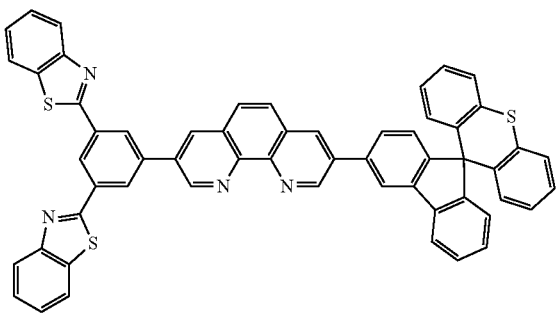
187
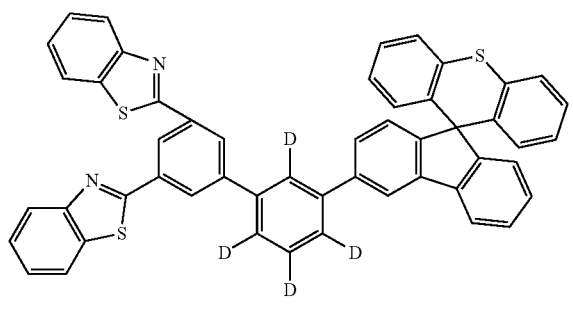
188
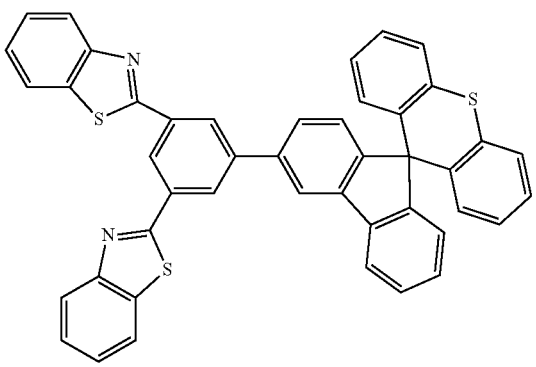
189
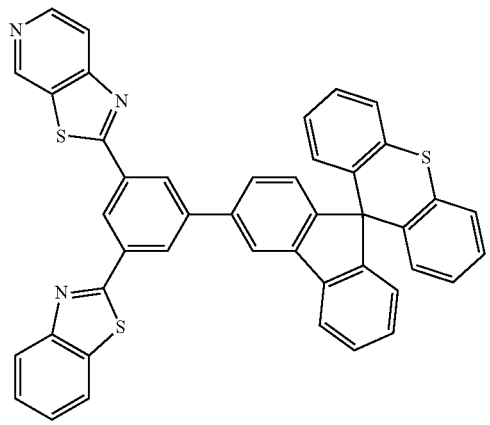
190
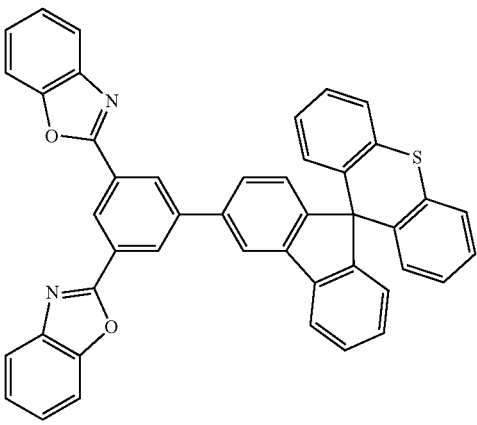
191
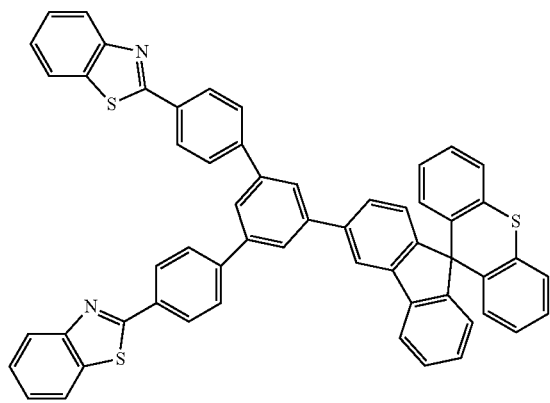
192
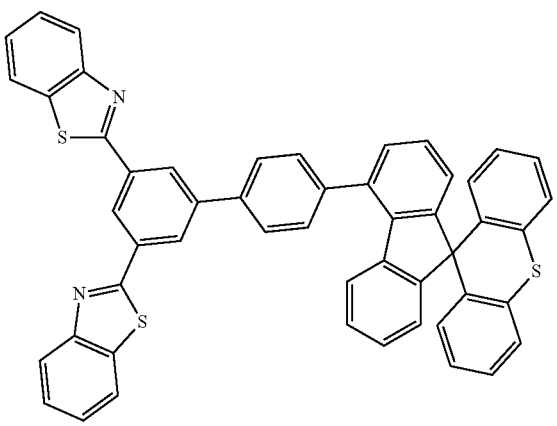

-continued
193
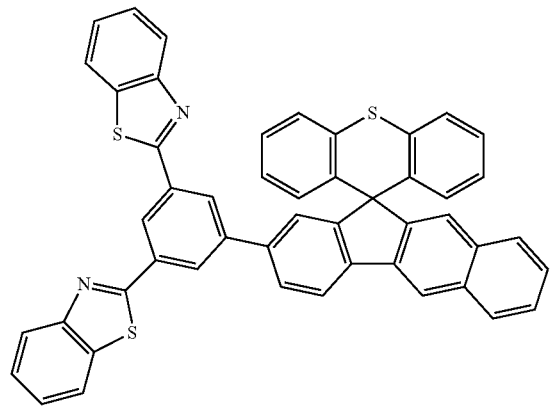
194
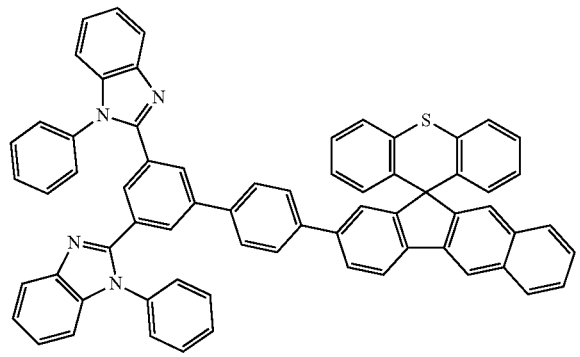
195
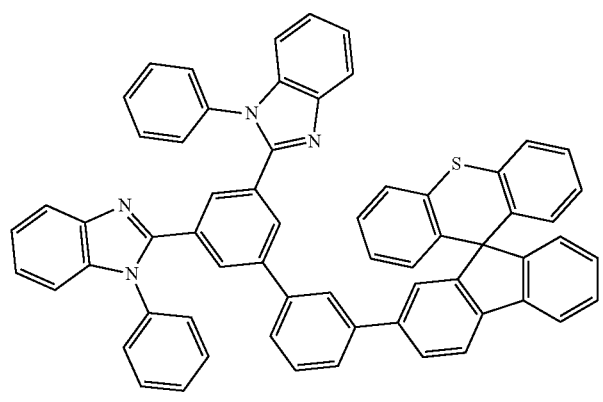
196
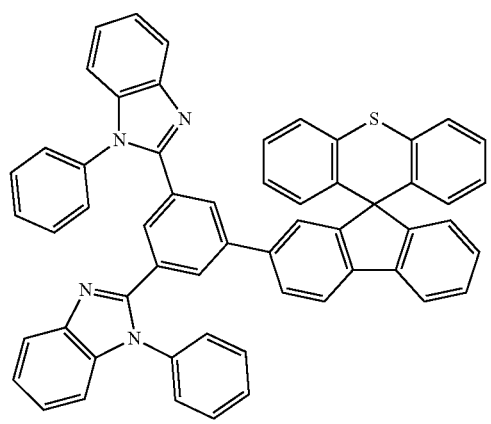
197
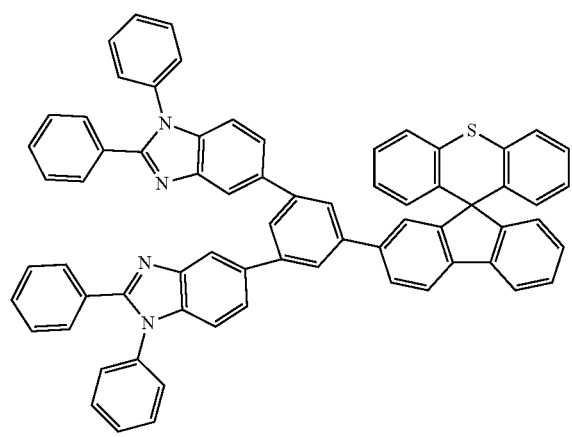
198
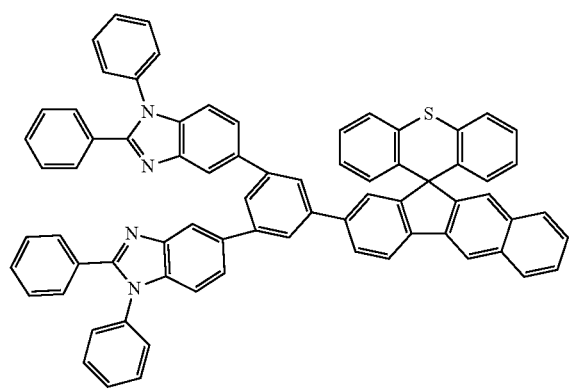

-continued
199
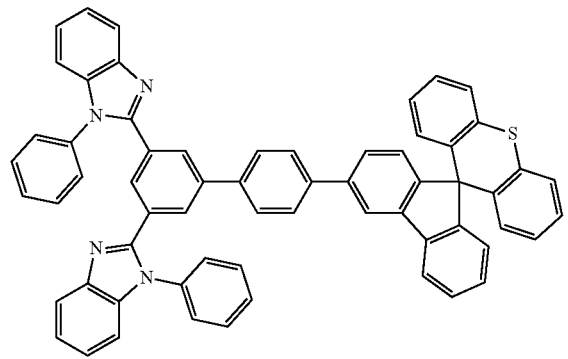
200
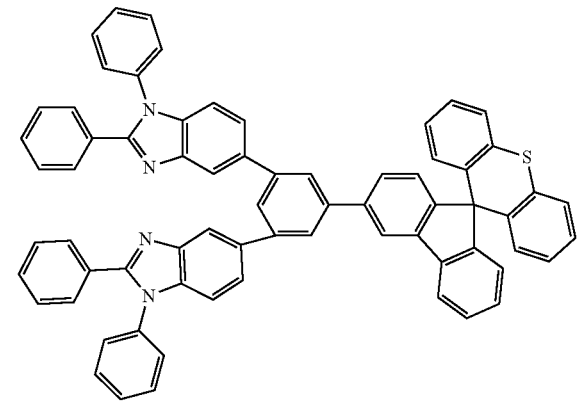
201
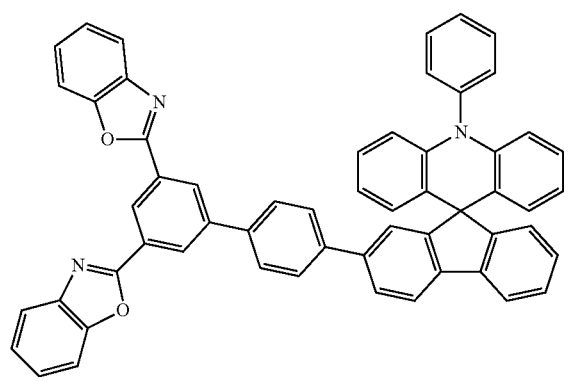
202
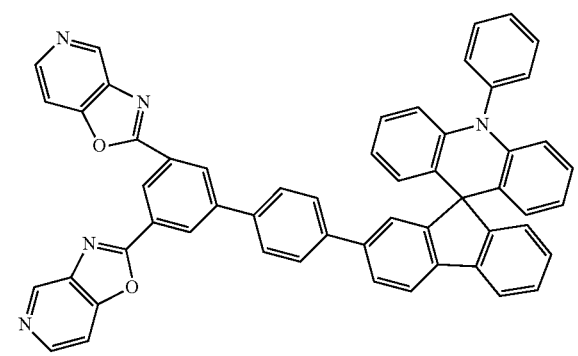
203
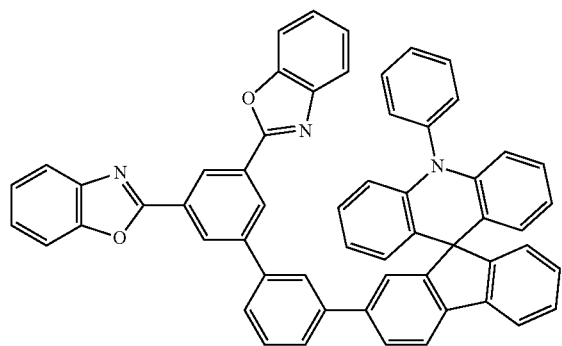
204
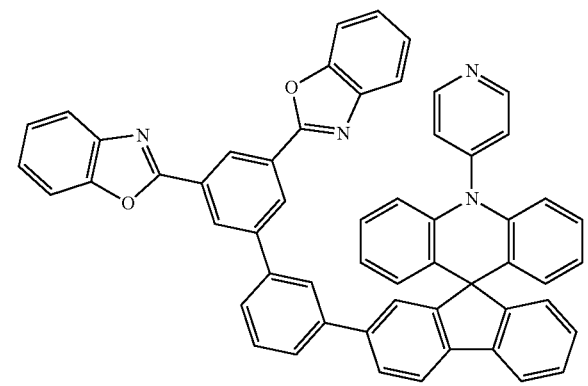
205
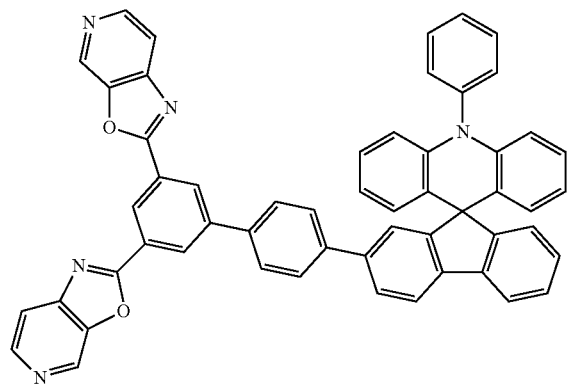
206
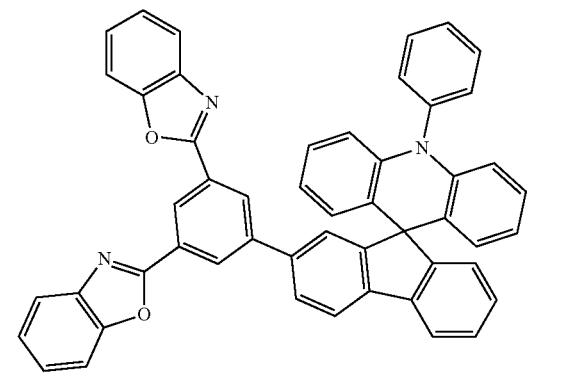

-continued
207
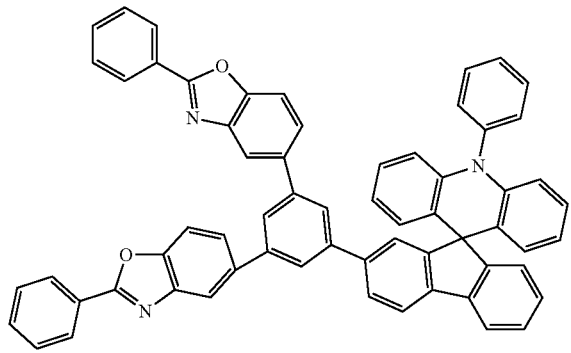
208
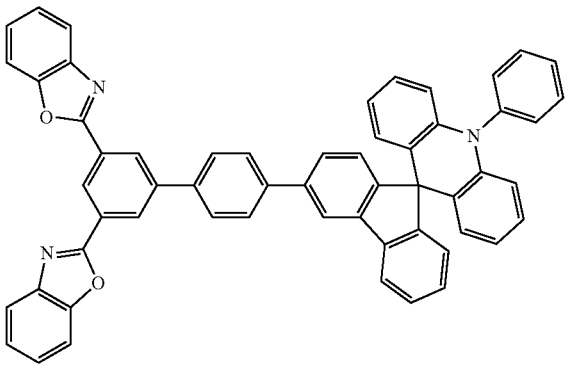
209
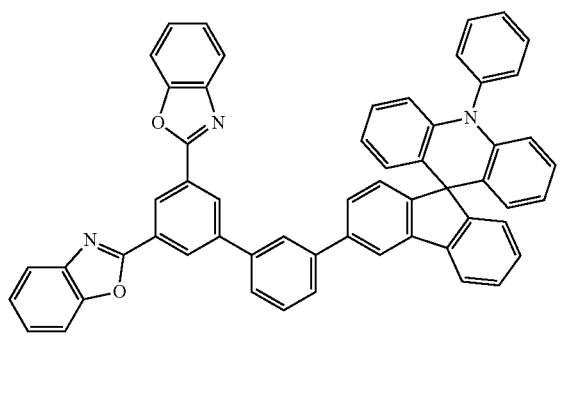
210
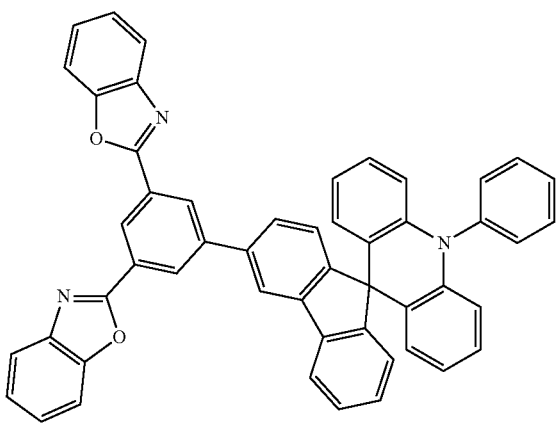
211
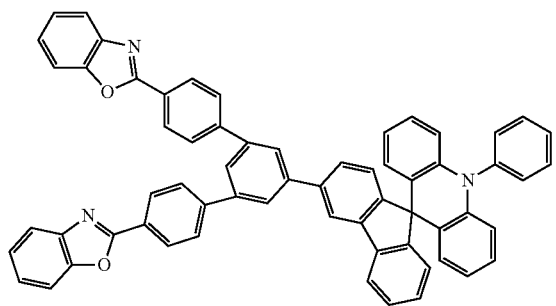
212
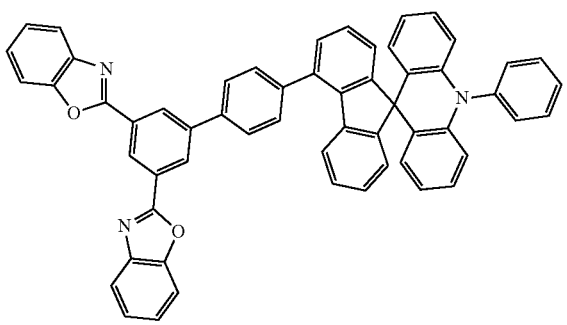
213
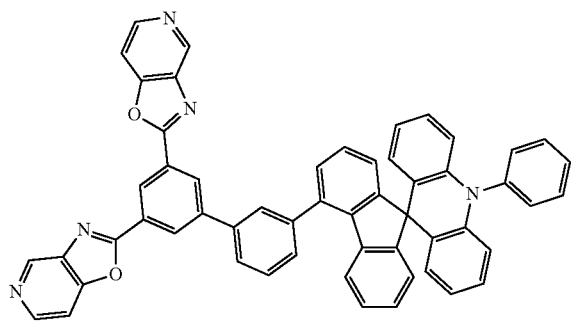
214
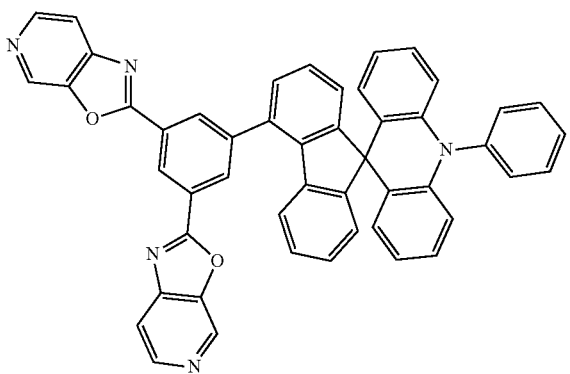

-continued
215
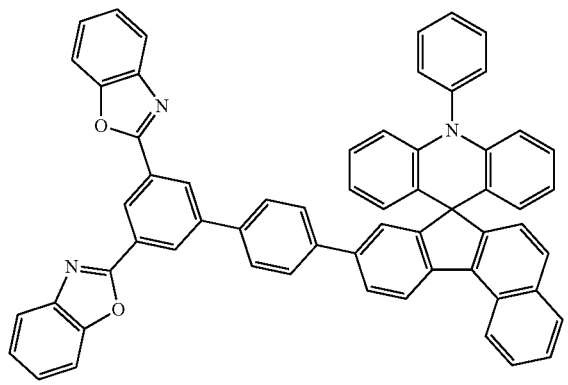
216
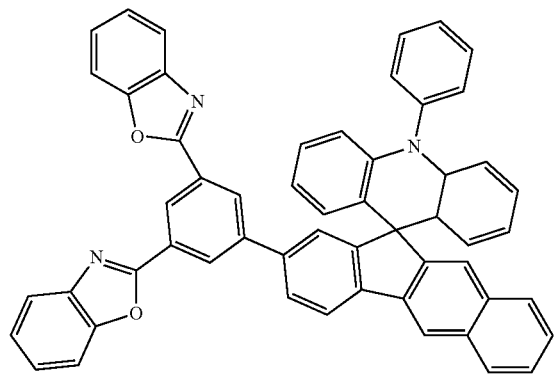
217
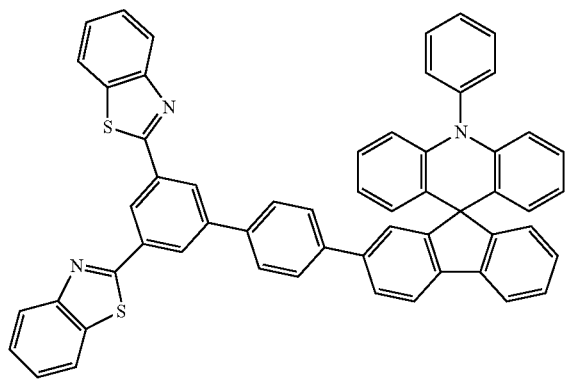
218
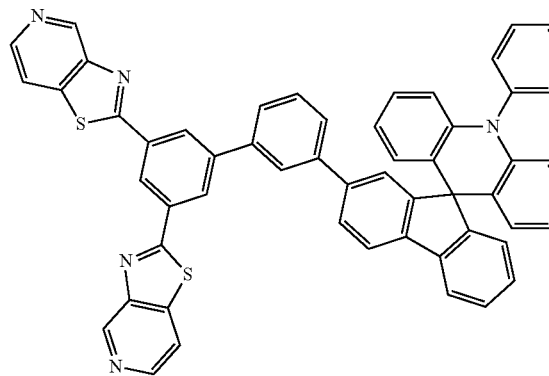
219
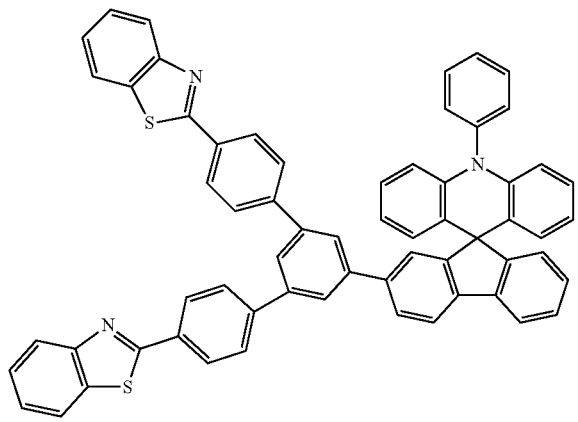
220
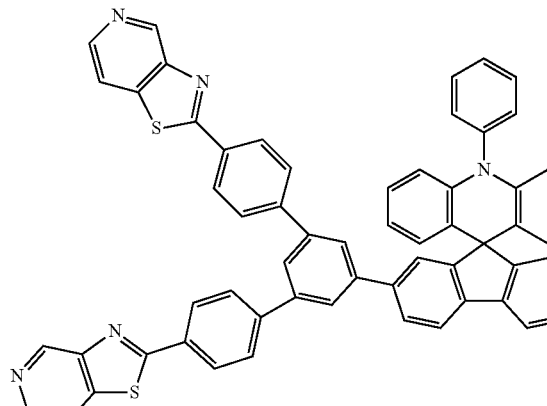
221
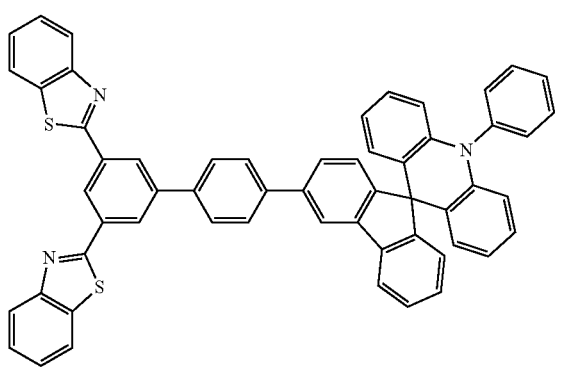
222
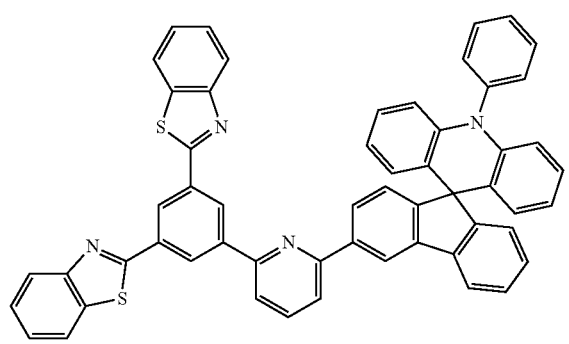

-continued
223
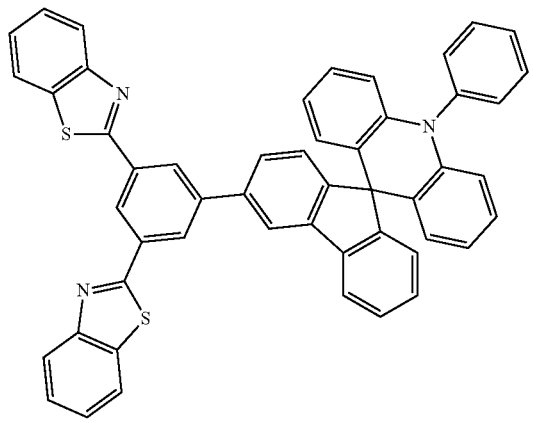
224
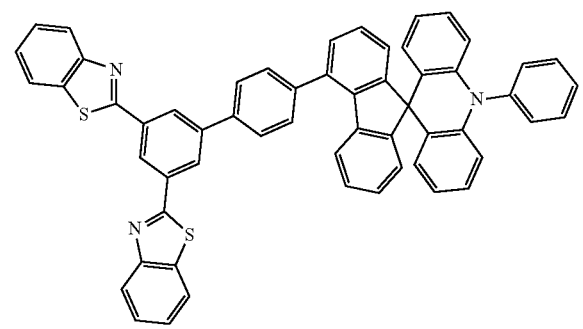
225
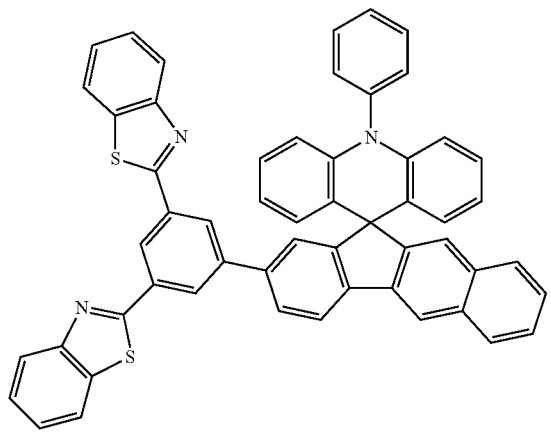
226
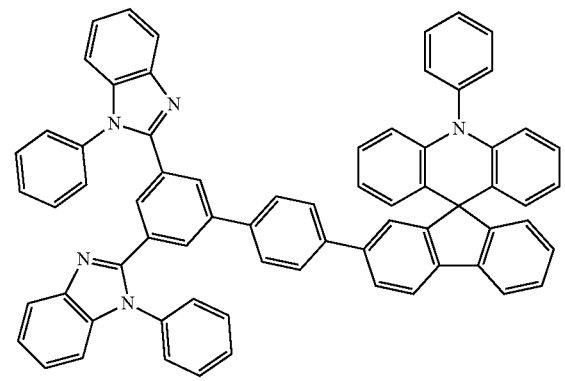
227
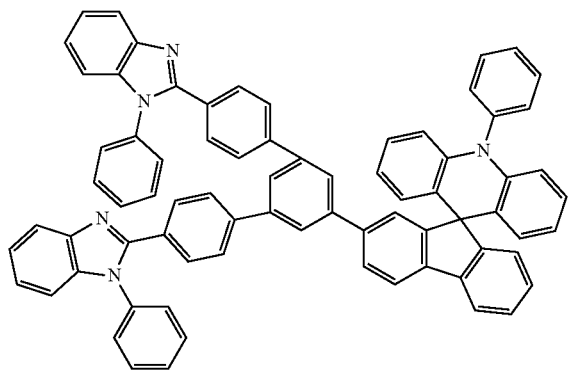
228
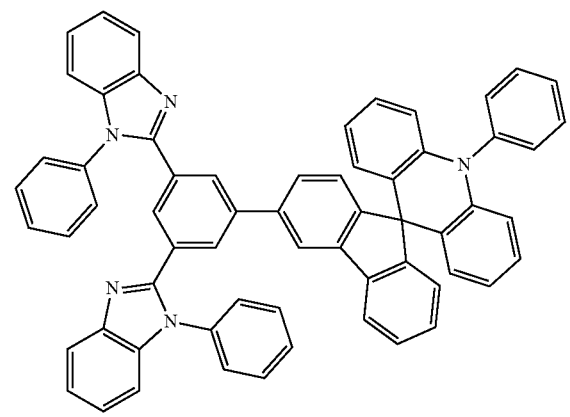

-continued
229
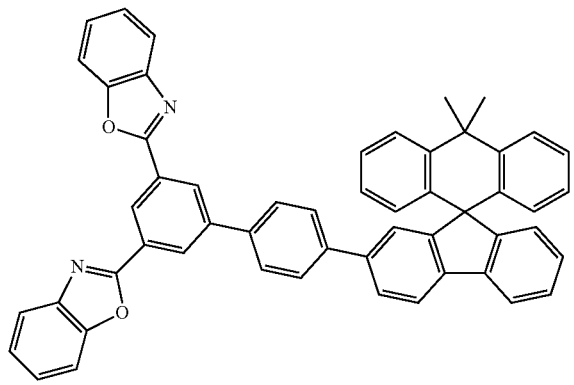
230
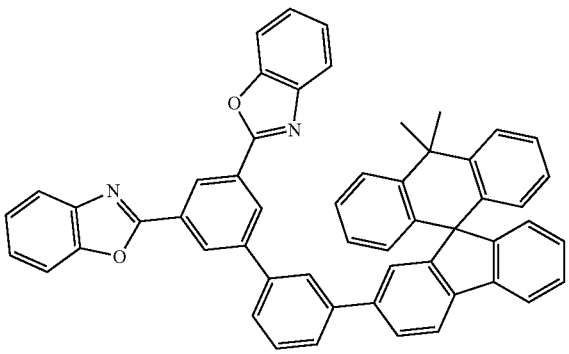
231
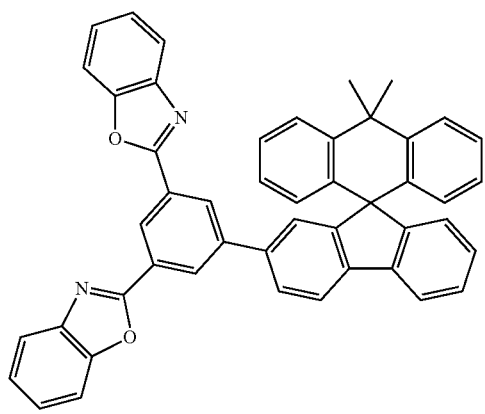
232
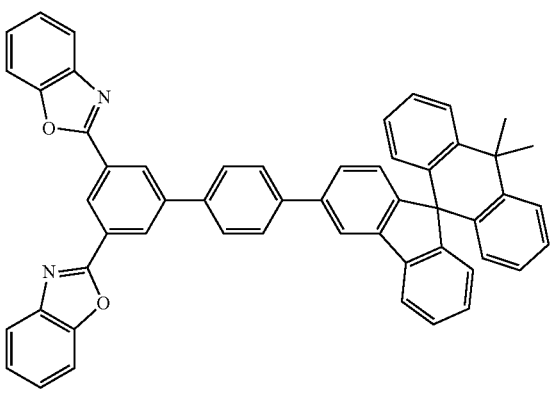
233
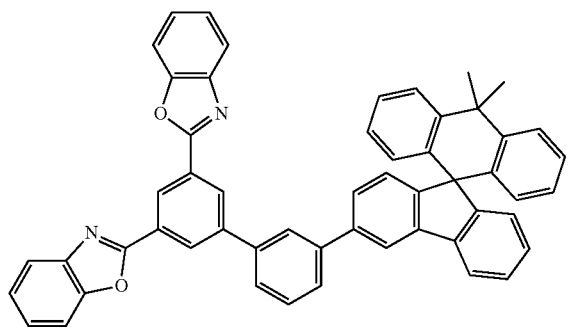
234
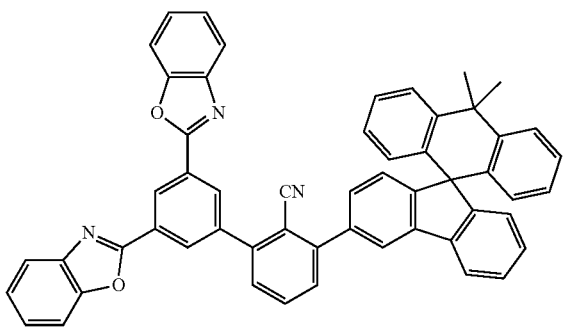
235
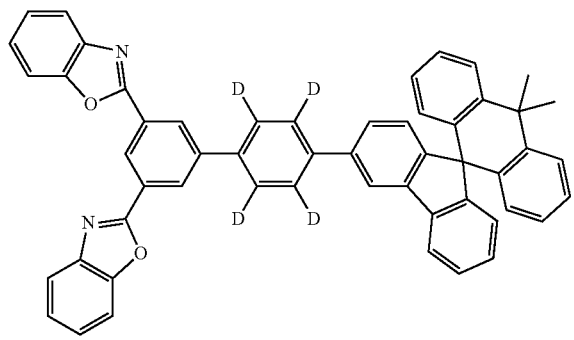
236
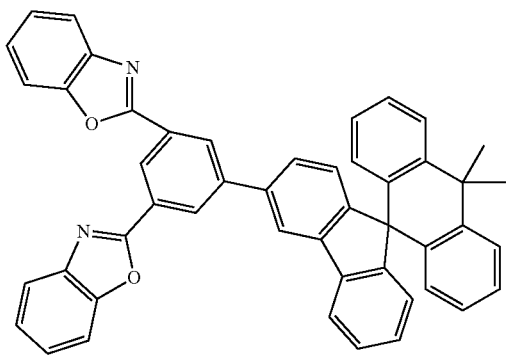

-continued
237
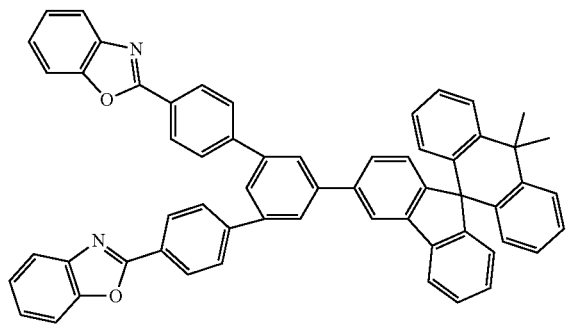
238
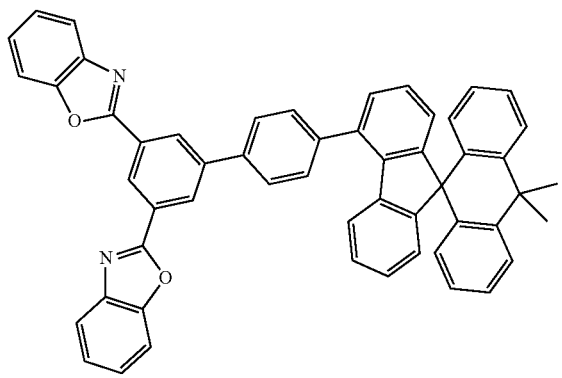
239
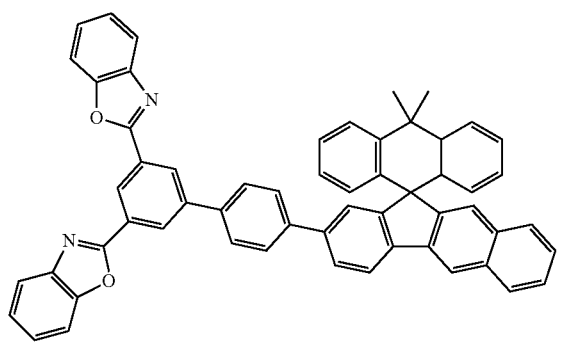
240
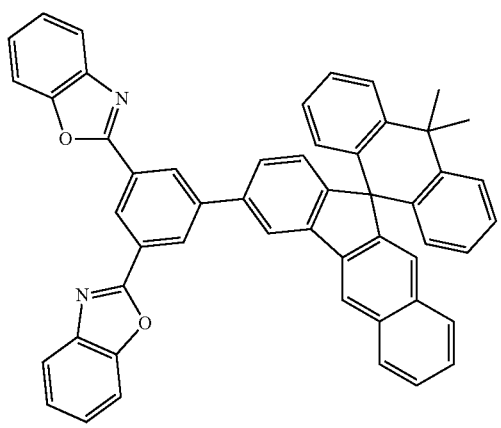
241
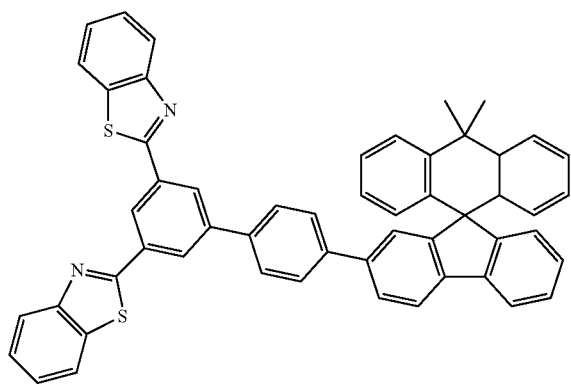
242
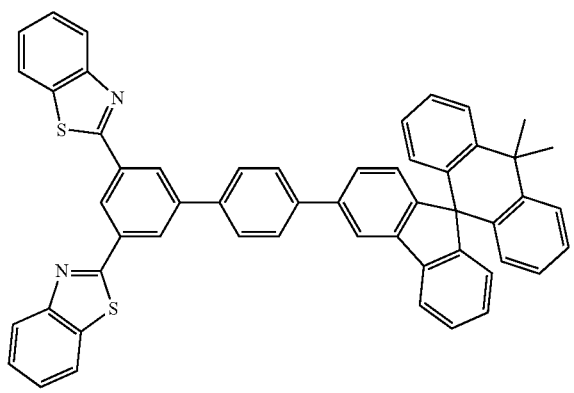

-continued
243
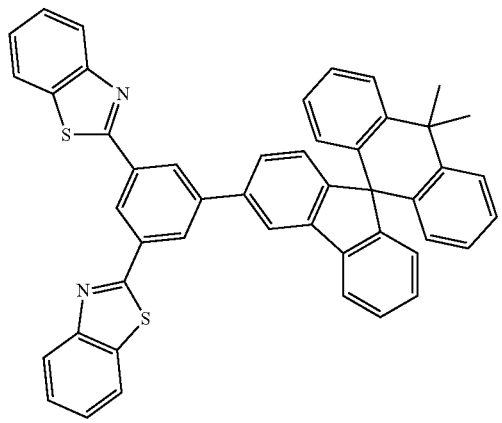
244
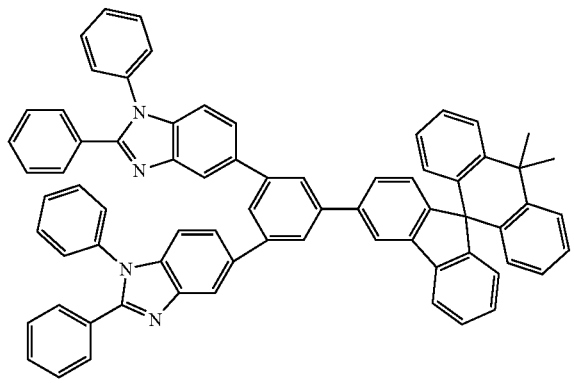
245
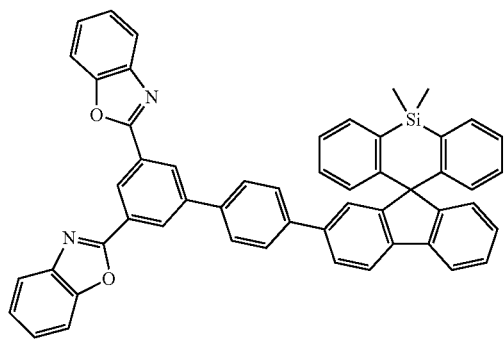
246
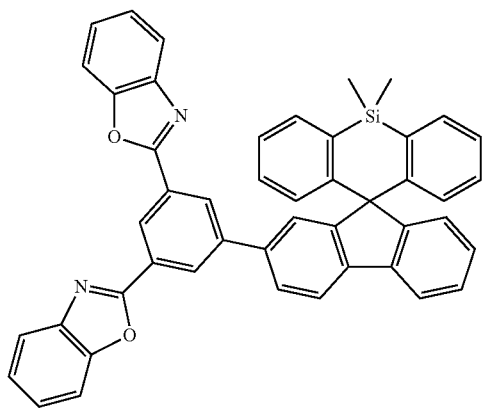
247
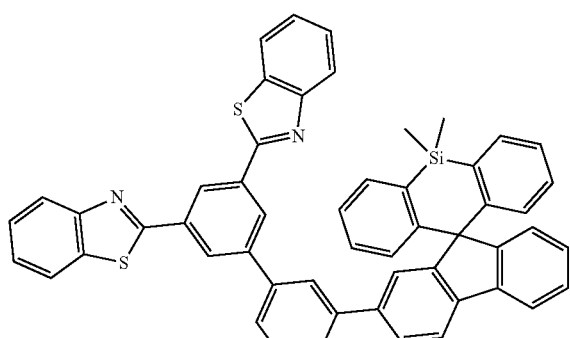
248
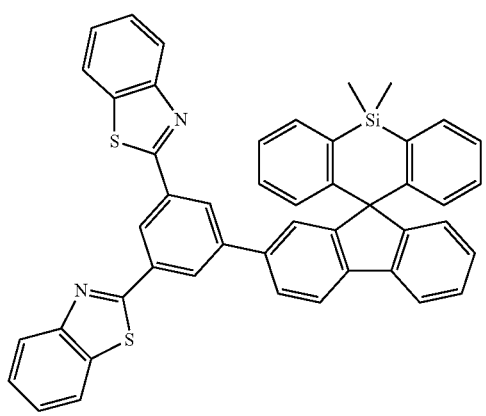

-continued
249
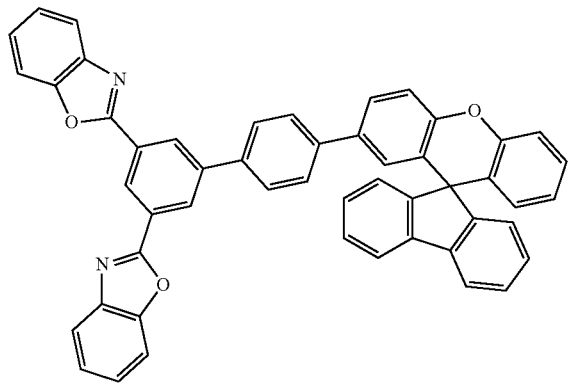
250
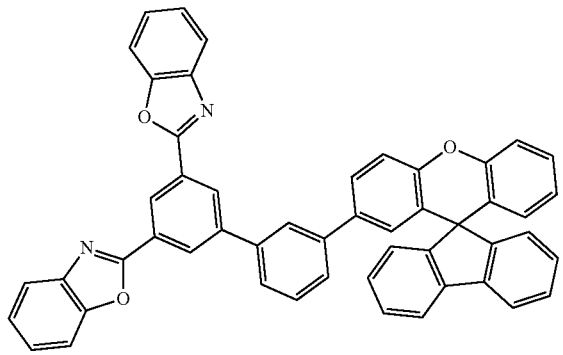
251
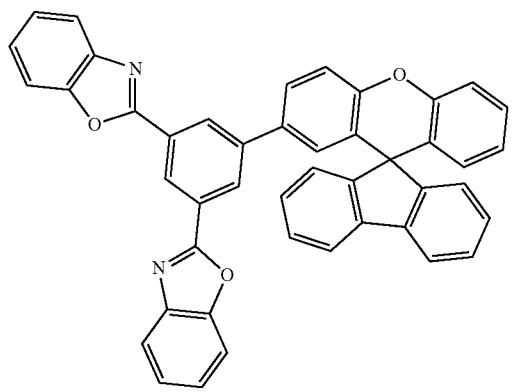
252
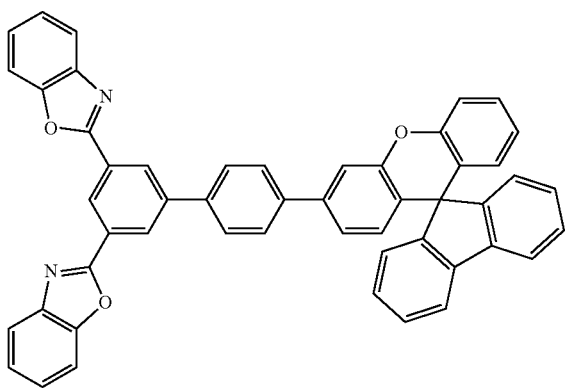
253
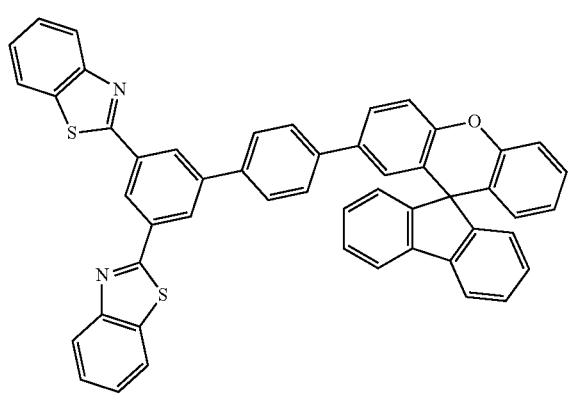
254
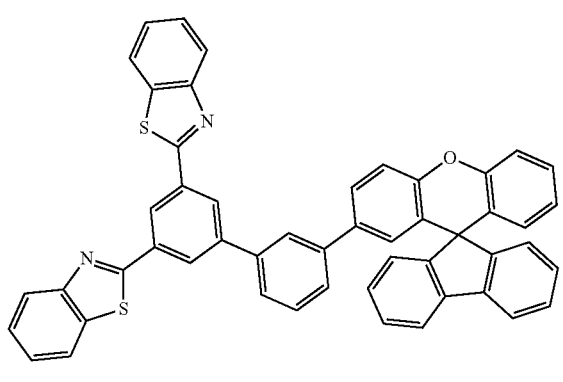
255
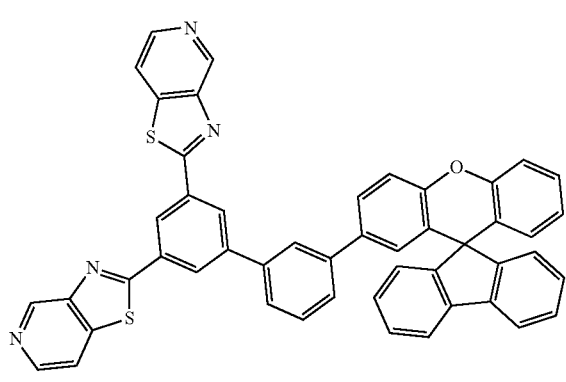
256
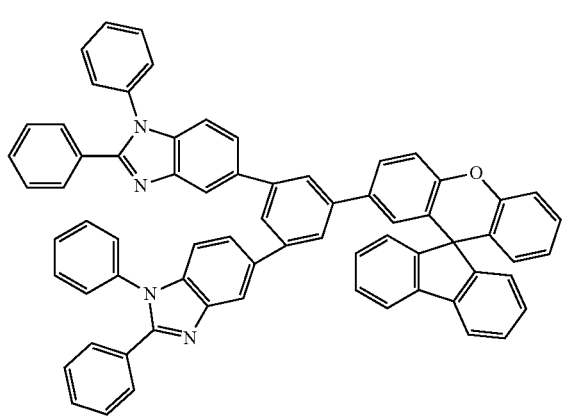

257

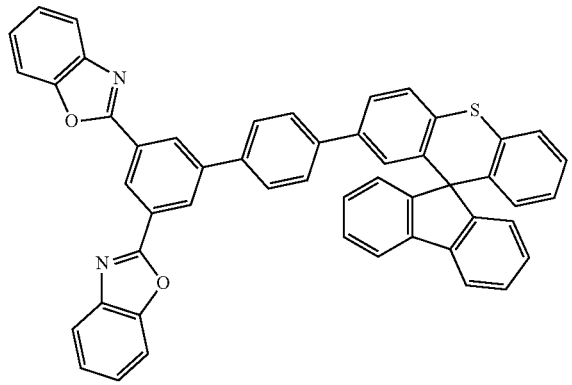

258

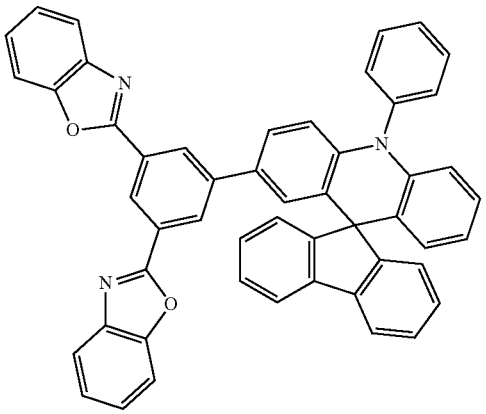

259

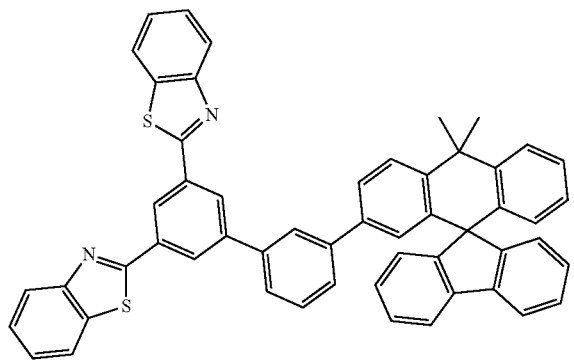

260

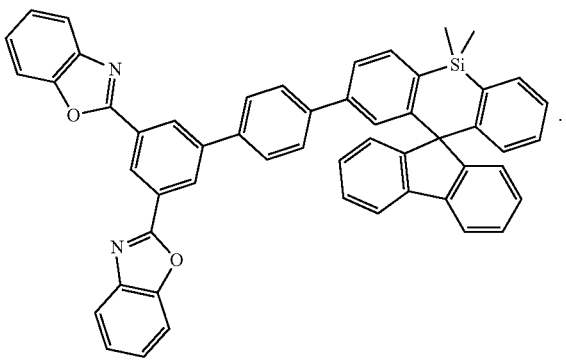

Some specific chemical structures of the heterocyclic derivative as shown in Formula I of the present disclosure are listed above, but the present disclosure is not limited to these chemical structures. Any group based on the structure shown in Formula I and having a substituent as defined above shall be included.

Further, the present disclosure further provides an organic electroluminescent device including an anode, an organic layer, and a cathode, wherein the organic layer is disposed between the anode and the cathode, and the organic layer includes an electron transport region containing the heterocyclic derivative of the above-mentioned present disclosure.

The electron transport region of the present disclosure is composed of one or more of a hole blocking layer, an electron transport layer, an electron injection layer or a functional layer having an electron injection/transport property. Preferably, the hole blocking layer and/or the electron transport layer contain the heterocyclic derivative of the present disclosure, and most preferably, the hole blocking layer contains the heterocyclic derivative of the present disclosure.

Preferably, the organic layer further includes a hole transport region containing a triarylamine compound as shown in Formula II, and the hole transport region of the present disclosure is composed of one or more of an electron blocking layer, an emissive auxiliary layer, a hole transport layer, a hole injection layer or a functional layer having a hole injection/transport property. Preferably, the electron blocking layer, the emissive auxiliary layer and/or the hole transport layer contain the triarylamine compound as shown in Formula II of the present disclosure, and most preferably, the emissive auxiliary layer and/or the hole transport layer contain the triarylamine compound as shown in Formula II of the present disclosure:

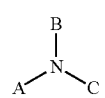

Formula II wherein A and B are independently selected from one of the following substituents:

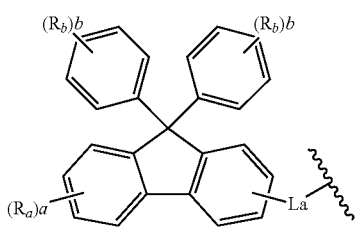

-continued

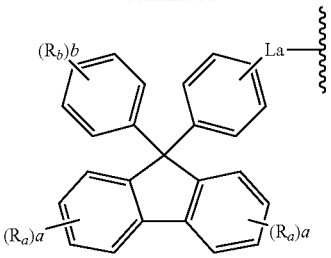

wherein $R_a$ is identically or differently selected from one of hydrogen, deuterium, substituted or unsubstituted C1 to C15 alkyl, substituted or unsubstituted C3 to C15 cycloalkyl, substituted or unsubstituted C2 to C30 alkenyl, substituted or unsubstituted C6 to C30 aryl or substituted or unsubstituted C3 to C30 heteroaryl, or two adjacent groups are joined to form a ring;

$R_b$ is identically or differently selected from one of hydrogen, deuterium, substituted or unsubstituted C1 to C15 alkyl, substituted or unsubstituted C3 to C15 cycloalkyl, substituted or unsubstituted C2 to C30 alkenyl, substituted or unsubstituted C6 to C30 aryl or substituted or unsubstituted C3 to C30 heteroaryl, or two adjacent groups are joined to form a ring;

$L_a$ is selected from one of a single bond, substituted or unsubstituted C6 to C30 arylene or substituted or unsubstituted C3 to C30 heteroarylene;

a is selected from 0, 1, 2, 3 or 4, and b is selected from 0, 1, 2, 3, 4 or 5; and C is selected from one of the following groups:

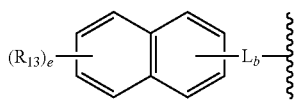

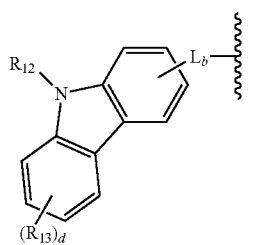
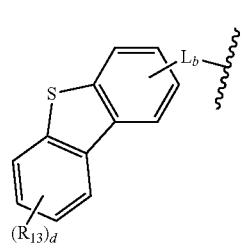

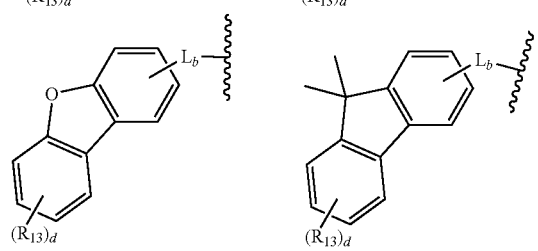

-continued

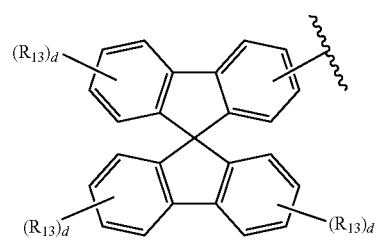

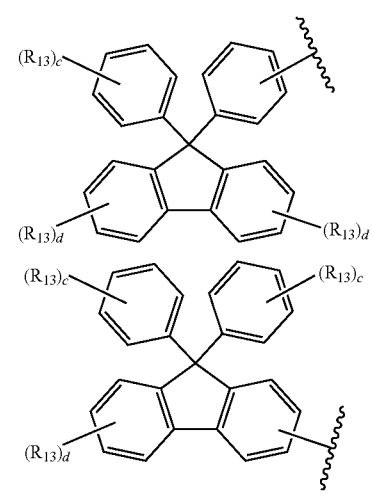

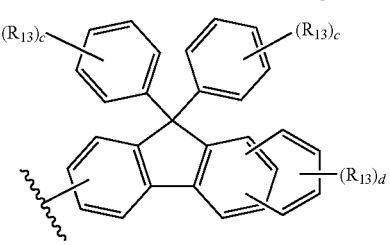

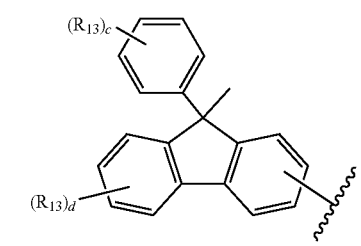

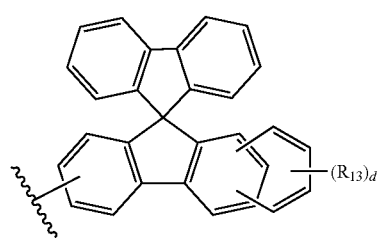

-continued

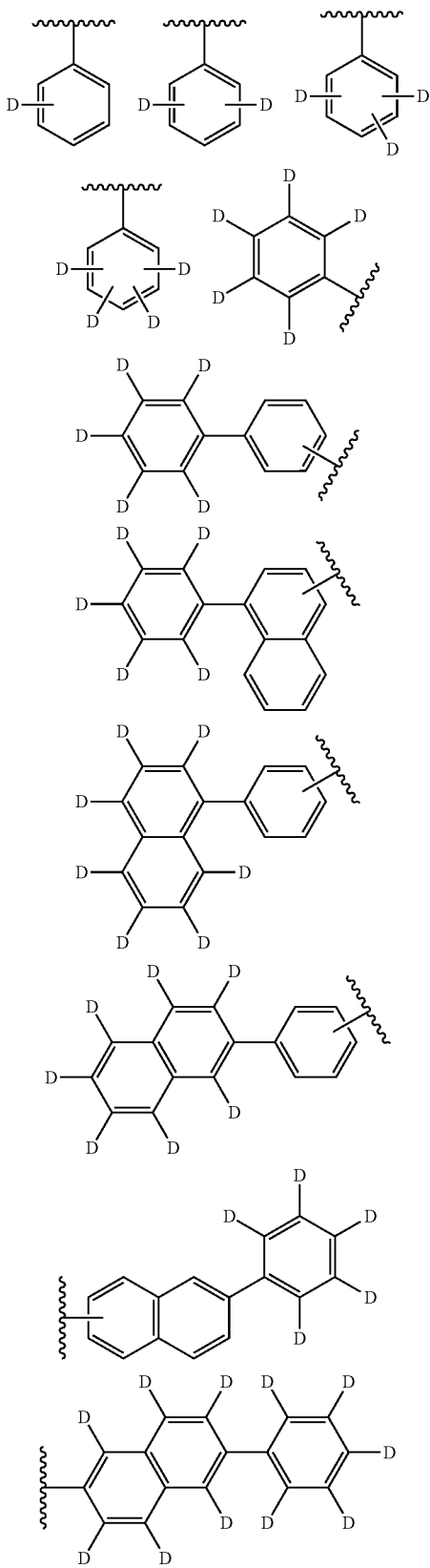

Preferably, C is selected from one of the following groups:

wherein $R_{12}$ is selected from one of methyl, ethyl, propyl, butyl, phenyl, tolyl, biphenyl or naphthyl;

$R_{13}$ is selected from one of deuterium, methyl, ethyl, propyl, butyl, cyclohexyl, adamantyl, phenyl, tolyl, biphenyl, terphenyl, naphthyl, anthryl, phenanthryl, triphenylenyl, acridyl, spirodifluorenyl, 9,9-dimethylfluorenyl, 9,9-diphenylfluorenyl, 9-phenylcarbazolyl, pyrenyl, indolyl, benzothiophenyl, benzofuranyl, dibenzothiophenyl or dibenzofuranyl;

$L_b$ is selected from one of a single bond, phenylene, deuterated phenylene, deuterated naphthylene, tolylene, biphenylene, naphthylene, terphenylene, dibenzofuranylene, fluorenylene or dibenzothienylene; and c is selected from 0, 1, 2, 3, 4 or 5; d is selected from 0, 1, 2, 3 or 4; e is selected from 0, 1, 2, 3, 4, 5, 6 or 7; f is selected from 0, 1, 2, 3, 4, 5, 6, 7, 8 or 9.

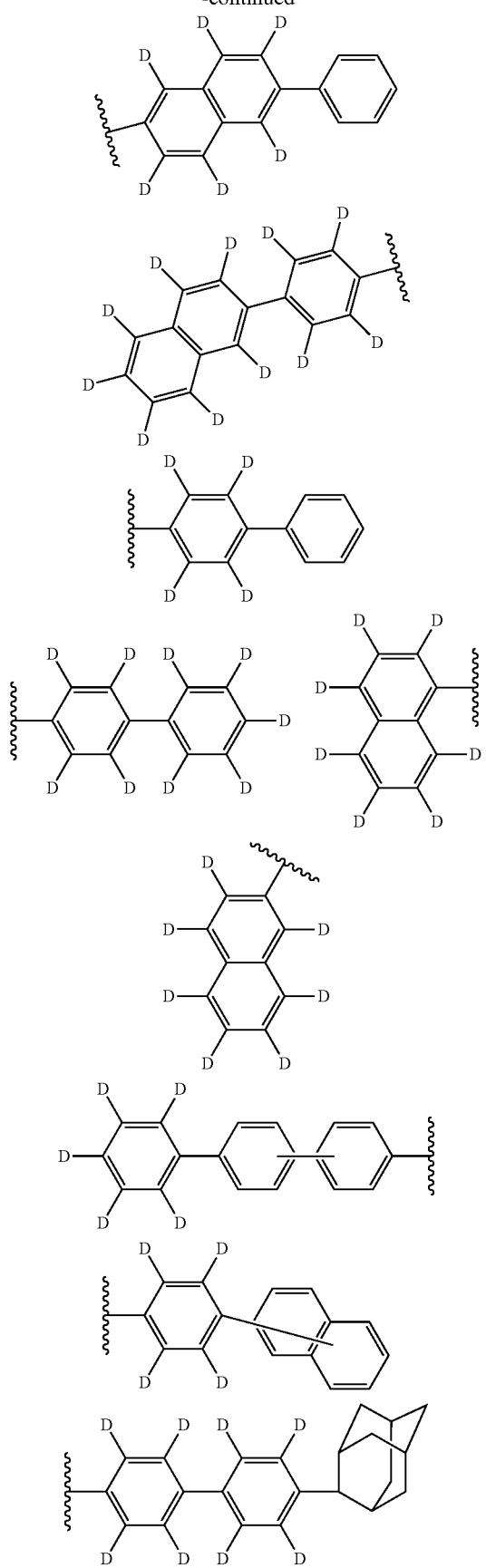
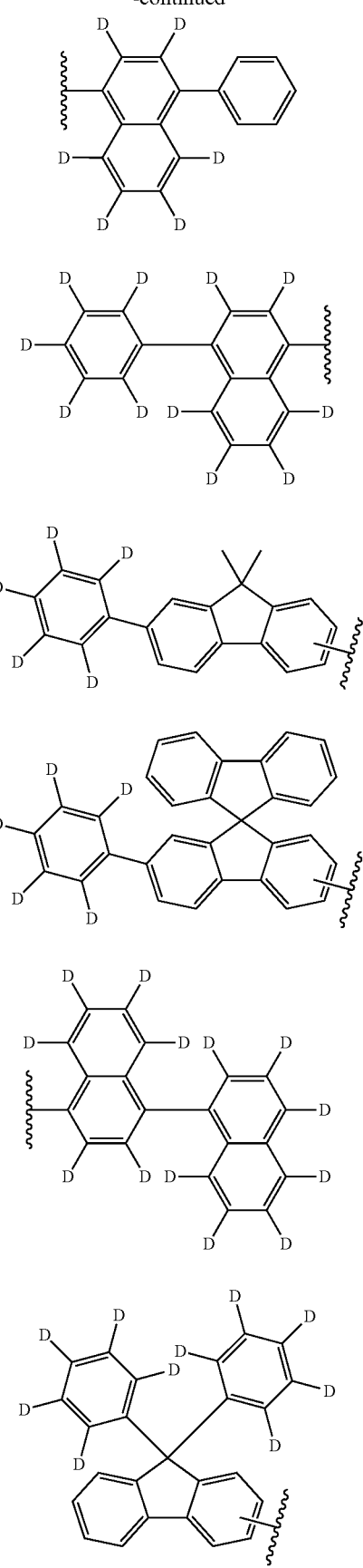

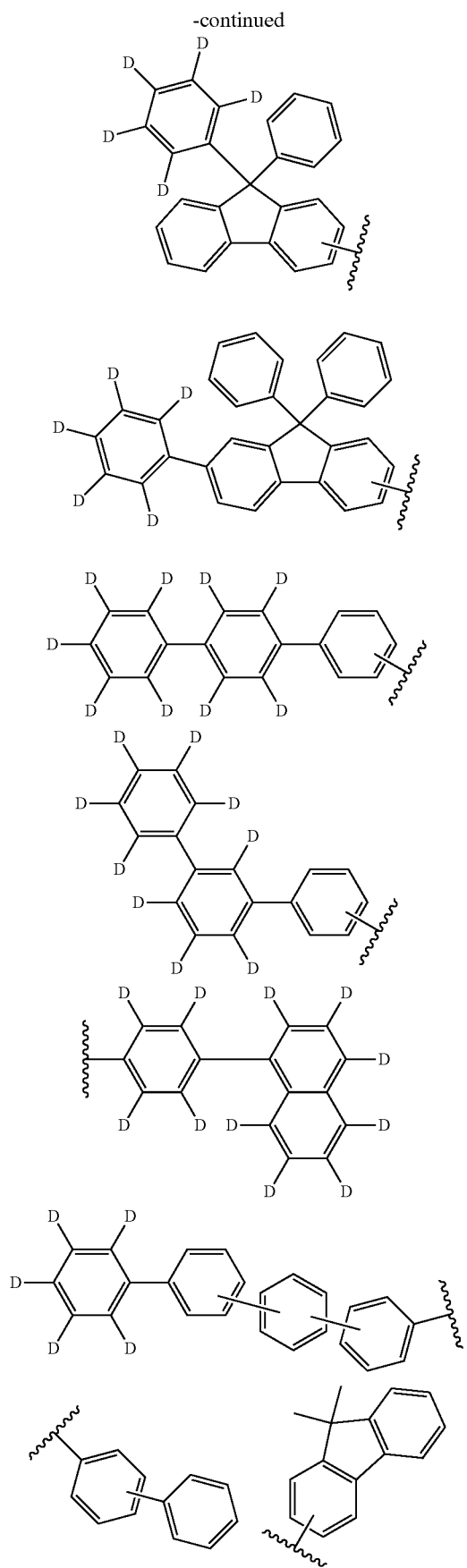
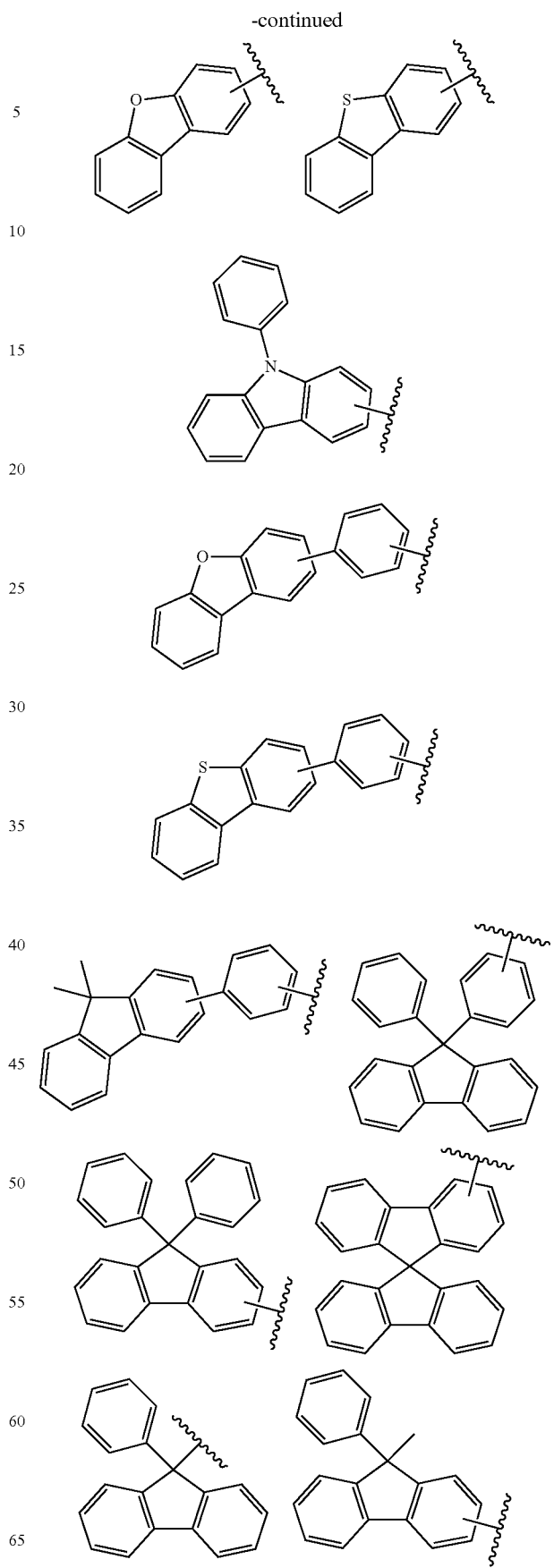

-continued
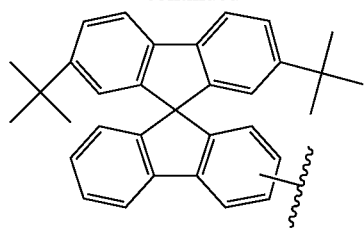
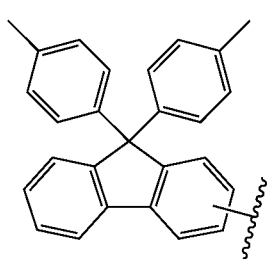
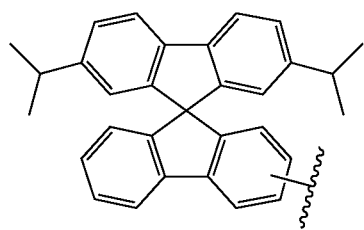
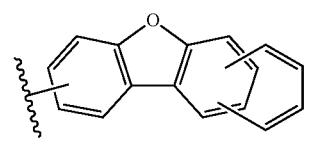
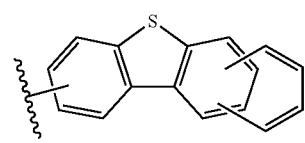
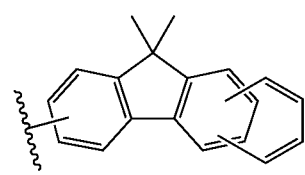
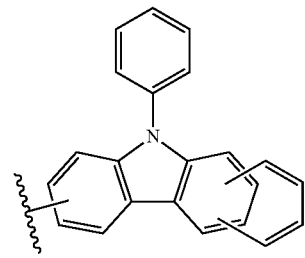
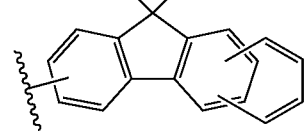
-continued
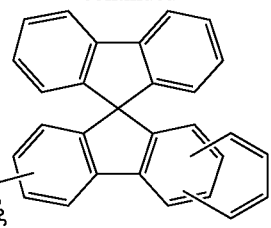
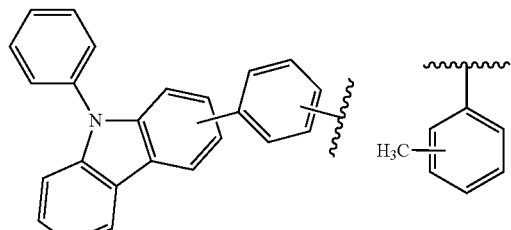
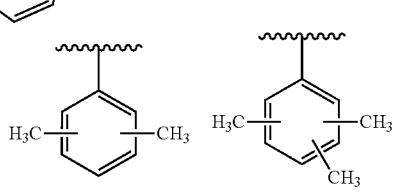
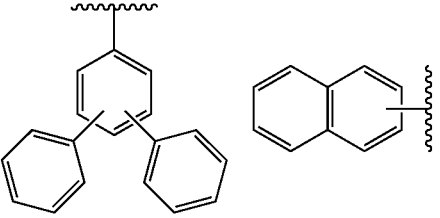
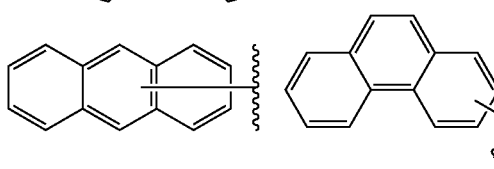
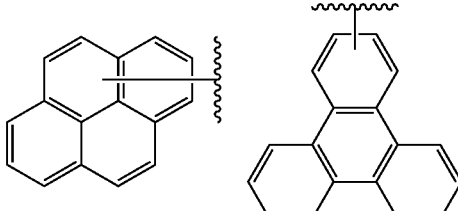
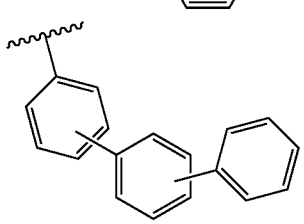
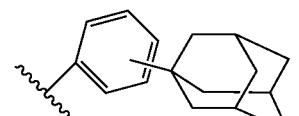
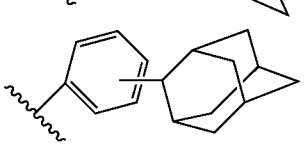

109
-continued
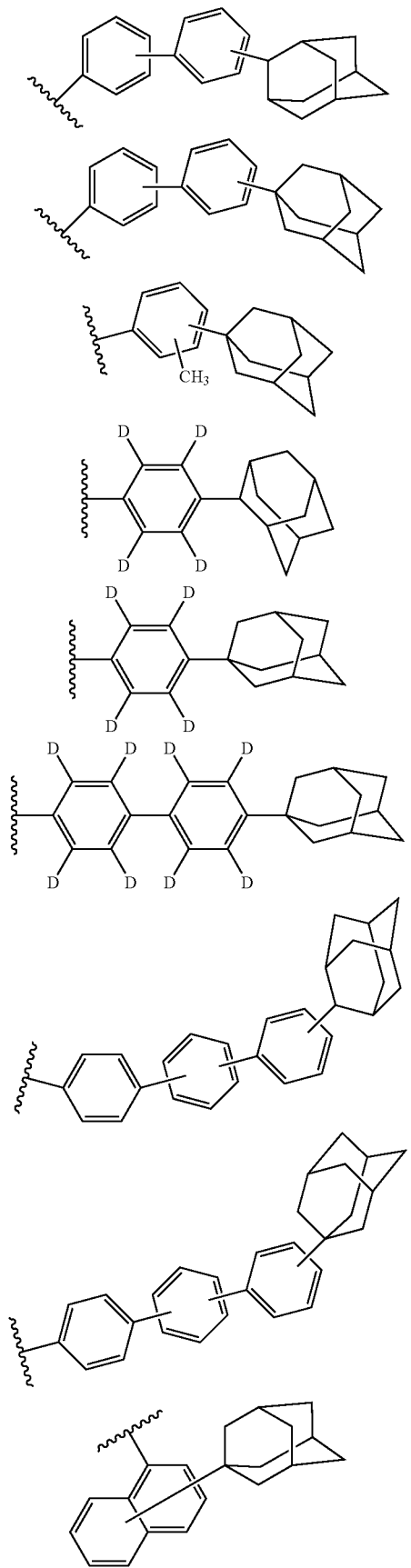
110
-continued
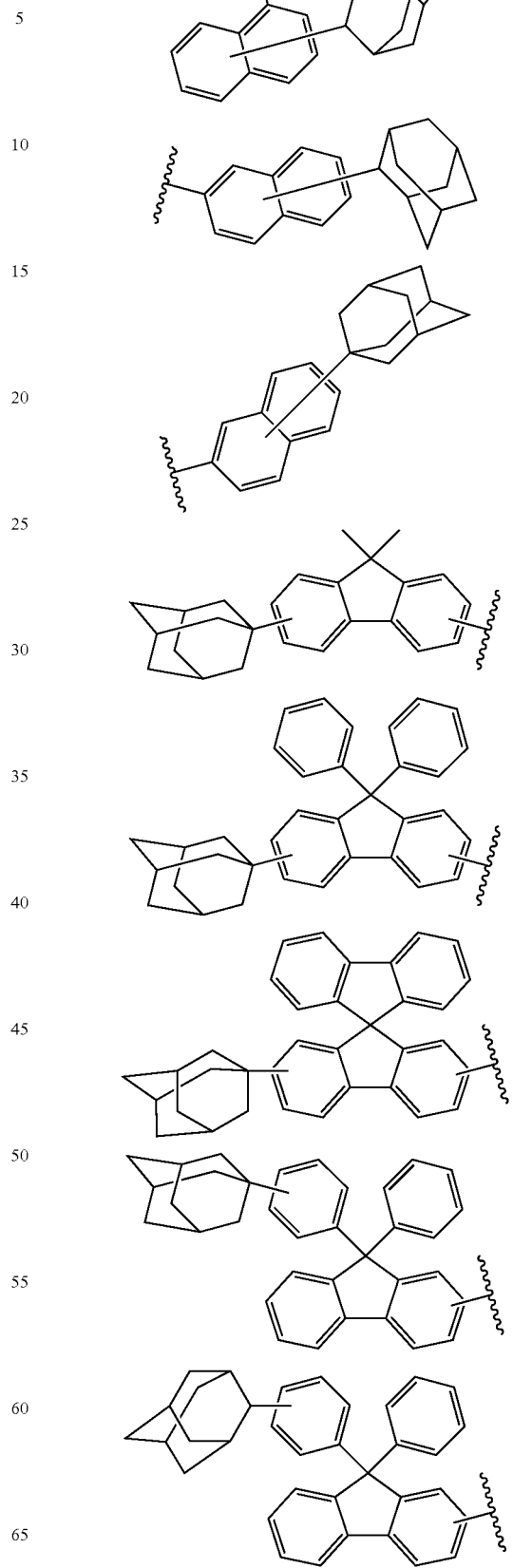

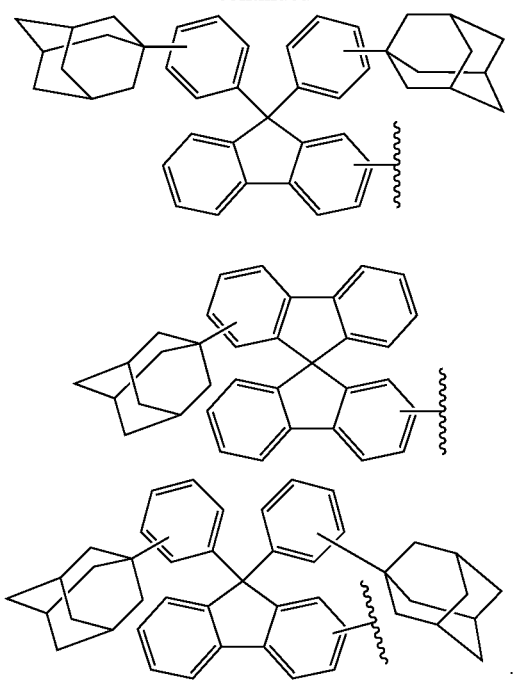

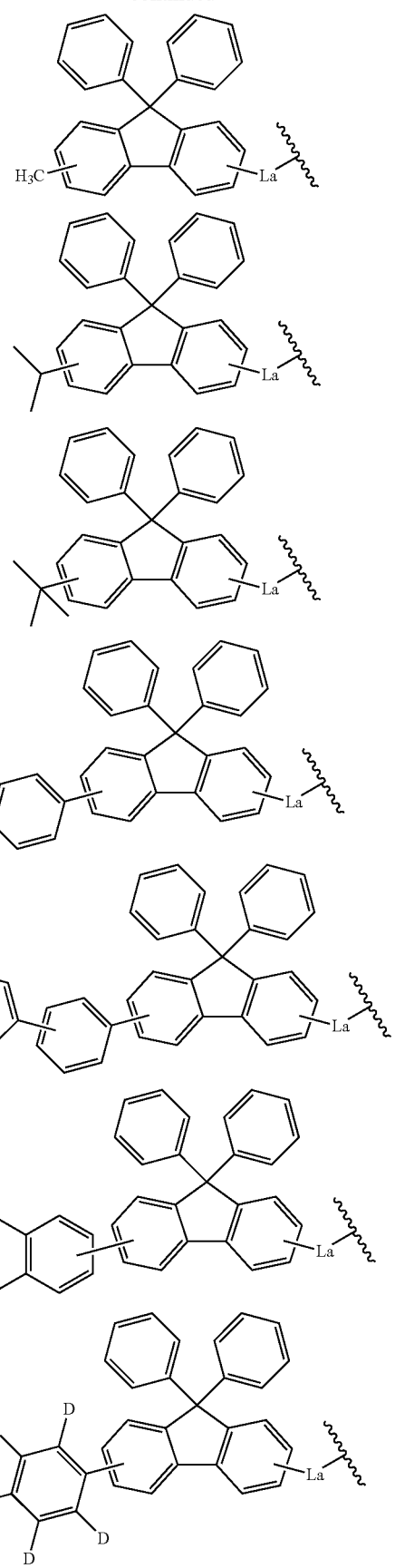

Preferably, $R_a$ is independently selected from one of hydrogen, deuterium, methyl, ethyl, propyl, butyl, adamantyl, camphanyl, norbornyl, phenyl, tolyl, biphenyl, triphenyl, naphthyl, anthryl, phenanthryl, triphenylenyl, acridinyl, spirodifluorenyl, 9,9-dimethylfluorenyl, 9,9-diphenylfluorenyl, 9-phenylcarbazolyl, pyrenyl, indolyl, benzothiophenyl, benzofuranyl, dibenzothiophenyl or dibenzofuranyl, or two adjacent groups are joined to form a ring;

$L_a$ is selected from one of a single bond, phenylene, tolylene, biphenylene, naphthylene, terphenylene, dibenzofuranylene, fluorenylene or dibenzothienylene; and $R_b$ is identically or differently selected from one of hydrogen, deuterium, methyl, ethyl, propyl, butyl, adamantyl, camphanyl, norbornyl, phenyl, tolyl, biphenyl or triphenyl, or two adjacent groups are joined to form a ring.

Preferably, in the triarylamine compound as shown in Formula II, at least one of the substituents A, B or C contains deuterium.

Preferably, in the triarylamine compound as shown in Formula II, at least one of the substituents A, B or C contains adamantyl.

Preferably, the groups A and B are independently selected from one of the following groups:

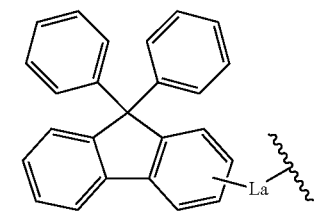

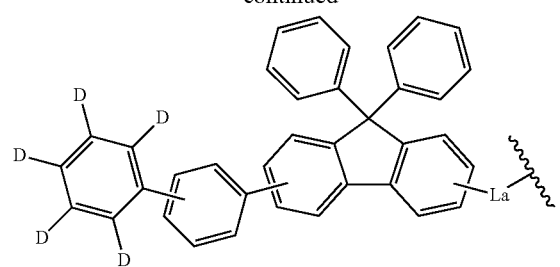
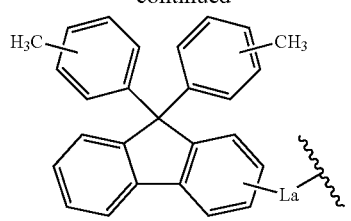
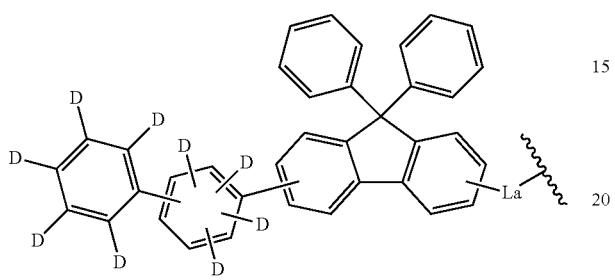
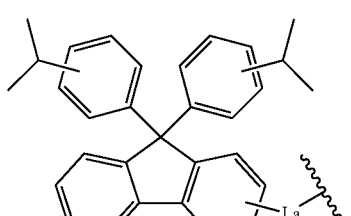
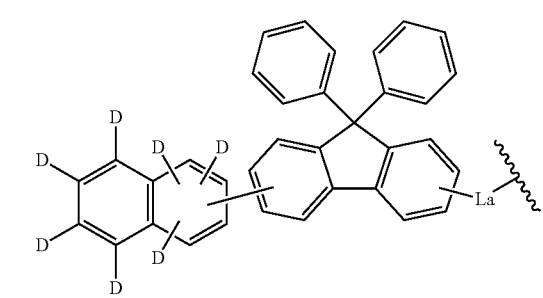
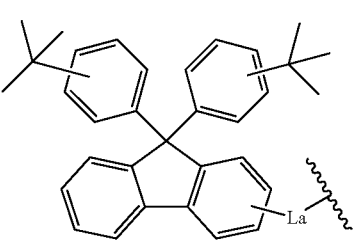
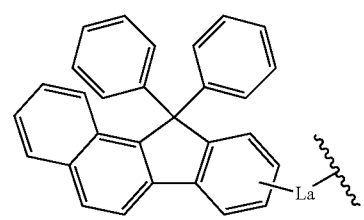
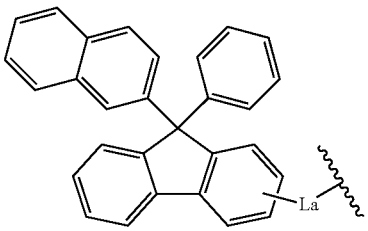
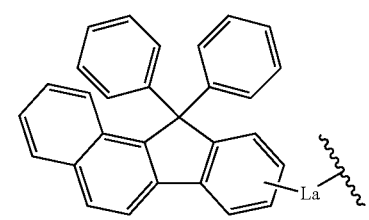
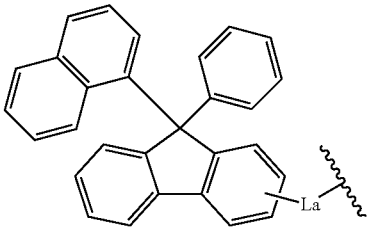
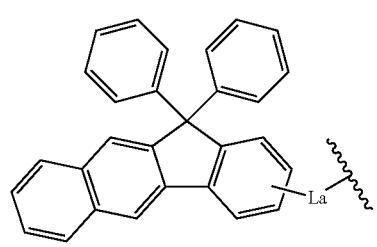
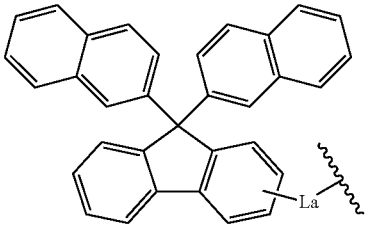
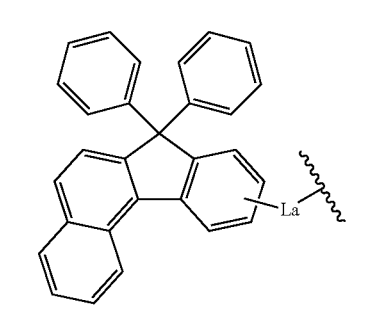
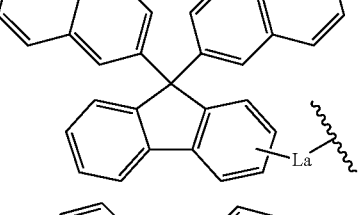
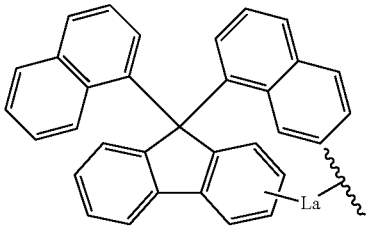

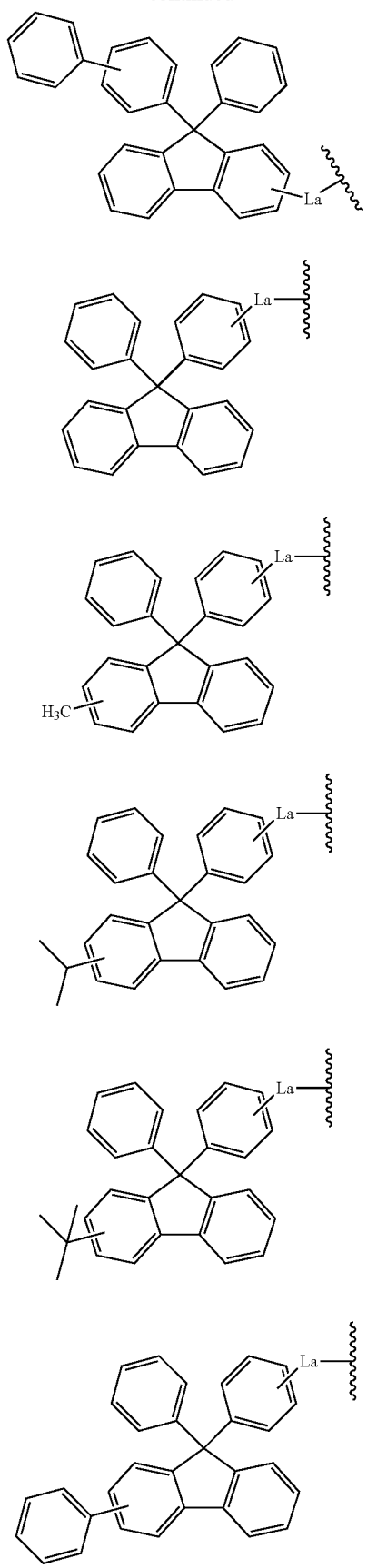
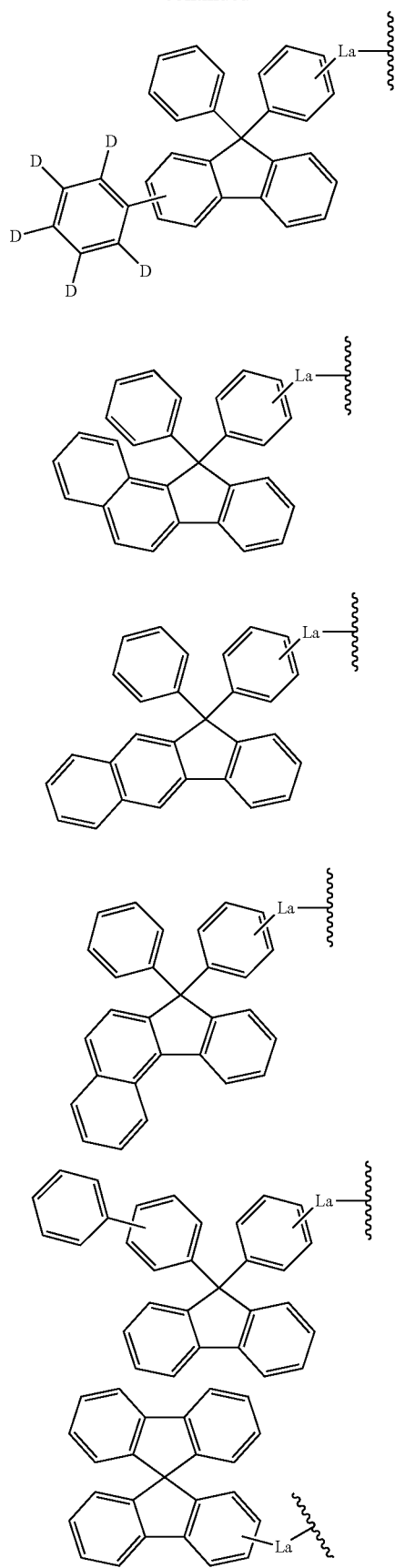

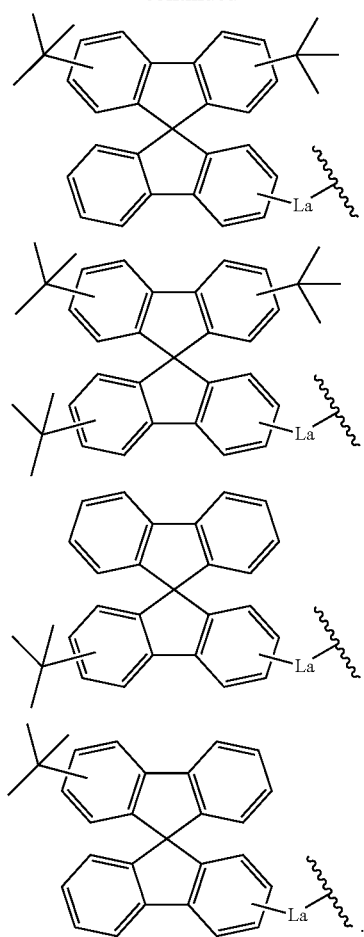
Preferably, the group C is independently selected from one of the following groups:
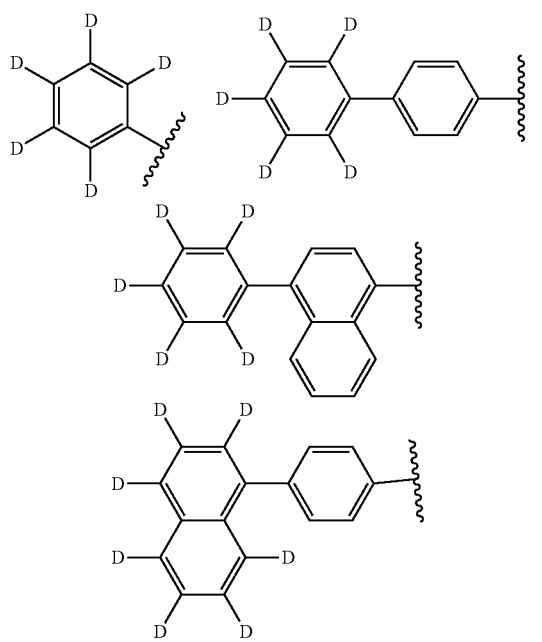
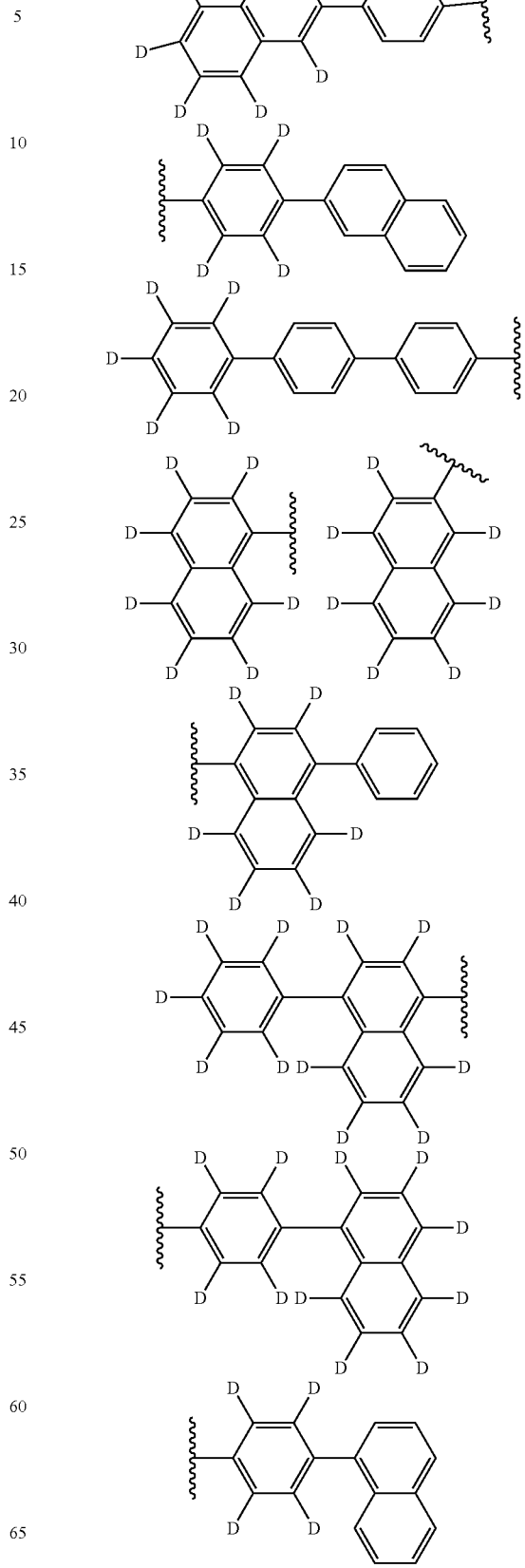

119
-continued
120
-continued
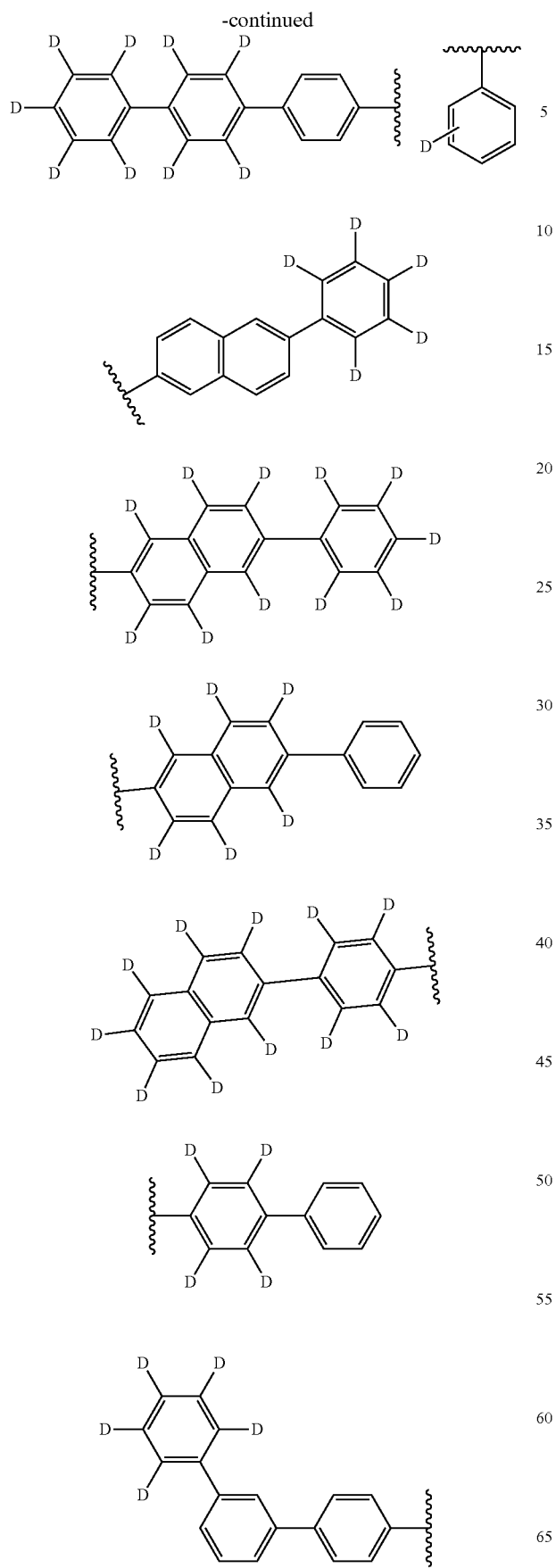
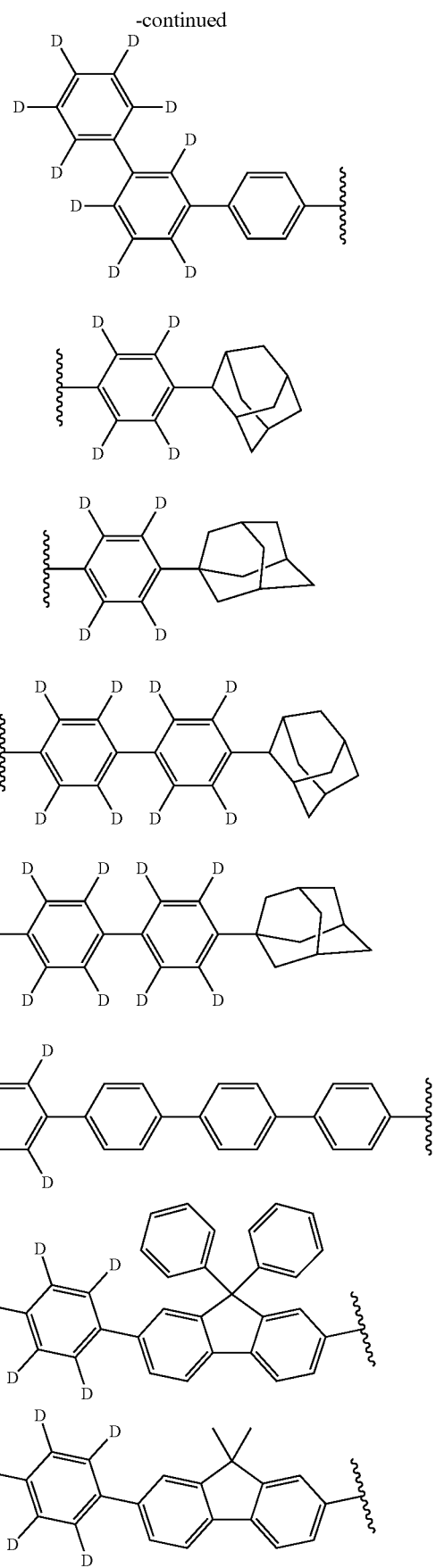

121
-continued
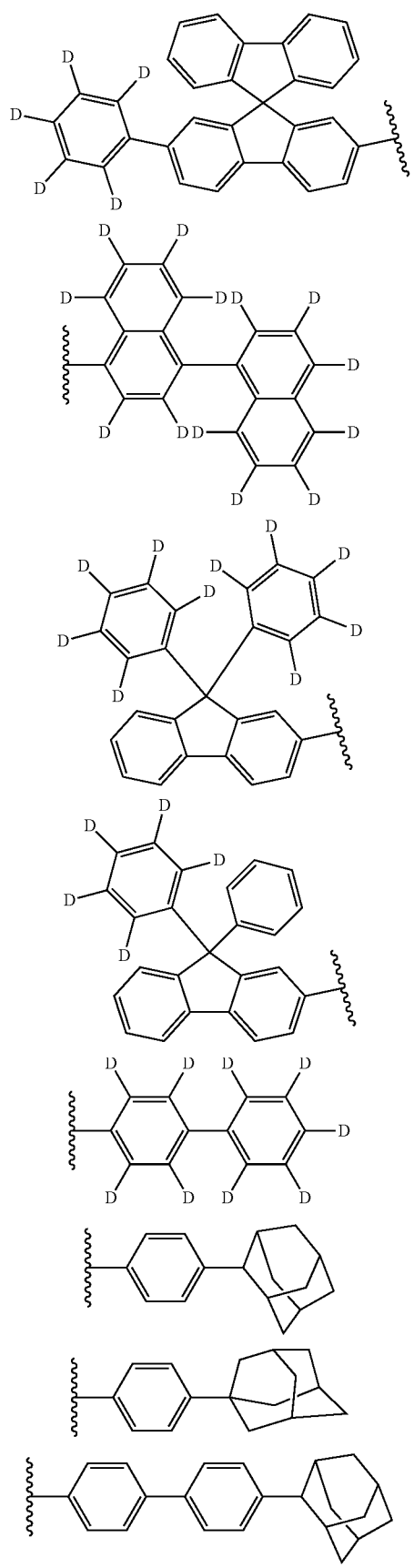
122
-continued
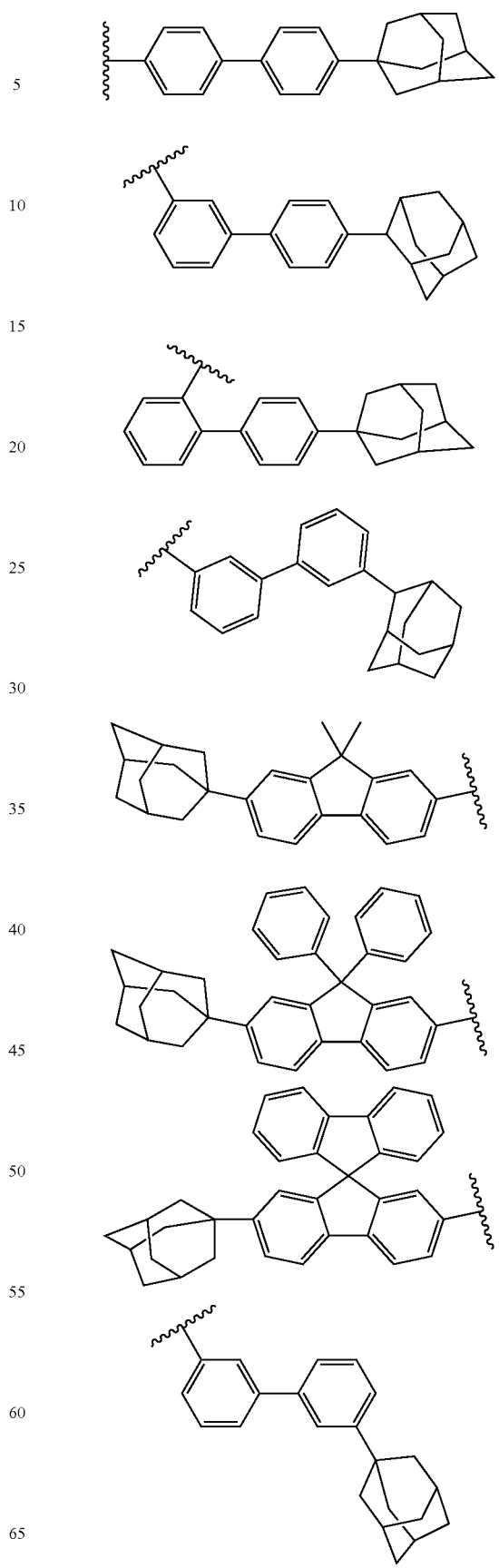

123
-continued
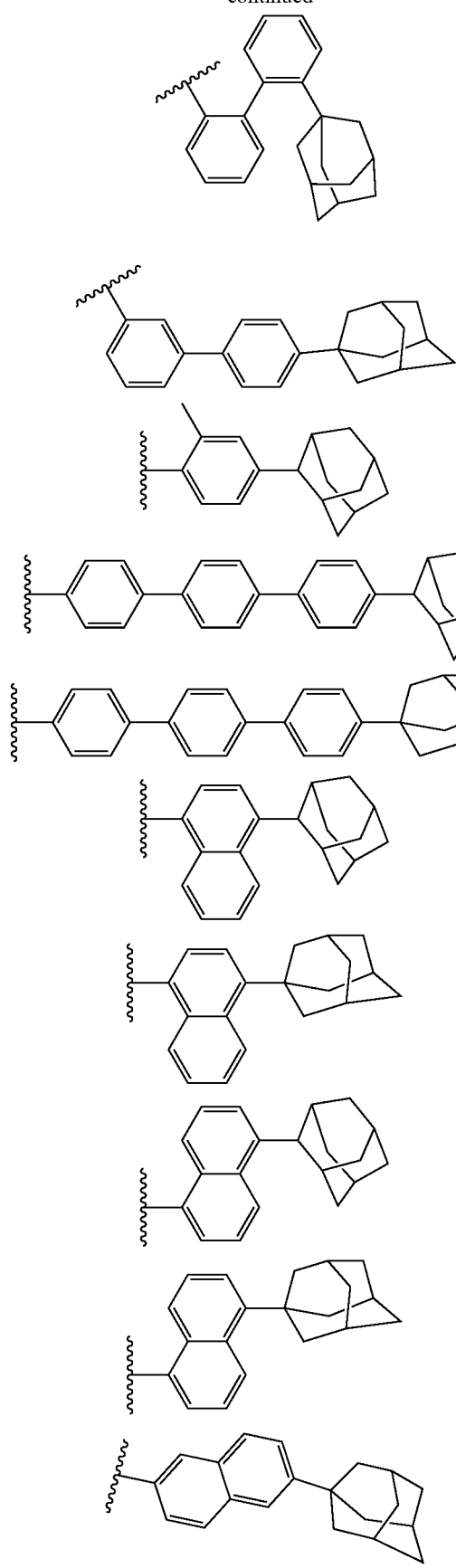
124
-continued
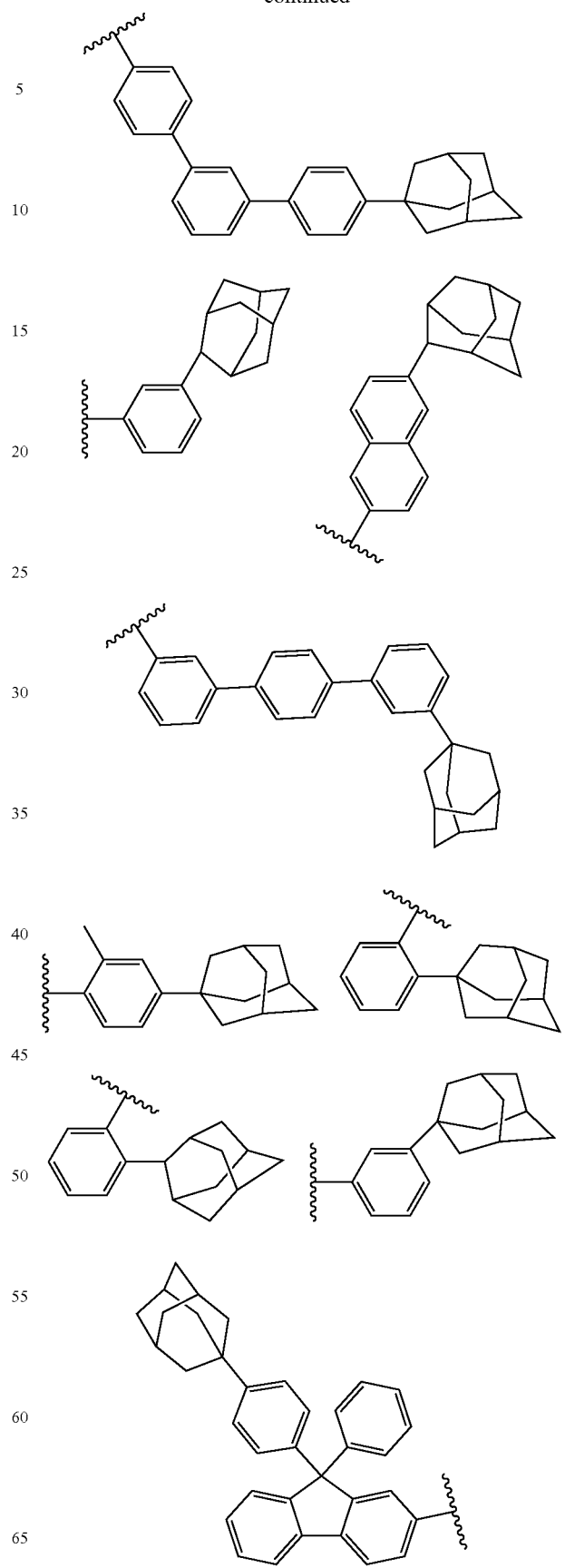

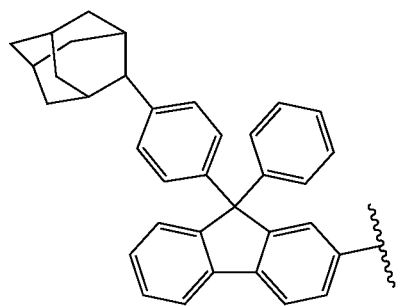
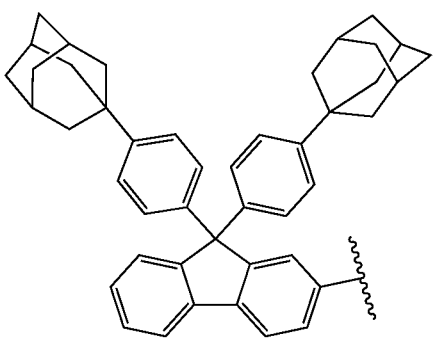
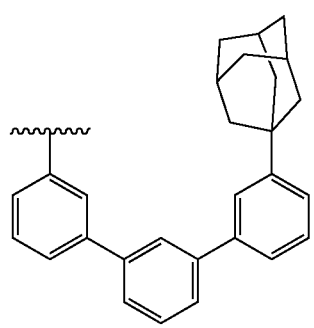
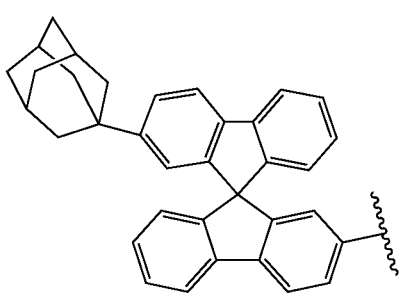
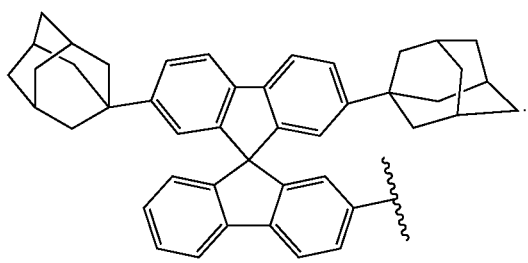
Preferably, the triarylamine compound as shown in Formula II is selected from one of the following structures:
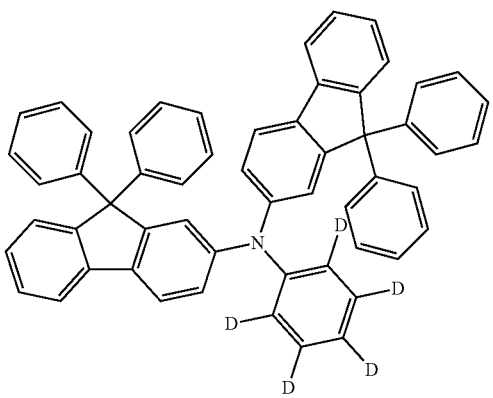
II-1
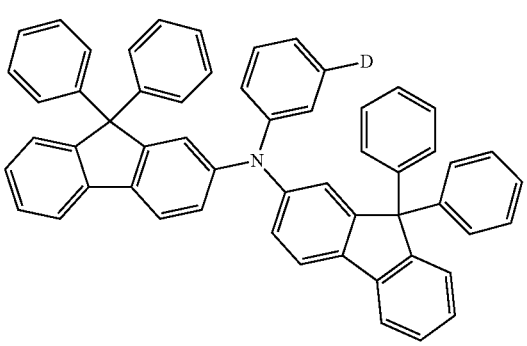
II-2
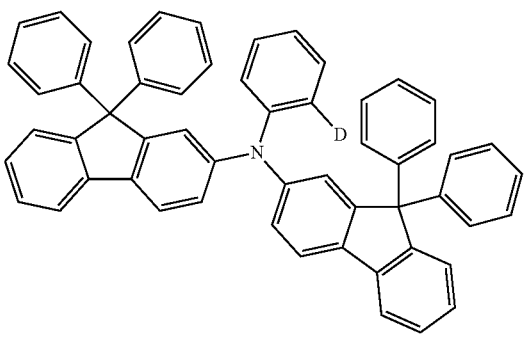
II-3
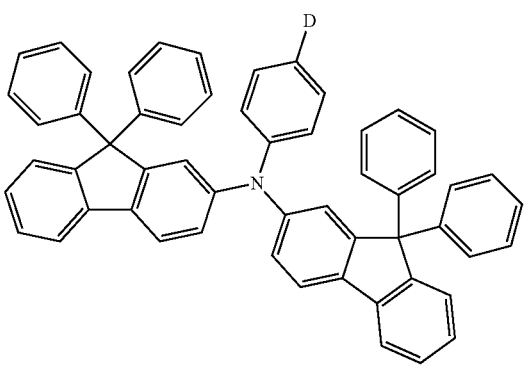
II-4

II-5
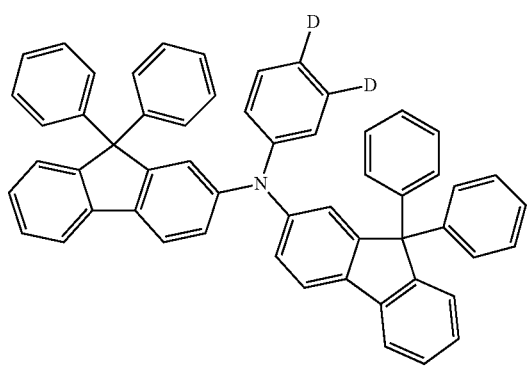
II-6
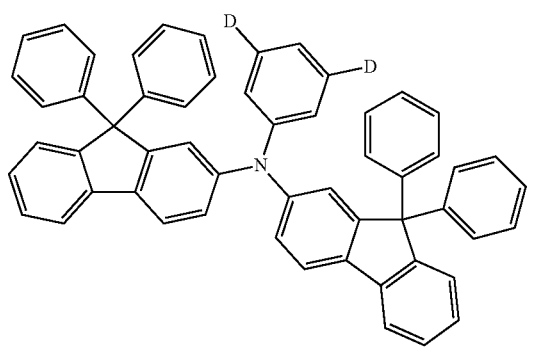
II-7
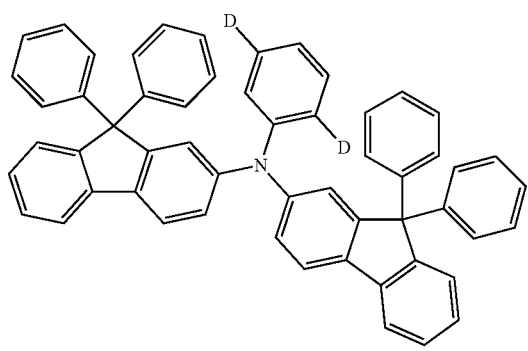
II-8
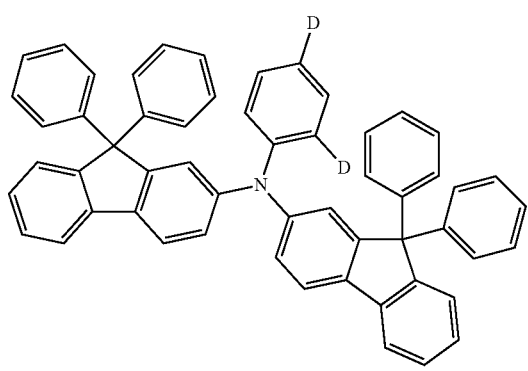
II-9
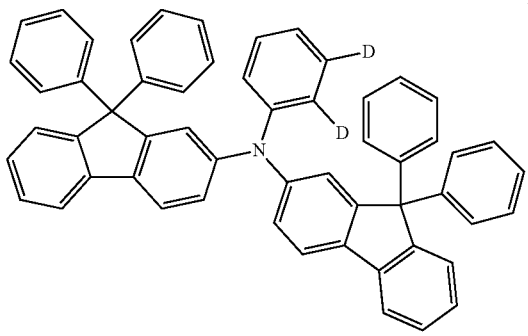
II-10
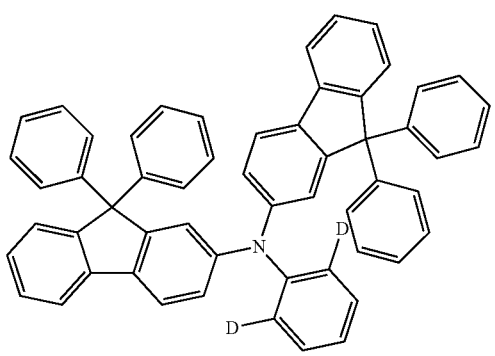
II-11
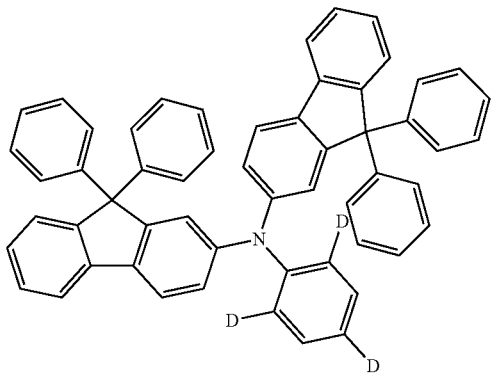
II-12
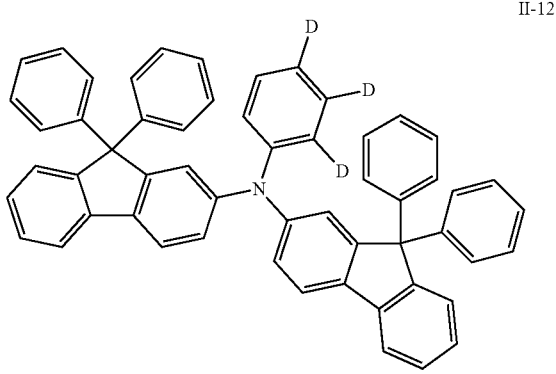

-continued
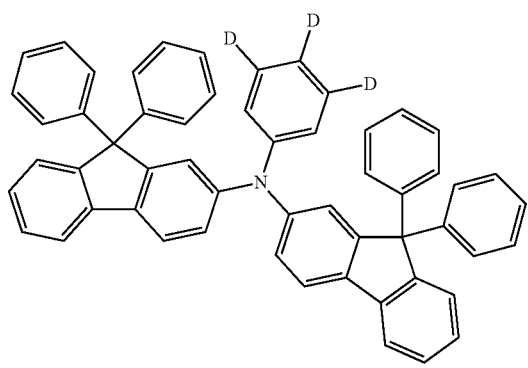
II-13
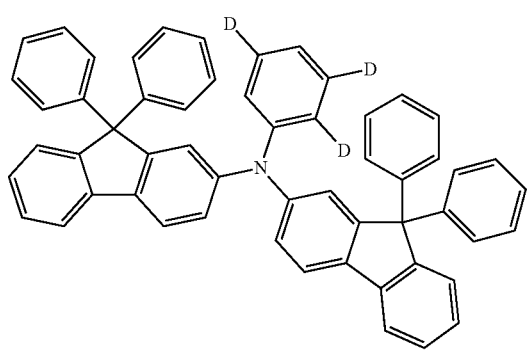
II-14
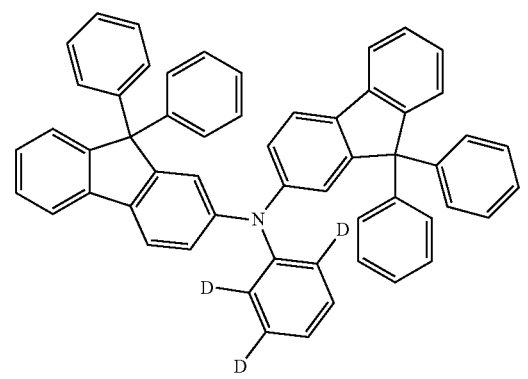
II-15
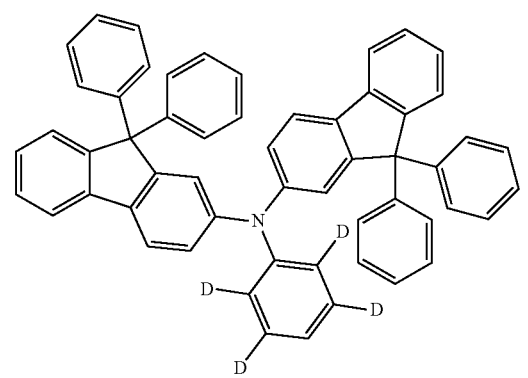
II-16
-continued
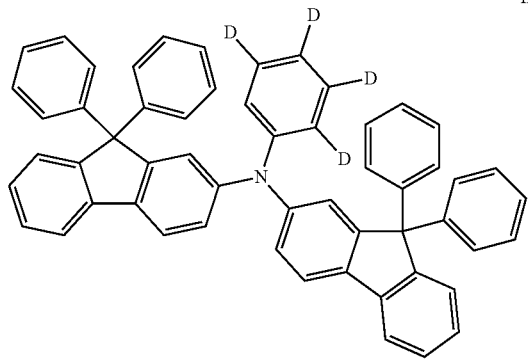
II-17
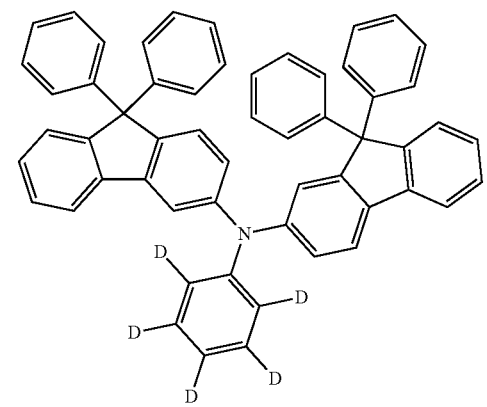
II-18
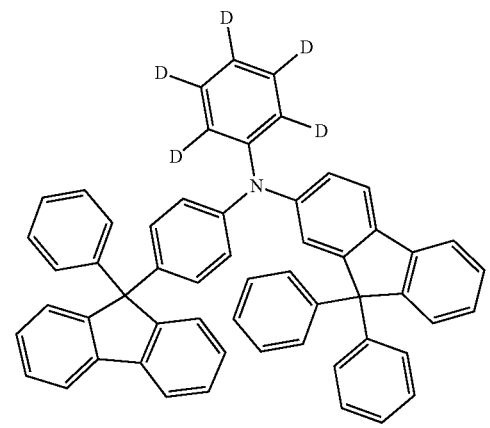
II-19
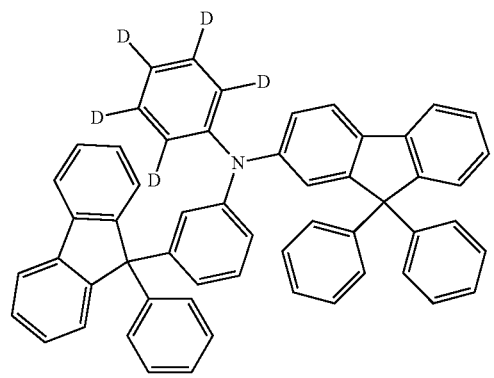
II-20

II-21
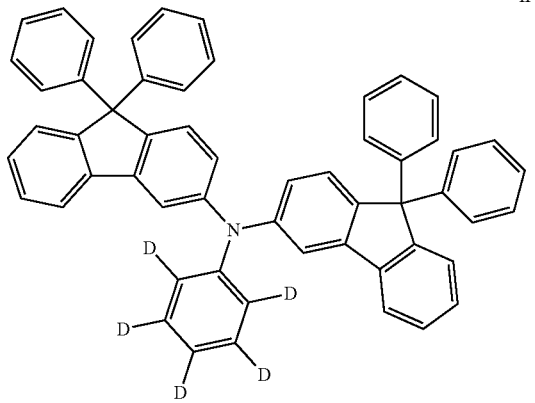
II-22
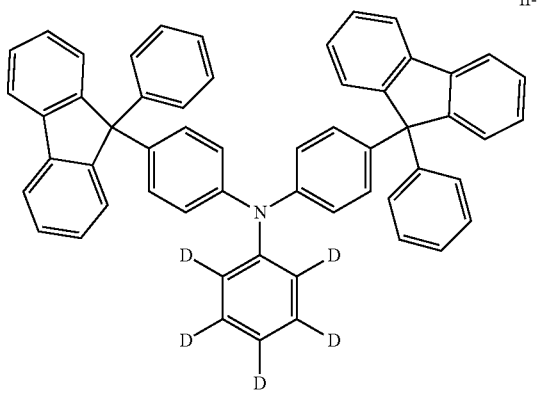
II-23
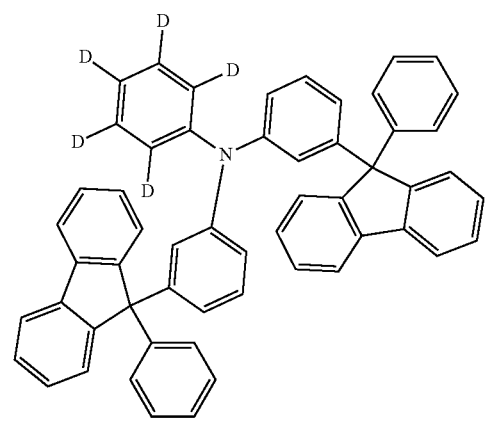
II-24
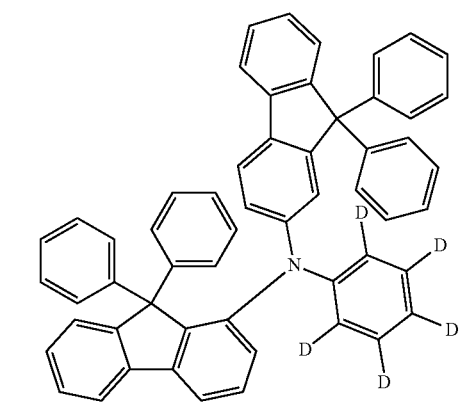
II-25
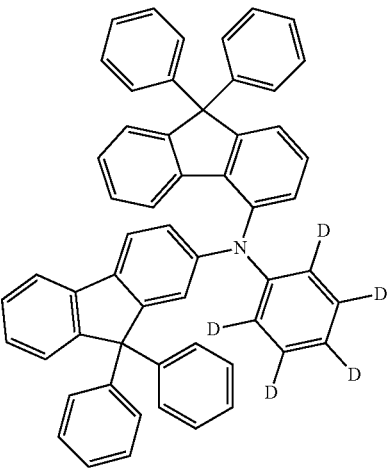
II-26
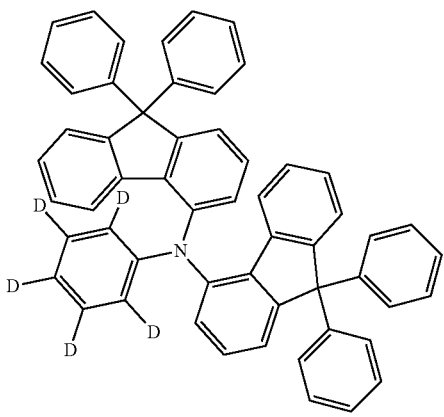
II-27
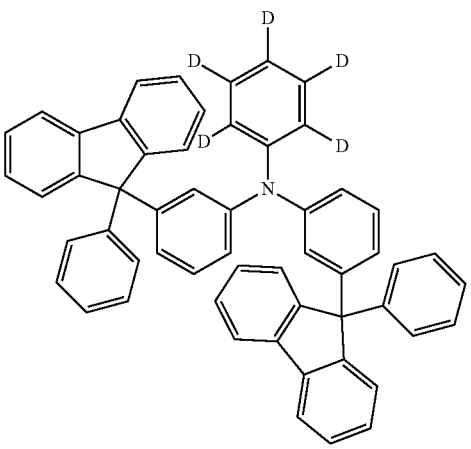

II-28
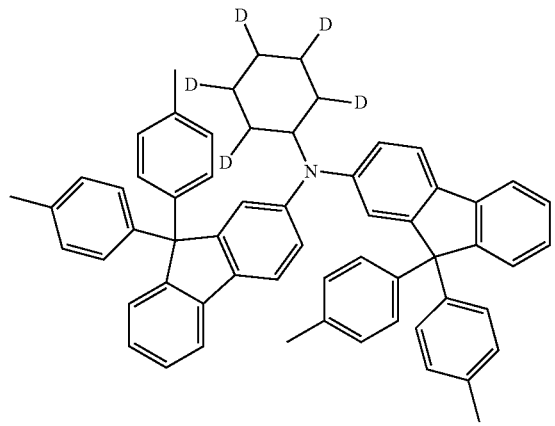
II-29
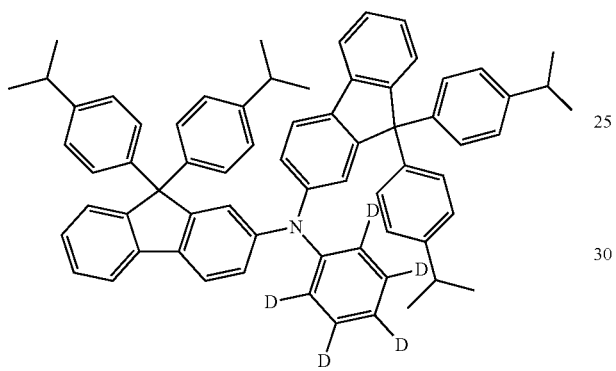
II-30
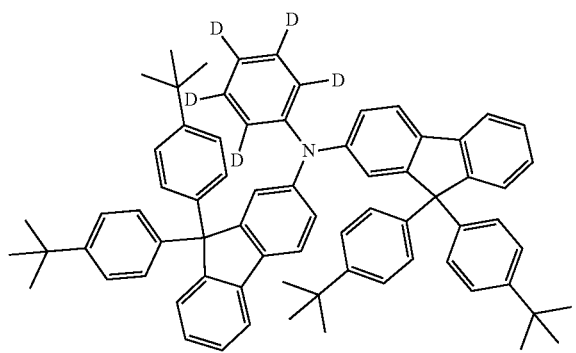
II-31
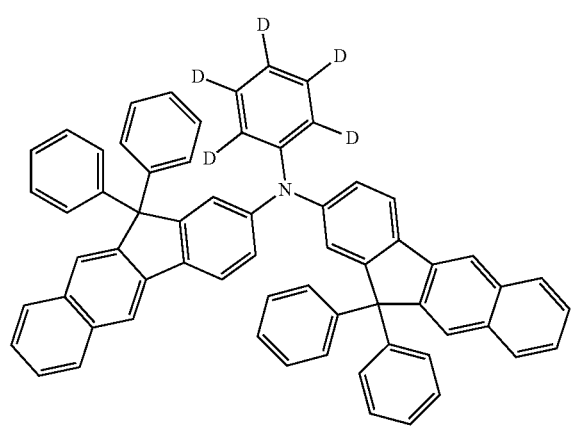
II-32
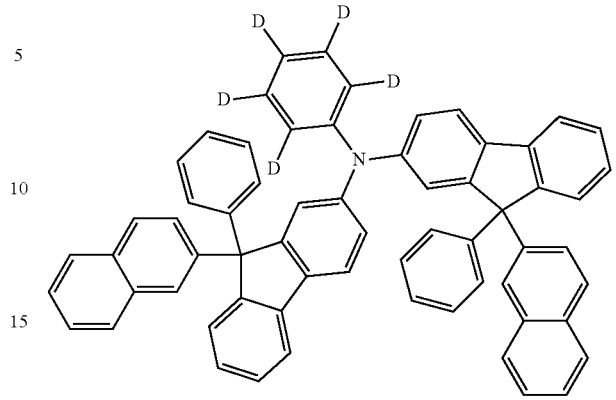
II-33
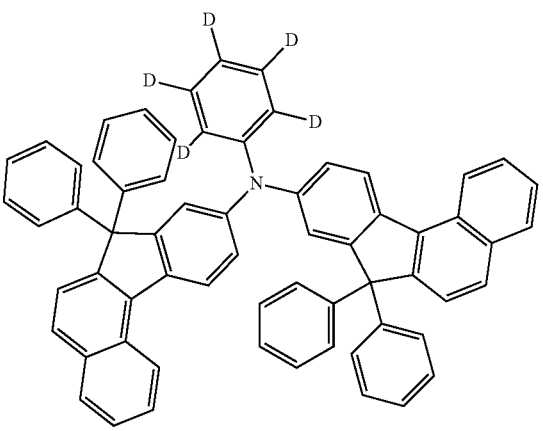
II-34
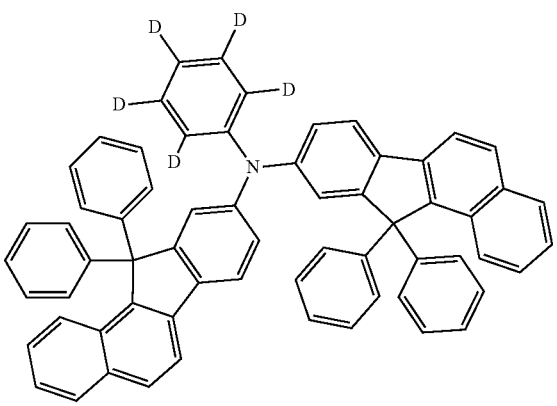

II-35
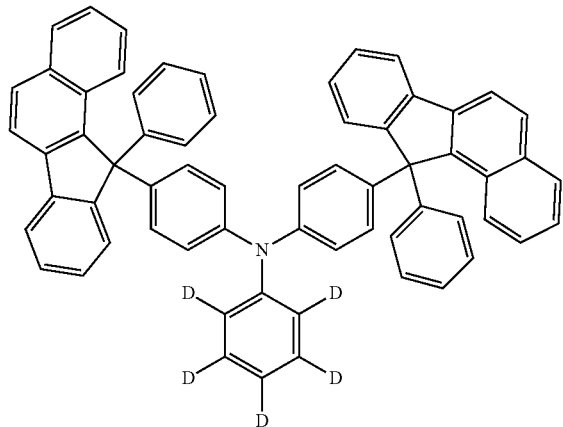
II-36
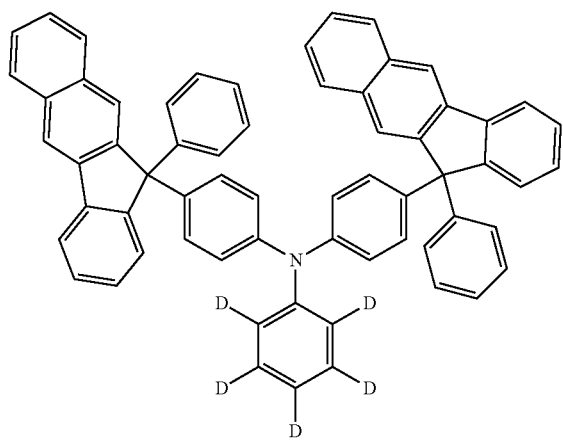
II-37
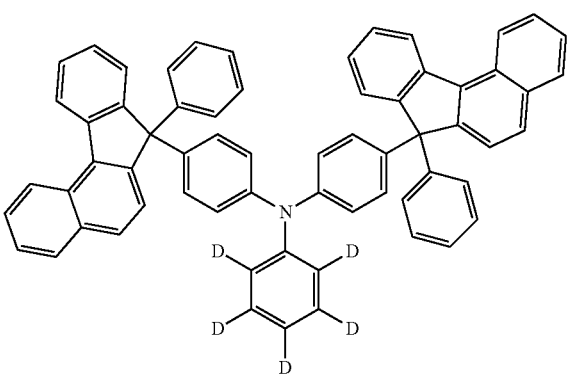
II-38
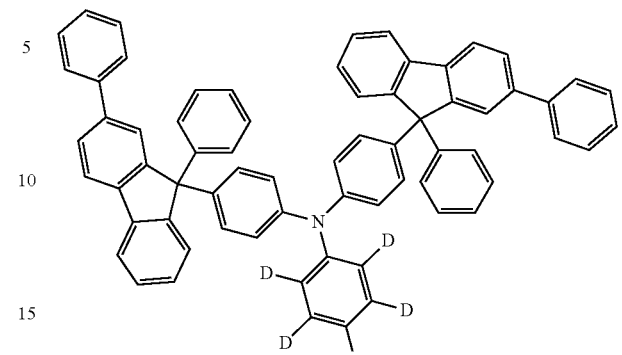
II-39
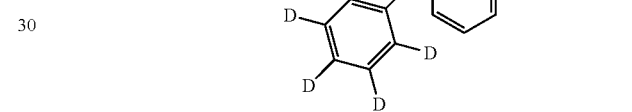
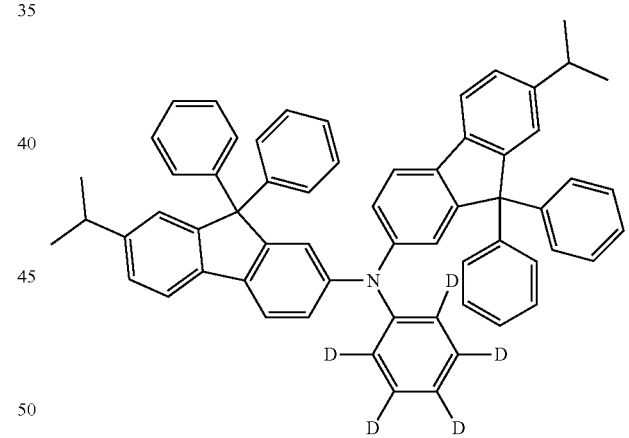
II-40
II-41
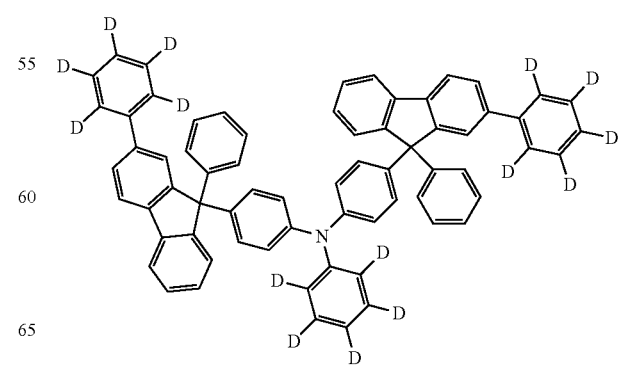

II-42
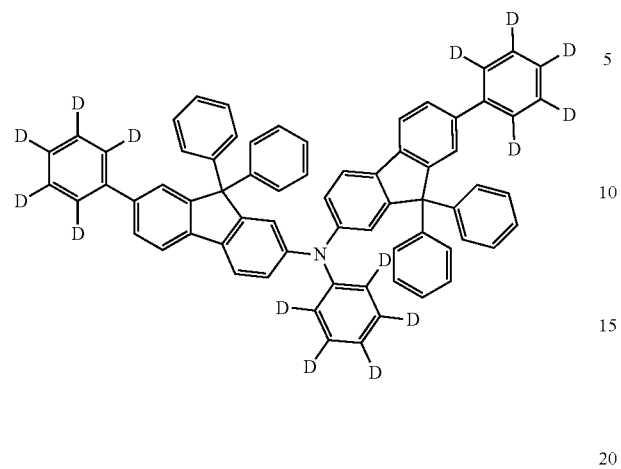
II-45
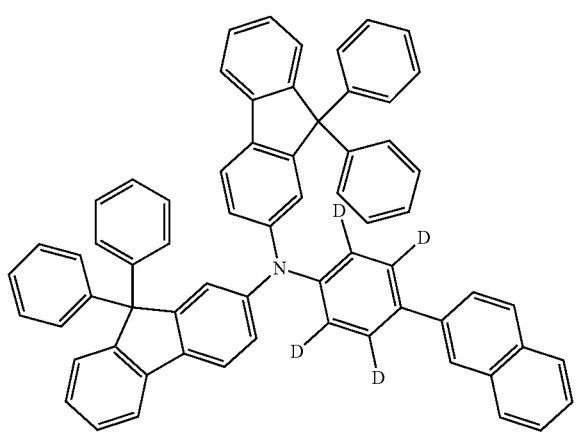
II-43
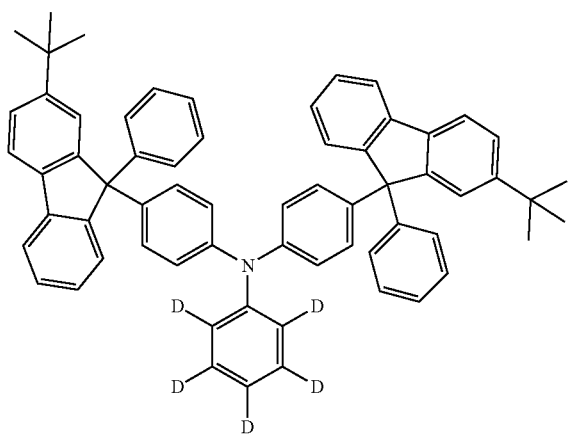
II-46
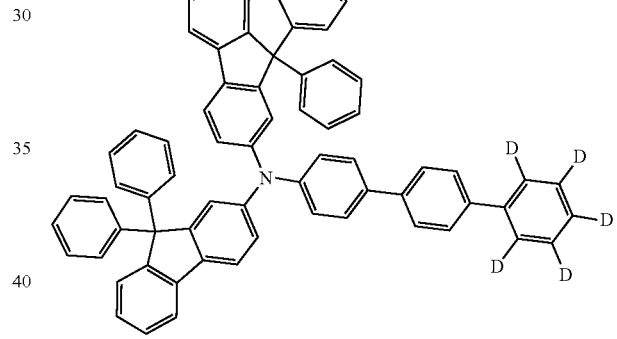
II-44
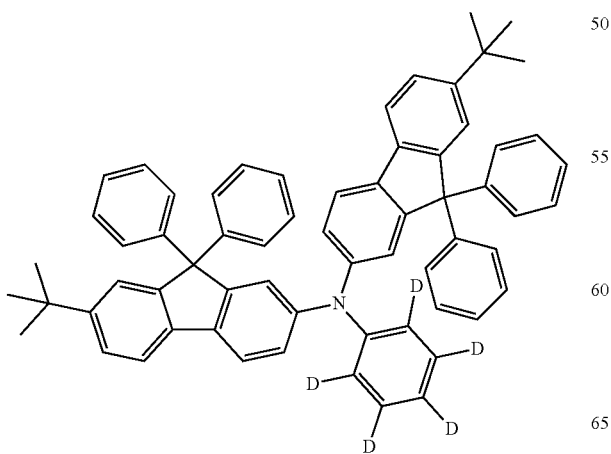
II-47
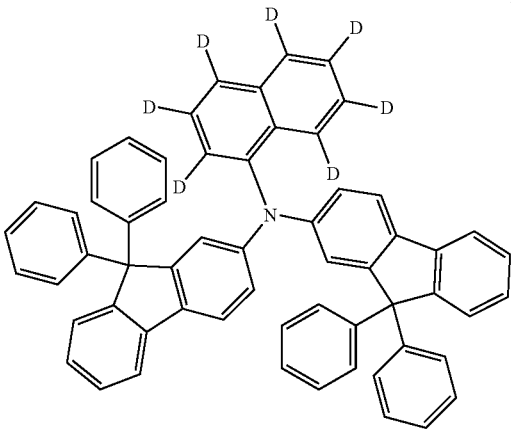

II-48
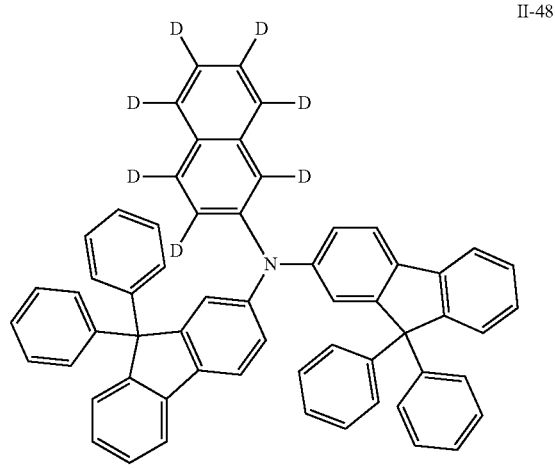
II-49
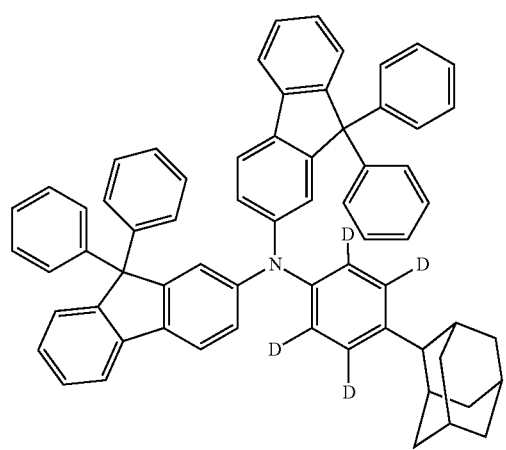
II-50
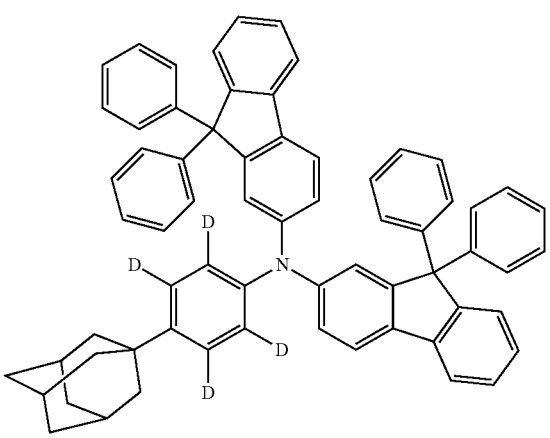
II-51
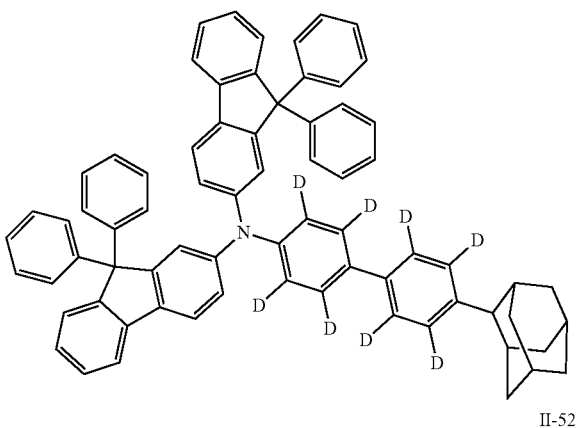
II-52
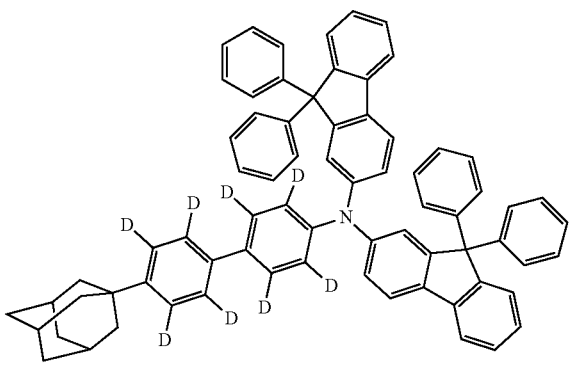
II-53
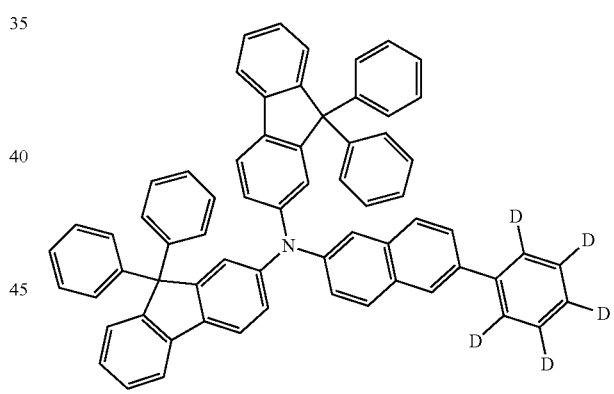
II-54
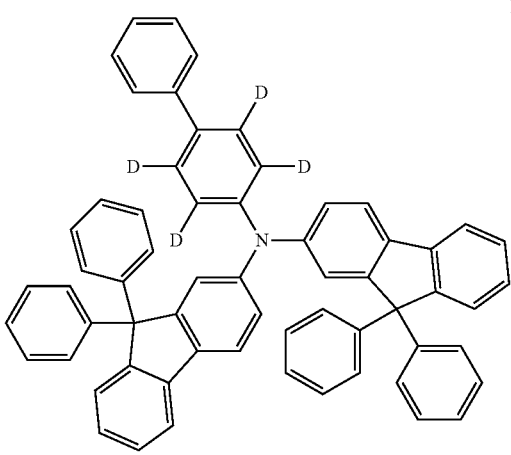

II-55
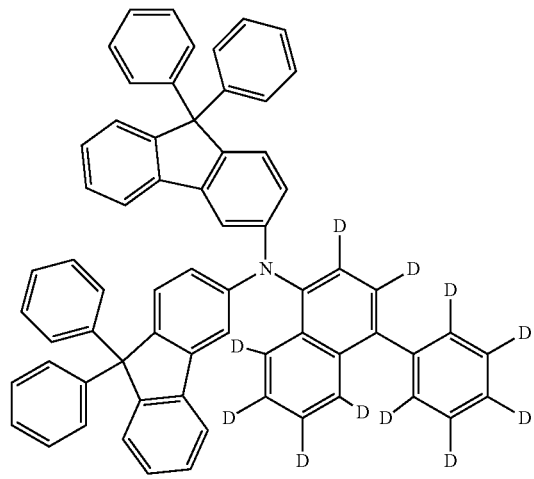
II-58
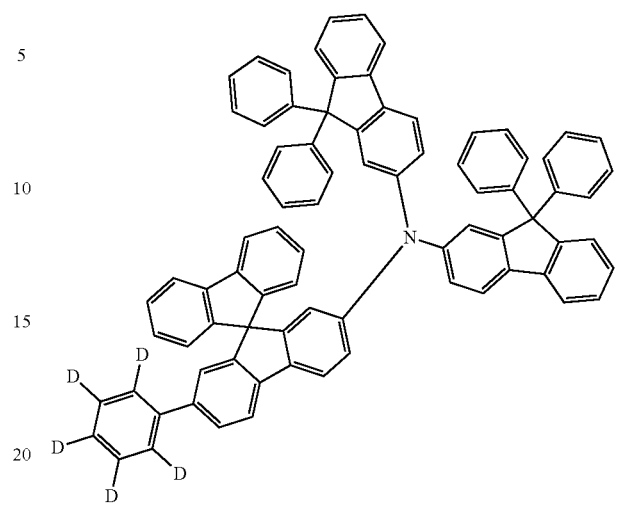
II-56
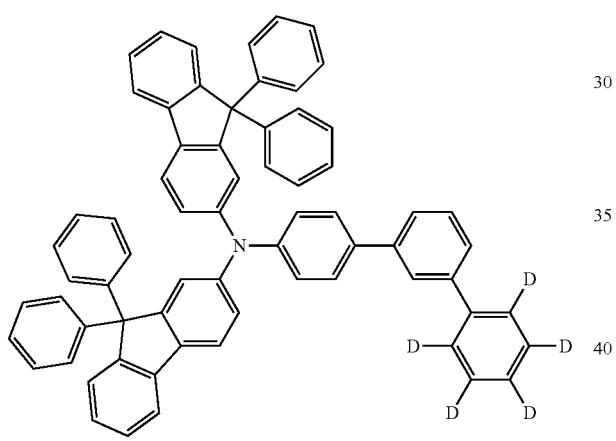
II-59
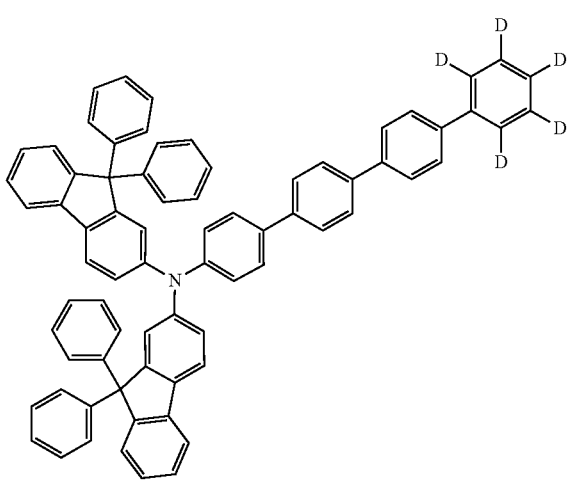
II-57
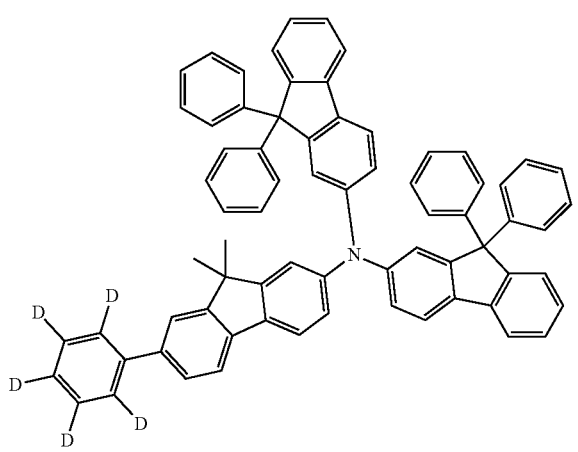
II-60
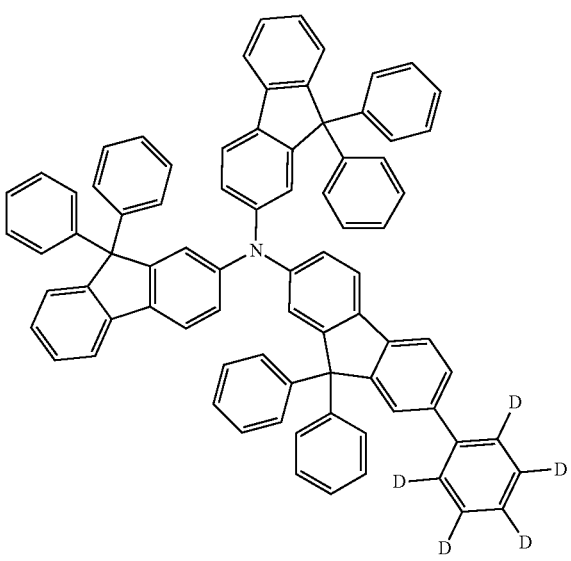

II-61
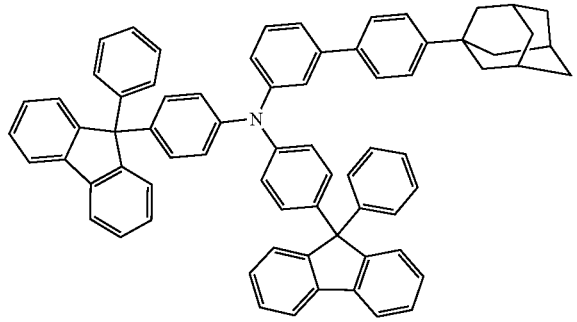
II-62
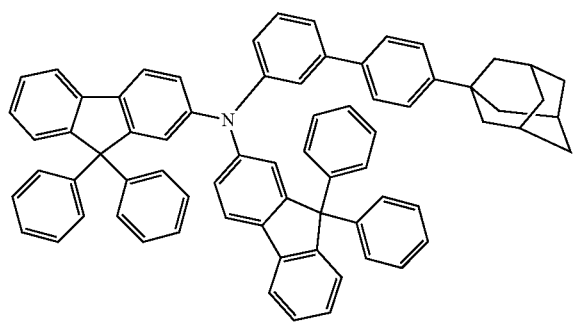
II-63
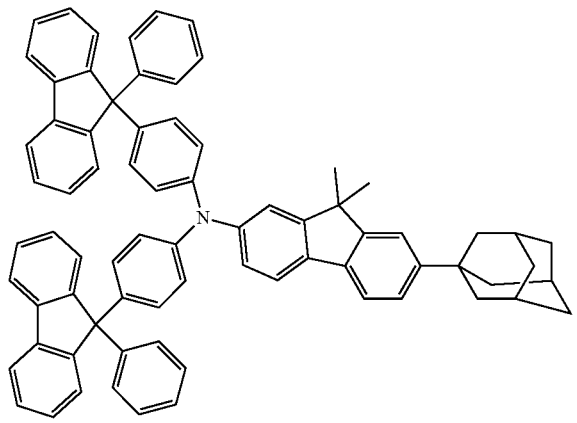
II-64

II-65

II-66

II-67
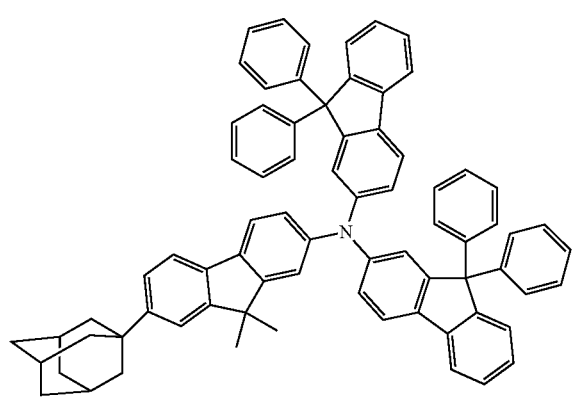

II-68
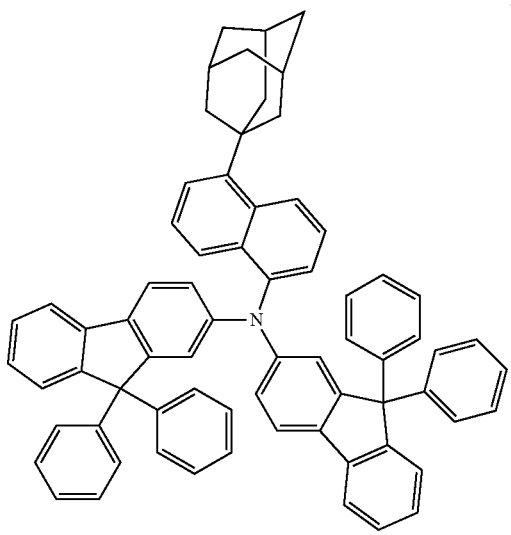
II-69
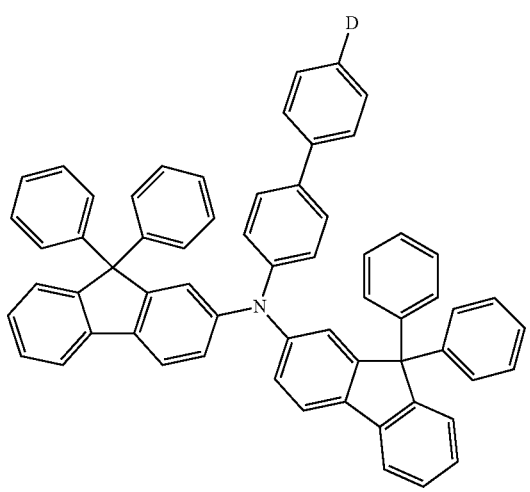
II-70
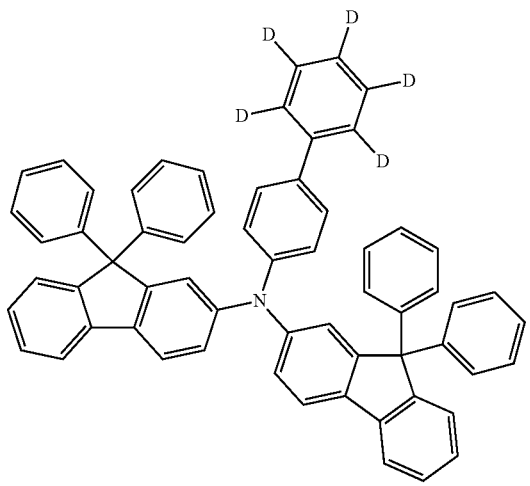
II-71
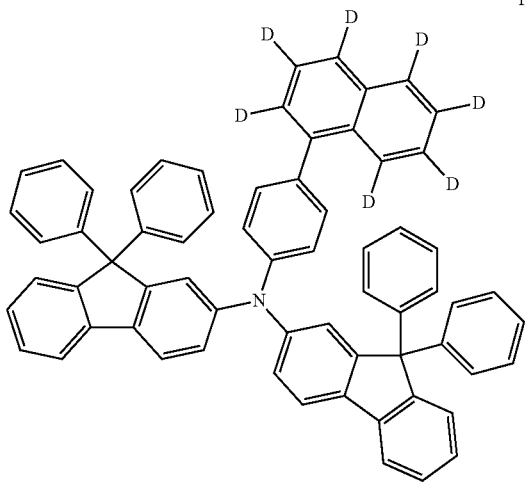
II-72
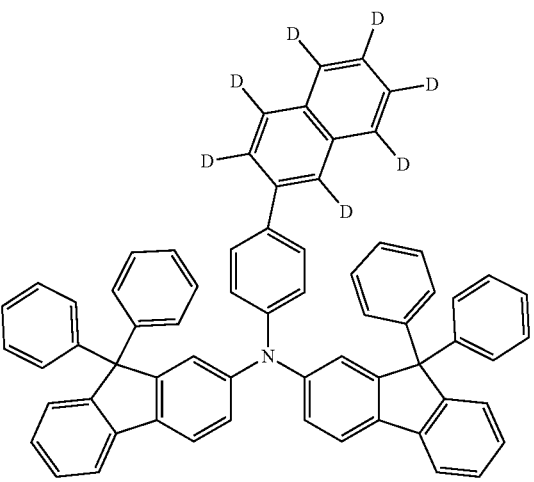
II-73
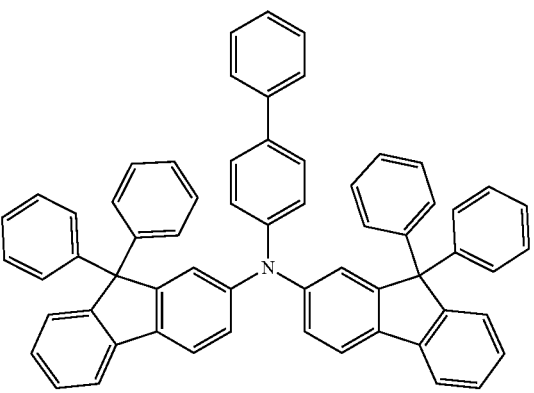

II-74
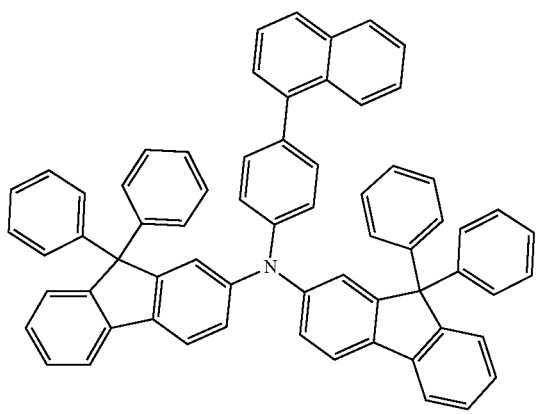
II-75
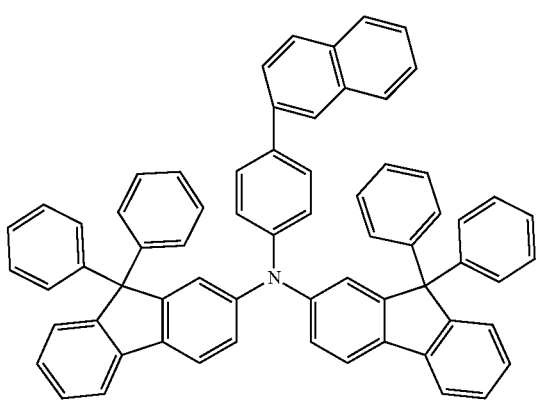
II-76
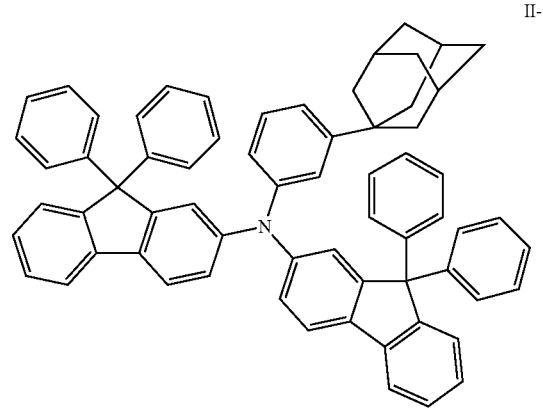
II-77
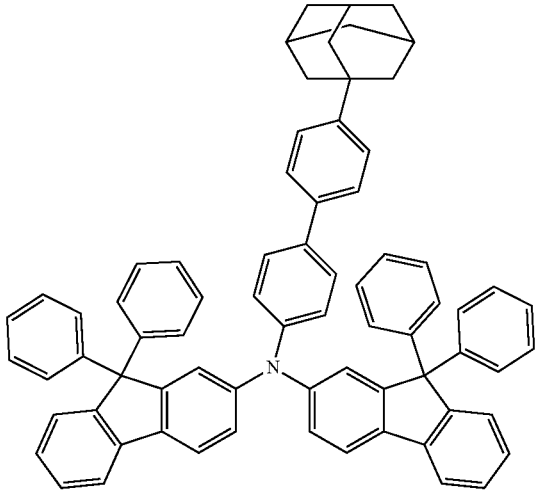
II-78
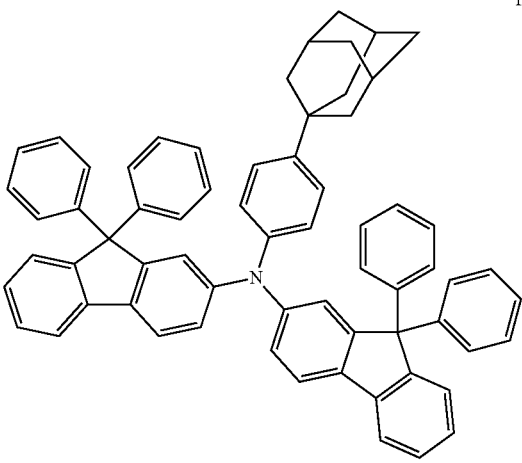
II-79
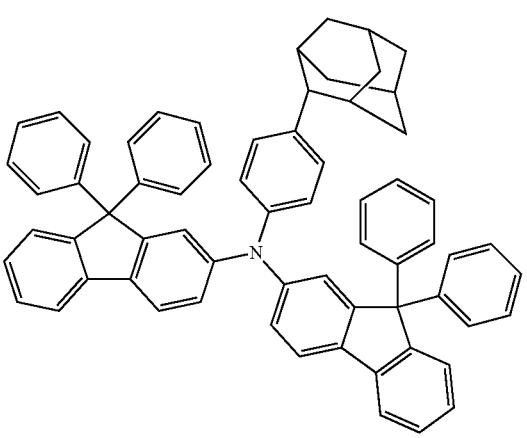

II-80
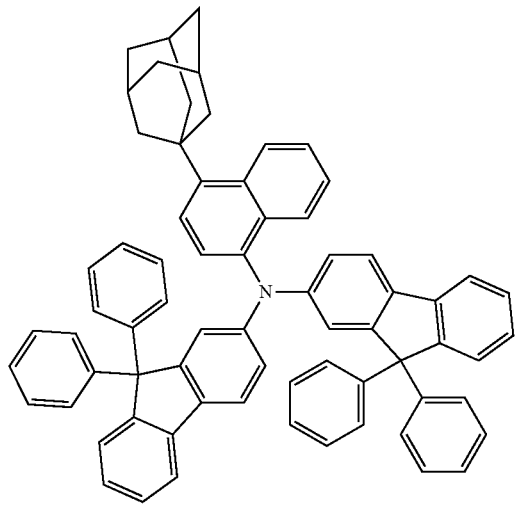
II-83
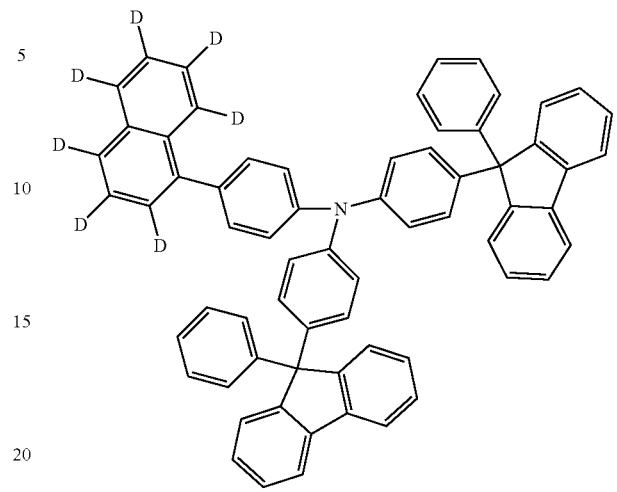
II-81
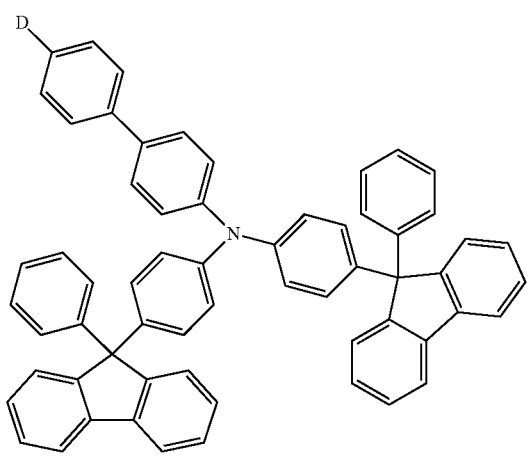
II-84
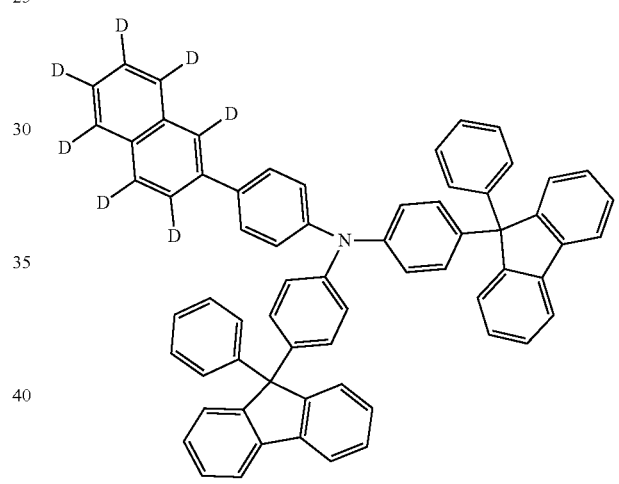
II-82
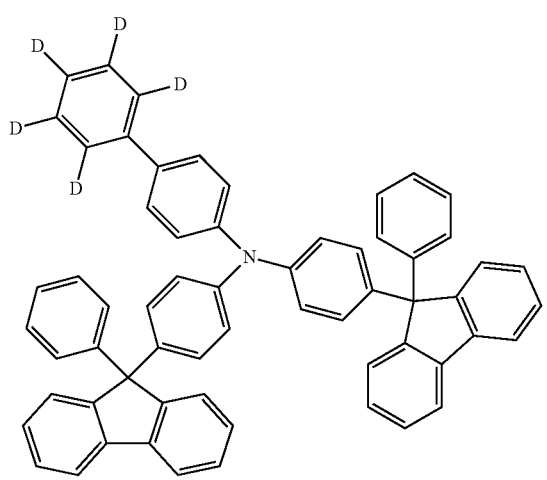
II-85
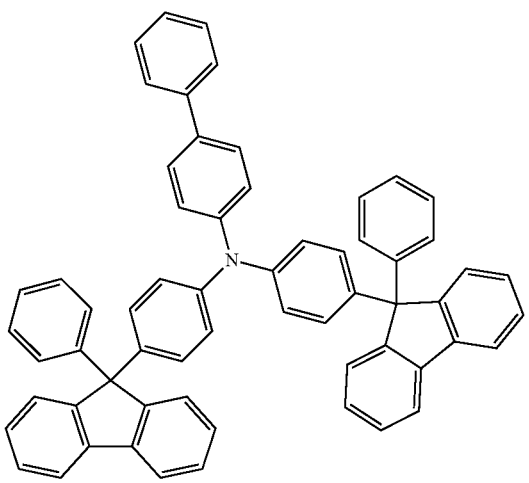

II-86
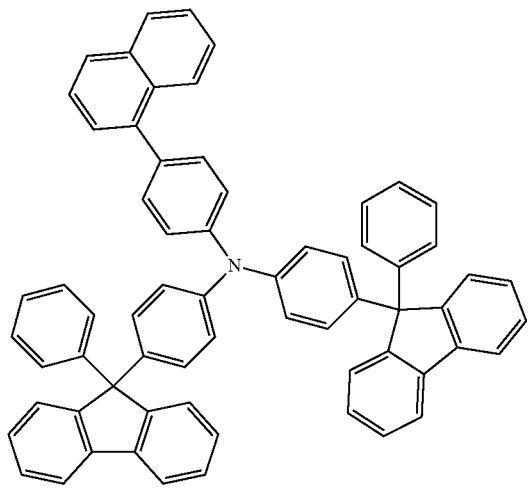
II-87
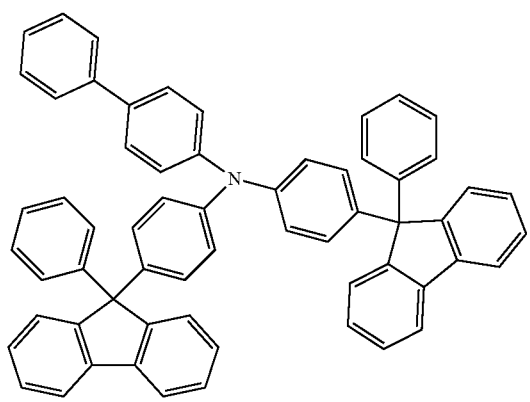
II-88
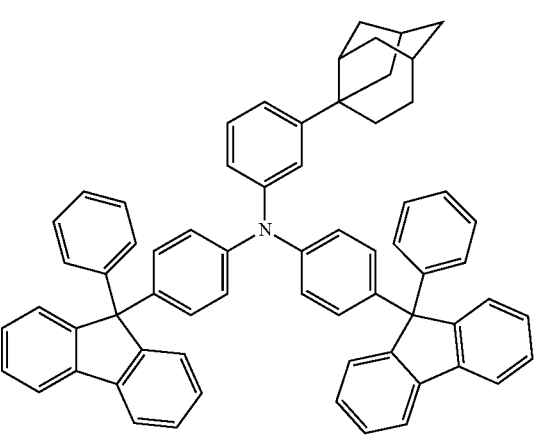
II-89
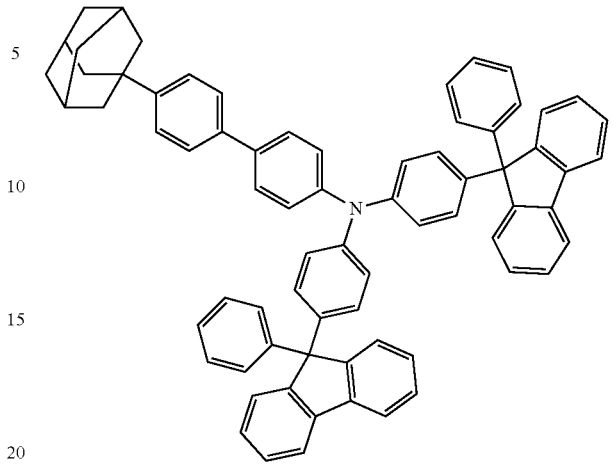
II-90
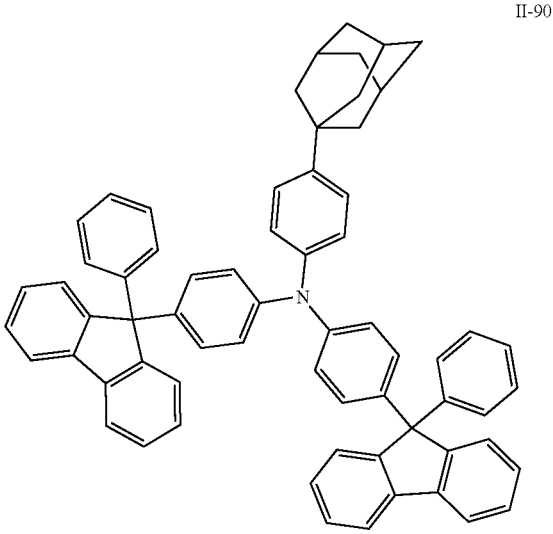
II-91
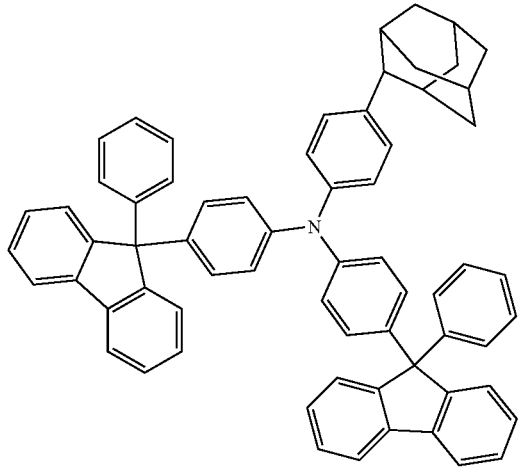

II-92
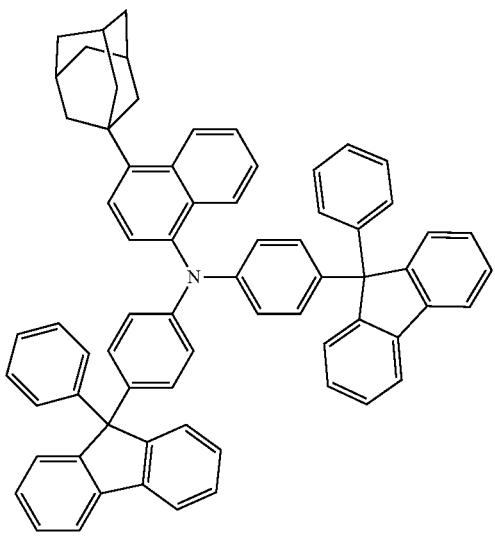
II-93
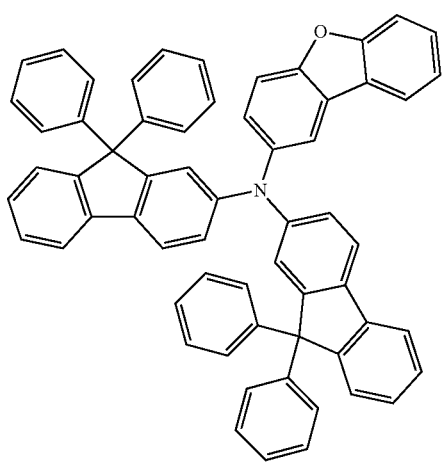
II-94
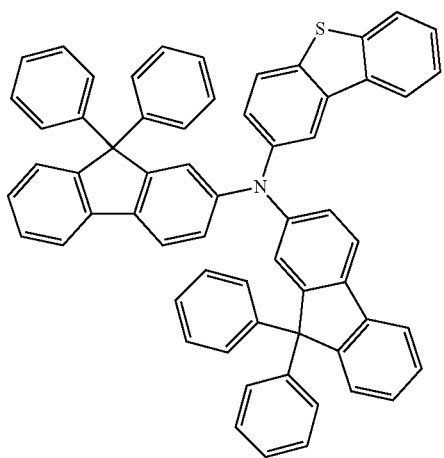
II-95
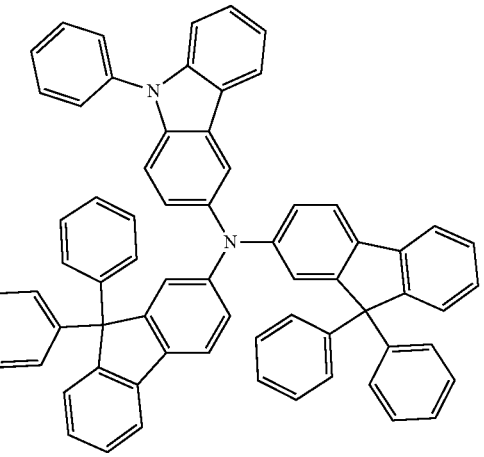
II-96
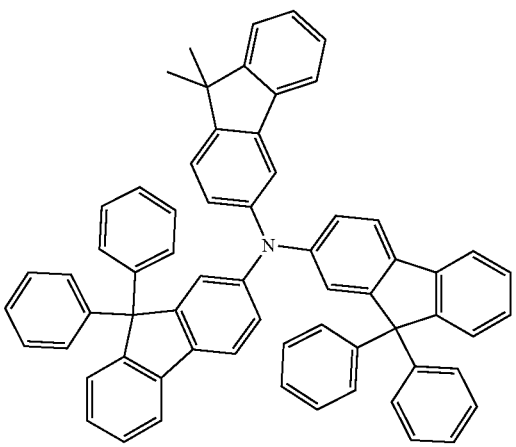
II-97
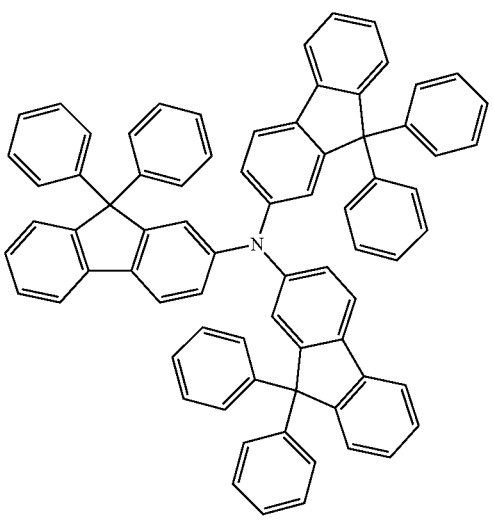

II-98
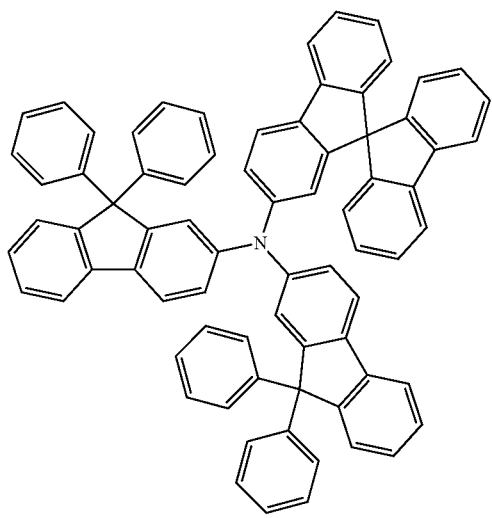
II-101
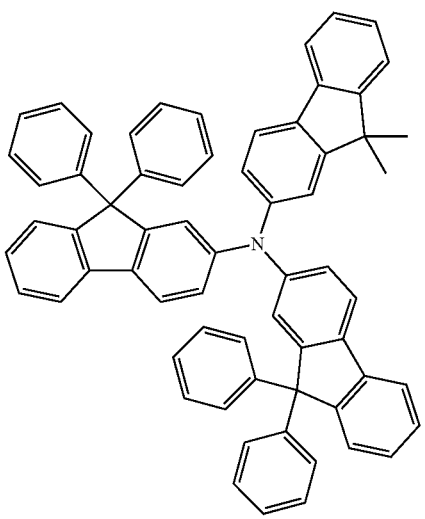
II-99
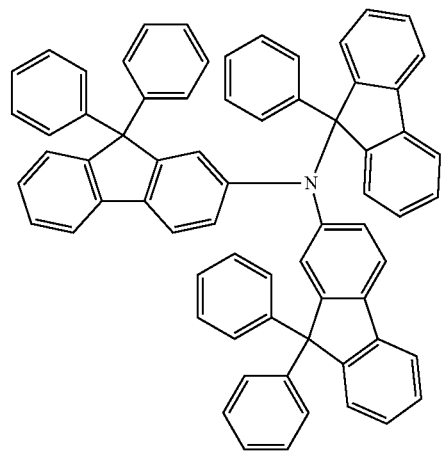
II-102
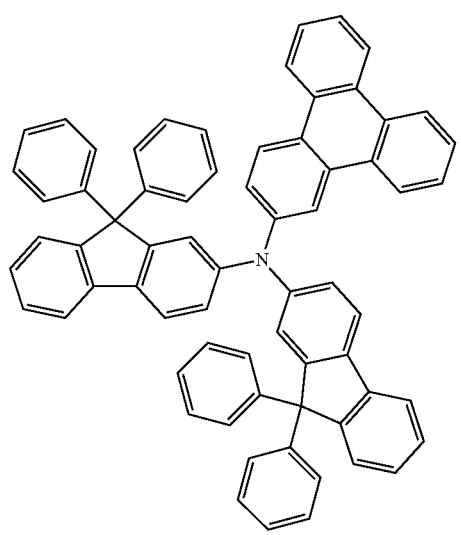
II-100
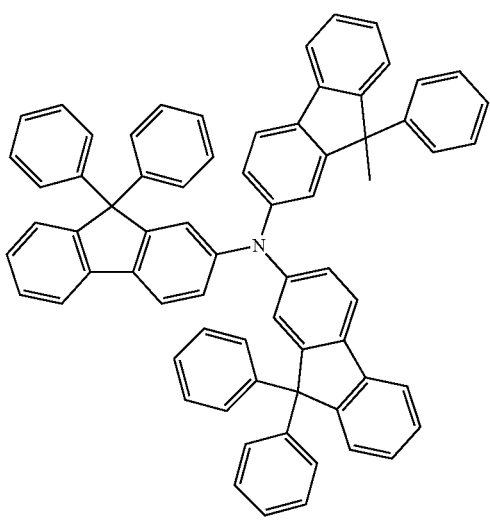
II-103
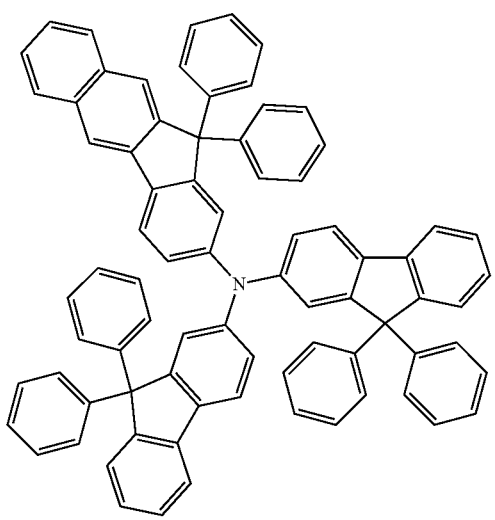

II-104
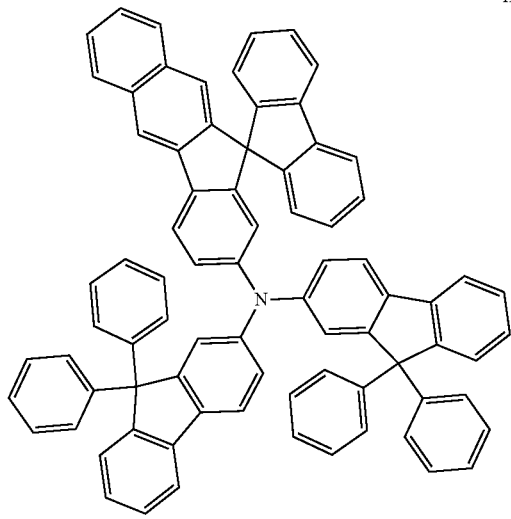
II-105
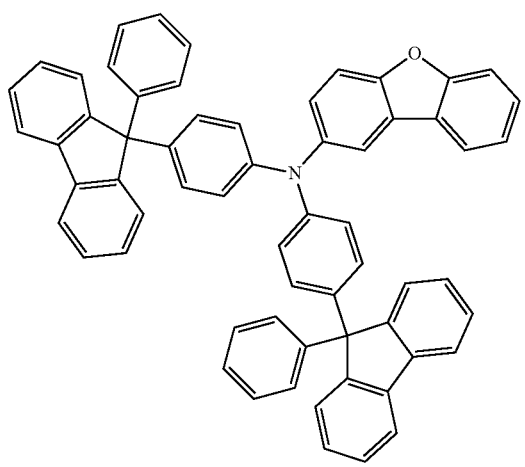
II-106
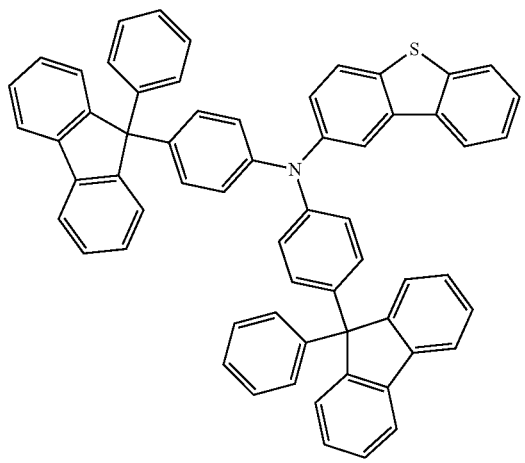
II-107
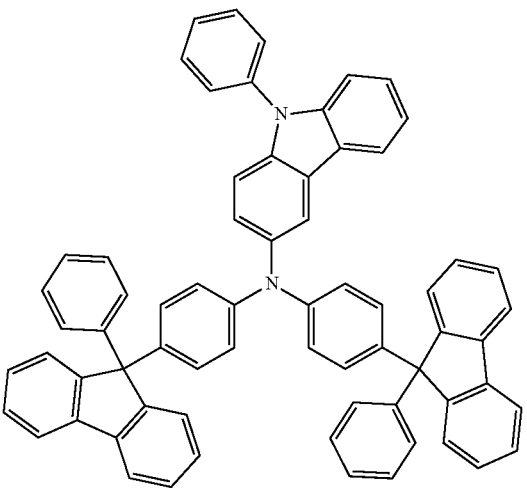
II-108
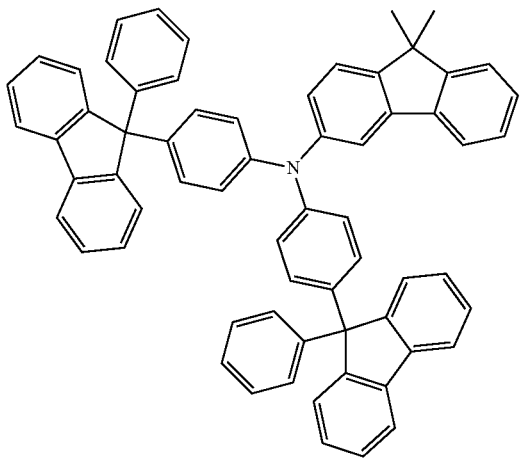
II-109
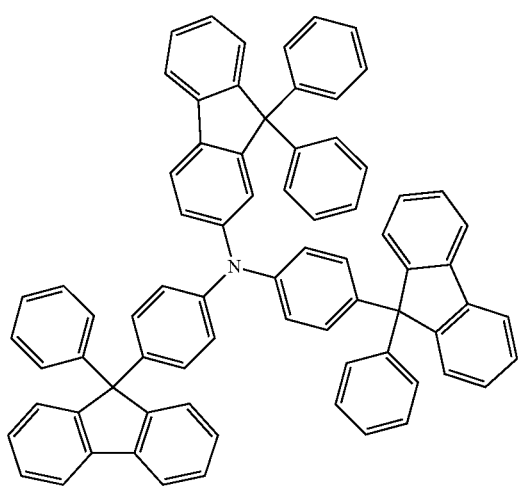

II-110
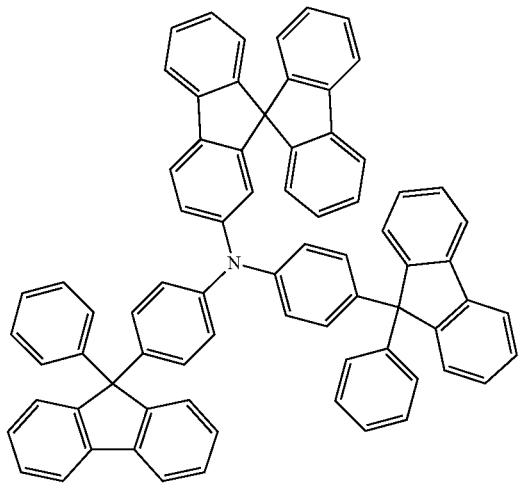
II-111
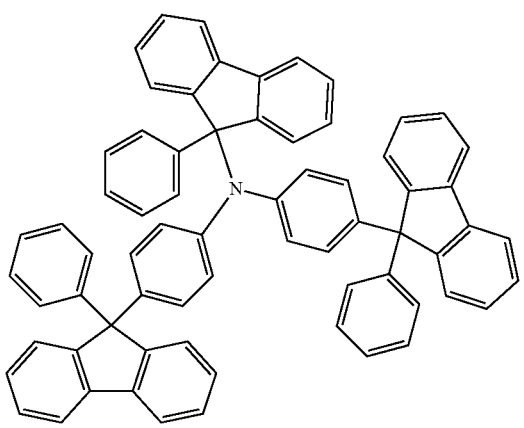
II-112
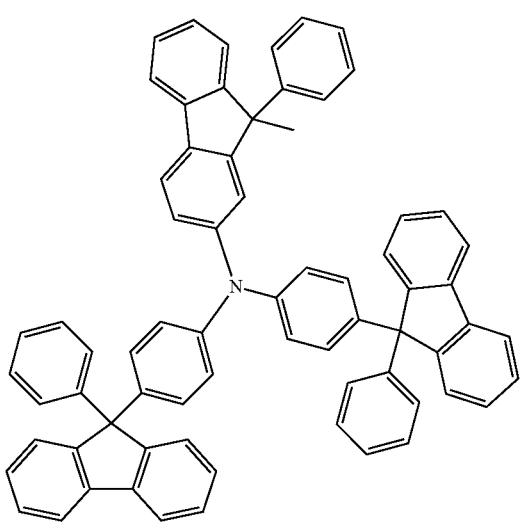
II-113
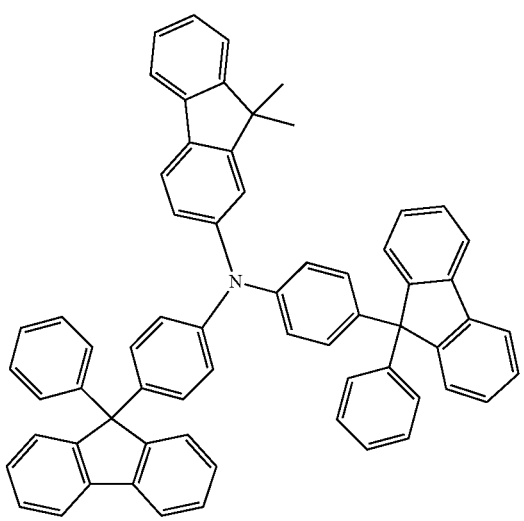
II-114
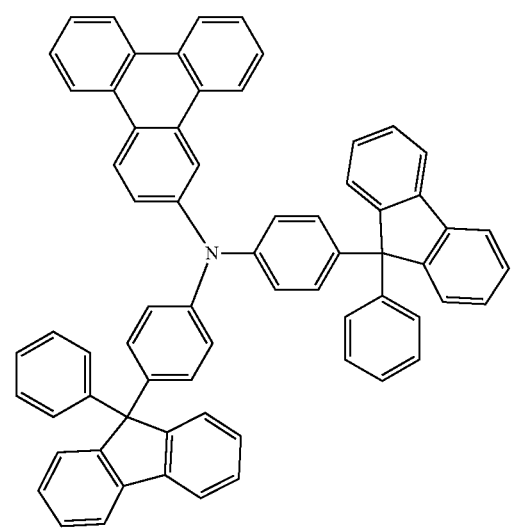
II-115
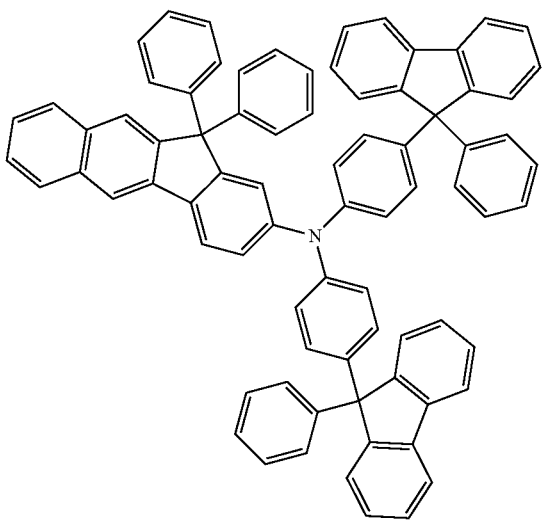

-continued
II-116
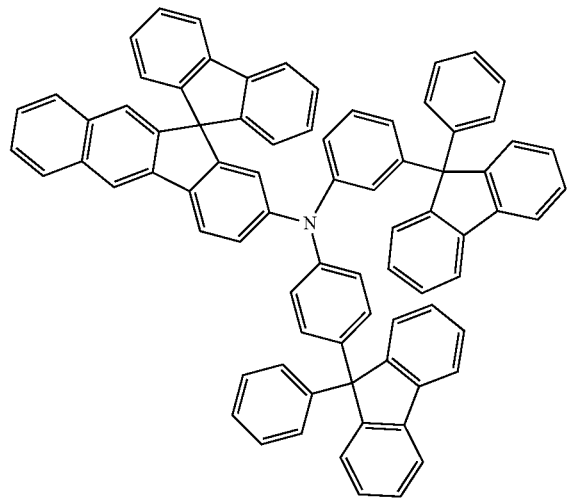
II-117
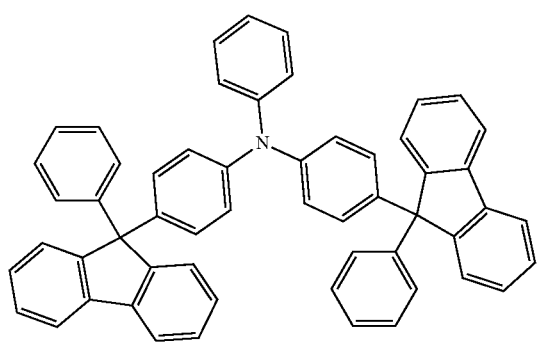
II-118
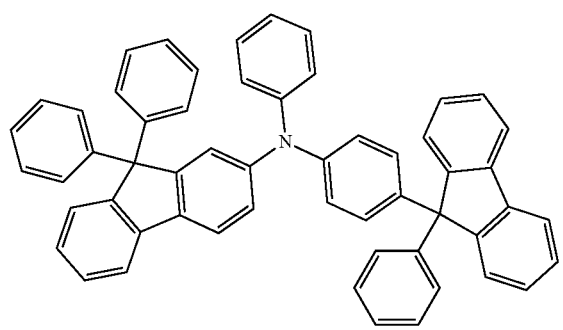
-continued
II-120
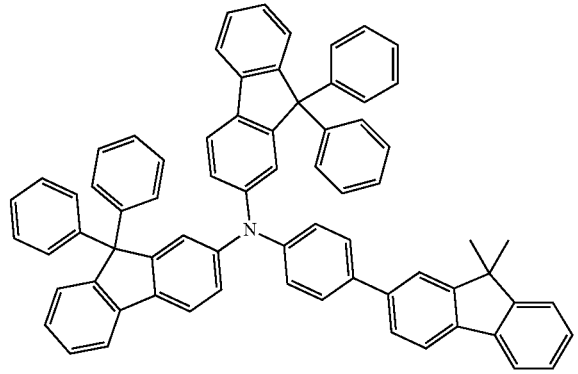
II-121
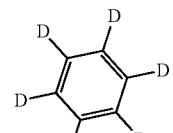
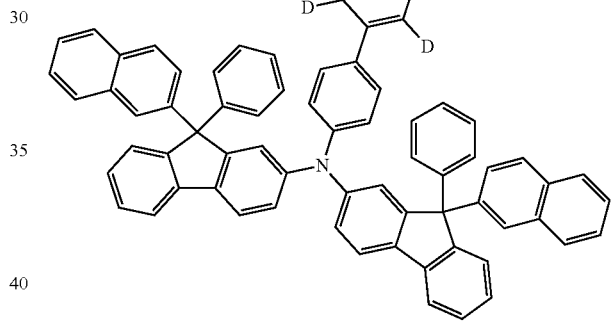
II-122
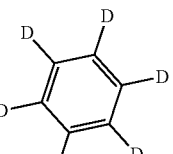
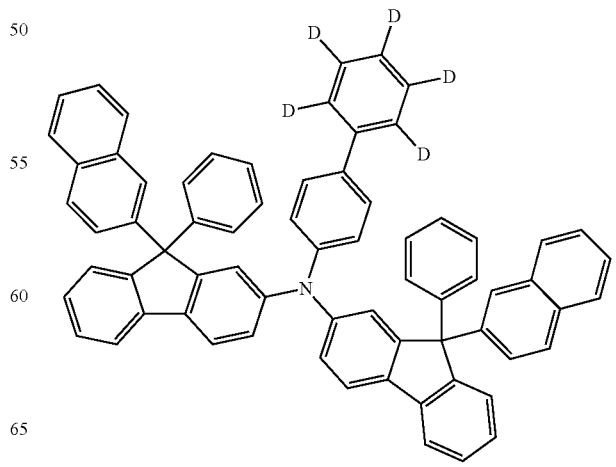

II-123
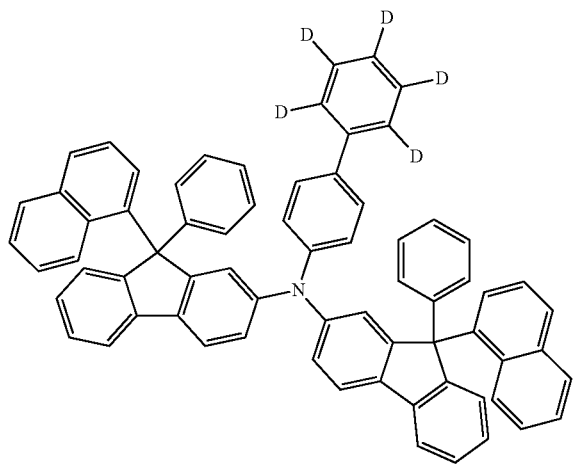
II-126
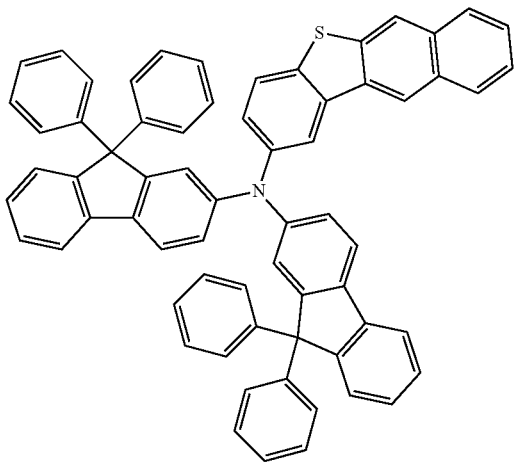
II-124
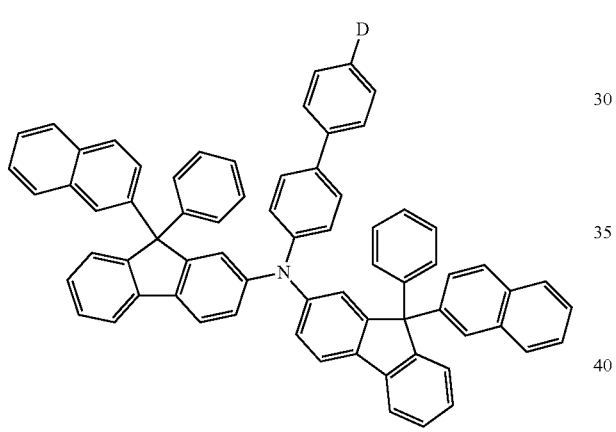
II-127
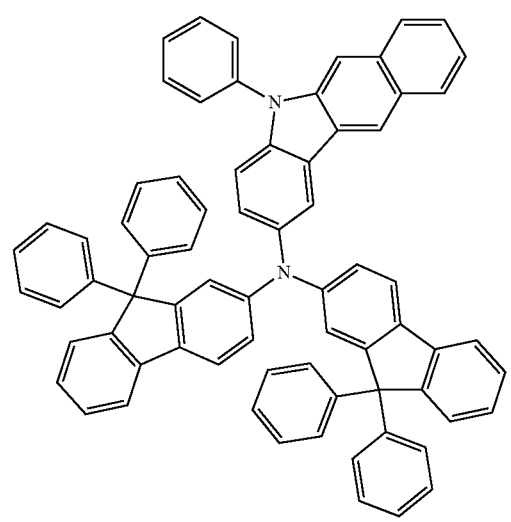
II-125
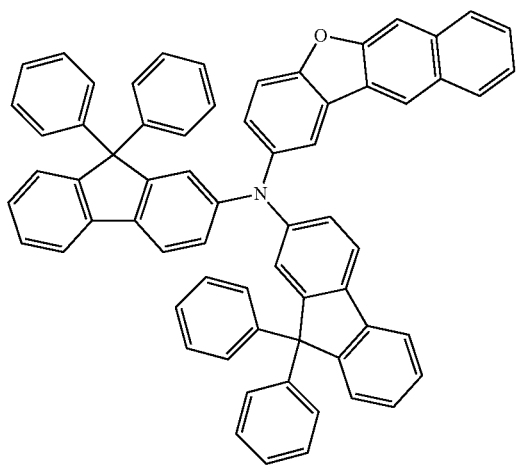
II-128
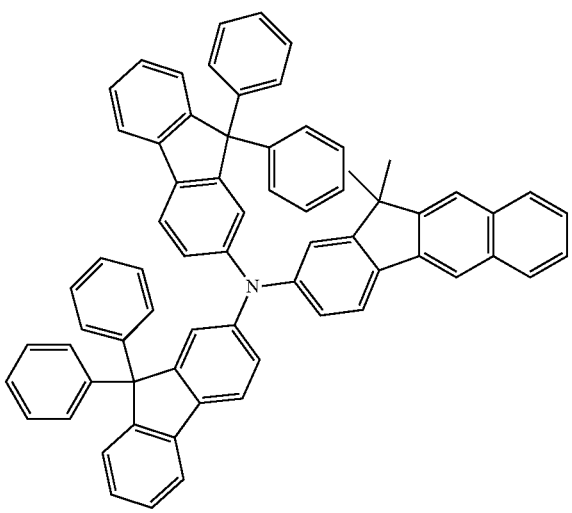

II-129
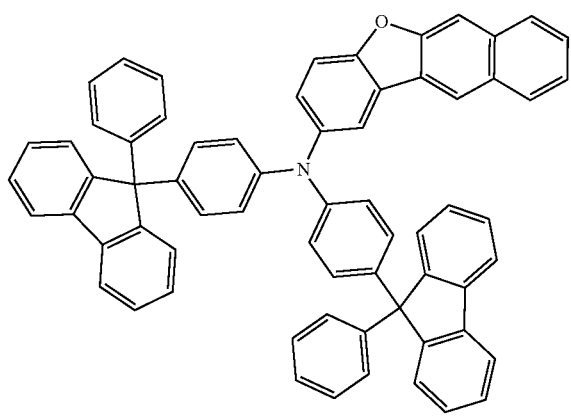
II-132
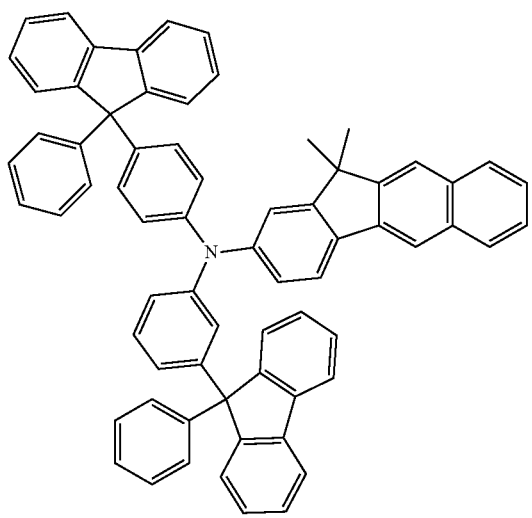
II-130
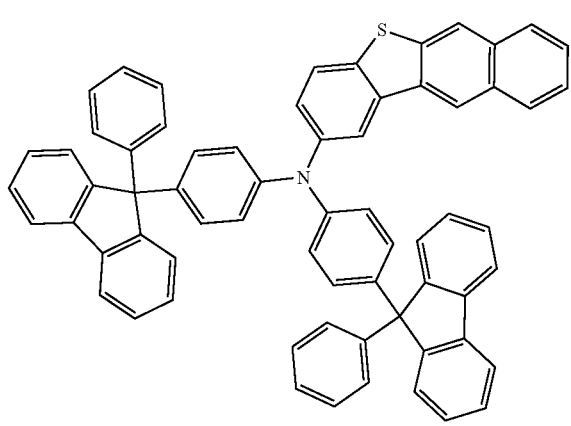
II-133
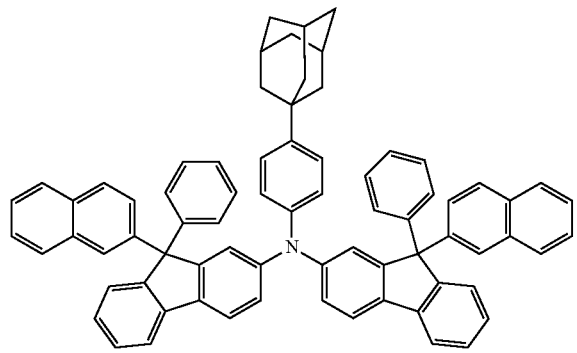
II-131
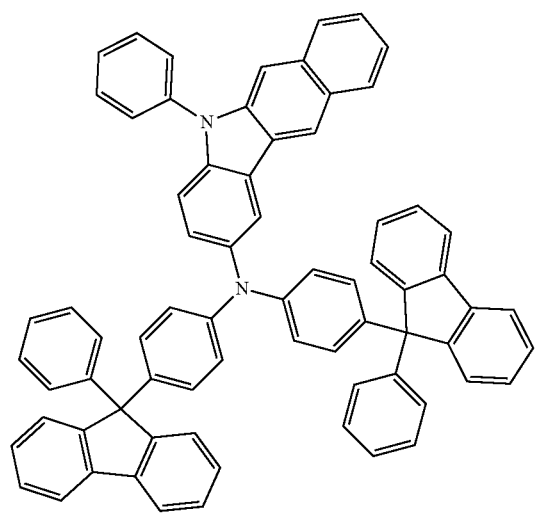
II-134
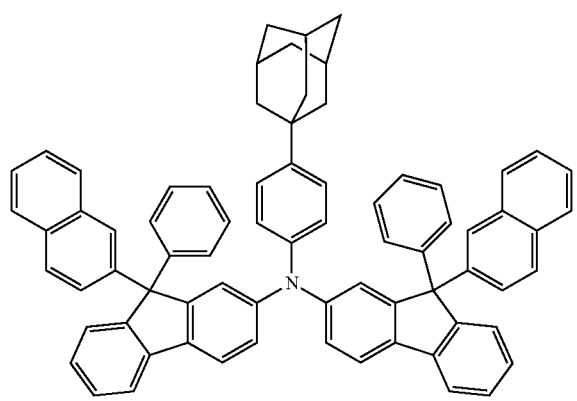

II-135
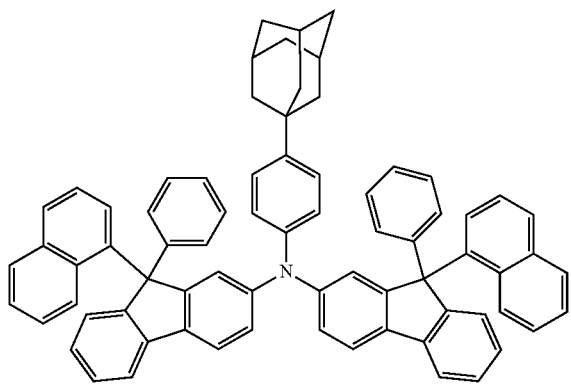
II-136
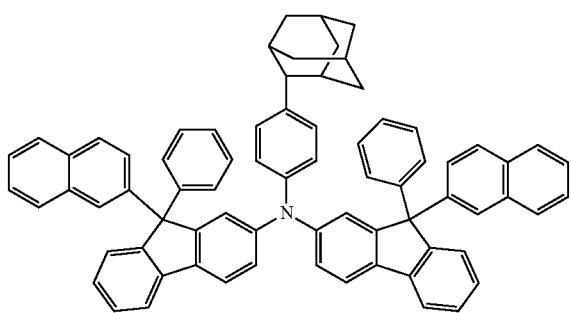
II-137
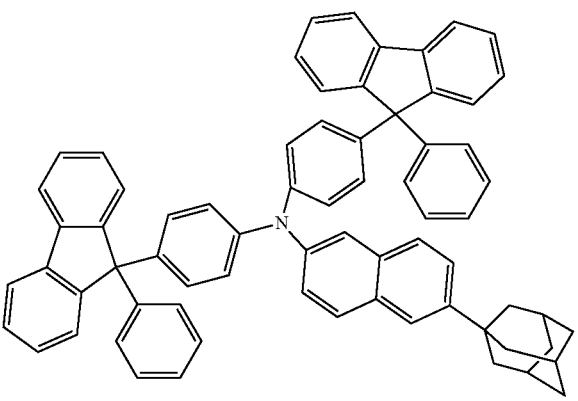
II-138
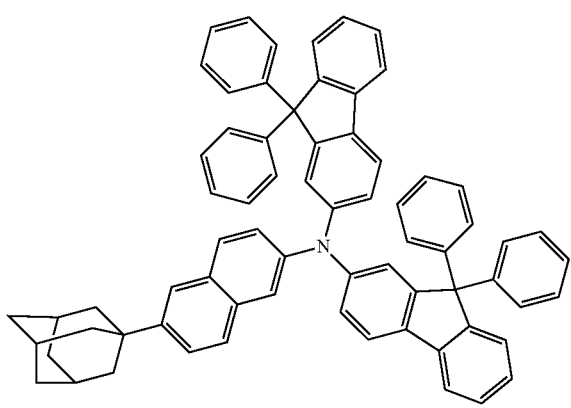
II-139
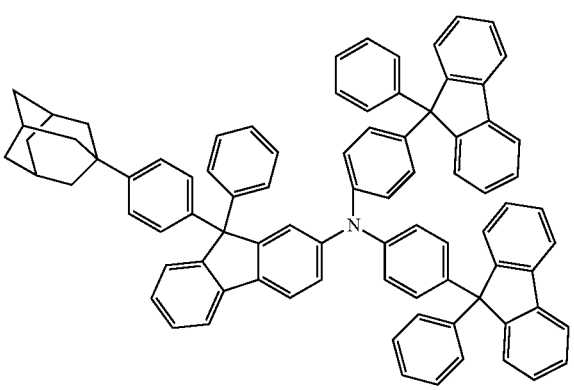
II-140
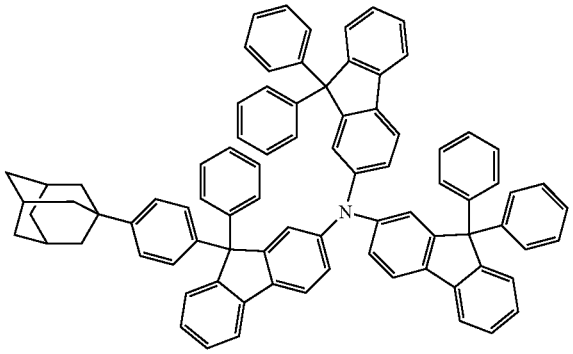
II-141
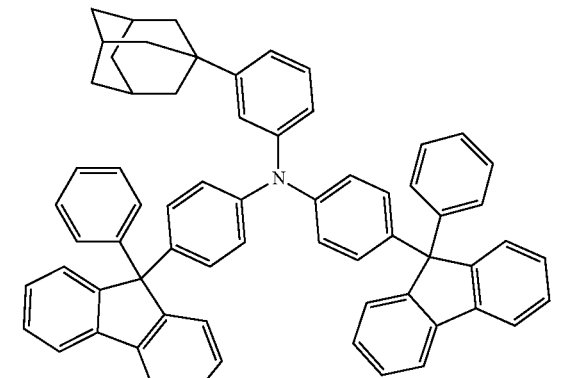
II-142
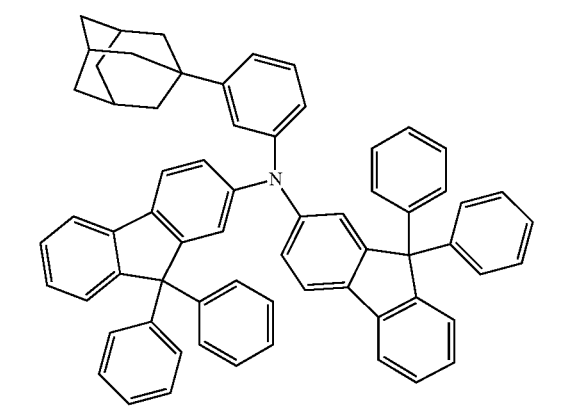

II-143
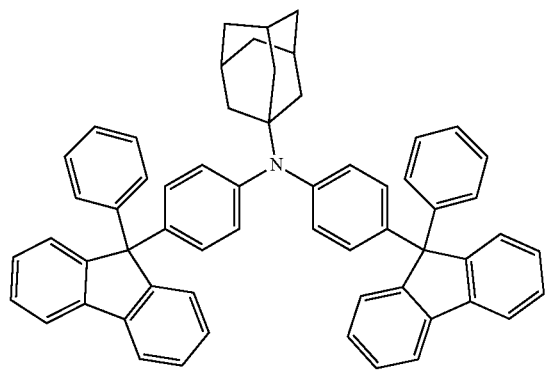
II-144
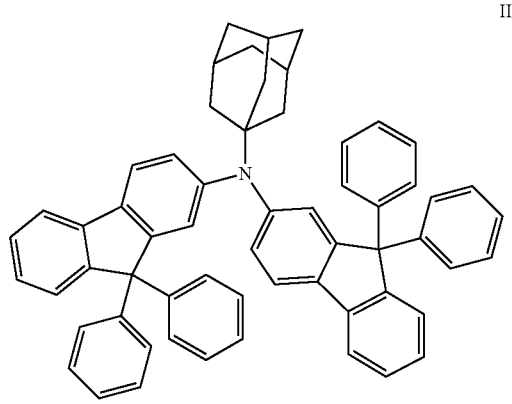
II-145
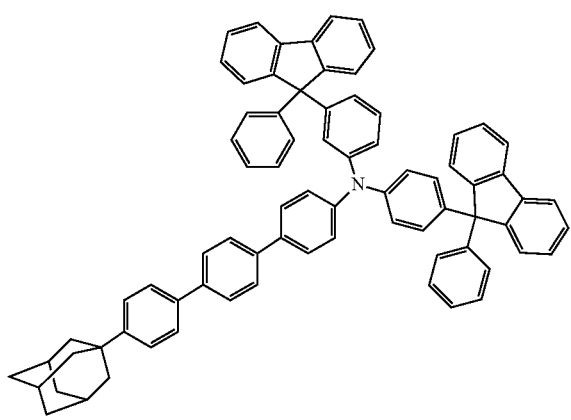
II-146
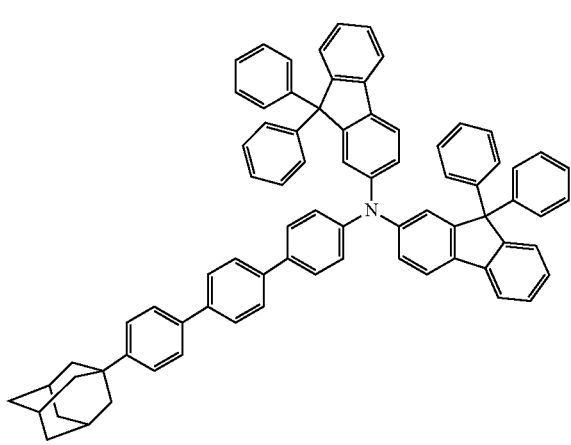
II-147
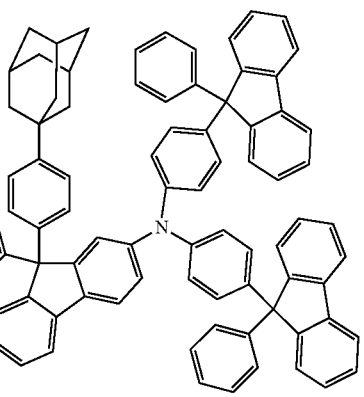
II-148
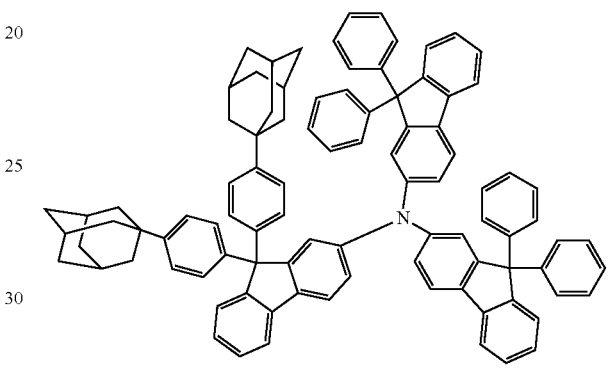
II-149
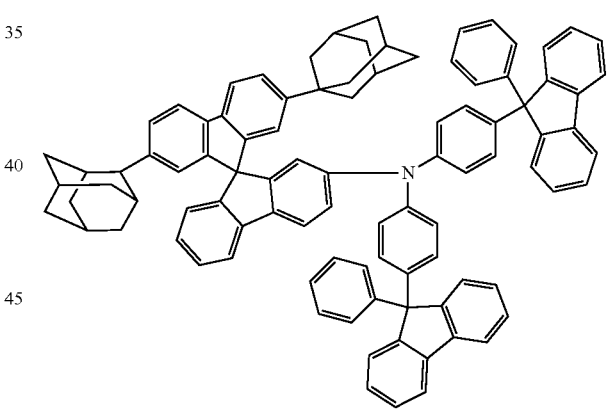
II-150
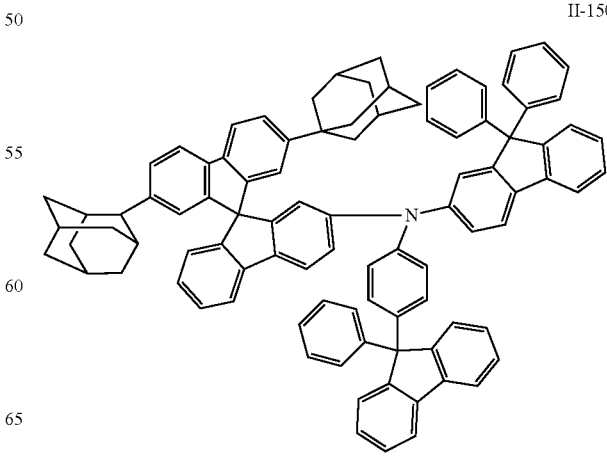

II-151
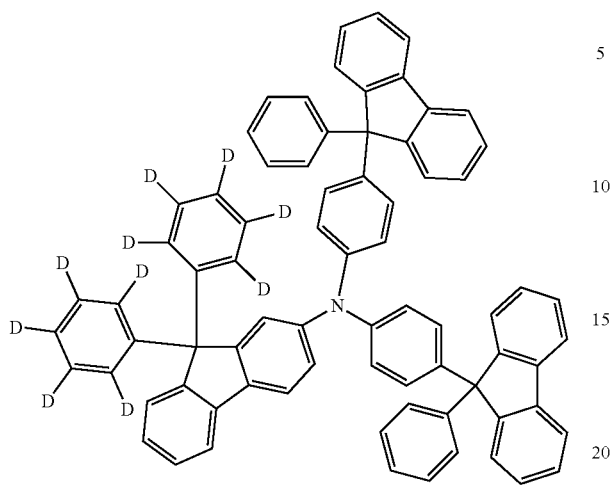
II-154
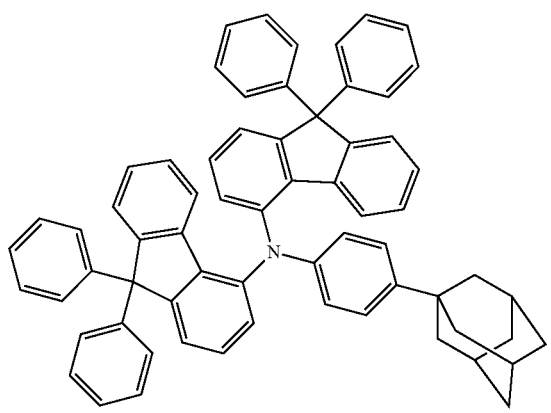
II-152
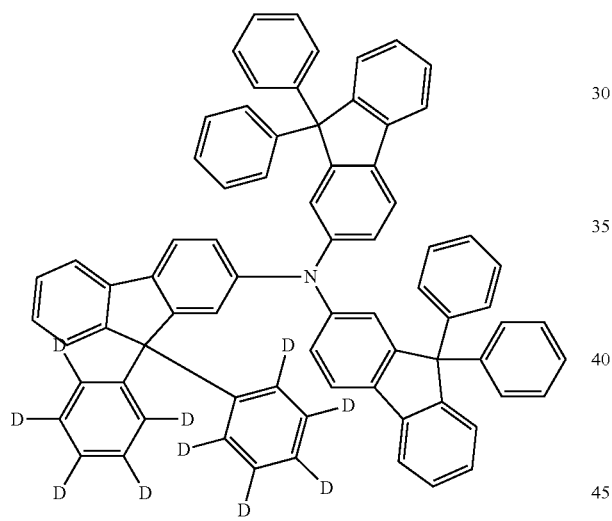
II-155
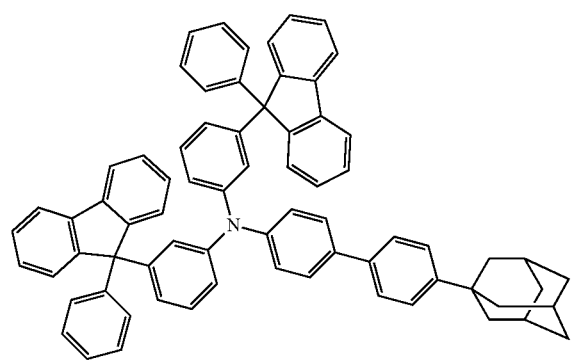
II-153
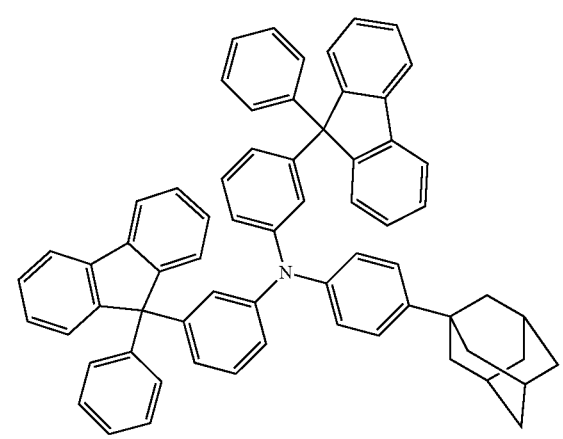
II-156
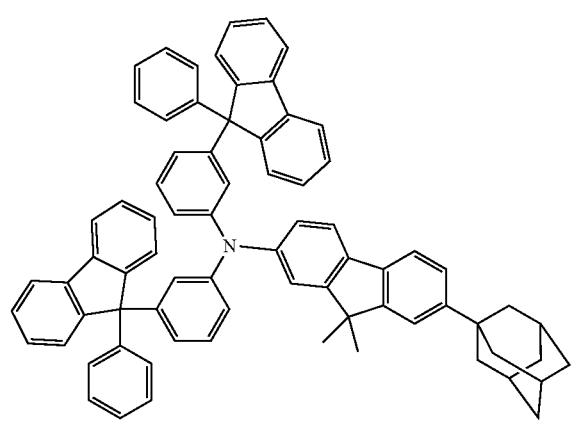

I-157
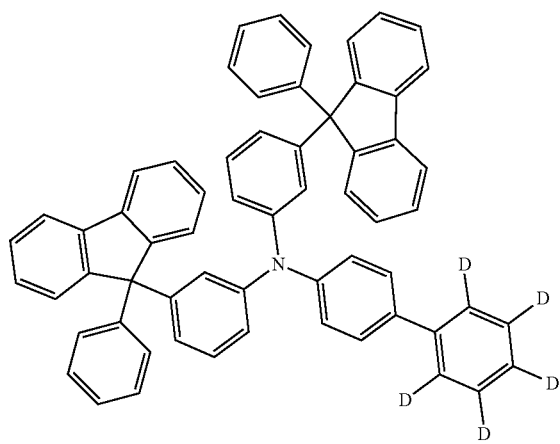
II-160
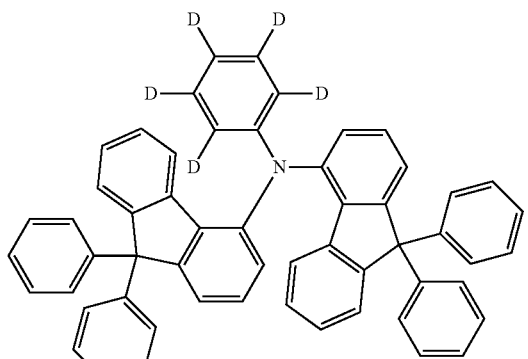
I-158
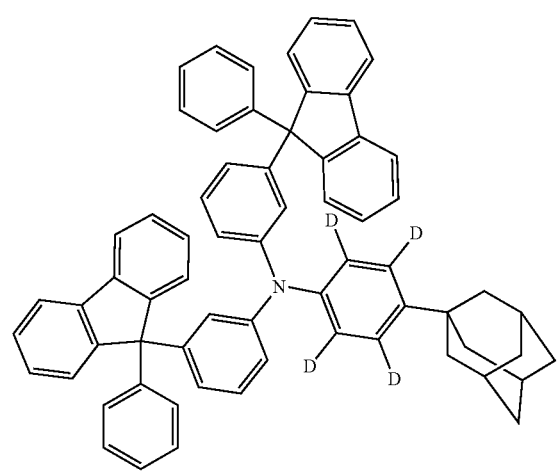
II-161
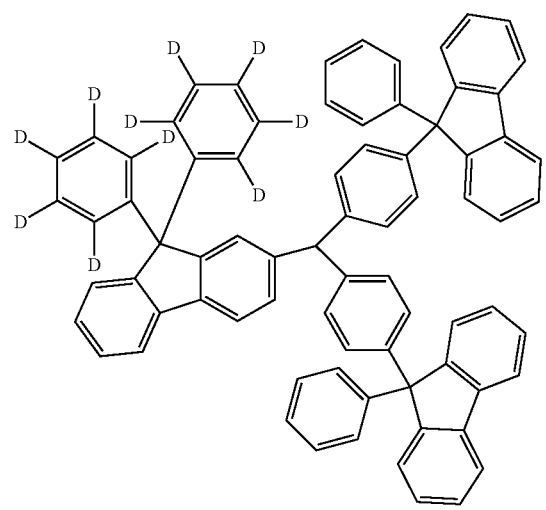
I-159
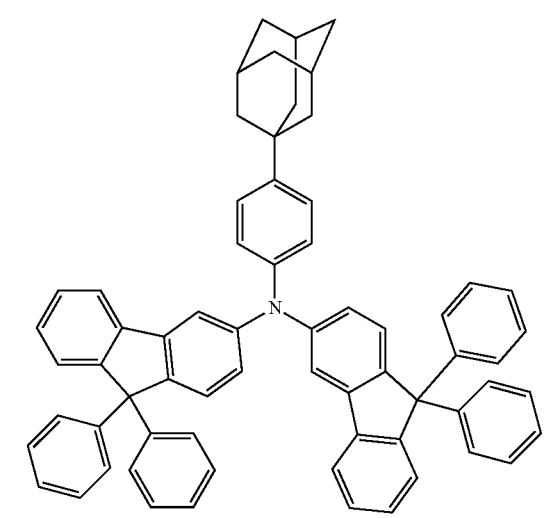
II-162
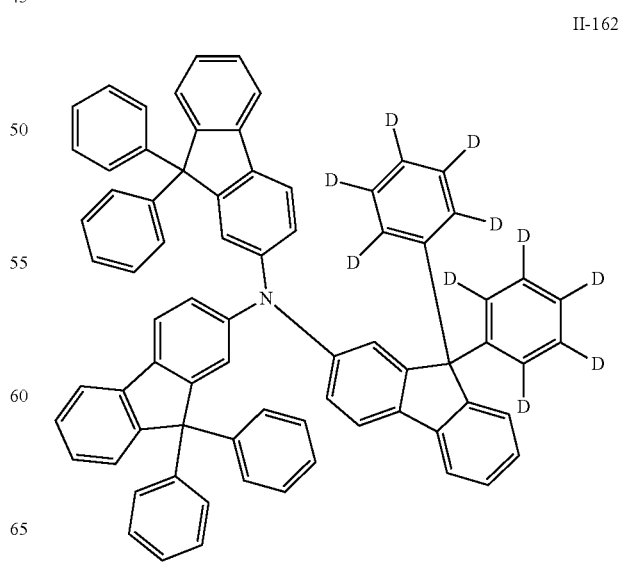

-continued

II-163
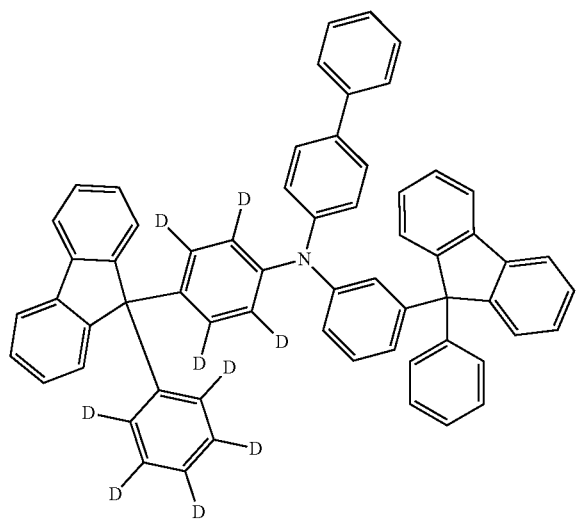

II-164
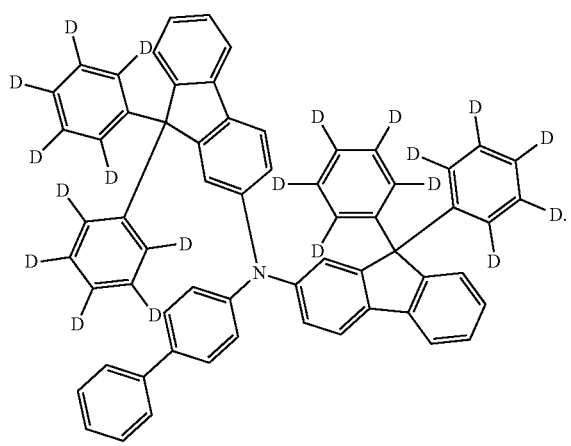

Some specific chemical structures of the triarylamine compound as shown in Formula II of the present disclosure are listed above, but the present disclosure is not limited to these chemical structures. Any group based on the structure shown in Formula I and having a substituent as defined above shall be included.

The organic layer of the organic electroluminescent device of the present disclosure can include one or more of the following functional layers: a hole injection layer, an emissive auxiliary layer, a hole transport layer, an electron blocking layer, an emissive layer, a hole blocking layer, an electron transport layer, an electron injection layer, etc. Each functional layer can consist of a single film or a plurality of films, and each film can include one material or a plurality of materials. The film thickness of each functional layer is not particularly limited and is preferably 0.01 nm to 1 μm. At least one functional layer includes the heterocyclic derivative as shown in Formula I, and preferably, the electron transport region, that is, the hole blocking layer, the electron transport layer and/or the electron injection layer, contains the heterocyclic derivative as shown in Formula I. Preferably, the hole transport region, that is, the electron blocking layer, the emissive auxiliary layer, the hole transport layer and/or the hole injection layer, contains the triarylamine compound as shown in Formula II of the present disclosure.

The present disclosure does not particularly limit the material of each film in the organic electroluminescent device, and in addition to the above-mentioned heterocyclic derivative as shown in Formula I or the triarylamine compound as shown in Formula II of the present disclosure, substances known in the art can be used. The materials in each organic functional layer of the above-mentioned organic electroluminescent device and the electrode materials on both sides of the device are introduced respectively below.

The anode material is preferably a material having a high work function to facilitate the injection of holes into the organic layer. The anode material of the present disclosure includes metals, metal oxides, metal alloys, combinations of metals and oxides, conductive polymers, etc. The anode materials include, but are not limited to, the following examples: gold, vanadium, chromium, copper, palladium, nickel, indium tin oxide (ITO), indium zinc oxide (IZO), zinc oxide, indium oxide, tin oxide:antimony ($SnO_2$:Sb), polypyrrole, etc.

The hole injection material has the function of injecting holes into the organic layer, including metal oxides, phthalocyanine compounds, aromatic amine compounds, conjugated organic materials containing multicyanos, polymer materials, etc. Examples of the hole transport material include, but are not limited to, molybdenum trioxide ($MoO_3$), copper phthalocyanine (CuPc), 4,4',4"-tris(N-3-methylphenyl-N-phenylamino)triphenylamine (m-MTDATA), 4,4',4"-tris(2-naphthyl(phenyl)amino]triphenylamine (2T-NATA), 1,4,5,8,9,11-hexaazatriphenylene (HAT-CN), (2E,2'E,2"E)-2,2',2"-(cyclopropane-1,2,3-triylene)tris(2-(perfluorophenyl)-acetonitrile), poly(3,4-ethylenedioxythiophene)/poly(styrenesulfonate) (PEDOT/PSS), etc.

The hole transport material has the function of injecting holes and balancing carriers, including aromatic amine compounds, carbazole compounds, etc. Examples of the hole transport material include, but are not limited to, the following materials: N,N'-biphenyl-N,N'-(1-naphthalenyl)-1,1'-biphenyl-4,4'-diamine (NPB), N4,N4,N4',N4'-tetrakis([1,1'-biphenyl]-4-yl)-[1,1'-biphenyl]-4,4'-diamine, 4,4'-cyclohexylidenebis[N,N-bis(4-methylphenyl)aniline] (TAPC), N,N'-diphenyl-N,N'-bis(3-methylphenyl)-[1,1'-biphenyl]-4,4'-diamine (TPD), 2,2,7,7-tetrakis(diphenylamino)-9,9-spirobifluorene (Spiro-TAD), 4,4',4"-tris(carbazol-9-yl)-triphenylamine (TCTA), etc.

The emissive auxiliary material has the function of injecting holes and balancing carriers and may also have the function of blocking electrons. The emissive auxiliary material includes aromatic amine compounds, carbazole compounds, etc. Examples of the emissive auxiliary material include, but are not limited to, the following materials: tri(biphenyl-4-yl)amine (TBA), 4,4',4"-tris(N-3-methylphenyl-N-phenylamino)triphenylamine (MTDATA), N,N'-biphenyl-N,N'-(1-naphthalenyl)-1,1'-biphenyl-4,4'-diamine (NPB), 4,4'-cyclohexylidenebis[N,N-bis(4-methylphenyl)aniline] (TAPC), 2,2,7,7-tetrakis(diphenylamino)-9,9-spirobifluorene (Spiro-TAD), 4,4',4"-tris(carbazol-9-yl)-triphenylamine (TCTA), etc.

The electron blocking material has the function of blocking electrons in the emissive layer, including aromatic amine compounds, etc. Examples of the electron blocking material include, but are not limited to, the following materials: 4,4',4"-tris(carbazol-9-yl)-triphenylamine (TCTA), N,N'-biphenyl-N,N'-(1-naphthalenyl)-1,1'-biphenyl-4,4'-diamine (NPB), etc.

The light-emitting material has the function of receiving holes and electrons and enabling them to combine to emit visible light, and according to the emitting color, can be divided into red light-emitting materials, green light-emitting materials, and blue light-emitting materials. The light-emitting material can be fluorescent materials or phosphorescent materials. The light-emitting material can act as the emissive layer alone or may be doped into the host material as the emissive layer.

The blue light-emitting material includes perylene derivatives, styrene amine derivatives, anthracene derivatives, fluorene derivatives, metal complexes, organosilicon, organoboron, etc. Examples of the blue light-emitting material include, but are not limited to, the following materials: 2,5,8,11-tetra-tert-butylperylene (TBPe), 4,4'-bis[4-(ditolylamino)styryl]biphenyl (BDAVBi), 9-[4-(2-(7-(N,N-diphenylamino)-9,9-diethylfluoren-2-yl)vinyl)phenyl]-9-phenyl-fluorene (DPAFVF), 9,10-di(2-naphthyl)anthracene (AND), bis(4,6-difluorophenylpyridine-C2,N)picolinatoiridium (FIrpic), etc.

The green light-emitting material includes coumarin dyes, quinacridone derivatives, polycyclic aromatic hydrocarbons, organosilicon compounds, pyrazoloquinoxaline derivatives, amino anthracene derivatives, hexabenzobenzene, imidazolone derivatives, thiophenopyrrole, naphthalimide, metal complexes, etc. Examples of the green light-emitting material include, but are not limited to, the following materials: coumarin 545T, N,N'-dimethylquinacridone (DMQA), 5,12-diphenylnaphthonaphthalene (DPT), tris(2-phenylpyridine)iridium (Ir(ppy)$_3$), etc.

The red light-emitting material includes DCM series materials, metal complexes, etc. Examples of the red light-emitting material include, but are not limited to, the following materials: 4-(dicyanomethylene)-2-methyl-6-(4-dimethylaminostyryl)-4h-pyran (DCM), 4-(dicyanomethylene)-2-tert-butyl-6-(1,1,7,7-tetramethyljulolidin-9-yl-vinyl)-4H-pyran (DCJTB), bis(1-phenyl-isoquinoline)(acetylacetonato)iridium(III) (Ir(piq)$_2$(acac), octaethylporphine platin (PtOEP), etc.

The hole blocking material has the function of blocking holes in the emissive layer, including heterocyclic compounds such as imidazole compounds and phenanthroline compounds. Examples of the hole blocking material include, but are not limited to, the following materials: 1,3,5-tris(N-phenyl-2-benzimidazol)benzene (TPBi), 4,7-diphenyl-1,10-phenanthroline (Bphen), etc. The hole blocking material is preferably the heterocyclic derivative as shown in Formula I of the present disclosure.

The electron transport material has the function of injecting electrons and balancing carriers, including heterocyclic compounds such as pyridine derivatives, imidazole derivatives, oxadiazole derivatives, triazole derivatives, phenanthroline derivatives and other, etc., and metal complexes. Examples of the electron transport material include, but are not limited to, the following materials: tris-(8-hydroxyquinoline)aluminum(III) (Alq$_3$), 3,3'-[5'-[3-(3-pyridinyl)phenyl] (TmPyPB), 1,3,5-tris(N-phenyl-2-benzimidazol)benzene (TPBi), 2-(4-biphenyl)-5-(4-tert-butylphenyl)-1,3,4-oxadiazole (PBD), 3-(biphenyl-4-yl)-4-phenyl-5-(4-tert-butylphenyl)-1,2,4-triazole (TAZ), 4,7-diphenyl-1,10-phenanthroline (Bphen), etc.

The electron injection material has the function of injecting electrons into the organic layer, including inorganic salts of alkali metals, alkali metal oxides, organic salts of alkali metals, alkali metal fluorides, alkali metal complexes, etc. Examples of the electron injection material include, but are not limited to, the following materials: cesium carbonate (Cs$_2$CO$_3$), lithium oxide (Li$_2$O), potassium acetate (CH$_3$COOK), lithium fluoride (LiF), 8-hydroxyquinolinolato-lithium (Liq), etc.

The cathode material is preferably a material having a low work function to facilitate the injection of electrons into the organic layer. The cathode material of the present disclosure includes metals, metal alloys, etc. The cathode includes, but is not limited to, the following examples: aluminum, silver, magnesium, calcium, magnesium-silver alloys, etc.

The preparation method of each film in the organic electroluminescent device of the present disclosure is not particularly limited, which may be a vacuum evaporation method, a sputtering method, a spin coating method, a spraying method, a silk-screen printing method, a laser transfer printing method, but is not limited thereto.

The organic electroluminescent device of the present disclosure is mainly applied to the technical field of information display and is widely applied to various information displays in the aspect of information display, such as tablet computers, flat-panel televisions, mobile phones, smart watches, digital cameras, VR, vehicle-mounted systems, wearable devices, etc.

SYNTHESIS EXAMPLE

The method for preparing the heterocyclic derivative as shown in Formula I of the present disclosure is not particularly limited, and conventional methods well known to those skilled in the art can be adopted. For example, a carbon-carbon coupling reaction, more specifically, Suzuki reaction, may be adopted, and the heterocyclic derivatives of Formula I of the present disclosure can be prepared according to the following synthetic routes.

Route one: $L_x$ and $L_y$ are not single bonds at the same time

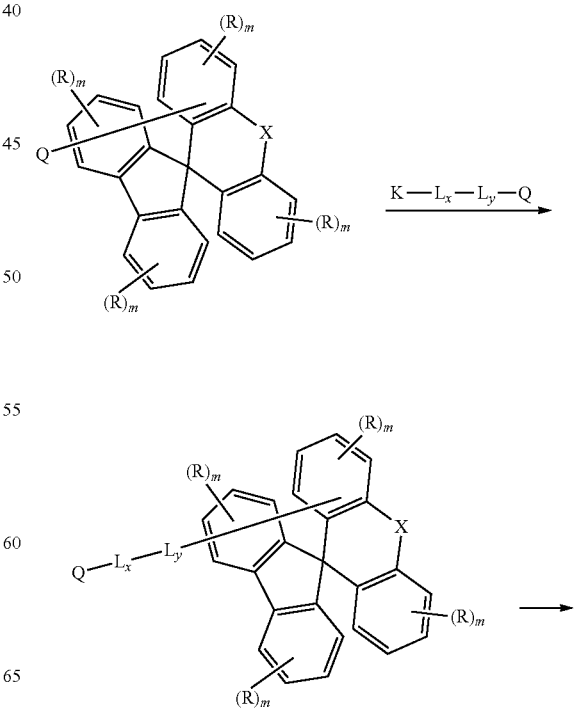

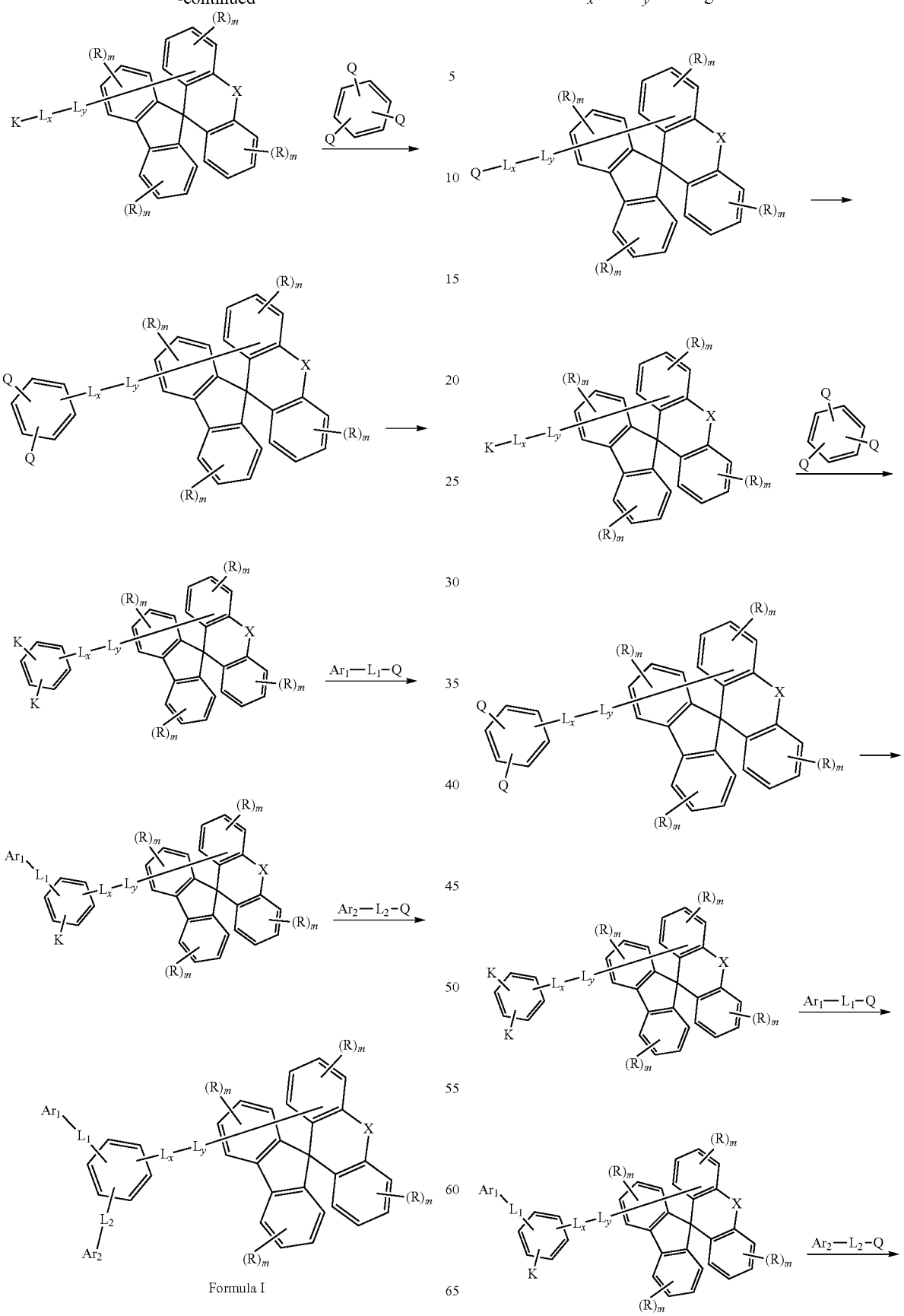

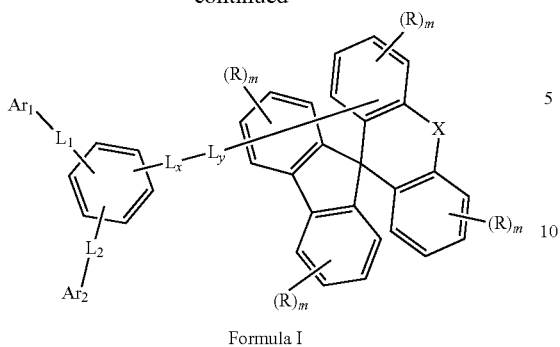

Formula I wherein, each Q is identical or different and is selected from F, Cl, Br, and I; each K is identical or different and is selected from

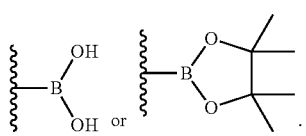

The method for preparing the triarylamine compound as shown in Formula II of the present disclosure is not particularly limited, and conventional methods well known to those skilled in the art can be adopted. For example, a carbon-nitrogen coupling reaction, more specifically, Buchwald reaction or Ullman reaction, can be adopted.

Raw materials and reagents: The raw materials and reagents used in the present disclosure are pure reagents. The raw materials or reagents used in the following synthesis examples are not particularly limited in the present disclosure and may be commercially available products or be prepared in a preparation method known to those skilled in the art.

Instruments: (1) G2-Si quadrupole-time-of-flight mass spectrometry (WATER CORPORATION, UK); (2) Vario EL cube elemental analyzer (ELEMENTAR CO., GERMANY); (3) Bruker-510 nuclear magnetic resonance spectrometer (BRUKER CO., GERMANY).

Synthesis Example 1: Synthesis of Compound 1

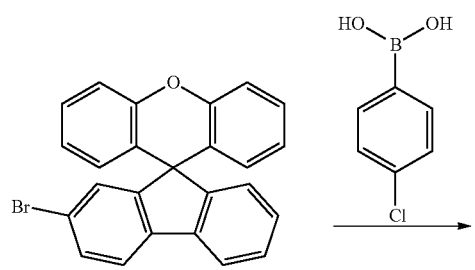

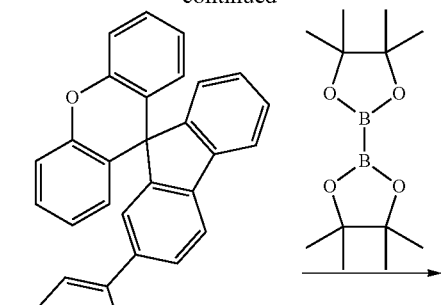

D1

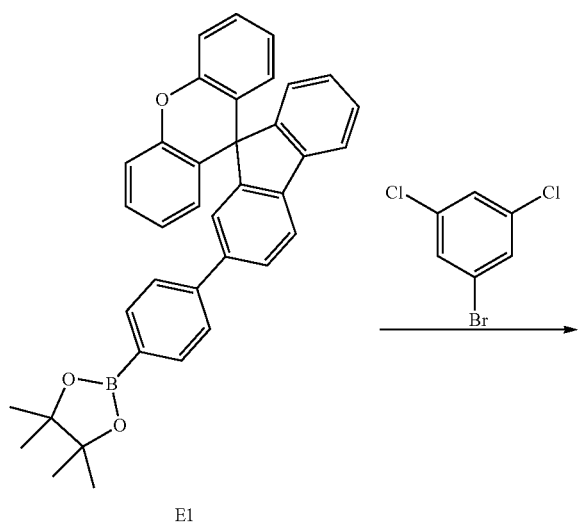

E1

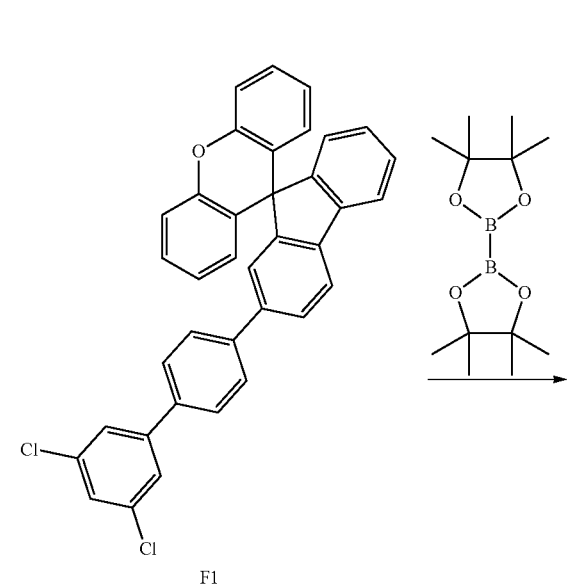

F1

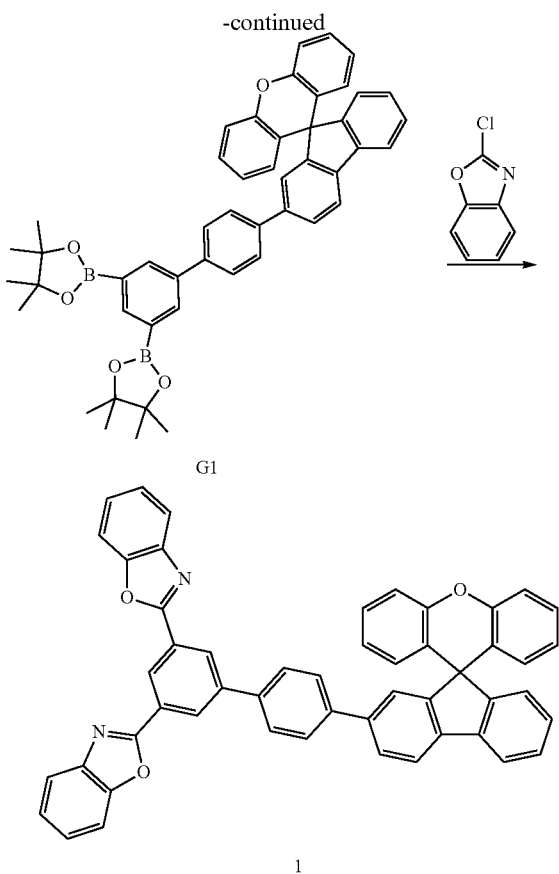

(1) Under N$_2$ atmosphere, tricyclohexyl phosphine (0.280 g, 1.0 mmol) and tris(dibenzylideneacetone)dipalladium (0.458 g, 0.5 mmol) were added to a mixed solution of 2-bromospiro[fluoren-9,9'-xanthene] (12.3 g, 30 mmol), 4-chlorophenylboronic acid (3.91 g, 25 mmol), dioxane (80 ml), and sodium carbonate solution (1.25 M, 40 ml) and refluxed overnight. The reaction solution was cooled to room temperature and extracted with ethyl acetate. The organic layer was dried with anhydrous magnesium sulfate, filtered, distilled under reduced pressure to remove the solvent, and then separated by silica gel column with dichloromethane and n-hexane (2:1) as the eluent to give 8.42 g of Compound D1 in 76% yield.

(2) Under N$_2$ atmosphere, bis(triphenylphosphine)palladium(II) dichloride (0.245 g, 0.35 mmol) was added to a mixed solution of bis(pinacolato)diboron (5.33 g, 21.0 mmol), Compound D1 (7.79 g, 17.5 mmol), potassium acetate (5.15 g, 52.5 mmol), and tetrahydrofuran (230 ml) and reacted for 4 hours under reflux. The reaction solution was cooled to room temperature, and the tetrahydrofuran solution was removed by distillation under reduced pressure. Chloroform and distilled water were added to separate the organic layer. Then, the water layer was extracted with chloroform, and the organic layer was dried with anhydrous magnesium sulfate, filtered, distilled under reduced pressure to remove the solvent, and separated by silica gel column with dichloromethane and petroleum ether (3:1) as the eluent to give 7.76 g of compound E1 in 83% yield.

(3) Under N$_2$ atmosphere, tetrakis(triphenylphosphine) palladium (0.162 g, 0.14 mmol) was added to a mixed solution of 1-bromo-3,5-dichlorobenzene (3.16 g, 14 mmol), Compound E1 (7.48 g, 14 mmol), sodium carbonate solution (2 M, 24.5 ml), ethanol (25 ml), and toluene (250 ml) and stirred under reflux overnight. The reaction solution was cooled to room temperature and extracted with chloroform. The organic layer was dried with anhydrous magnesium sulfate, filtered, distilled under reduced pressure to remove the solvent, and then separated by silica gel column with ethyl acetate and n-hexane (2:1) as the eluent to give 6.28 g of Compound F1 in 81% yield.

(4) Under N$_2$ atmosphere, tris(dibenzylideneacetone)dipalladium (0.366 g, 0.4 mmol) and tricyclohexyl phosphine (0.244 g, 0.8 mmol) were added to a mixed solution of Compound F1 (5.54 g, 10 mmol), bis(pinacolato)diboron (5.08 g, 20 mmol), sodium carbonate solution (1.25 M, 32 ml), and dioxane (65 ml) and refluxed overnight. The reaction solution was cooled to room temperature and extracted with dichloromethane. The organic layer was dried with anhydrous magnesium sulfate, filtered, distilled under reduced pressure to remove the solvent, and then separated by silica gel column with dichloromethane and n-hexane (5:2) as the eluent to give 5.38 g of Compound G1 in 73% yield.

(5) Under N$_2$ atmosphere, [1,1'-bis(diphenylphosphino)ferrocene]dichloropalladium(II) (0.732 g, 0.1 mmol) was added to a mixed solution of Compound G1 (3.68 g, 5 mmol), 2-chlorobenzoxazole (1.84 g, 12 mmol), potassium phosphate solution (2 M, 10 ml), and toluene (50 ml) and reacted for one day under reflux. The reaction solution was cooled to room temperature and extracted with dichloromethane. The organic layer was dried with anhydrous magnesium sulfate, filtered, distilled under reduced pressure to remove the solvent, and then separated by silica gel column with dichloromethane and ethanol (3:1) as the eluent to give 2.84 g of Compound 1 in 79% yield. The purity of the solid detected by HPLC was greater than or equal to 99.9%. Mass spectrum m/z, theoretical value: 718.2256, measured value: 718.2267. Theoretical element content (%) of $C_{51}H_{30}N_2O_3$: C, 85.22; H, 4.21; N, 3.90, measured element content (%): C, 85.20; H, 4.27; N, 3.94. $^1$H NMR (600 MHz, CDCl$_3$, ppm) δ: 8.28 (s, 1H), 8.22-8.19 (m, 2H), 8.07 (d, 1H), 8.02 (s, 1H), 7.95-7.90 (m, 3H), 7.89-7.83 (m, 3H), 7.66-7.62 (m, 5H), 7.60-7.57 (m, 1H), 7.46-7.42 (m, 1H), 7.40-7.33 (m, 6H), 7.31-7.24 (m, 2H), 7.11-7.06 (m, 2H), 7.02-6.95 (m, 2H). The above results confirmed that the obtained product was the target product.

Synthesis Example 2: Synthesis of Compound 6

2.58 g of Compound 6 was given according to the same steps as described in Synthesis Example 1 except that 2-chlorobenzoxazole in Synthesis Example 1 was replaced with an equimolar amount of 2-chloro-6-methyl-benzooxazole. The purity of the solid detected by HPLC was greater than or equal to 99.9%. Mass spectrum m/z, theoretical value: 746.2569, measured value: 746.2593. Theoretical element content (%) of $C_{53}H_{34}N_2O_3$: C, 85.23; H, 4.59; N, 3.75, measured element content (%): C, 85.12; H, 4.76; N, 3.83.

Synthesis Example 3: Synthesis of Compound 19

3.05 g of Compound 19 was given according to the same steps as described in Synthesis Example 1 except that 2-chlorobenzoxazole in Synthesis Example 1 was replaced with an equimolar amount of 6-bromo-2-phenylbenzo[D] oxazole. The purity of the solid detected by HPLC was greater than or equal to 99.9%. Mass spectrum m/z, theoretical value: 870.2882, measured value: 870.2894. Theoretical element content (%) of $C_{63}H_{38}N_2O_3$: C, 86.88; H, 4.40; N, 3.22, measured element content (%): C, 86.97; H, 4.30; N, 3.21.

Synthesis Example 4: Synthesis of Compound 22

2.59 g of Compound 22 was given according to the same steps as described in Synthesis Example 1 except that 4-chlorophenylboronic acid in Synthesis Example 1 was replaced with an equimolar amount of 3-chlorophenylboronic acid and 2-chlorobenzoxazole was replaced with an equimolar amount of 2-chlorooxazolo[5,4-C]pyridine. The purity of the solid detected by HPLC was greater than or equal to 99.9%. Mass spectrum m/z, theoretical value: 720.2161, measured value: 720.2180. Theoretical element content (%) of $C_{49}H_{28}N_4O_3$: C, 81.65; H, 3.92; N, 7.77, measured element content (%): C, 81.74; H, 3.98; N, 7.63. $^1$H NMR (600 MHz, $CDCl_3$, ppm) δ: 8.70 (s, 1H), 8.67 (s, 1H), 8.42 (d, 1H), 8.39 (d, 1H), 8.27 (t, 1H), 8.20 (d, 2H), 8.09-8.04 (m, 2H), 8.02 (t, 1H), 7.93 (d, 1H), 7.88-7.85 (m, 1H), 7.78-7.70 (m, 4H), 7.67-7.63 (m, 2H), 7.61-7.56 (m, 1H), 7.47-7.41 (m, 1H), 7.37-7.33 (m, 2H), 7.30-7.25 (m, 2H), 7.14-7.10 (m, 2H), 7.01-6.95 (m, 2H).

Synthesis Example 5: Synthesis of Compound 29

3.26 g of Compound 29 was given according to the same steps as described in Synthesis Example 1 except that 4-chlorophenylboronic acid in Synthesis Example 1 was replaced with an equimolar amount of 4-chloro-4-biphenylboronic acid. The purity of the solid detected by HPLC was greater than or equal to 99.9%. Mass spectrum m/z, theoretical value: 794.2569, measured value: 794.2585. Theoretical element content (%) of $C_{57}H_{34}N_2O_3$: C, 86.13; H, 4.31; N, 3.52, measured element content (%): C, 86.09; H, 4.25; N, 3.60.

Synthesis Example 6: Synthesis of Compound 37

3.03 g of Compound 37 was given according to the same steps as described in Synthesis Example 1 except that 4-chlorophenylboronic acid in Synthesis Example 1 was replaced with an equimolar amount of 7-chlorodibenzo[B,D]furan-3-ylboronic acid. The purity of the solid detected by HPLC was greater than or equal to 99.9%. Mass spectrum m/z, theoretical value: 808.2362, measured value: 808.2382. Theoretical element content (%) of $C_{57}H_{32}N_2O_4$: C, 84.64; H, 3.99; N, 3.46, measured element content (%): C, 84.70; H, 3.92; N, 3.43.

Synthesis Example 7: Synthesis of Compound 42

2.53 g of Compound 42 was given according to the same steps as described in Synthesis Example 1 except that 4-chlorophenylboronic acid in Synthesis Example 1 was replaced with an equimolar amount of 3-chloro-5-cyanophenylboronic acid. The purity of the solid detected by HPLC was greater than or equal to 99.9%. Mass spectrum m/z, theoretical value: 743.2209, measured value: 743.2237. Theoretical element content (%) of $C_{52}H_{29}N_3O_3$: C, 83.97; H, 3.93; N, 5.65, measured element content (%): C, 83.94; H, 3.98; N, 5.70.

Synthesis Example 8: Synthesis of Compound 43

2.64 g of Compound 43 was given according to the same steps as described in Synthesis Example 1 except that 4-chlorophenylboronic acid in Synthesis Example 1 was replaced with an equimolar amount of (4-chlorophenyl-2,3,5,6-d4)boronic acid. The purity of the solid detected by HPLC was greater than or equal to 99.9%. Mass spectrum m/z, theoretical value: 722.2507, measured value: 722.2533. Theoretical element content (%) of $C_{51}H_{26}D_4N_2O_3$: C, 84.74; H, 4.74; N, 3.88, measured element content (%): C, 84.69; H, 4.77; N, 3.85.

Synthesis Example 9: Synthesis of Compound 51

Under $N_2$ atmosphere, bis(triphenylphosphine)palladium (II) dichloride (0.123 g, 0.175 mmol) was added to a mixed solution of 2-bromospiro[fluoren-9,9'-xanthene] (7.20 g, 17.5 mmol), bis(pinacolato)diboron (5.33 g, 21.0 mmol), potassium acetate (4.29 g, 43.75 mmol), and tetrahydrofuran (200 ml) and reacted for 3 hours under reflux. The reaction solution was cooled to room temperature, and the tetrahydrofuran solution was removed by distillation under reduced pressure. Dichloromethane and distilled water were added to separate the organic layer. Then, the water layer was extracted with dichloromethane, and the organic layer was dried with anhydrous magnesium sulfate, filtered, distilled under reduced pressure to remove the solvent, and separated by silica gel column with dichloromethane and petroleum ether (3:1) as the eluent to give 6.98 g of compound E5 in 87% yield.

3.50 g of Compound 51 was given according to the same steps as described in Synthesis Example 1 except that Compound E5 in step (3) in Synthesis Example 1 was replaced with an equimolar amount of Compound E5, and 2-chlorobenzoxazole in step (5) was replaced with an equimolar amount of 6-bromo-2-phenylbenzo[D]oxazole. The purity of the solid detected by HPLC was greater than or equal to 99.9%. Mass spectrum m/z, theoretical value: 794.2569, measured value: 794.2597. Theoretical element content (%) of $C_{57}H_{34}N_2O_3$: C, 86.13; H, 4.31; N, 3.52, measured element content (%): C, 86.02; H, 4.39; N, 3.48. $^1$H NMR (600 MHz, $CDCl_3$, ppm) δ: 8.16 (s, 2H), 8.11-8.05 (m, 7H), 7.94 (d, 1H), 7.90 (dd, 1H), 7.80-7.74 (m, 4H), 7.69-7.63 (m, 3H), 7.61-7.57 (m, 1H), 7.46-7.39 (m, 7H), 7.38-7.34 (m, 2H), 7.30-7.26 (m, 2H), 7.12-7.07 (m, 2H), 7.03-6.96 (m, 2H).

Synthesis Example 10: Synthesis of Compound 57

3.38 g of Compound 57 was given according to the same steps as described in Synthesis Example 1 except that 2-bromospiro[fluoren-9,9'-xanthene] in Synthesis Example 1 was replaced with an equimolar amount of 3-bromospiro[fluorene-9,9'-xanthene] and 4-chlorophenylboronic acid was replaced with an equimolar amount of 3'-chloro-3-biphenylboronic acid. The purity of the solid detected by HPLC was greater than or equal to 99.9%. Mass spectrum m/z, theoretical value: 794.2569, measured value: 794.2634. Theoretical element content (%) of $C_{57}H_{34}N_2O_3$: C, 86.13; H, 4.31; N, 3.52, measured element content (%): C, 86.16; H, 4.27; N, 3.50.

Synthesis Example 11: Synthesis of Compound 65

2.41 g of Compound 65 was given according to the same steps as described in Synthesis Example 9 except that 2-bromospiro[fluoren-9,9'-xanthene] in Synthesis Example 9 was replaced with an equimolar amount of 3-bromospiro[fluorene-9,9'-xanthene] and 6-bromo-2-phenylbenzo[D]oxazole was replaced with an equimolar amount of 2-chlorobenzoxazole. The purity of the solid detected by HPLC was greater than or equal to 99.9%. Mass spectrum m/z, theoretical value: 642.1943, measured value: 642.1964. Theoretical element content (%) of $C_{45}H_{26}N_2O_3$: C, 84.10; H, 4.08; N, 4.36, measured element content (%): C, 84.21; H, 4.19; N, 4.28.

Synthesis Example 12: Synthesis of Compound 71

2.73 g of Compound 71 was given according to the same steps as described in Synthesis Example 1 except that 2-bromospiro[fluoren-9,9'-xanthene] in Synthesis Example 1 was replaced with an equimolar amount of 3-bromospiro [fluorene-9,9'-xanthene] and 4-chlorophenylboronic acid was replaced with an equimolar amount of 6-chloro-2-naphthaleneboronic acid. The purity of the solid detected by HPLC was greater than or equal to 99.9%. Mass spectrum m/z, theoretical value: 768.2413, measured value: 768.2446. Theoretical element content (%) of $C_{55}H_{32}N_2O_3$: C, 85.92; H, 4.20; N, 3.64, measured element content (%): C, 85.80; H, 4.15; N, 3.68.

Synthesis Example 13: Synthesis of Compound 77

2.69 g of Compound 77 was given according to the same steps as described in Synthesis Example 1 except that 2-bromospiro[fluoren-9,9'-xanthene] in Synthesis Example 1 was replaced with an equimolar amount of 2-bromospiro [benzo[B]fluorene-11,9'-xanthene]. The purity of the solid detected by HPLC was greater than or equal to 99.9%. Mass spectrum m/z, theoretical value: 768.2413, measured value: 768.2448. Theoretical element content (%) of $C_{55}H_{32}N_2O_3$: C, 85.92; H, 4.20; N, 3.64, measured element content (%): C, 85.96; H, 4.27; N, 3.73.

Synthesis Example 14: Synthesis of Compound 95

2.88 g of Compound 95 was given according to the same steps as described in Synthesis Example 1 except that 2-chlorobenzoxazole in Synthesis Example 1 was replaced with an equimolar amount of 2-chloro-6-trifluoromethyl-benzothiazole. The purity of the solid detected by HPLC was greater than or equal to 99.9%. Mass spectrum m/z, theoretical value: 886.1547, measured value: 886.1565. Theoretical element content (%) of $C_{53}H_{28}F_6N_2OS_2$: C, 71.77; H, 3.18; N, 3.16, measured element content (%): C, 71.61; H, 3.21; N, 3.09.

Synthesis Example 15: Synthesis of Compound 102

2.70 g of Compound 102 was given according to the same steps as described in Synthesis Example 1 except that 4-chlorophenylboronic acid in Synthesis Example 1 was replaced with an equimolar amount of 3'-chloro-3-biphenylboronic acid and 2-chlorobenzoxazole was replaced with an equimolar amount of 2-chlorobenzothiazole. The purity of the solid detected by HPLC was greater than or equal to 99.9%. Mass spectrum m/z, theoretical value: 826.2113, measured value: 826.2126. Theoretical element content (%) of $C_{57}H_{34}N_2OS_2$: C, 82.78; H, 4.14; N, 3.39, measured element content (%): C, 82.91; H, 4.18; N, 3.30.

Synthesis Example 16: Synthesis of Compound 106

2.95 g of Compound 106 was given according to the same steps as described in Synthesis Example 1 except that 2-bromospiro[fluoren-9,9'-xanthene] in Synthesis Example 1 was replaced with an equimolar amount of 3-bromospiro [fluorene-9,9'-xanthene], 4-chlorophenylboronic acid was replaced with an equimolar amount of (7-chloro-9,9-dimethyl-9H-fluoren-2-yl)boronic acid, and 2-chlorobenzoxazole was replaced with an equimolar amount of 2-chlorobenzothiazole. The purity of the solid detected by HPLC was greater than or equal to 99.9%. Mass spectrum m/z, theoretical value: 866.2426, measured value: 866.2451. Theoretical element content (%) of $C_{60}H_{38}N_2OS_2$: C, 83.11; H, 4.42; N, 3.23, measured element content (%): C, 83.10; H, 4.45; N, 3.28.

Synthesis Example 17: Synthesis of Compound 108

Under $N_2$ atmosphere, tetrakis(triphenylphosphine)palladium (0.104 g, 0.09 mmol) was added to a mixed solution of Compound G2 (13.3 g, 18 mmol), 2-chlorobenzothiazole (3.66 g, 21.6 mmol), potassium carbonate (2 M, 18 ml), and dioxane (60 ml) and reacted for 5 hours under reflux. The reaction solution was cooled to room temperature and extracted with chloroform. The organic layer was dried with anhydrous magnesium sulfate, filtered, distilled under reduced pressure to remove the solvent, and then separated by silica gel column with chloroform and n-hexane (3:2) as the eluent to give 6.16 g of Compound G2-1 in 46% yield.

Under $N_2$ atmosphere, bis(triphenylphosphine)palladium (II) dichloride (0.104 g, 0.09 mmol) was added to a mixed solution of Compound G2-1 (13.3 g, 5 mmol), 2-chlorobenzothiazole (3.66 g, 6 mmol), sodium carbonate (1.25 M, 8 ml), and dioxane (25 ml) and reacted for 8 hours under reflux. The reaction solution was cooled to room temperature and extracted with dichloromethane. The organic layer was dried with anhydrous magnesium sulfate, filtered, distilled under reduced pressure to remove the solvent, and then separated by silica gel column with dichloromethane and n-hexane (2:1) as the eluent to give 3.16 g of Compound 108 in 86% yield. The purity of the solid detected by HPLC was greater than or equal to 99.9%. Mass spectrum m/z, theoretical value: 734.2028, measured value: 734.2046. Theoretical element content (%) of $C_{51}H_{30}N_2O_2S$: C, 83.36; H, 4.11; N, 3.81, measured element content (%): C, 83.47; H, 4.12; N, 3.79. $^1$H NMR (600 MHz, CDCl$_3$, ppm) δ: 8.33 (s, 1H), 8.29 (s, 1H), 8.23-8.20 (m, 2H), 8.15-8.10 (m, 2H), 8.09-8.05 (m, 2H), 7.93 (d, 1H), 7.87 (dd, 1H), 7.80-7.77 (m, 1H), 7.74-7.70 (m, 1H), 7.68-7.62 (m, 4H), 7.61-7.56 (m, 2H), 7.52-7.48 (m, 1H), 7.46-7.42 (m, 1H), 7.41-7.33 (m, 4H), 7.30-7.25 (m, 2H), 7.22 (dd, 1H), 7.12 (dd, 1H), 7.01-6.95 (m, 2H).

Synthesis Example 18: Synthesis of Compound 153

2.65 g of Compound 153 was given according to the same steps as described in Synthesis Example 1 except that 2-bromospiro[fluoren-9,9'-xanthene] in Synthesis Example 1 was replaced with an equimolar amount of 3-bromospiro [fluorene-9,9'-thioxanthene] and 4-chlorophenylboronic acid was replaced with an equimolar amount of 3-chlorophenylboronic acid. The purity of the solid detected by HPLC was greater than or equal to 99.9%. Mass spectrum m/z, theoretical value: 734.2028, measured value: 734.2032. Theoretical element content (%) of $C_{51}H_{30}N_2O_2S$: C, 83.36; H, 4.11; N, 3.81, measured element content (%): C, 83.22; H, 4.07; N, 3.71.

Synthesis Example 19: Synthesis of Compound 164

3.02 g of Compound 164 was given according to the same steps as described in Synthesis Example 1 except that 2-bromospiro[fluoren-9,9'-xanthene] in Synthesis Example 1 was replaced with an equimolar amount of 3-bromospiro[fluorene-9,9'-thioxanthene] and 4-chlorophenylboronic acid was replaced with an equimolar amount of (7-chloro-9,9-dimethyl-9H-fluoren-2-yl)boronic acid. The purity of the solid detected by HPLC was greater than or equal to 99.9%. Mass spectrum m/z, theoretical value: 850.2654, measured value: 850.2647. Theoretical element content (%) of $C_{60}H_{38}N_2O_2S$: C, 84.68; H, 4.50; N, 3.29, measured element content (%): C, 84.59; H, 4.45; N, 3.26.

Synthesis Example 20: Synthesis of Compound 173

2.56 g of Compound 173 was given according to the same steps as described in Synthesis Example 1 except that 2-bromospiro[fluoren-9,9'-xanthene] in Synthesis Example 1 was replaced with an equimolar amount of 3-bromospiro[fluorene-9,9'-thioxanthene] and 2-chlorobenzothiazole was replaced with an equimolar amount of 2-chlorobenzothiazole. The purity of the solid detected by HPLC was greater than or equal to 99.9%. Mass spectrum m/z, theoretical value: 766.1571, measured value: 766.1585. Theoretical element content (%) of $C_{51}H_{30}N_2S_3$: C, 79.87; H, 3.94; N, 3.65, measured element content (%): C, 79.68; H, 3.83; N, 3.75.

Synthesis Example 21: Synthesis of Compound 201

3.33 g of Compound 201 was given according to the same steps as described in Synthesis Example 1 except that 2-bromospiro[fluoren-9,9'-xanthene] in Synthesis Example 1 was replaced with an equimolar amount of 2'-bromo-10-phenyl-10H-spiro[acridine-9,9'-fluorene]. The purity of the solid detected by HPLC was greater than or equal to 99.9%. Mass spectrum m/z, theoretical value: 793.2729, measured value: 793.2815. Theoretical element content (%) of $C_{57}H_{35}N_3O_2$: C, 86.23; H, 4.44; N, 5.29, measured element content (%): C, 86.32; H, 4.38; N, 5.20.

Synthesis Example 22: Synthesis of Compound 219

3.14 g of Compound 219 was given according to the same steps as described in Synthesis Example 9 except that 2-bromospiro[fluoren-9,9'-xanthene] in Synthesis Example 9 was replaced with an equimolar amount of 2'-bromo-10-phenyl-10H-spiro[acridine-9,9'-fluorene] and 2-chlorobenzothiazole was replaced with an equimolar amount of 2-(4-chlorophenyl)benzothiazole. The purity of the solid detected by HPLC was greater than or equal to 99.9%. Mass spectrum m/z, theoretical value: 901.2585, measured value: 901.2607. Theoretical element content (%) of $C_{63}H_{39}N_3S_2$: C, 83.88; H, 4.36; N, 4.66, measured element content (%): C, 83.74; H, 4.41; N, 4.74.

Synthesis Example 23: Synthesis of Compound 244

3.11 g of Compound 244 was given according to the same steps as described in Synthesis Example 9 except that 2-bromospiro[fluoren-9,9'-xanthene] in Synthesis Example 9 was replaced with an equimolar amount of 3'-bromo-10,10-dimethyl-spiro[anthracene-9(10H),9'-[9H]fluorene] and 2-chlorobenzothiazole was replaced with an equimolar amount of 5-bromo-1,2-diphenyl-1H-benzoimidazole. The purity of the solid detected by HPLC was greater than or equal to 99.9%. Mass spectrum m/z, theoretical value: 970.4035, measured value: 970.4072. Theoretical element content (%) of $C_{72}H_{50}N_4$: C, 89.04; H, 5.19; N, 5.77, measured element content (%): C, 89.18; H, 5.08; N, 5.72.

Synthesis Example 24: Synthesis of Compound 250

2.88 g of Compound 201 was given according to the same steps as described in Synthesis Example 1 except that 2-bromospiro[fluoren-9,9'-xanthene] in Synthesis Example 1 was replaced with an equimolar amount of 2-bromo-spiro[9H-fluorene-9,9'-[9H]xanthene] and 4-chlorophenylboronic acid was replaced with an equimolar amount of 3-chlorophenylboronic acid. The purity of the solid detected by HPLC was greater than or equal to 99.9%. Mass spectrum m/z, theoretical value: 718.2256, measured value: 718.2291. Theoretical element content (%) of $C_{51}H_{30}N_2O_3$: C, 85.22; H, 4.21; N, 3.90, measured element content (%): C, 85.33; H, 4.26; N, 3.80.

The target compounds in Synthesis Examples 2 to 24 are as follows:

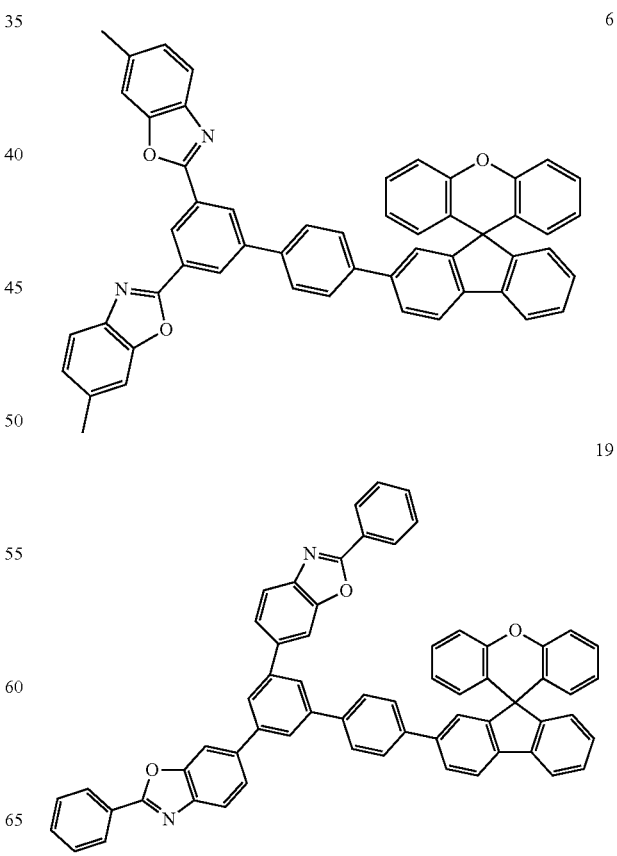

22
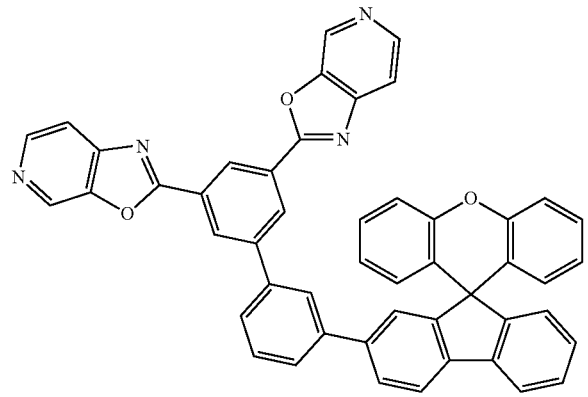
29
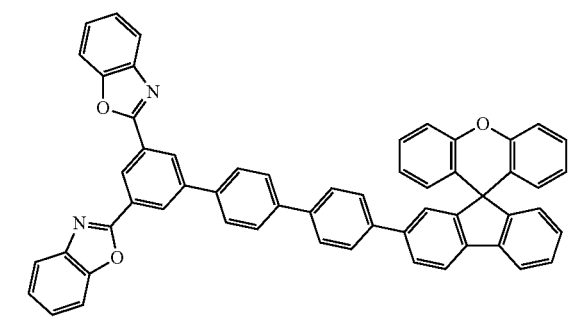
37
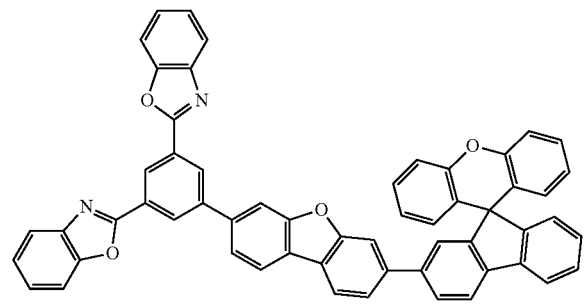
42
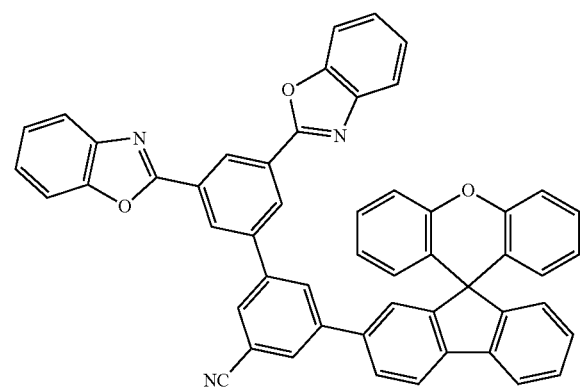
43
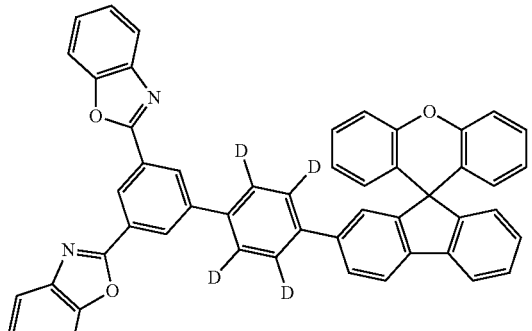
51
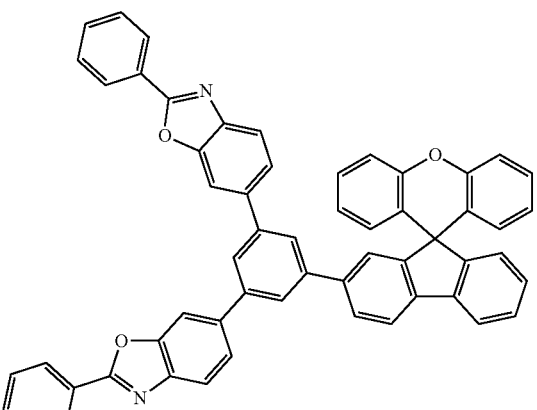
57
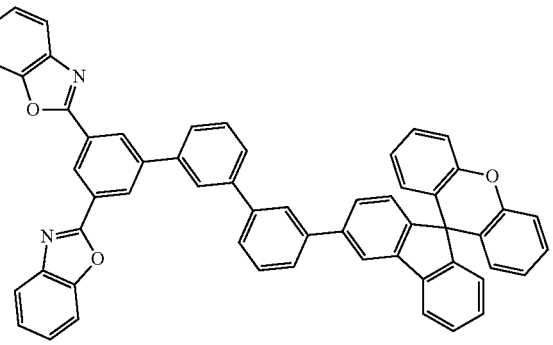
65
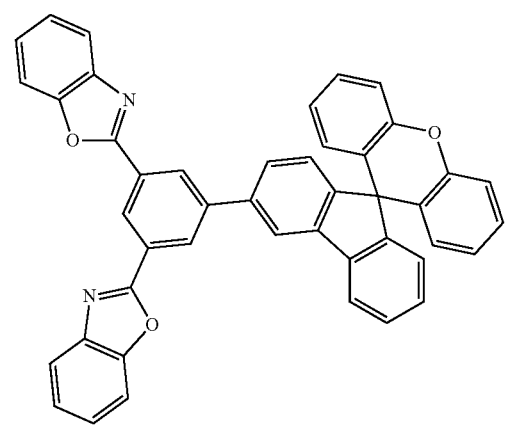

71
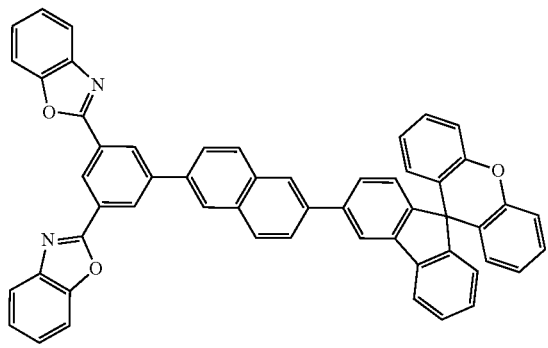
77
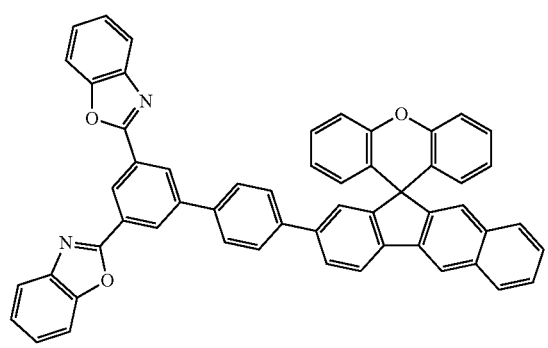
95
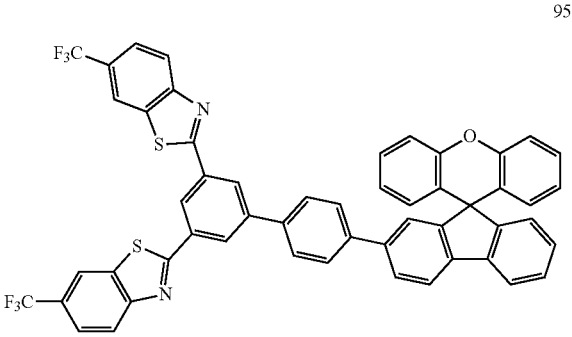
102
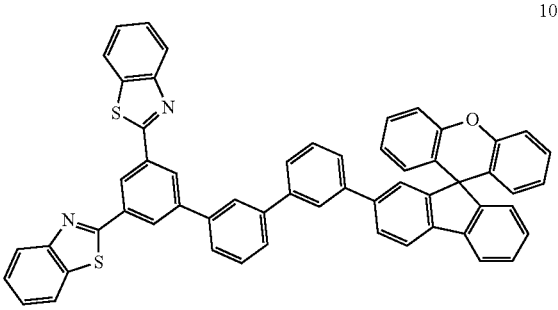
106
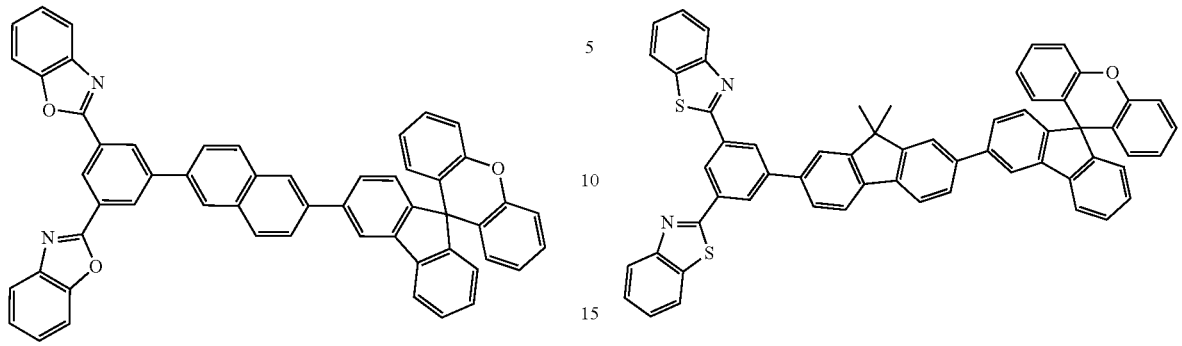
108
153
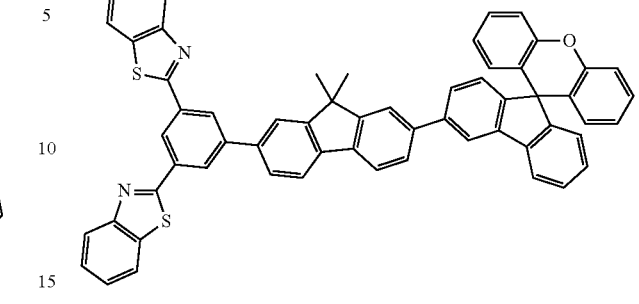
164
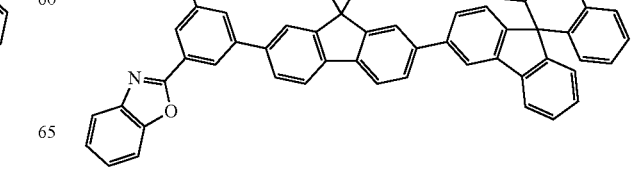

173
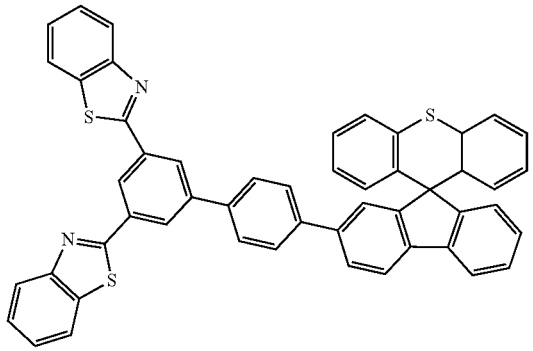
250
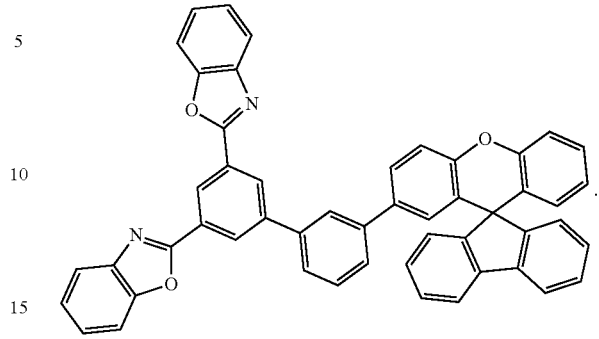
Synthesis Example 25: Synthesis of Compound II-1
201
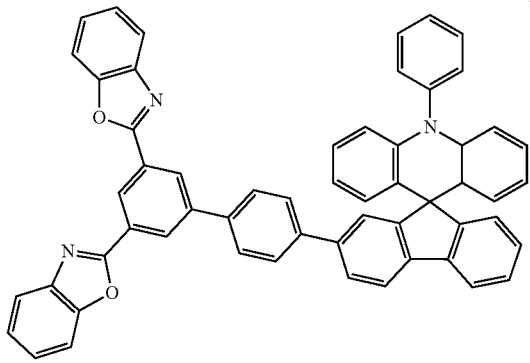
Step 1
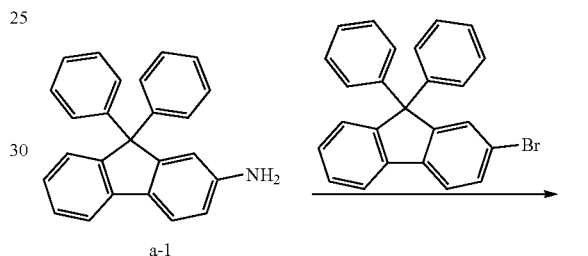
219
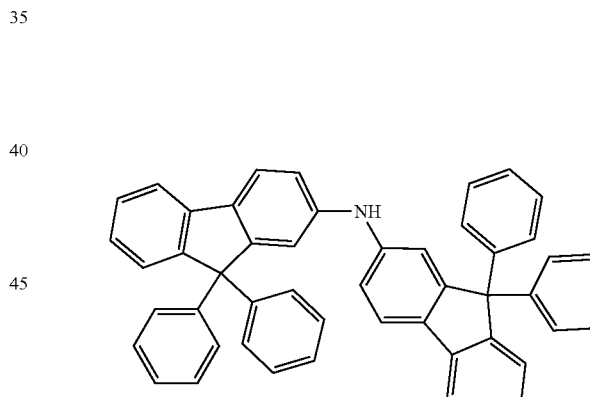
Intermediate A-1
244
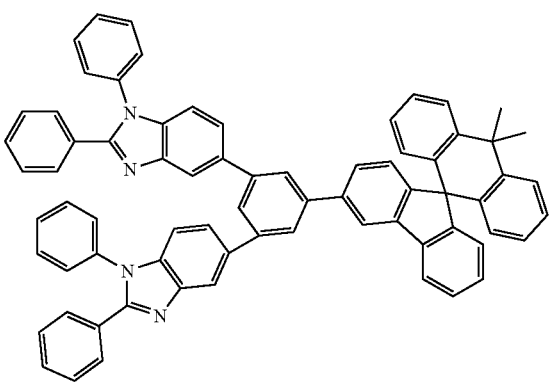
Step 2
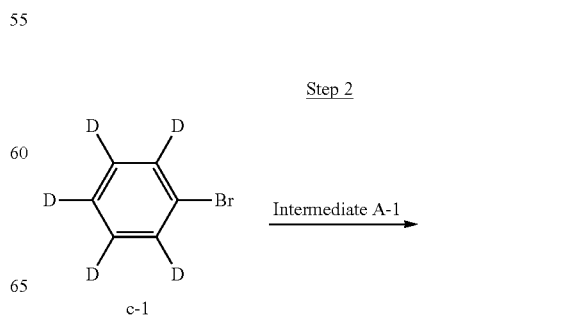

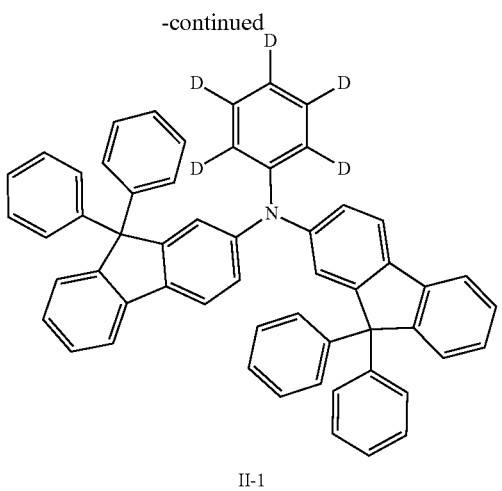

II-1

Under nitrogen protection, toluene (600 mL), a-1 (20.00 g, 0.06 mol), b-1 (23.83 g, 0.06 mol), palladium acetate (0.21 g, 0.93 mmol), sodium t-butoxide (11.3 g, 0.117 mol), and tri-tert-butyl phosphine (8 mL of toluene solution) were successively added to a 1 L flask, and reacted under reflux for 2 h. After the reaction stopped, the mixture was cooled to room temperature and filtered with Celite, and the filtrate was concentrated, recrystallized with methanol, filtered by suction, and leached with methanol to give recrystallized solid to give Intermediate A-1 (30.41 g, 78 yield). The purity of the solid detected by HPLC was greater than or equal to 99.7%.

Under nitrogen protection, toluene solvent (600 ml), c-1 (5.83 g, 36 mmol), Intermediate A-1 (23.39 g, 36 mmol), Pd$_2$(dba)$_3$ (330 mg, 0.36 mmol), BINAP (0.67 g, 1.08 mmol), and sodium t-butoxide (3.23 g, 33.6 mmol) were successively added into a 1 L flask, stirred to dissolve, and reacted for 24 hours under reflux under nitrogen protection. After the reaction was complete, the reaction solution was washed with dichloromethane and distilled water. Layers were separated and extracted. The organic layer was dried with anhydrous magnesium sulfate, filtered to remove the solvent, and then separated, purified and refined by silica gel column with cyclohexane:ethyl acetate=10:1 as the eluent to give Compound II-1 (17.89 g, 68% yield). The purity of the solid detected by HPLC was greater than or equal to 99.1%.

Mass spectrum m/z, theoretical value: 730.3396, measured value: 730.3425. Theoretical element content (%) of C$_{56}$H$_{34}$D$_5$N: C, 92.02; H, 6.07; N, 1.92, measured element content (%): C, 92.02; H, 6.08; N, 1.89.

The following target compounds were prepared according to the same method as described in Synthesis Example 25: Compound II-47 (17.43 g), with the purity of the solid detected by HPLC of greater than or equal to 99.2%. Mass spectrum m/z: 782.3693 (theoretical value: 782.3678). Theoretical element content (%) of C$_{60}$H$_{34}$D$_7$N: C, 92.03; H, 6.18; N, 1.79, measured element content (%): C, 92.05; H, 6.18; N, 1.78.

Compound II-70 (19.18 g), with the purity of the solid detected by HPLC of greater than or equal to 99.2%. Mass spectrum m/z: 806.3798 (theoretical value: 806.3709). Theoretical element content (%) of C$_{62}$H$_{38}$D$_5$N: C, 92.27; H, 5.99; N, 1.74, measured element content (%): C, 92.29; H, 5.99; N, 1.74.

Compound II-78 (19.82 g), with the purity of the solid detected by HPLC of greater than or equal to 99.6%. Mass spectrum m/z: 859.4209 (theoretical value: 859.4178). Theoretical element content (%) of C$_{66}$H$_{53}$N: C, 92.16; H, 6.21; N, 1.63, measured element content (%): C, 92.16; H, 6.28; N, 1.60.

Compound II-85 (18.19 g), with the purity of the solid detected by HPLC of greater than or equal to 99.7%. Mass spectrum m/z: 801.3411 (theoretical value: 801.3396). Theoretical element content (%) of C$_{62}$H$_{43}$N: C, 92.85; H, 5.40; N, 1.75, measured element content (%): C, 92.83; H, 5.40; N, 1.70.

Compound II-90 (20.13 g), with the purity of the solid detected by HPLC of greater than or equal to 98.8%. Mass spectrum m/z: 859.4197 (theoretical value: 859.4178). Theoretical element content (%) of C$_{66}$H$_{53}$N: C, 92.16; H, 6.21; N, 1.63, measured element content (%): C, 92.10; H, 6.20; N, 1.62.

Compound II-102 (18.92 g), with the purity of the solid detected by HPLC of greater than or equal to 99.3%. Mass spectrum m/z: 875.3584 (theoretical value: 875.3552). Theoretical element content (%) of C$_{68}$H$_{45}$N: C, 93.22; H, 5.18; N, 1.60, measured element content (%): C, 93.24; H, 5.15; N, 1.53.

The above target compounds are as follows:

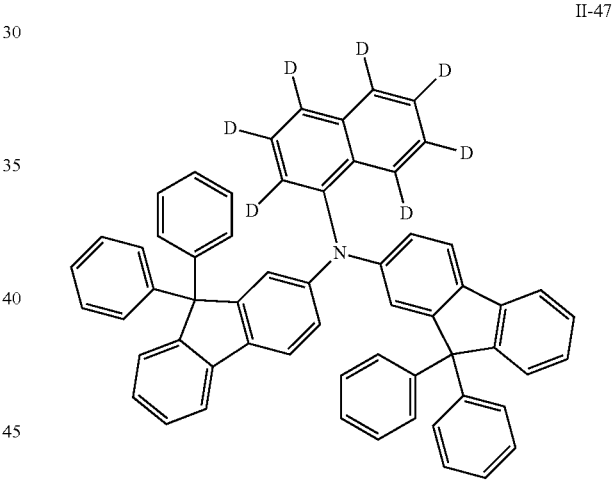

II-47

II-70

II-78

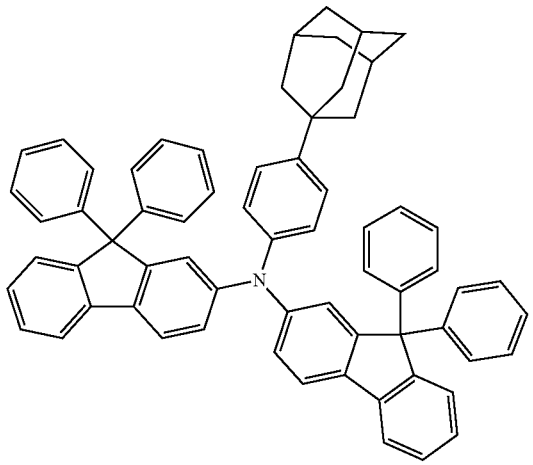

II-85

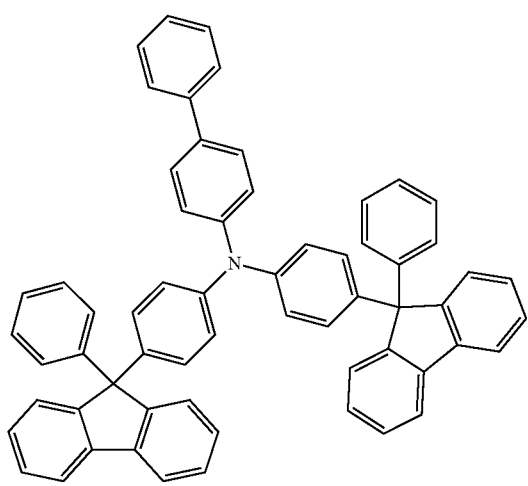

II-90

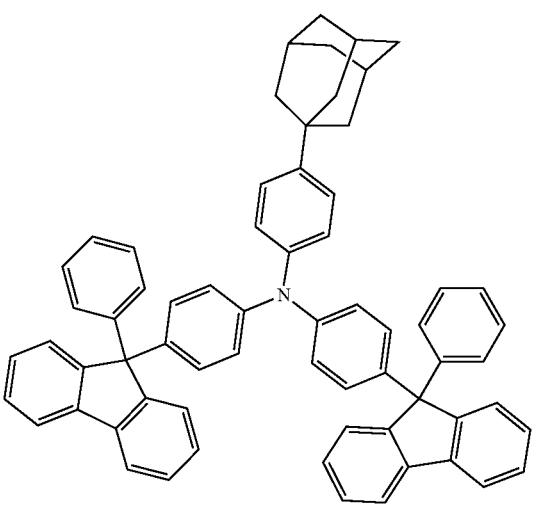

II-102

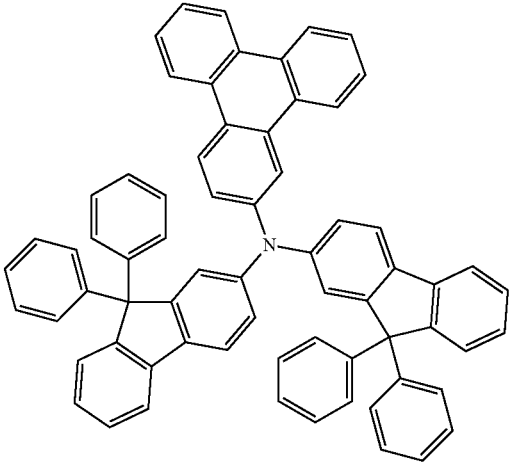

Device Example

Organic materials: all organic materials were sublimated, achieving a purity above 99.99%.

Substrate: a glass substrate was subjected to ultrasonic cleaning twice with 5% glass cleaning liquid for 20 minutes each time and then subjected to ultrasonic cleaning twice with deionized water for 10 minutes each time. The glass substrate was subjected to ultrasonic cleaning sequentially with acetone and isoacetone for 20 minutes and dried at 120° C.

Evaporation system: the devices were prepared by using a vacuum evaporation system, and the preparation was completed by consecutive evaporation under uninterrupted vacuum. The materials used herein were respectively placed in quartz crucibles with different evaporation sources, and the temperature of evaporation sources could be controlled independently. The thermal evaporation rate of the organic materials or the doped parent organic materials was generally set at 0.1 nm/s, and the evaporation rate of the doped materials was adjusted according to the doping ratio; the evaporation rate of the electrode metals was 0.4 nm/s to 0.6 nm/s. The processed glass substrate was placed in an OLED vacuum coating machine. In the film manufacture process, the vacuum degree of the system was maintained below ($5\times10^{-5}$) Pa, the organic layers and the metal electrodes were respectively evaporated by replacing mask plates, the evaporation rate was detected by an SQM160 quartz crystal film thickness detector produced by INFICON, and the film thickness was detected by a quartz crystal oscillator.

Test system: test software, a computer, K2400 SourceMeter produced by KEITHLEY, USA, and PR788 SpectraScan produced by PHOTO RESEARCH, USA were combined into a joint IVL test system to test the drive voltage, the luminous efficiency and the like of the organic electroluminescent devices.

Example 1: Preparation of Organic Electroluminescence Device 1

HAT-CN was deposited on the ITO transparent electrode by thermal evaporation as the hole injection layer with an evaporation thickness of 10 nm; NPB was deposited on the hole injection layer by thermal evaporation as the hole transport layer with an evaporation thickness of 50 nm; GH-1:GH-2:GD=47.5:47.5:5 were deposited on the hole transport layer by thermal evaporation as the emissive layer with an evaporation thickness of 30 nm; Compound 1 of the present disclosure was deposited on the emissive layer by thermal evaporation as the hole blocking layer with an evaporation thickness of 5 nm; ET-1:Liq=50:50 were deposited on the hole blocking layer by thermal evaporation as the electron transport layer with an evaporation thickness of 30 nm; Liq was deposited on the electron transport layer by thermal evaporation as the electron injection layer with an evaporation thickness of 1 nm; Al was deposited on the electron injection layer by thermal evaporation as the cathode with an evaporation thickness of 150 nm.

The device structure of the organic electroluminescent device 1 is as follows:
ITO/HAT-CN (10 nm)/NPB (50 nm)/GH-1:GH-2:GD=47.5: 47.5:5 (30 nm)/Compound 1 (5 nm)/ET-1:Liq=50:50 (30 nm)/Liq (1 nm)/Al (150 nm).

Examples 2 to 11: Preparation of Organic Electroluminescence Devices 2 to 11

The organic electroluminescent devices 2 to 11 were prepared according to the same steps as described in Example 1 except that Compound 1 in the hole blocking layer in Example 1 was replaced with Compound 6, Compound 19, Compound 22, Compound 29, Compound 37, Compound 57, Compound 77, Compound 173, Compound 219, and Compound 244 respectively.

Example 12: Preparation of Organic Electroluminescence Device 12

HAT-CN was deposited on the ITO transparent electrode by thermal evaporation as the hole injection layer with an evaporation thickness of 10 nm; NPB was deposited on the hole injection layer by thermal evaporation as the hole transport layer with an evaporation thickness of 50 nm; Compound II-21 of the present disclosure was deposited on the hole transport layer by thermal evaporation as the emissive auxiliary layer with an evaporation thickness of 10 nm; GH-1:GH-2:GD=47.5:47.5:5 were deposited on the emissive auxiliary layer by thermal evaporation as the emissive layer with an evaporation thickness of 30 nm; Compound 1 of the present disclosure was deposited on the emissive layer by thermal evaporation as the hole blocking layer with an evaporation thickness of 5 nm; ET-1:Liq=50: 50 were deposited on the hole blocking layer by thermal evaporation as the electron transport layer with an evaporation thickness of 30 nm; Liq was deposited on the electron transport layer by thermal evaporation as the electron injection layer with an evaporation thickness of 1 nm; Al was deposited on the electron injection layer by thermal evaporation as the cathode with an evaporation thickness of 150 nm.

The device structure of the organic electroluminescent device 12 is as follows:
ITO/HAT-CN (10 nm)/NPB (50 nm)/Compound II-21 (10 nm)/GH-1:GH-2:GD=47.5:47.5:5 (30 nm)/Compound 1(5 nm)/ET-1:Liq=50:50 (30 nm)/Liq(1 nm)/Al (150 nm).

Examples 13 to 25: Preparation of Organic Electroluminescence Devices 13 to 25

The organic electroluminescent devices 13 to 25 were prepared according to the same steps as described in Example 12 except that Compound 1 in the hole blocking layer in Example 12 was replaced with Compound 42, Compound 43, Compound 51, Compound 65, Compound 71, Compound 95, Compound 102, Compound 106, Compound 108, Compound 153, Compound 164, Compound 201, and Compound 250 respectively and Compound II-21 in the emissive auxiliary layer was replaced with Compound II-102, Compound II-1, Compound II-47, Compound II-70, Compound II-119, Compound II-85, Compound II-77, Compound II-79, Compound II-76, Compound II-159, Compound II-90, Compound II-73, and Compound II-78 respectively.

Comparative Examples 1 to 3: Preparation of Comparative Organic Electroluminescence Devices 1 to 3

The comparative organic electroluminescent devices 1 to 3 were prepared according to the same steps as described in Example 1 except that Compound 1 in the hole blocking layer in Example 1 was replaced with Compound R-1, Compound R-2, and Compound R-3 respectively.

Comparative Examples 4 to 6: Preparation of Comparative Organic Electroluminescence Devices 4 to 6

The comparative organic electroluminescent devices 4 to 6 were prepared according to the same steps as described in Example 12 except that Compound 1 in the hole blocking layer in Example 12 was replaced with Compound 1, Compound R-1 and Compound R-1 respectively and Compound II-1 in the emissive auxiliary layer was replaced with Compound HT-1, Compound HT-2, and Compound HT-2 respectively.

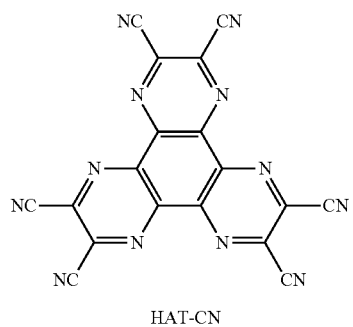

HAT-CN

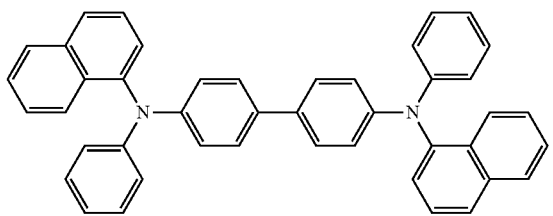

NPB

-continued
ET-1
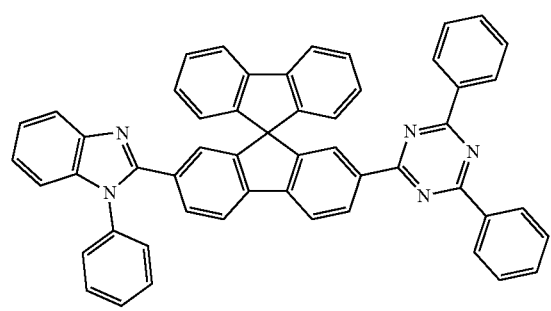
GH-1
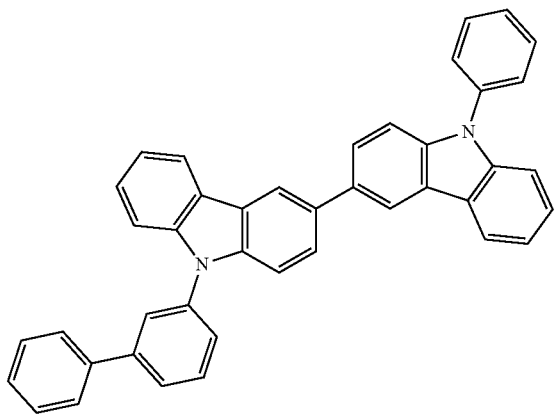
GH-2
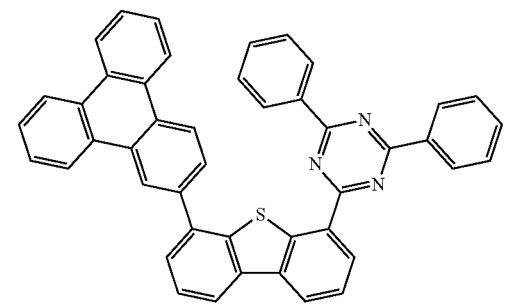
GD
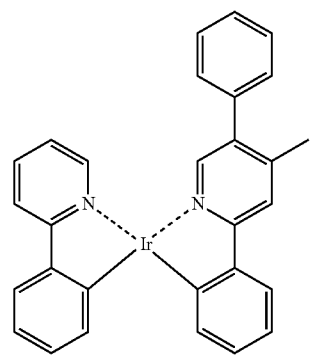
-continued
R-1
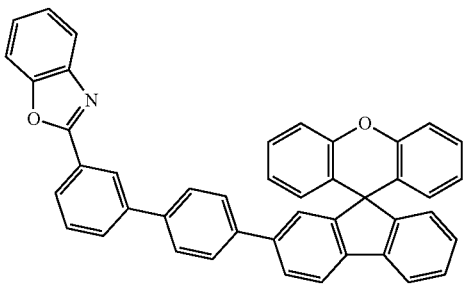
R-2
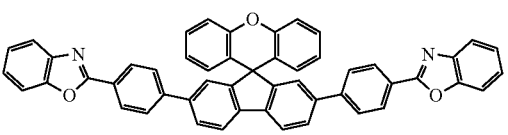
R-3
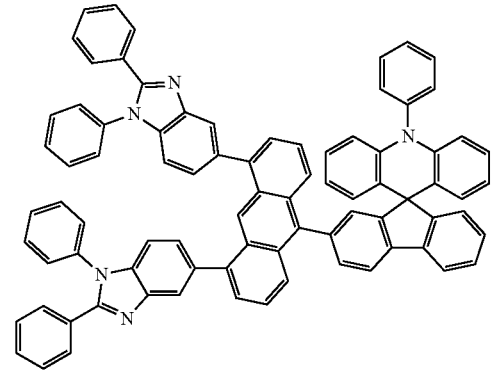
HT-1
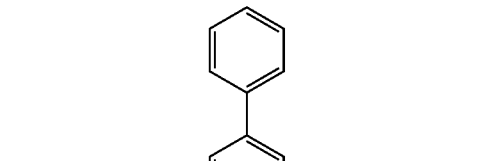
HT-2
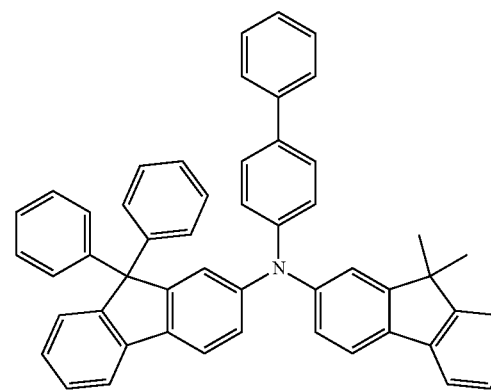

The test results of luminescence characteristics of the organic electroluminescence devices prepared in Examples 1 to 25 and Comparative Examples 1 to 6 of the present disclosure are shown in Table 1.

TABLE 1

Luminescence characteristic test data of organic electroluminescent devices

| Example | Hole blocking material | Emissive auxiliary material | Drive voltage (V) (@10 mA/cm$^2$) | luminous efficiency [cd/A] (@10 mA/cm$^2$) |
|---|---|---|---|---|
| Example 1 | Compound 1 | — | 4.23 | 66.35 |
| Example 2 | Compound 6 | — | 4.39 | 63.12 |
| Example 3 | Compound 19 | — | 4.28 | 65.51 |
| Example 4 | Compound 22 | — | 4.46 | 61.45 |
| Example 5 | Compound 29 | — | 4.25 | 66.14 |
| Example 6 | Compound 37 | — | 4.40 | 62.59 |
| Example 7 | Compound 57 | — | 4.26 | 66.07 |
| Example 8 | Compound 77 | — | 4.48 | 60.27 |
| Example 9 | Compound 173 | — | 4.24 | 66.29 |
| Example 10 | Compound 219 | — | 4.49 | 60.06 |
| Example 11 | Compound 244 | — | 4.50 | 59.24 |
| Example 12 | Compound 1 | Compound II-21 | 3.82 | 76.42 |
| Example 13 | Compound 42 | Compound II-102 | 4.01 | 72.91 |
| Example 14 | Compound 43 | Compound II-1 | 3.81 | 76.86 |
| Example 15 | Compound 51 | Compound II-47 | 3.85 | 75.71 |
| Example 16 | Compound 65 | Compound II-70 | 3.84 | 76.01 |
| Example 17 | Compound 71 | Compound II-119 | 3.97 | 73.67 |
| Example 18 | Compound 95 | Compound II-85 | 4.03 | 72.08 |
| Example 19 | Compound 102 | Compound II-77 | 3.89 | 74.94 |
| Example 20 | Compound 106 | Compound II-79 | 3.93 | 74.12 |
| Example 21 | Compound 108 | Compound II-76 | 3.91 | 74.41 |
| Example 22 | Compound 153 | Compound II-159 | 3.88 | 75.02 |
| Example 23 | Compound 164 | Compound II-90 | 3.96 | 73.93 |
| Example 24 | Compound 201 | Compound II-73 | 3.99 | 73.04 |
| Example 25 | Compound 250 | Compound II-78 | 3.87 | 75.33 |
| Comparative Example 1 | R-1 | — | 5.14 | 50.67 |
| Comparative Example 2 | R-2 | — | 5.10 | 52.10 |
| Comparative Example 3 | R-3 | — | 5.12 | 51.84 |
| Comparative Example 4 | Compound 1 | HT-1 | 4.18 | 68.74 |
| Comparative Example 5 | Compound 1 | HT-2 | 4.16 | 69.15 |
| Comparative Example 6 | R-1 | HT-2 | 4.85 | 55.34 |

As can be seen from Table 1, devices 1 to 11 had lower drive voltages and higher luminous efficiency than comparative devices 1 to 3. This shows that the heterocyclic derivative of Formula I of the present disclosure has good electron mobility and good hole blocking performance and can effectively block holes in the emissive layer to enable electrons and holes to effectively form excitons in the emissive layer.

Compared with the comparative devices 4 to 6, the organic electroluminescent devices 12 to 25 had lower drive voltages and higher luminous efficiency. This shows that the triarylamine compound as shown in Formula II of the present disclosure has high hole mobility and can effectively transport holes. Meanwhile, it also shows that the electron transport region where the hole blocking layer containing the heterocyclic derivative of Formula I is located and the hole transport region where the emissive auxiliary layer containing the triarylamine compound of Formula II is located balance the injection and transport of electrons and holes well, which reduces the quenching of excitons and improves the recombination probability of carriers, and thus the device has low drive voltage and high luminous efficiency.

It is to be noted that the present disclosure has been described in particular through some embodiments, but without departing from the principle of the present disclosure, modifications in various forms or details may be made to the present disclosure by those of ordinary skill in the art, and such modifications fall within the scope of the present disclosure.

What is claimed is:
1. A heterocyclic derivative, having a structure as shown in Formula I:

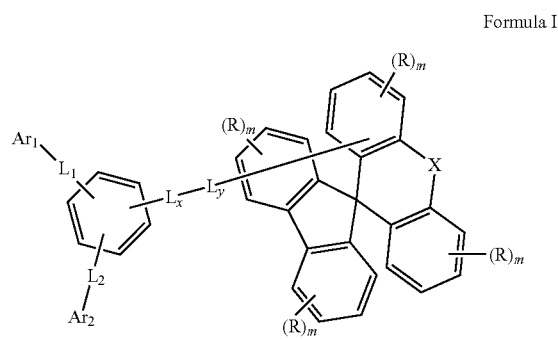

Formula I wherein Ar$_1$ and Ar$_2$ are identical or different and selected from the following group:

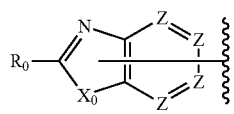

wherein $R_0$ is selected from one of hydrogen, deuterium, halogen, cyano, nitro, C1 to C30 alkyl, C3 to C30 cycloalkyl, C6 to C60 aryl or C3 to C60 heteroaryl, $X_0$ is selected from one of O, S, N($R_x$) or C($R_x$)$_2$, wherein $R_x$ is selected from one of C1 to C30 alkyl, C3 to C30 cycloalkyl, C6 to C60 aryl or C3 to C60 heteroaryl, Z is selected from C($R_y$) or N, wherein $R_y$ is selected from one of hydrogen, deuterium, halogen, cyano, nitro, C1 to C30 alkyl, C3 to C30 cycloalkyl, C2 to C30 alkenyl, C2 to C30 alkynyl, C6 to C60 aryl or C3 to C60 heteroaryl, or two adjacent groups are joined to form a ring;

X is selected from one of O, S, N(Art), C(Ar)$_2$ or Si(Ar)$_2$, wherein Ar is selected from one of C1 to C30 alkyl, C3 to C30 cycloalkyl, C6 to C60 aryl or C3 to C60 heteroaryl;

m is selected from 0, 1, 2, 3 or 4, and R is identically or differently selected from one of deuterium, cyano, nitro, C1 to C30 alkyl, C3 to C30 cycloalkyl, C2 to C30 alkenyl, C2 to C30 alkynyl, C6 to C60 aryl or C3 to C60 heteroaryl, or two adjacent groups are joined to form a ring;

$L_x$ and $L_y$ are independently selected from one of a single bond, C1 to C30 alkylene, C1 to C30 cycloalkylene, C6 to C60 arylene or C3 to C60 heteroarylene; and $L_1$ and $L_2$ are independently selected from one of a single bond, C6 to C60 arylene or C3 to C60 heteroarylene;

wherein said alkyl, cycloalkyl, aryl, heteroaryl, alkenyl, alkynyl, alkylene, cycloalkylene, arylene, and heteroarylene are unsubstituted or substituted with at least one substituent selected from deuterium, halogen, cyano, nitro, C1 to C30 alkyl, C3 to C30 cycloalkyl, C6 to C60 aryl, C3 to C60 heteroaryl and C6 to C60 amine.

2. The heterocyclic derivative according to claim 1, wherein $L_x$ and $L_y$ are independently selected from one of a single bond, adamantylene, camphanylene, norbornylene, phenylene, biphenylene, terphenylene, naphthylene, phenanthrylene, triphenylenylene, fluorenylene, benzofluorenylene, spirodifluorenylene, benzospirodifluorenylene, dibenzofuranylene, dibenzothiophenylene, carbazolylene, quinolinylene, isoquinolinylene, naphthyridinylene, quinoxalinylene, quinazolinylene or phenanthrolinylene; and $L_1$ and $L_2$ are independently selected from a single bond or one of the following groups:

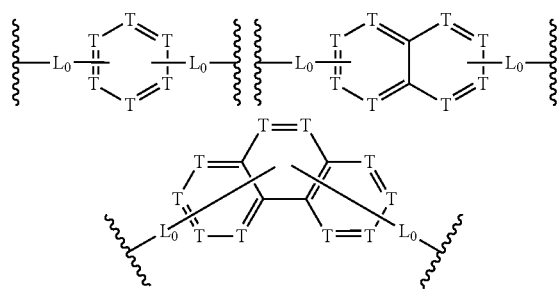

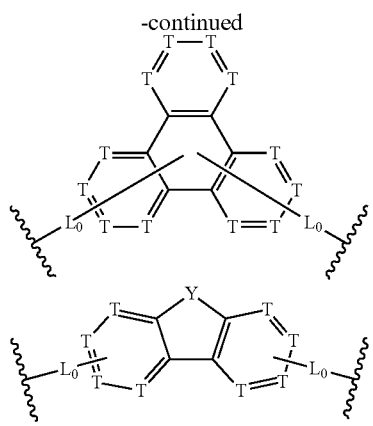

wherein T is identically or differently selected from N or C($R_m$), wherein $R_m$ is selected from one of hydrogen, deuterium, cyano, nitro, C1 to C30 alkyl, C3 to C30 cycloalkyl, C6 to C60 aryl C3 to C60 heteroaryl;

Y is selected from O, S, N($R_n$) or C($R_n$)$_2$, wherein $R_n$ is selected from one of hydrogen, deuterium, C1 to C30 alkyl, C3 to C30 cycloalkyl, C2 to C30 alkenyl, C2 to C30 alkynyl, C6 to C60 aryl or C3 to C60 heteroaryl, or two adjacent groups are joined to form a ring; and $L_0$ is identically or differently selected from one of a single bond, C6 to C60 arylene or C3 to C60 heteroarylene.

3. The heterocyclic derivative according to claim 1, wherein $Ar_1$ and $Ar_2$ are independently selected from one of the following groups:

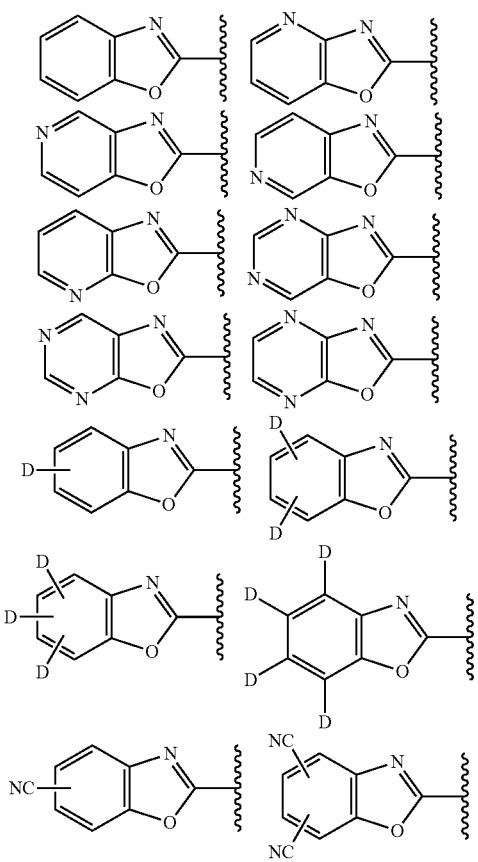

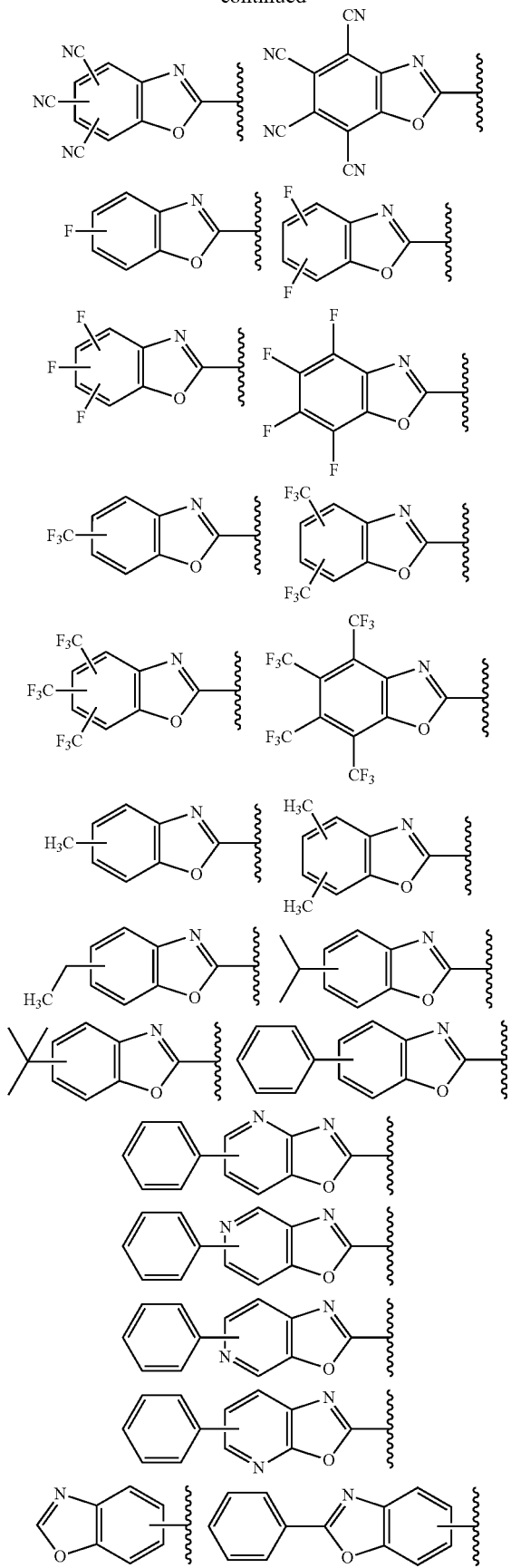
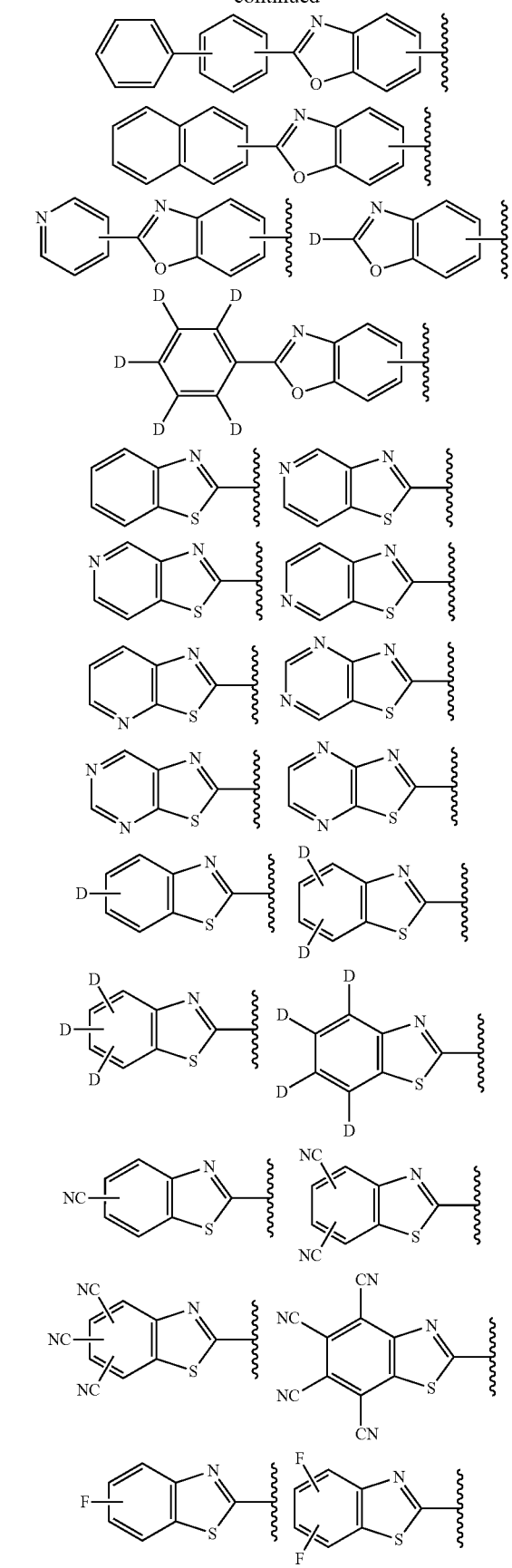

-continued
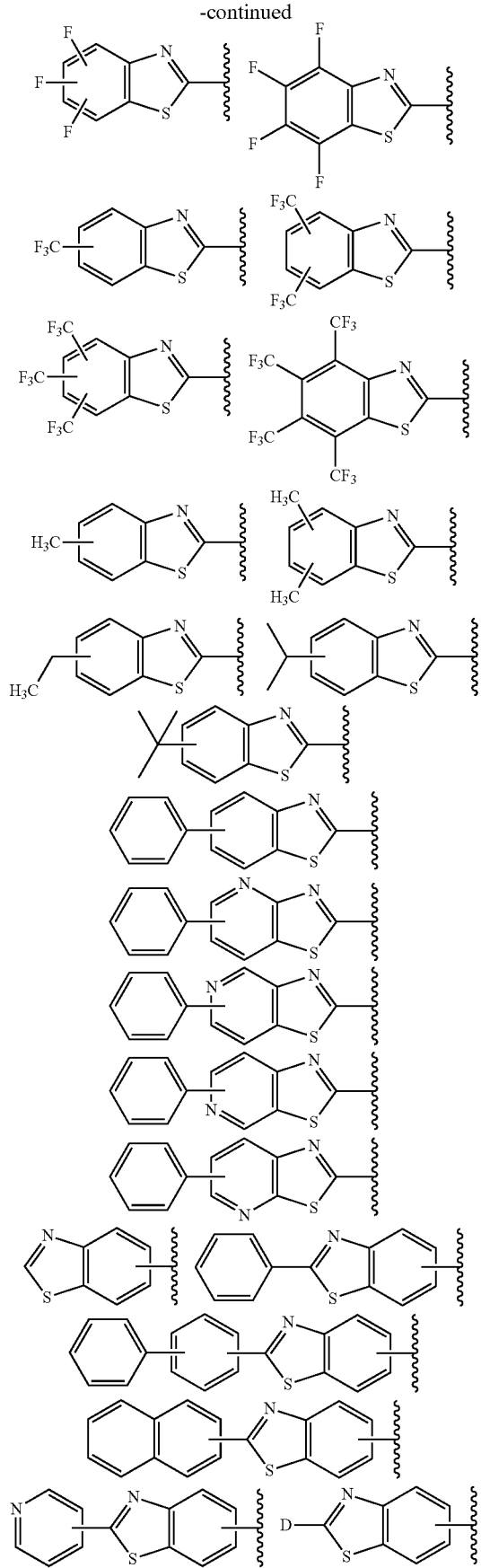
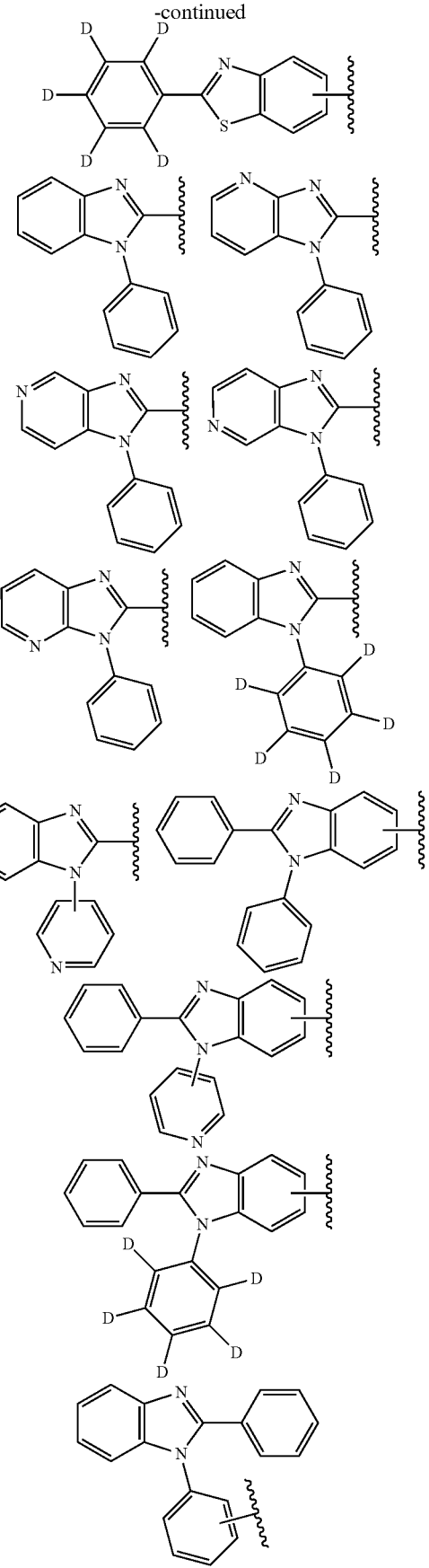

213
-continued
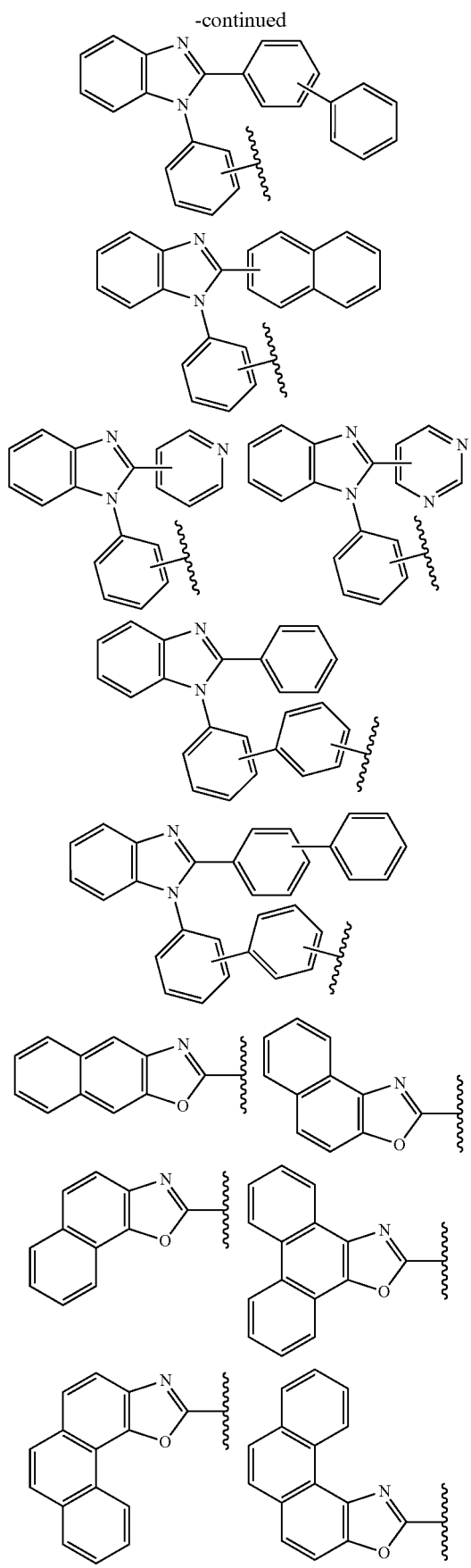
214
-continued
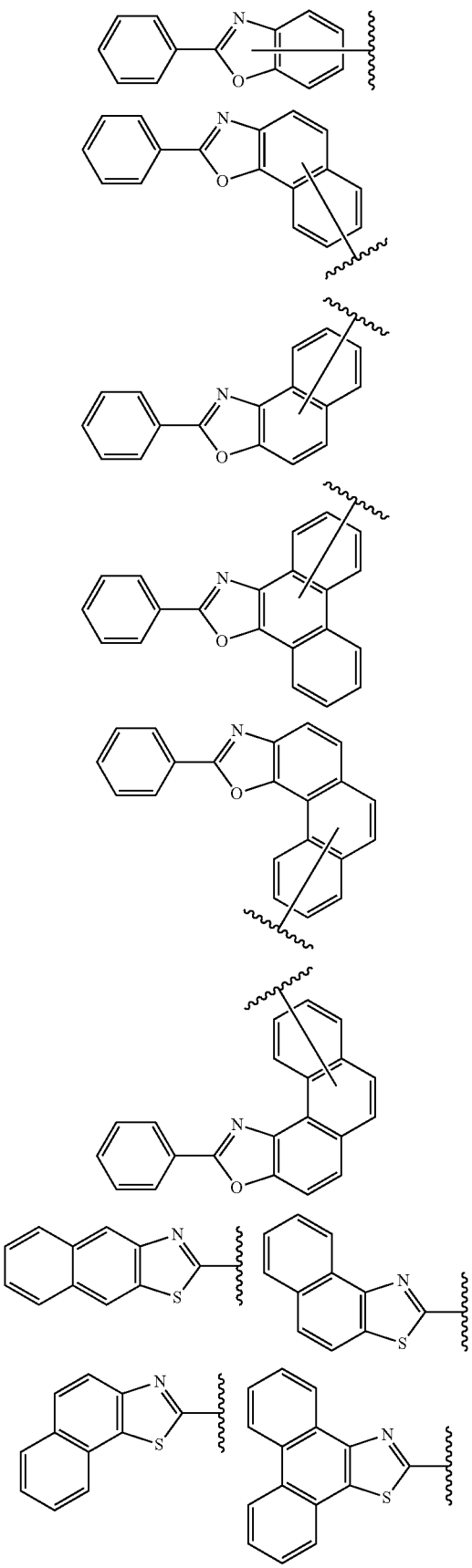

-continued
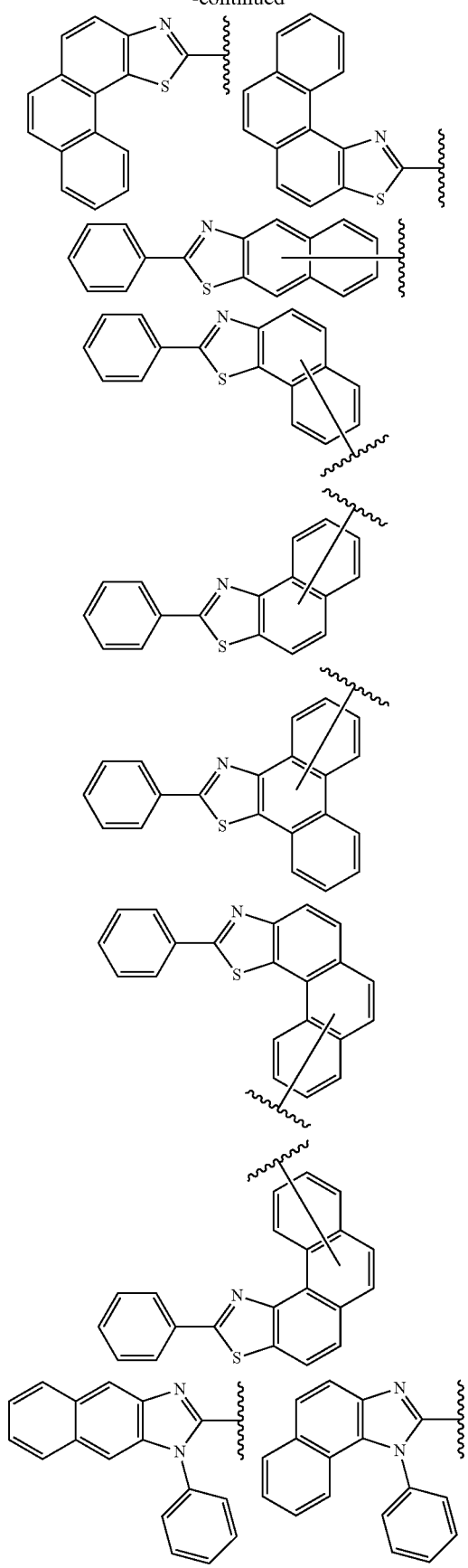
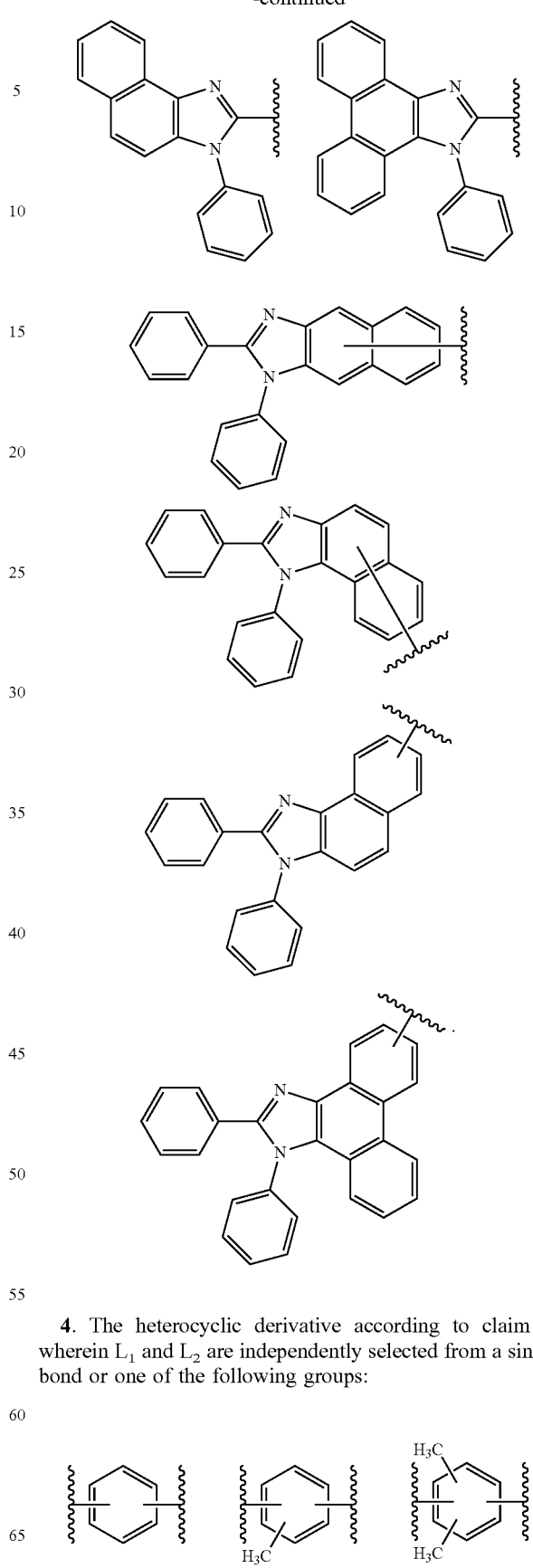
4. The heterocyclic derivative according to claim 1, wherein $L_1$ and $L_2$ are independently selected from a single bond or one of the following groups:
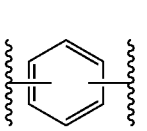 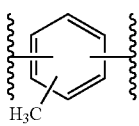 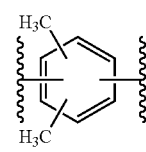

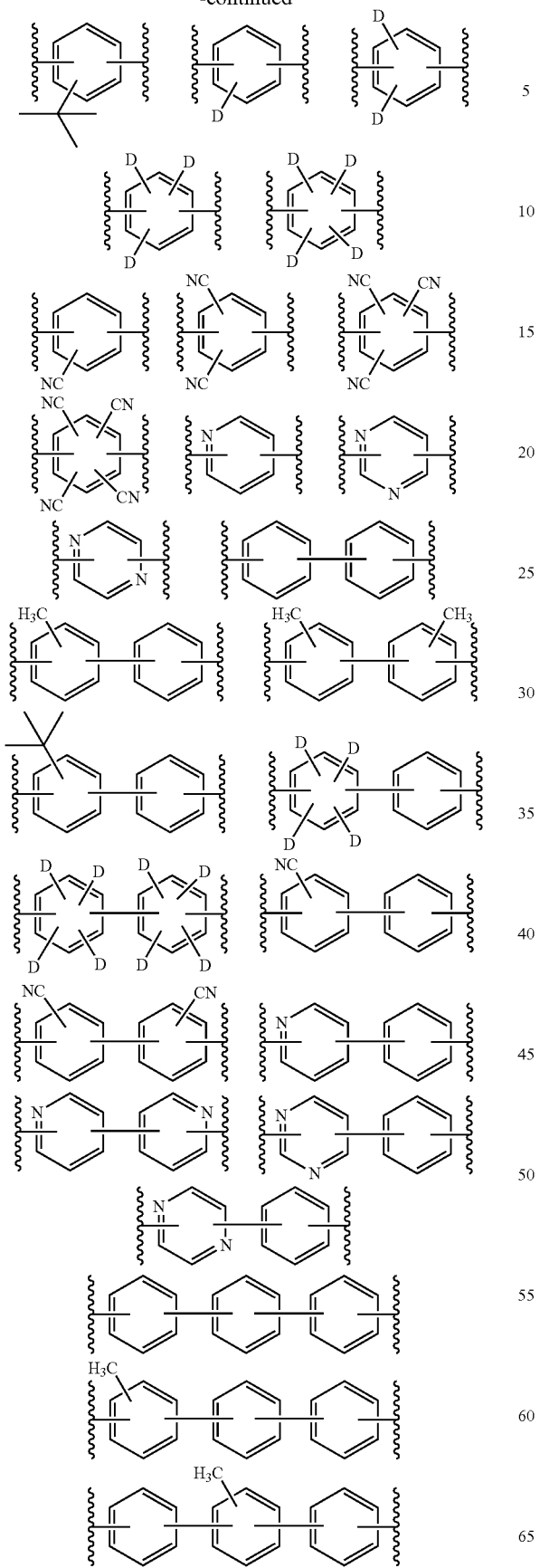
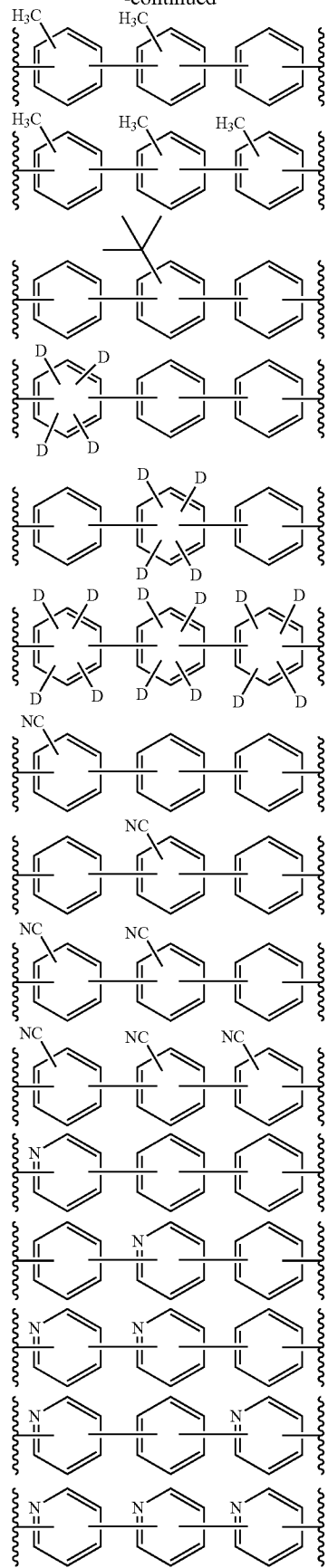

219
-continued
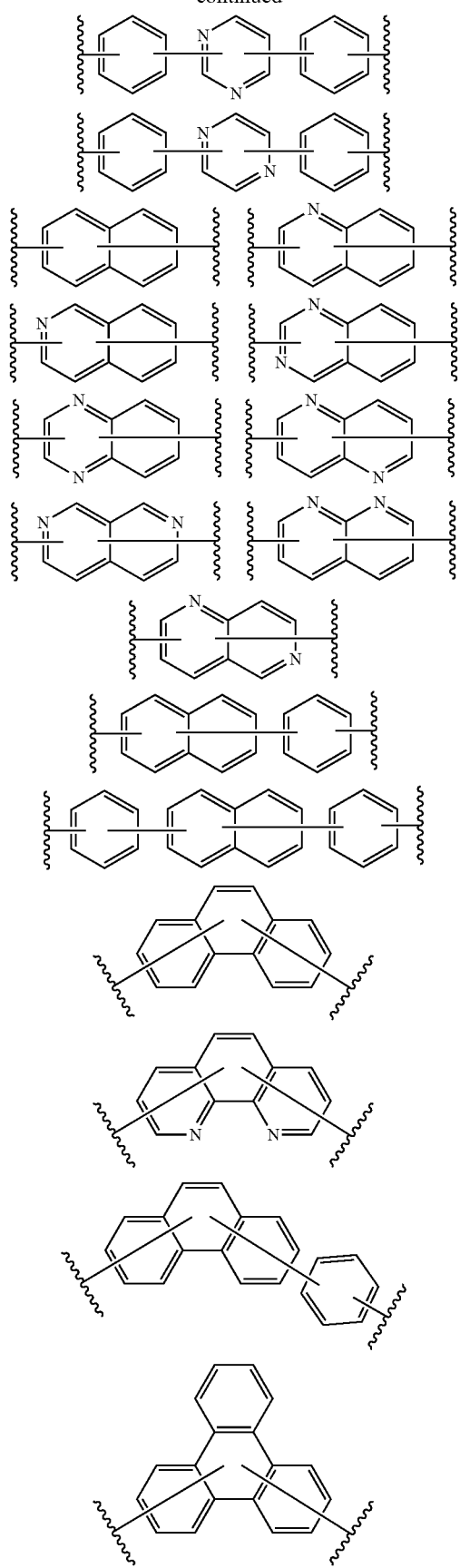
220
-continued
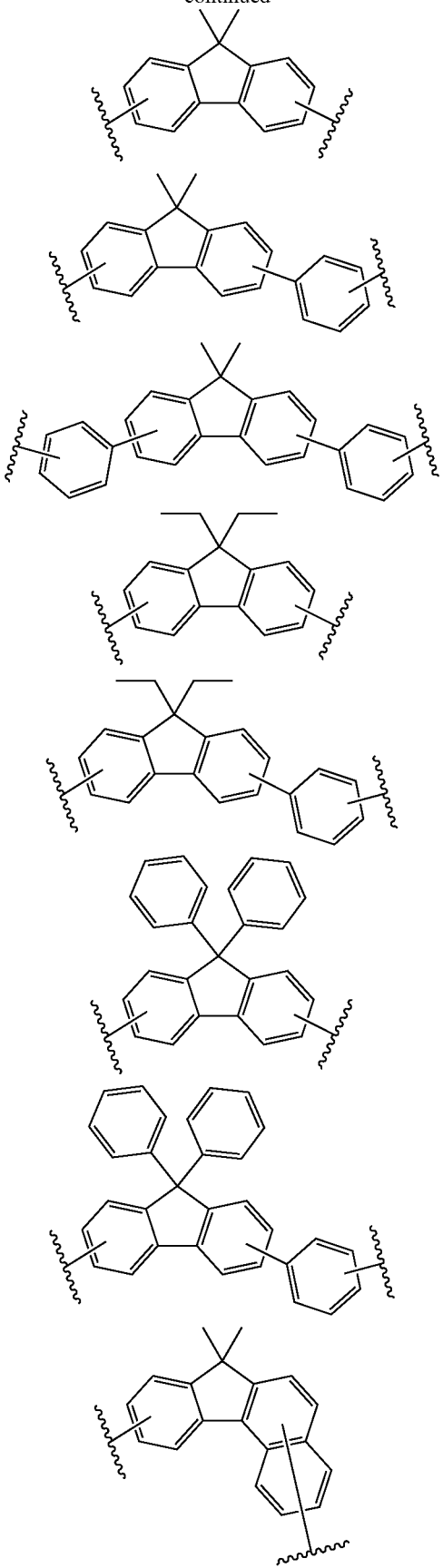

221
-continued
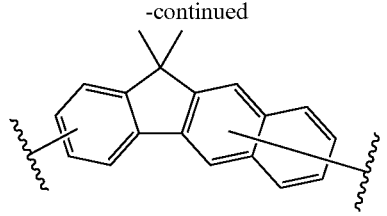
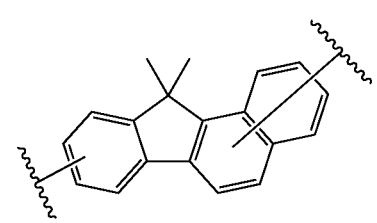
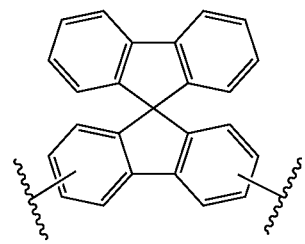
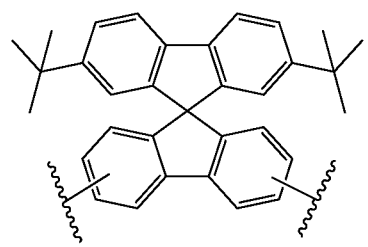
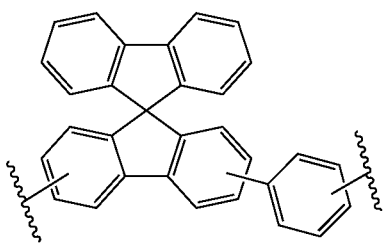
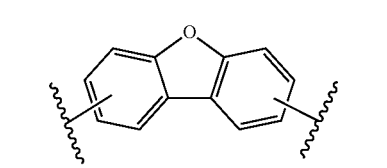
222
-continued
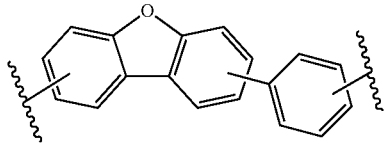
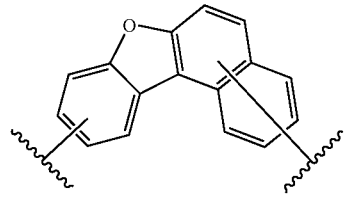
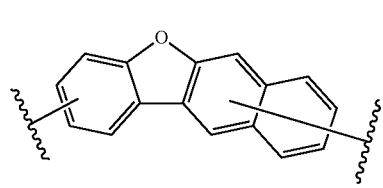
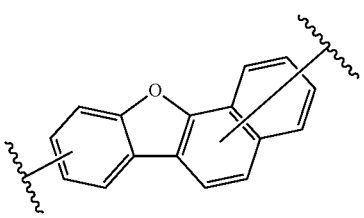
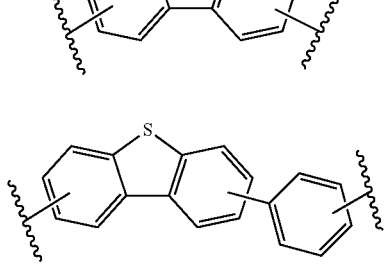
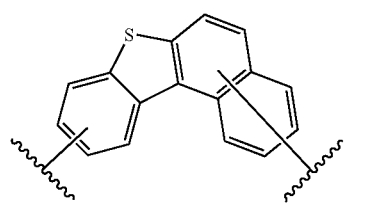
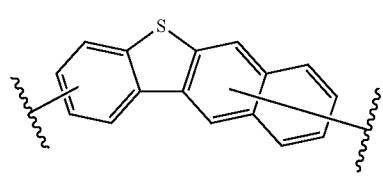

223
-continued
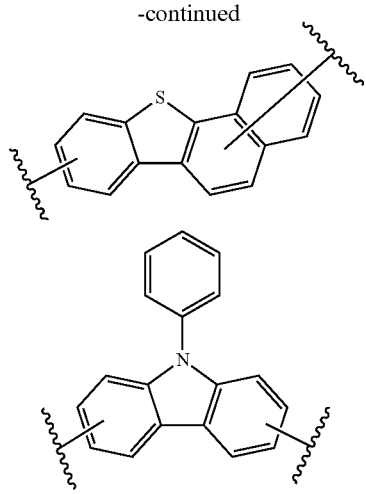
224
-continued
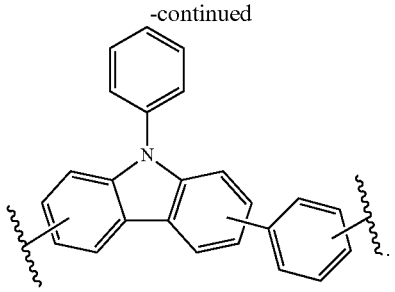
5. The heterocyclic derivative according to claim 1, selected from the following compounds:
1
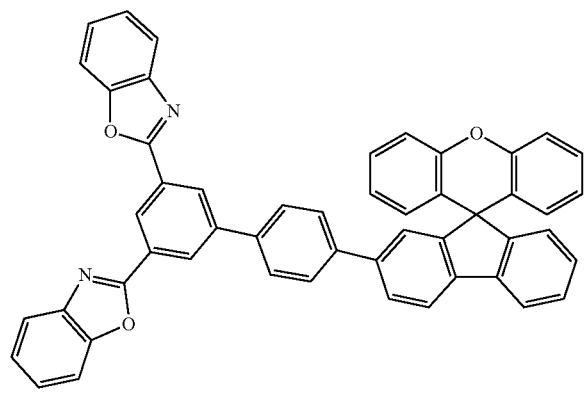
2
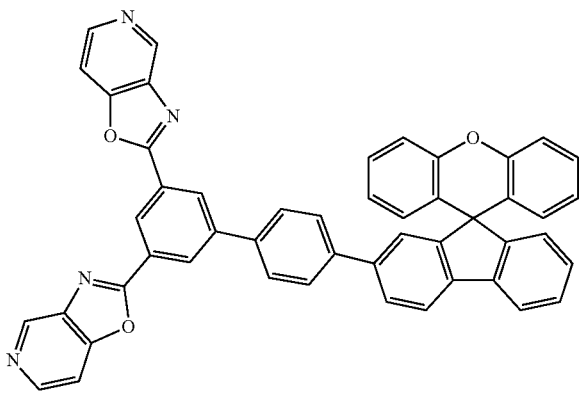
3
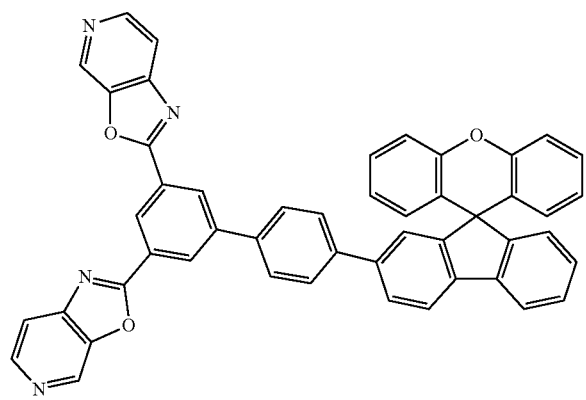
4
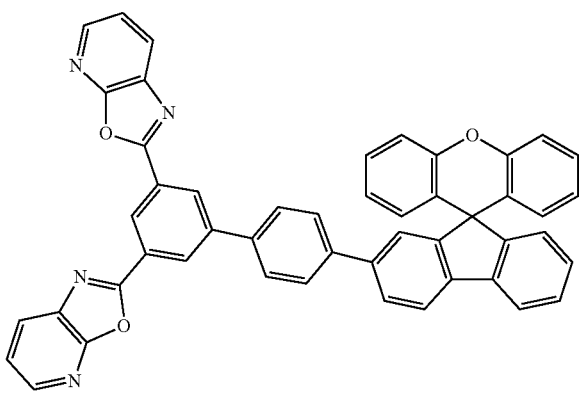

-continued
5
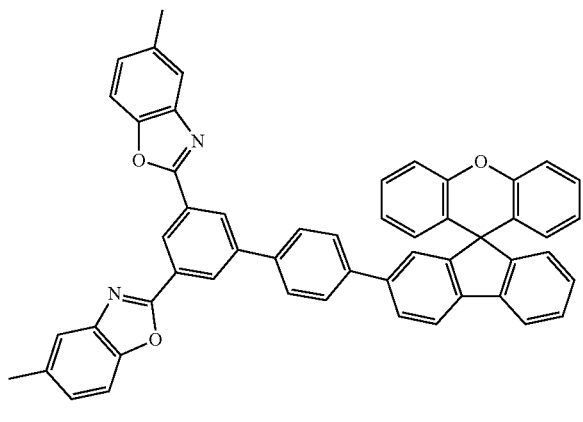
6
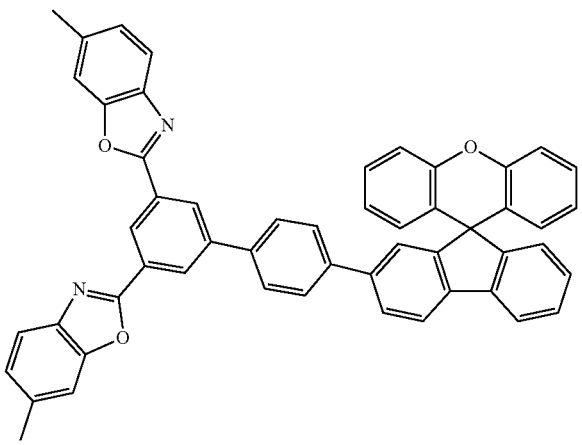
7
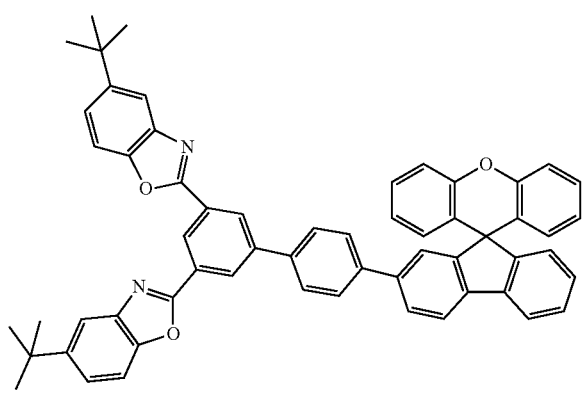
8
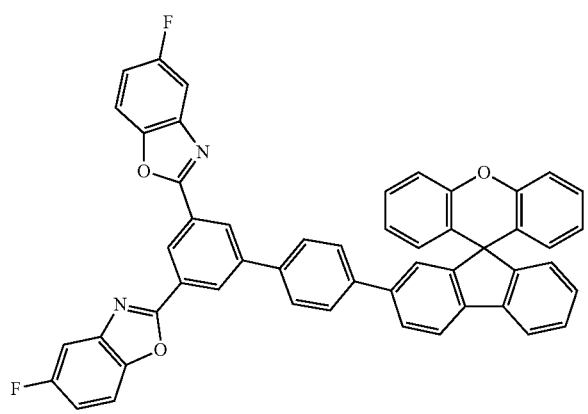
9
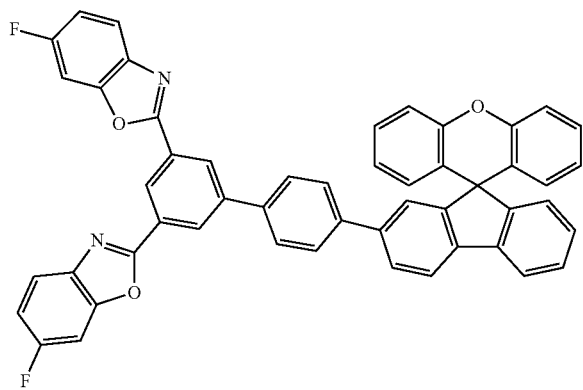
10
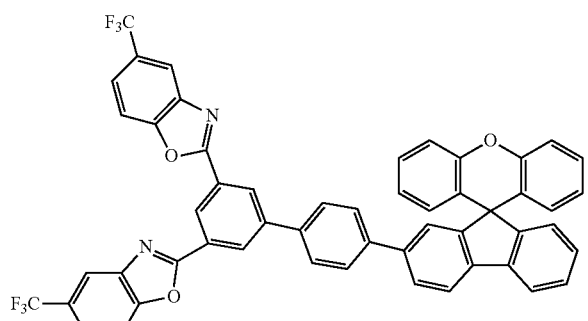

-continued
11
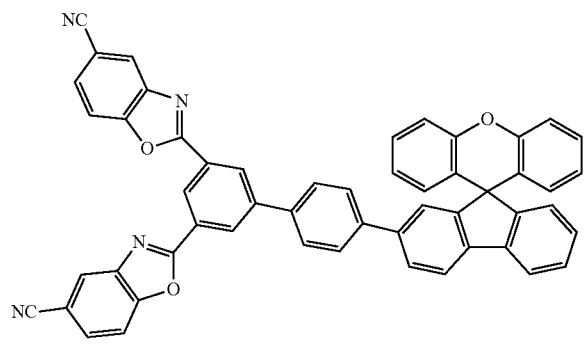
12
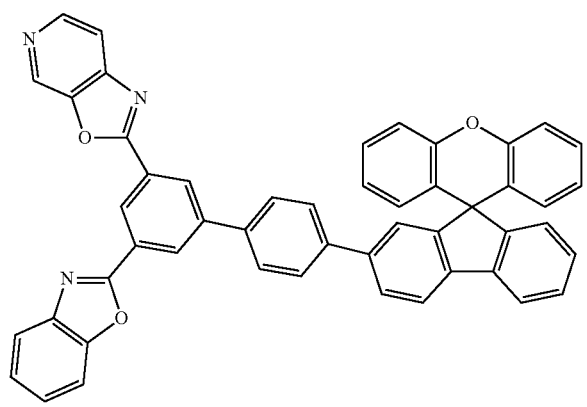
13
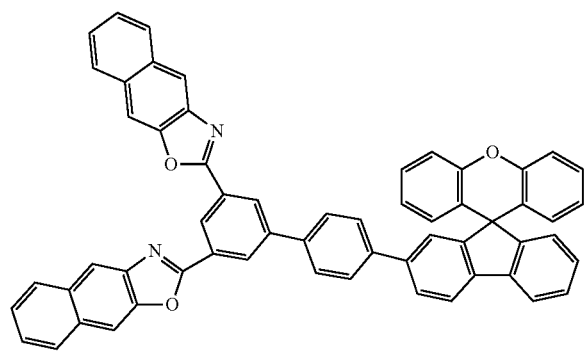
14
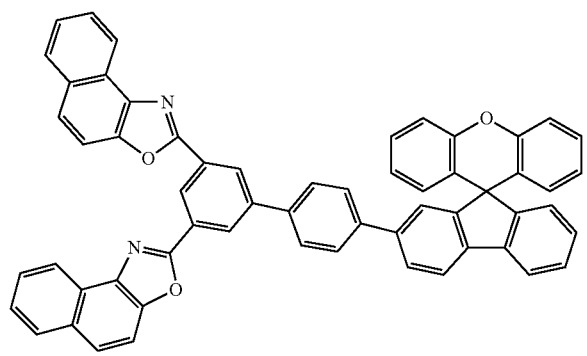
15
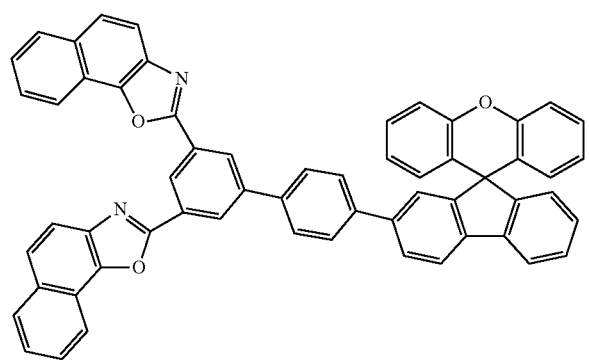
16
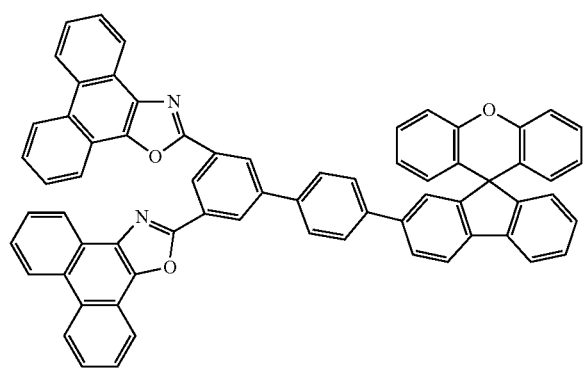

17
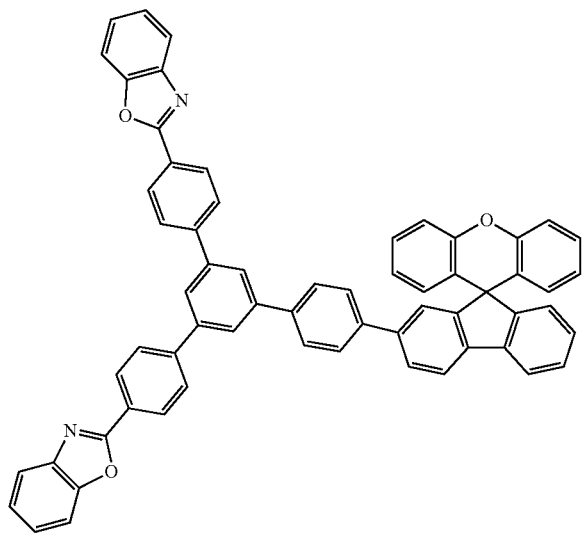
18
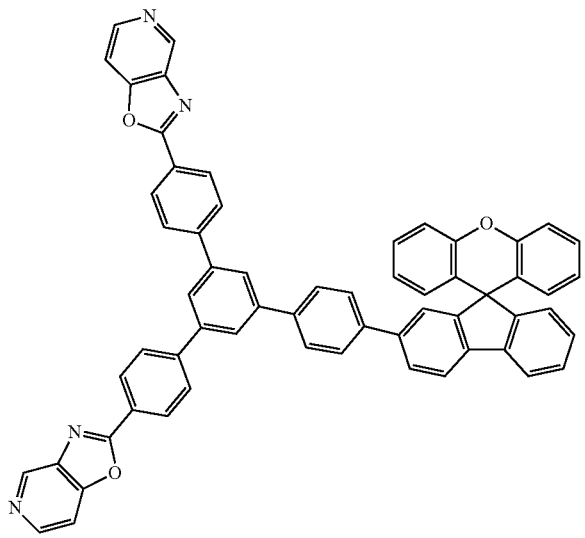
19
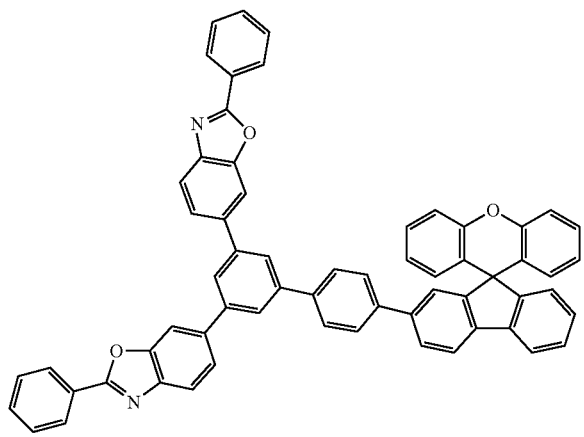
20
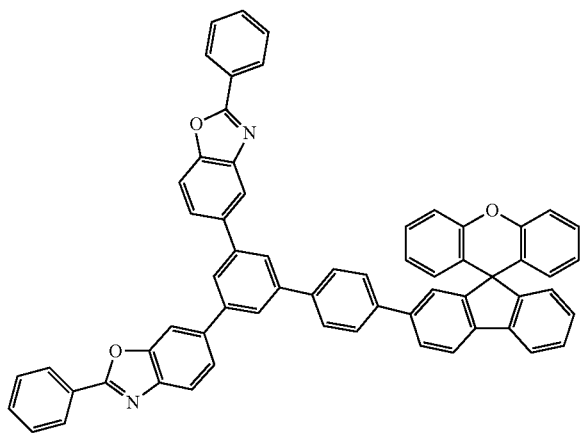
21
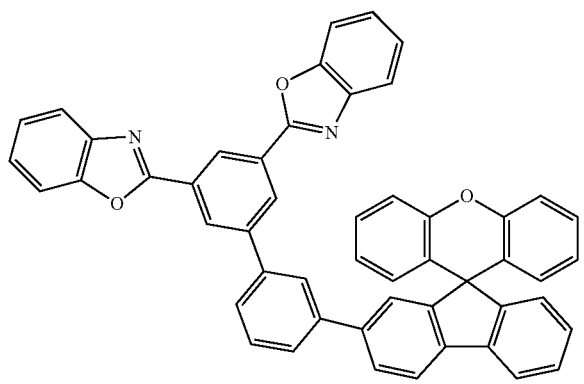
22
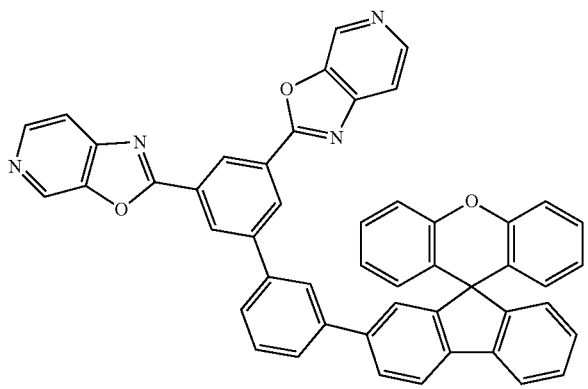

-continued
23
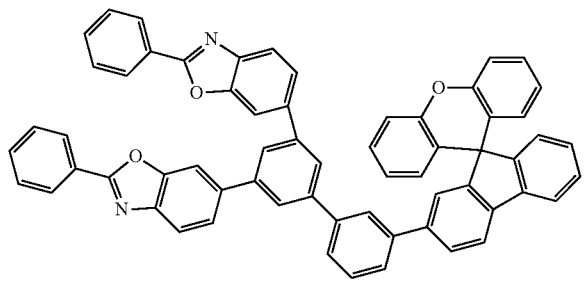
24
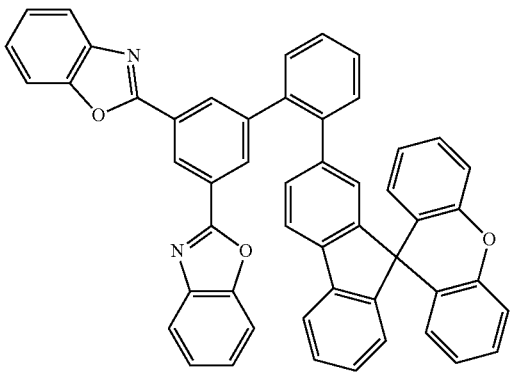
25
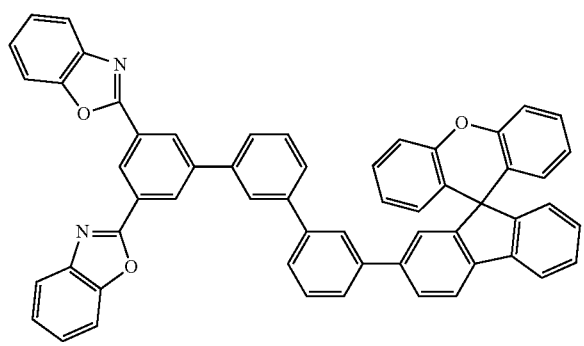
26
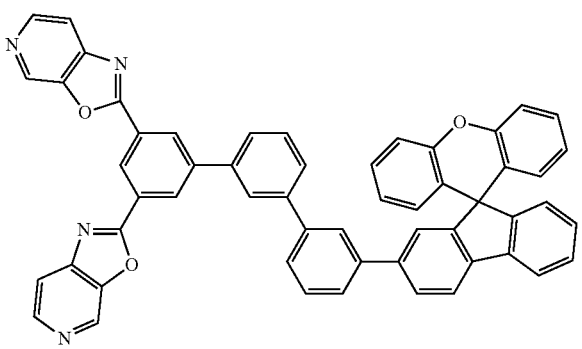
27
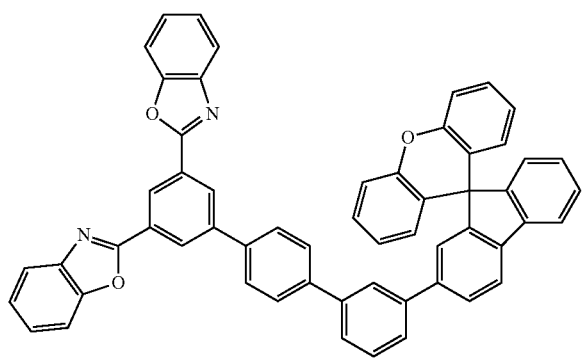
28
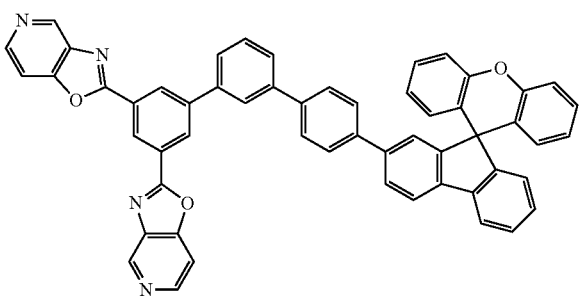
29
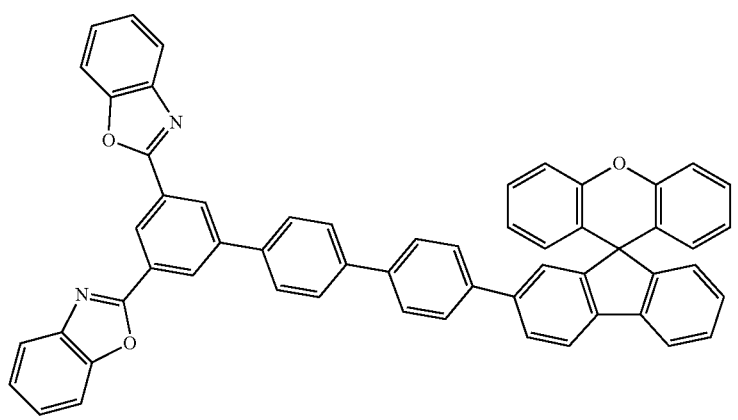

30
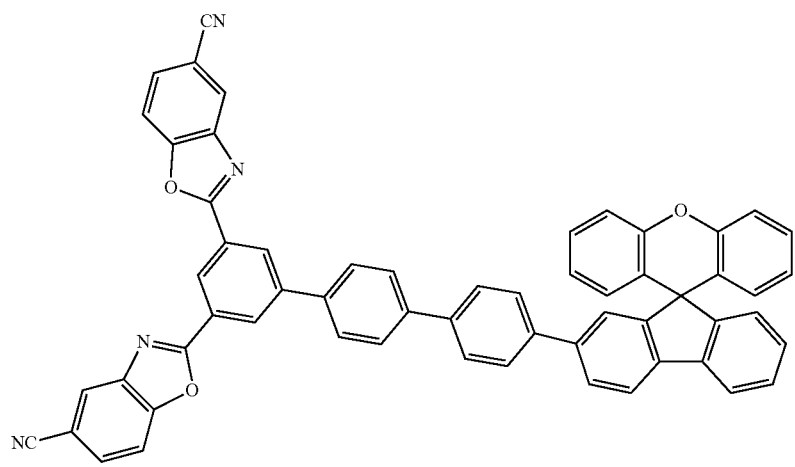
31
32
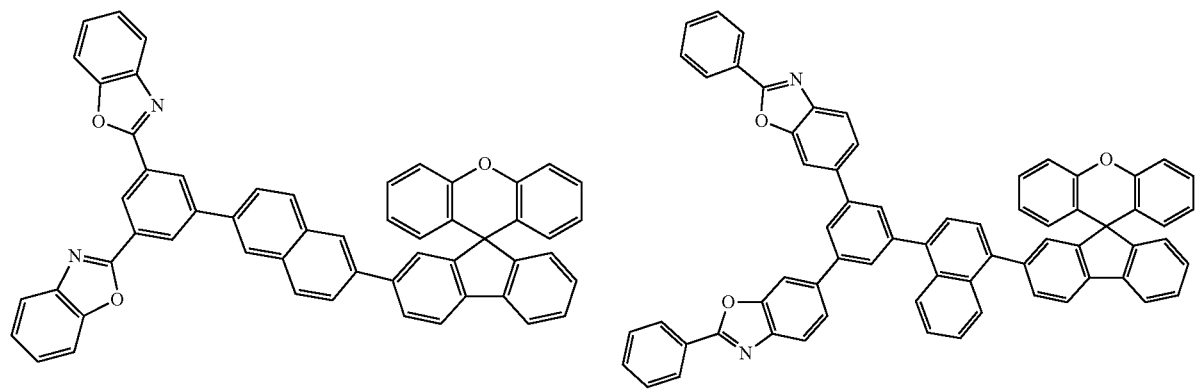
33
34
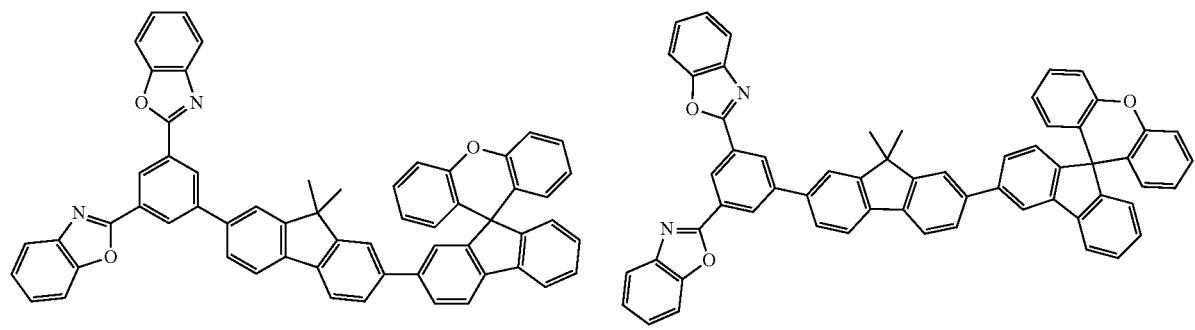
35
36
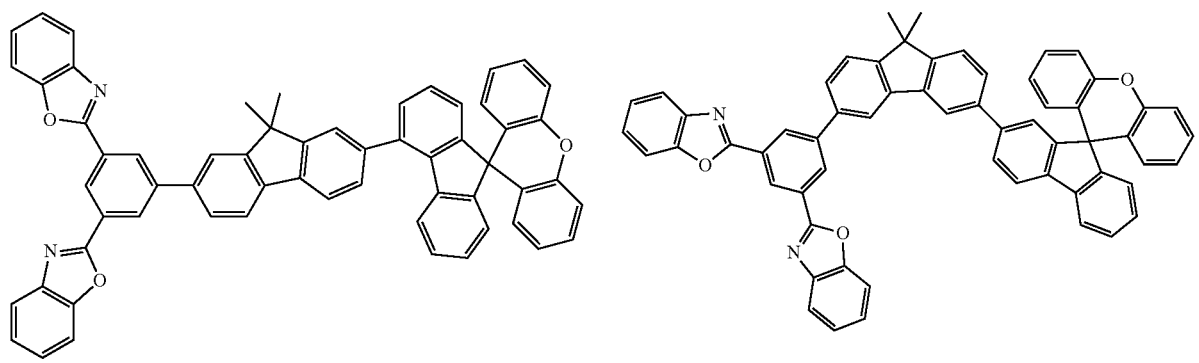

-continued
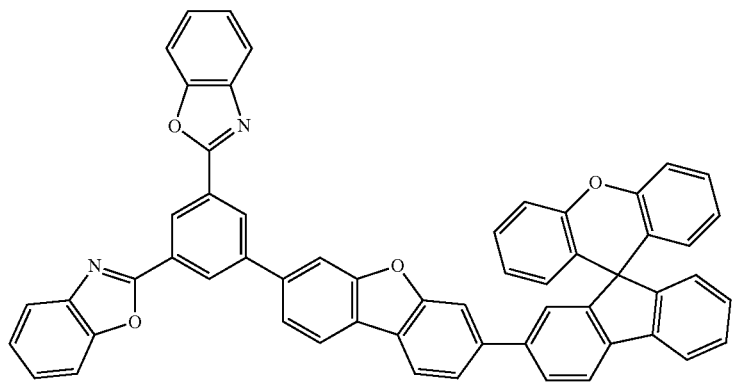
37
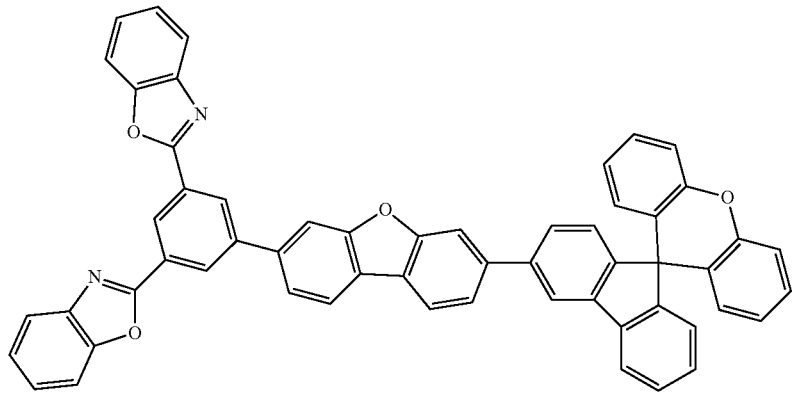
38
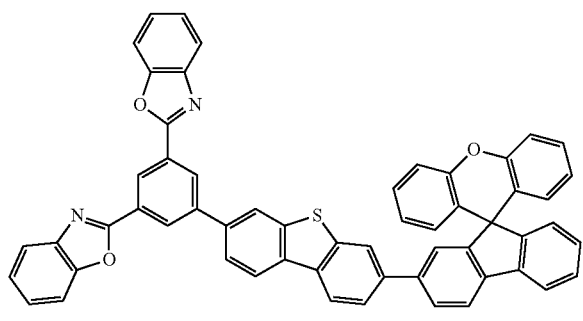
39
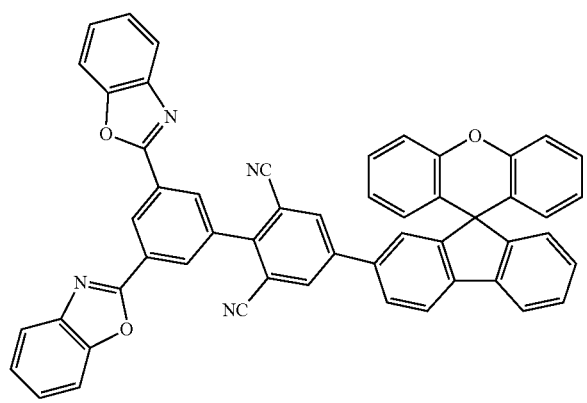
40
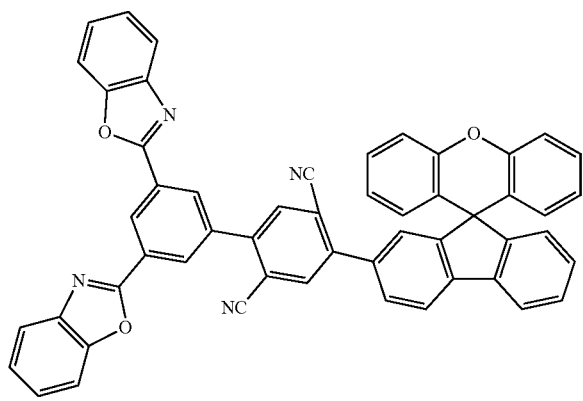
41
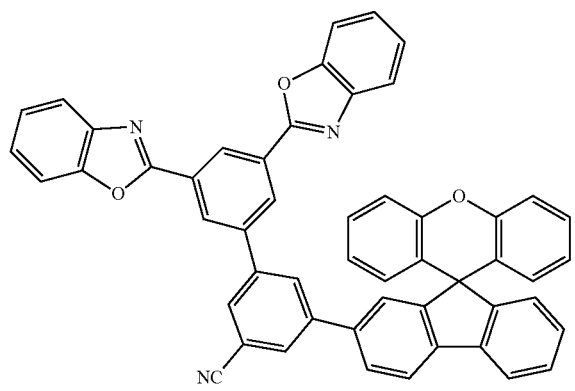
42

43
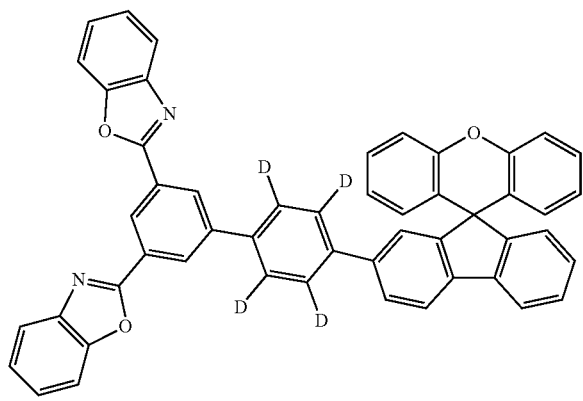
44
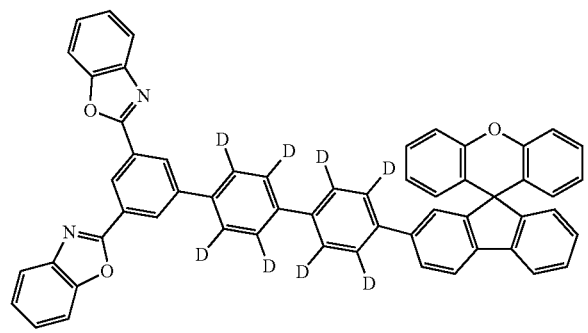
45
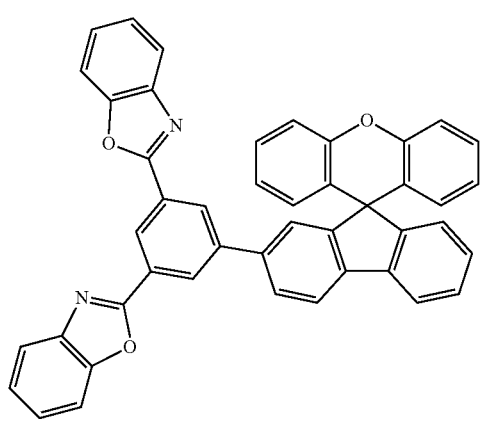
46
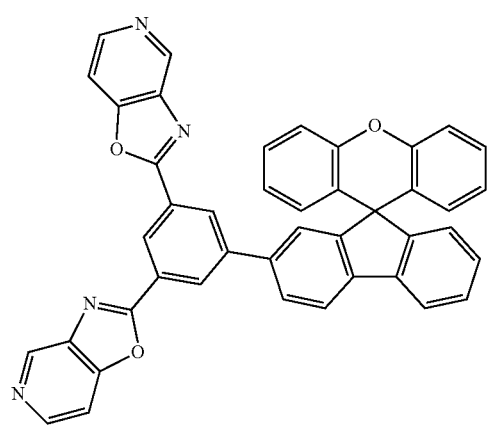
47
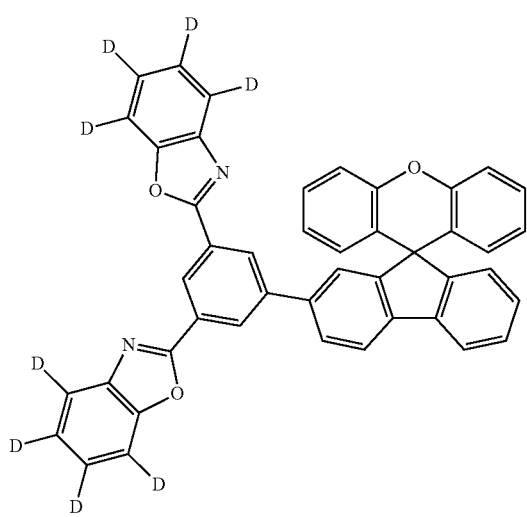
48
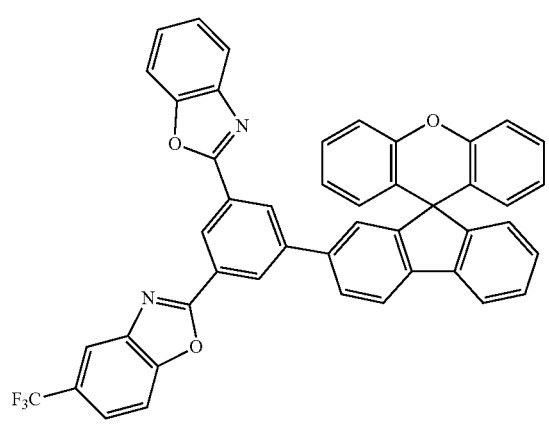

49
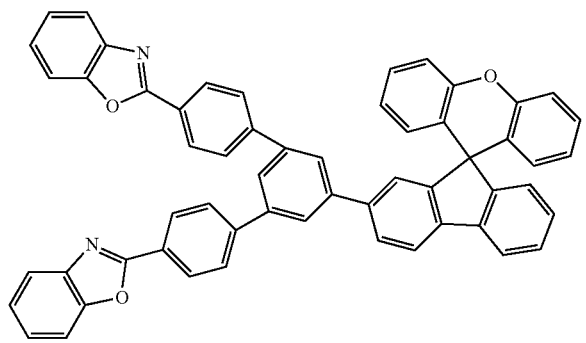
50
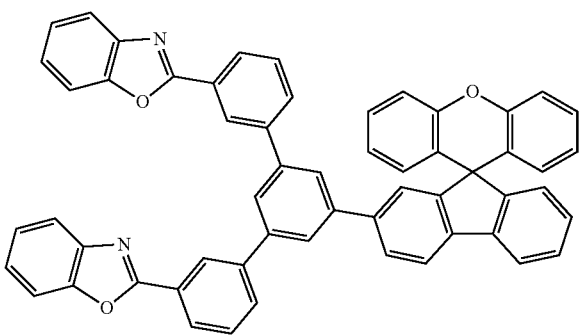
51
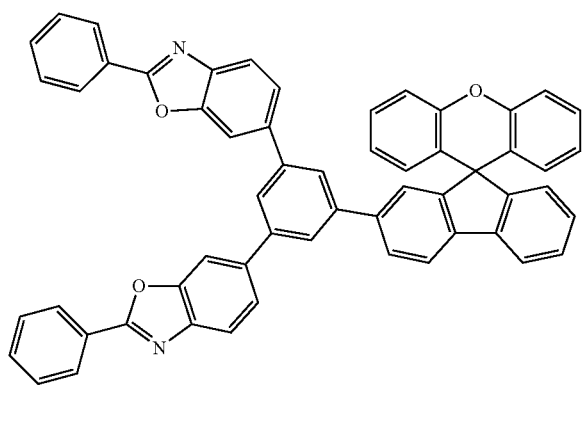
52
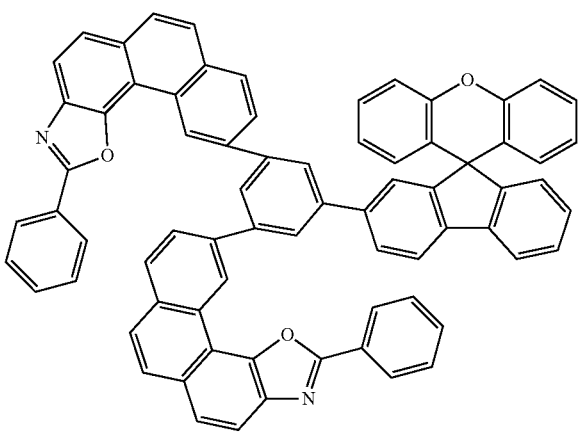
53
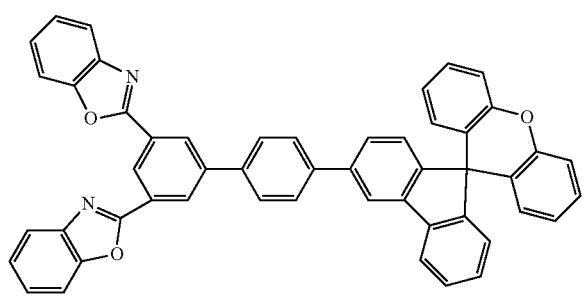
54
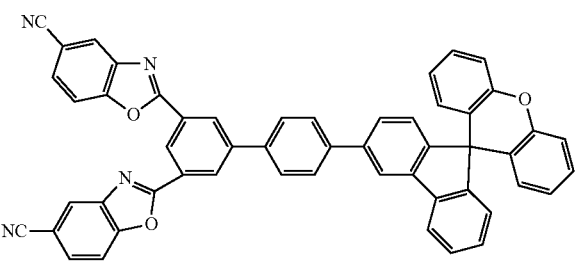
55
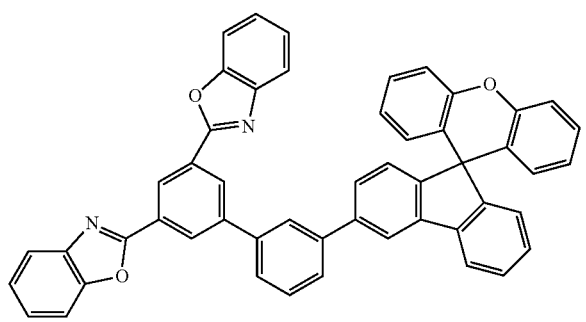
56
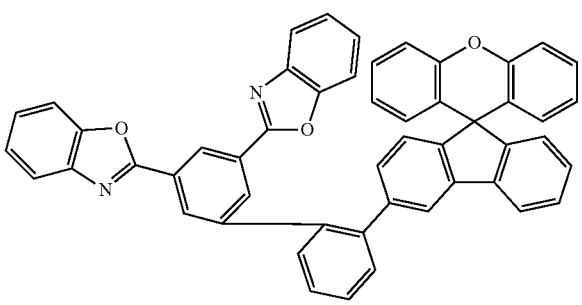

-continued
57
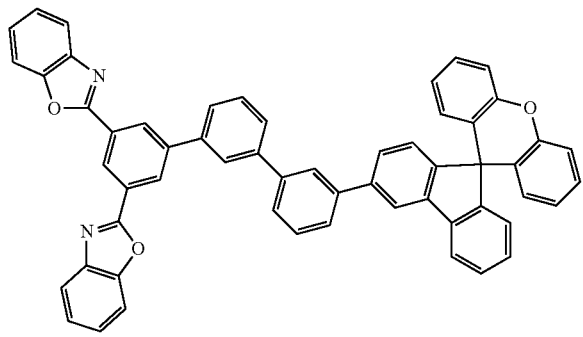
58
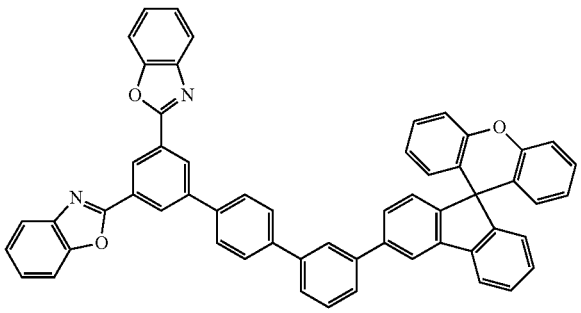
59
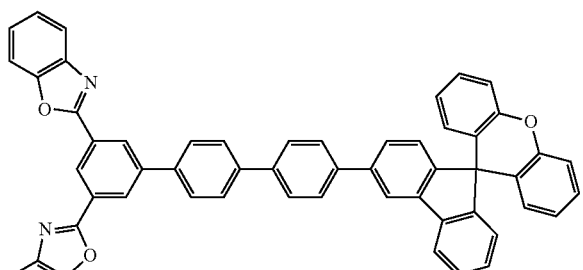
60
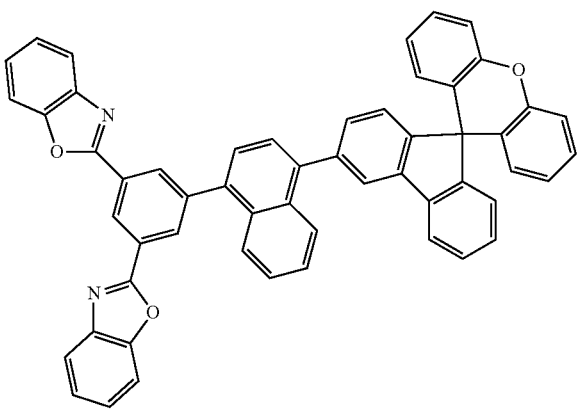
61
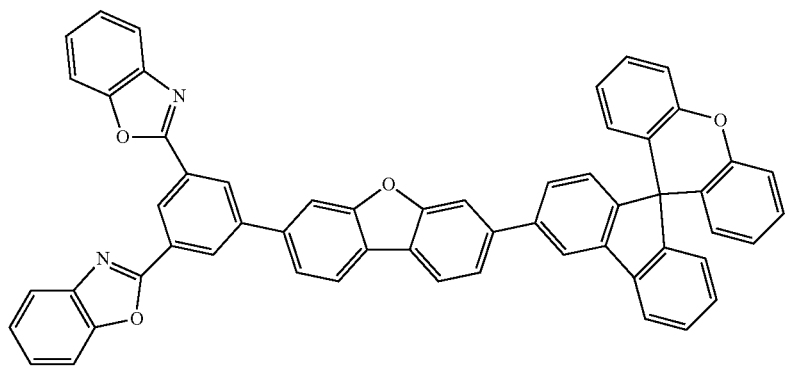
62
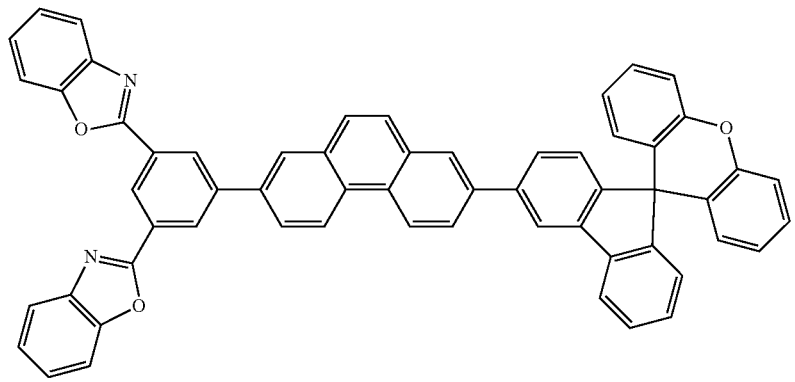

63
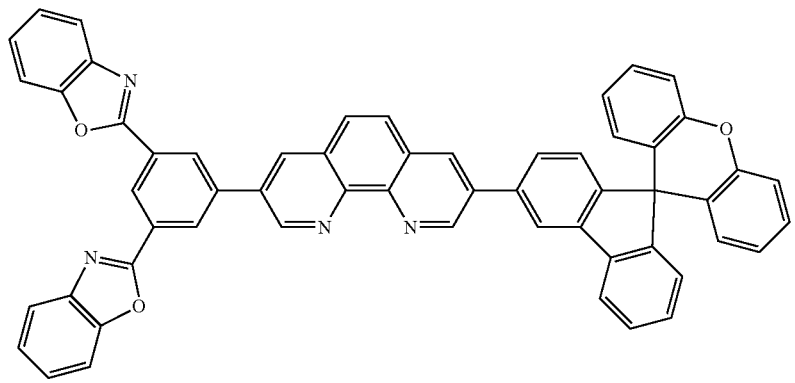
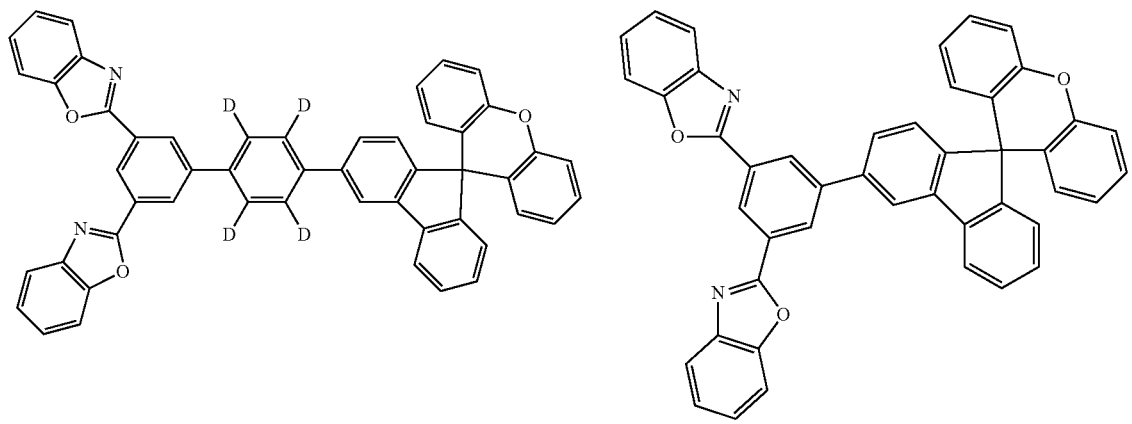
64
65
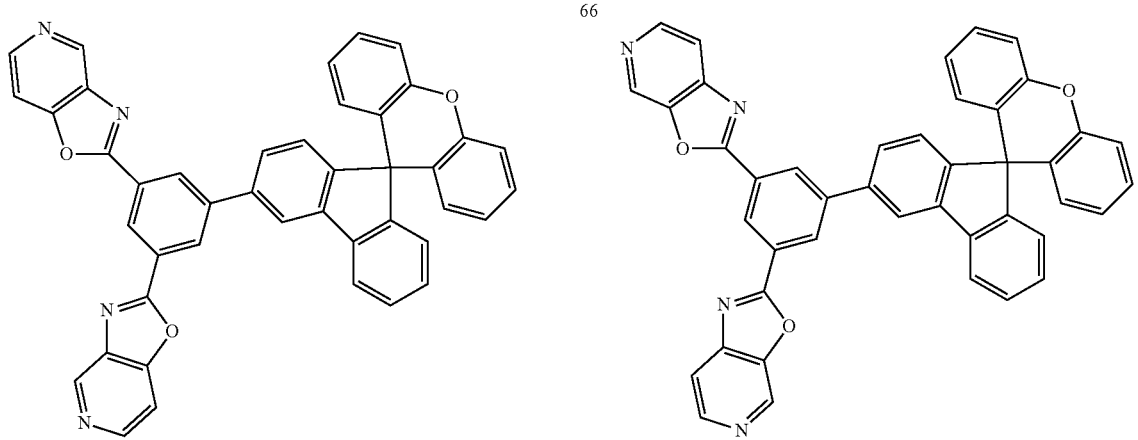
66
67

68
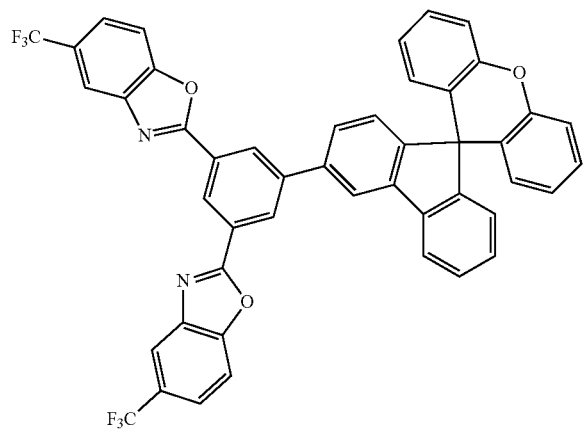
69
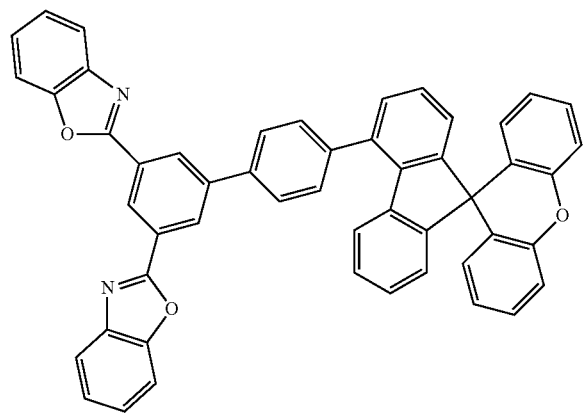
70
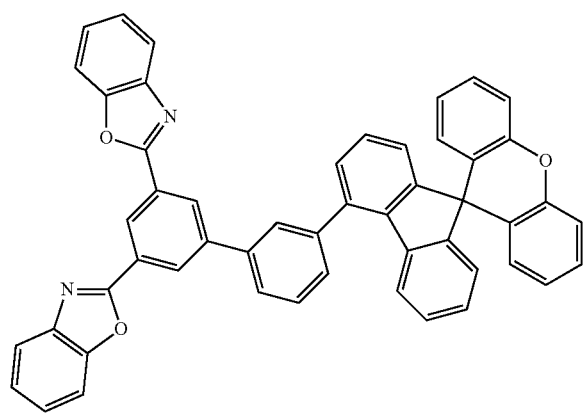
71
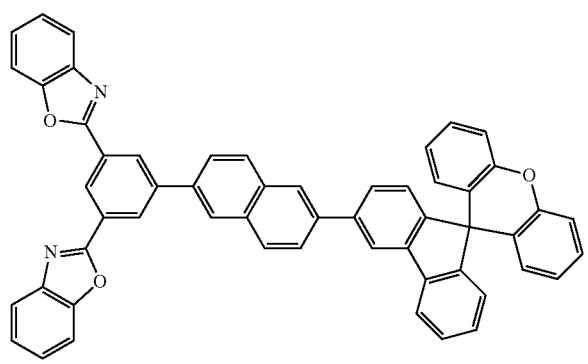
72
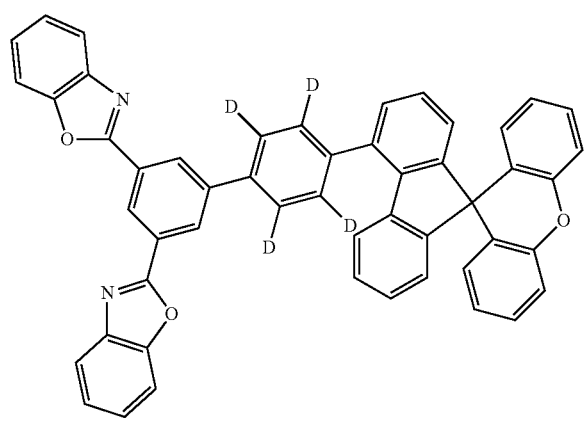
73
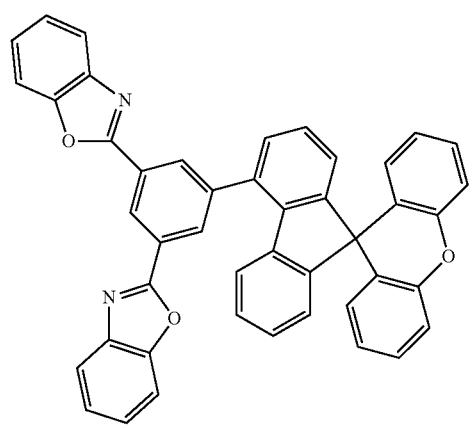

-continued
74
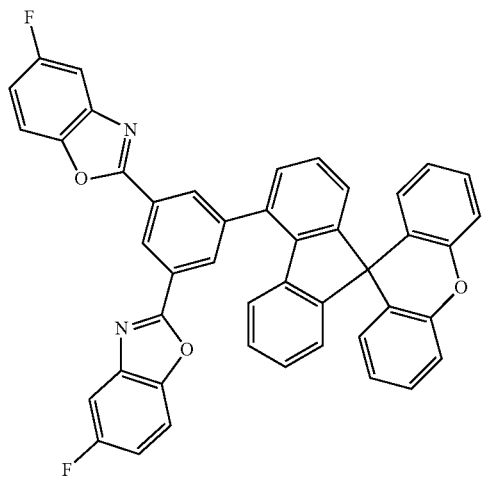
75
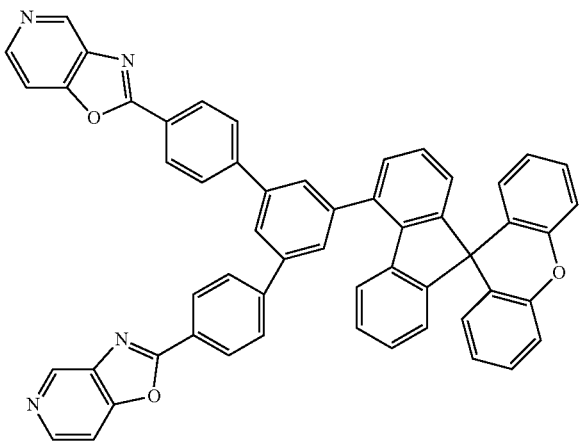
76
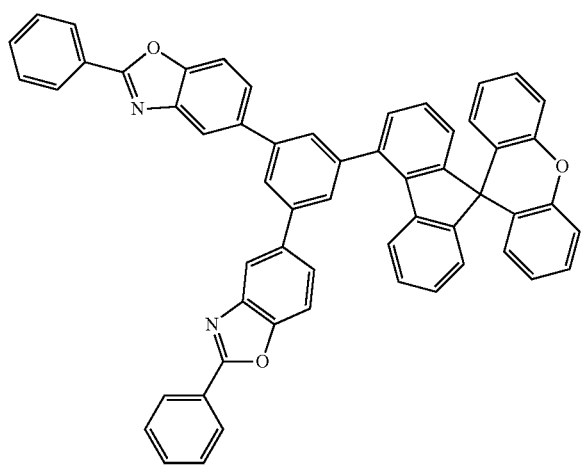
77
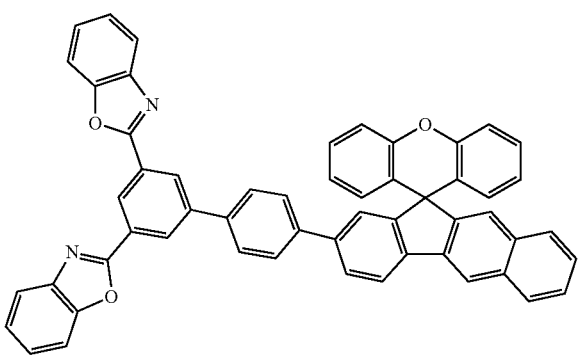
78
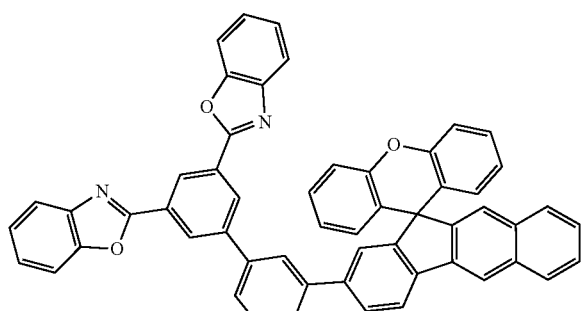
79
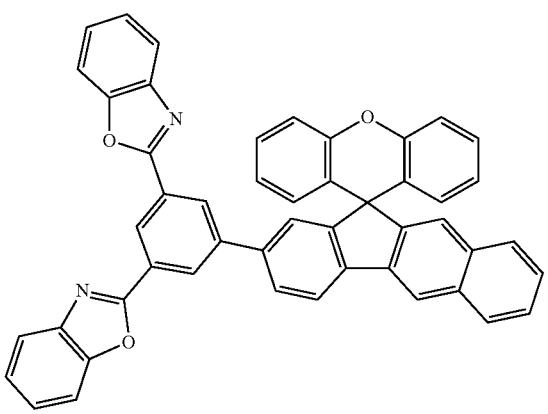

-continued
80
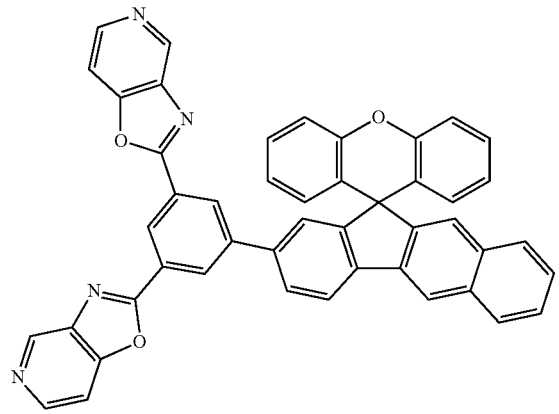
81
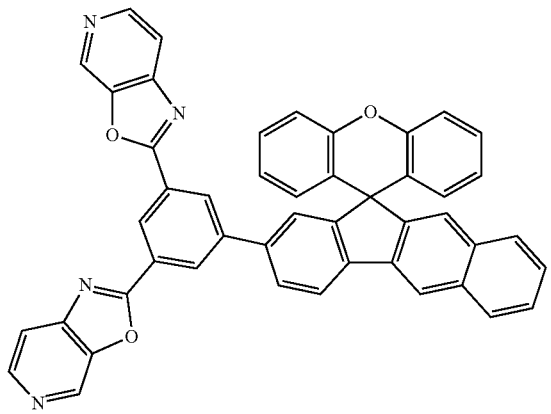
82
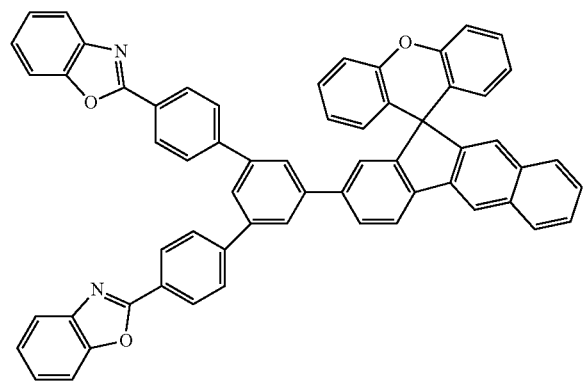
83
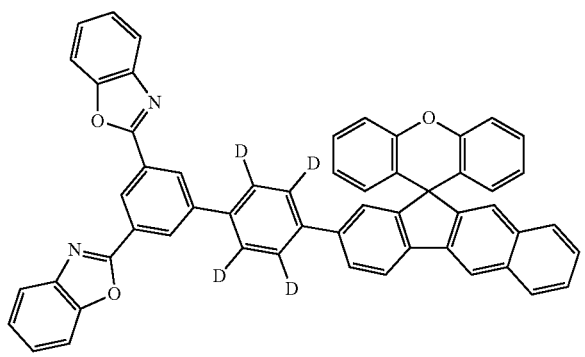
84
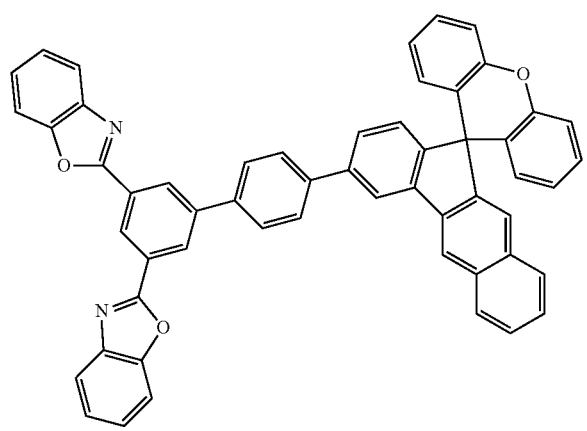
85
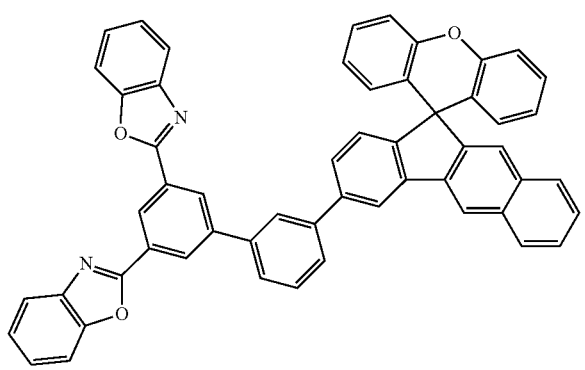

-continued
86
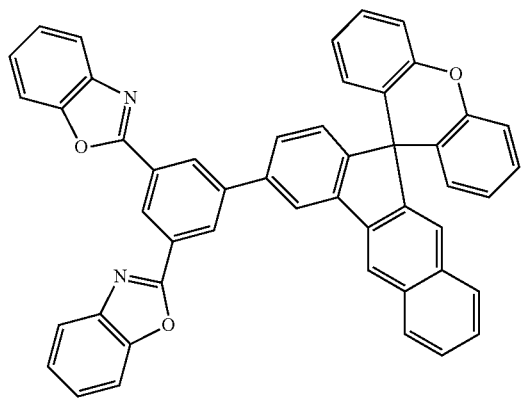
87
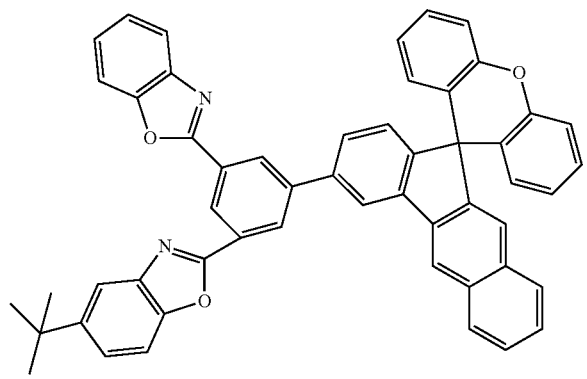
88
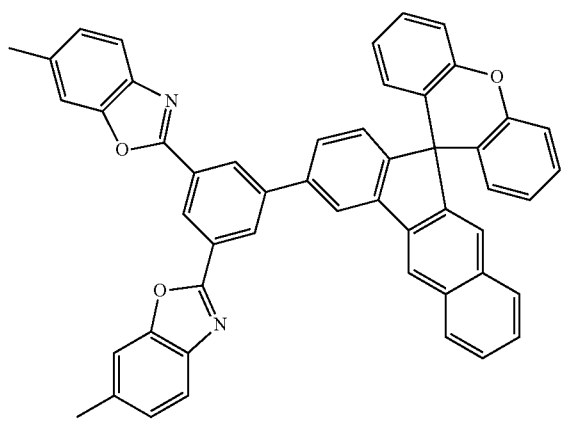
89
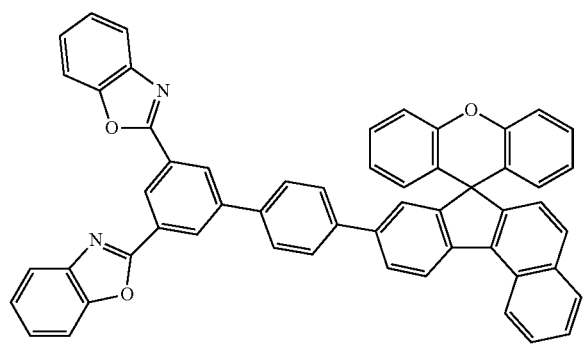
90
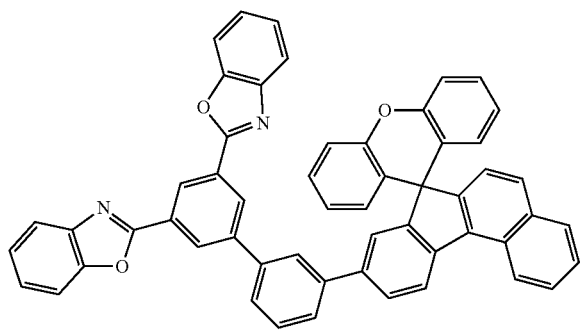
91
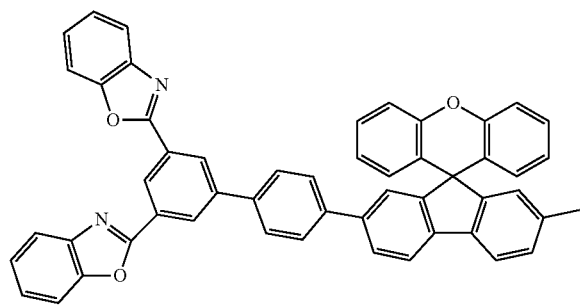
92
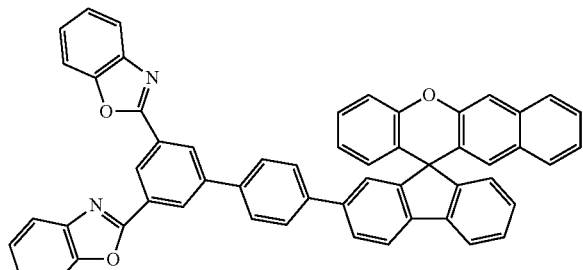
93
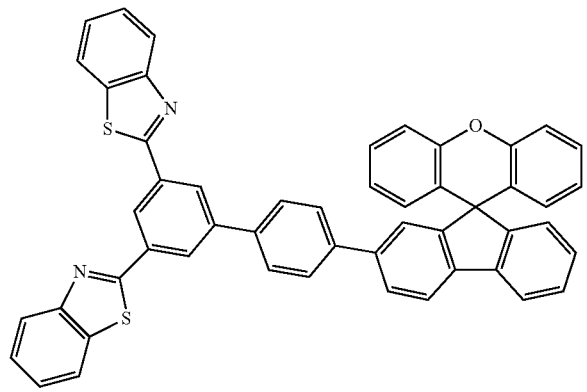

-continued
94
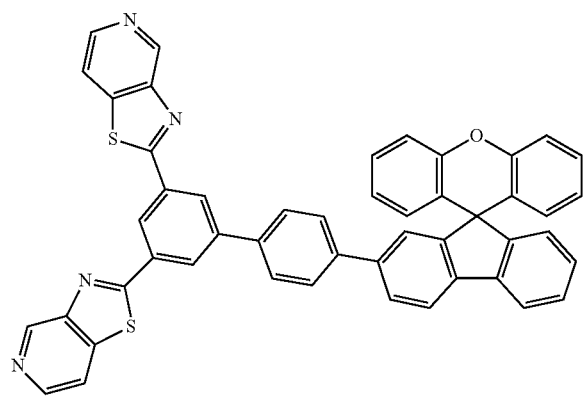
95
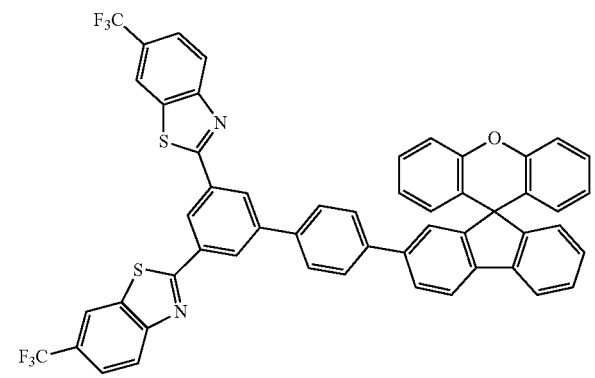
96
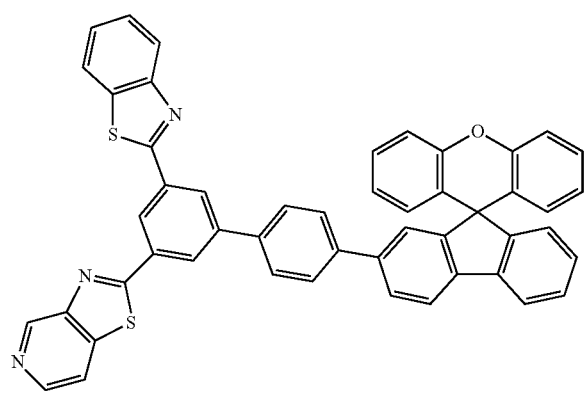
97
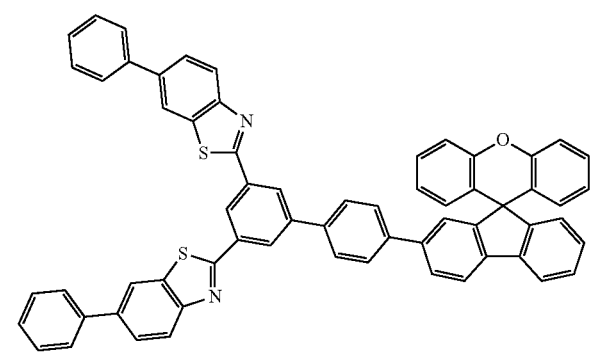
98
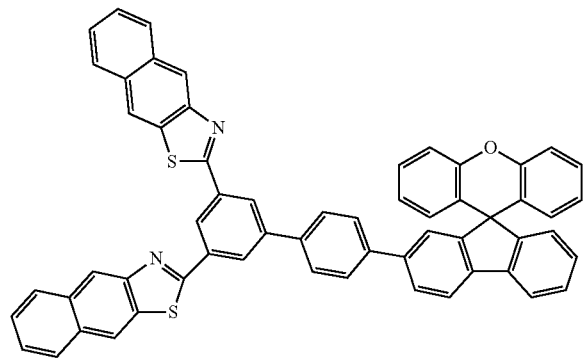
99
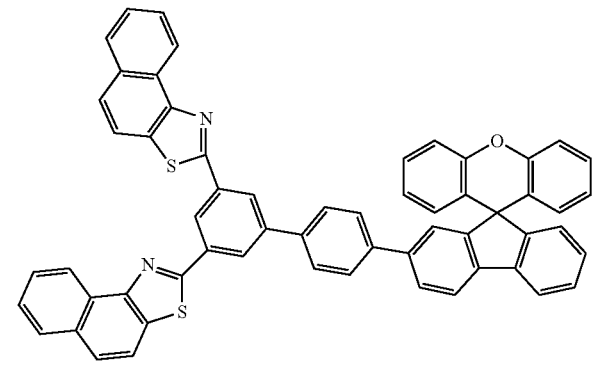
100
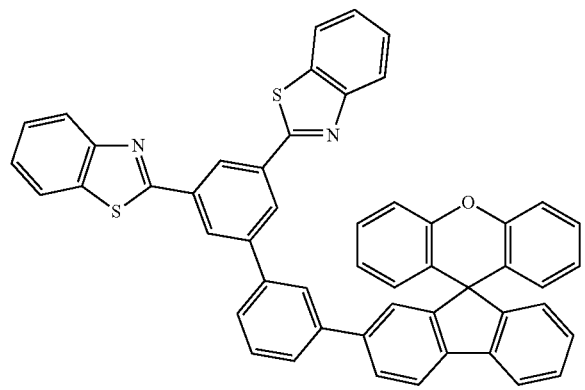
101
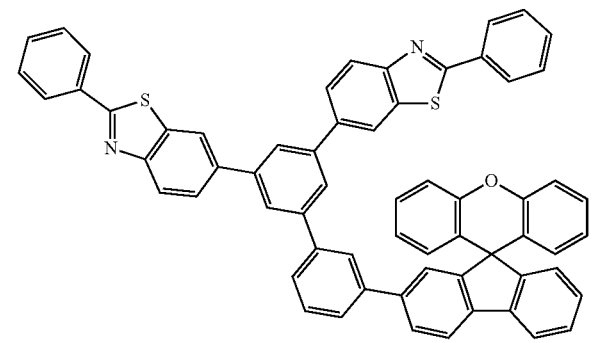

-continued
102
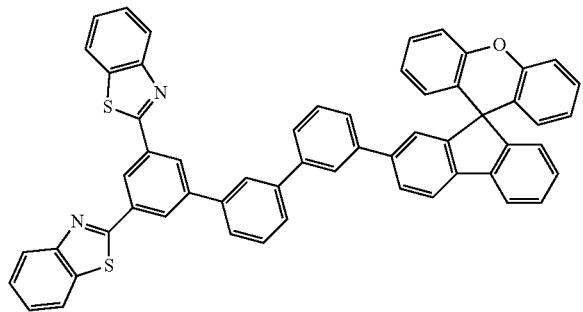
103
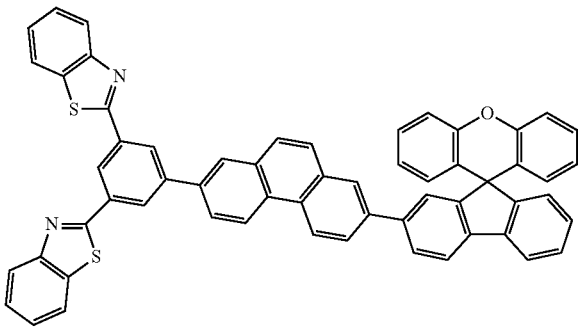
104
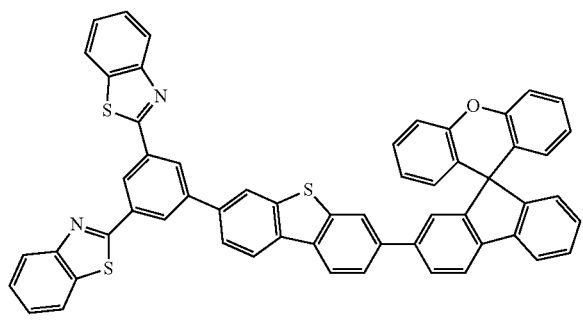
105
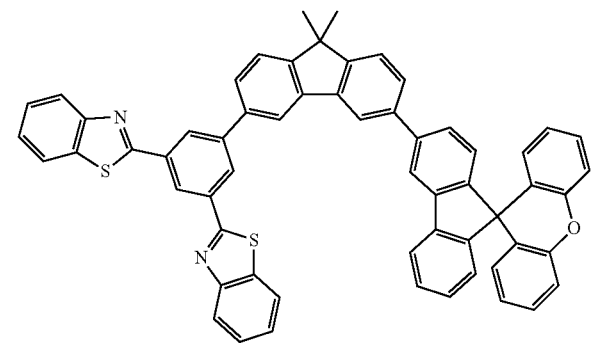
106
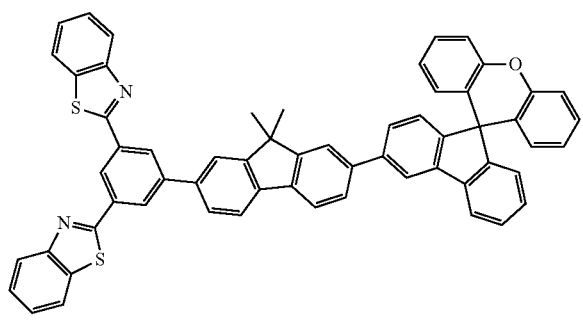
107
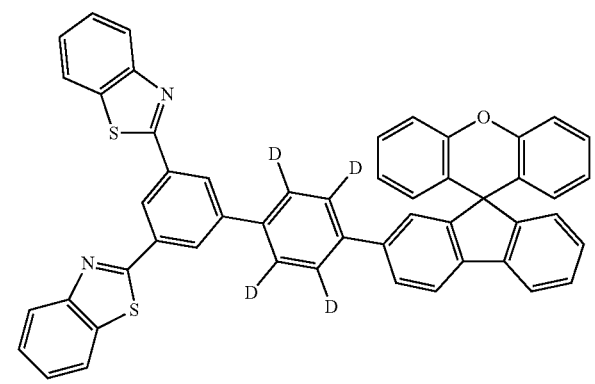
108
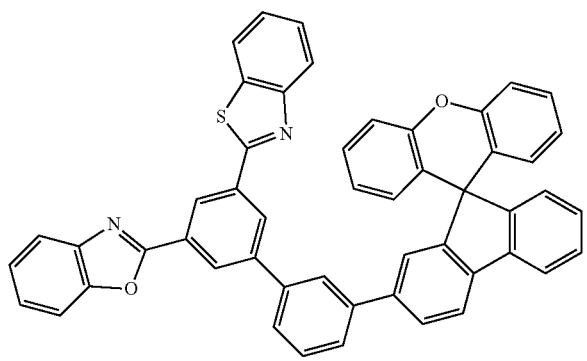
109
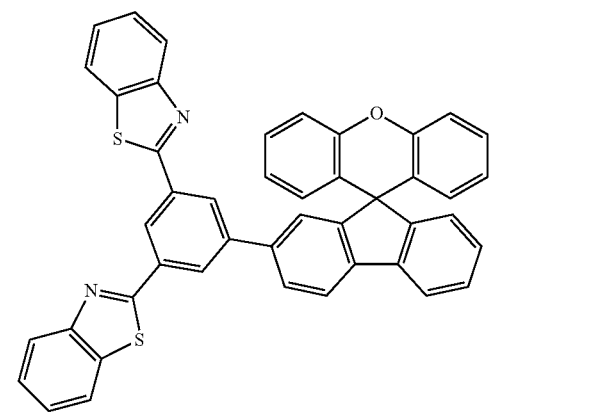

-continued
110
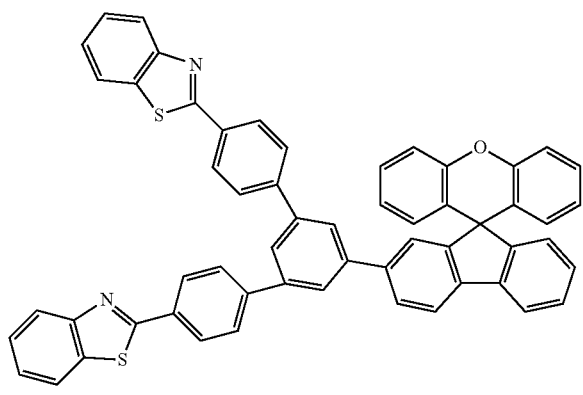
111
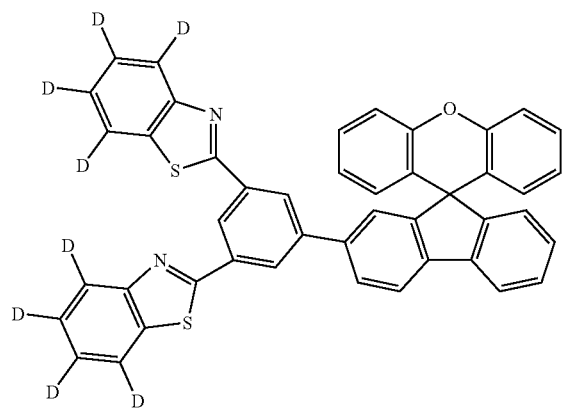
112
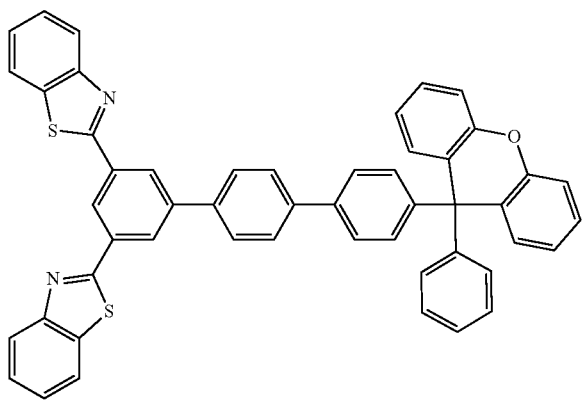
113
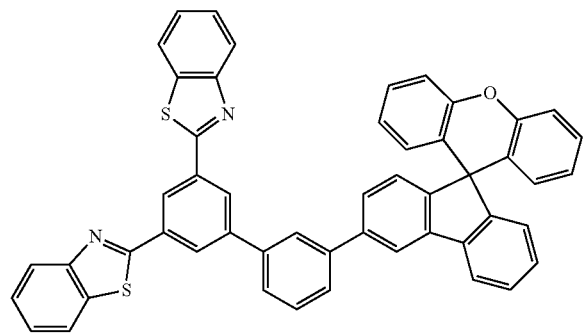
114
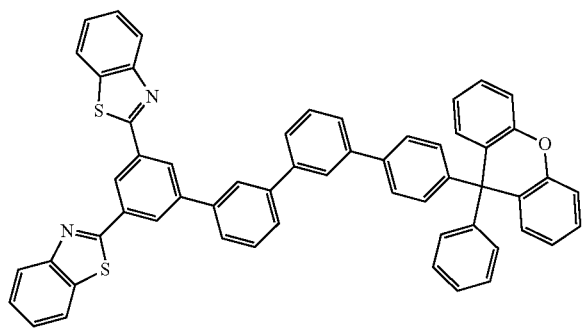
115
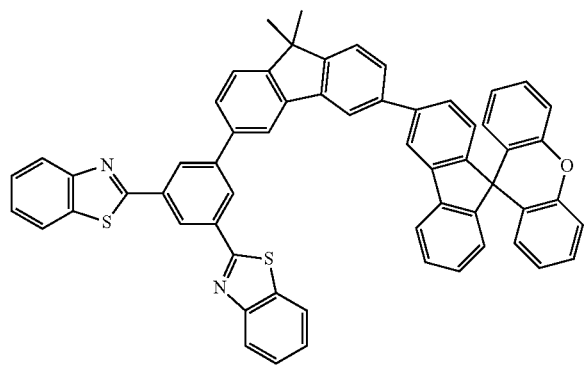
116
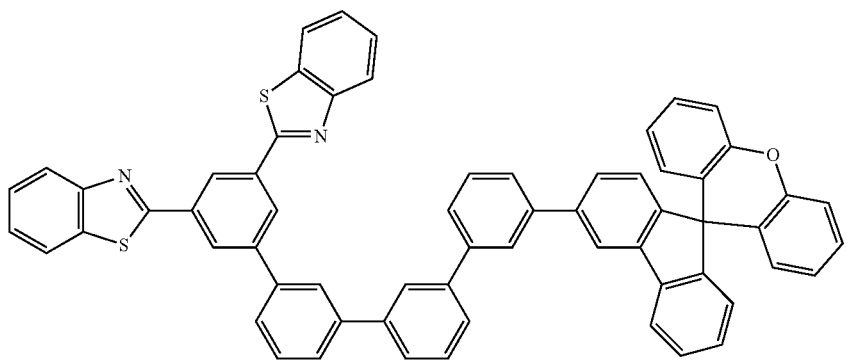

-continued
117
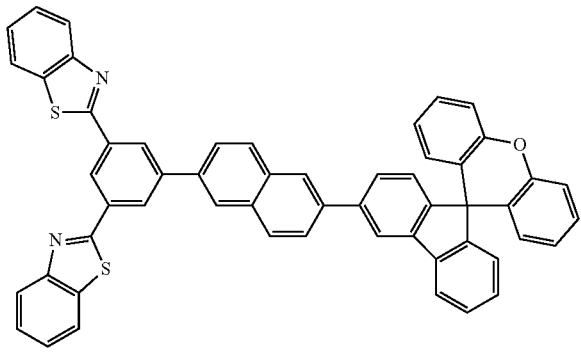
118
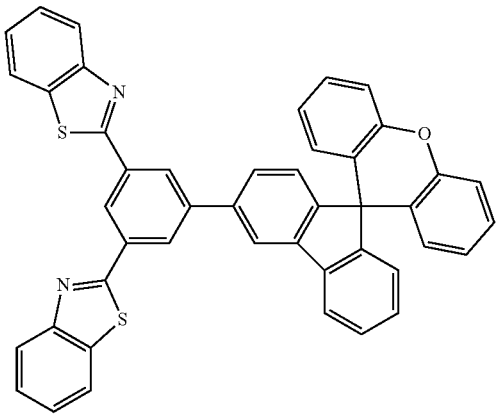
119
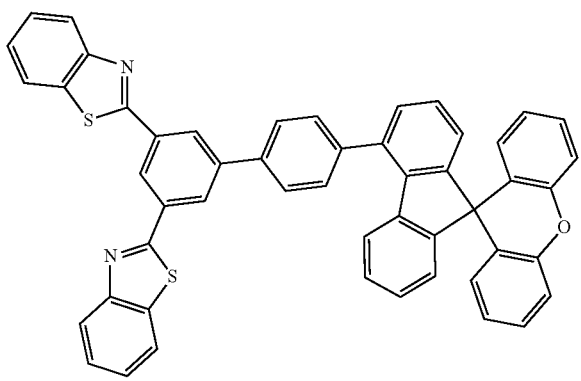
120
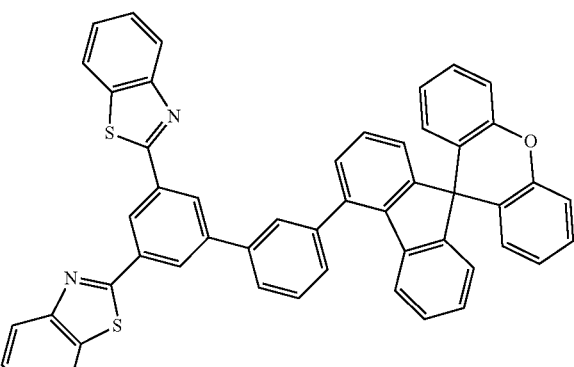
121
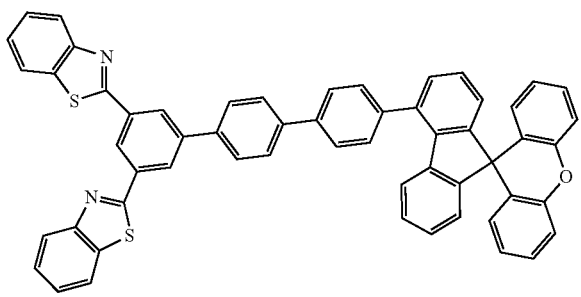
122
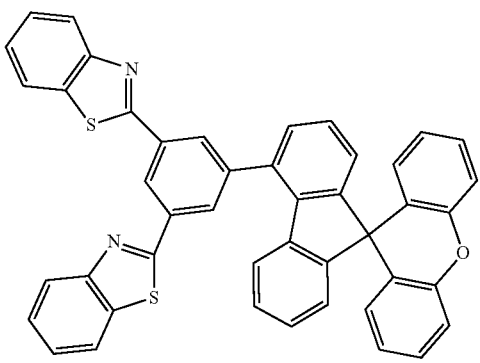
123
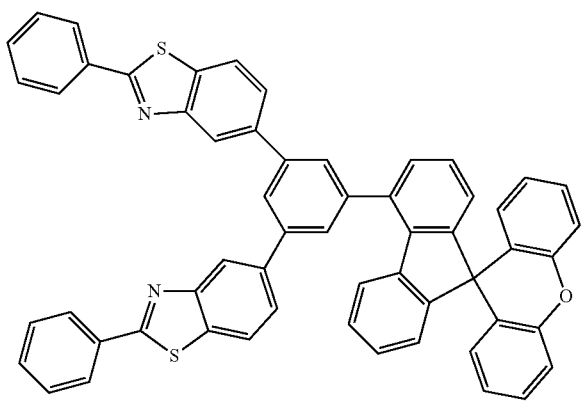
124
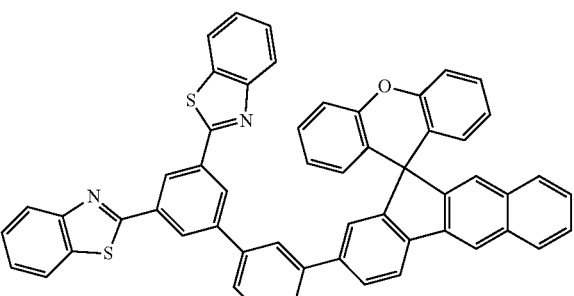

-continued
125
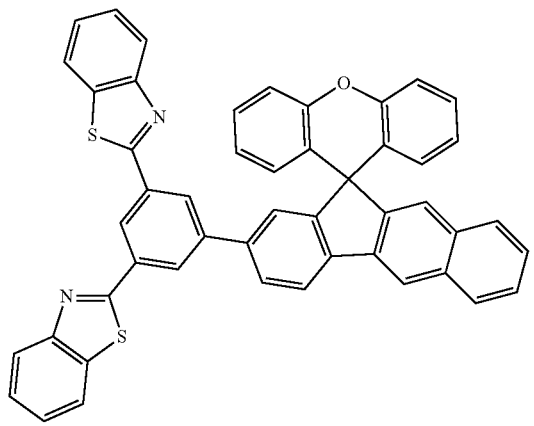
126
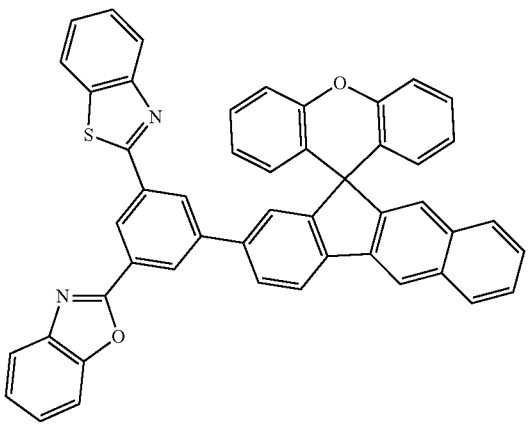
127
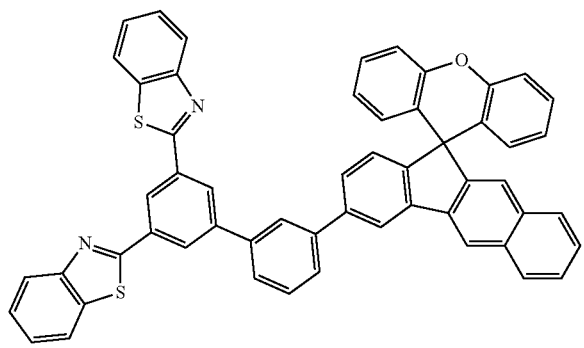
128
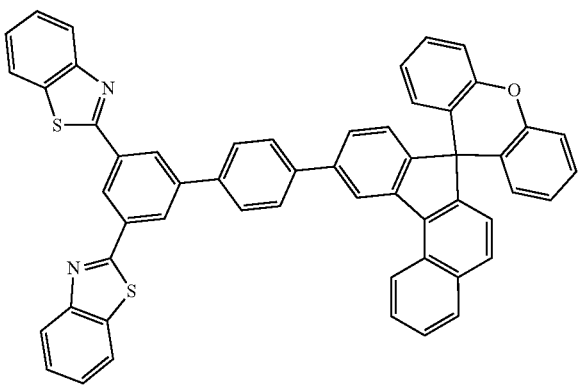
129
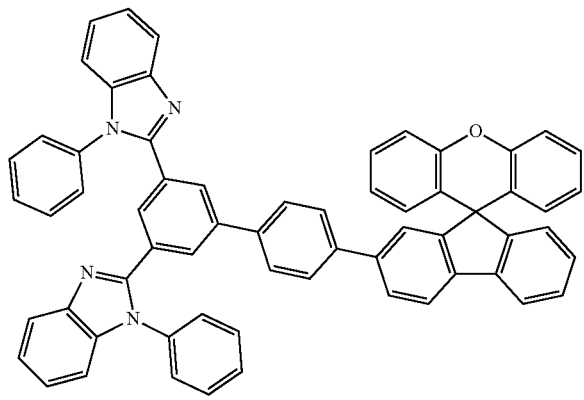
130
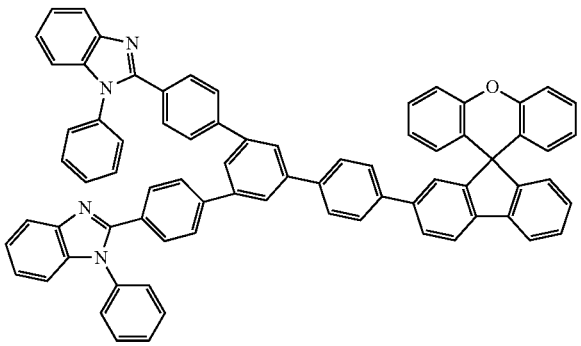
131
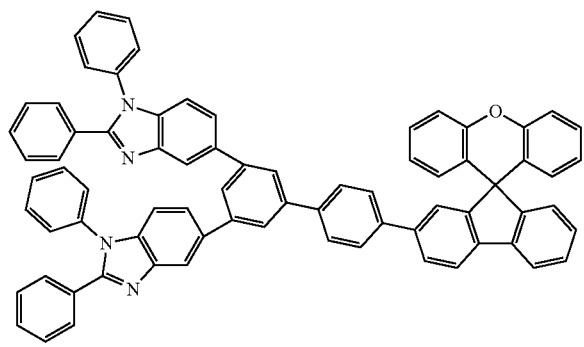
132
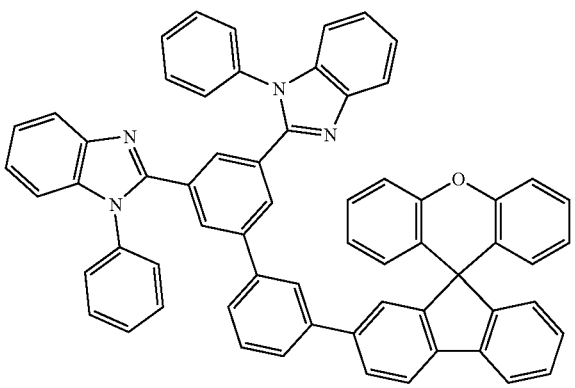

-continued
133
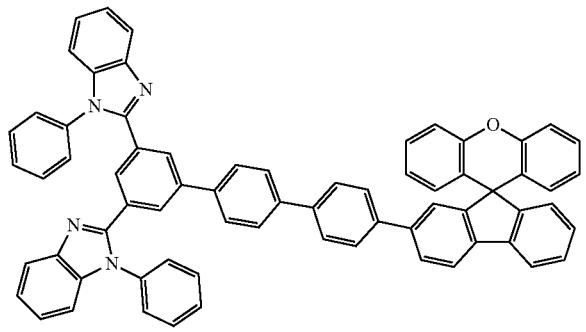
134
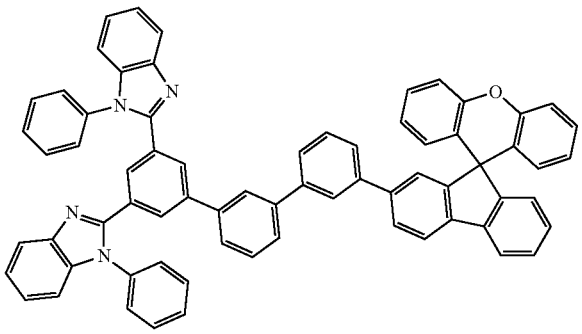
135
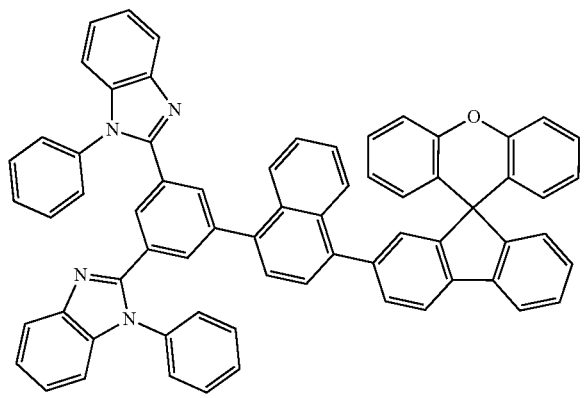
136
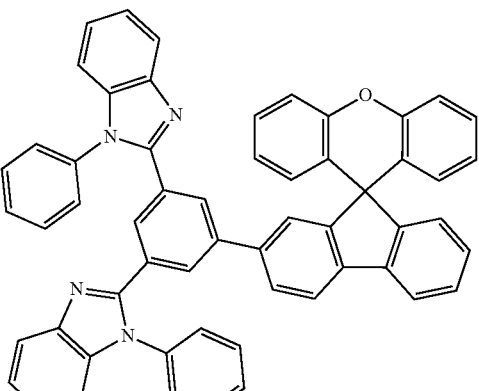
137
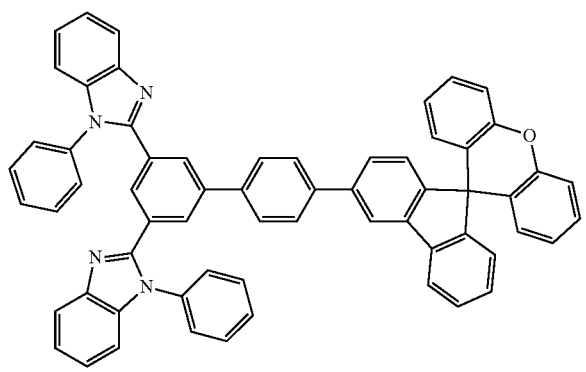
138
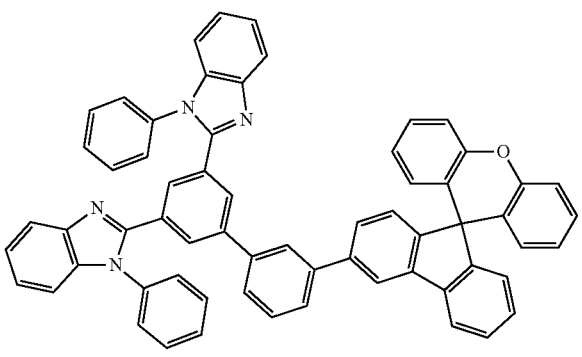
139
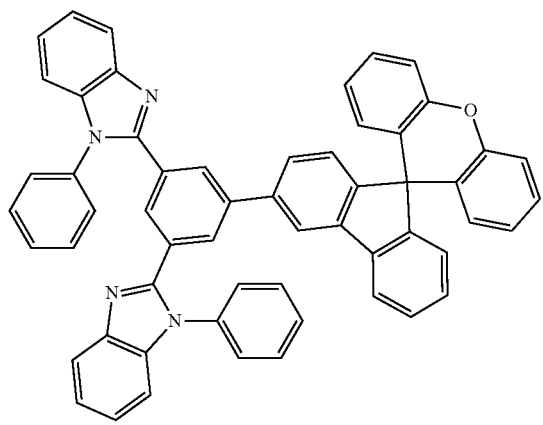
140
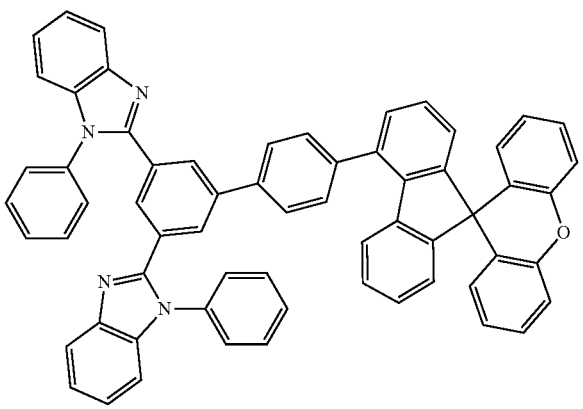

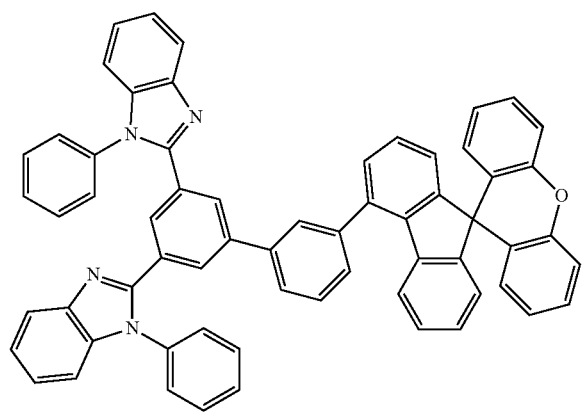
141
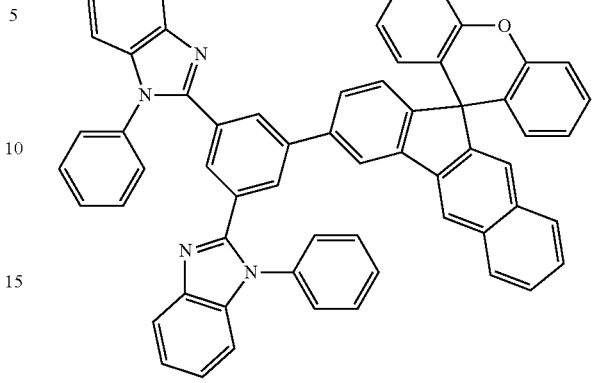
144
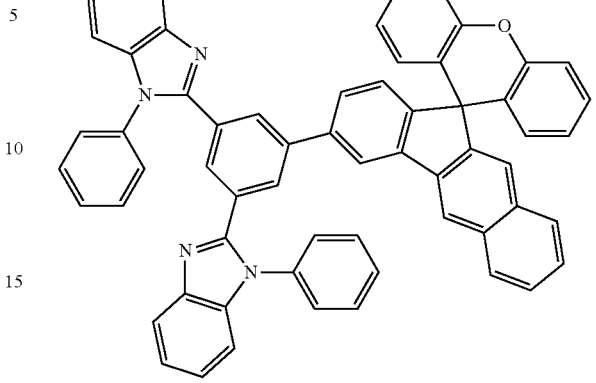
142
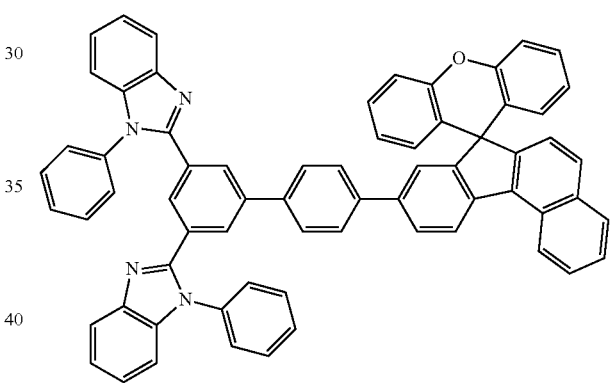
145
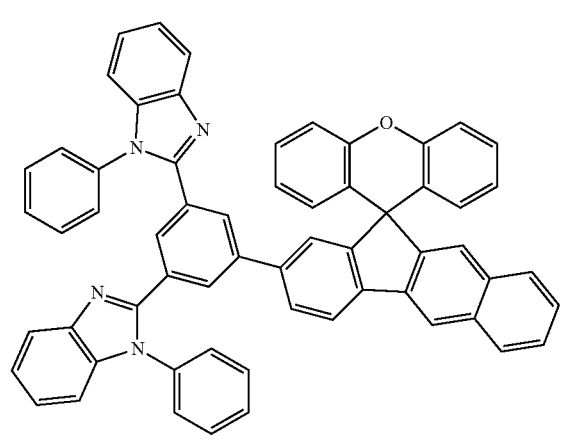
143
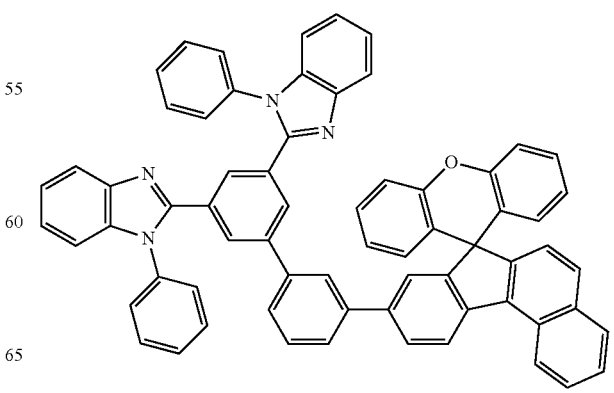
146

147
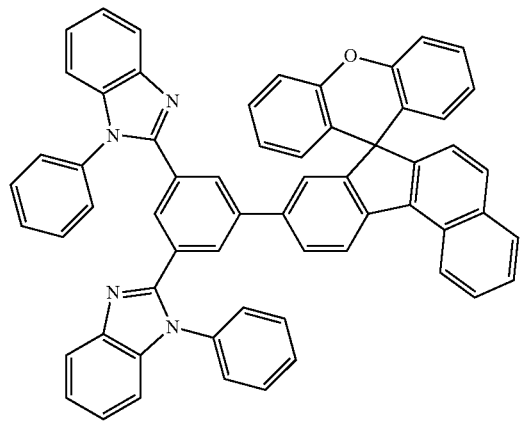
148
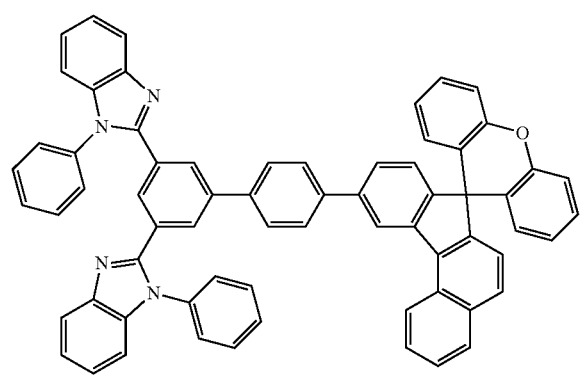
149
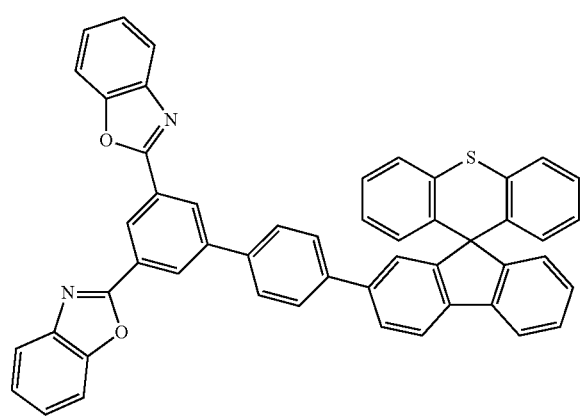
150
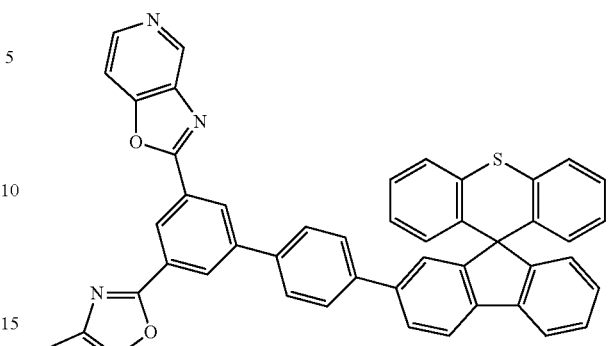
151
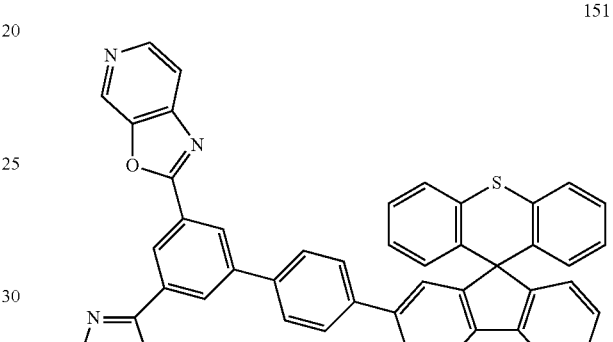
152
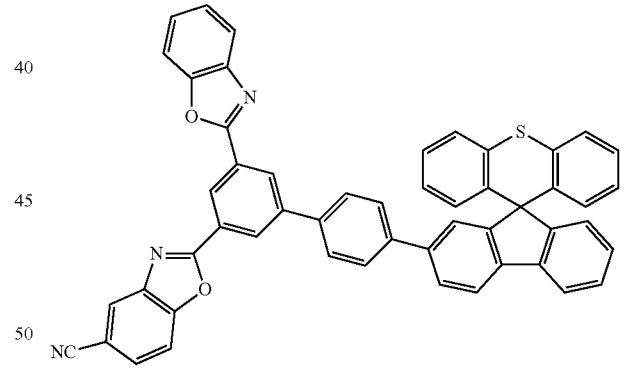
153
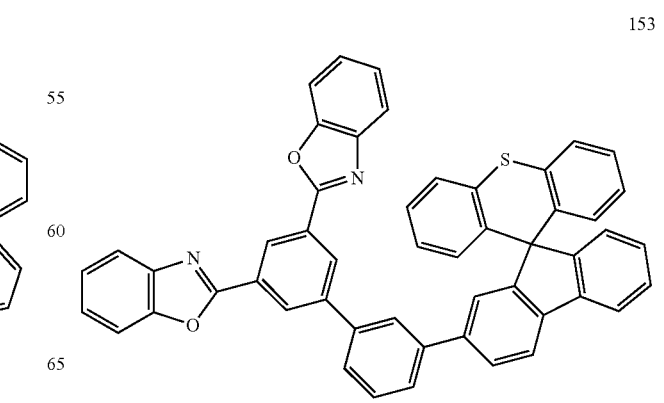

-continued
154
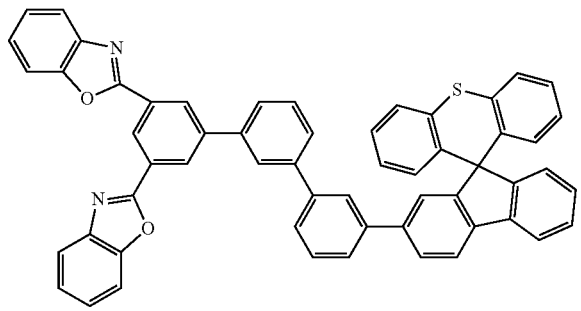
155
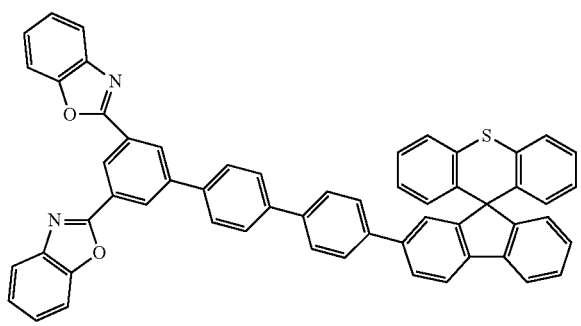
156
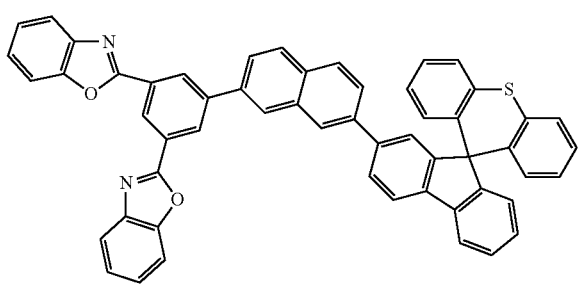
157
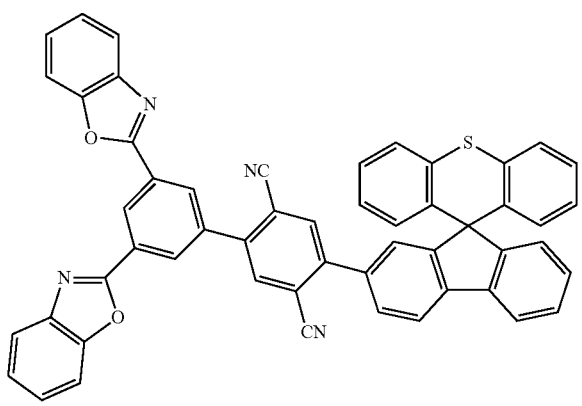
-continued
158
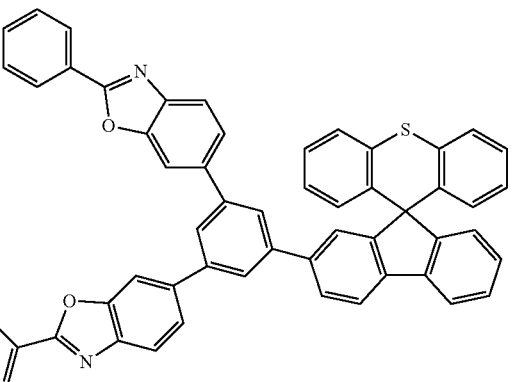
159
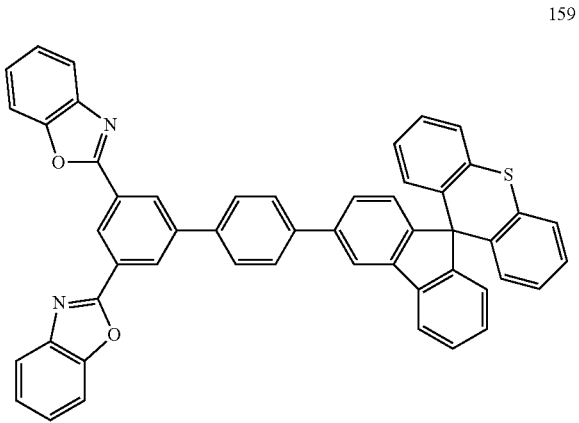
160
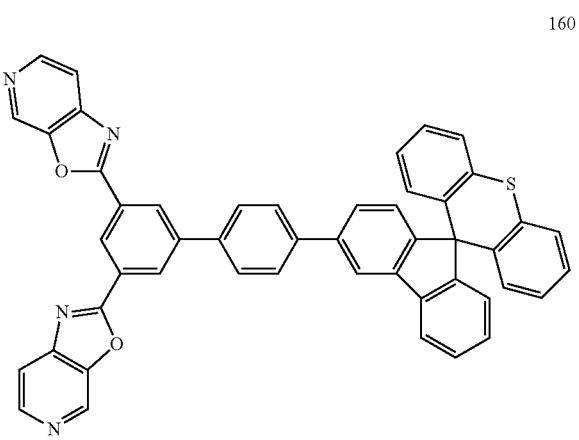
161
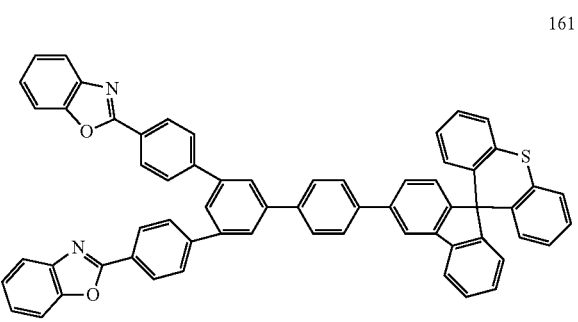

162
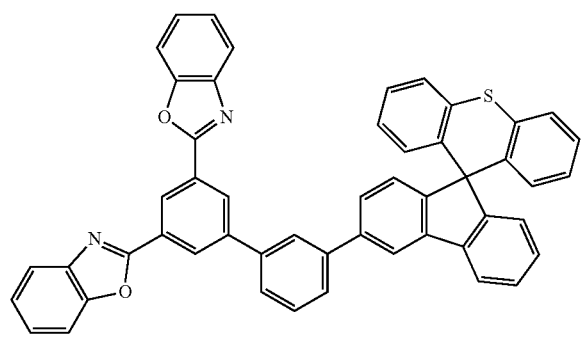
163
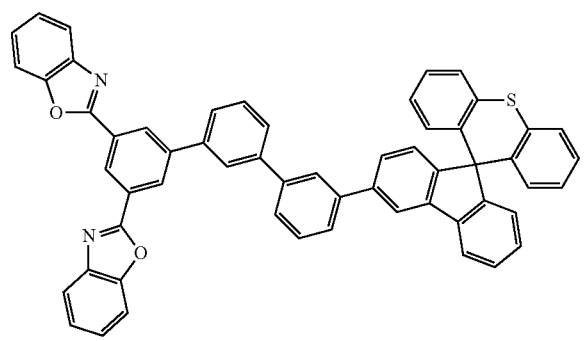
164
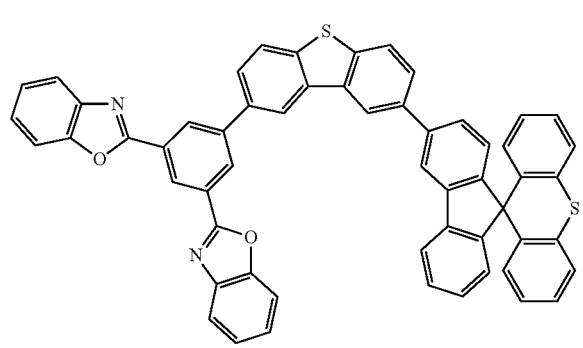
165
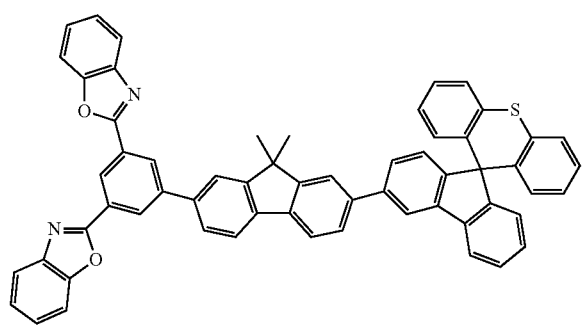
166
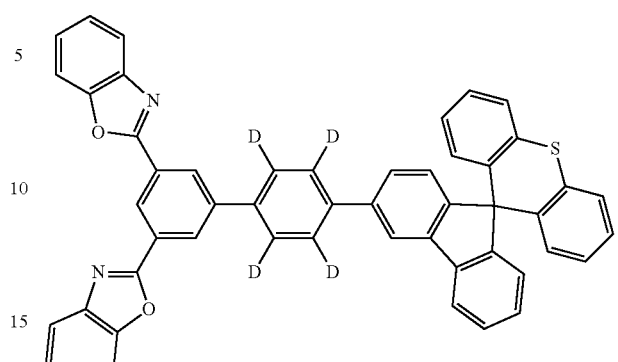
167
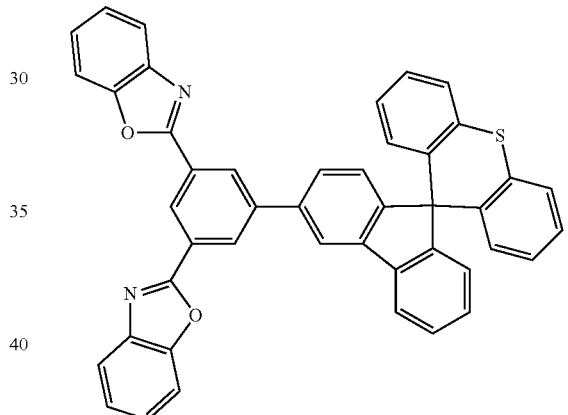
168
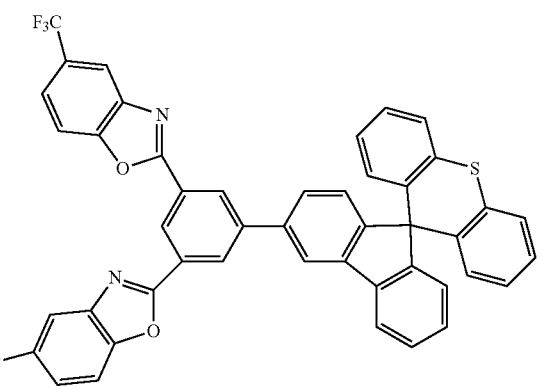

169
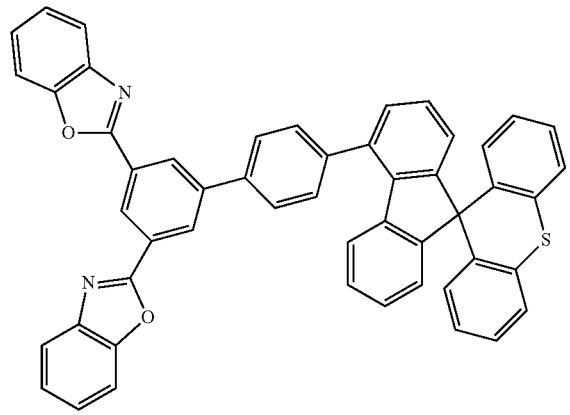
170
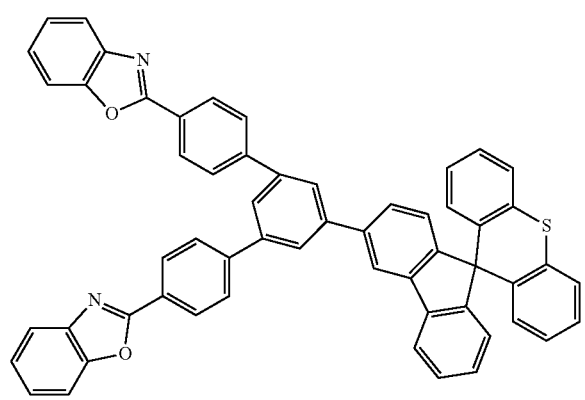
171
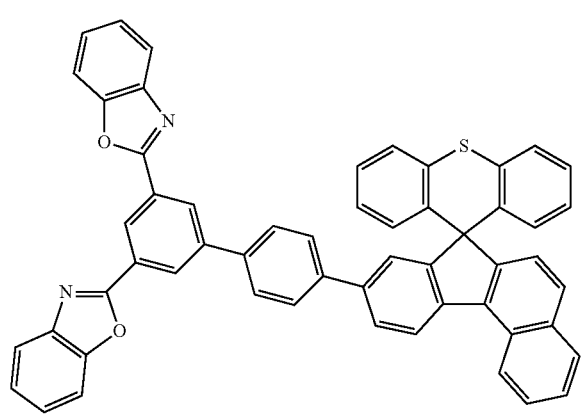
172
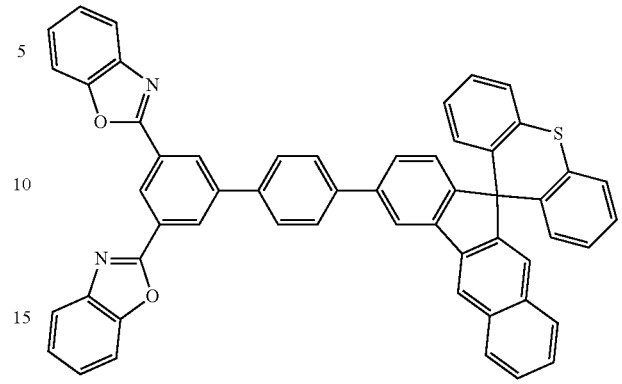
173
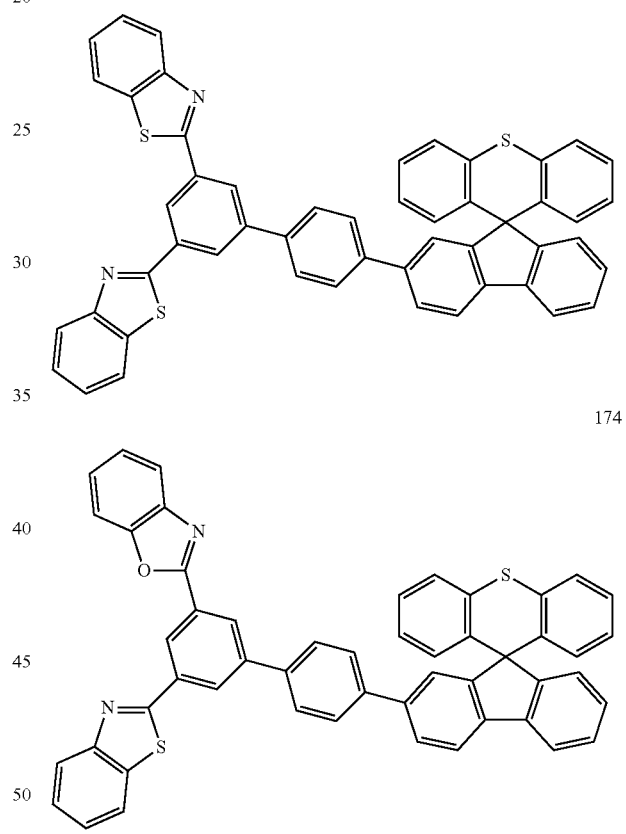
174
175
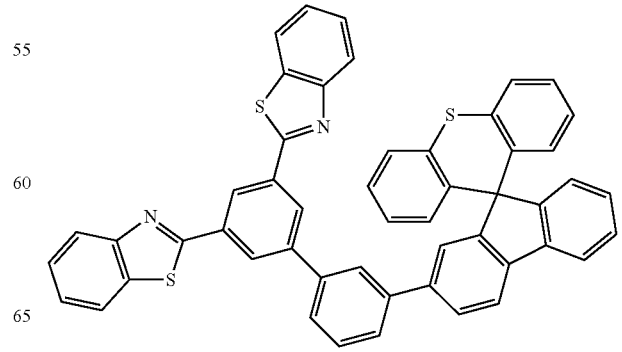

176
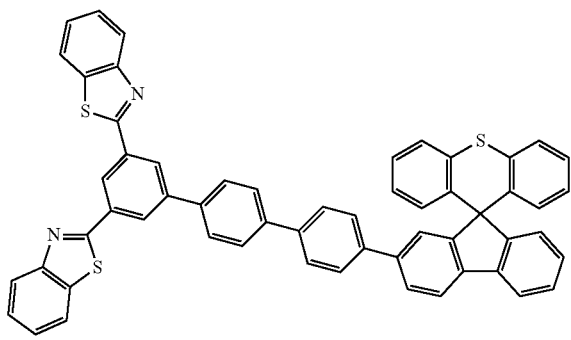
177
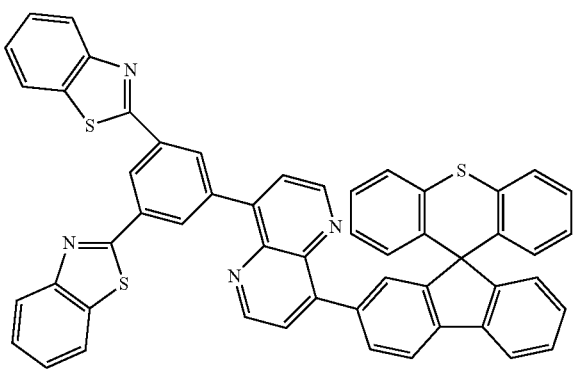
178
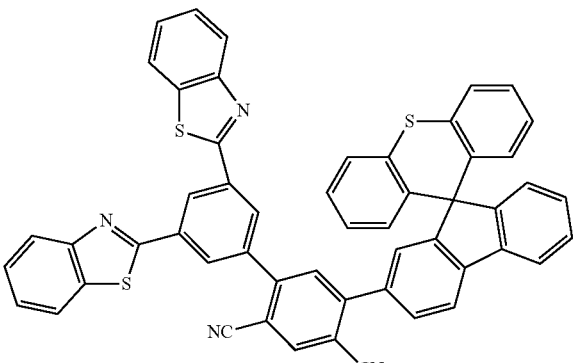
179
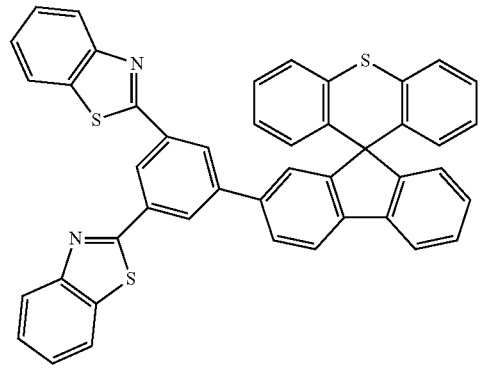
180
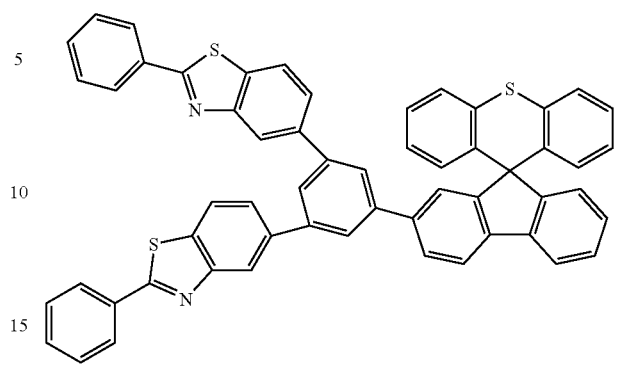
181
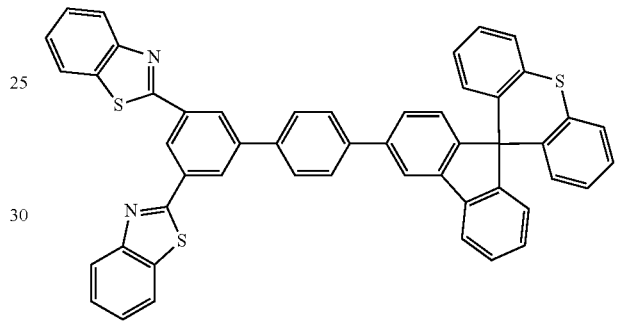
182
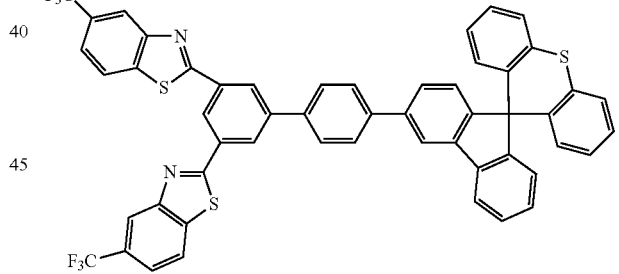
183
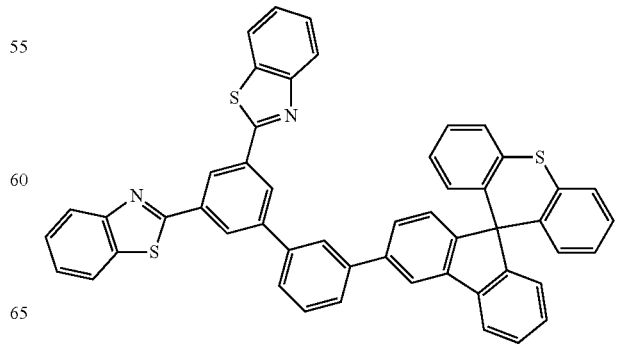

184
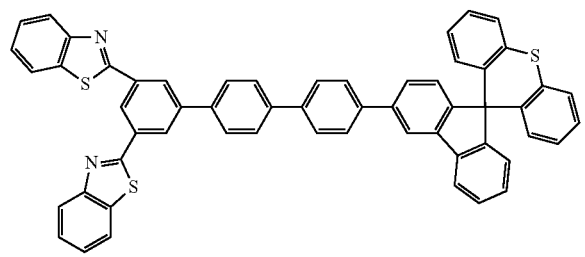
185
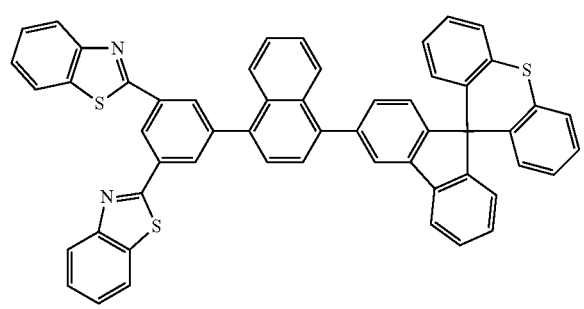
186
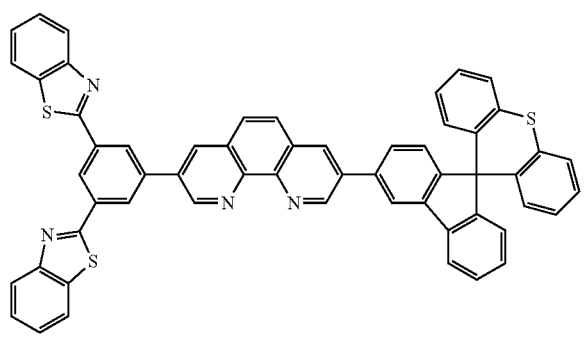
187
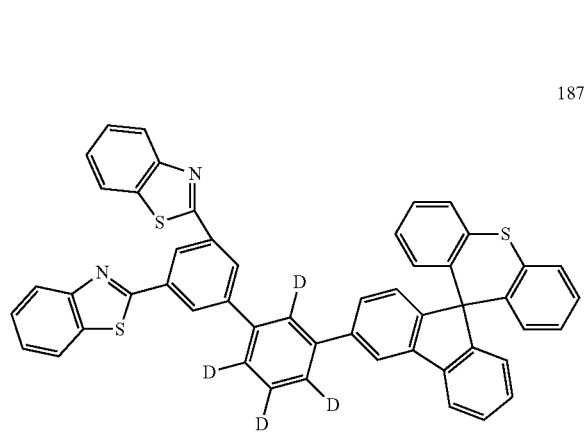
188
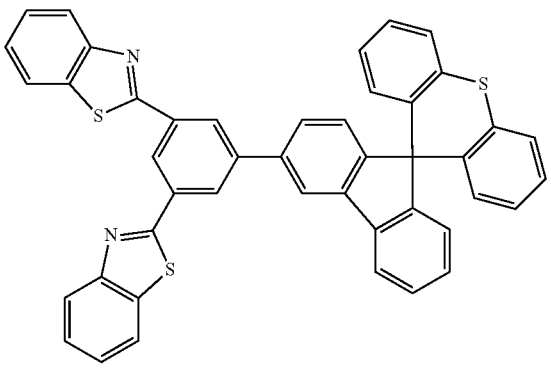
189
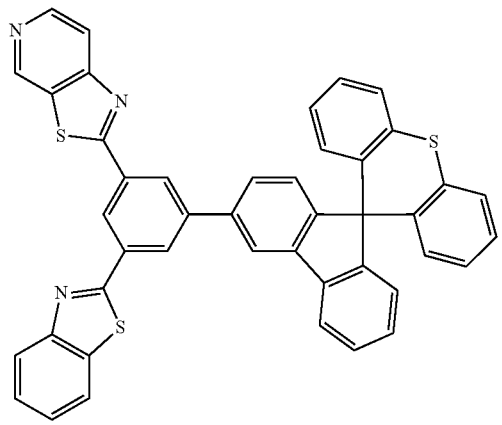
190
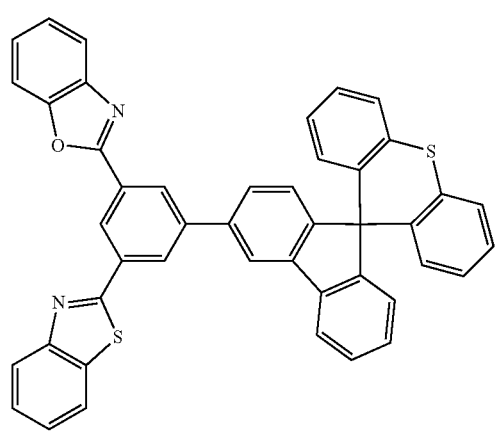

191
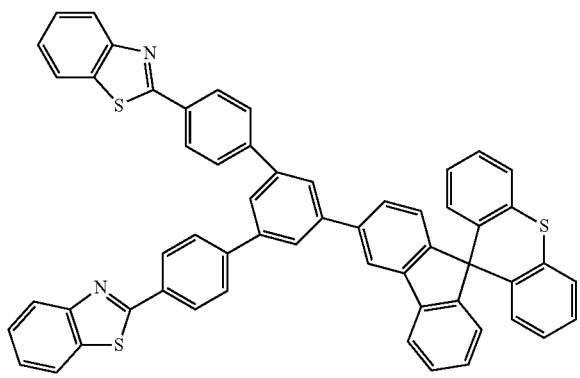
192
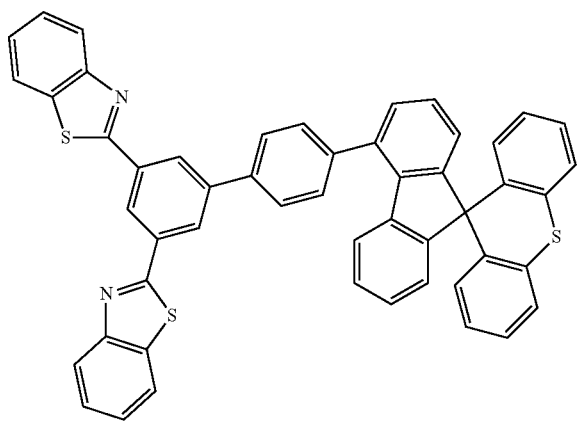
193
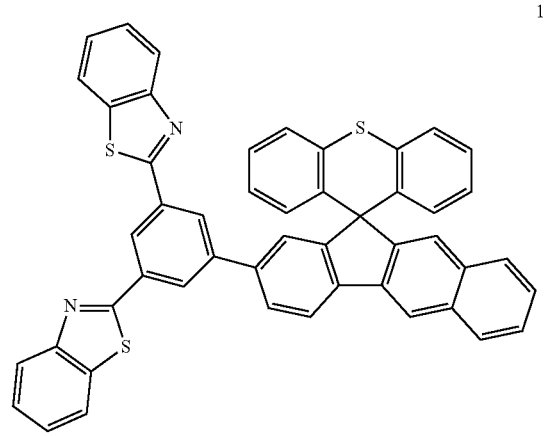
194
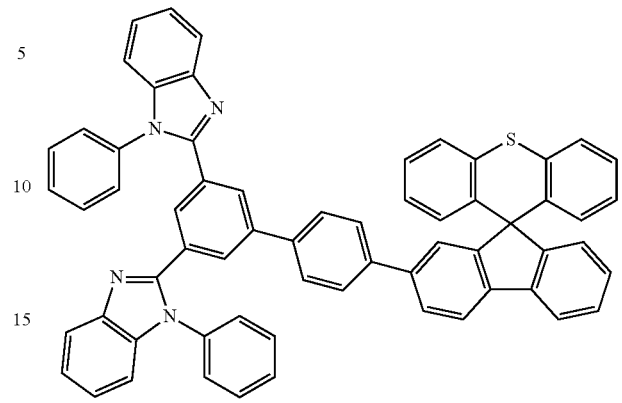
195
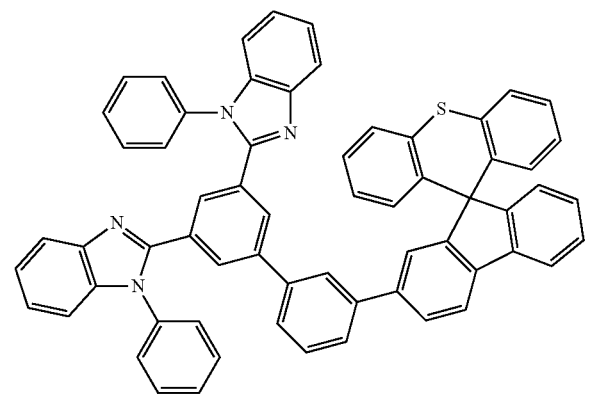
196
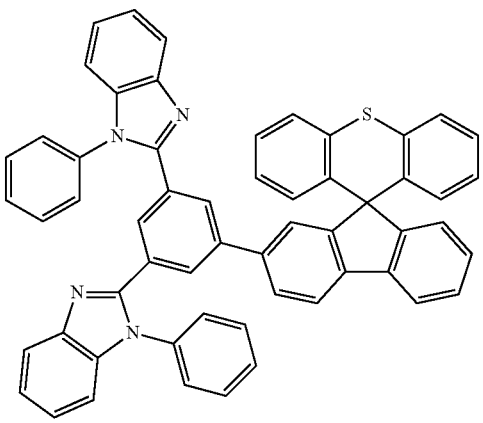

197
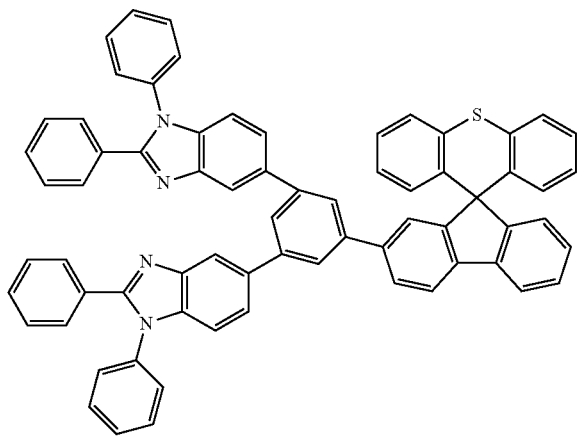
200
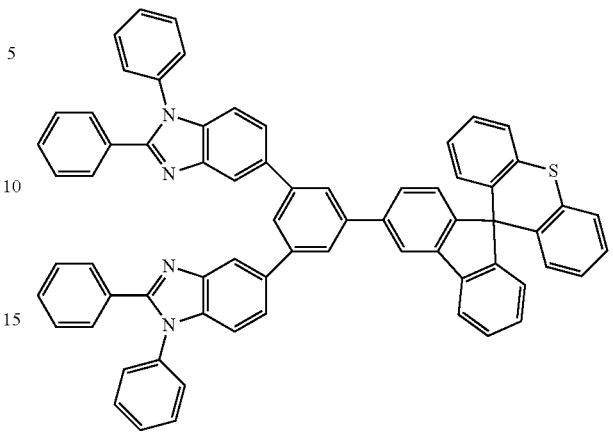
198
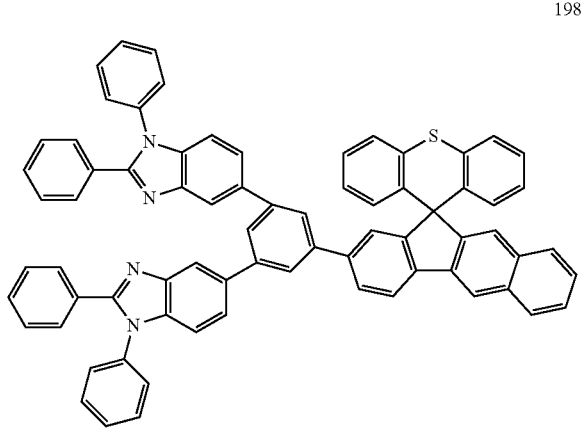
201
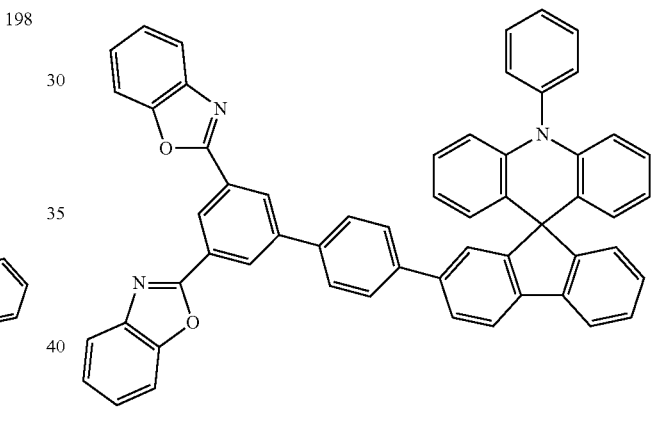
199
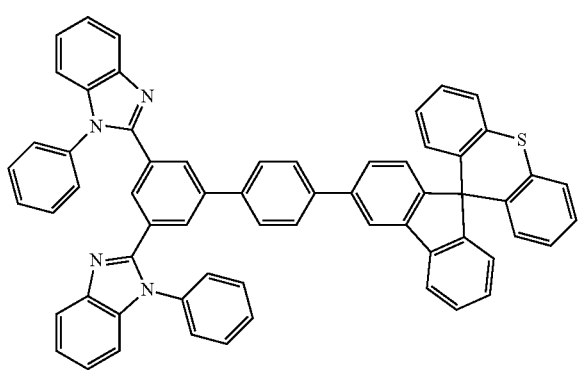
202
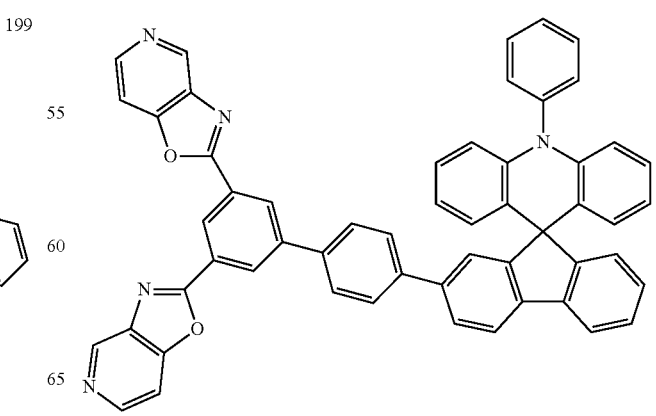

203
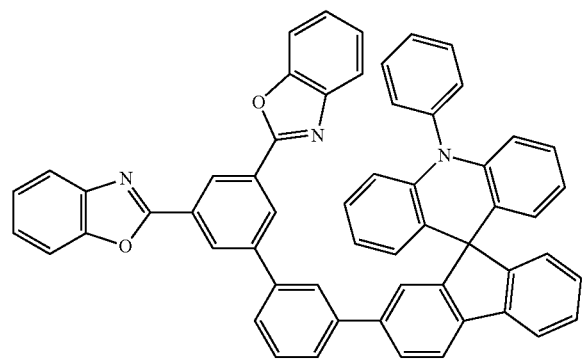
204
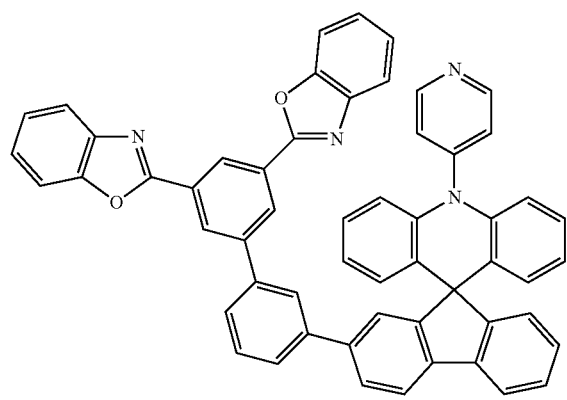
205
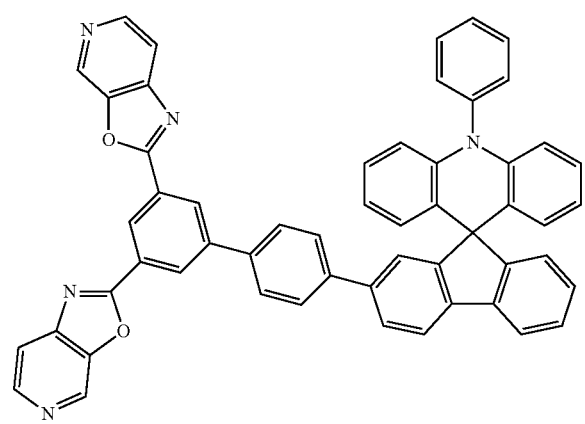
206
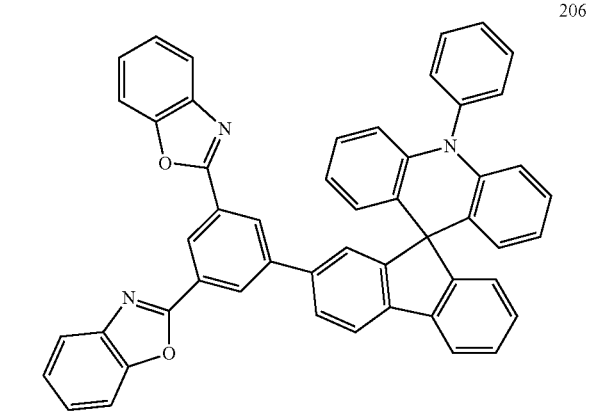
207
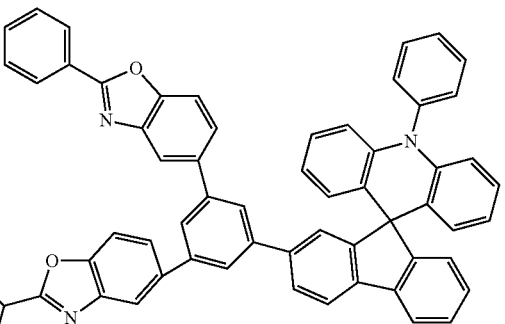
208
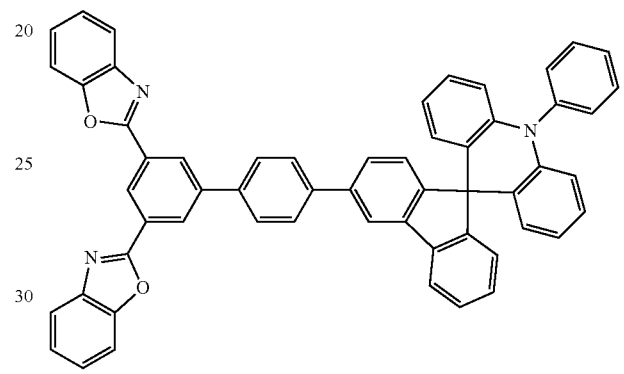
209
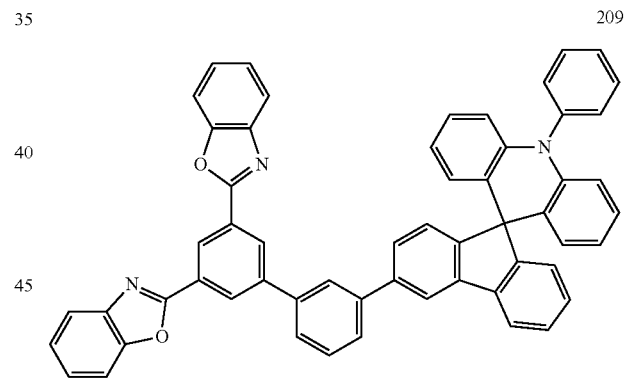
210
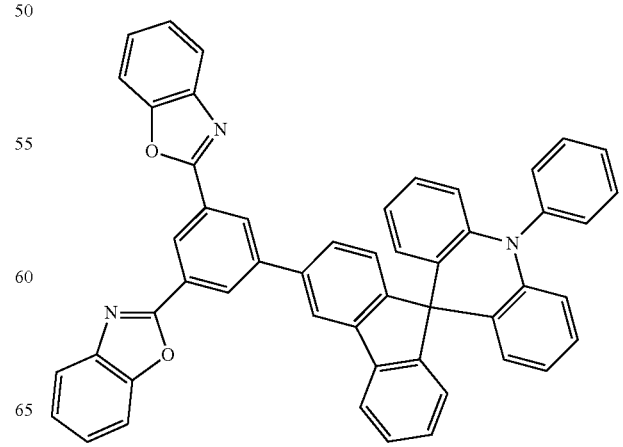

211
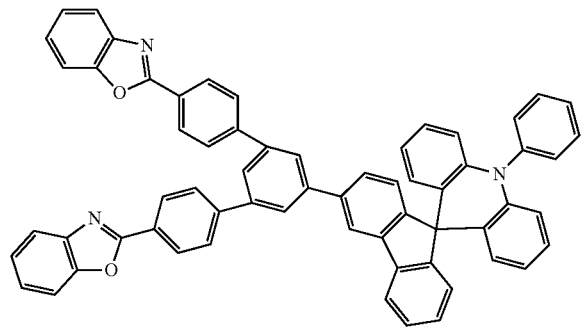
212
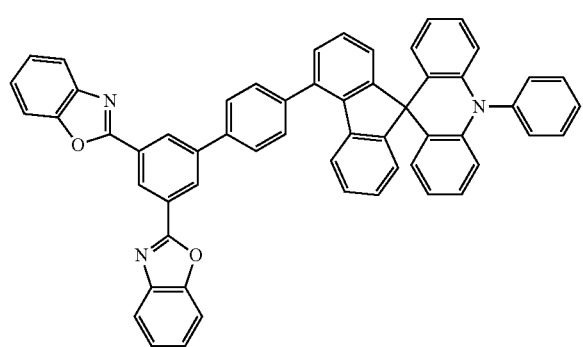
213
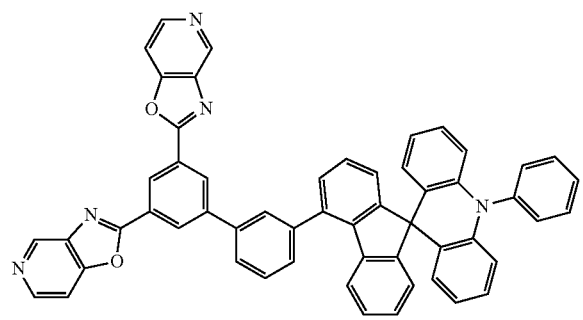
214
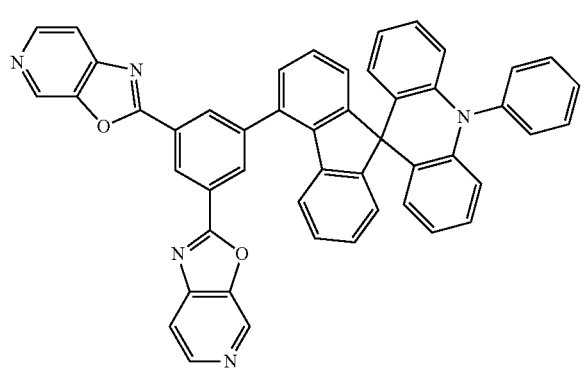
215
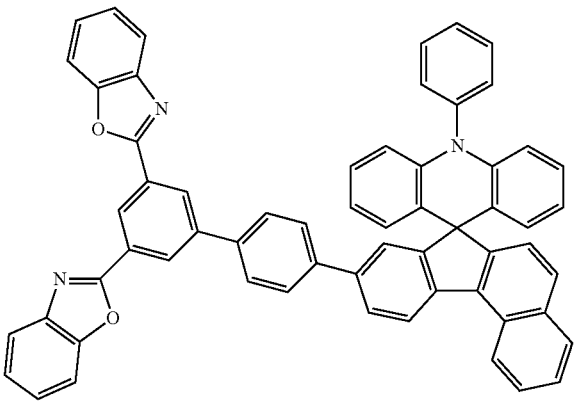
216
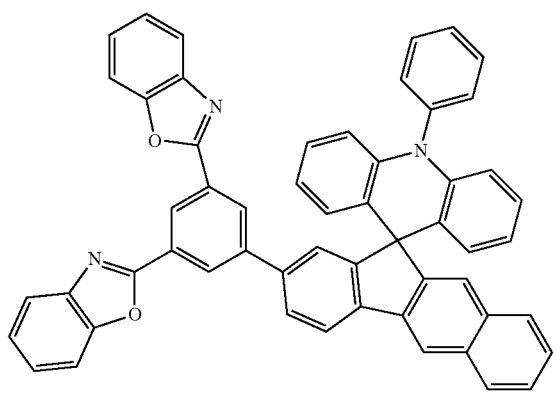
217
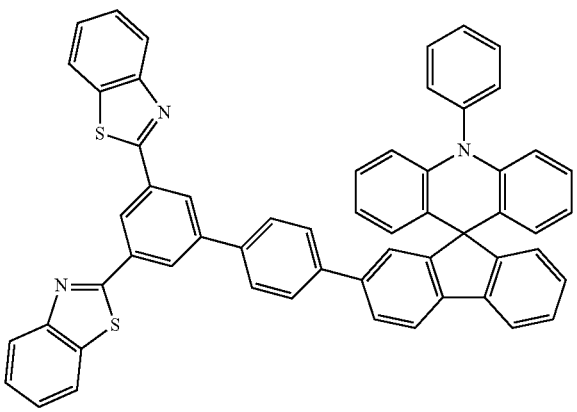
218
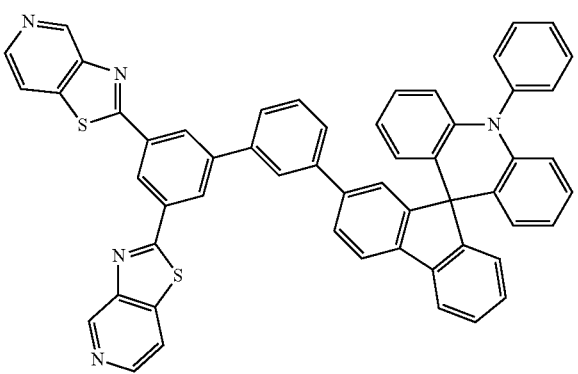

219
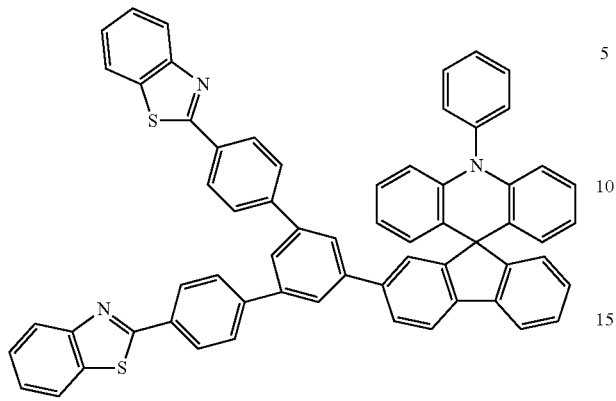
220
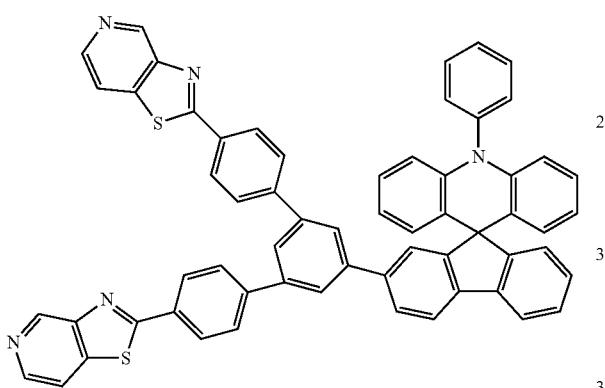
221
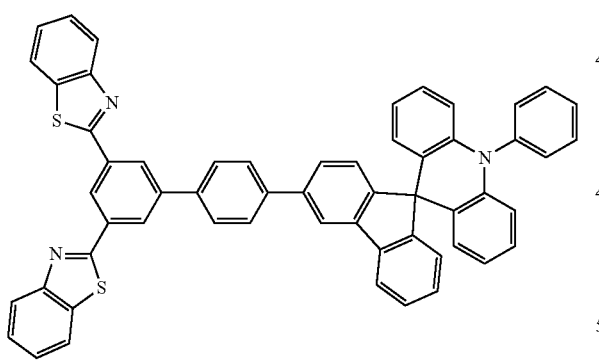
222
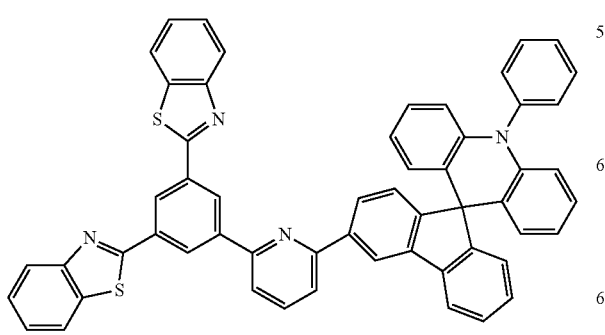
223
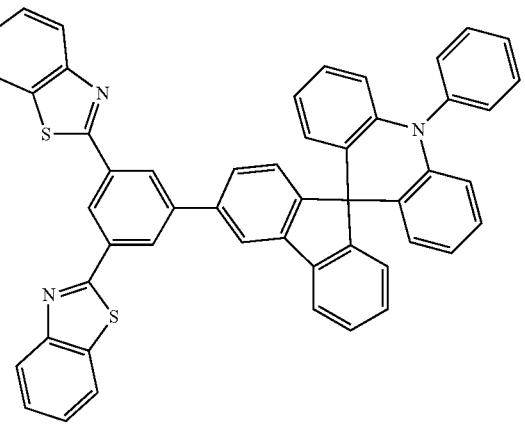
224
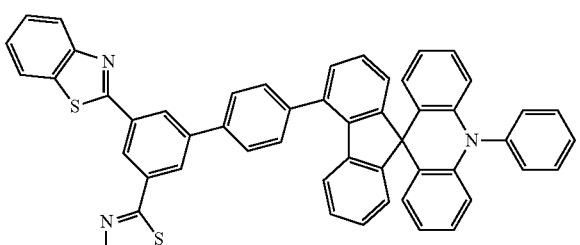
225
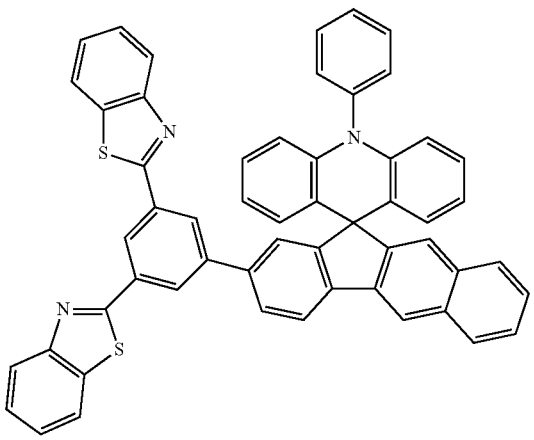

226
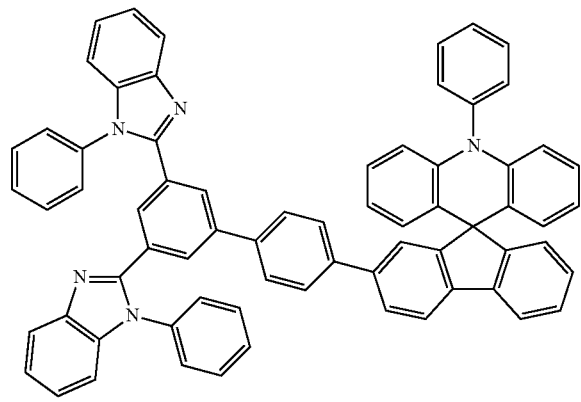
227
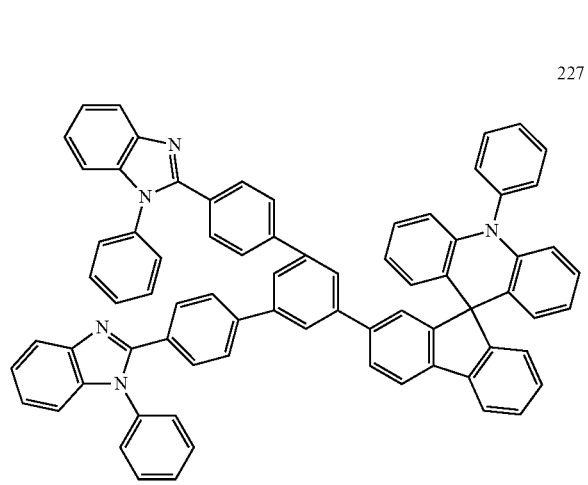
228
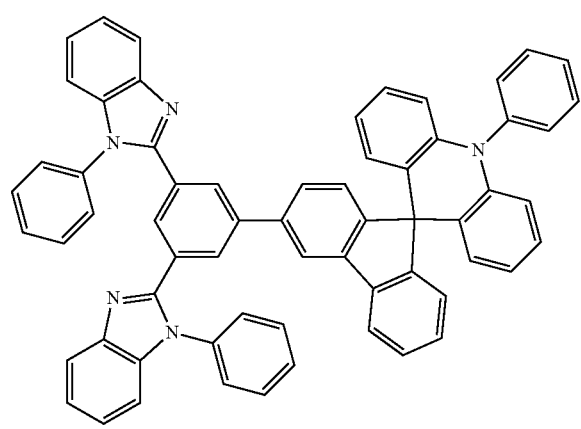
229
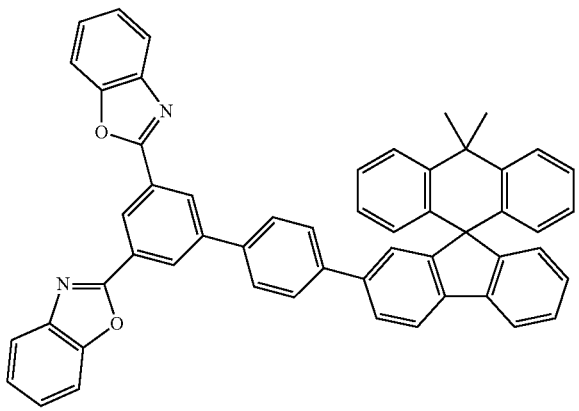
230
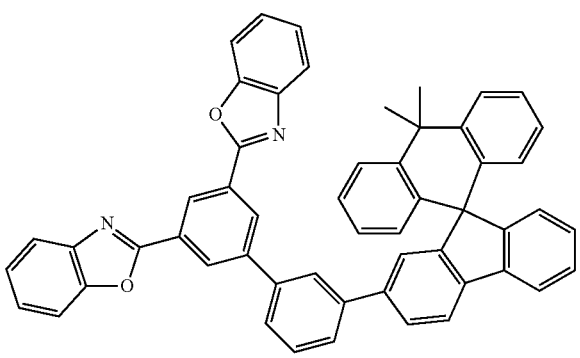
231
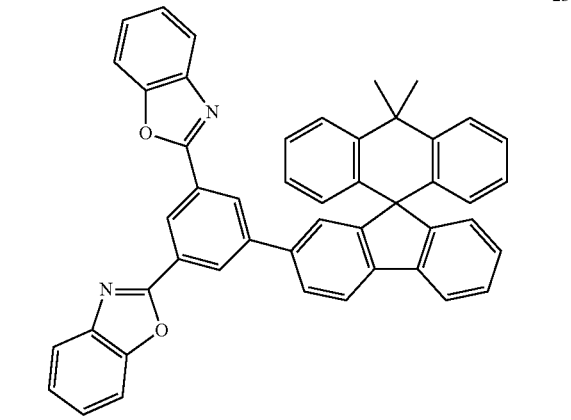
232
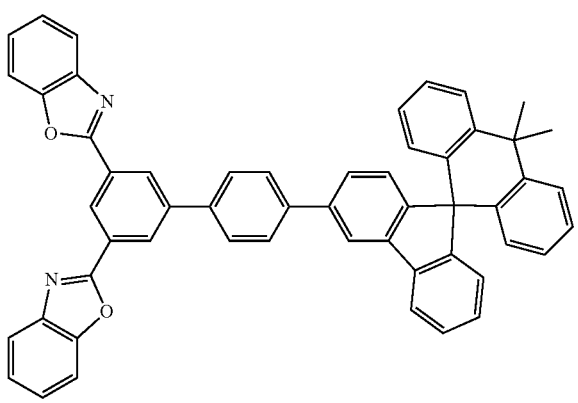

233
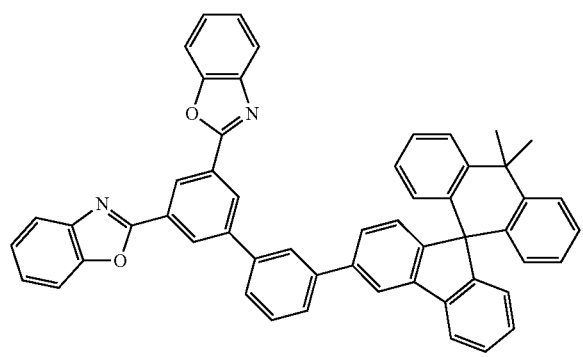
234
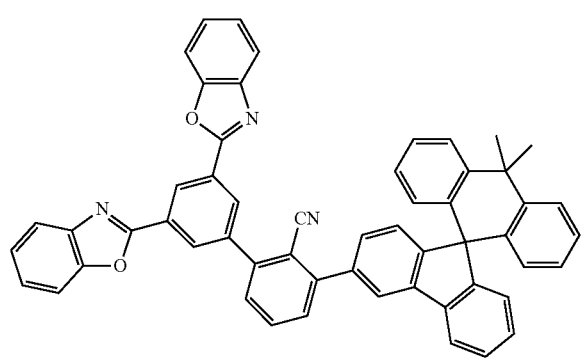
235
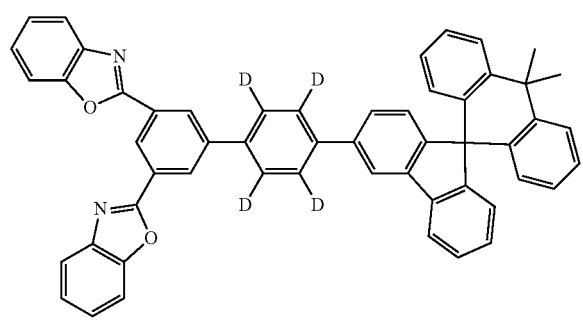
236
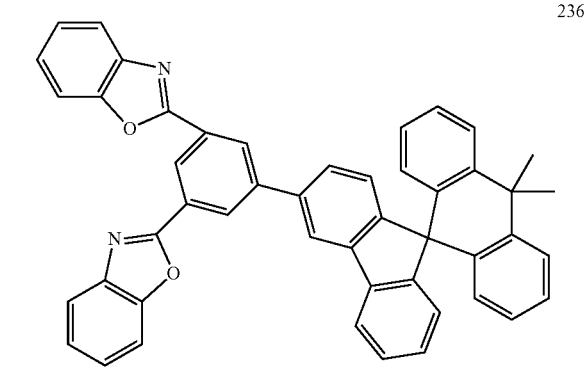
237
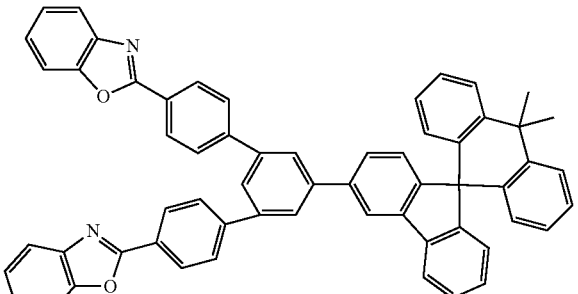
238
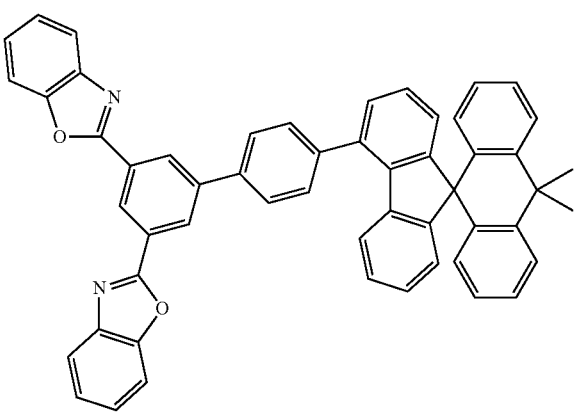
239
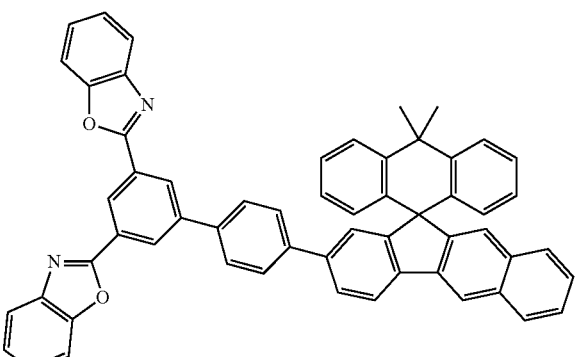
240
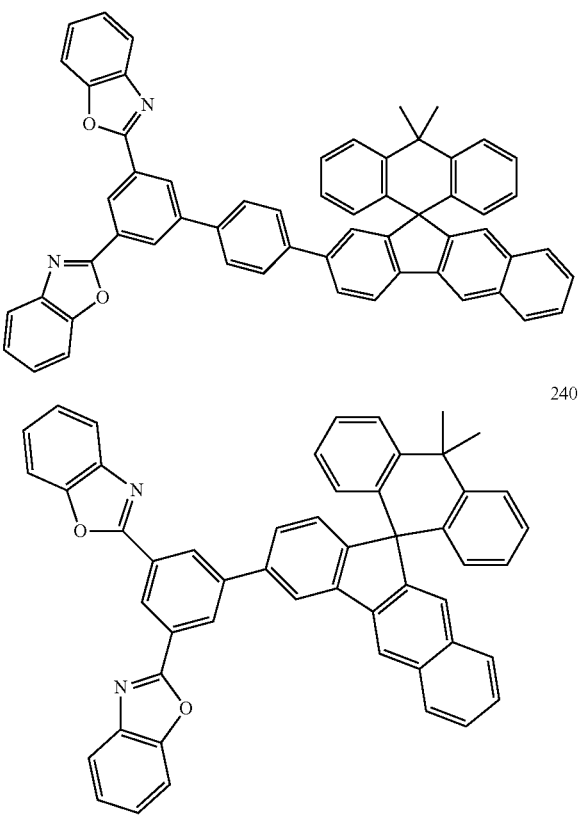

-continued
241
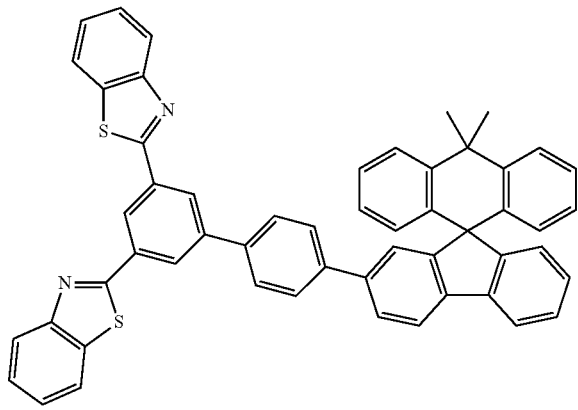
242
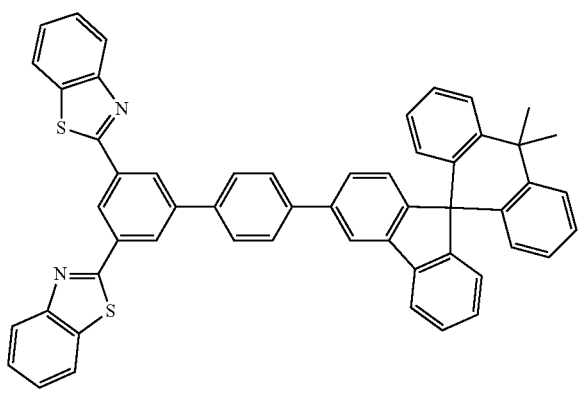
243
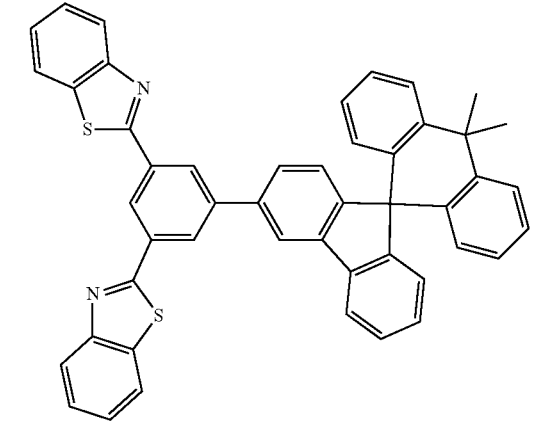
244
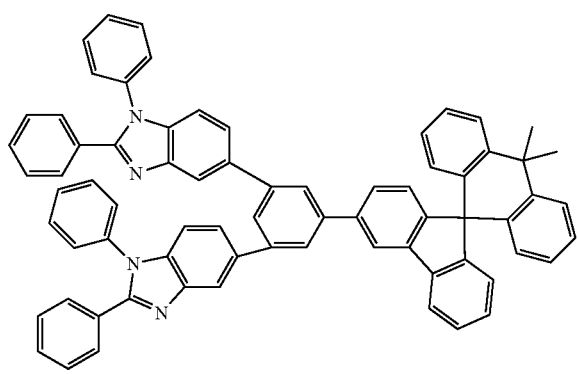
-continued
245
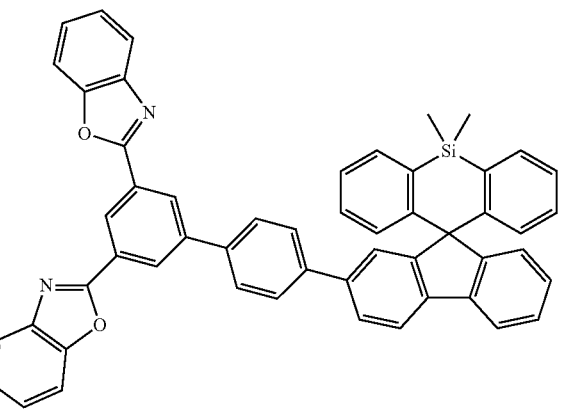
246
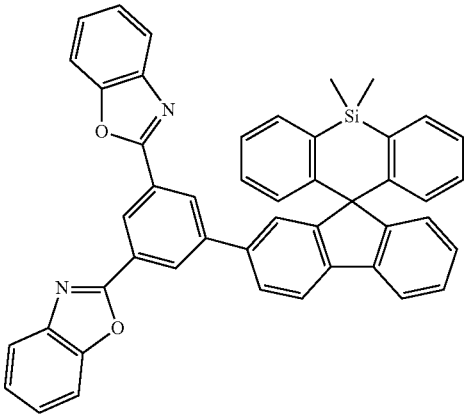
247
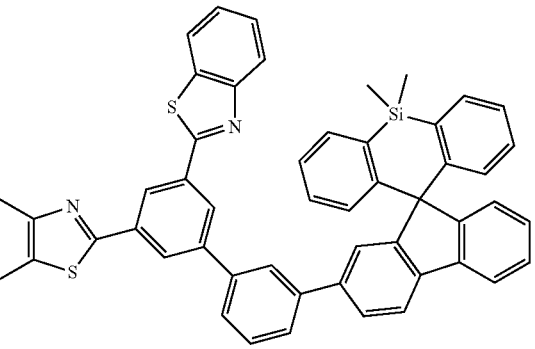
248
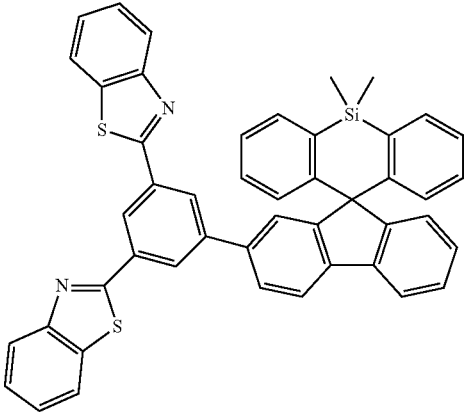

249
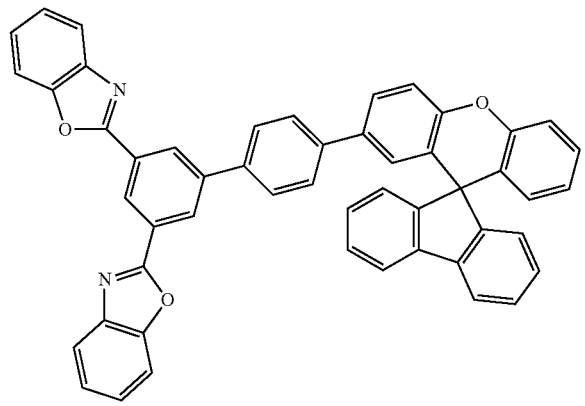
250
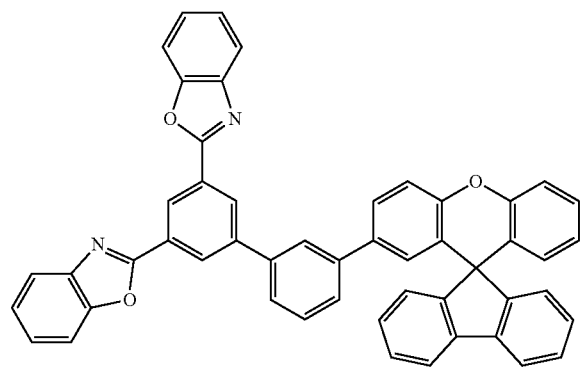
251
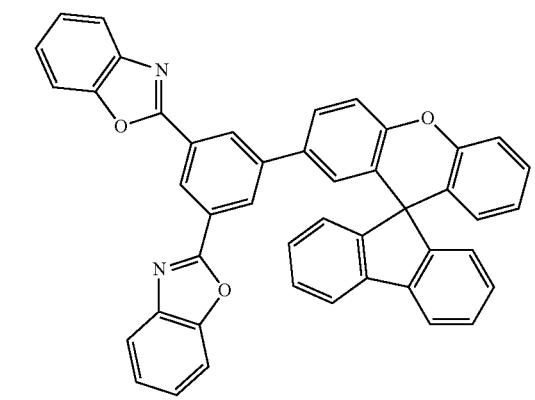
252
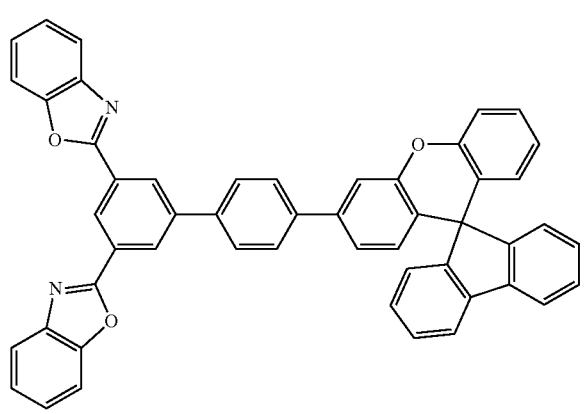
253
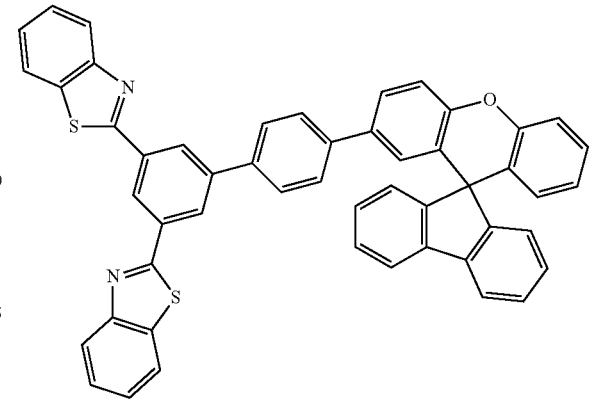
254
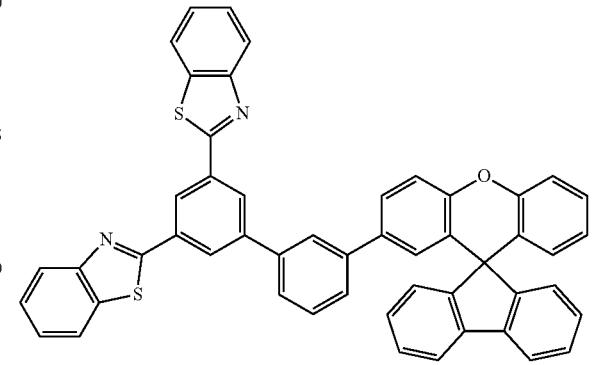
255
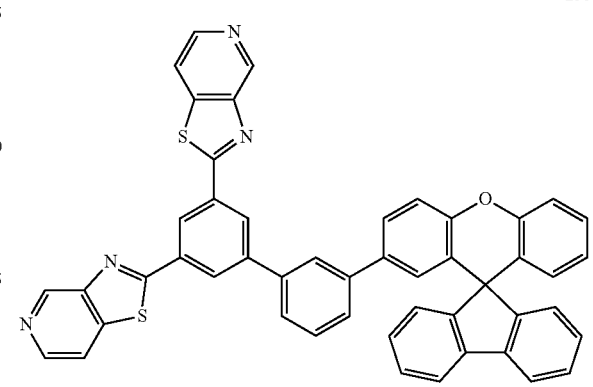
256
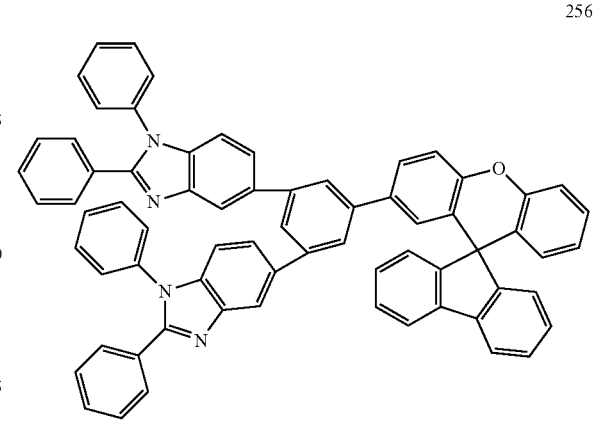

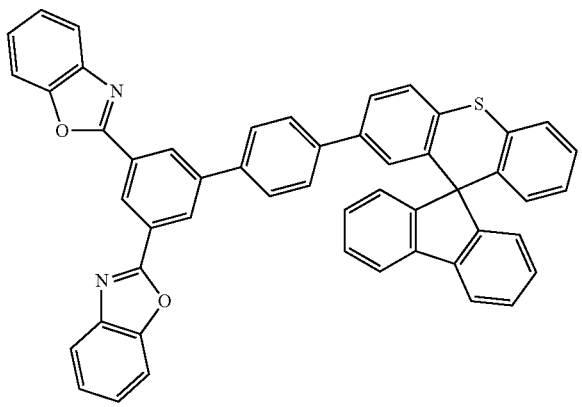

257

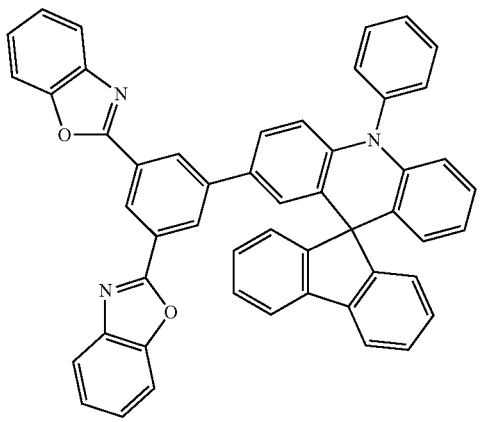

258

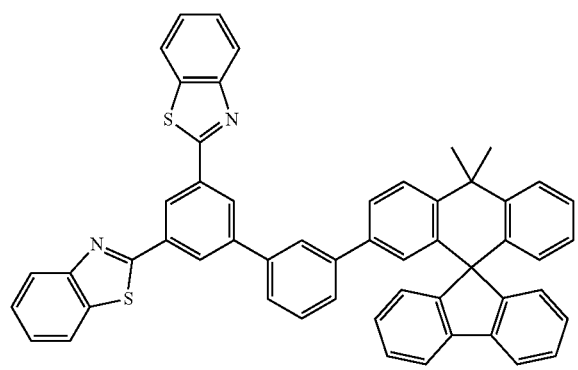

259

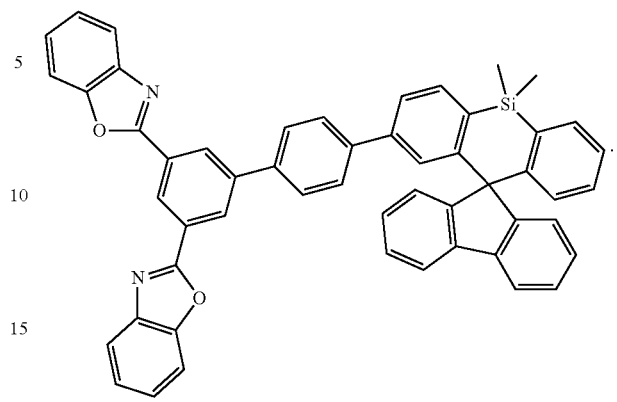

260

6. An organic electroluminescent device, comprising an anode, an organic layer, and a cathode, wherein the organic layer is disposed between the anode and the cathode, and the organic layer comprises an electron transport region containing the heterocyclic derivative according to claim 1.

7. The organic electroluminescent device according to claim 6, wherein the organic layer further comprises a hole transport region containing a triarylamine compound as shown in Formula II:

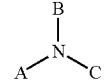

Formula II wherein A and B are independently selected from one of the following substituents:

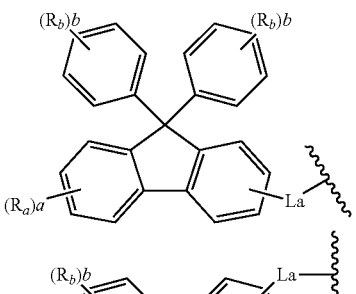

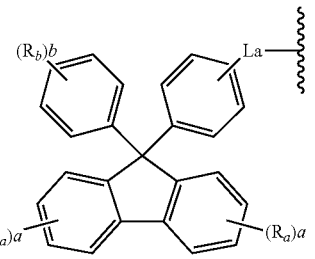

wherein $R_a$ is identically or differently selected from one of hydrogen, deuterium, C1 to C15 alkyl, C3 to C15 cycloalkyl, C2 to C30 alkenyl, C6 to C30 aryl or C3 to C30 heteroaryl, or two adjacent groups are joined to form a ring;

$R_b$ is identically or differently selected from one of hydrogen, deuterium, C1 to C15 alkyl, C3 to C15 cycloalkyl, C2 to C30 alkenyl, C6 to C30 aryl or C3 to C30 heteroaryl, or two adjacent groups are joined to form a ring;
$L_a$ is selected from one of a single bond, C6 to C30 arylene or C3 to C30 heteroarylene;
a is selected from 0, 1, 2, 3 or 4, and b is selected from 0, 1, 2, 3, 4 or 5; and
C is selected from one of the following groups:
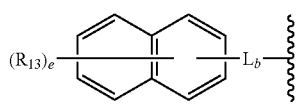
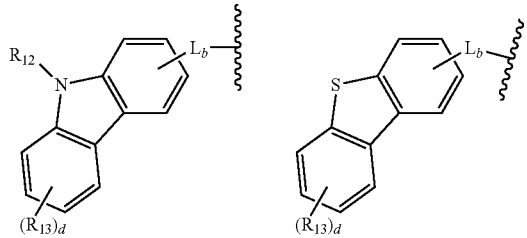
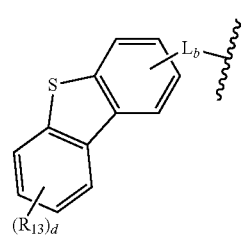
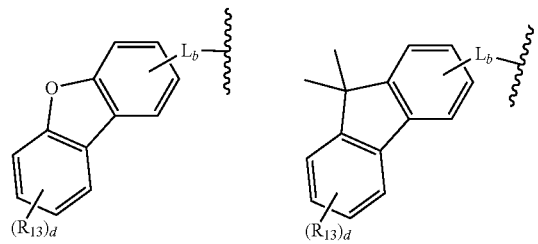
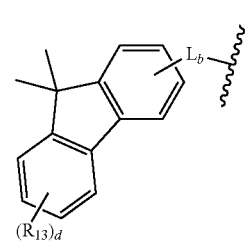
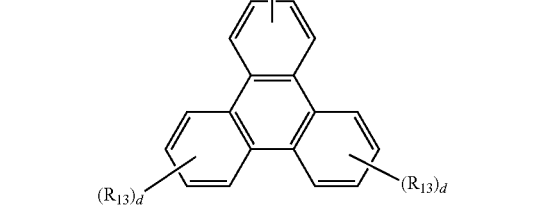
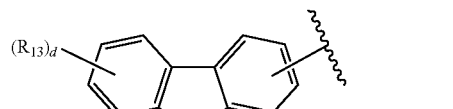
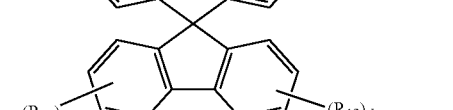
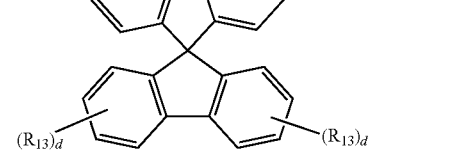
-continued
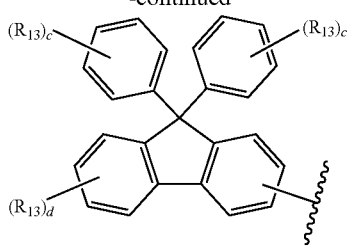
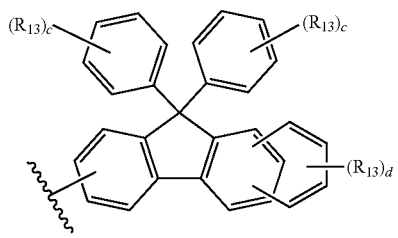
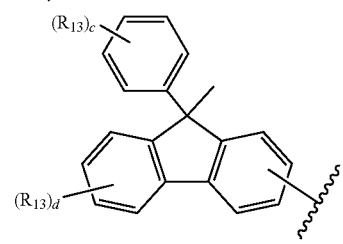
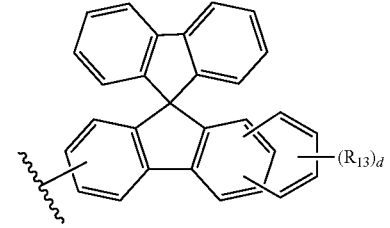
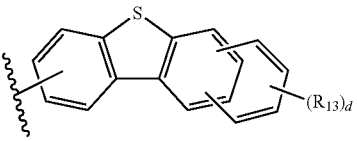
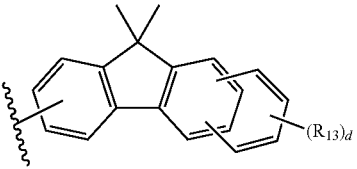
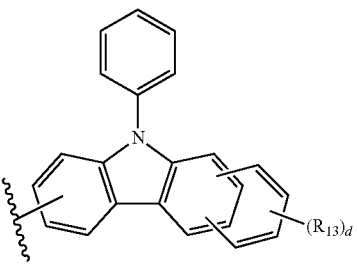
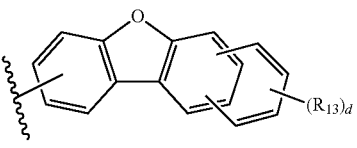

301

-continued

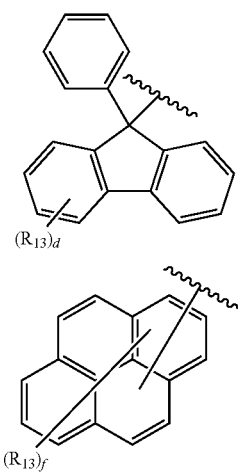

wherein $R_{12}$ is selected from one of methyl, ethyl, propyl, butyl, phenyl, tolyl, biphenyl or naphthyl;

$R_{13}$ is selected from one of deuterium, methyl, ethyl, propyl, butyl, cyclohexyl, adamantyl, phenyl, tolyl, biphenyl, terphenyl, naphthyl, anthryl, phenanthryl, triphenylenyl, acridyl, spirodifluorenyl, 9,9-dimethyl-fluorenyl, 9,9-diphenylfluorenyl, 9-phenylcarbazolyl, pyrenyl, indolyl, benzothiophenyl, benzofuranyl, dibenzothiophenyl or dibenzofuranyl;

$L_b$ is selected from one of a single bond, phenylene, deuterated phenylene, deuterated naphthylene, tolylene, biphenylene, naphthylene, terphenylene, dibenzofuranylene, fluorenylene or dibenzothiophenylene; and c is selected from 0, 1, 2, 3, 4 or 5; d is selected from 0, 1, 2, 3 or 4; e is selected from 0, 1, 2, 3, 4, 5, 6 or 7; f is selected from 0, 1, 2, 3, 4, 5, 6, 7, 8 or 9.

8. The organic electroluminescent device according to claim 7, wherein C is selected from one of the following groups:

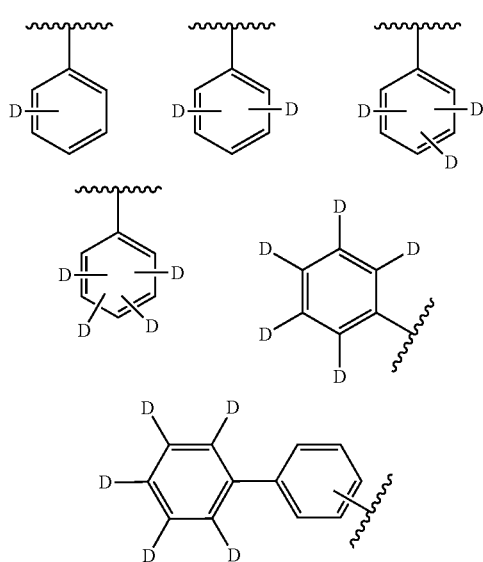

302

-continued

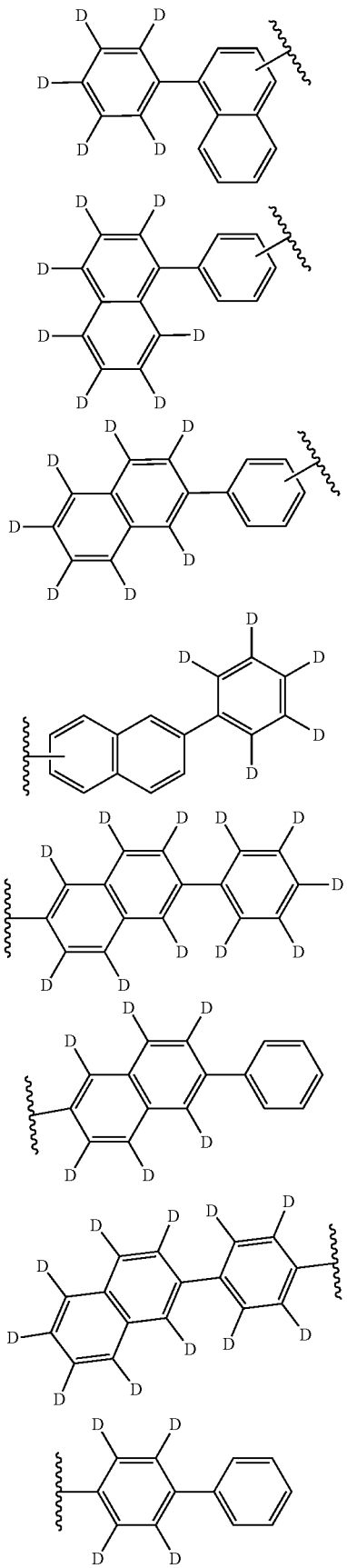

303
-continued
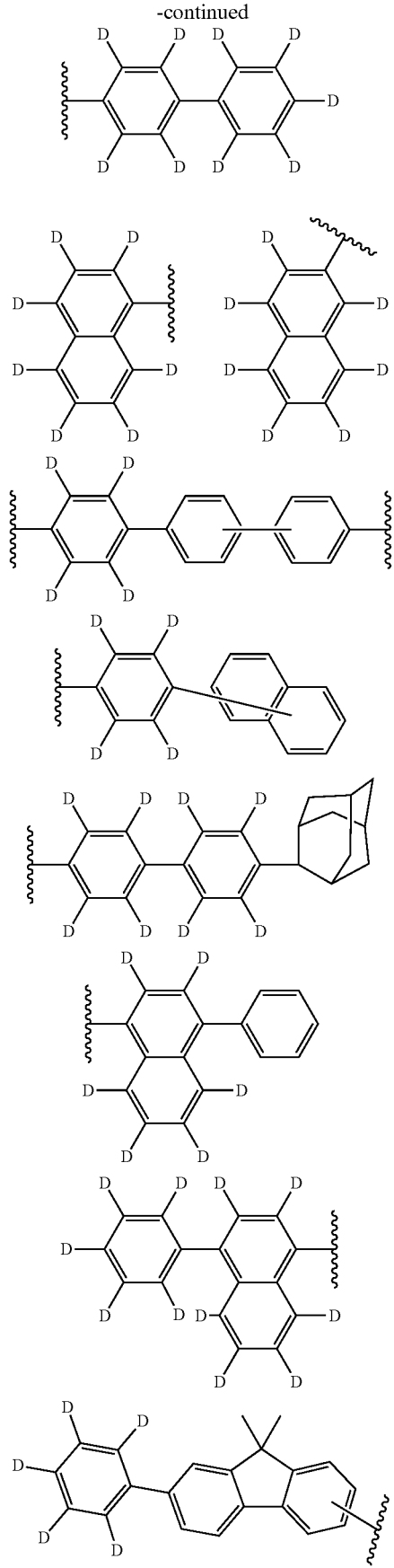
304
-continued
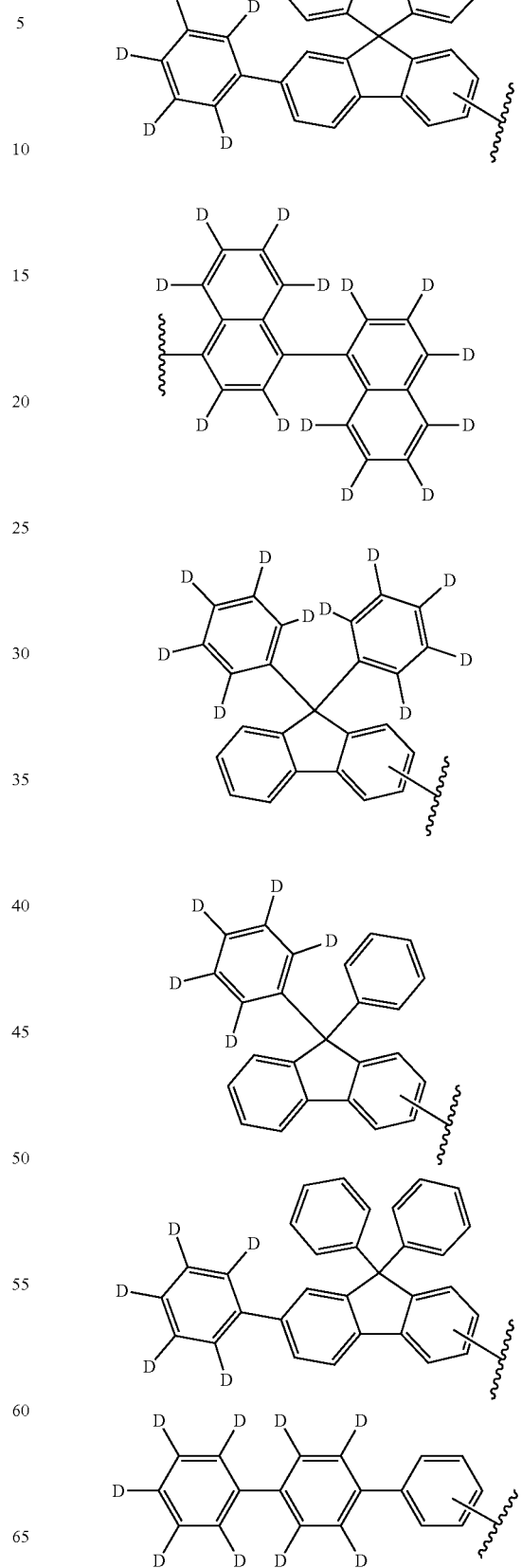

305
-continued
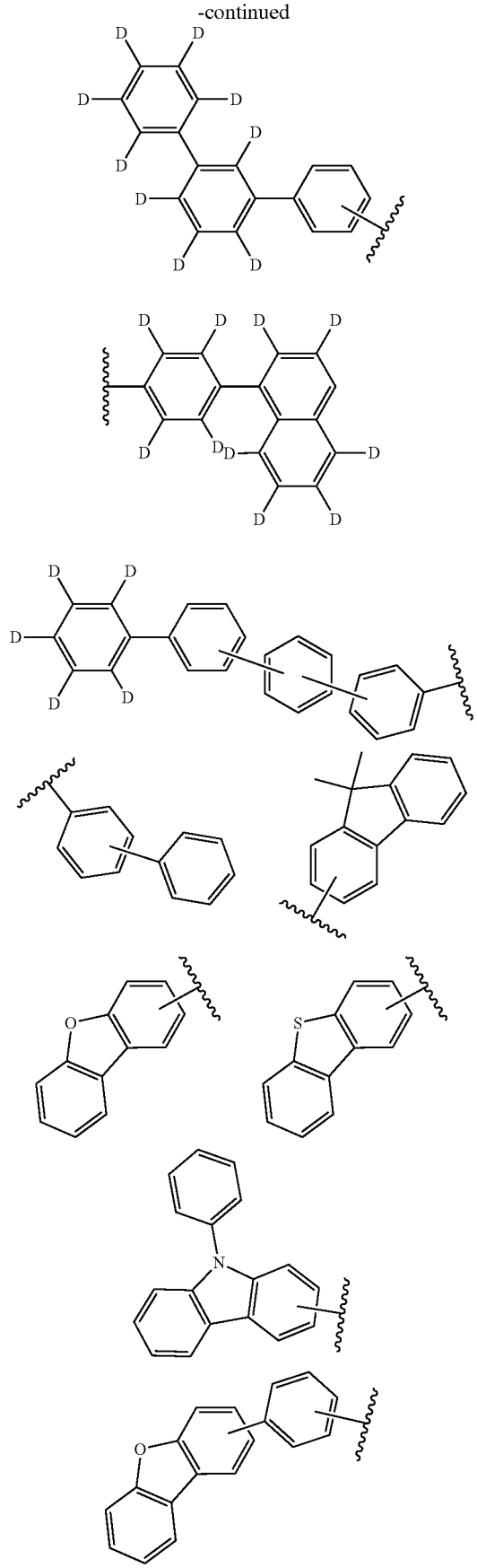
306
-continued
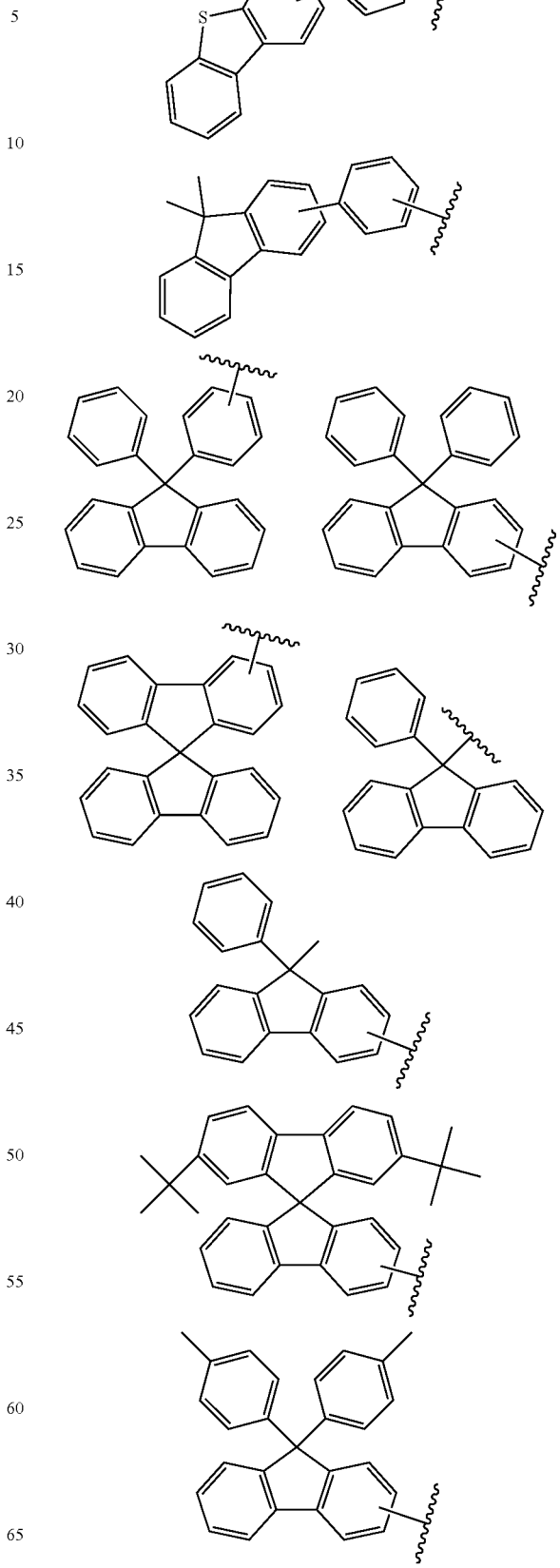

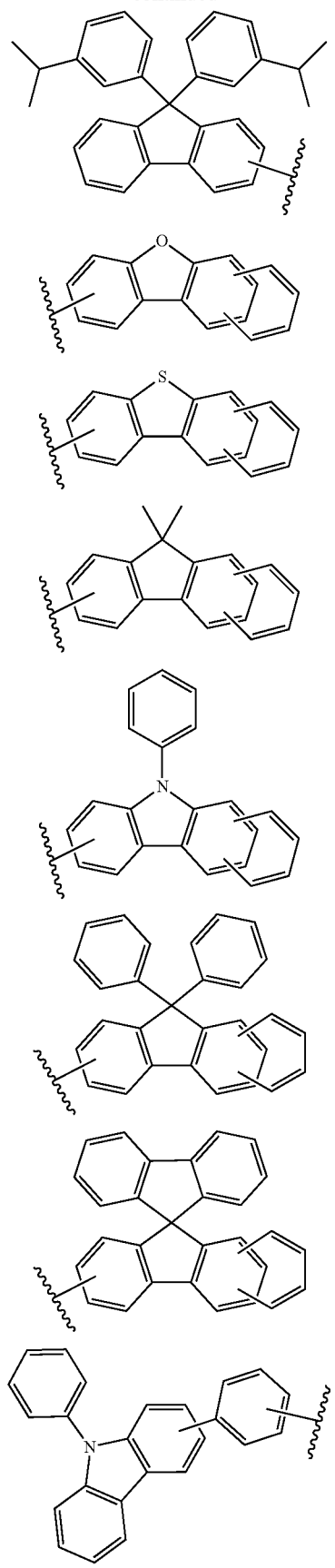
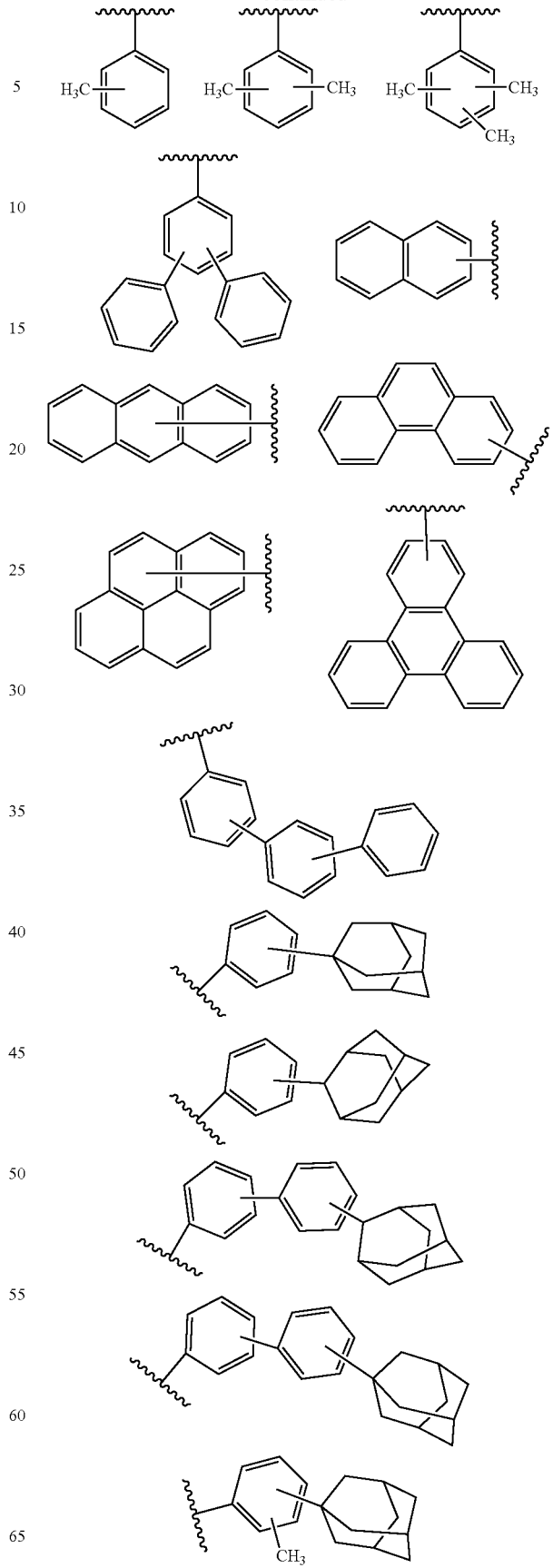

309
-continued
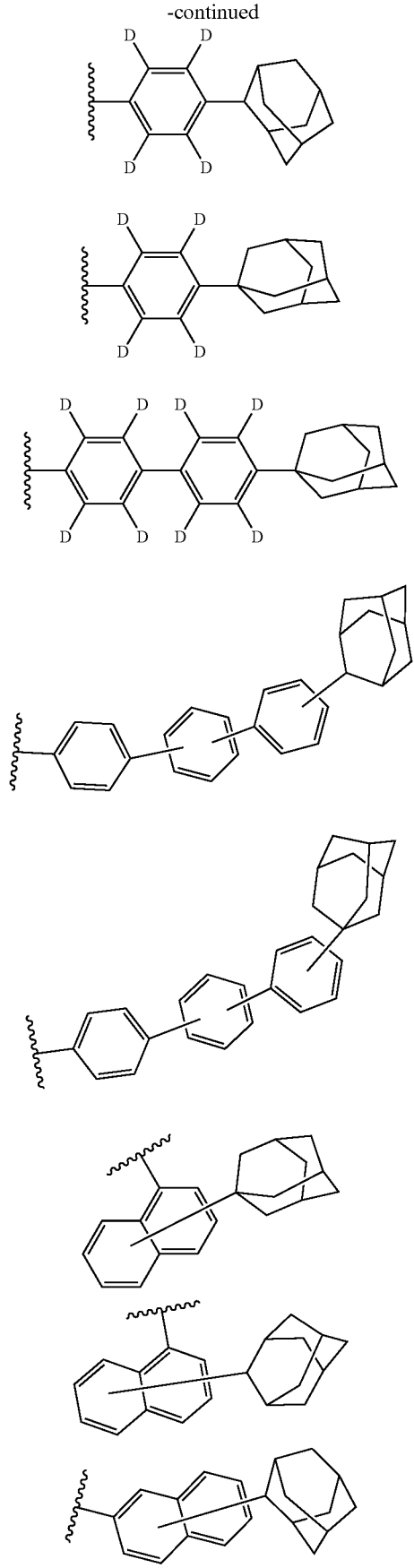
310
-continued
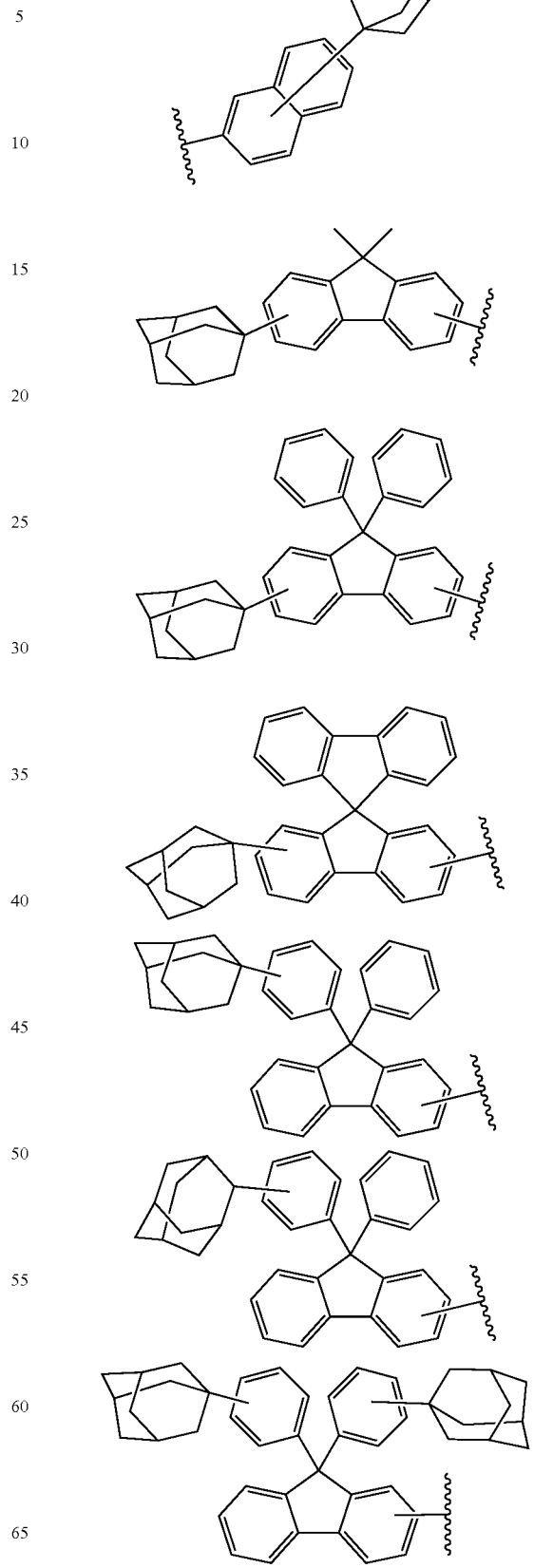

-continued

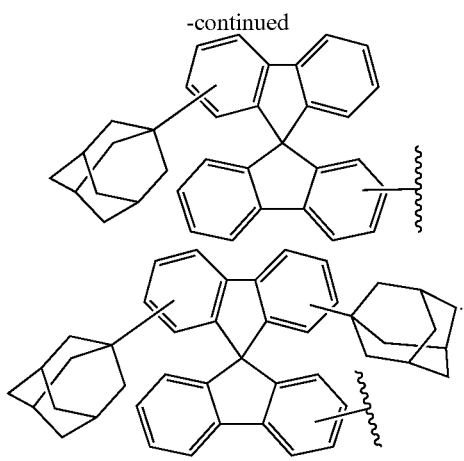

9. The organic electroluminescent device according to claim 7, wherein $R_a$ is independently selected from one of hydrogen, deuterium, methyl, ethyl, propyl, butyl, adamantyl, camphanyl, norbornyl, phenyl, tolyl, biphenyl, triphenyl, naphthyl, anthryl, phenanthryl, triphenylenyl, acridinyl, spirodifluorenyl, 9,9-dimethylfluorenyl, 9,9-diphenylfluorenyl, 9-phenylcarbazolyl, pyrenyl, indolyl, benzothiophenyl, benzofuranyl, dibenzothiophenyl or dibenzofuranyl, or two adjacent groups are joined to form a ring;

$L_a$ is selected from one of a single bond, phenylene, tolylene, biphenylene, naphthylene, terphenylene, dibenzofuranylene, fluorenylene or dibenzothiophenylene; and $R_b$ is identically or differently selected from one of hydrogen, deuterium, methyl, ethyl, propyl, butyl, adamantyl, camphanyl, norbornyl, phenyl, tolyl, biphenyl or triphenyl, or two adjacent groups are joined to form a ring.

10. The organic electroluminescent device according to claim 7, wherein the triarylamine compound as shown in Formula II is selected from one of the following structures:

II-1

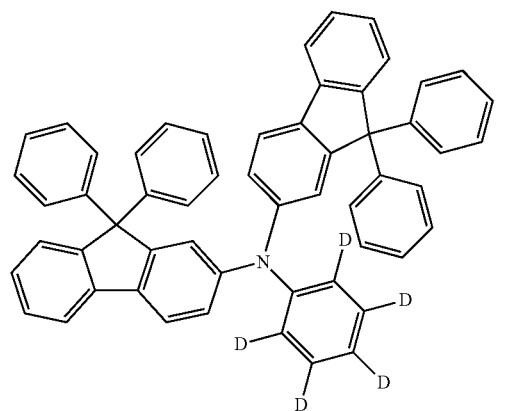

II-2

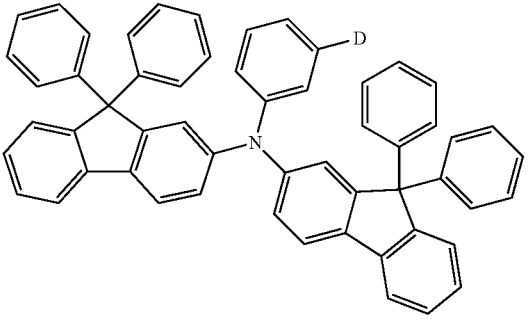

II-3

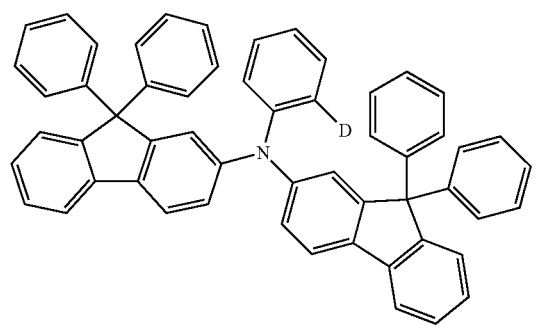

II-4

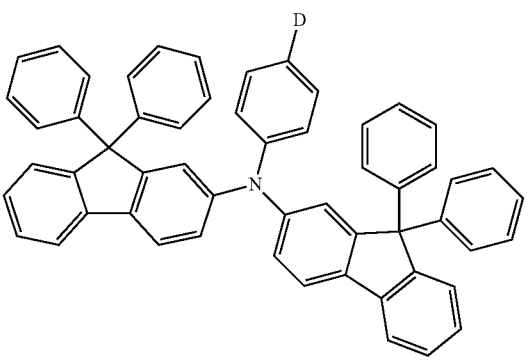

-continued
II-5
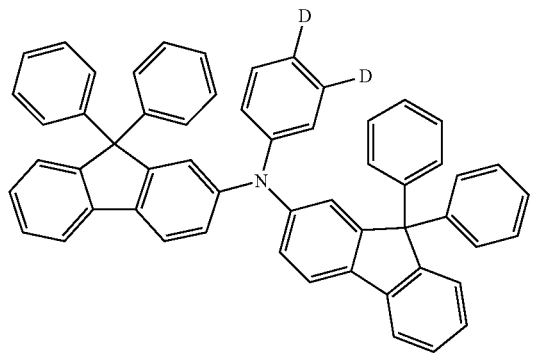
II-6
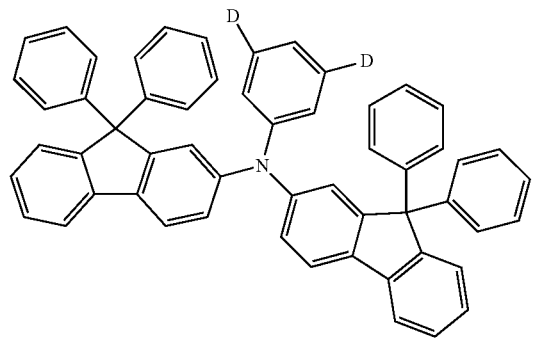
II-7
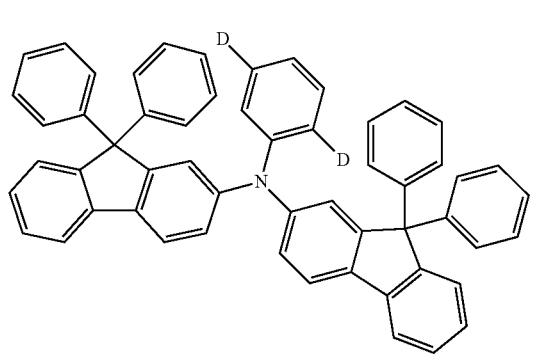
II-8
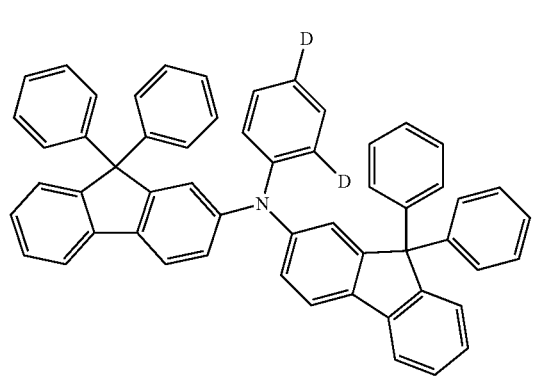
II-9
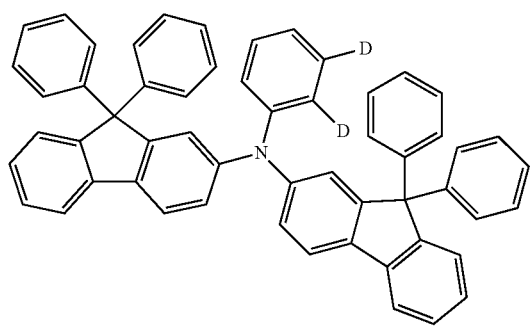
II-10
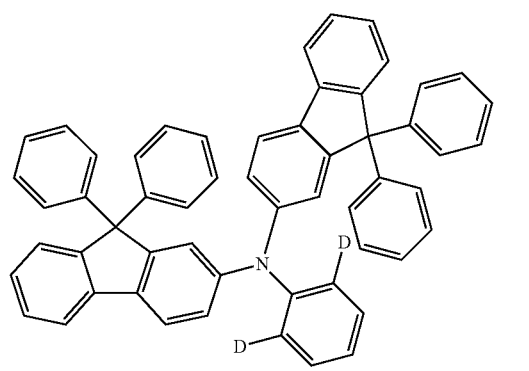
II-11
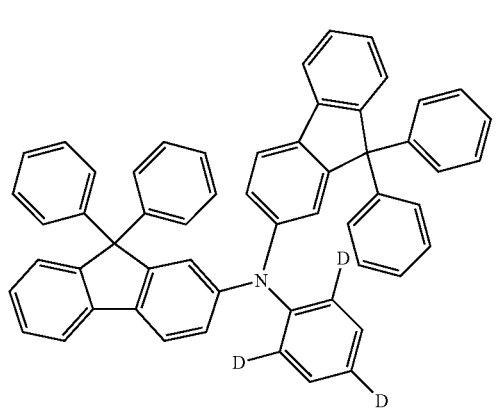
II-12
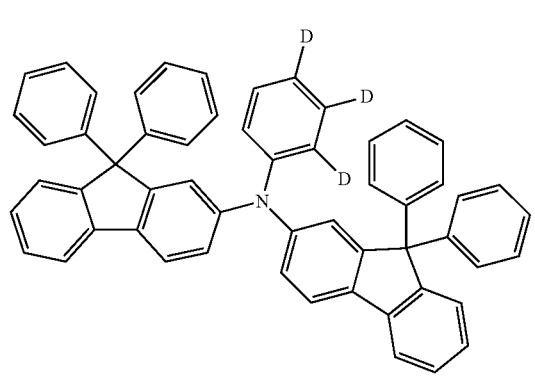

-continued
II-13
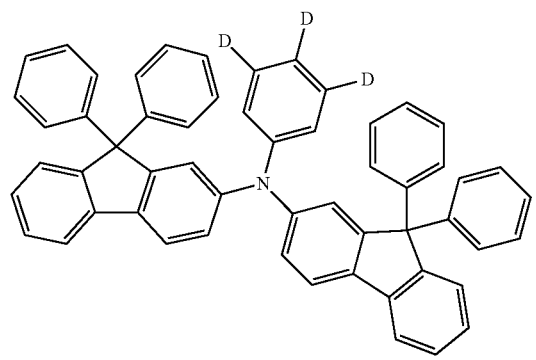
II-14
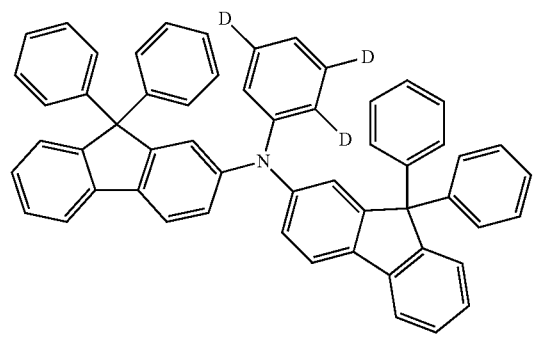
II-15
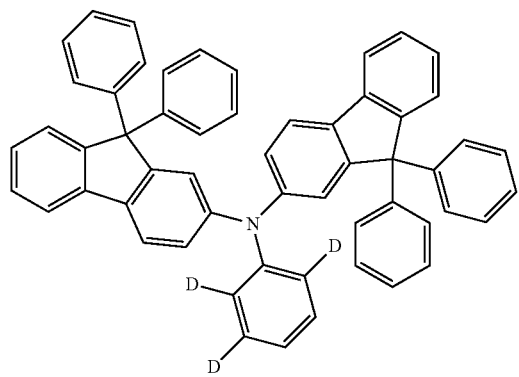
II-16
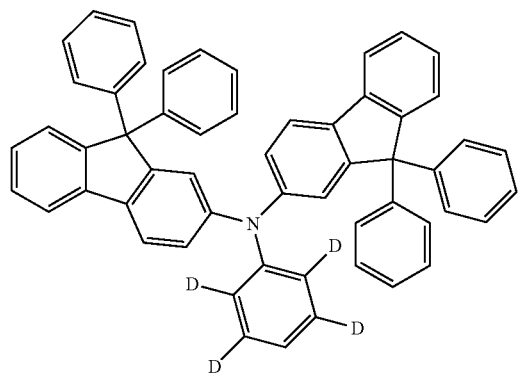
II-17
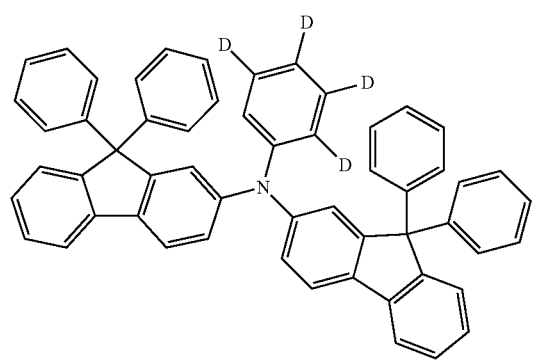
II-18
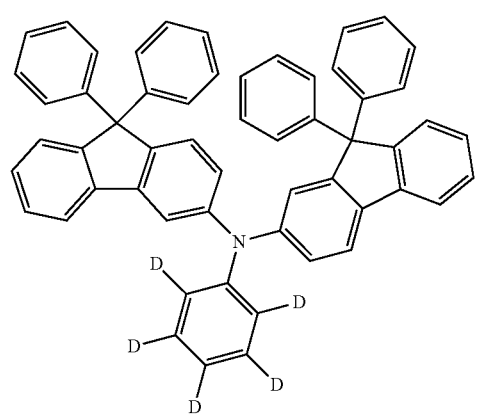
II-19
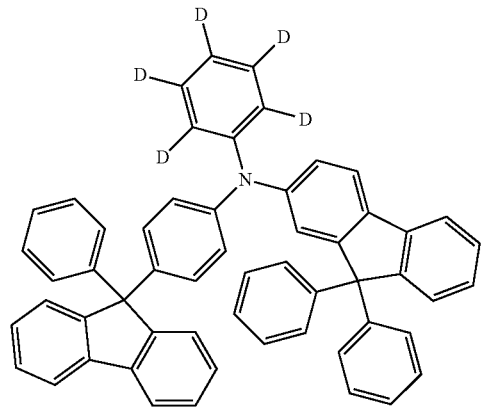
II-20
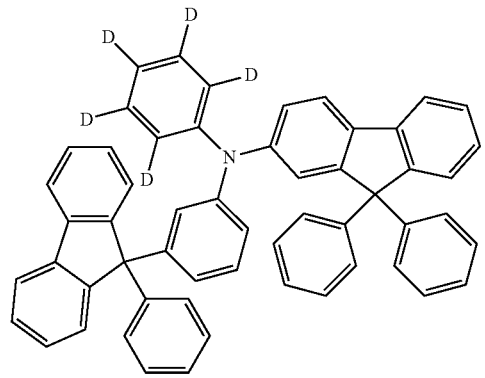

-continued
II-21
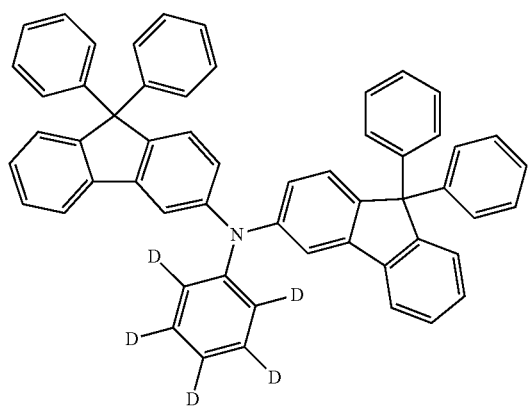
II-22
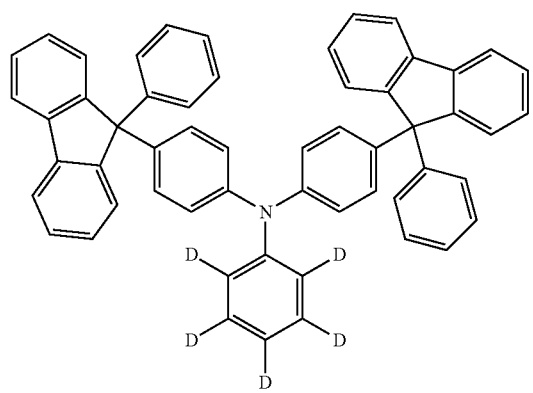
II-23
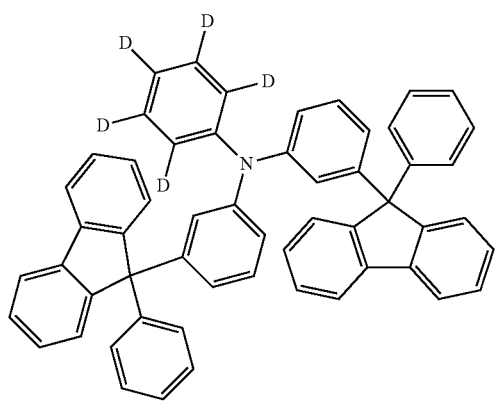
II-24
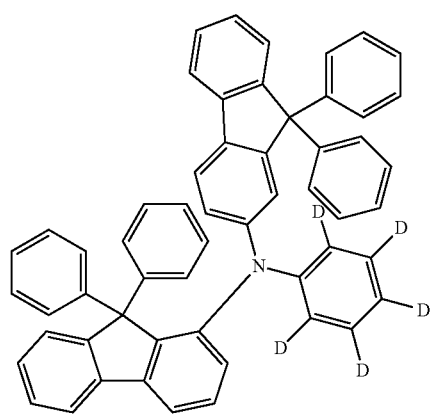
II-25
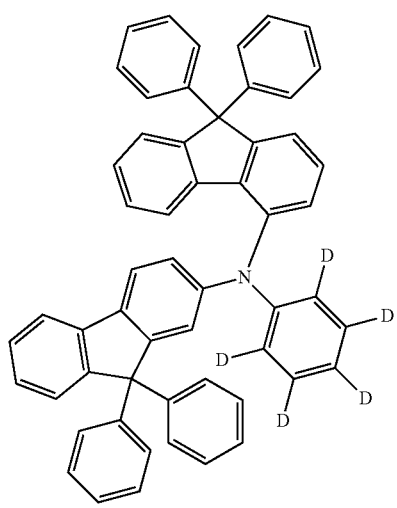
II-26
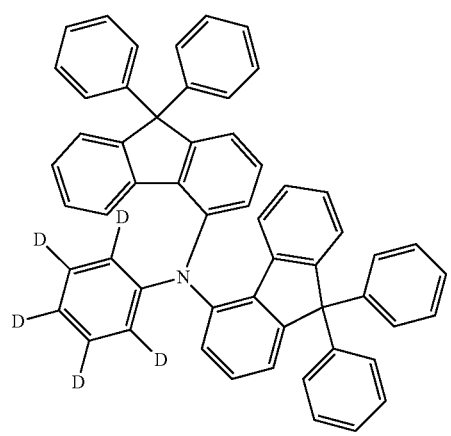

-continued
II-27
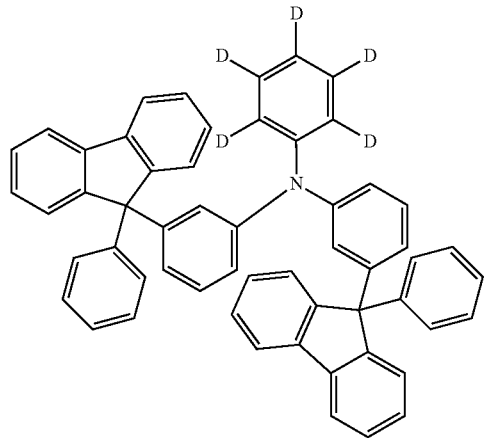
II-28
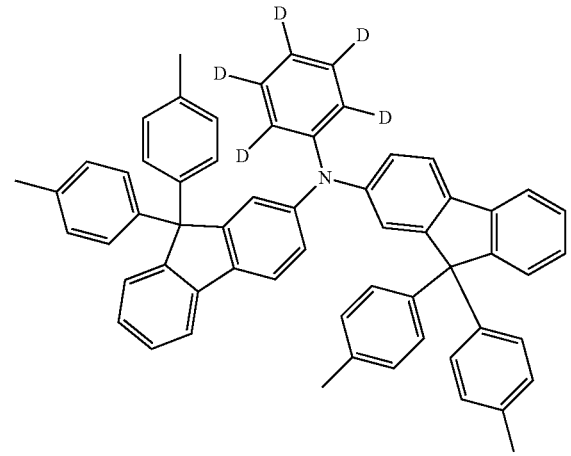
II-29
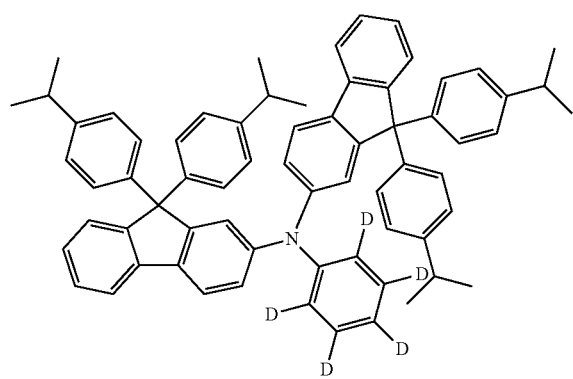
II-30
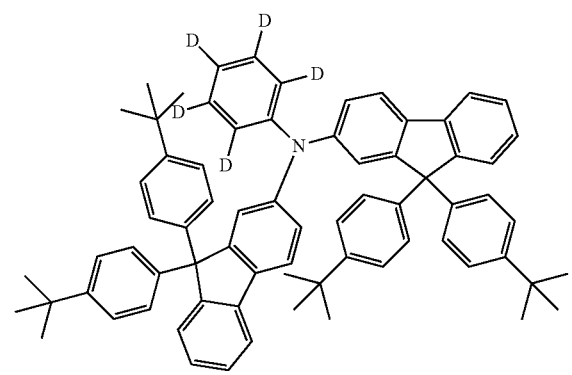
II-31
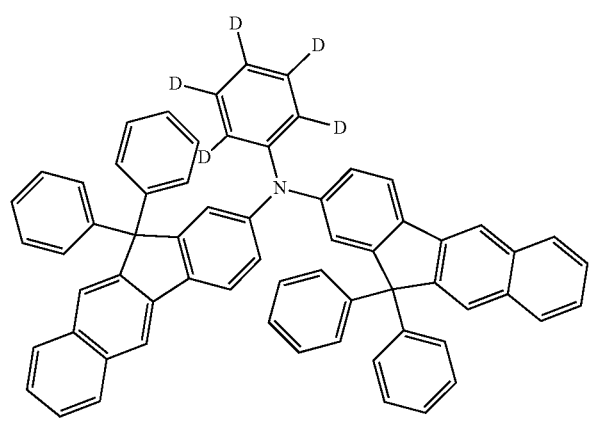
II-32
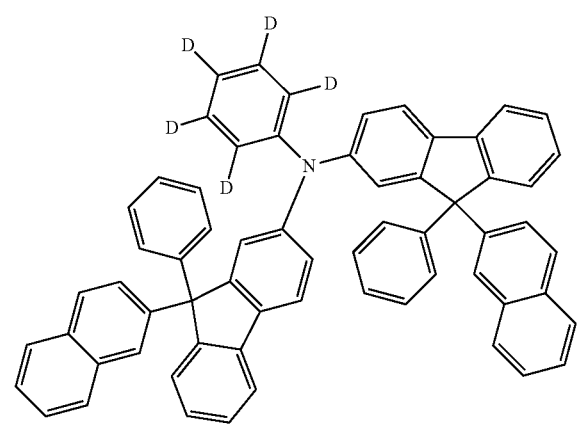

-continued
II-33
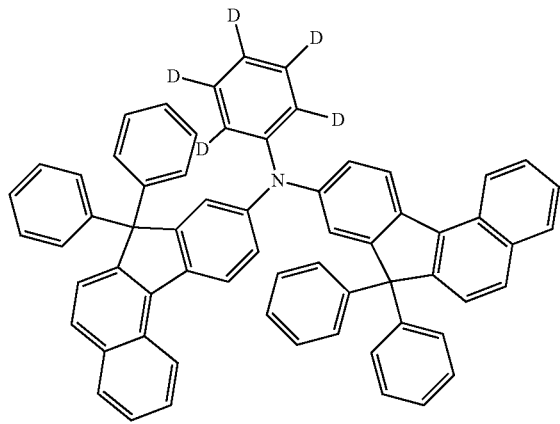
II-34
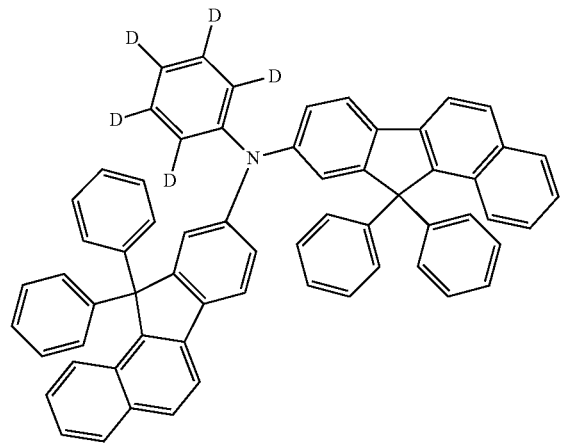
II-35
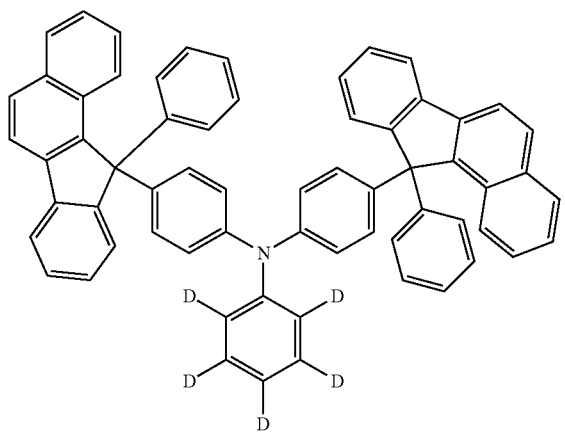
II-36
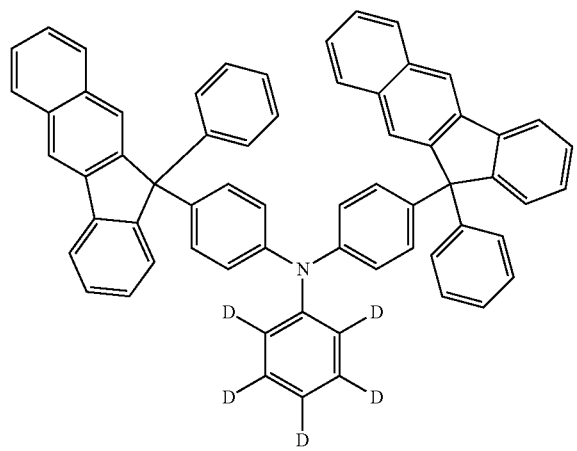
II-37
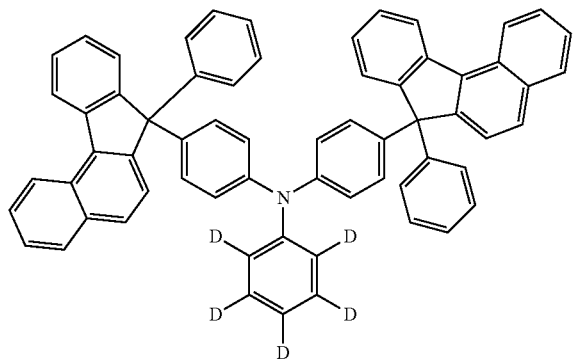
II-38
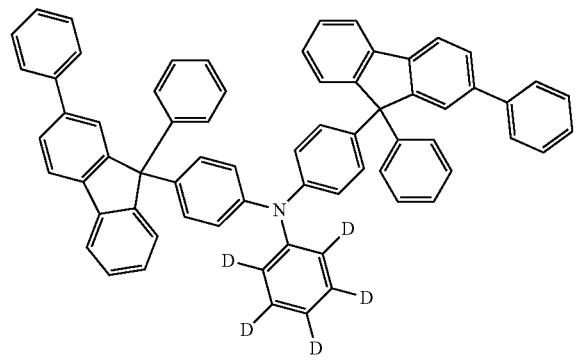

-continued
II-39
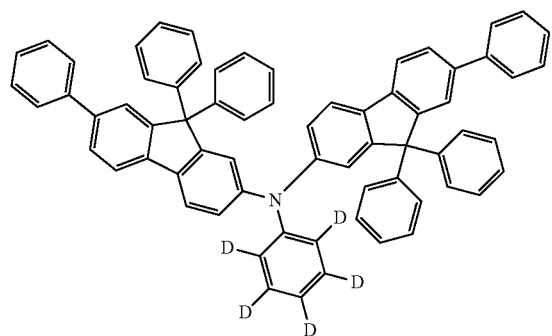
II-40
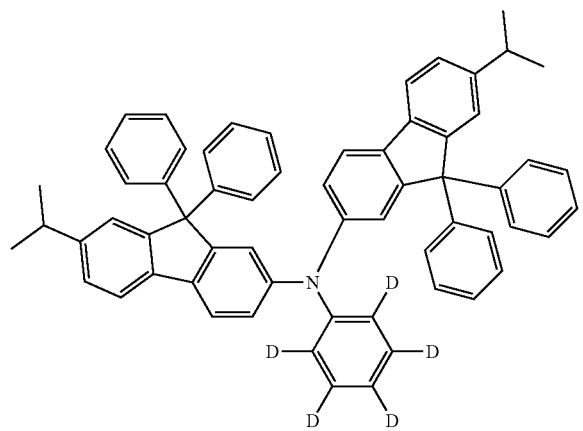
II-41
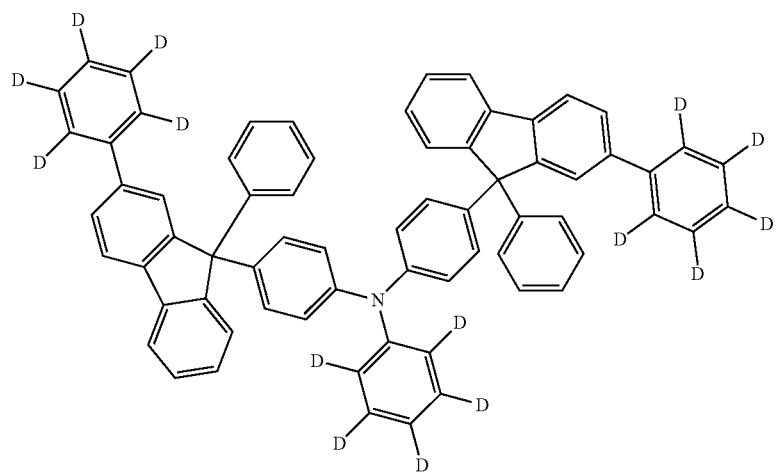
II-42
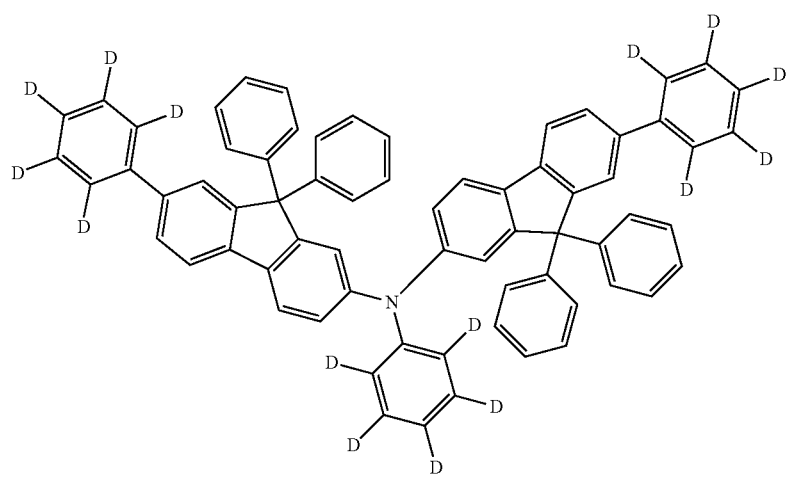

-continued
II-43
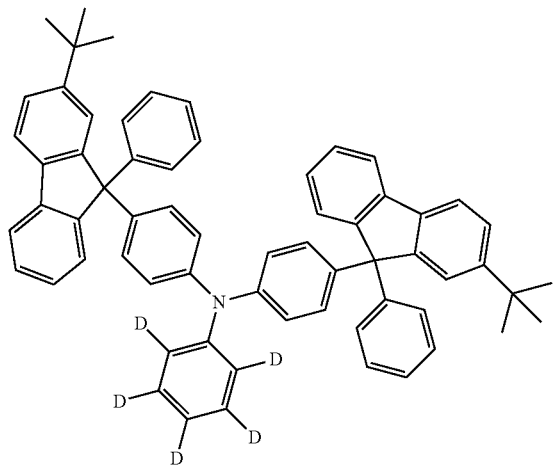
II-44
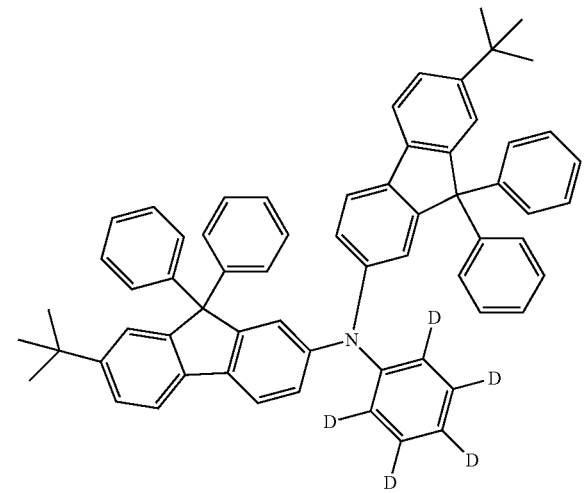
II-45
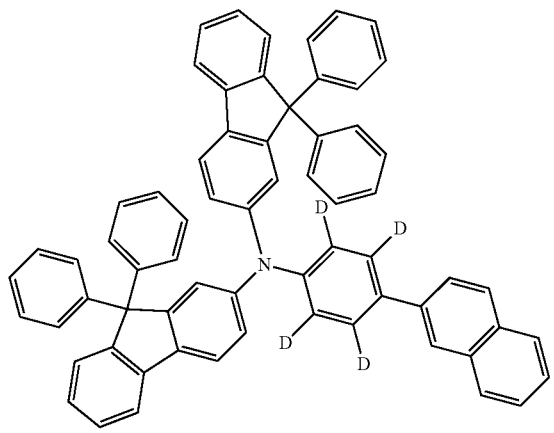
II-46
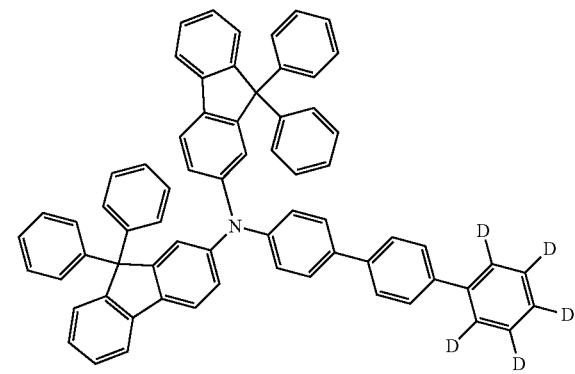
II-47
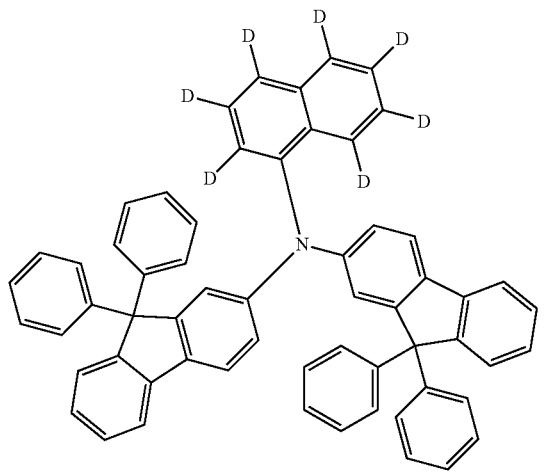
II-48
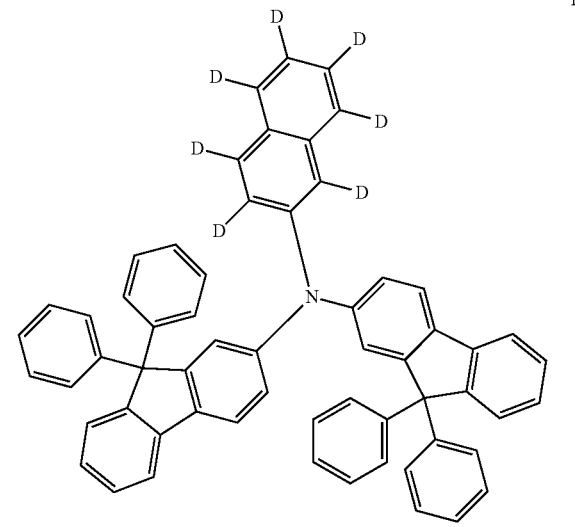

-continued
II-49
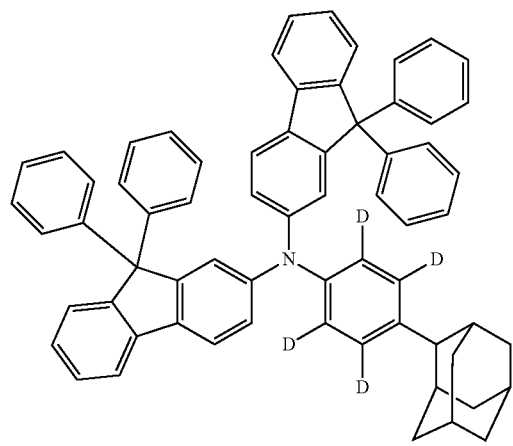
II-50
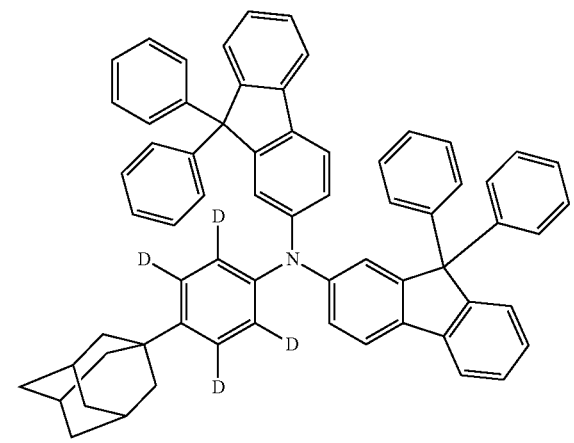
II-51
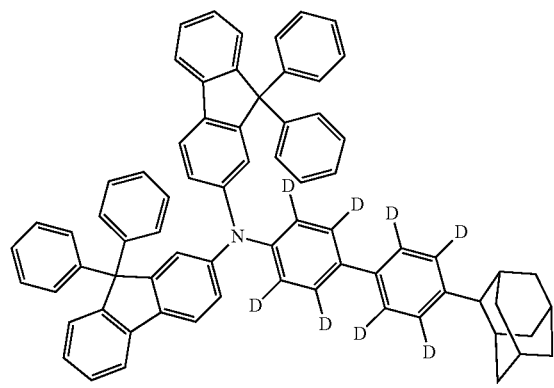
II-52
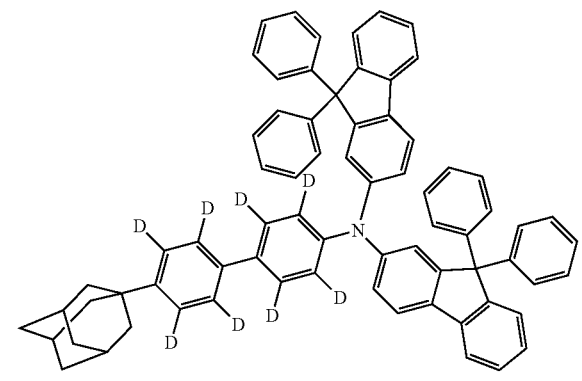
II-53
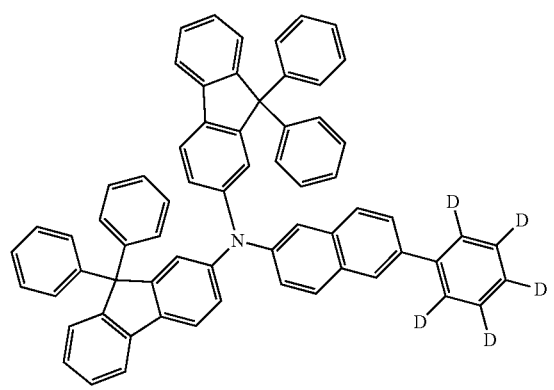
II-54
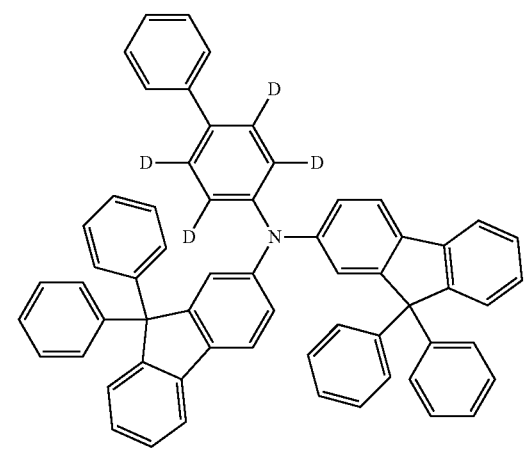

-continued
II-55
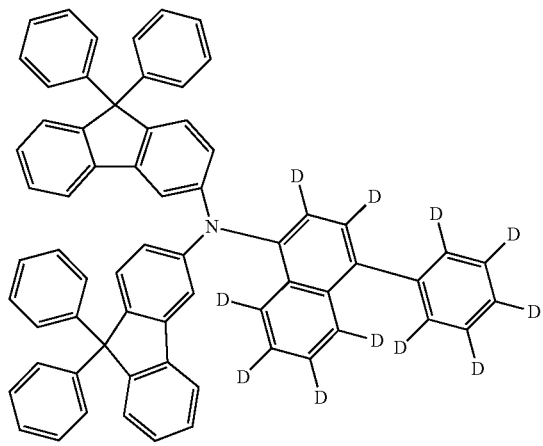
II-56
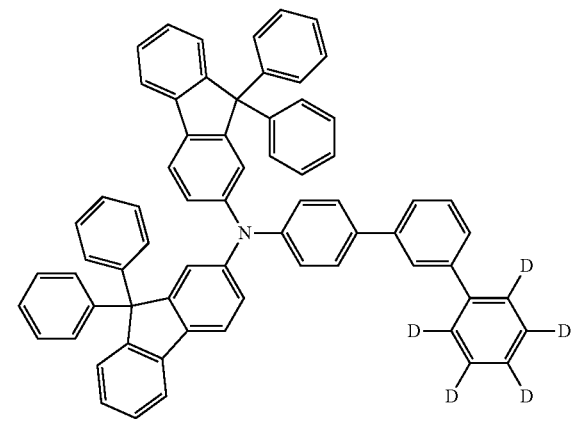
II-57
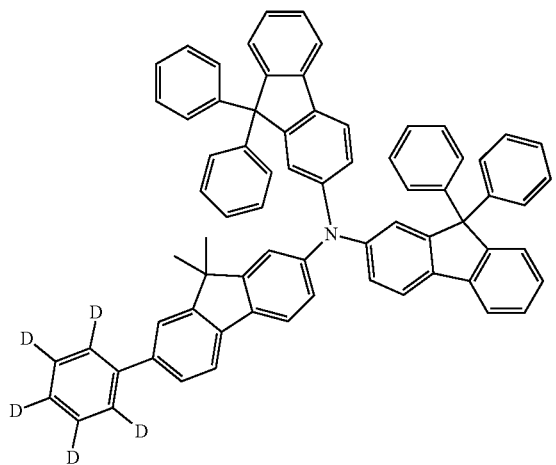
II-58
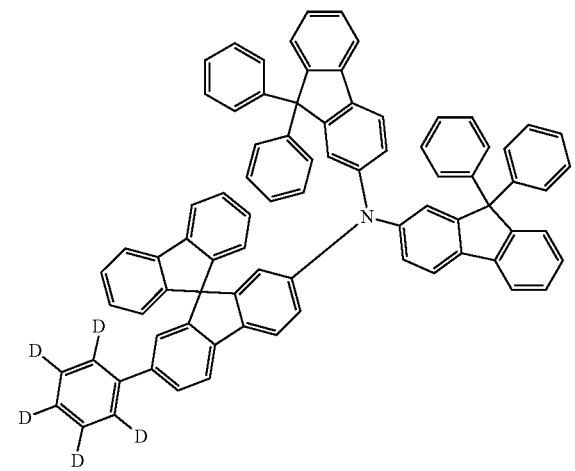
II-59
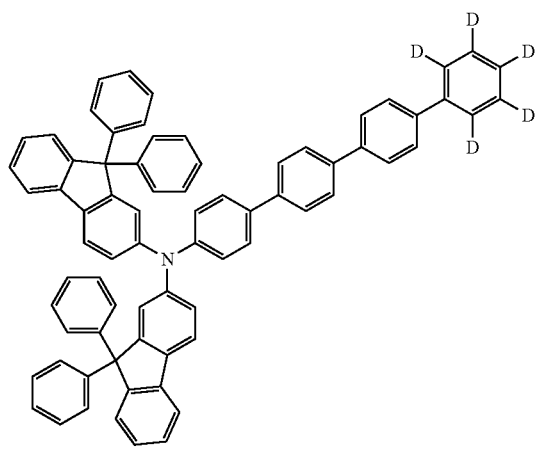
II-60
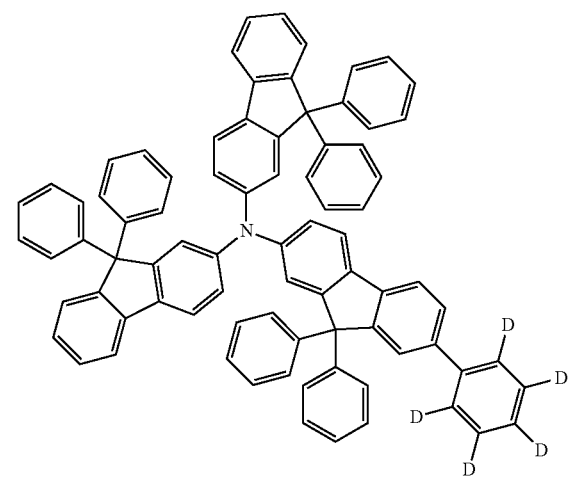

-continued
II-61
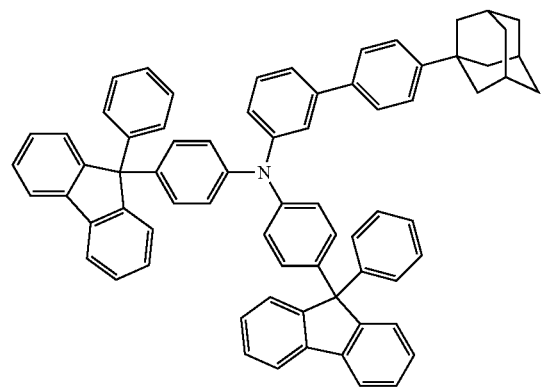
II-62
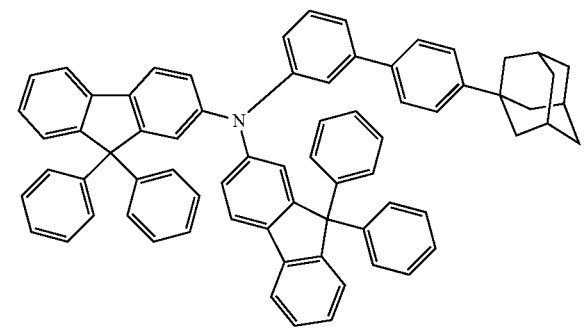
II-63
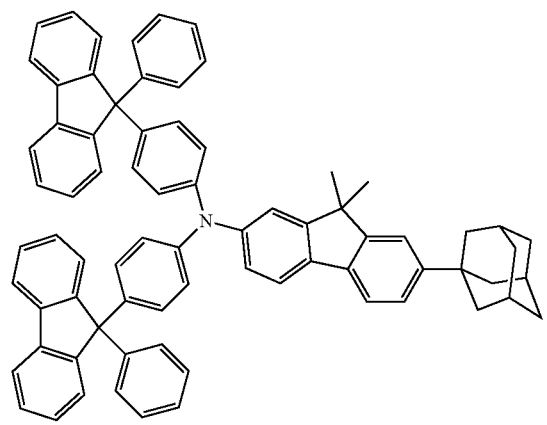
II-64
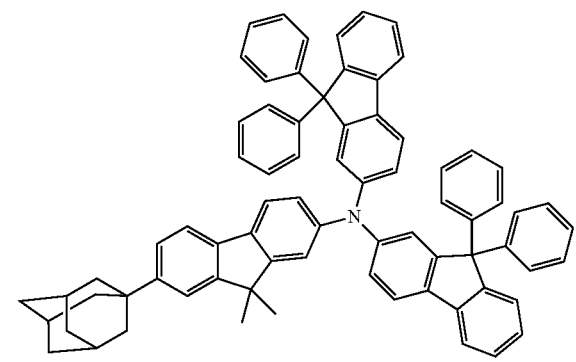
II-65
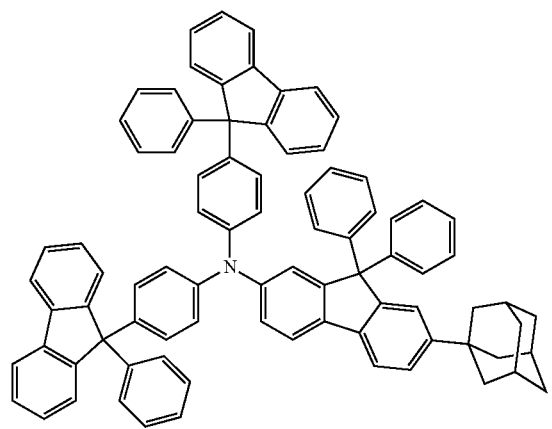
II-66
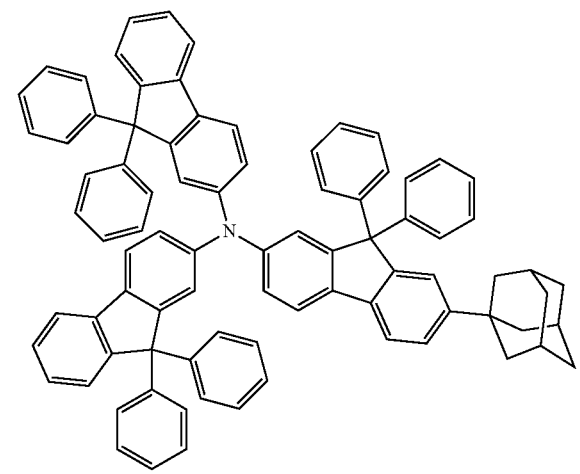

-continued
II-67
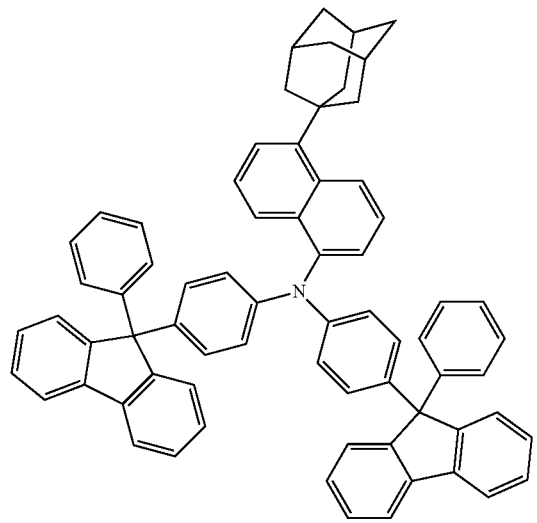
II-68
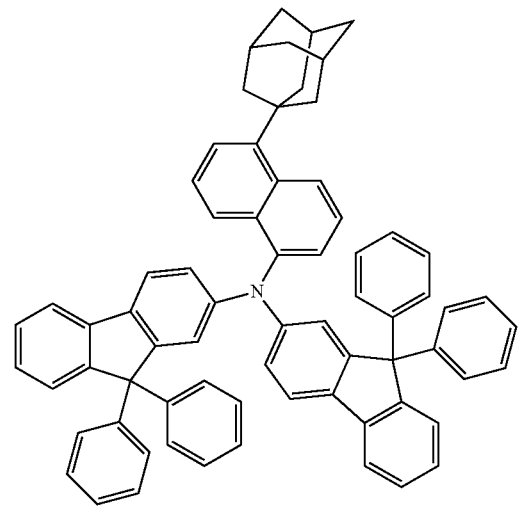
II-69
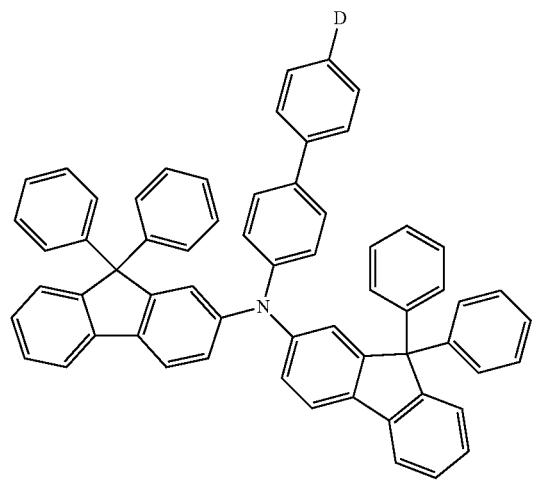
II-70
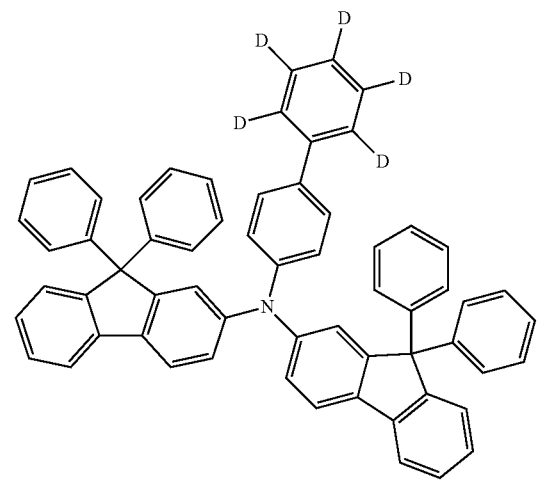
II-71
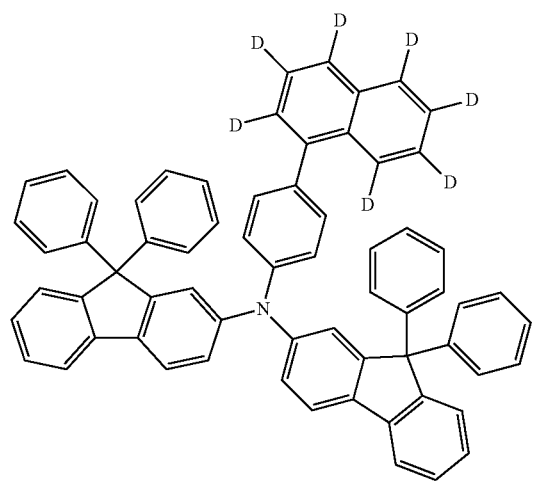
II-72
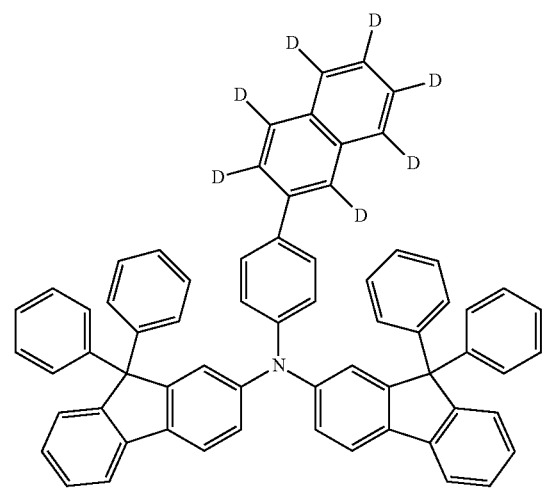

-continued
II-73
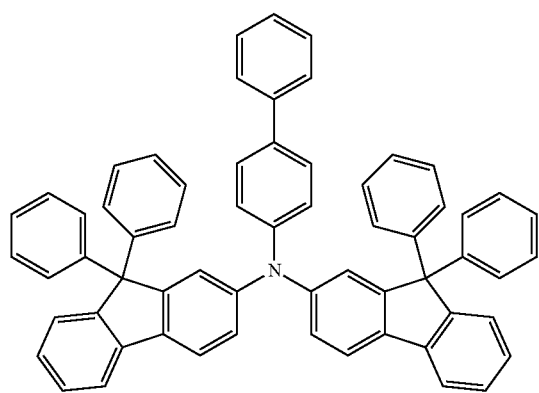
II-74
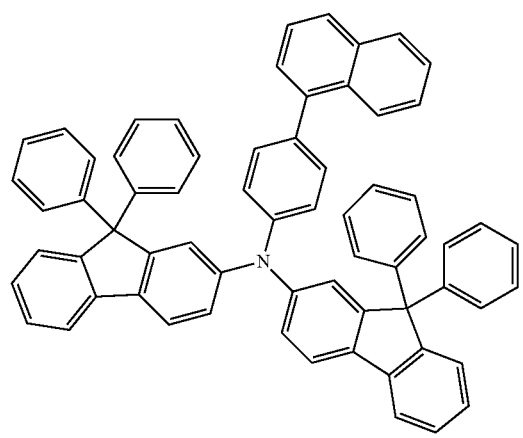
II-75
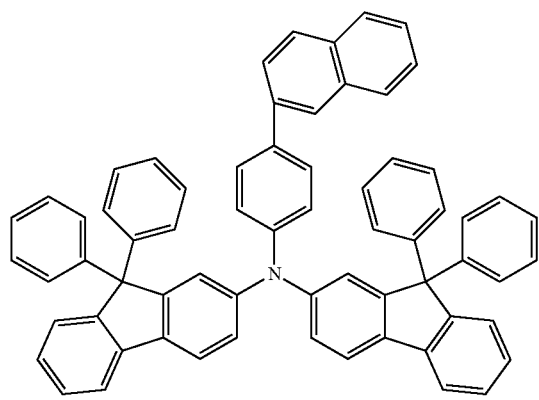
II-76
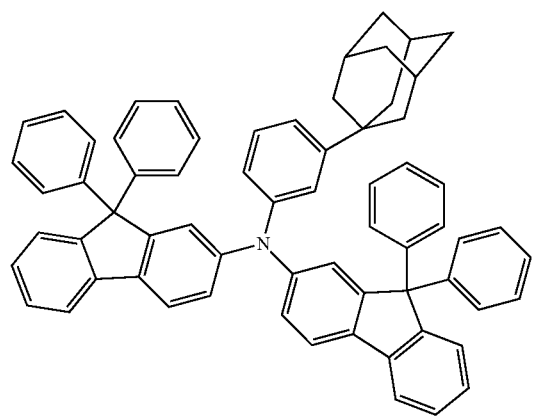
II-77
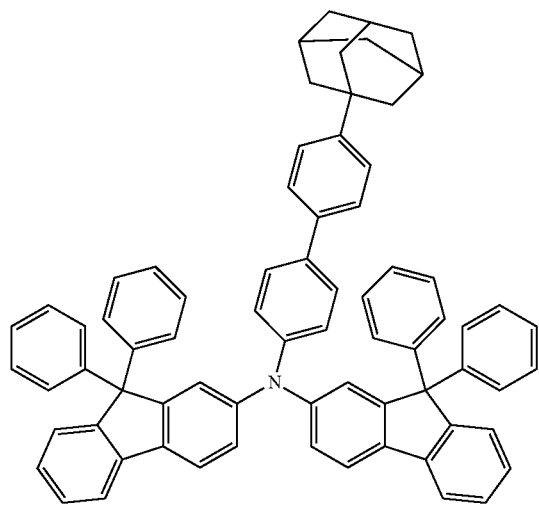
II-78
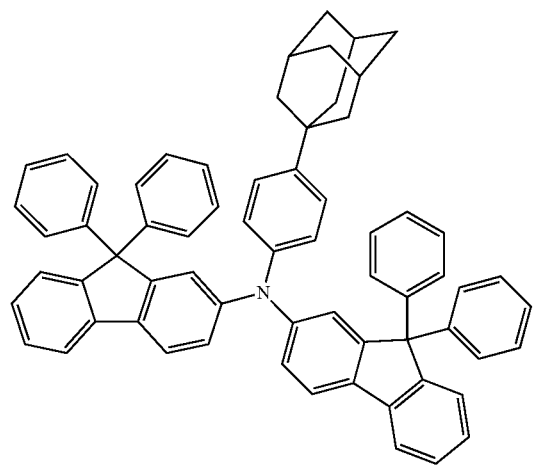

-continued
II-79
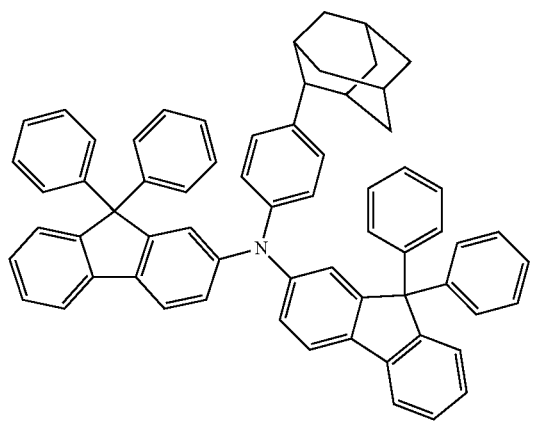
II-80
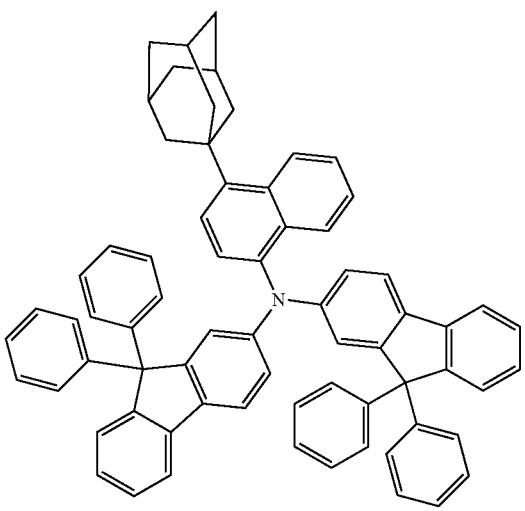
II-81
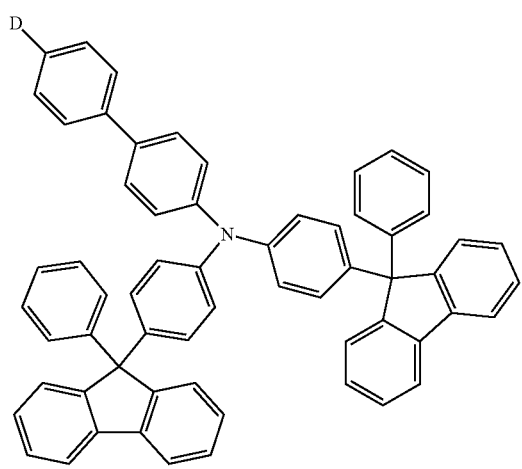
II-82
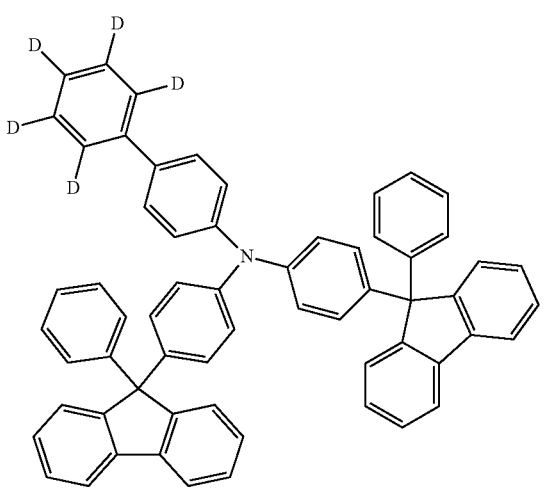
II-83
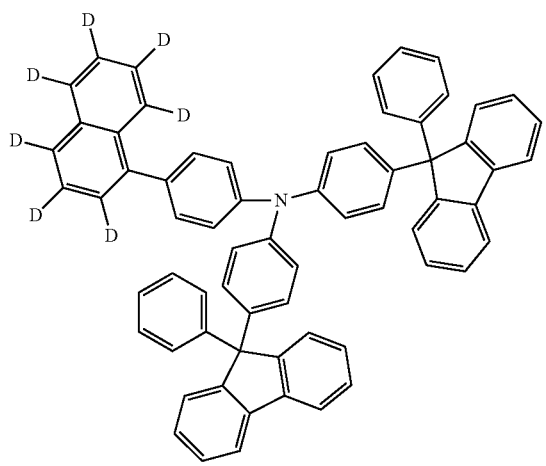
II-84
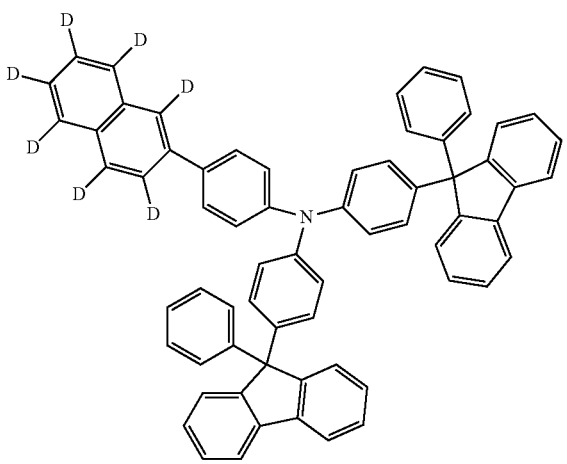

-continued
II-85
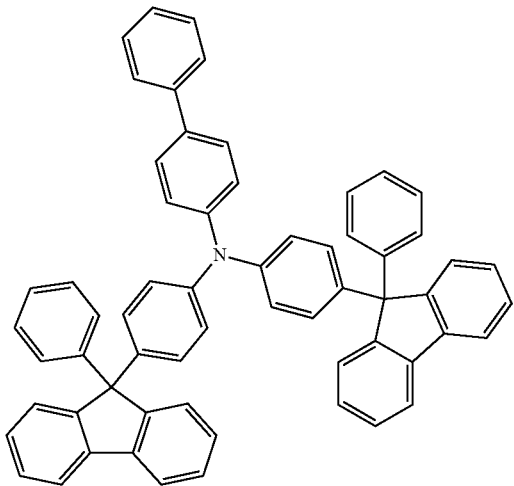
II-86
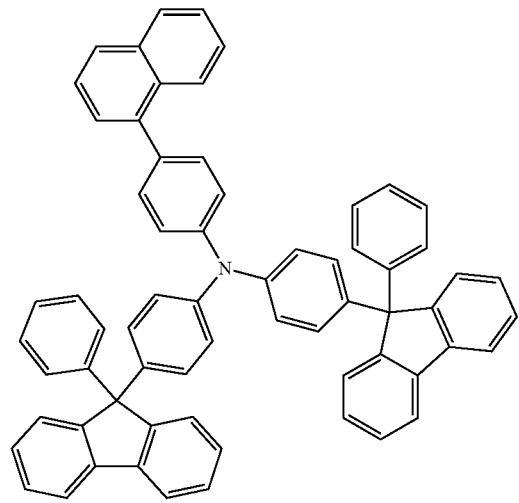
II-87
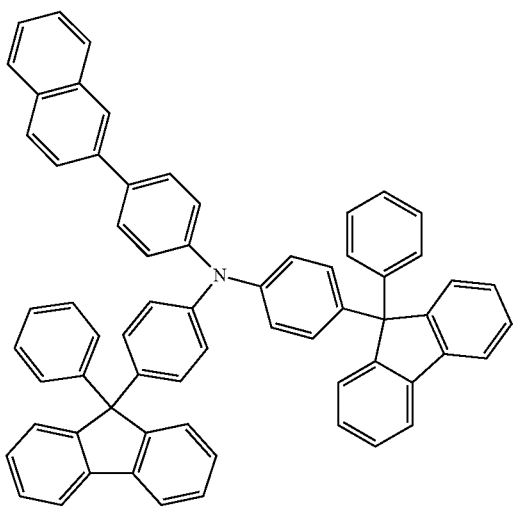
II-88
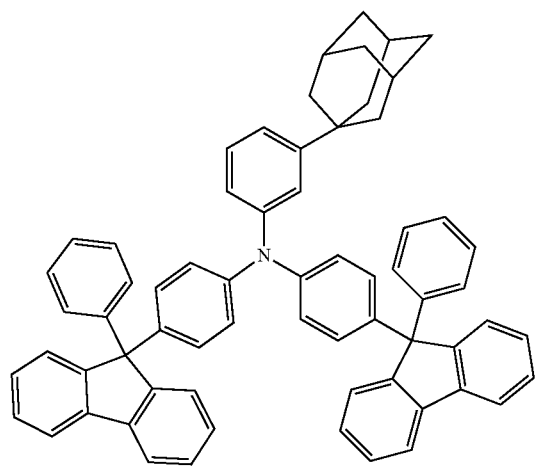
II-89
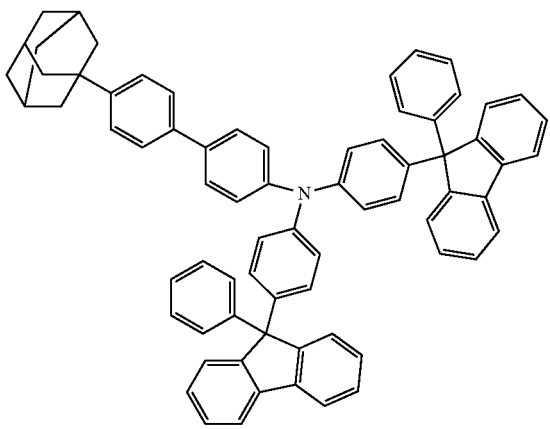
II-90
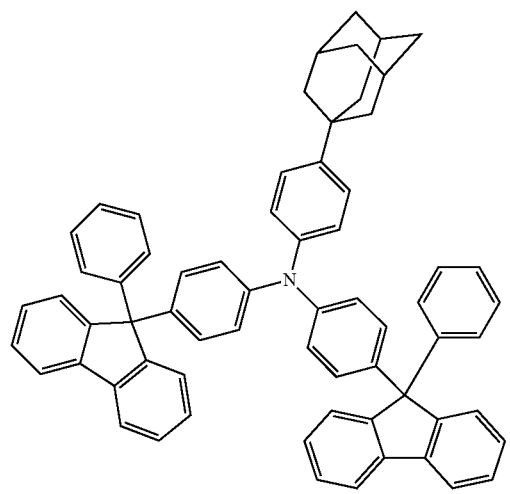

-continued
II-91
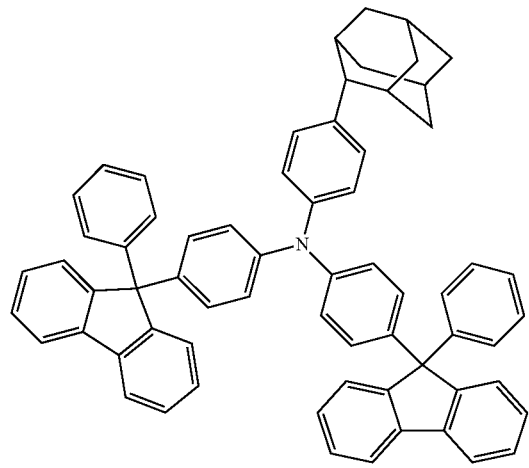
II-92
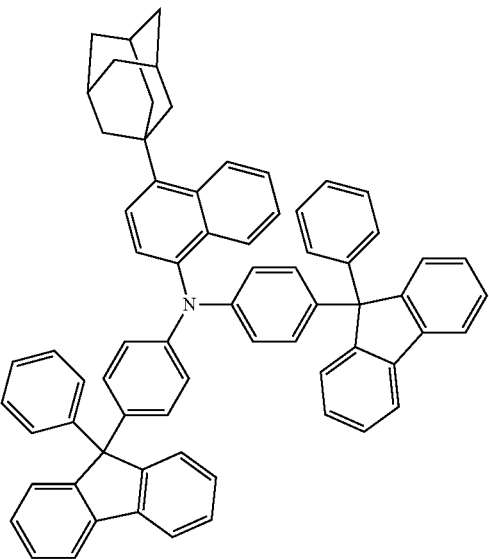
II-93
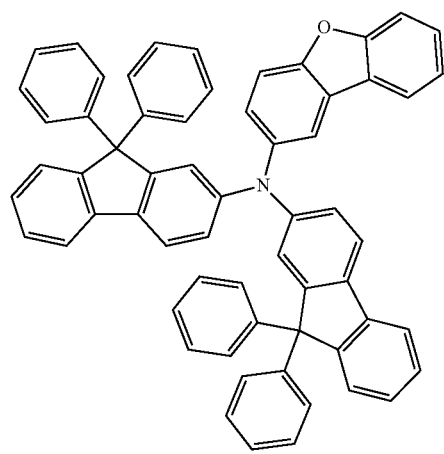
II-94
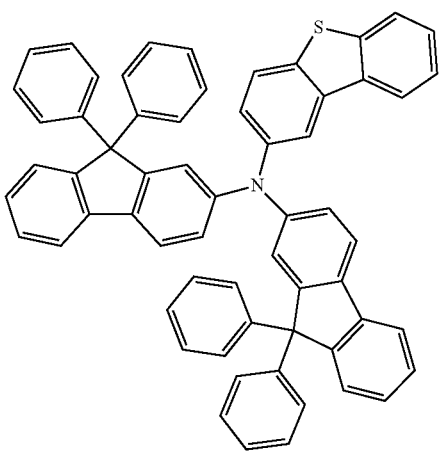
II-95
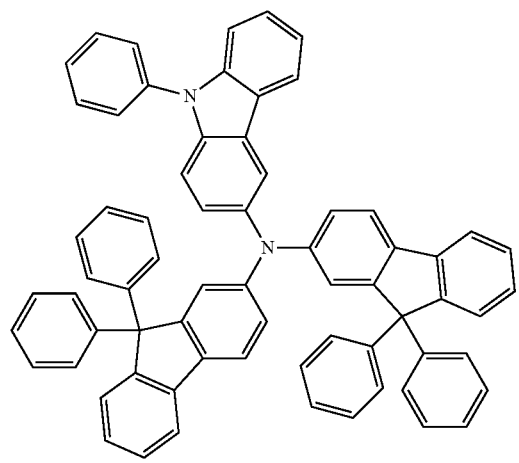
II-96
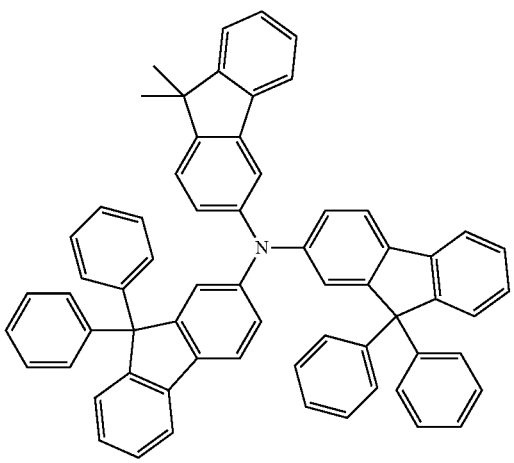

-continued
II-97
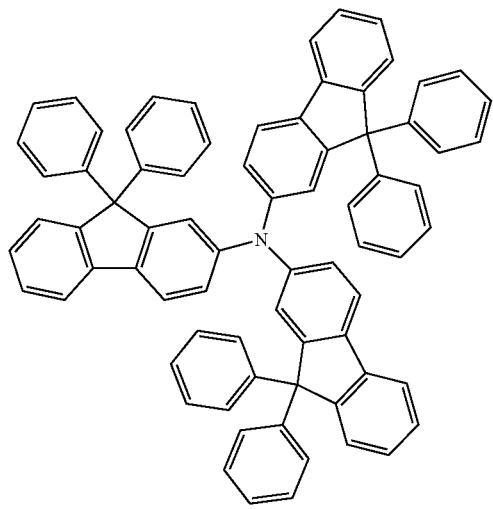
II-98
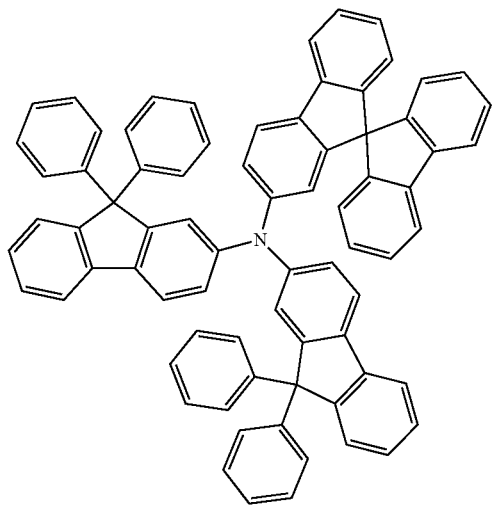
II-99
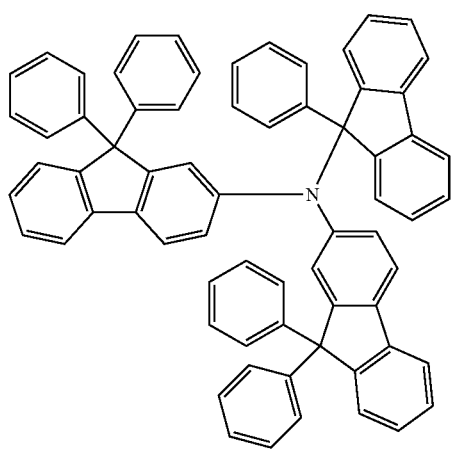
II-100
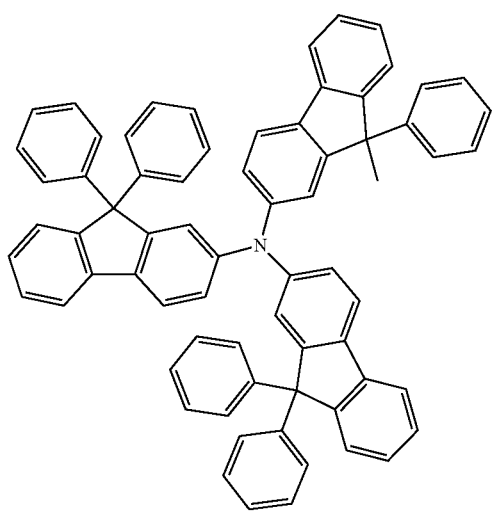
II-101
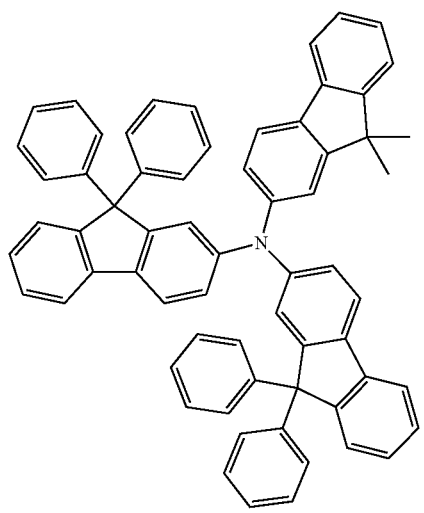
II-102
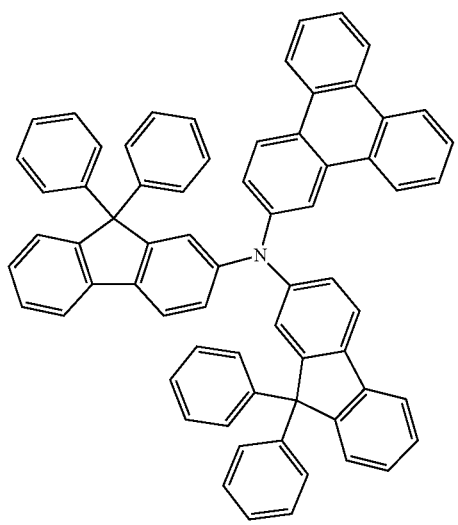

-continued
II-103
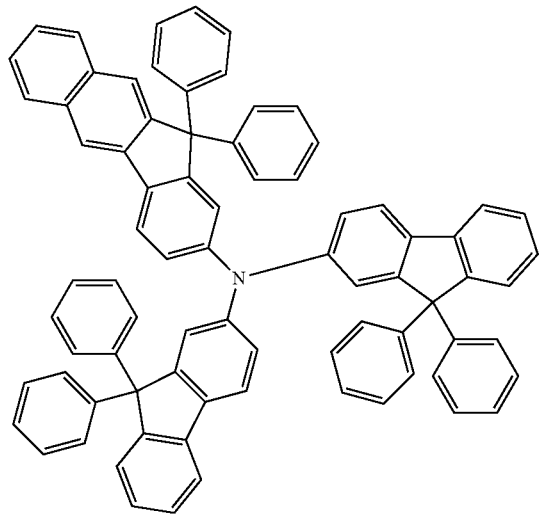
II-104
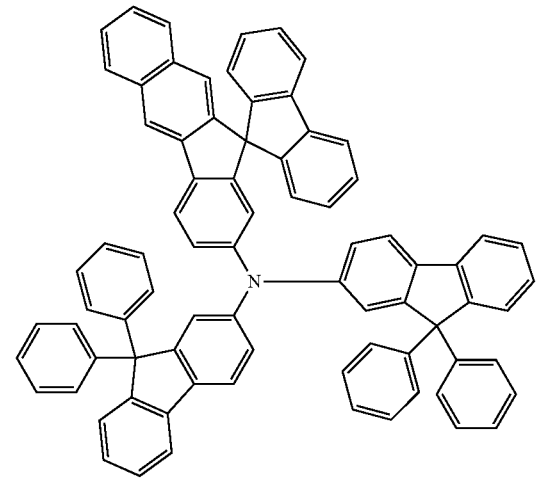
II-105
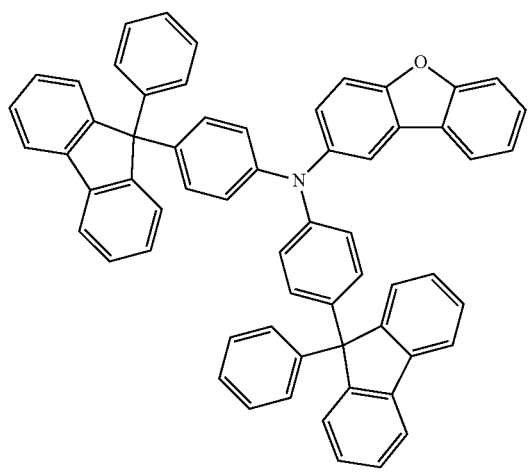
II-106
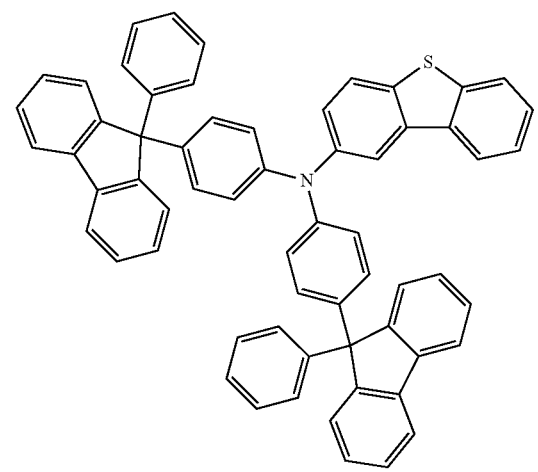
II-107
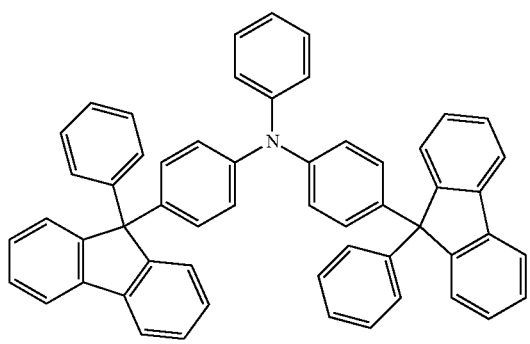
II-108
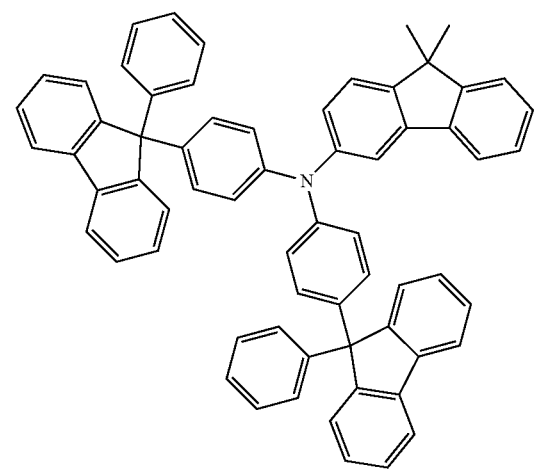

-continued
II-109
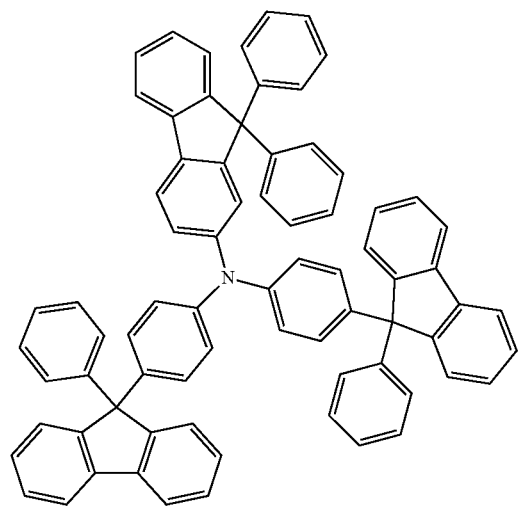
II-110
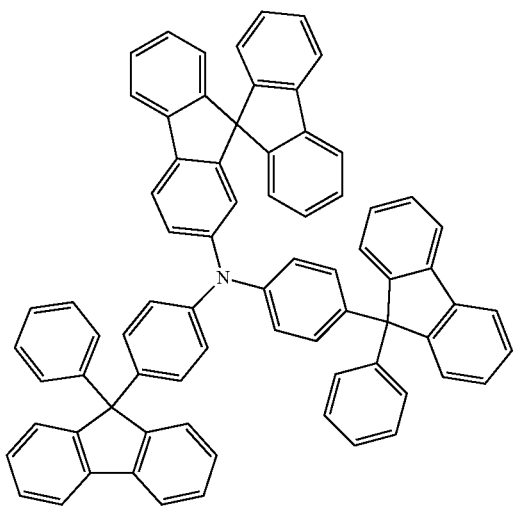
II-111
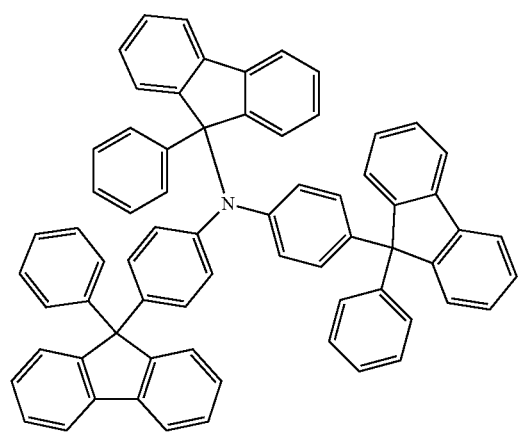
II-112
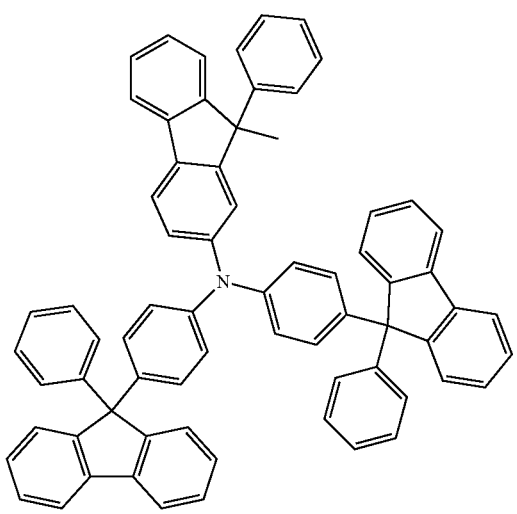
II-113
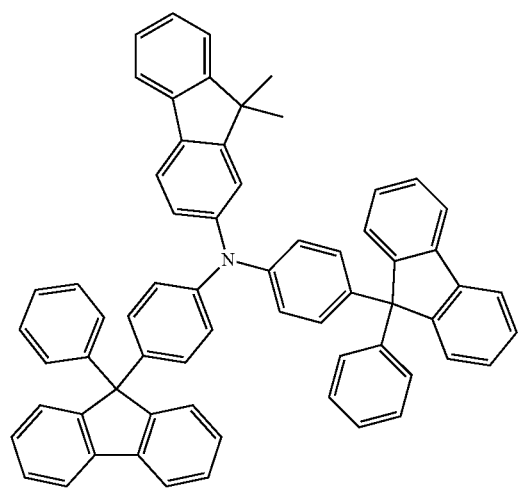
II-114
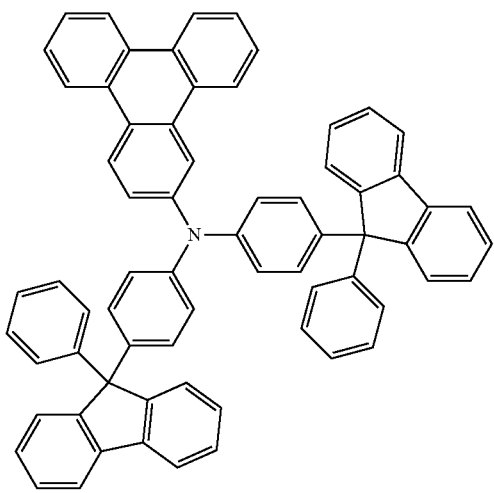

-continued
II-115
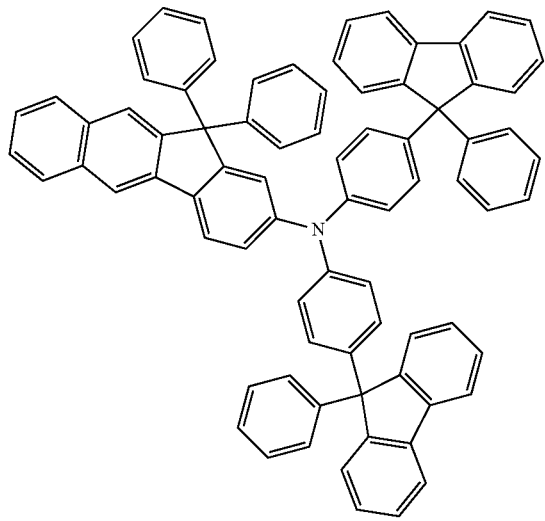
II-116
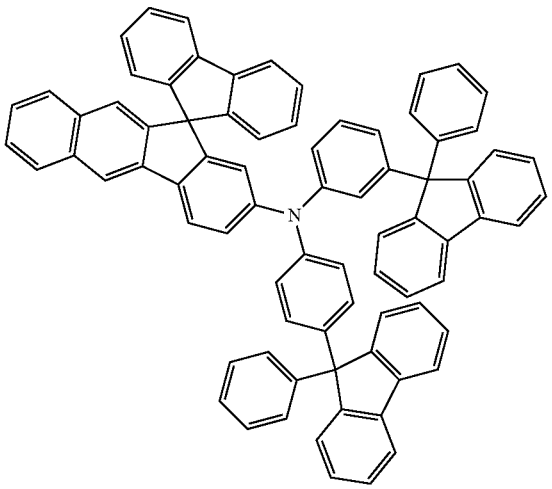
II-117
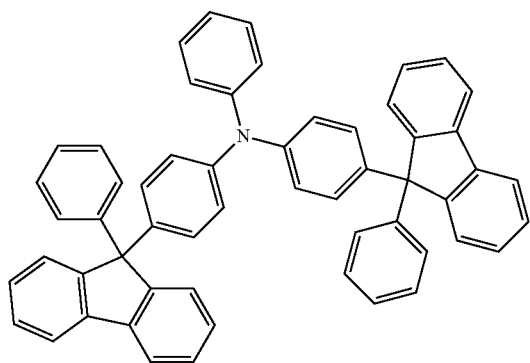
II-118
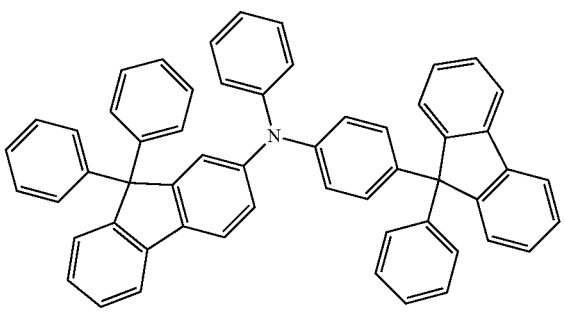
II-119
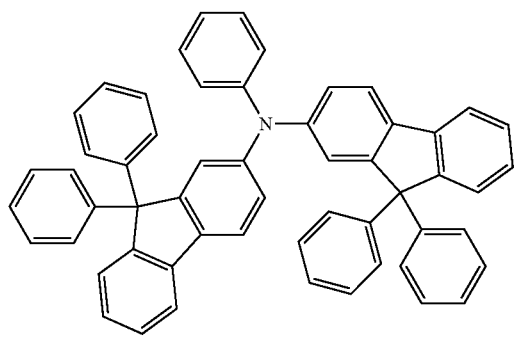
II-120
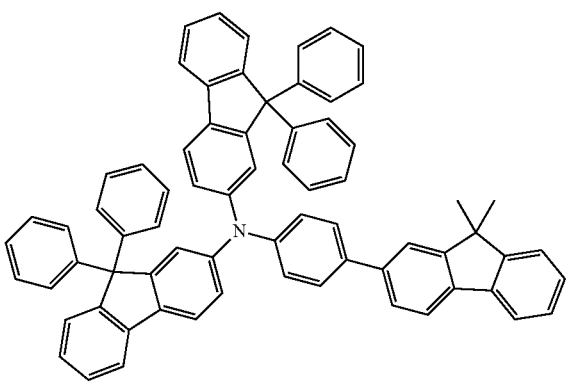

-continued
II-121
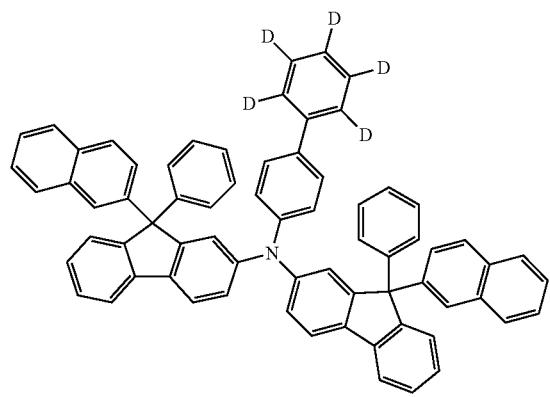
II-122
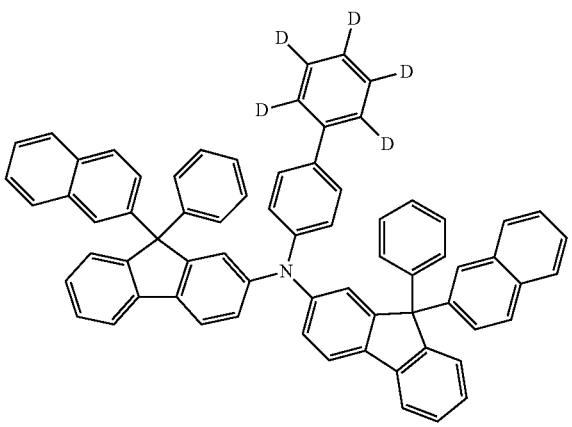
II-123
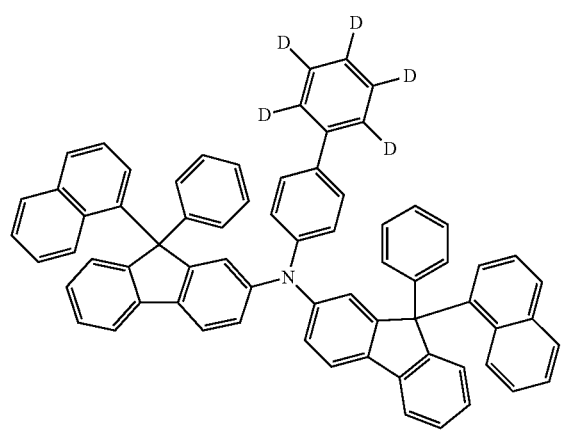
II-24
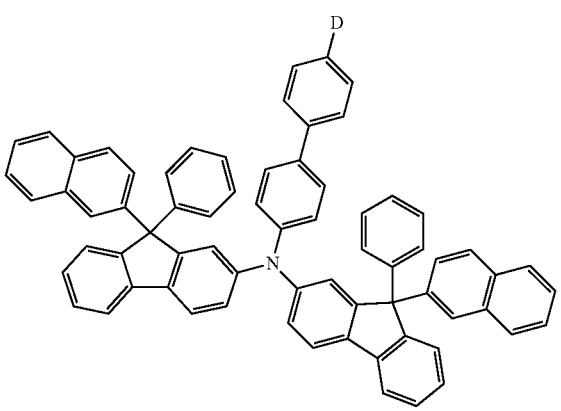
II-125
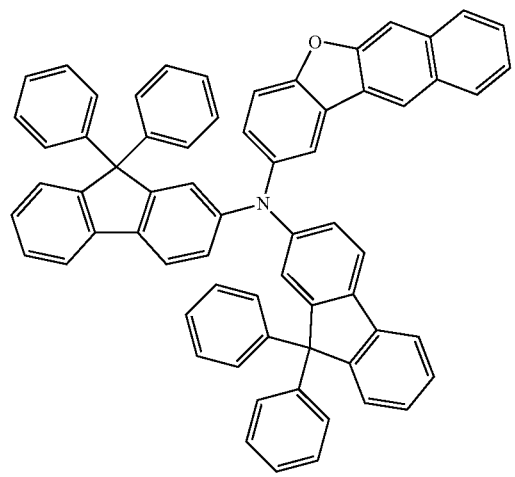
II-126
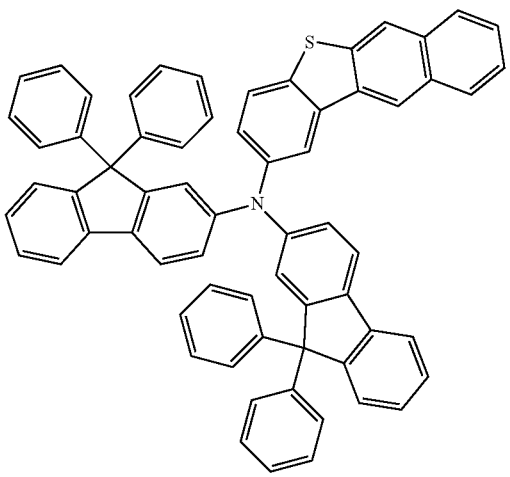

-continued
II-127
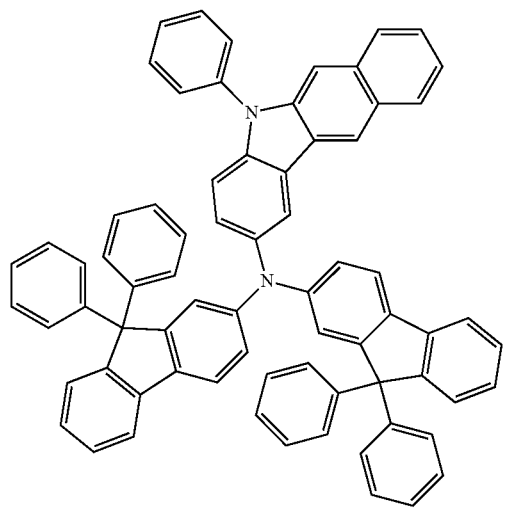
II-128
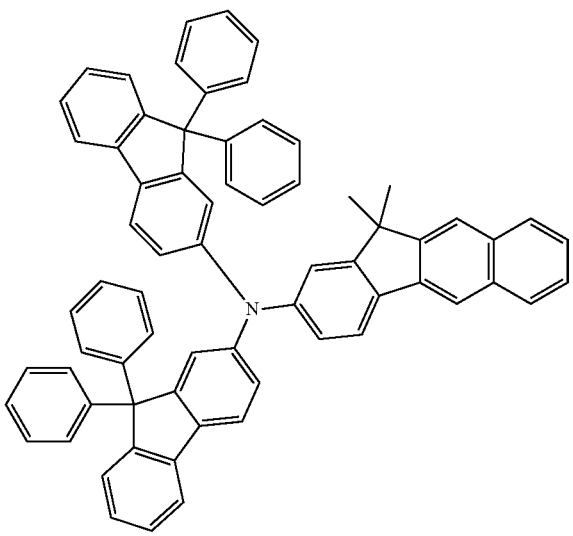
II-129
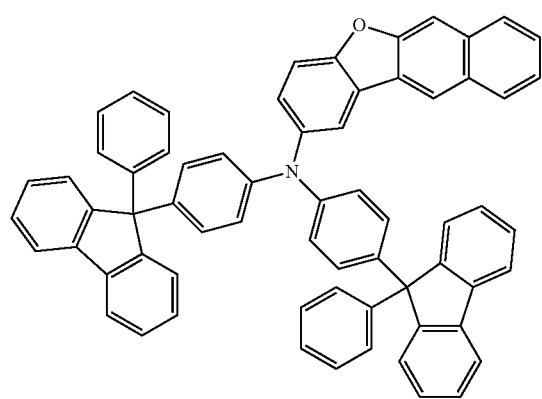
II-130
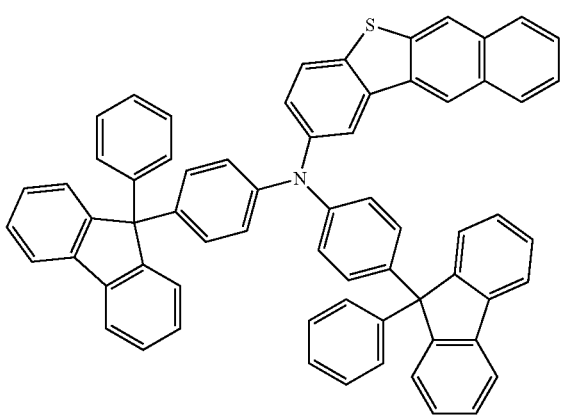
II-131
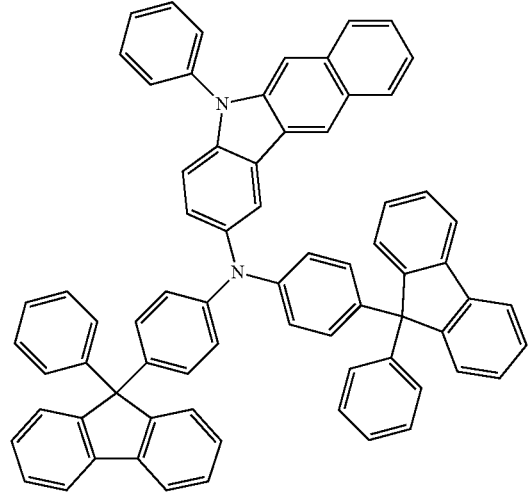
II-132
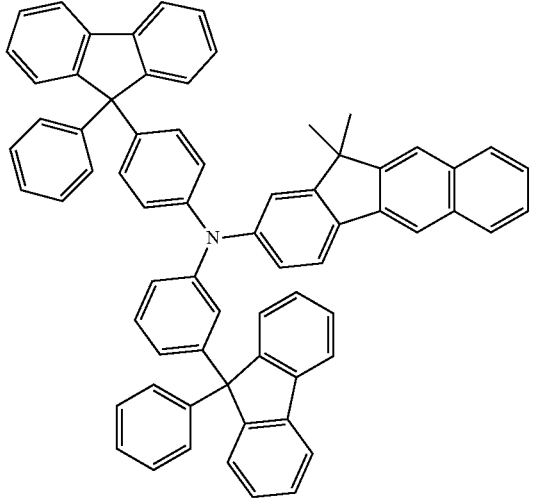

-continued
II-133
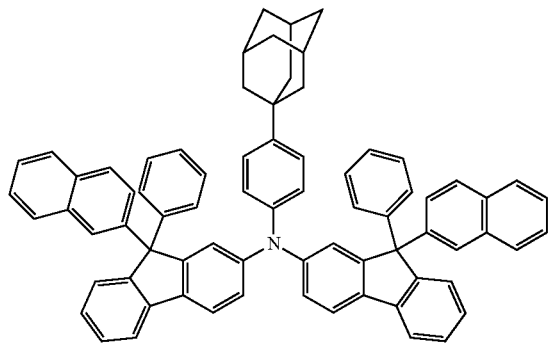
II-134
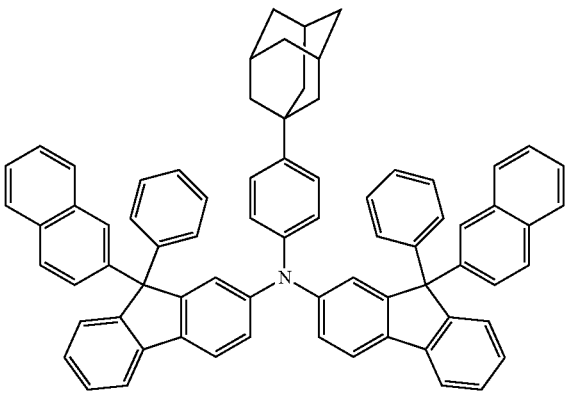
II-135
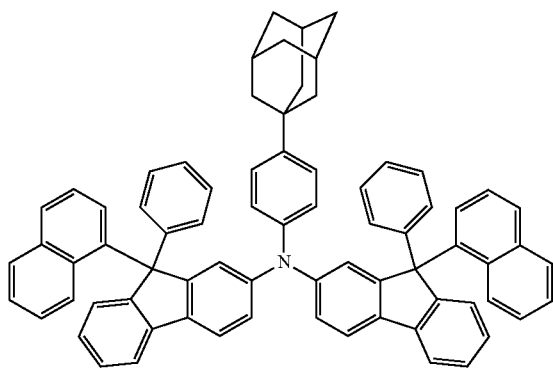
II-136
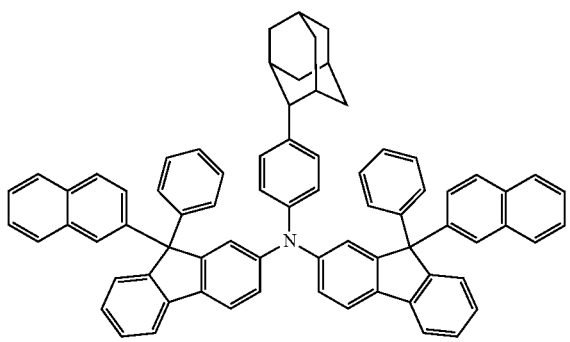
II-137
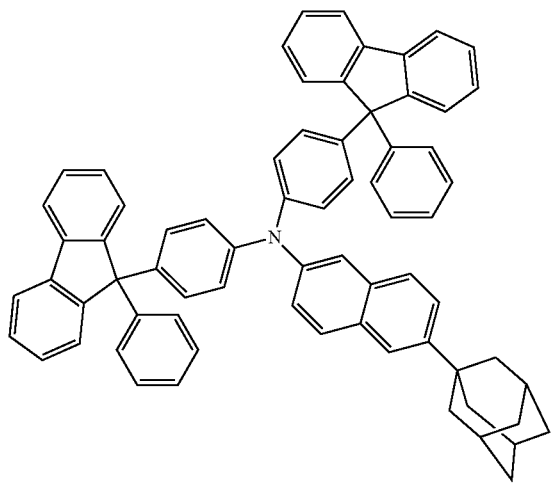
II-138
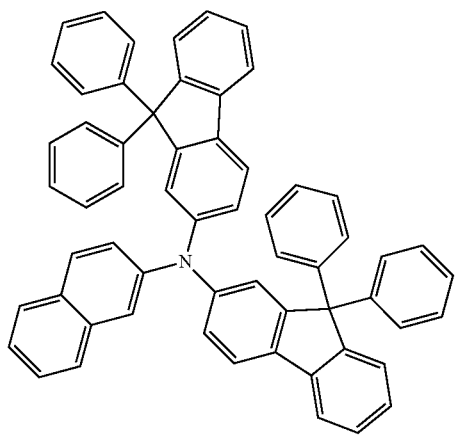

-continued
II-139
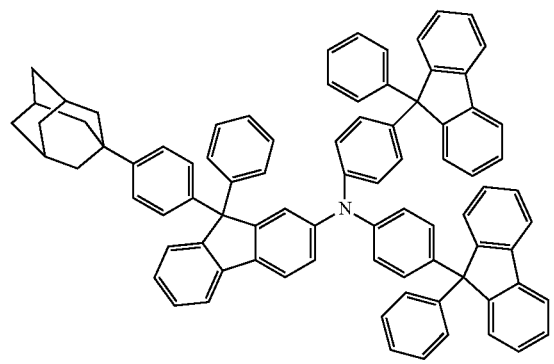
II-140
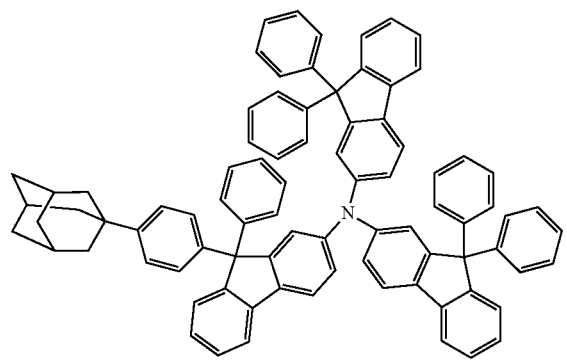
II-141
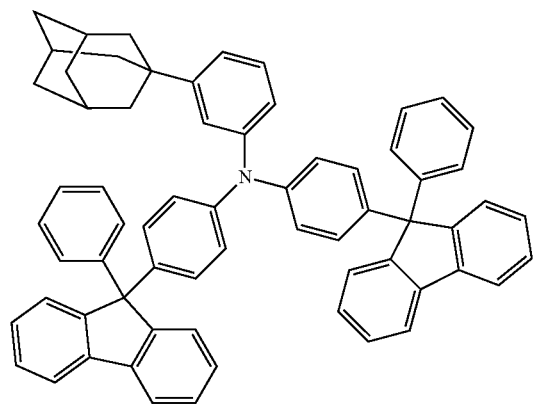
II-142
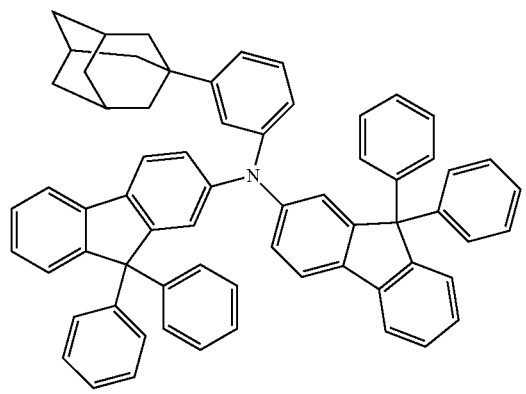
II-143
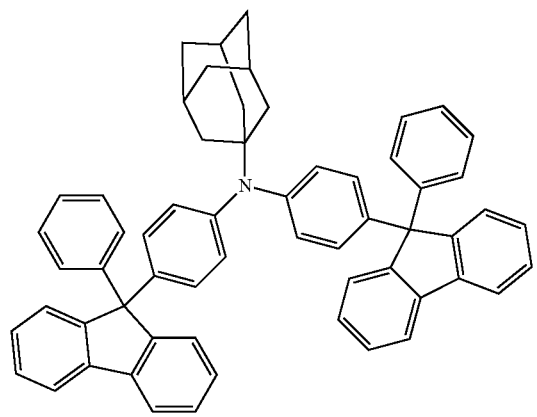
II-144
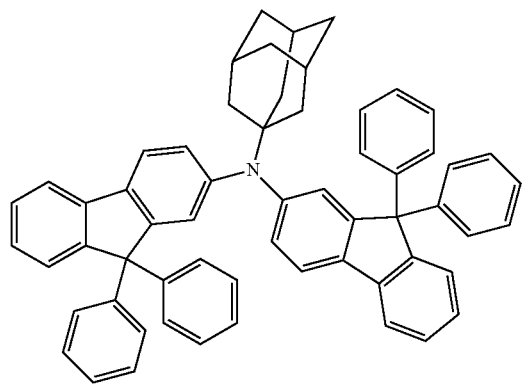

-continued
II-145
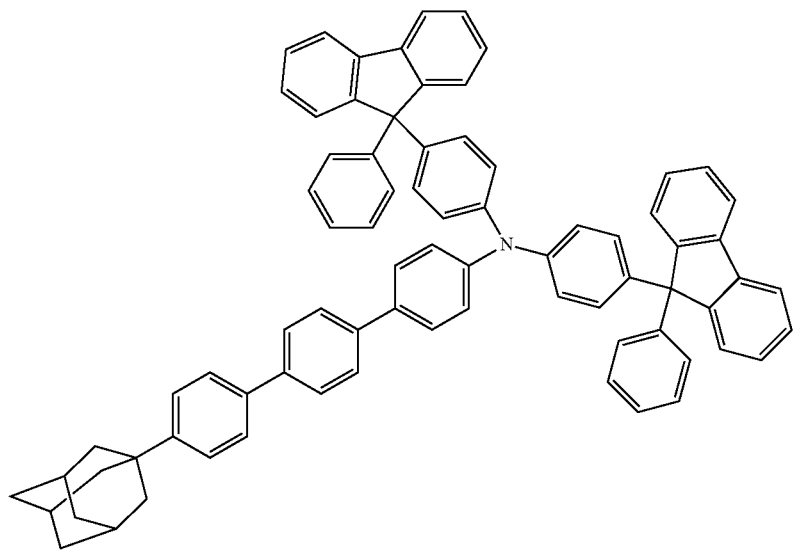
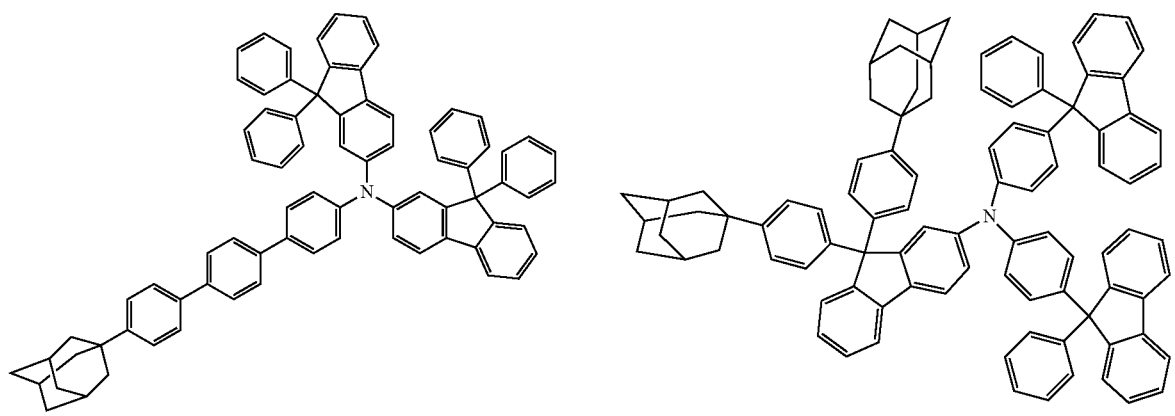
II-146    II-147
II-148
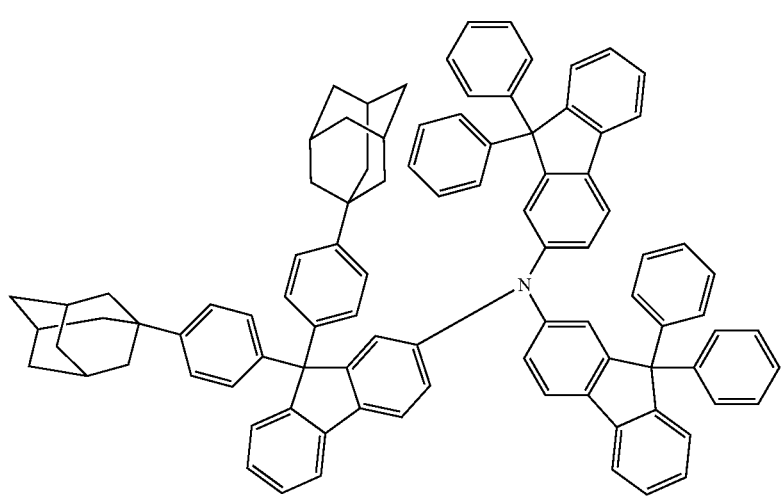

-continued
II-149
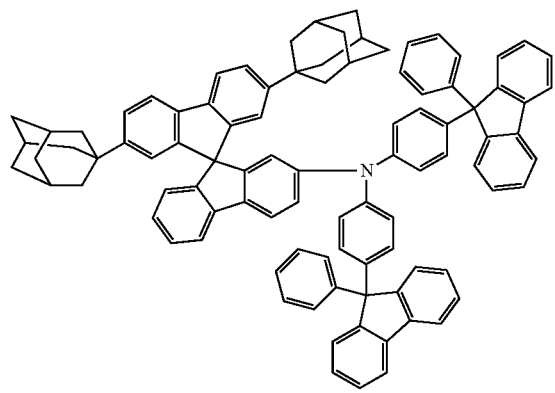
II-150
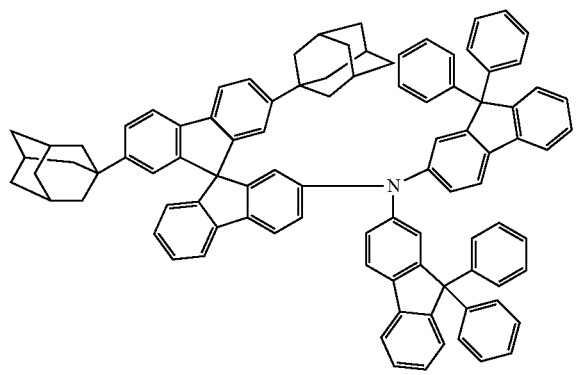
II-151
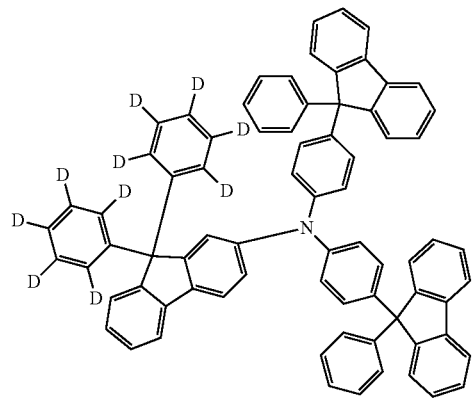
II-152
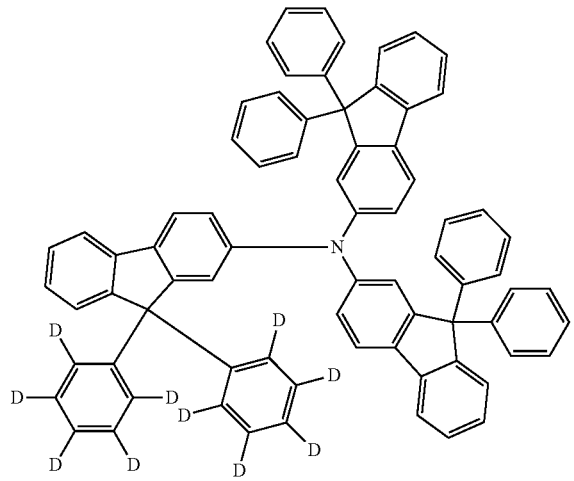
II-153
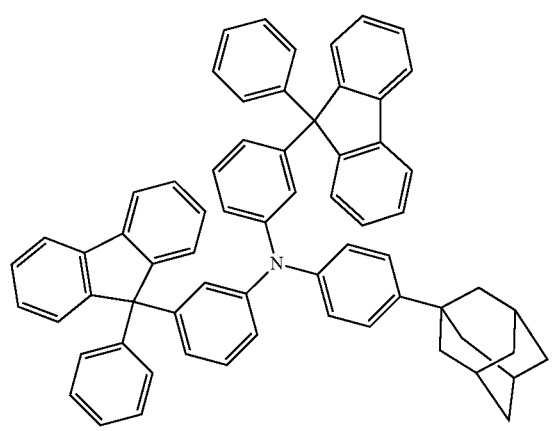
II-154
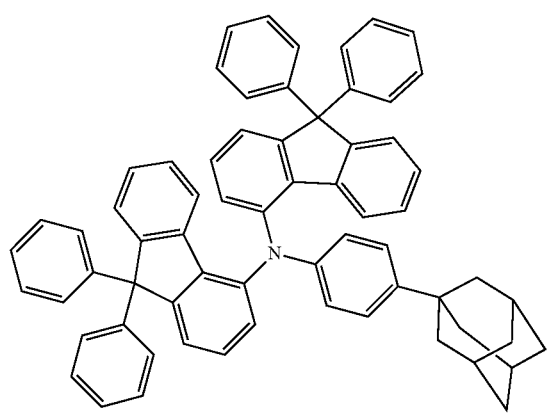

-continued
II-155
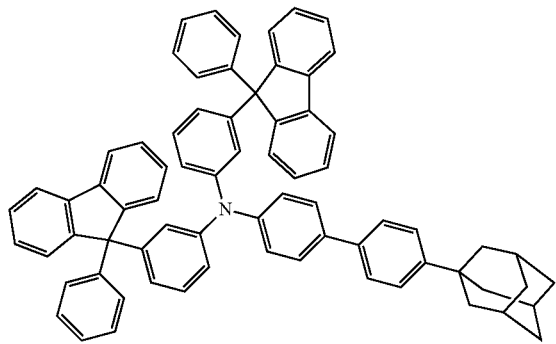
II-156
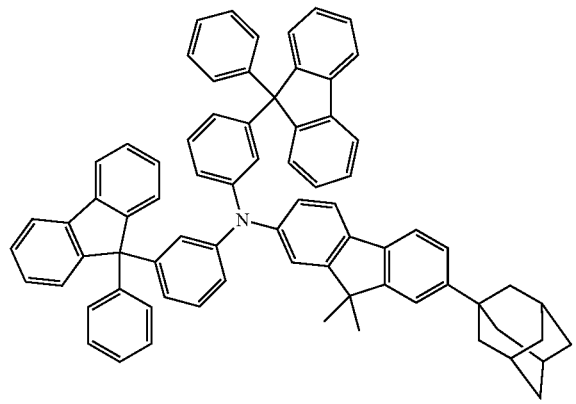
II-157
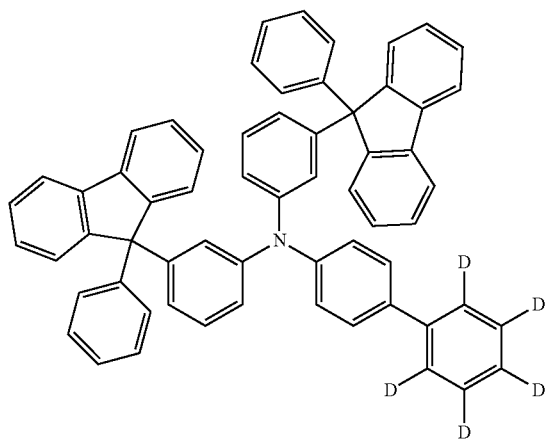
II-158
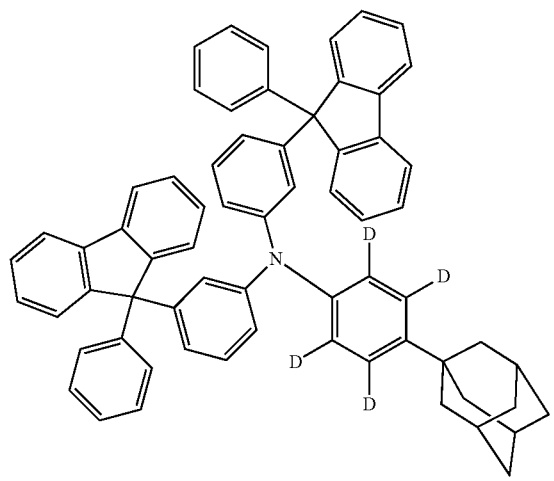
II-159
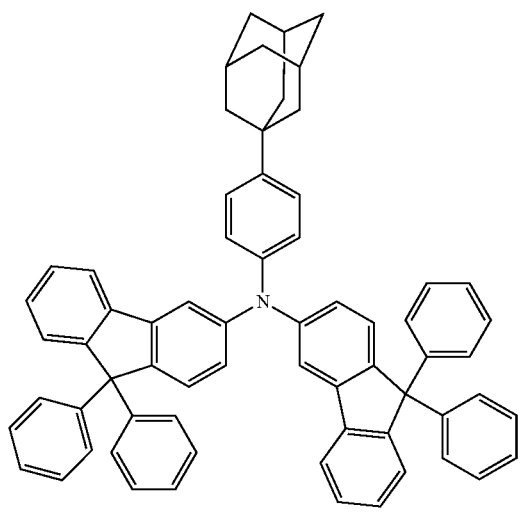
II-160
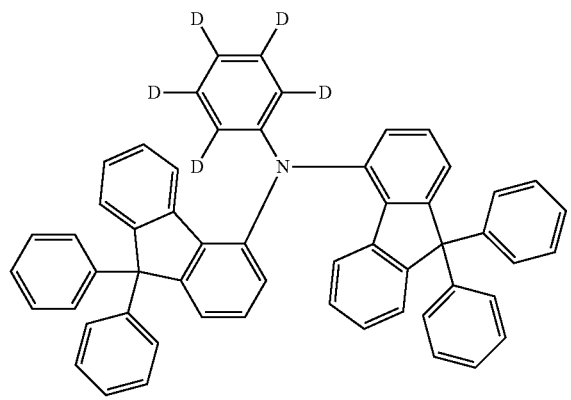

-continued
II-161
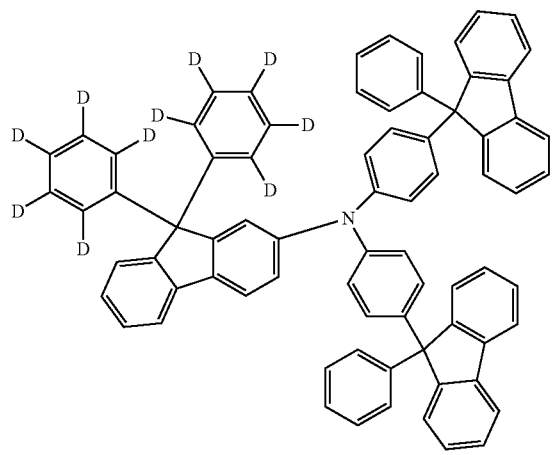
II-162
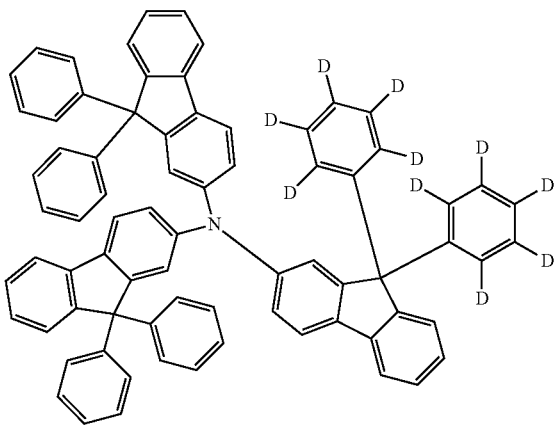
II-163
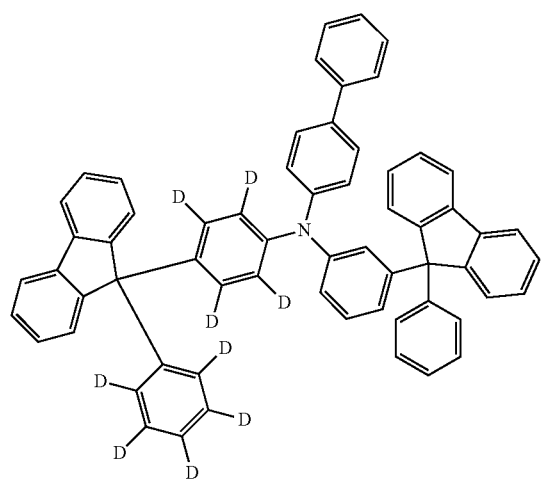
II-164
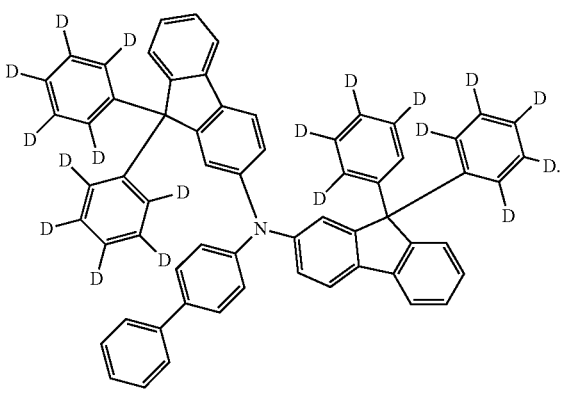
* * * * *